US010844076B2

(12) United States Patent
Sharma et al.

(10) Patent No.: US 10,844,076 B2
(45) Date of Patent: Nov. 24, 2020

(54) DERIVATIVES OF 6-(2,3-DICHLOROPHENYL)-1,2,4-TRIAZIN-5-AMINE

(71) Applicant: Nektar Therapeutics, San Francisco, CA (US)

(72) Inventors: Pankaj Sharma, New Delhi (IN); Vijay Kumar Khatri, Secunderabad Andhra Pradesh (IN); Xuyuan Gu, Foster City, CA (US); Yuan Song, Redwood City, CA (US); Michael Lixin Shen, San Bruno, CA (US); Jennifer Riggs-Sauthier, Huntsville, AL (US); Neel K. Anand, San Mateo, CA (US); Antoni Kozlowski, Huntsville, AL (US); Aleksandrs Odinecs, San Carlos, CA (US); Timothy A. Riley, Worcester, MA (US); Zhongxu Ren, Foster City, CA (US); YongQi Mu, Los Altos, CA (US); Xiaoming Shen, Millbrae, CA (US); Xuejun Yuan, San Ramon, CA (US); Natalia Aurrecoechea, Oakland, CA (US); Donogh John Roger O'Mahony, San Mateo, CA (US); Bo-Liang Deng, San Ramon, CA (US)

(73) Assignee: Nektar therapeutics, San Francisco, CA (US)

( * ) Notice: Subject to any disclaimer, the term of this patent is extended or adjusted under 35 U.S.C. 154(b) by 0 days.

(21) Appl. No.: 16/182,387

(22) Filed: Nov. 6, 2018

(65) Prior Publication Data
US 2019/0071454 A1  Mar. 7, 2019

Related U.S. Application Data

(62) Division of application No. 15/106,741, filed as application No. PCT/IN2014/000789 on Dec. 19, 2014, now Pat. No. 10,189,859.

(30) Foreign Application Priority Data

Dec. 21, 2013  (IN) ............................ 3732/DEL/2013
Jul. 3, 2014    (IN) ............................ 1799/DEL/2014
Oct. 17, 2014   (IN) ............................ 2966/DEL/2014

(51) Int. Cl.
| C07D 253/075 | (2006.01) |
| C07D 401/04  | (2006.01) |
| C07D 401/12  | (2006.01) |
| C07D 403/04  | (2006.01) |
| C07D 403/12  | (2006.01) |
| C07D 498/04  | (2006.01) |
| C07D 471/10  | (2006.01) |
| A61K 31/53   | (2006.01) |
| A61P 25/02   | (2006.01) |
| A61P 25/28   | (2006.01) |
| A61P 33/06   | (2006.01) |
| A61K 31/496  | (2006.01) |
| C07D 405/12  | (2006.01) |

(52) U.S. Cl.
CPC .......... *C07D 498/04* (2013.01); *A61K 31/496* (2013.01); *A61K 31/53* (2013.01); *A61P 25/02* (2018.01); *A61P 25/28* (2018.01); *A61P 33/06* (2018.01); *C07D 253/075* (2013.01); *C07D 401/04* (2013.01); *C07D 401/12* (2013.01); *C07D 403/04* (2013.01); *C07D 403/12* (2013.01); *C07D 405/12* (2013.01); *C07D 471/10* (2013.01)

(58) Field of Classification Search
CPC .. C07D 253/75; C07D 401/04; C07D 403/04; A61K 31/53; A61P 25/02; A61P 25/28; A61P 33/06
USPC ........................................... 544/182; 514/242
See application file for complete search history.

(56) References Cited

U.S. PATENT DOCUMENTS

| 3,391,197 | A |   | 7/1968  | Frump et al. |
| 3,637,688 | A |   | 1/1972  | Rees et al. |
| 4,486,354 | A |   | 12/1984 | Baxter et al. |
| 4,810,646 | A |   | 3/1989  | Jamas et al. |
| 4,992,540 | A |   | 2/1991  | Jamas et al. |
| 5,028,703 | A |   | 7/1991  | Jamas et al. |
| 5,607,677 | A |   | 3/1997  | Jamas et al. |
| 5,741,495 | A |   | 4/1998  | Jamas et al. |
| 6,420,354 | B1| * | 7/2002  | Marquess ............ C07D 239/48  514/183 |
| 6,916,867 | B2|   | 7/2005  | Gugumus |
| 7,678,551 | B2| * | 3/2010  | Ouyang ............. C07D 253/075  435/7.1 |

(Continued)

FOREIGN PATENT DOCUMENTS

| DE | 226454     | 8/1908  |
| EP | 0 963 980 A2 | 12/1999 |

(Continued)

OTHER PUBLICATIONS

Sinha et al. Chemical Papers (2011), 65(1), 70-76; CA 155: 449249, 2010. CAPLUS Abstract provided.*

(Continued)

*Primary Examiner* — Venkataraman Balasubramanian
(74) *Attorney, Agent, or Firm* — Jacqueline F. Mahoney

(57) ABSTRACT

The instant disclosure relates to (among other things) compounds that are derivatives of 6-(2,3-dichlorophenyl)-1,2,4-triazin-5-amine. The compounds provided possess unique effects and differences over other phenyltriazines known in the art.

17 Claims, No Drawings

(56) References Cited

U.S. PATENT DOCUMENTS

| | | | |
|---|---|---|---|
| 8,772,479 B2* | 7/2014 | Riggs-Sauthier | ............................ C07D 253/075 544/182 |
| 10,189,859 B2* | 1/2019 | Sharma | ................ C07D 401/04 |
| 2005/0281781 A1 | 12/2005 | Ostroff | |
| 2006/0046967 A1* | 3/2006 | Satyam | ................ C07C 323/12 548/400 |
| 2006/0115865 A1* | 6/2006 | Ouyang | ............... C07D 249/14 435/7.92 |
| 2008/0044438 A1 | 2/2008 | Ostroff et al. | |
| 2012/0122871 A1* | 5/2012 | Riggs-Sauthier | ............................ C07D 253/075 514/242 |
| 2017/0066782 A1 | 3/2017 | Sharma et al. | |
| 2017/0204080 A1 | 7/2017 | Chen et al. | |

FOREIGN PATENT DOCUMENTS

| | | |
|---|---|---|
| WO | WO 2006/047372 A2 | 5/2006 |
| WO | WO 2007/097470 A2 | 8/2007 |
| WO | WO 2010/132691 A1 | 11/2010 |
| WO | WO 2015/107493 A1 | 7/2015 |

OTHER PUBLICATIONS

Venkanna et. al, Pharma Chemica (2012), 4(1), 100-105; CA 156: 560579, 2012. CAPLUS Abstract provided.*
Berge et al., "Pharmaceutical Salts", Journal of Pharmaceutical Sciences, vol. 66, No. 1, pp. 1-19, (Jan. 1977).
Dermer, "Another Anniversary for the War on Cancer", Bio/Technology, vol. 12, pp. 320, Mar. 12, 1994.
Ertl et al., "Fast Calculating of Molecular Polar Surface Area as a Sum of Fragment-Based Contributions and Its Application to the Prediction of Drug Transport", J. Med. Chem., vol. 43, pp. 3714-3717, (2000).
Freshney, "Culture of Animal Cells", A Manual of Basic Technique, Alan R. Liss, Inc., New York, pp. 1-6, (1983).
Garcia et al., "Quantitative structure-property relationships prediction of some physico-chemical properties of glycerol based solvents", Green Chem., Vo. 15, pp. 2283-2293, (2013).
Hartman et al., "Dimethyl Sulfide Ditriflate: A New Reagent for the Conversion of Amino Heterocycles to Iminosulfuranes", Tetrahedron Letters, vol. 24, No. 10, pp. 1011-1014, (1983).
Jain et al., "Mutual prodrugs containing bio-cleavable and drug releasable disulfide linkers", Bioorganic Chemistry, vol. 49, pp. 40-48, (2013).
Kelder et al., "Polar Molecular Surface as a Dominating Determinant for Oral Absorption and Brain Penetration of Drugs", Pharmaceutical Research, vol. 16, No. 10, pp. 1514-1519, (1999).
Shirini et al., "Poly(4-vinylpyridine) catalyzed Chemoselective O-TMS protection of alcohols and phenols and N-Boc protection of amines", J. Iran Chem. Soc., vol. 9, pp. 495-502, (2012).
Sinha et al., "Synthesis, characterisation, and biological activity of three new amide prodrugs of lamotrigine with reduced hepatotoxicity", Chemical Papers, vol. 65, No. 1, pp. 70-76, (2011).
Wagner et al., "Mepyramine-JNJ7777120—hybrid compounds show high affinity to $hH_1R$, but low affinity to $hH_4R$", Bioorganic & Medicinal Chemistry Letters, vol. 21, pp. 6274-6280, (2011).
Woodbury et al., "Design and Use of a New Electroshock Seizure Apparatus, and Analysis of Factors Altering Seizure Threshold and Pattern", Arch. Int. Pharmacodyn., XCII, No. 1, pp. 97-107, (1952).
XP002739497, Database Reaxys [Online], Elsevier Information Systems, GmbH, Frankfurt/Main (DE), Database accession No. 639503, Abstract, 1 page.
XP002739498, Database Reaxys [Online] Elsevier Information Systems, GmbH, Frankfurt/Main (DE), Database accession No. 4799025, Abstract, 10 pages.
XP002739499, Database Reaxys [Online] Elsevier Information Systems, GmbH, Frankfurt/Main (DE), Database accession No. 1734308, Abstract, 8 pages.
XP002739500, Database Reaxys [Online] Elsevier Information Systems, GmbH, Frankfurt/Main (DE), Database accession No. 7705020, Abstract, 6 pages.
XP002739539, Database Reaxys [Online] Elsevier Information Systems, GmbH, Frankfurt/Main (DE), Database accession No. 7589268, Abstract, 2 pages.
PCT International Search Report and Written Opinion in corresponding PCT Application No. PCT/IN2014/000789 date of dated Aug. 10, 2015.
PCT International Preliminary Report on Patentability corresponding to PCT Application No. PCT/IN2014/000789 dated Jun. 30, 2016.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

* cited by examiner

DERIVATIVES OF 6-(2,3-DICHLOROPHENYL)-1,2,4-TRIAZIN-5-AMINE

CROSS REFERENCE TO RELATED APPLICATIONS

This application is a divisional application of U.S. patent application Ser. No. 15/106,741, filed Jun. 20, 2016, now U.S. Pat. No. 10,189,859, which is a 35 U.S.C. § 371 application of International Application No. PCT/IN2014/000789, filed Dec. 19, 2014, which claims the benefit of priority to Indian Provisional Patent Application No. 2966/DEL/2014, filed Oct. 17, 2014; Indian Provisional Patent Application No. 1799/DEL/2014, filed Jul. 3, 2014; and Indian Provisional Patent Application No. 3732/DEL/2013, filed Dec. 21, 2013, each of which are hereby incorporated by reference in their entireties.

FIELD

This disclosure comprises (among other things) derivatives of 6-(2,3-dichlorophenyl)-1,2,4-triazin-5-amine that possess unique properties. The derivatives of 6-(2,3-dichlorophenyl)-1,2,4-triazin-5-amine described herein relate to and/or have application(s) in (among others) the fields of drug discovery, pharmacotherapy, physiology, and organic chemistry.

BACKGROUND

As the name suggests, phenyltriazines are a class of molecules that contain both a phenyl group and a triazine group. The phenyltriazine class of molecules has a variety of activities and uses. For example, one of the most well-known members of the phenyltriazines in the field of pharmacology is lamotrigine [3,5-diamino-6-(2,3-dichlorophenyl)-1,2,4-triazine], which has been shown to be useful for treating patients suffering from epileptic and bipolar disorders. Other phenyltriazines have been used as UV absorbers. See U.S. Pat. No. 6,916,867. Still other phenyltriazines have been shown to have activity against malarial infections. See U.S. Pat. No. 3,637,688. Thus, in view of their myriad activities and uses, phenyltriazines represent an important class of molecules.

In view of the above, there remains a need to continue to identify new phenyltriazines, with the aim of finding new uses within this class of active molecules or improving the properties of currently known phenyltriazines.

By way of example, individuals being treated with the phenyltriazine, lamotrigine, may experience many side effects, including life threatening skin reactions, including Stevens-Johnson syndrome, toxic epidermal necrolysis, headaches, dizziness and insomnia. Other side effects may include acne and skin irritation, vivid dreams or nightmares, night sweats, body aches and cramps, muscle aches, dry mouth, fatigue, memory problems, cognitive problems, irritability, weight changes, hair loss, changes in libido, frequent urination, and nausea. Therefore, pharmacotherapy with such phenyltriazine would be notably improved if these and/or other adverse or side effects associated with their use could be lessened or if their pharmacology could be improved. Thus, there is a large unmet need for additional novel phenyltriazine compounds having beneficial and or improved properties over lamotrigine.

The present disclosure seeks to address these and other needs in the art.

SUMMARY

In one aspect, provided herein are derivatives of 6-(2,3-dichlorophenyl)-1,2,4-triazine-5 amine. The compounds provided herein each possess an N-bonded substituent at the 3-position of the triazine ring and an amino ($-NH_2$) group at the 5-position of the triazine ring, based upon the numbering scheme provided below. The N-bonded substituent is an amino nitrogen covalently attached to the 3-carbon of the triazine ring, where the amino nitrogen may be comprised within a substituted acyclic amino moiety, or may form part of a substituted or unsubstituted nitrogen-containing heterocycle such as a substituted or unsubstituted piperazine moiety, a substituted or unsubstituted piperidine, a substituted or an unsubstituted pyrrolidine moiety, a substituted or an unsubstituted azetidine, or a substituted or an unsubstituted diazetidine, where any of the foregoing nitrogen-containing heterocycles may also form part of a bi- or a tricyclic ring structure. Generally, the compounds provided herein have the following general structure:

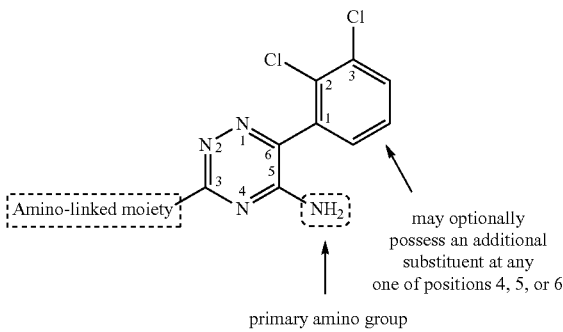

Formula A primary amino group

The amino linked moiety is attached to the 3-carbon of the triazine ring by an amino-linkage, where the amino group may be a primary amino group ($-NH_2$), or may be a secondary or a tertiary amino group (comprising one or no hydrogens, respectively). The amino group is generally but not necessarily a substituted amino group, i.e., having one or no hydrogens. The amino group may, for example, be substituted with an alkyl chain(s) that is linear or branched, and/or may comprise an oligomeric ethylene oxide chain, both of which may be further substituted. In one or more embodiments, substituents include one or more functional groups selected from, for example, oxygen (ether), amino, hydroxyl, carboxyl, carbonyl, sulfonyl, aldehyde, alkylsulfone, tetrazole, carbonyl, oxetane, carbonate, alkyl ester, sulfoxide, halo, amido, sulfonamide, cycloalkyl, heterocyclyl, $-CF_3$, $-CF_2H$, $CFH_2$, and the like.

In some embodiments, the amino group linked to the 3-carbon of the triazine ring may also be comprised within a ring structure. The amino group may, for example, be comprised within a substituted or unsubstituted piperazine moiety, or within a substituted or unsubstituted pyrrolidine moiety, or within a substituted or unsubstituted piperidine, or within a substituted or unsubstituted azetidine, or within a substituted or unsubstituted diazetidine, and the like, or may be comprised within a bicyclic ring comprising one of the foregoing heterocycles, such as a hexahydropyrazino-oxazin-one, or hexahydropyrazino-oxazine, diazaspiro-octane, diazaspiro-nonane, and the like. Substituted ring structures include rings as described above substituted with an alkyl chain that is linear or branched, and/or with an oligomeric ethylene oxide chain (that may comprise a substituent on an alkyl chain) both of which may be further substituted. In one or more embodiments, substituents include one or more functional groups selected from, for example, oxygen (ether), amino, hydroxyl, carboxyl, carbonyl, sulfonyl, aldehyde, alkylsulfone, tetrazole, carbonyl, oxetane, carbonate, alkyl ester, sulfoxide, halo, amido, sulfonamide, cycloalkyl, heterocyclyl, —$CF_3$, —$CF_2H$, $CFH_2$, and the like.

In some embodiments, the dichlorophenyl ring may possess an additional substituent at any one of positions 4, 5 or 6, where the substituent is selected from halo, hydroxyl, and oligomeric ethylene oxide (—$OCH_2CH_2)_nOR$, where n is in a range from 1-7 and R is selected from H, -lower alkyl, preferably methyl, and fluoro-substituted methyl (e.g., —$CF_3$, —$CHF_2$, —$CH_2F$).

In one or more embodiments, derivatives of 6-(2,3-dichlorophenyl)-1,2,4-triazine-5 amine of the following structure are provided:

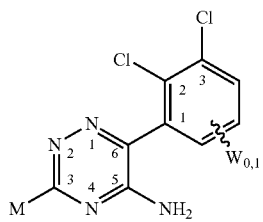

Formula B where M is a substituted amino moiety —$NR_6R_7$, wherein $R_6$ and $R_7$ are each independently selected from the group consisting of H, lower alkyl, —$(CH_2CH_2O)_mR_8$, —$CH_2CH_2$-(3-7 membered heterocycloalkyl), —$C(O)$—$CH_2(CH_2CH_2O)_mR_{10}$, —$CH_2CR_9HCH_2O(CH_2CH_2O)_m(CH_2)_{0,1}R_{10}$, —$CR_{11}R_{12}CH_2OH$, —$CR_{11}R_{12}CH_2O(CH_2CH_2O)_{1-7}R_{10}$, —$CH$—$[CH_2OH]_2$; —$CCH_3(CH_2OH)_2$, —$CCH_3(CH_2OH)CH_2O(CH_2CH_2O)_{1-7}R_{10}$, alkylamino, hydroxyalkylamino, —$CH_2CH_2NCH_3C(O)CH_2(OCH_2CH_2)_{1-7}R_{10}$, —$CH_2CH_2NCH_3C(O)CH_2OCH_2C(O)NH_2$, —$CH_2CH_2NCH_3(CH_2CH_2O)_{1-7}R_{10}$, —$CR_{11}R_{12}CH(O)$, —$CR_{11}R_{12}(CH_2)_{1\ or\ 2}SO_2$—$CH_2CH_2O)_{1-7}R_{10}$, —$CCH_3(CH_2OCH_2CH_2OCH_3)_2$, —$OCH_2CR_9HCH_2OR_{10}$—$CH_2CR_9HCH_2NHC(O)CH_2O(CH_2CH_2O)_mR_{10}$, —$CH_2CR_9HCH_2NHC(O)CH_2OCH_2C(O)NH_2$, and —$(OCH_2CH_2)_mOR_{10}$, with the proviso that $R_6$ and $R_7$ are not both H, or wherein $R_6$ and $R_7$ taken together with N form a heterocycloalkyl ring selected from piperazine, piperidine, and azetidine, which may optionally form part of a bicyclic ring structure, where the heterocycloalkyl ring or bicyclic ring is either unsubstituted or is substituted with a group selected from lower alkyl, —$(CH_2CH_2O)_mR_8$, —$C(O)$—$CH_2(CH_2CH_2O)_mR_{10}$, —$CH_2CR_9HCH_2O(CH_2CH_2O)_m(CH_2)_{0,1}R_{10}$, —$CH_2CH_2SO_2CH_3$, —$NR_9(CH_2CH_2O)_mR_{10}$, tetra-hydro-2H-pyranyl, piperidinyl, —$CH_2OH$, —$CH_2R_{10}$, amino, —$CHCH_3CH_2OH$, hydroxyl, —$CR_{11}R_{12}CH_2OH$, —$C(O)OCH_3$, —$CF_3$, —$CH_2C(OH)CF_3$, —$CH_2OCH_2$—$C_6H_5F$, and —$CH_2CR_9HCH_2O(CH_2CH_2O)_m(CH_2)_{0,1}R_{13}$, m is in a range from 0-29, $R_8$ is selected from H, C1-C6 alkyl, fluoro-substituted methyl (e.g., —$CF_3$, —$CF_2H$, or —$CFH_2$), —$CH_2COOR_{10}$, —$CH_2COCH_3$, 3-7 membered heterocycloalkyl, 3-7 membered heteroaryl, heteroarylalkyl, —$C(O)OCH_3$, C1-C6 alkyl substituted with one or more of hydroxyl, amino, alkylamino, amido, alkylamide, amidoalkylamine, acylamino, carboxyalkylamino, sulfonamide, sulfone, alkylsulfone, alkoxyalkyl sulfone, alkyloxyalklsulfoxide, 3-7 membered heterocycloalkyl, 5-6 membered heteroaryl, carboxyl, —$NHCH_2CH_2OCH_3$, —$NHCHR_9COOR_{11}$; and —$CH$—$[CH_2O$—$(CH_2CH_2O)_{2-8}CH_3]_2$;

$R_9$ is H, lower alkyl, hydroxyl, $R_{10}$ is selected from H, lower alkyl and fluoro-substituted methyl, $R_{11}$ and $R_{12}$ are each independently selected from H and lower alkyl, $R_{13}$ is cyclopropyl or cyclobutyl, and W is an optional substituent (where the subscript zero indicates its absence and the subscript 1 indicates its presence) selected from halo, hydroxyl, and oligomeric ethylene oxide (—$OCH_2CH_2)_nOR$, where n ranges from 1-7 and R is selected from H, -lower alkyl, preferably methyl, and fluoro-substituted methyl (e.g., —$CF_3$, —$CHF_2$, —$CH_2F$). In some embodiments, W is fluoro. In some additional embodiments, W is a fluoro group positioned at the 5-position of the phenyl ring, based upon the numbering provided herein.

In one or more embodiments, when $R_6$ is H and W is absent, $R_7$ does not equal —$(CH_2CH_2O)_{2-11}CH_3$.

In one or more embodiments, $R_6$ is H.

In some embodiments, $R_6$ and $R_7$ are each independently selected from the group consisting of H, lower alkyl, —$(CH_2CH_2O)_mR_8$, —$CH_2CH_2$-(3-7 membered heterocycloalkyl), —$C(O)$—$CH_2(CH_2CH_2O)_mR_{10}$, —$CH_2CR_9HCH_2O(CH_2CH_2O)_m(CH_2)_{0,1}R_{10}$, —$CR_{11}R_{12}CH_2OH$, —$CR_{11}R_{12}CH_2O(CH_2CH_2O)_{1-7}R_{10}$, —$CH$—$[CH_2OH]_2$; —$CCH_3(CH_2OH)_2$, —$CCH_3(CH_2OH)CH_2O(CH_2CH_2O)_{1-7}R_{10}$, alkylamino, hydroxyalkylamino, —$CH_2CH_2NCH_3C(O)CH_2(OCH_2CH_2)_{1-7}R_{10}$, —$CH_2CH_2NCH_3C(O)CH_2OCH_2C(O)NH_2$, —$CH_2CH_2NCH_3(CH_2CH_2O)_{1-7}R_{10}$, —$CR_{11}R_{12}CH(O)$, —$CR_{11}R_{12}(CH_2)_{1\ or\ 2}SO_2$—$CH_2CH_2O)_{1-7}R_{10}$, —$CCH_3(CH_2OCH_2CH_2OCH_3)_2$, —$OCH_2CR_9HCH_2OR_{10}$—$CH_2CR_9HCH_2NHC(O)CH_2O(CH_2CH_2O)_mR_{10}$, —$CH_2CR_9HCH_2NHC(O)CH_2OCH_2C(O)NH_2$, and —$(OCH_2CH_2)_mOR_{10}$, where variables possess the values provided above, and with the proviso that $R_6$ and $R_7$ are not both H.

In yet some further embodiments, $R_6$ is H and $R_7$ is selected from the group consisting of H, lower alkyl, —$(CH_2CH_2O)_mR_8$, —$CH_2CH_2$-(3-7 membered heterocycloalkyl), —$C(O)$—$CH_2(CH_2CH_2O)_mR_{10}$, —$CH_2CR_9HCH_2O(CH_2CH_2O)_m(CH_2)_{0,1}R_{10}$, —$CR_{11}R_{12}CH_2OH$, —$CR_{11}R_{12}CH_2O(CH_2CH_2O)_{1-7}R_{10}$, —$CH$—$[CH_2OH]_2$; —$CCH_3(CH_2OH)_2$, —$CCH_3(CH_2OH)CH_2O(CH_2CH_2O)_{1-7}R_{10}$, alkylamino, hydroxyalkylamino, —$CH_2CH_2NCH_3C(O)CH_2(OCH_2CH_2)_{1-7}R_{10}$, —$CH_2CH_2NCH_3C(O)CH_2OCH_2C(O)NH_2$, —$CH_2CH_2NCH_3(CH_2CH_2O)_{1-7}R_{10}$, —$CR_{11}R_{12}CH(O)$, —$CR_{11}R_{12}(CH_2)_{1\ or\ 2}SO_2$—$CH_2CH_2O)_{1-7}R_{10}$, —$CCH_3(CH_2OCH_2CH_2OCH_3)_2$, —$OCH_2CR_9HCH_2OR_{10}$—$CH_2CR_9HCH_2NHC(O)CH_2O(CH_2CH_2O)_mR_{10}$, —$CH_2CR_9HCH_2NHC(O)CH_2OCH_2C(O)NH_2$, and —$(OCH_2CH_2)_mOR_{10}$, where variables possess the values provided above.

In some preferred embodiments, m is selected from 0, 1, 2, 3, 4, 5, 6, and 7.

In some additional embodiments, $R_6$ and $R_7$ taken together with N form a heterocycloalkyl ring selected from piperazine, piperidine, and azetidine, which may optionally form part of a bicyclic ring structure, where the heterocycloalkyl ring or bicyclic ring is either unsubstituted or is substituted with a group selected from lower alkyl, —(CH₂CH₂O)ₘR₈, —C(O)—CH₂(CH₂CH₂O)ₘR₁₀, —CH₂CR₉HCH₂O(CH₂CH₂O)ₘ(CH₂)₀,₁R₁₀, —CH₂CH₂SO₂CH₃, —NR₉(CH₂CH₂O)ₘR₁₀, tetra-hydro-2H-pyranyl, piperidinyl, —CH₂OH, —CH₂R₁₀, amino, —CHCH₃CH₂OH, hydroxyl, —CR₁₁R₁₂CH₂OH, —C(O)OCH₃, —CF₃, —CH₂C(OH)CF₃, —CH₂OCH₂—C₆H₅F, and —CH₂CR₉HCH₂O(CH₂CH₂O)ₘ(CH₂)₀,₁R₁₃, where variables such as m, R₈, R₉, R₁₀, R₁₁, R₁₂, and R₁₃ posssess the values provided above.

In one or more embodiments, R₆ is H and R₇ is —(CH₂CH₂O)ₘR₈, where m is selected from 1, 2, 3, 4, 5, 6, and 7, and R₈ is selected from H, methyl, isopropyl, fluoro-substituted methyl, carboxyl, and 3-7 membered heterocycloalkyl. In one or more related embodiments, the 3-7 membered ring heterocycloalkyl is selected from tetrazole, oxetane and piperazine.

In some embodiments, R₆ and R₇ taken together with N form a heterocycloalkyl ring selected from piperazine, piperidine, and azetidine. In some particular embodiments, R₆ and R₇ taken together with N form an unsubstituted or a substituted piperazine. Exemplary substituted piperazines include those having a N-substituent selected from —(CH₂CH₂O)₁₋₇C1-C6 alkyl or fluoro-substituted methyl, —(CH₂CH₂O)₁₋₇CH₂CH₂NHSO₂CH₃, —(CH₂CH₂O)₁₋₇CH₂CH₂—N(tetrazole), —C(O)CH₂O(CH₂CH₂O)₁₋₇CH₃, —CH₂CHOHCH₂OCF₃, —CH₂CHOHCH₂OCH₂CF₃—CH₂CHOHCH₂OCH₃, —CH₂OH, —(CH₂CH₂O)₂OH, —CH₂CH₂SO₂CH₃, —CH₂CH₂OCH₂COOH, —CH₂CH₂OCH₂COOC(CH₃)₃, —CH₂CH(OH)CH₂OH, —C(CH₃)₂CH₂OCH₂CH₂OH, (tetrahydropyranyl), (piperidinyl-NH), —CH₂CF₃, —CHCH₃CH₂OH, —C(CH₃)₂CH₂OH, and —CH₂CH(OH)CH₂Cl. Exemplary compounds wherein R₆ and R₇ taken together with N form an unsubstituted or a substituted piperazine include compounds 92, 103, 104, 105, 106, 113, 120, 121, 122, 123, 96, 97, 87, 89, 88, 90, 94, 207, 98, 13, 136, 137, 208, 124, 27, 200, 201, 202, 203, 204, 138, 139, 140, 55, 73, 78, 80, and 83.

In some additional embodiments, R₆ and R₇ taken together with N form a ring selected from substituted pyrrolidine, substituted piperazine, and substituted piperazine forming part of a bicyclic ring system, e.g., tetrahydro-1H-oxazolo[3,4-a]pyrazin-3(5H)-one (as in compound 128), tetrahydro-1H-oxazolo[3,4-a]pyrazin-3(5H)-one (as in compound 127), and hexahydropyrazino[2,1-c][1,4]oxazin-4(3H)-one (as in compound 130), and azetidine.

In some particular embodiments, the compound is selected from the group consisting of: (2S,4R)-Methyl 1-(5-amino-6-(2,3-dichlorophenyl)-1,2,4-triazin-3-yl)-4-hydroxypyrrolidine-2-carboxylate (Compound 65), (S)-1-(4-(5-amino-6-(2,3-dichlorophenyl)-1,2,4-triazin-3-yl)piperazin-1-yl)-3-methoxypropan-2-ol (Compound 97), (S)-7-(5-amino-6-(2,3-dichlorophenyl)-1,2,4-triazin-3-yl)tetrahydro-1H-oxazolo[3,4-a]pyrazin-3(5H)-one HCl salt (Compound 128), (S)-1-(4-(5-amino-6-(2,3-dichlorophenyl)-1,2,4-triazin-3-yl)-piperazin-1-yl)-3-(2,2,2-trifluoroethoxy)-propan-2-ol.2HCl (Compound 95), (R)-1-((1-(5-Amino-6-(2,3-dichlorophenyl)-1,2,4-triazin-3-yl)azetidin-3-yl)oxy)-3-methoxypropan-2-ol (Compound 75), 3-N-(3-hydroxyazetin-1-yl) lamotrigine (Compound 129), 1-(4-(5-Amino-6-(2,3-dichlorophenyl)-1,2,4-triazin-3-yl)piperazin-1-yl)-3-(trifluoromethoxy)propan-2-ol (Compound 27), (R)-7-(5-amino-6-(2,3-dichlorophenyl)-1,2,4-triazin-3-yl) tetrahydro-1H-oxazolo[3,4-a]pyrazin-3(5H)-one (Compound 127), (R)-1-(4-(5-amino-6-(2,3-dichlorophenyl)-1,2,4-triazin-3-yl)-piperazin-1-yl)-3-(2,2,2-trifluoroethoxy)-propan-2-ol (Compound 94), (S)-1-(4-(5-amino-6-(2,3-dichlorophenyl)-1,2,4-triazin-3-yl)piperazin-1-yl)-3-methoxypropan-2-ol (Compound 98), (R)-1-(4-(5-amino-6-(2,3-dichlorophenyl)-1,2,4-triazin-3-yl)piperazin-1-yl)-3-methoxypropan-2-ol (Compound 96), 3-N-(4-(tetrahydro-2H-pyran-4-yl)piperazin-1-yl) lamotrigine di HCl (Compound 120), and (R)-8-(5-amino-6-(2,3-dichlorophenyl)-1,2,4-triazin-3-yl)hexahydropyrazino[2,1-c][1,4]oxazin-4(3H)-one HCl salt (Compound 130).

In one or more embodiments, derivatives of 6-(2,3-dichlorophenyl)-1,2,4-triazine-5 amine of the following structure are provided:

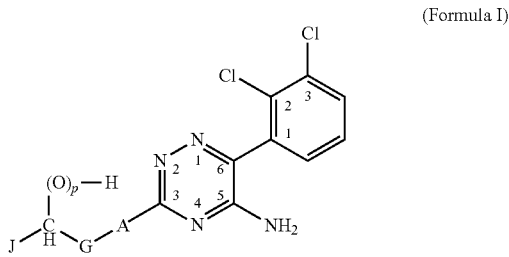

(Formula I)

wherein:

A is selected from the group consisting of

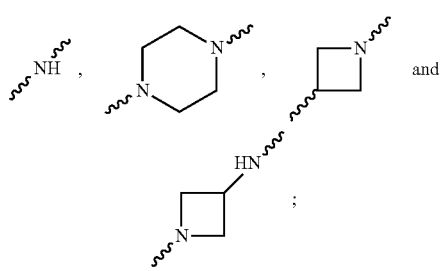

G is selected from the group consisting of ~O~, ~CH₂~,

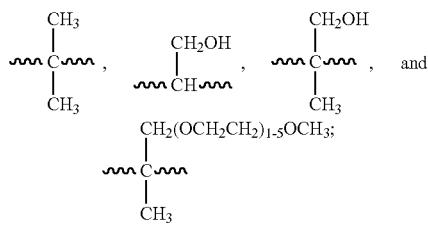

p is 0 or 1 (where a value of 0 indicates the absence of oxygen and a value of 1 indicates its presence); and J is selected from the group consisting of ~CH(OH)CH$_2$OH, ~CH(OH)CH$_2$OCH$_3$, ~OCH$_2$CH$_2$OH, ~CH$_2$OCF$_3$, ~CH$_2$OCH$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$, ~CH$_2$OCH(CH$_3$)$_2$,

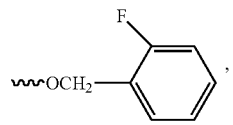

and ~OCH$_2$C(OH)HCH$_2$OCH$_3$, and pharmaceutically acceptable salts thereof.

In one or more embodiments of formula (I), G is

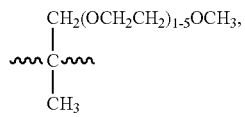

where G is selected from

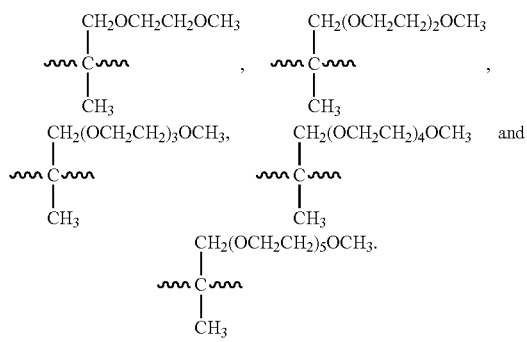

In one or more additional embodiments, when J is ~(OCH$_2$CH$_2$)$_{0-29}$OR$^1$, J is further selected from ~OR$^1$ and ~(OCH$_2$CH$_2$)$_{1-10}$OR$^1$.

In yet one or more further embodiments, when J is ~(OCH$_2$CH$_2$)$_{0-29}$OR$^1$, J is selected from ~(OCH$_2$CH$_2$)OR$^1$, ~(OCH$_2$CH$_2$)$_2$OR$^1$, ~(OCH$_2$CH$_2$)$_3$OR$^1$, ~(OCH$_2$CH$_2$)$_4$OR$^1$, ~(OCH$_2$CH$_2$)$_5$OR$^1$, ~(OCH$_2$CH$_2$)$_6$OR$^1$, ~(OCH$_2$CH$_2$)$_6$ OR$^1$, ~(OCH$_2$CH$_2$)$_8$OR$^1$, ~(OCH$_2$CH$_2$)$_9$OR$^1$, and ~(OCH$_2$CH$_2$)$_{10}$OR$^1$.

In one or more further embodiments, compounds of the following structure are provided:

(Formula II)

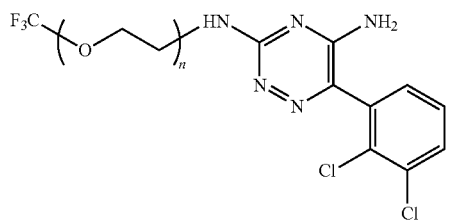

wherein (n) is an integer of 1 to 30, and pharmaceutically acceptable salts thereof. Compounds in accordance with Formula II fall within Formula I above where G is ~CH$_2$~, p equals zero, and J is ~(OCH$_2$CH$_2$)$_{1-29}$OR$^1$, where R$^1$ is —CF$_3$, and the number of ethylene oxide subunits is selected from 1, 2, 3, 4, 5, 6, 7, 8, 9, 10, 11, 12, 13, 14, 15, 16, 17, 18, 19, 20, 21, 22, 23, 24, 25, 26, 27, 28, and 29.

In one or more embodiments, a compound having the following formula is provided:

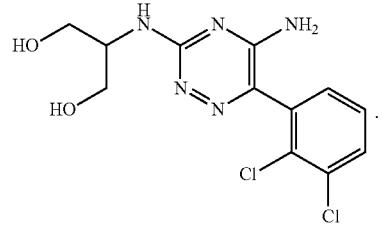 [SMILES: Nc1nc(NC(CO)CO)nnc1-c1cccc(Cl)c1Cl]

In the compound above, in reference to Formula I, G is

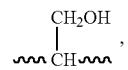

p is zero, and J is ~OH.

In yet one or more additional embodiments, a compound in accordance with the following structure is provided, where the substituent covalently attached to the 3-carbon of the triazine ring is a substituted pyrrolidine moiety:

(Formula III)

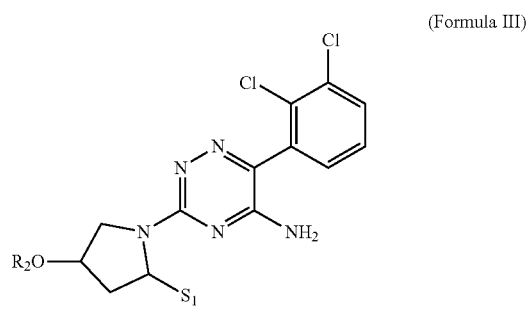

wherein R$_2$ is either H or ~CH$_2$C(OH)CH$_2$OCH$_3$, and S$_1$ is an optional substituent selected from ~OCH$_2$CH$_3$ and

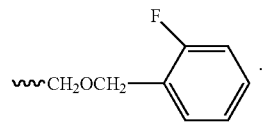

In one or more additional embodiments of the compound of formula (I), A is

and the compound is selected from the group consisting of:
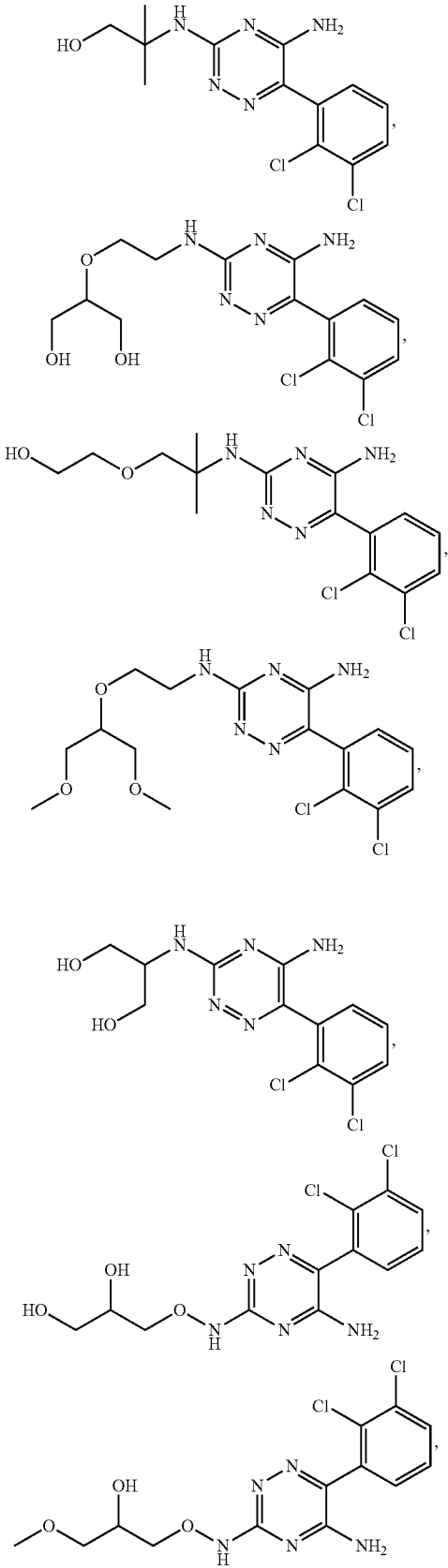
-continued
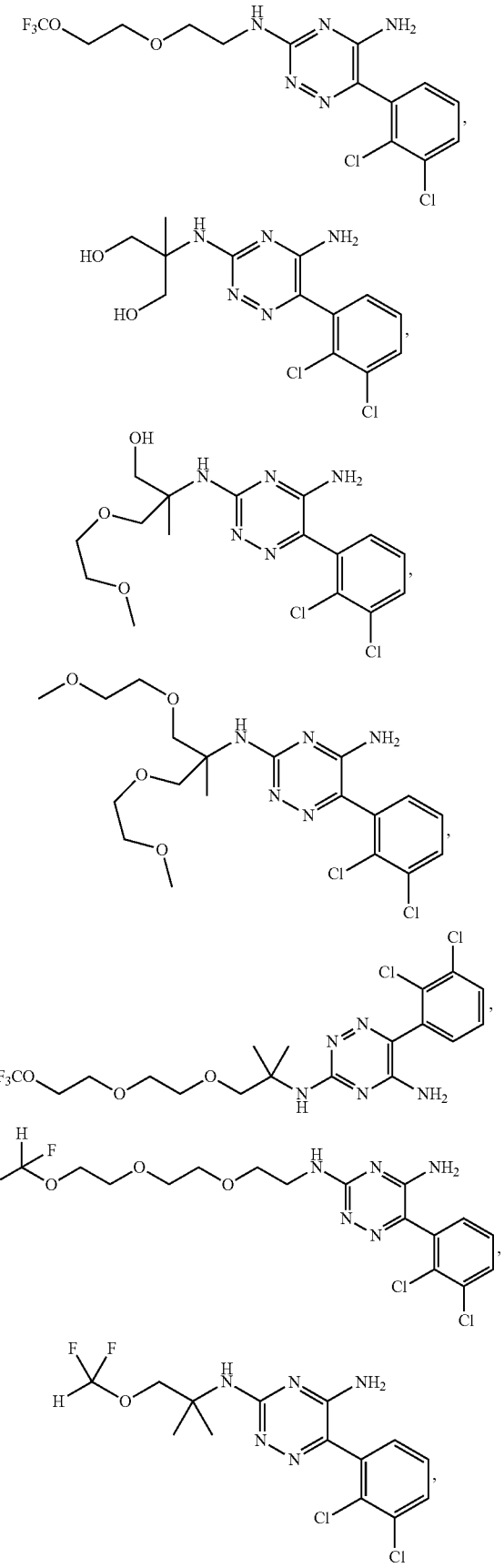

-continued

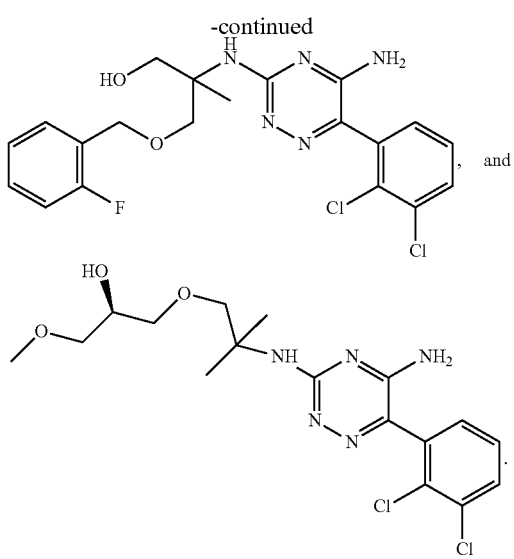

In yet one or more further embodiments of the compound of Formula (I), A is

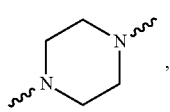

and the compound is selected from the group consisting of

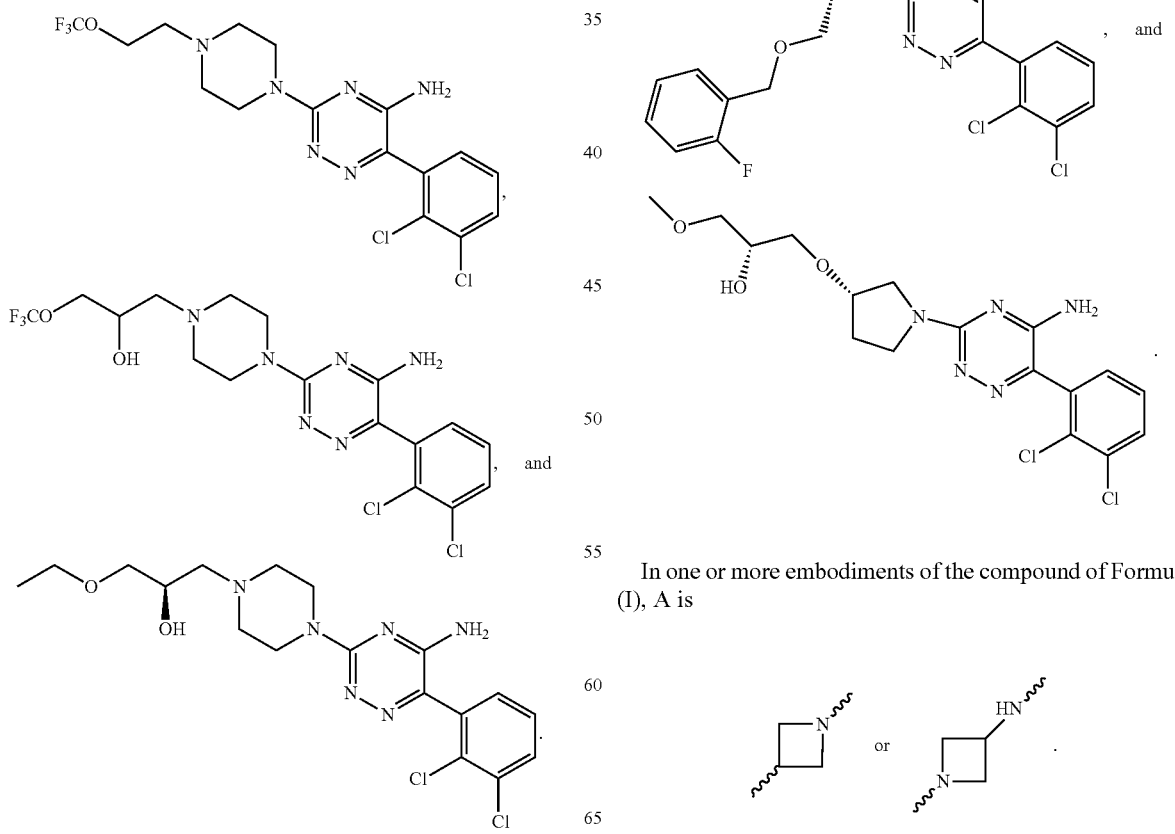

In one or more embodiments of the compound of Formula (I), A is

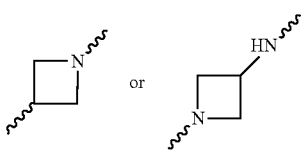

In one or more additional embodiments, the 6-(2,3-dichlorophenyl)-1,2,4-triazin-5-amine derivative compound comprises a substituted pyrrolidine at the 3-position of the triazine ring and is selected from the group consisting of:

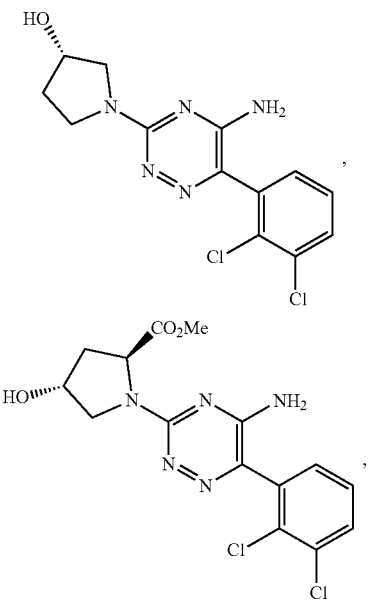

In one or more embodiments of the compound of Formula (I), A is

G is

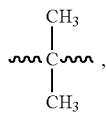

p is 0, and J is selected from ~CH(OH)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

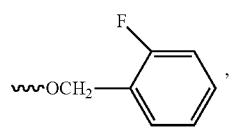

and ~OCH$_2$C(OH)HCH$_2$OCH$_3$.

In one or more additional embodiments of the compound of Formula (I), A is

G is

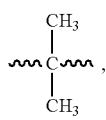

p is 0, and J is selected from ~OH, ~OCH$_2$CH$_2$OH, ~OCF$_2$H, ~OCH$_2$C(OH)HCH$_2$OCH$_3$ and ~(OCH$_2$CH$_2$)$_2$OCF$_3$.

In one or more further embodiments, A is either

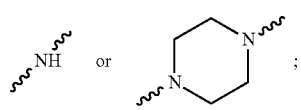

G is ~CH$_2$~, p is 0 or 1, and J is selected from ~CH(OH)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

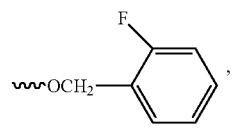

and ~OCH$_2$C(OH)HCH$_2$OCH$_3$.

In yet one or more additional embodiments, A is either

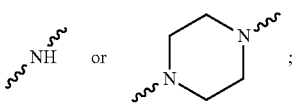

G is ~CH$_2$~, p is 0, and J is selected from ~OCH(CH$_2$OH)$_2$, ~OCH(CH$_2$OCH$_3$)$_2$, ~OCF$_3$, ~(OCH$_2$CH$_2$)OCF$_3$, ~CH(OH)CH$_2$OCH$_3$, ~CH$_2$OCH$_2$CH$_3$, ~(OCH$_2$CH$_2$)$_2$OCF$_2$H.

In yet one or more additional embodiments, A is

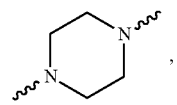

G is ~CH$_2$~, p is 1, and J is ~CH$_2$OCF$_3$.

In yet one or more further embodiments, A is

G is

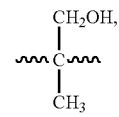

p is 0, and J is selected from the group consisting of ~CH(OF)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

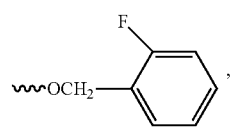

and ~OCH$_2$C(OH)HCH$_2$OCH$_3$.

In yet one or more further embodiments, A is

G is

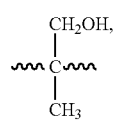

p is 0, and J is selected from the group consisting of ~OH, ~(OCH₂CH₂)OCH₃, and

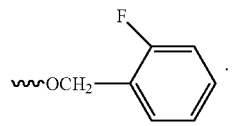

In yet one or more additional embodiments, the compound is

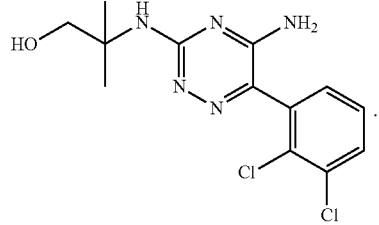 [SMILES: CC(C)(CO)Nc1nnc(-c2cccc(Cl)c2Cl)c(N)n1]

In yet one or more additional embodiments, the compound is

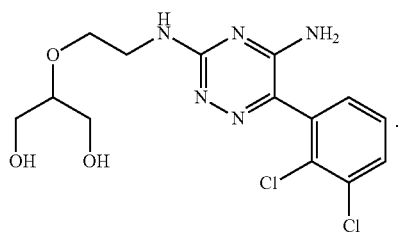 [SMILES: Nc1nc(NCCOC(CO)CO)nnc1-c1cccc(Cl)c1Cl]

In yet one or more additional embodiments, the compound is

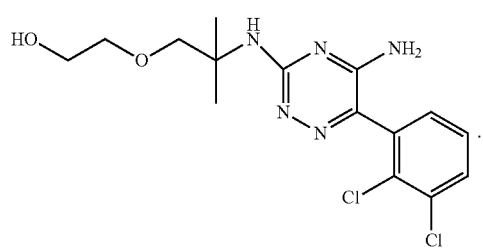 [SMILES: CC(C)(COCCO)Nc1nnc(-c2cccc(Cl)c2Cl)c(N)n1]

In yet one or more additional embodiments, the compound is

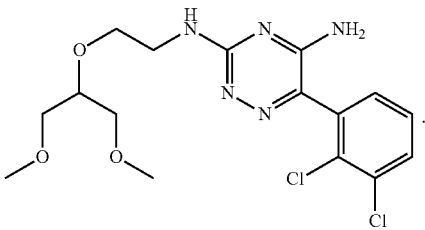 [SMILES: COCC(COC)OCCNc1nnc(-c2cccc(Cl)c2Cl)c(N)n1]

In yet one or more additional embodiments, the compound is

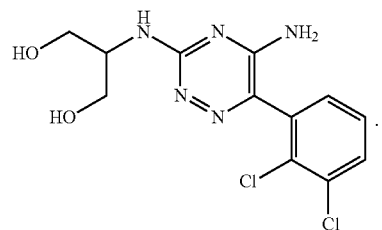 [SMILES: Nc1nc(NC(CO)CO)nnc1-c1cccc(Cl)c1Cl]

In yet one or more further embodiments, the compound is

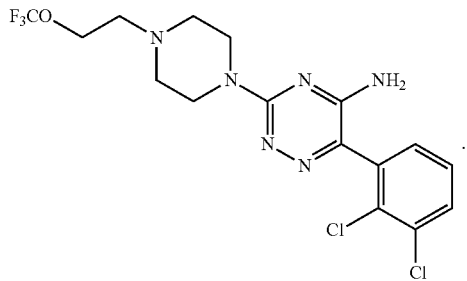 [SMILES: Nc1nc(N2CCN(CCOC(F)(F)F)CC2)nnc1-c1cccc(Cl)c1Cl]

In yet one or more additional embodiments, the compound is

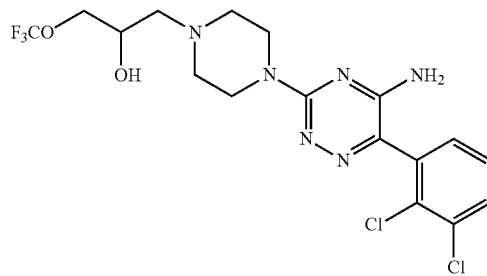

In yet one or more further embodiments, the compound is

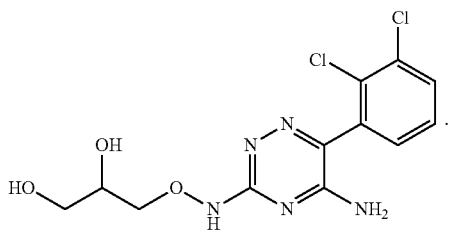 [SMILES: Nc1nc(NOCC(O)CO)nnc1-c1cccc(Cl)c1Cl]

In yet one or more additional embodiments, the compound is

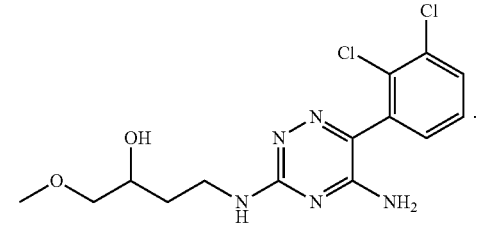 [SMILES: COCC(O)CCNc1nnc(-c2cccc(Cl)c2Cl)c(N)n1]

In yet one or more further embodiments, the compound is

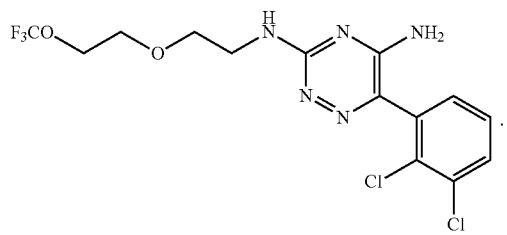 [SMILES: Nc1nc(NCCOCCOC(F)(F)F)nnc1-c1cccc(Cl)c1Cl]

In yet one or more additional embodiments, the compound is

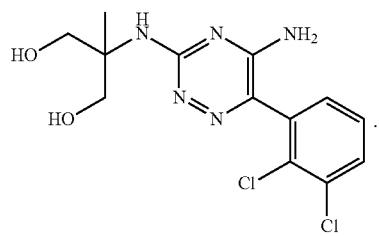 [SMILES: CC(CO)(CO)Nc1nnc(-c2cccc(Cl)c2Cl)c(N)n1]

In yet one or more further embodiments, the compound is

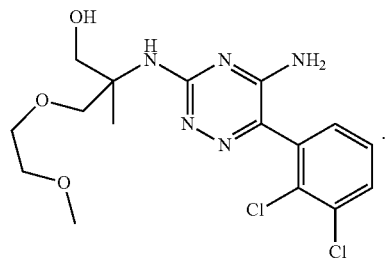 [SMILES: COCCOCC(C)(CO)Nc1nnc(-c2cccc(Cl)c2Cl)c(N)n1]

In yet one or more additional embodiments, the compound is

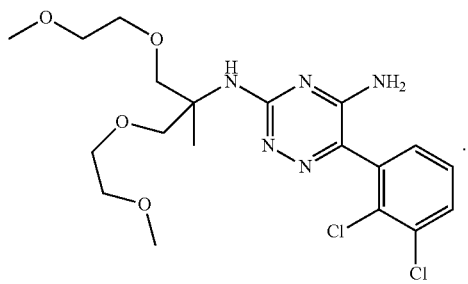 [SMILES: COCCOCC(C)(COCCOC)Nc1nnc(-c2cccc(Cl)c2Cl)c(N)n1]

In yet one or more additional embodiments, the compound is

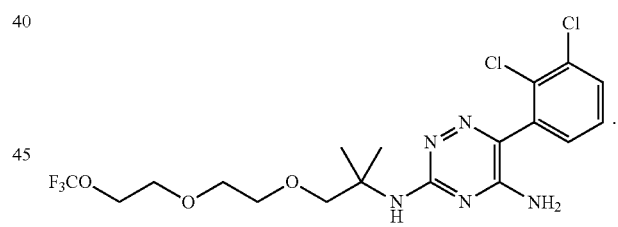

In yet one or more further embodiments, the compound is

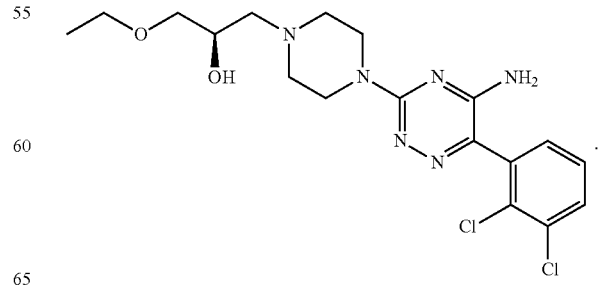

In yet one or more further embodiments, the compound is

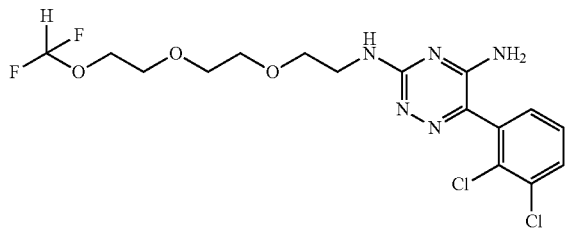

In yet one or more additional embodiments, the compound is

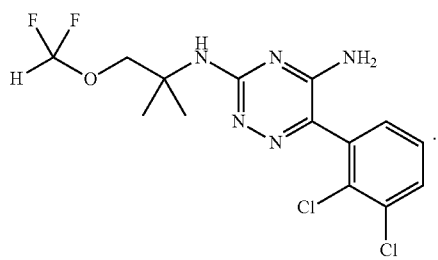 [SMILES: CC(C)(COC(F)F)Nc1nnc(-c2cccc(Cl)c2Cl)c(N)n1]

In some embodiments, the compound is selected from the group consisting of compounds 1-209. In one or more embodiments, provided is a compound selected from the group consisting of Compounds 1, 2, 3, 4, 5, 6, 7, 8, 9, 10, 11, 12, 13, 14, 15, 16, 17, 18, 19, and 20.

In one or more additional embodiments, provided is a compound selected from the group consisting of Compounds 21, 22, 23, 24, 25, 26, 27, 28, 29, 30, 31, 32, 33, 34, 35, 36, 3, 38, 39, and 40.

In one or more additional embodiments, provided is a compound selected from the group consisting of Compounds 41, 42, 43, 44, 45, 46, 47, 48, 49, 50, 51, 52, 53, 54, 55, 56, 57, 58, 59, and 60.

In one or more additional embodiments, provided is a compound selected from the group consisting of Compounds 61, 62, 63, 64, 65, 66, 67, 68, 69, 70, 71, 72, 73, 74, 75, 76, 77, 78, 79, and 80.

In one or more additional embodiments, provided is a compound selected from the group consisting of Compounds 81, 82, 83, 84, 85, 86, 87, 88, 89, 90, 91, 92, 93, 94, 95, 96, 97, 98, 99 and 100.

In one or more additional embodiments, provided is a compound selected from the group consisting of Compounds 101, 102, 103, 104, 105, 106, 107, 108, 109, 110, 111, 112, 113, 114, 115, 116, 117, 118, 119, and 120.

In one or more additional embodiments, provided is a compound selected from the group consisting of Compounds 121, 122, 123, 124, 125, 126, 127, 128, 129, 130, 131, 132, 133, 134, 135, 136, 137, 138, 139, and 140.

In one or more additional embodiments, provided is a compound selected from the group consisting of Compounds 141, 142, 143, 144, 145, 146, 147, 148, 149, 150, 151, 152, 153, 154, 155, 156, 157, 158, 159, and 160.

In one or more additional embodiments, provided is a compound selected from the group consisting of Compounds 161, 162, 163, 164, 165, 166, 167, 168, 169, 170, 171, 172, 13, 174, 175, 176, 177, 178, 179, and 180.

In one or more additional embodiments, provided is a compound selected from the group consisting of Compounds 181, 182, 183, 184, 185, 186, 187, 188, 189, 190, 191, 192, 193, 194, 195, 196, 197, 198, 199, and 200.

In one or more additional embodiments, provided is a compound selected from the group consisting of Compounds 201, 202, 203, 204, 205, 206, 207, 208, and 209.

In one or more embodiments, a composition is provided, the composition comprising a compound as provided herein and optionally, a pharmaceutically acceptable excipient.

In some particular embodiments, a composition is provided, the composition comprising a compound encompassed by Formula A or Formula B, or by Formula I or Formula III, and optionally, a pharmaceutically acceptable excipient.

In one or more particular embodiments, provided is a composition comprising a compound selected from the group consisting of compounds 1-209, and a pharmaceutically acceptable excipient.

In one or more embodiments, a composition is provided, the composition comprising a compound having the formula

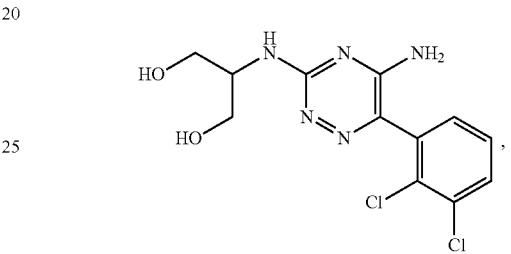

and optionally, a pharmaceutically acceptable excipient.

In one or more embodiments, a dosage form is provided, the dosage form comprising a compound encompassed by Formula A or Formula B, or by Formula I or Formula III, wherein the compound is present in the dosage form. In some embodiments, the dosage form comprises a compound selected from the group consisting of compounds 1-209. In some further embodiments, the dosage form is an oral dosage form.

In one or more embodiments, a dosage form is provided, the dosage form comprising a compound having the formula

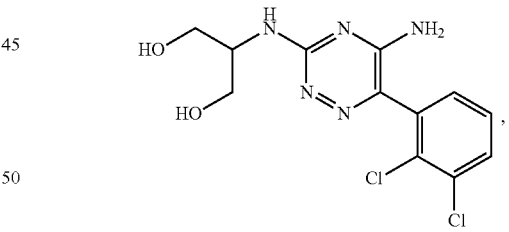

wherein the compound is present in a dosage form.

In one or more embodiments, a method is provided, the method comprising administering a compound encompassed by Formula A or Formula B, or by Formula I or Formula III to a mammal in need thereof. In some embodiments, the method comprises administering a compound selected from the group consisting of compounds 1-209.

In some embodiments, provided is a method for treating neuropathic pain by administering a compound encompassed by Formula A or Formula B, or by Formula I or Formula III to a mammal in need thereof. In some embodiments, the method comprises administering a compound selected from the group consisting of compounds 1-209 for treating neuropathic pain.

In one or more embodiments, a method is provided, the method comprising administering a compound having the formula

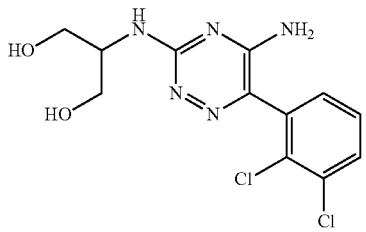 [SMILES: Nc1nc(NC(CO)CO)nnc1-c1cccc(Cl)c1Cl]

to a mammal in need thereof.

Additional embodiments of the compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION

As used in this specification, the singular forms "a," "an," and "the" include plural referents unless the context clearly dictates otherwise.

In describing and claiming the present invention, the following terminology will be used in accordance with the definitions described below.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "heteroatom" refers to an atom of any element other than carbon or hydrogen. Illustrative heteroatoms include boron, nitrogen, oxygen, phosphorus, sulfur and selenium. Preferred heteroatoms are nitrogen and oxygen.

The term "alkyl" includes saturated aliphatic groups, including straight-chain alkyl groups and branched-chain alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and preferably, about 20 or fewer. Likewise, cycloalkyls have from about 3 to about 10 carbon atoms in their ring structure, and preferably, have 5, 6 or 7 carbons in the ring structure. Alkyl and cycloalkyl groups, unless otherwise specified, may optionally be substituted with suitable substituents. The number of substituents is typically limited by the number of available valences on the alkyl group; thus an alkyl group may be substituted by replacement of one or more of the hydrogen atoms that would be present on the unsubstituted group.

Suitable substituents for alkyl groups include but are not limited to, for example, halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; and wherein two R' on the same substituent or on adjacent atoms can be linked to form a 3-7 membered ring optionally containing up to three heteroatoms selected from N, O and S;

Unless the number of carbons is otherwise specified, "lower alkyl" refers to an alkyl group, as defined above, having from one to about six carbons in its backbone structure.

The terms ortho, meta and para are art-recognized and refer to 1,2-, 1,3- and 1,4-disubstituted benzene rings, respectively. For example, the names 1,2-dimethylbenzene and ortho-dimethylbenzene are synonymous.

The terms "heterocyclyl", "heteroaryl", or "heterocyclic group" refer to 3- to about 10-membered ring structures, alternatively 3- to about 7-membered rings, whose ring structures typically include one to four heteroatoms. Heterocycles may also be bi-cycles or tri-cycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "subject" as used herein, refers to an animal, typically a mammal or a human, that is the generally the object of treatment, observation, and/or experiment. When the term is used in conjunction with administration of a compound as provided herein, then the subject has been the object of treatment, observation, and/or administration of the compound or drug. The phrase "therapeutically-effective amount" as used herein means that amount of a compound, material, or composition comprising a compound as provided herein which is effective for producing a desired therapeutic effect in at least a sub-population of cells in an animal at a reasonable benefit/risk ratio applicable to any medical treatment.

The phrases "parenteral administration" and "administered parenterally" as used herein refer to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

A functional group in "protected form" refers to a functional group bearing a protecting group. As used herein, the term "functional group" or any synonym thereof encompasses protected forms thereof.

Certain compounds of may exist in particular geometric or stereoisomeric forms. The present invention contemplates all such compounds, including where applicable, cis- and trans-isomers, R- and S-enantiomers, diastereomers, (D)-isomers, (L)-isomers, racemic mixtures thereof, and other mixtures thereof, as falling within the scope of the invention As set forth above, the present compounds contain a basic amino functional group and are therefore capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a compound as provided herein in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some cases, the phenyltriazine compounds provided herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the compound with the acidic group in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it ever reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a compound of the invention may provide a reduced rate of metabolism [relative to a compound lacking any water-soluble, non-peptidic oligomer(s)] satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Pharmaceutically acceptable excipient" or "pharmaceutically acceptable carrier" refers to component that may be included in the compositions of the invention causes no significant adverse toxicological effects to a patient.

"Pharmacologically effective amount," "physiologically effective amount," and "therapeutically effective amount" are used interchangeably herein to mean the amount of the compound of the invention present in a composition that is needed to provide a desired level of the compound (or desired metabolite thereof) the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A basic reactant or an acidic reactant described herein include neutral, charged, and any corresponding salt forms thereof.

The term "patient," refers to a living organism suffering from or prone to a condition that can be prevented or treated by administration of a compound of the invention described herein, and includes both humans and animals.

"Optional" or "optionally" means that the subsequently described circumstance may but need not necessarily occur, so that the description includes instances where the circumstance occurs and instances where it does not.

As indicated above, the present disclosure is directed to (among other things) derivatives of 6-(2,3-dichlorophenyl)-1,2,4-triazine-5 amine having a substituent at the 3-position of the triazine ring. The compounds provided herein each possess an N-bonded substituent at the 3-position of the triazine ring and an amino (—$NH_2$) group at the 5-position of the triazine ring, based upon the numbering scheme provided herein. The N-bonded substituent is an amino nitrogen covalently attached to the 3-carbon of the triazine ring, where the amino nitrogen may be comprised within a substituted acyclic amino moiety, or may form part of a substituted or unsubstituted nitrogen-containing heterocycle. Illustrative heterocycles include a substituted or unsubstituted piperazine moiety, a substituted or unsubstituted piperidine, a substituted or an unsubstituted pyrrolidine moiety, a substituted or an unsubstituted azetidine, or a substituted or unsubstituted diazetidine, where any of the foregoing nitrogen-containing heterocycles may also form part of a bi- or a tricylic ring structure (see for example, compounds 130, 131 (fused ring systems), and compounds 141 and 161).

Generally, the compounds provided herein possess the following general structure:

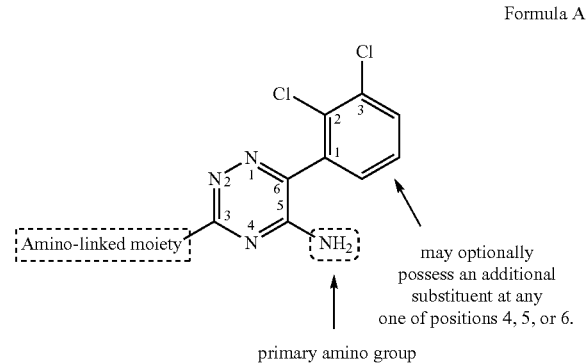

Formula A primary amino group may optionally possess an additional substituent at any one of positions 4, 5, or 6.

The amino linked moiety as shown in Formula A is attached to the 3-carbon of the triazine ring by an amino-linkage, where the amino group may be a primary amino group (—$NH_2$), or may be a secondary or a tertiary amino group (comprising one or no hydrogens, respectively). The amino group is generally but not necessarily a substituted amino group, i.e., having one or no hydrogens. The amino group may, for example, be substituted with an alkyl chain(s) that is linear or branched, and/or may comprise an oligomeric ethylene oxide chain, both of which may be further substituted. In one or more embodiments, substituents include one or more functional groups selected from, for example, oxygen (ether), amino, hydroxyl, carboxyl, carbonyl, sulfonyl, aldehyde, alkylsulfone, tetrazole, carbonyl, oxetane, carbonate, alkyl ester, sulfoxide, halo, amido, sulfonamide, cycloalkyl, heterocyclyl, —$CF_3$, —$CF_2H$, $CFH_2$, and the like.

In some embodiments, the amino group linked to the 3-carbon of the triazine ring may also be comprised within a ring structure. The amino group may, for example, be comprised within a substituted or unsubstituted piperazine moiety, or within a substituted or unsubstituted pyrrolidine moiety, or within a substituted or unsubstituted piperidine, or within a substituted or unsubstituted azetidine, or within a substituted or unsubstituted diazetidine, and the like, or may be comprised within a bicyclic ring comprising one of the foregoing heterocycles, such as a hexahydropyrazino-oxazin-one, or hexahydropyrazino-oxazine, diazaspiro-octane, diazaspiro-nonane, and the like. Substituted ring structures include rings as described above substituted with an alkyl chain that is linear or branched, and/or with an oligomeric ethylene oxide chain (that may comprise a substituent on an alkyl chain) both of which may be further substituted. In one or more embodiments, substituents include one or more functional groups selected from, for example, oxygen (ether), amino, hydroxyl, carboxyl, carbonyl, sulfonyl, aldehyde, alkylsulfone, tetrazole, carbonyl, oxetane, carbonate, alkyl ester, sulfoxide, halo, amido, sulfonamide, cycloalkyl, heterocyclyl, —$CF_3$, —$CF_2H$, $CFH_2$, and the like.

In some embodiments, the dichlorophenyl ring of the compounds may possess an additional substituent at any one of positions 4, 5 or 6, where the substituent is selected from halo, hydroxyl, and oligomeric ethylene oxide (—$OCH_2CH_2)_n$OR, where n is in a range from 1-7 and R is selected from H, -lower alkyl, preferably methyl, and fluoro-substituted methyl (e.g., —$CF_3$, —$CHF_2$, —$CH_2F$). Exemplary compounds having an additional substituent on the phenyl ring include compounds 104, 106, 109, 110, 119, 123 (5-fluoro substituted compounds), compound 164 (4-hydroxy substituted), and compound 112 (having a oligomeric ethylene oxide group at the 4-ring position, —(OCH$_2$CH$_2$)$_3$OCH$_3$.

In some embodiments, derivatives of 6-(2,3-dichlorophenyl)-1,2,4-triazine-5 amine having the following structure are provided:

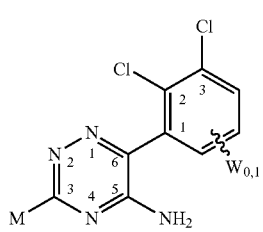

Formula B where M is a substituted amino moiety NR$_6$R$_7$, wherein:
(i) R$_6$ and R$_7$ are each independently selected from the group consisting of H, lower alkyl, —(CH$_2$CH$_2$O)$_m$R$_8$, —CH$_2$CH$_2$-(3-7 membered heterocycloalkyl), —C(O)—CH$_2$(CH$_2$CH$_2$O)$_m$R$_{10}$, —CH$_2$CR$_9$HCH$_2$O(CH$_2$CH$_2$O)$_m$(CH$_2$)$_{0,1}$R$_{10}$, —CR$_{11}$R$_{12}$CH$_2$OH, —CR$_{11}$R$_{12}$CH$_2$O(CH$_2$CH$_2$O)$_{1-7}$R$_{10}$, —CH—[CH$_2$OH]$_2$; —CCH$_3$(CH$_2$OH)$_2$, —CCH$_3$(CH$_2$OH)CH$_2$O(CH$_2$CH$_2$O)$_{1-7}$R$_{10}$, alkylamino, hydroxyalkylamino, —CH$_2$CH$_2$NCH$_3$C(O)CH$_2$(OCH$_2$CH$_2$)$_{1-7}$R$_{10}$, —CH$_2$CH$_2$NCH$_3$C(O)CH$_2$OCH$_2$C(O)NH$_2$, —CH$_2$CH$_2$NCH$_3$(CH$_2$CH$_2$O)$_{1-7}$R$_{10}$, —CR$_{11}$R$_{12}$CH(O), —CR$_{11}$R$_{12}$(CH$_2$)$_1$ $_{or}$ $_2$SO$_2$—CH$_2$CH$_2$O)$_{1-7}$R$_{10}$, —CCH$_3$(CH$_2$OCH$_2$CH$_2$OCH$_3$)$_2$, —OCH$_2$CR$_9$HCH$_2$OR$_{10}$—CH$_2$CR$_9$HCH$_2$NHC(O)CH$_2$O(CH$_2$CH$_2$O)$_m$R$_{10}$, —CH$_2$CR$_9$HCH$_2$NHC(O)CH$_2$OCH$_2$C(O)NH$_2$, and —(OCH$_2$CH$_2$)$_m$OR$_{10}$, with the proviso that R$_6$ and R$_7$ are not both H, or, (ii) wherein R$_6$ and R$_7$ taken together with N form a heterocycloalkyl ring selected from piperazine, piperidine, and azetidine, which may optionally form part of a bicyclic ring structure, where the heterocycloalkyl ring or bicyclic ring is either unsubstituted or is substituted with a group selected from lower alkyl, —(CH$_2$CH$_2$O)$_m$R$_8$, —C(O)—CH$_2$(CH$_2$CH$_2$O)$_m$R$_{10}$, —CH$_2$CR$_9$HCH$_2$O(CH$_2$CH$_2$O)$_m$(CH$_2$)$_{0,1}$R$_{10}$, —CH$_2$CH$_2$SO$_2$CH$_3$, —NR$_9$(CH$_2$CH$_2$O)$_m$R$_{10}$, tetra-hydro-2H-pyranyl, piperidinyl, —CH$_2$OH, —CH$_2$R$_{10}$, amino, —CHCH$_3$CH$_2$OH, hydroxyl, —CR$_{11}$R$_{12}$CH$_2$OH, —C(O)OCH$_3$, —CF$_3$, —CH$_2$C(OH)CF$_3$, —CH$_2$OCH$_2$—C$_6$H$_5$F, and —CH$_2$CR$_9$HCH$_2$O(CH$_2$CH$_2$O)$_m$(CH$_2$)$_{0,1}$R$_{13}$, with variables having the values as set forth below:

m is in a range from 0-29,

R$_8$ is selected from H, C1-C6 alkyl, fluoro-substituted methyl (e.g., —CF$_3$, —CF$_2$H, or —CFH$_2$), —CH$_2$COOR$_{10}$, —CH$_2$COCH$_3$, 3-7 membered heterocycloalkyl, 3-7 membered heteroaryl, heteroarylalkyl, —C(O)OCH$_3$, C1-C6 alkyl substituted with one or more of hydroxyl, amino, alkylamino, amido, alkylamide, amidoalkylamine, acylamino, carboxyalkylamino, sulfonamide, sulfone, alkylsulfone, alkoxyalkyl sulfone, alkyloxyalklsulfoxide, 3-7 membered heterocycloalkyl, 5-6 membered heteroaryl, carboxyl, —NHCH$_2$CH$_2$OCH$_3$, —NHCHR$_9$COOR$_{11}$; and —CH—[CH$_2$O—(CH$_2$CH$_2$O)$_{2-8}$CH$_3$]$_2$;

R$_9$ is H, lower alkyl, hydroxyl,

R$_{10}$ is selected from H, lower alkyl and fluoro-substituted methyl,

R$_{11}$ and R$_{12}$ are each independently selected from H and lower alkyl,

R$_{13}$ is cyclopropyl or cyclobutyl, and

W is an optional substituent (where the subscript zero indicates its absence and the subscript 1 indicates its presence) selected from halo, hydroxyl, and oligomeric ethylene oxide (—OCH$_2$CH$_2$)$_n$OR, where n ranges from 1-7 and R is selected from H, -lower alkyl, preferably methyl, and fluoro-substituted methyl (e.g., —CF$_3$, —CHF$_2$, —CH$_2$F).

In some embodiments, when R$_6$ is H and W is absent, and R$_7$ does not equal —(CH$_2$CH$_2$O)$_{2-11}$CH$_3$.

In one or more embodiments, R$_6$ is H.

In some embodiments, R$_6$ and R$_7$ are each independently selected from the group consisting of H, lower alkyl, —(CH$_2$CH$_2$O)$_m$R$_8$, —CH$_2$CH$_2$-(3-7 membered heterocycloalkyl), —C(O)—CH$_2$(CH$_2$CH$_2$O)$_m$R$_{10}$, —CH$_2$CR$_9$HCH$_2$O(CH$_2$CH$_2$O)$_m$(CH$_2$)$_{0,1}$R$_{10}$, —CR$_{11}$R$_{12}$CH$_2$OH, —CR$_{11}$R$_{12}$CH$_2$O(CH$_2$CH$_2$O)$_{1-7}$R$_{10}$, —CH—[CH$_2$OH]$_2$; —CCH$_3$(CH$_2$OH)$_2$, —CCH$_3$(CH$_2$OH)CH$_2$O(CH$_2$CH$_2$O)$_{1-7}$R$_{10}$, alkylamino, hydroxyalkylamino, —CH$_2$CH$_2$NCH$_3$C(O)CH$_2$(OCH$_2$CH$_2$)$_{1-7}$R$_{10}$, —CH$_2$CH$_2$NCH$_3$C(O)CH$_2$OCH$_2$C(O)NH$_2$, —CH$_2$CH$_2$NCH$_3$(CH$_2$CH$_2$O)$_{1-7}$R$_{10}$, —CR$_{11}$R$_{12}$CH(O), —CR$_{11}$R$_{12}$(CH$_2$)$_1$ $_{or}$ $_2$SO$_2$—CH$_2$CH$_2$O)$_{1-7}$R$_{10}$, —CCH$_3$(CH$_2$OCH$_2$CH$_2$OCH$_3$)$_2$, —OCH$_2$CR$_9$HCH$_2$OR$_{10}$—CH$_2$CR$_9$HCH$_2$NHC(O)CH$_2$O(CH$_2$CH$_2$O)$_m$R$_{10}$, —CH$_2$CR$_9$HCH$_2$NHC(O)CH$_2$OCH$_2$C(O)NH$_2$, and —(OCH$_2$CH$_2$)$_m$OR$_{10}$, where variables possess the values provided above, and with the proviso that R$_6$ and R$_7$ are not both H.

In yet some further embodiments, R$_6$ is H and R$_7$ is selected from the group consisting of H, lower alkyl, —(CH$_2$CH$_2$O)$_m$R$_8$, —CH$_2$CH$_2$-(3-7 membered heterocycloalkyl), —C(O)—CH$_2$(CH$_2$CH$_2$O)$_m$R$_{10}$, —CH$_2$CR$_9$HCH$_2$O(CH$_2$CH$_2$O)$_m$(CH$_2$)$_{0,1}$R$_{10}$, —CR$_{11}$R$_{12}$CH$_2$OH, —CR$_{11}$R$_{12}$CH$_2$O(CH$_2$CH$_2$O)$_{1-7}$R$_{10}$, —CH—[CH$_2$OH]$_2$; —CCH$_3$(CH$_2$OH)$_2$, —CCH$_3$(CH$_2$OH)CH$_2$O(CH$_2$CH$_2$O)$_{1-7}$R$_{10}$, alkylamino, hydroxyalkylamino, —CH$_2$CH$_2$NCH$_3$C(O)CH$_2$(OCH$_2$CH$_2$)$_{1-7}$R$_{10}$, —CH$_2$CH$_2$NCH$_3$C(O)CH$_2$OCH$_2$C(O)NH$_2$, —CH$_2$CH$_2$NCH$_3$(CH$_2$CH$_2$O)$_{1-7}$R$_{10}$, —CR$_{11}$R$_{12}$CH(O), —CR$_{11}$R$_{12}$(CH$_2$)$_1$ $_{or}$ $_2$SO$_2$—CH$_2$CH$_2$O)$_{1-7}$R$_{10}$, —CCH$_3$(CH$_2$OCH$_2$CH$_2$OCH$_3$)$_2$, —OCH$_2$CR$_9$HCH$_2$OR$_{10}$—CH$_2$CR$_9$HCH$_2$NHC(O)CH$_2$O(CH$_2$CH$_2$O)$_m$R$_{10}$, —CH$_2$CR$_9$HCH$_2$NHC(O)CH$_2$OCH$_2$C(O)NH$_2$, and —(OCH$_2$CH$_2$)$_m$OR$_{10}$, where variables possess the values provided above.

In some preferred embodiments, m is selected from 0, 1, 2, 3, 4, 5, 6, and 7.

In some additional embodiments, R$_6$ and R$_7$ taken together with N form a heterocycloalkyl ring selected from piperazine, piperidine, and azetidine, which may optionally form part of a bicyclic ring structure, where the heterocycloalkyl ring or bicyclic ring is either unsubstituted or is substituted with a group selected from lower alkyl, —(CH$_2$CH$_2$O)$_m$R$_8$, —C(O)—CH$_2$(CH$_2$CH$_2$O)$_m$R$_{10}$, —CH$_2$CR$_9$HCH$_2$O(CH$_2$CH$_2$O)$_m$(CH$_2$)$_{0,1}$R$_{10}$, —CH$_2$CH$_2$SO$_2$CH$_3$, —NR$_9$(CH$_2$CH$_2$O)$_m$R$_{10}$, tetra-hydro-2H-pyranyl, piperidinyl, —CH$_2$OH, —CH$_2$R$_{10}$, amino, —CHCH$_3$CH$_2$OH, hydroxyl, —CR$_{11}$R$_{12}$CH$_2$OH, —C(O)OCH$_3$, —CF$_3$, —CH$_2$C(OH)CF$_3$, —CH$_2$OCH$_2$—C$_6$H$_5$F, and —CH$_2$CR$_9$HCH$_2$O(CH$_2$CH$_2$O)$_m$(CH$_2$)$_{0,1}$R$_{13}$, where variables such as m, R$_8$, R$_9$, R$_{10}$, R$_{11}$, R$_{12}$, and R$_{13}$ posssess the values provided above.

In one or more embodiments, R$_6$ is H and R$_7$ is —(CH$_2$CH$_2$O)$_m$R$_8$, where m is selected from 1, 2, 3, 4, 5, 6, and 7, and R$_8$ is selected from H, methyl, isopropyl, fluoro-substituted methyl, carboxyl, and 3-7 membered heterocycloalkyl. In one or more related embodiments, the 3-7 membered ring heterocycloalkyl is selected from tetrazole, oxetane and piperazine.

In some embodiments, $R_6$ and $R_7$ taken together with N form a heterocycloalkyl ring selected from piperazine, piperidine, and azetidine. In some particular embodiments, $R_6$ and $R_7$ taken together with N form an unsubstituted or a substituted piperazine. Exemplary substituted piperazines include those having a N-substituent selected from —(CH$_2$CH$_2$O)$_{1-7}$C1-C6 alkyl or fluoro-substituted methyl, —(CH$_2$CH$_2$O)$_{1-7}$CH$_2$CH$_2$NHSO$_2$CH$_3$,

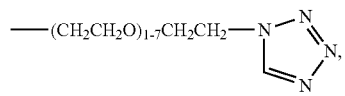

—C(O)CH$_2$O(CH$_2$CH$_2$O)$_{1-7}$CH$_3$, —CH$_2$CHOHCH$_2$OCF$_3$, —CH$_2$CHOHCH$_2$OCH$_2$CF$_3$ —CH$_2$CHOHCH$_2$OCH$_3$, —CH$_2$OH, —(CH$_2$CH$_2$O)$_2$OH, —CH$_2$CH$_2$SO$_2$CH$_3$, —CH$_2$CH$_2$OCH$_2$COOH, —CH$_2$CH$_2$OCH$_2$COOC(CH$_3$)$_3$, —CH$_2$CH(OH)CH$_2$OH, —C(CH$_3$)$_2$CH$_2$OCH$_2$CH$_2$OH,

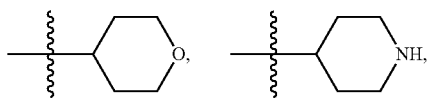

—CH$_2$CF$_3$, —CHCH$_3$CH$_2$OH, —C(CH$_3$)$_2$CH$_2$OH, and —CH$_2$CH(OH)CH$_2$Cl. Exemplary compounds wherein $R_6$ and $R_7$ taken together with N form an unsubstituted or a substituted piperazine include compounds 92, 103, 104, 105, 106, 113, 120, 121, 122, 123, 96, 97, 87, 89, 88, 90, 94, 207, 98, 13, 136, 137, 208, 124, 27, 200, 201, 202, 203, 204, 138, 139, 140, 55, 73, 78, 80, and 83.

In some additional embodiments, $R_6$ and $R_7$ taken together with N form a ring selected from substituted pyrrolidine, substituted piperazine, and substituted piperazine forming part of a bicyclic ring system, e.g., tetrahydro-1H-oxazolo[3,4-a]pyrazin-3(5H)-one (as in compound 128), tetrahydro-1H-oxazolo[3,4-a]pyrazin-3(5H)-one (as in compound 127), and hexahydropyrazino[2,1-c][1,4]oxazin-4(3H)-one (as in compound 130), and azetidine.

In some preferred embodiments, the compound is selected from the group consisting of: (2S,4R)-Methyl 1-(5-amino-6-(2,3-dichlorophenyl)-1,2,4-triazin-3-yl)-4-hydroxypyrrolidine-2-carboxylate (Compound 65), (S)-1-(4-(5-amino-6-(2,3-dichlorophenyl)-1,2,4-triazin-3-yl)piperazin-1-yl)-3-methoxypropan-2-ol (Compound 97), (S)-7-(5-amino-6-(2,3-dichlorophenyl)-1,2,4-triazin-3-yl)tetrahydro-1H-oxazolo[3,4-a]pyrazin-3(5H)-one HCl salt (Compound 128), (S)-1-(4-(5-amino-6-(2,3-dichlorophenyl)-1,2,4-triazin-3-yl)-piperazin-1-yl)-3-(2,2,2-trifluoroethoxy)-propan-2-ol.2HCl (Compound 95), (R)-1-((1-(5-Amino-6-(2,3-dichlorophenyl)-1,2,4-triazin-3-yl)azetidin-3-yl)oxy)-3-methoxypropan-2-ol (Compound 75), 3-N-(3-hydroxyazetin-1-yl) lamotrigine (Compound 129), 1-(4-(5-Amino-6-(2,3-dichlorophenyl)-1,2,4-triazin-3-yl)piperazin-1-yl)-3-(trifluoromethoxy)propan-2-ol (Compound 27), (R)-7-(5-amino-6-(2,3-dichlorophenyl)-1,2,4-triazin-3-yl)tetrahydro-1H-oxazolo[3,4-a]pyrazin-3(5H)-one (Compound 127), (R)-1-(4-(5-amino-6-(2,3-dichlorophenyl)-1,2,4-triazin-3-yl)-piperazin-1-yl)-3-(2,2,2-trifluoroethoxy)-propan-2-ol (Compound 94), (S)-1-(4-(5-amino-6-(2,3-dichlorophenyl)-1,2,4-triazin-3-yl)piperazin-1-yl)-3-methoxypropan-2-ol (Compound 98), (R)-1-(4-(5-amino-6-(2,3-dichlorophenyl)-1,2,4-triazin-3-yl)piperazin-1-yl)-3-methoxypropan-2-ol (Compound 96), 3-N-(4-(tetrahydro-2H-pyran-4-yl)piperazin-1-yl) lamotrigine di HCl (Compound 120), and (R)-8-(5-amino-6-(2,3-dichlorophenyl)-1,2,4-triazin-3-yl)hexahydropyrazino[2,1-c][1,4]oxazin-4(3H)-one HCl salt (Compound 130).

In some further embodiments, compounds as provided herein contain an amino nitrogen covalently attached to the 3-carbon of the triazine ring, where the amino nitrogen may be comprised within a substituted acyclic amino moiety, within a substituted piperazine moiety, or within a substituted pyrrolidine moiety. Compounds falling within the particular molecular scaffolds described herein possess unique properties, to be described in greater detail herein.

In one or more embodiments, a derivative of 6-(2,3-dichlorophenyl)-1,2,4-triazine-5 amine having a substituent at the 3-position of the triazine ring may fall within the following generalized structure:

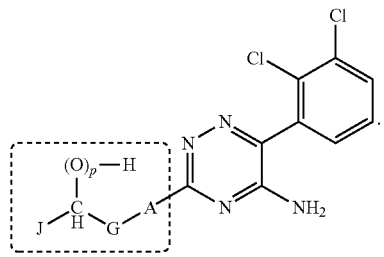

(Formula I)

In the foregoing structure, the overall boxed moiety represents a substituted amino moiety, wherein the moiety comprises an amino nitrogen covalently attached to the 3-carbon of the triazine ring, where the amino nitrogen may be comprised within a substituted acyclic amino moiety, within a substituted piperazine moiety, or within a substituted pyrrolidine moiety. Thus, one feature of the instant compounds is the presence of an amino nitrogen covalently attached to the 3-ring position of the triazine ring.

Representative compounds possess the following features. For example in one or more embodiments, A is one of

(piperazinyl).

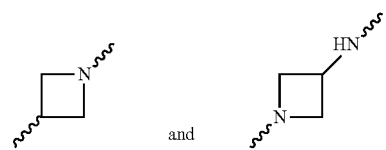

Turning now to variable G, exemplary G groups are oxygen, methylene (~CH$_2$~), substituted methylene where the methylene group may be substituted with alkyl groups such as lower alkyl (methyl, ethyl, propyl, butyl, pentyl, and hexyl, or branched forms thereof) or substituted lower alkyl, where the alkyl substituent may comprise a hydroxyl, or an ethylene oxide segment comprising from 1-5 repeat units, and having a terminal hydroxy or methoxy group, or lower alkylene or substituted lower alkylene as described above. Illustrative G groups include the following: ~O~, ~CH₂~,

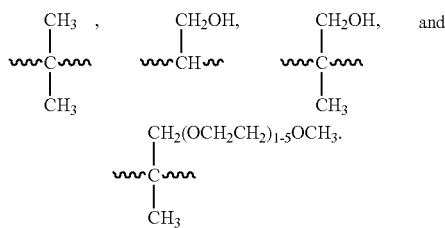

For example, when G is

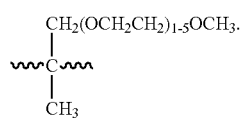

where G is selected from the following:

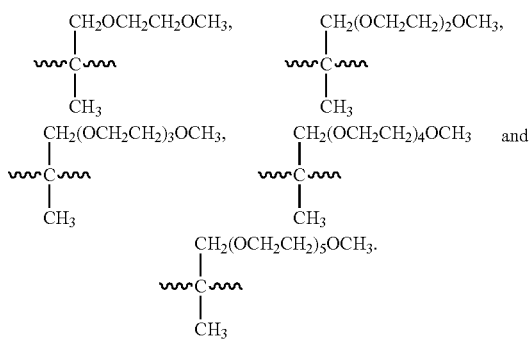

Turning now to the substituent adjacent to the G in Formula (I), "~CH(O)$_p$H~," p is 0 or 1 (where a value of 0 indicates the absence of oxygen and a value of 1 indicates its presence), such that this moiety is either methylene or ~CH(OH)~.

Variable J in reference to Formula (I) is typically a substituted alkyl or substituted araalkyl, optionally comprising an ether oxygen or an ether, where each J generally includes one or more oxygen atoms. Illustrative J groups are selected from ~CH(OF)CH₂OH, ~CH(OH)CH₂OCH₃, ~OCH₂CH₂OH, ~CH₂OCF₃, ~OCF₃, ~OH, ~OCH(CH₂OCH₃)₂, ~OCH(CH₂OH)₂, ~(OCH₂CH₂)$_{0-29}$OR¹, where R¹ equals methyl or fluoro-substituted methyl (e.g., —CF₃, —CF₂H, or —CFH₂), ~CH₂OCH₂CH₃,

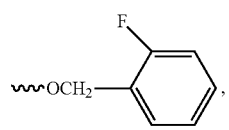

and ~OCH₂C(OH)HCH₂OCH₃.

In yet one or more further embodiments, when J is ~(OCH₂CH₂)$_{0-29}$OR¹, J is selected from ~(OCH₂CH₂)OR¹, ~(OCH₂CH₂)₂OR¹, ~(OCH₂CH₂)₃OR¹, ~(OCH₂CH₂)₄OR¹, ~(OCH₂CH₂)₅OR¹, ~(OCH₂CH₂)₆OR¹, ~(OCH₂CH₂)₆ OR¹, ~(OCH₂CH₂)₈OR¹, ~(OCH₂CH₂)₉OR¹, and ~(OCH₂CH₂)₁₀OR¹.

In yet one or more additional embodiments, when J is ~(OCH₂CH₂)$_{0-29}$OR¹, J is further selected from ~OR¹ and ~(OCH₂CH₂)$_{1-10}$OR¹.

In reference to the variables provided above for A, G, p, and J, compounds in accordance with the disclosure are meant to encompass each and every combination of illustrative A, G, p, and J moieties as provided above.

A representative structure is provided below as Formula II, where the amino group substituted at the 3-position of the triazine ring comprises a trifluoromethoxy terminal group and ethyoxy-subunits (from 1 to 30) within the alkyl chain.

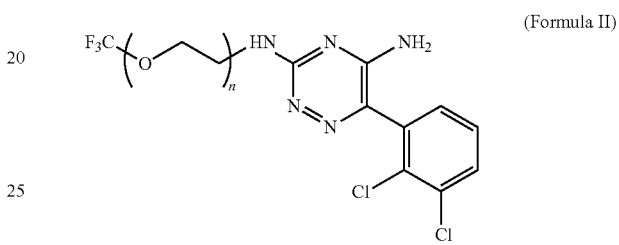
(Formula II)

The number of ethoxy subunits is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

In yet one or more embodiments related to the foregoing, n is an integer selected from 1-15 or from 1-10.

Also provided herein is a compound having the formula:

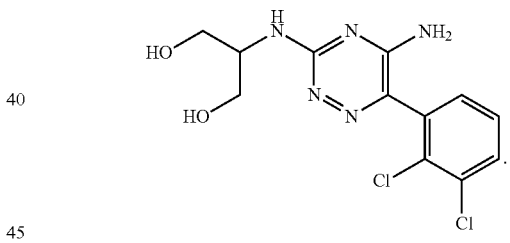

Additional compounds provided herein are those comprising a pyrrolidine substituent at the 3-position of the triazine ring. Generally, such compounds are described by Formula III,

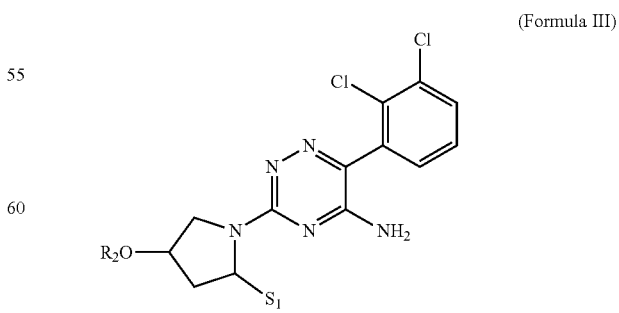
(Formula III)

where R₂ is either H or ~CH₂C(OH)CH₂OCH₃, and S₁ is an optional substituent selected from ~OCH₂CH₃ and

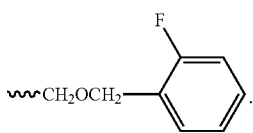

Illustrative compounds in accordance with Formula (I) are those in which A is

G is

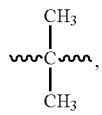

p is 0, and J is selected from ~CH(OH)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

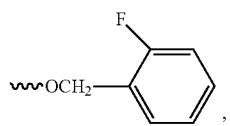

and ~OCH$_2$C(OH)HCH$_2$OCH$_3$.

Additional compounds in accordance with Formula (I) are those in which A is

G is

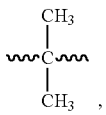

p is 0, and J is selected from ~OH, ~OCH$_2$CH$_2$OH, ~OCF$_2$H, ~OCH$_2$C(OH)HCH$_2$OCH$_3$ and ~(OCH$_2$CH$_2$)$_2$OCF$_3$.

Yet additional compounds in accordance with Formula (I) are those in which A is either

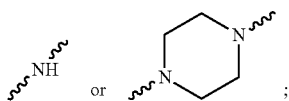

G is ~CH$_2$~, p is 0 or 1, and J is selected from ~CH(OH)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

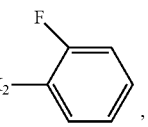

and ~OCH$_2$C(OH)HCH$_2$OCH$_3$.

Yet additional compounds in accordance with Formula (I) are those in which A is either

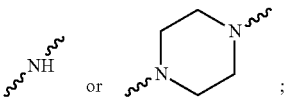

G is ~CH$_2$~, p is 0, and J is selected from ~OCH(CH$_2$OH)$_2$, ~OCH(CH$_2$OCH$_3$)$_2$, ~OCF$_3$, ~(OCH$_2$CH$_2$)OCF$_3$, ~CH(OH)CH$_2$OCH$_3$, ~CH$_2$OCH$_2$CH$_3$, ~(OCH$_2$CH$_2$)$_2$OCF$_2$H.

Additional representative compounds include those in accordance with Formula (I), where A is

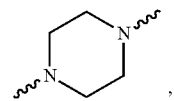

G is ~CH$_2$~, p is 1, and J is ~CH$_2$OCF$_3$.

Further compounds are those in which A is

G is

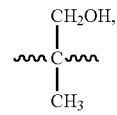

p is 0, and J is selected from the group consisting of ~CH(OH)CH$_2$OH, ~CH(OH)CH$_2$OCH$_3$, ~OCH$_2$CH$_2$OH, ~CH$_2$OCF$_3$, ~OCF$_3$, ~OH, ~OCH(CH$_2$OCH$_3$)$_2$, ~OCH(CH$_2$OH)$_2$, ~(OCH$_2$CH$_2$)$_{0-29}$OR$^1$, where R$^1$ equals methyl or fluoro-substituted methyl (e.g., —CF$_3$, —CF$_2$H, or —CFH$_2$), ~CH$_2$OCH$_2$CH$_3$,

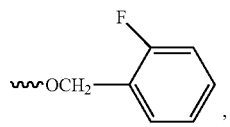

and ~OCH$_2$C(OH)HCH$_2$OCH$_3$.

Additional exemplary compounds include those in which A is
G is
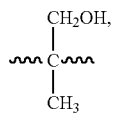
p is 0, and J is selected from the group consisting of ~OH, ~(OCH₂CH₂)OCH₃, and
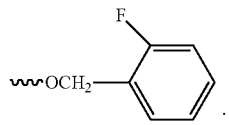
Exemplary compounds of formula (I) include those in which A is
such as the following:
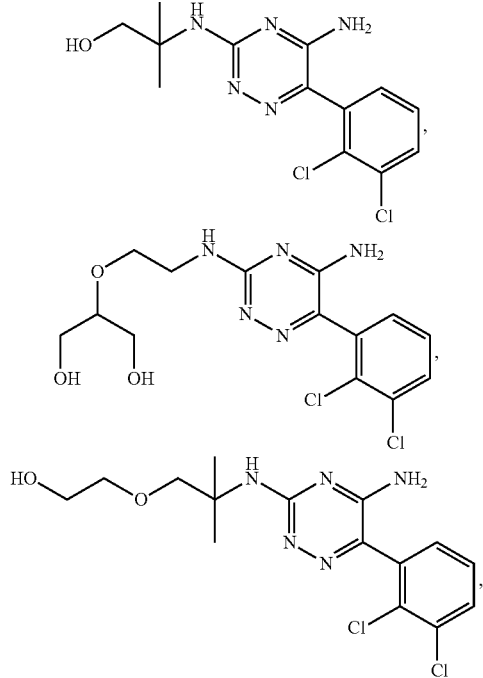
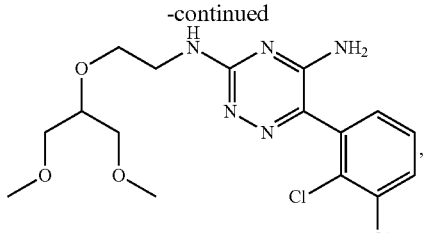
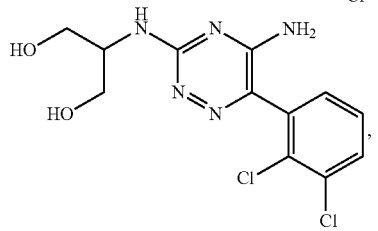
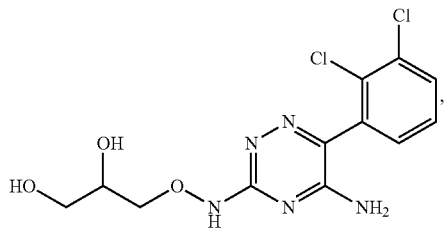
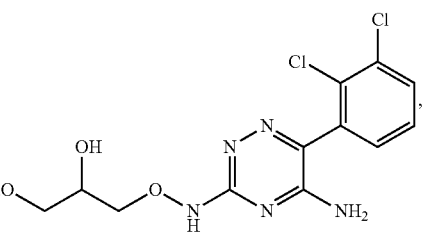
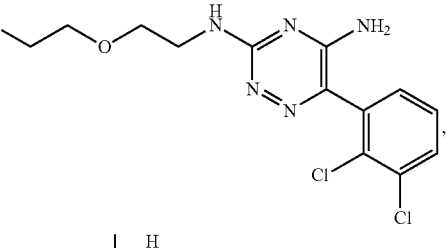
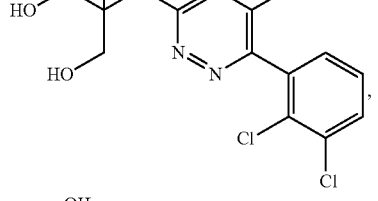
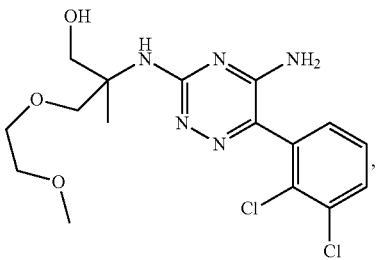

-continued
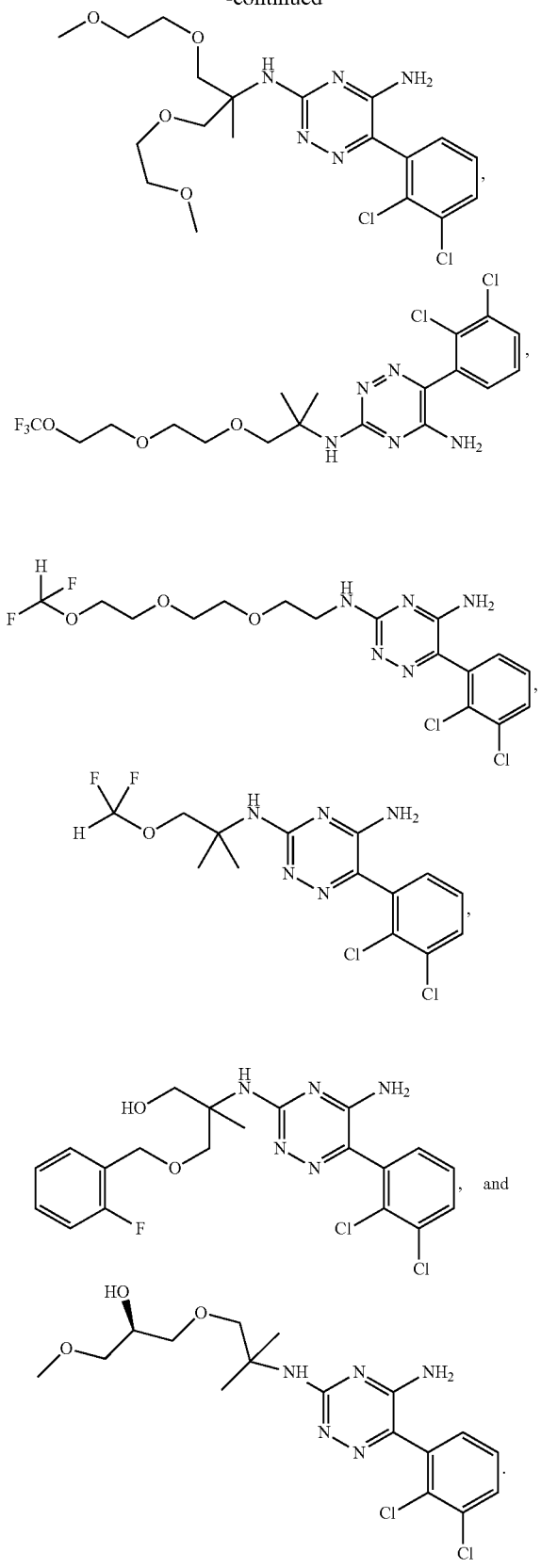
Additional compounds as provided herein are those wherein, in reference to Formula (I), A is
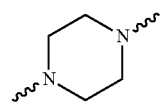
Illustrative compounds include the following:
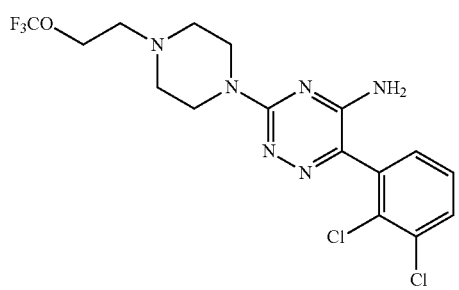
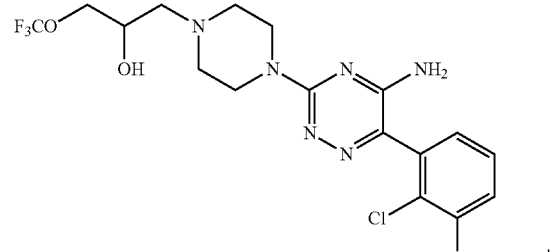
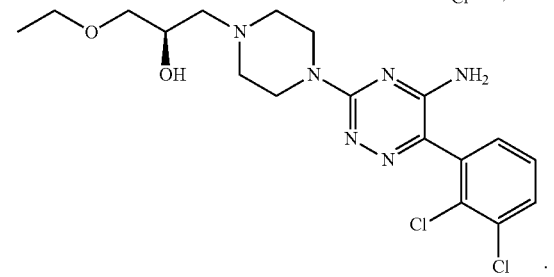
Representative 6-(2,3-dichlorophenyl)-1,2,4-triazin-5-amine derivative compounds comprising a substituted pyrrolidine at the 3-position of the triazine ring include:
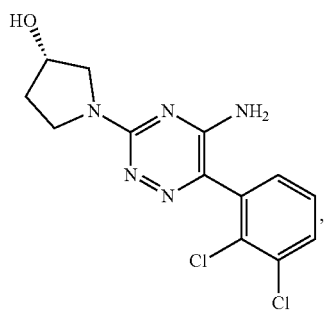

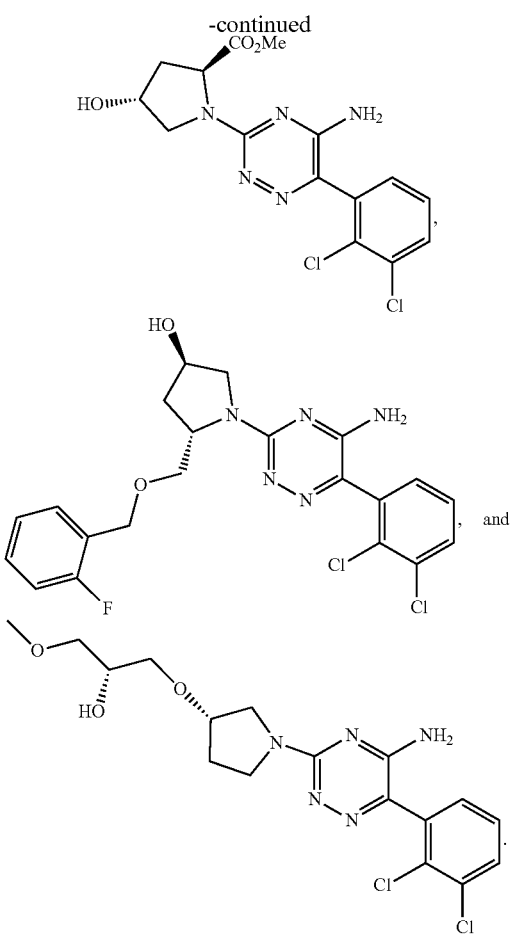

Further compounds as described generally above are provided in the accompanying Examples.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatography with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., Ertl et al. (2000) *J. Med. Chem.* 43:3714-3717 and Kelder et al. (1999) *Pharm. Res.* 16:1514-1519.

With respect to the blood-brain barrier, a 6-(2,3-dichlorophenyl)-1,2,4-triazin-5-amine derivative compound as provided herein exhibits a blood-brain barrier crossing rate. It is preferred that such a rate is relatively reduced (e.g., reduced when compared to the rate of lamotrigine). Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of lamotrigine.

Assays for determining whether a given phenyltriazine compound such as those provided herein has anticonvulsant activity (e.g., as evidenced through a maximal electroshock test) are known. One such assay is described in L. A. Woodbury and V. D. Davenport (1952) *Design and Use of a New Electroshock Seizure Apparatus, and Analysis of Factors Altering Seizure Threshold and Pattern Arch Int Pharmacodyn Ther* 92:97-104.

The compounds described herein can be present in a racemic mixture and in an optically active form, for example, a single optically active enantiomer, or any combination or ratio of enantiomers (e.g., scalemic and racemic mixtures). In addition, the 6-(2,3-dichlorophenyl)-1,2,4-triazin-5-amine derivative compound may possess one or more geometric isomers. With respect to geometric isomers, a composition can comprise a single geometric isomer or a mixture of two or more geometric isomers. A small molecule drug for use as set forth herein can be in its customary active form, or may possess some degree of modification.

Animal models (rodents and dogs) can be used to study oral drug transport. In addition, non-in vivo methods include rodent everted gut excised tissue and Caco-2 cell monolayer tissue-culture models. These models are useful in predicting oral drug bioavailability.

To determine whether a 6-(2,3-dichlorophenyl)-1,2,4-triazin-5-amine derivative compound has potential pharmacological activity, the compound may be evaluated using, for example, the various approaches as set forth in the Examples section. For example, in vitro binding studies to receptors using various cell lines expressing these receptors that have become routine in pharmaceutical industry, and can be used to determine whether a given compound has potential pharmacological activity.

Turning now to the examples, Example 154 describes the efficacy of certain exemplary compounds as sodium channel blockers. Preferred compounds, in terms of sodium channel blocking activity, are those compounds described in Table 2 that demonstrate an $IC_{50}$ tonic state value as indicated in the table of greater than (>) a value that is 200 μM. In one or more additional embodiments, preferred are compounds that demonstrate an $IC_{50}$ inactivated state value as provided in the table of less than (<) a value that is 50 μM. Such compounds are described in the example.

In terms of pharmacokinetics, Example 155 describes certain pharmacokinetic properties of illustrative compounds as provided herein. As provided in Example 155, clearance parameters (CL), bioavailabilities (F) and half-lives were calculated. Particularly preferred compounds are those described in Table 3, having a single asterisk. Of the compounds evaluated, these compounds exhibited the most favorable pharmacokinetics. Each of the compounds possesses a substituted tertiary amino group attached at the 3-position of the triazine ring, where the tertiary amino group forms part of a ring system. The substituted ring systems include substituted pyrrolidine, substituted piperazine, and substituted piperazine forming part of a bicyclic ring system, e.g., tetrahydro-1H-oxazolo[3,4-a]pyrazin-3(5H)-one (compound 128), tetrahydro-1H-oxazolo[3,4-a]pyrazin-3(5H)-one (compound 127), and hexahydropyrazino[2,1-c][1,4]oxazin-4(3H)-one (compound 130), and azetidine.

Specifically, compounds demonstrating the most favorable pharmacokinetics include: (2S,4R)-Methyl 1-(5-amino-6-(2,3-dichlorophenyl)-1,2,4-triazin-3-yl)-4-hydroxypyrrolidine-2-carboxylate (Compound 65), (S)-1-(4-(5-amino-6-(2,3-dichlorophenyl)-1,2,4-triazin-3-yl)piperazin-1-yl)-3-methoxypropan-2-ol (Compound 97), (S)-7-(5-amino-6-(2,3-dichlorophenyl)-1,2,4-triazin-3-yl)tetrahydro-1H-oxazolo[3,4-a]pyrazin-3(5H)-one HCl salt (Compound 128), (S)-1-(4-(5-amino-6-(2,3-dichlorophenyl)-1,2,4-triazin-3-yl)-piperazin-1-yl)-3-(2,2,2-trifluoroethoxy)-propan-2-ol.2HCl (Compound 95), (R)-1-((1-(5-Amino-6-(2,3-dichlorophenyl)-1,2,4-triazin-3-yl)azetidin-3-yl)oxy)-3-methoxypropan-2-ol (Compound 75), 3-N-(3-hydroxyazetin-1-yl) lamotrigine (Compound 129), 1-(4-(5-Amino-6-(2,3-dichlorophenyl)-1,2,4-triazin-3-yl)piperazin-1-yl)-3-(trifluoromethoxy)propan-2-ol (Compound 27), (R)-7-(5-amino-6-(2,3-dichlorophenyl)-1,2,4-triazin-3-yl)tetrahydro-1H-oxazolo[3,4-a]pyrazin-3(5H)-one (Compound 127), (R)-1-(4-(5-amino-6-(2,3-dichlorophenyl)-1,2,4-triazin-3-yl)-piperazin-1-yl)-3-(2,2,2-trifluoroethoxy)-propan-2-ol (Compound 94), (S)-1-(4-(5-amino-6-(2,3-dichlorophenyl)-1,2,4-triazin-3-yl)piperazin-1-yl)-3-methoxypropan-2-ol (Compound 98), (R)-1-(4-(5-amino-6-(2,3-dichlorophenyl)-1,2,4-triazin-3-yl)piperazin-1-yl)-3-methoxypropan-2-ol (Compound 96), 3-N-(4-(tetrahydro-2H-pyran-4-yl)piperazin-1-yl) lamotrigine di HCl (Compound 120), and (R)-8-(5-amino-6-(2,3-dichlorophenyl)-1,2,4-triazin-3-yl)hexahydropyrazino[2,1-c][1,4]oxazin-4(3H)-one HCl salt (Compound 130).

Still, in reference to Example 155, compounds that exhibited the best exposure after oral dosing are indicated in the table by (**). These compounds are, in some embodiments, preferred.

Additionally, provided in Example 156 is data related to potencies of certain illustrative compounds as provided herein in treating chronic or acute pain. In one or more embodiments, the compounds are effective in treating neuropathic pain. Animal models used to assess the ability of the compounds for treating pain included mechanical allodynia, AFP, RR, and hyperalgesia models. Some preferred compounds, based upon potency indications, include compounds 167 (6-(2,3-dichlorophenyl)-$N^3$-(2-(2-(2-(trifluoromethoxy)ethoxy)ethyl)-1,2,4-triazine-3,5-diamine) and 98 ((S)-1-(4-(5-amino-6-(2,3-dichlorophenyl)-1,2,4-triazin-3-yl)piperazin-1-yl)-3-methoxypropan-2-ol).

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

Also provided are pharmaceutical preparations comprising a 6-(2,3-dichlorophenyl)-1,2,4-triazin-5-amine derivative compound as described herein in combination with a pharmaceutical excipient. Generally, the compound itself will be in a solid form (e.g., a precipitate, in crystalline form, optionally in the form of a hydrate or solvate), which can be combined with a suitable pharmaceutical excipient that may be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the 6-(2,3-dichlorophenyl)-1,2,4-triazin-5-amine derivative compound will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compounds of the invention can also be administered through the skin using conventional transdermal patch or other transdermal delivery system, wherein the conjugate is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compounds of the invention can also be formulated into a suppository for rectal administration. With respect to suppositories, the compound is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the compounds of the invention may further be incorporated into a suitable delivery vehicle. Such delivery vehicles may provide controlled and/or continuous release of the compounds and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), Rhodotorula yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703, 5,607,677, and U.S. Patent Application Publication Nos. 2005/0281781 and 2008/0044438.

The invention also provides a method for administering a compound of the invention as provided herein to a patient suffering from a condition that is responsive to treatment with the compound. The method comprises administering, generally orally, a therapeutically effective amount of the compound (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method of administering may be used to treat any condition that can be remedied or prevented by administration of a particular compound of the invention. Those of ordinary skill in the art appreciate which conditions a specific compound can effectively treat. Exemplary conditions include conditions requiring anticonvulsant therapy and/or prophylaxis and pain. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

In some embodiments, the compounds provided herein act as sodium channel blockers. See, e.g., Example 154. The instant compounds, may, for example, be useful for the treatment of neuropathic pain. Neuropathic pain, also known as nerve pain or neuropathy, is the result of nerve damage and can be caused by such diverse conditions as diabetes, shingles, cancer, HIV, multiple sclerosis and fibromyalgia, as well as physical trauma to the nerves. According to the Neuropathy Association, an estimated 1 in 15 Americans suffer from peripheral neuropathy. Its prevalence is particularly high among diabetes patients and incidence increases with age. Though neuropathic pain is a very common condition, its symptoms, including numbness, tingling, and pricking sensations, sensitivity to touch, or burning sensations, can be highly variable, making diagnosis difficult. If left untreated, neuropathy can lead to permanent nerve damage and significant disability.

Chronic neuropathic pain arises from nerves injured or damaged by systemic disease, infection, toxins, or physical trauma. The damaged nerves are in a continuous state of hyper-excitability, often due to aberrant sodium channel firing. This hyper-excitability results in transmission of abnormal pain signals from the periphery to the central nervous system (CNS). Existing therapies that block sodium channels to treat neuropathic pain have been shown to provide effective pain relief, but are typically associated with significant unwanted CNS side effects, including dizziness, ataxia and somnolence. The compounds provided herein, may, in one or more embodiments, be able to selectively block hyper-excitable sodium channels without causing the CNS side effects that limit usage of current existing therapies. Thus, in some embodiments, the instant compounds are useful in treating neuropathic pain associated with one or more of the following: diabetes, shingles, cancer, HIV, multiple sclerosis, fibromyalgia, and physical trauma to the nerves.

The unit dosage of any given compound of the invention (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Example 1

Preparation of Compound 1

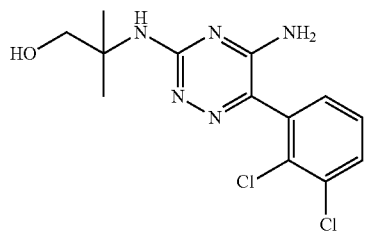 [SMILES: CC(C)(CO)Nc1nnc(-c2cccc(Cl)c2Cl)c(N)n1]

2-((5-amino-6-(2,3-dichlorophenyl)-1,2,4-triazin-3-yl)amino)-2-methylpropan-1-ol (Compound 1)

2-((5-Amino-6-(2,3-dichlorophenyl)-1,2,4-triazin-3-yl)amino)-2-methylpropan-1-ol (Compound 1) was prepared according to the following steps.

Step 1: Preparation of 3,6-dichloro-1,2,4-triazin-5-amine (Compound 2)

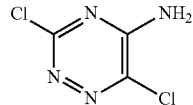

3,5,6-Trichloro-1,2,4-triazine (20 g, 108 mmol) was dissolved in acetonitrile (30 mL). This solution was added, slowly, to a 15% aq ammonia solution (50 mL, 433 mol of $NH_3$) at 5-20° C. The reaction mixture was stirred for one hour and progress of the reaction was monitored by thin layer chromatograghy ("TLC"). After completion of the reaction, 300 mL of water was added and the reaction mass stirred for an additional one hour at 10-15° C. The solid that precipitated was filtered, washed with water and dried under vacuum giving 3,6-dichloro-1,2,4-triazin-5-amine (Compound 2) (16.0 g; Yield: 90%).

Step 2: Preparation of 2-((5-amino-6-chloro-1,2,4-triazin-3-yl)amino)-2-methylpropan-1-ol (Compound 3)

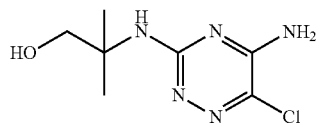

3,6-Dichloro-1,2,4-triazin-5-amine (Compound 2) (5.00 g, 30.3 mmol), 2-amino-2-methylpropan-1-ol (4.05 g, 45.5 mmol) and $NaHCO_3$ (5.09 g, 60.6 mmol) were added to a RB flask containing 50 mL of 1,4-dioxane. This mixture was degassed for 10-15 minutes. The degassed reaction mixture was stirred at 85-90° C. for 18-20 hours. Progress of the reaction was monitored by high performance liquid chromatography ("HPLC"). The reaction mixture was allowed to attain room temp (20-25° C.) and then filtered (to remove inorganic salt and unreacted $NaHCO_3$). A 1,4-dioxane solution was concentrated and the crude thus obtained was purified by column chromatography (using DCM/MeOH as eluent) giving 2-((5-amino-6-chloro-1,2,4-triazin-3-yl)amino)-2-methylpropan-1-ol (Compound 3) (1.00 g, 15.16% yield).

Step 3: Preparation of 2-((5-amino-6-(2,3-dichlorophenyl)-1,2,4-triazin-3-yl)amino)-2-methylpropan-1-ol (Compound 1)

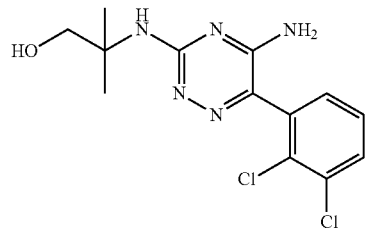 [SMILES: CC(C)(CO)Nc1nnc(-c2cccc(Cl)c2Cl)c(N)n1]

2-((5-Amino-6-chloro-1,2,4-triazin-3-yl)amino)-2-methylpropan-1-ol (Compound 3) (1.00 g, 4.59 mmol) and (2,3-dichlorophenyl)boronic acid (1.753 g, 9.19 mmol) were dissolved in 20 mL of 1,4-dioxane. $Pd(PPh_3)_4$ (531 mg, 0.459 mmol), $K_2HPO_4$ (1.761 g, 10.11 mmol) and 5 mL of DI water were added to the above reaction mixture. The reaction mixture was degassed for 10-15 minutes and then stirred under heating (at 85-90° C.) for 4-6 hours. The reaction mixture was concentrated, and to it, 5 mL of DI water and 10 mL of ethyl acetate, were added. The pH was adjusted to ~1-2 with aqueous HCl. The reaction mixture was then filtered through celite bed. The organic layer was separated and the aqueous layer was again washed with EtOAc (2×10 mL). The pH of the aqueous layer was adjusted to ~9-10 using aqueous KOH and the compound was extracted into dichloromethane ("DCM") (2×25 mL). The DCM solution was concentrated and the crude product thus obtained was purified by column chromatography, giving 2-((5-amino-6-(2,3-dichlorophenyl)-1,2,4-triazin-3-yl)amino)-2-methylpropan-1-ol (Compound 1). (1.00 g, 66.3% yield). $^1$H NMR (500 MHz, DMSO-$d_6$): δ 7.70 (d, 1H), 7.45 (t, 1H), 7.35 (d, 1H), 6.30-7.20 (br s, 2H), 6.1-6.30 (br s, 1H), 5.1-5.3 (br s, 1H), 3.45-3.55 (d, 2H), 1.25-1.50 (s, 6H); MS (ESI) for $C_{13}H_{15}Cl_2N_5O$: 328.05 (MH$^+$). The free base was dissolved in 4M hydrochloric acid in 2-propanol and stirred for two hours. The mixture was precipitated using MTBE to afford white solid as hydrochloride salt.

Example 2

Preparation of Compound 4

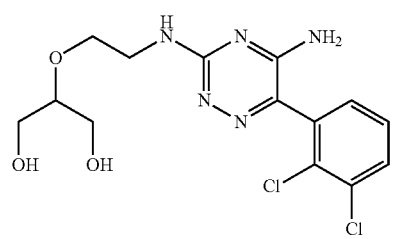 [SMILES: Nc1nc(NCCOC(CO)CO)nnc1-c1cccc(Cl)c1Cl]

2-(2-((5-amino-6-(2,3-dichlorophenyl)-1,2,4-triazin-3-yl)amino)ethoxy)propane-1,3-diol Compound 4

2-(2-((5-Amino-6-(2,3-dichlorophenyl)-1,2,4-triazin-3-yl)amino)ethoxy)propane-1,3-diol (Compound 4) was prepared according to the following steps.

Step 1: Preparation of 2-(2-((5-amino-6-chloro-1,2,4-triazin-3-yl)amino)ethoxy)propane-1,3-diol (Compound 5)

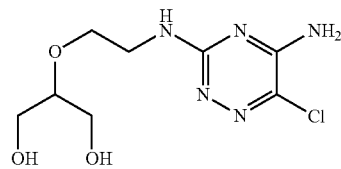 [SMILES: Nc1nc(NCCOC(CO)CO)nnc1Cl]

3,6-Dichloro-1,2,4-triazin-5-amine (Compound 2) (1.5 g, 9.09 mmol), 2-((2-phenyl-1,3-dioxan-5-yl)oxy)ethanamine (2.64 g, 11.64 mmol) and sodium bicarbonate (1.146 g, 13.64 mmol) were added to a round bottom flask containing 15 mL of 1,4-dioxane, and equipped with a condenser and a CaCl$_2$ guard tube. Nitrogen was purged into the reaction mixture for 10-15 minutes and then it was stirred at 80-85° C. for 4-5 hours. After completion of the reaction, the mixture was filtered, concentrated and the residue was heated with aqueous hydrochloric acid at 50° C. for 30 minutes. The crude product was purified by column chromatography to yield 2-(2-((5-amino-6-chloro-1,2,4-triazin-3-yl)amino)ethoxy)propane-1,3-diol (Compound 5) (400 mg, 20% yield).

Step 2: Preparation of 2-(2-((5-amino-6-(2,3-dichlorophenyl)-1,2,4-triazin-3-yl)amino)ethoxy)propane-1,3-diol (Compound 4)

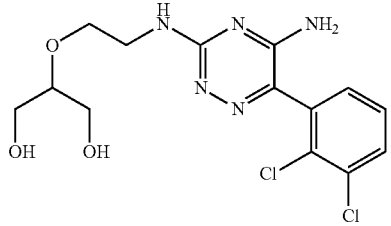 [SMILES: Nc1nc(NCCOC(CO)CO)nnc1-c1cccc(Cl)c1Cl]

2-(2-((5-Amino-6-chloro-1,2,4-triazin-3-yl)amino)ethoxy)propane-1,3-diol (Compound 5) (400 mg, 1.517 mmol) and (2,3-dichlorophenyl)boronic acid (492 mg, 2.58 mmol) were dissolved in 20 mL of 1,4-dioxane. Pd(PPh$_3$)$_4$ (175 mg, 0.152 mmol), K$_2$HPO$_4$ (581 mg, 3.34 mmol) and 5 mL of DI water were added to the above reaction mixture. Nitrogen was purged into the reaction mixture for 10-15 minutes and the mixture was stirred at 80-85° C. for 2-3 hours. The reaction mixture was concentrated and 5 mL of DI water and 10 mL of ethyl acetate were added. The pH of the reaction mixture was adjusted to 1-2 with aqueous HCl and the reaction mixture was subsequently filtered through a celite bed. The organic layer was separated and the aqueous layer was again washed with EtOAc (2×10 mL). The pH of the aqueous layer was adjusted to 9-10 using aqueous KOH and the compound was extracted into DCM (2×25 mL). The DCM layer was concentrated and the crude thus obtained was purified by column chromatography giving 2-(2-((5-amino-6-(2,3-dichlorophenyl)-1,2,4-triazin-3-yl)amino)ethoxy)propane-1,3-diol (Compound 4). The free base was dissolved in 4M HCl in 2-propanol. The mixture was concentrated to afford the product as a hydrochloride salt (100 mg, 18% yield). $^1$H NMR (500 MHz, DMSO-d$_6$+D$_2$O): δ 7.80 (d, 1H), 7.65 (m, 2H), 3.8 (m, 2H), 3.6-3.3 (m, 7H); MS (ESI) for C$_{14}$H$_{17}$Cl$_2$N$_5$O$_3$: 374.2 (MH$^+$).

Example 3

Preparation of Compound 6

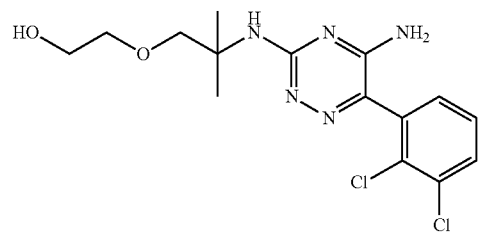 [SMILES: CC(C)(COCCO)Nc1nnc(-c2cccc(Cl)c2Cl)c(N)n1]

2-(2-((5-Amino-6-(2,3-dichlorophenyl)-1,2,4-triazin-3-yl)amino)-2-methylpropoxy)ethanol (Compound 6)

2-(2-((5-Amino-6-(2,3-dichlorophenyl)-1,2,4-triazin-3-yl)amino)-2-methylpropoxy)ethanol (Compound 6) is prepared in accordance with the following steps.

Step-1: Preparation of tert-butyl (1-hydroxy-2-methylpropan-2-yl)carbamate (Compound 7)

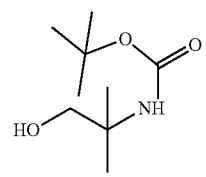

2-amino-2-methylpropan-1-ol is reacted with boc-anhydride, using triethylamine as base and DCM solvent to yield the tert-butyl (1-hydroxy-2-methylpropan-2-yl)carbamate (Compound 7a).

Step-2: Preparation of 2-((tert-butoxy carbonyl)amino)-2-methylpropyl methanesulfonate (Compound 8a)

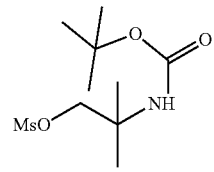

Tert-butyl (1-hydroxy-2-methylpropan-2-yl)carbamate (Compound 7) is reacted with 1.2 mol equivalent of mesyl chloride using triethylamine (1.5 eq) as base, in DCM as a solvent, to afford 2-((tert-butoxycarbonyl)amino)-2-methylpropyl methanesulfonate (Compound 8a).

Step-3: Preparation of tert-butyl (1-(2-(benzyloxy)ethoxy)-2-methylpropan-2-yl)carbamate (Compound 9a)

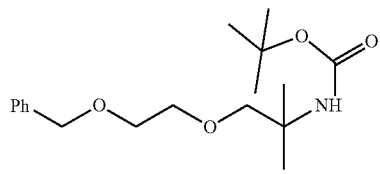 [SMILES: CC(C)(COCCOCc1ccccc1)NC(=O)OC(C)(C)C]

2-(Benzyloxy)ethanol is mixed with NaH (1.2 eq) in THF as a solvent and to this is added, slowly, 2-((tert-butoxycarbonyl)amino)-2-methylpropyl methanesulfonate (Compound 8a) to afford the synthesis of tert-butyl (1-(2-(benzyloxy)ethoxy)-2-methylpropan-2-yl)carbamate (Compound 9a) which, is further purified by column chromatography to obtain a pure compound.

Step-4: Preparation of 2-(2-amino-2-methylpropoxy)ethanol (Compound 10)

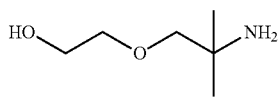

Tert-butyl (1-(2-(benzyloxy)ethoxy)-2-methylpropan-2-yl)carbamate (Compound 9) is reacted with TFA/DCM to remove the boc-group. In a subsequent step, debenzylation is carried out, using Pd/C, under $H_2$ pressure conditions, to afford 2-(2-amino-2-methylpropoxy)ethanol (Compound 10).

Step-5: Preparation of 2-(2-((5-amino-6-chloro-1,2,4-triazin-3-yl)amino)-2-methylpropoxy)ethanol (Compound 11a)

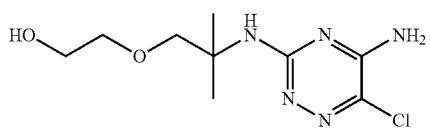 [SMILES: CC(C)(COCCO)Nc1nnc(Cl)c(N)n1]

3,6-Dichloro-1,2,4-triazin-5-amine (Compound 2) (1 eq), 2-(2-amino-2-methylpropoxy)ethanol (Compound 10) (1.5 eq) and $NaHCO_3$ (2 eq) are added together, in dioxane. The reaction mixture is stirred at 80-85° C. for 18-20 hours. The crude compound thus obtained is purified by column chromatography, to afford pure 2-(2-((5-amino-6-chloro-1,2,4-triazin-3-yl)amino)-2-methylpropoxy)ethanol (Compound 11a), which is characterized by mass and $^1$H NMR.

Step-6: Preparation of 2-(2-((5-amino-6-(2,3-dichlorophenyl)-1,2,4-triazin-3-yl)amino)-2-methylpropoxy)ethanol (Compound 6)

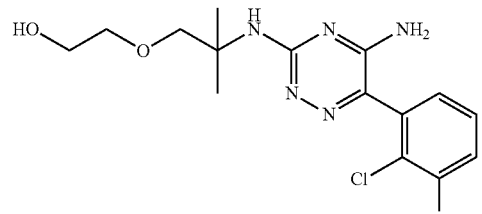

2-(2-((5-Amino-6-chloro-1,2,4-triazin-3-yl)amino)-2-methylpropoxy)ethanol (Compound 11a) is reacted, under Suzuki coupling conditions, with 2,3-dichlorophenyl boronic acid, using $K_2HPO_4$ as base and $Pd(PPh_3)_4$ as catalyst, in a dioxane/water medium at 85-90° C. The crude compound thus obtained is purified by column chromatography to afford 2-(2-((5-amino-6-(2,3-dichlorophenyl)-1,2,4-triazin-3-yl)amino)-2-methylpropoxy)ethanol (Compound 6). The free base is subjected to 4M HCl in 2-propanol to obtain the HCl salt of Compound 6.

Example 3A

Additional Approach for the Preparation of Compound 6

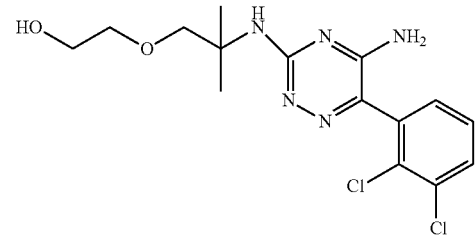 [SMILES: CC(C)(COCCO)Nc1nnc(-c2cccc(Cl)c2Cl)c(N)n1]

2-(2-((5-Amino-6-(2,3-dichlorophenyl)-1,2,4-triazin-3-yl)amino)-2-methylpropoxy)ethanol (Compound 6)

2-(2-((5-Amino-6-(2,3-dichlorophenyl)-1,2,4-triazin-3-yl)amino)-2-methylpropoxy)ethanol (Compound 6) was prepared in accordance with the following steps.

Step-1: Preparation of benzyl (1-hydroxy-2-methylpropan-2-yl)carbamate (Compound 7b)

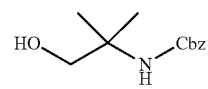

2-Amino-2-methylpropan-1-ol (5 g, 89.13 mmol) was reacted with benzyl chloroformate (8.61 g, 50.5 mmol), using triethylamine (7.38 g, 72.9 mmol) as base in DCM solvent (50 mL) at room temperature for 3 hours. After completion of the reaction, the organic layer was washed with water (2×20 mL) and dried over sodium sulfate. The DCM layer upon concentration under vaccum afforded benzyl (1-hydroxy-2-methylpropan-2-yl)carbamate (Compound 7b).

Step-2: Preparation of tert-butyl 2-(2-(((benzyloxy) carbonyl)-amino)-2-methylpropoxyl)acetate (Compound 8b)

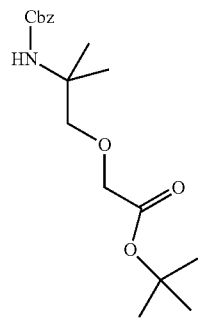 [SMILES: CC(C)(COCC(=O)OC(C)(C)C)NC(=O)OCc1ccccc1]

Benzyl (1-hydroxy-2-methylpropan-2-yl)carbamate (Compound 7b) (10 g, 26.9 mmol) and tert-butylbromoacetate (5.24 g, 26.9 mmol) were added to a round bottom flask containing 30% aqueous NaOH solution (30 mL) and toluene (50 mL). The reaction mixture was stirred for 18 hours at room temperature. After completion of the reaction, the toluene layer was separated and concentrated under vacuum to obtain a residue, which upon purification by column chromatography yielded tert-butyl 2-(2-(((benzyloxy)carbonyl)amino)-2-methylpropoxy)acetate (Compound 8b) (4.5 g, 49.6% yield).

Step-3: Preparation of tert-butyl 2-(2-amino-2-methylpropoxy)acetate (Compound 9b)

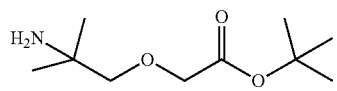

Tert-butyl 2-(2-(((benzyloxy)carbonyl)amino)-2-methylpropoxy)acetate (Compound 8b) (4.5 g, 13.34 mmol) and 50% wet Pd/C (0.50 g, 10% w/w) were added to a round bottom flask containing 45 mL of THF and subjected to hydrogenation for two hours. After completion of the reaction, the reaction mass was filtered through a celite bed, and the filtrate was concentrated under vacuum to give tert-butyl 2-(2-amino-2-methylpropoxy)acetate (Compound 9b) (2.5 g, 92% yield).

Step-4: Preparation of 2-(2-amino-2-methylpropoxy)ethanol (Compound 10)

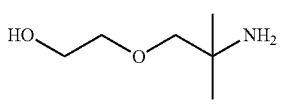

To a solution of tert-butyl 2-(2-amino-2-methylpropoxy) acetate (Compound 9b) (2.5 g, 12.3 mmol) in THF (20 mL) was added LiAlH$_4$ (0.93 g, 24.6 mmol) under a nitrogen atmosphere and the reaction mixture was stirred for 20 hours. After completion of the reaction, a 20% sodium sulfate solution (10 mL) and ethyl acetate (20 mL) were charged sequentially to the reaction mixture under stirring. After stirring for 30 minutes, the reaction mixture was filtered through a celite bed. The organic layer was separated and concentrated under vacuum to afford 2-(2-amino-2-methylpropoxy)ethanol (Compound 10).

Step-5: Preparation of 2-(2-((5-amino-6-chloro-1,2, 4-triazin-3-yl)amino)-2-methylpropoxy)ethanol (Compound 11)

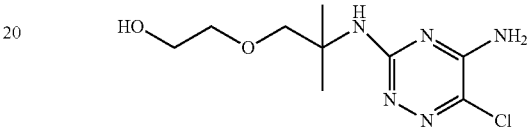

3,6-Dichloro-1,2,4-triazin-5-amine (Compound 2) (1.24 g, 7.51 mmol), 2-(2-amino-2-methylpropoxy)ethanol (Compound 10) (1.5 g, 11.26 mmol) and NaHCO$_3$ (1.26 g, 15.02 mmol) were added to a round bottom flask containing 30 mL of 1,4-dioxane. The mixture was degassed for 10-15 minutes. The degassed reaction mixture was stirred at 110° C. for 18-20 hours. After completion of the reaction, the reaction mixture was allowed to attain room temperature (20-25° C.) and then filtered (to remove inorganic salt and unreacted NaHCO$_3$). The filtrate 1,4-dioxane solution was concentrated under vacuum and the crude thus obtained was purified by column chromatography (using DCM/MeOH as eluent) giving 2-(2-((5-amino-6-chloro-1,2,4-triazin-3-yl) amino)-2-methylpropoxy)ethanol (Compound 11) (0.30 g, 15.27% yield).

Step-6: Preparation of 2-(2-((5-amino-6-(2,3-dichlorophenyl)-1,2,4-triazin-3-yl)amino)-2-methylpropoxy)ethanol (Compound 6)

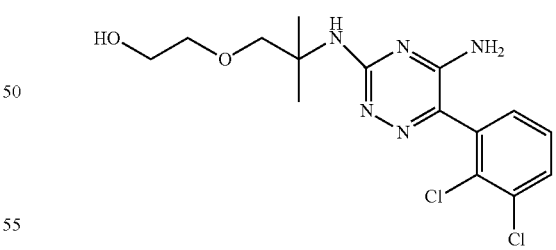

2-(2-((5-Amino-6-chloro-1,2,4-triazin-3-yl)amino)-2-methylpropoxy)ethanol (Compound 11) (0.30 g, 1.15 mmol) and (2,3-dichlorophenyl) boronic acid (0.437 g, 2.29 mmol) were dissolved in 10 mL of 1,4-dioxane, and Pd(PPh$_3$)$_4$ (0.083 g, 0.071 mmol), K$_2$HPO$_4$ (0.54 g, 3.1 mmol) and 5 ml of DI water were added to the mixture. The mixture was degassed for 10-15 minutes and then stirred under heating (at 85-90° C.) for 4 hours. After completion of the reaction, the reaction mass was allowed to attain room temperature. The reaction mixture was then filtered through a celite bed and the filtrate was concentrated under vacuum. To the residue, 20 mL of water was added and the product extracted into DCM (3×20 mL). The DCM solution was concentrated and the crude was subsequently purified by column chromatography (using DCM/MeOH as eluent), thereby yielding 2-(2-((5-amino-6-(2,3-dichlorophenyl)-1,2,4-triazin-3-yl)amino)-2-methylpropoxy)ethanol (Compound 6). (0.050 g, 11.72% yield). $^1$H NMR (500 MHz, DMSO-d$^6$): δ7.75-7.65 (d, 1H), 7.45-7.35 (dd, 1H), 7.35-7.25 (d, 1H), 6.30-6.10 (br s, 1H), 4.65-4.50 (t, 1H), 3.65-3.55 (s, 2H), 3.50-3.30 (m, 4H), 1.40-1.30 (s, 6H); MS(ESI) for $C_{15}H_{19}Cl_2N_5O_2$: 372.07 (MH$^+$). The free base is subjected to 4M HCl in 2-propanol to obtain the HCl salt of Compound 6.

Example 4

Preparation of Compound 12

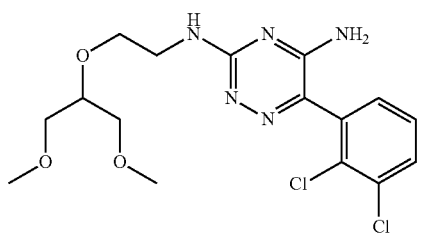 [SMILES: COCC(COC)OCCNc1nnc(-c2cccc(Cl)c2Cl)c(N)n1]

6-(2,3-Dichlorophenyl)-N3-(2-((1,3-dimethoxypropan-2-yl)oxy)ethyl)-1,2,4-triazine-3,5-diamine (Compound 12)

6-(2,3-Dichlorophenyl)-N3-(2-((1,3-dimethoxypropan-2-yl)oxy)ethyl)-1,2,4-triazine-3,5-diamine (Compound 12) is prepared in accordance with the following steps.

Step-1: Preparation of (((1,3-dimethoxypropan-2-yl)oxy)methyl)benzene (Compound 13)

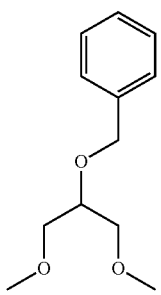

2-(Benzyloxy)propane-1,3-diol is reacted with methyl iodide (2 eq) in the presence of NaH (2.2 eq) as base, to afford (((1,3-dimethoxypropan-2-yl)oxy)methyl)benzene (Compound 13).

Step-2: Preparation of 1,3-dimethoxypropan-2-ol (Compound 14)

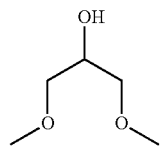

(((1,3-Dimethoxypropan-2-yl)oxy)methyl)benzene is debenzylated using Pd/C, under H$_2$ atomosphere to yield 1,3-dimethoxypropan-2-ol (Compound 14).

Step-3: Preparation of tert-butyl 2-((1,3-dimethoxypropan-2-yl)oxy)acetate (Compound 15)

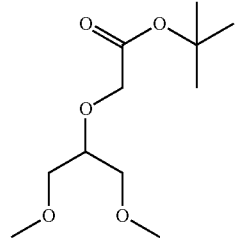 [SMILES: COCC(COC)OCC(=O)OC(C)(C)C]

1,3-Dimethoxypropan-2-ol (Compound 14) is reacted with tert-butylbromoacetate in the presence of NaH as base. The crude is purified by column chromatography to afford tert-butyl 2-((1,3-dimethoxypropan-2-yl)oxy)acetate (Compound 15).

Step-4: Preparation of 2-((1,3-dimethoxypropan-2-yl)oxy)ethanol (Compound 16)

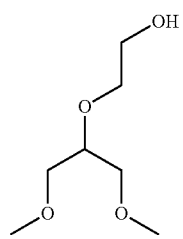

tert-Butyl 2-((1,3-dimethoxypropan-2-yl)oxy)acetate (Compound 15) is reacted with lithium aluminum hydride (LAH) in THF to afford 2-((1,3-dimethoxypropan-2-yl)oxy)ethanol (Compound 16).

Step-5: Preparation of 2-((1,3-dimethoxypropan-2-yl)oxy)ethyl methanesulfonate (Compound 17)

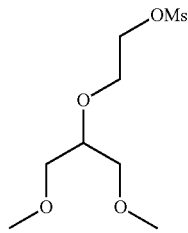

2-((1,3-Dimethoxypropan-2-yl)oxy)ethanol (Compound 16) is reacted with methanesulphonyl chloride (1 eq) in the presence of triethylamine (1.2 eq) as base, in DCM solvent. After completion of reaction, the resulting compound is isolated and purified to afford 2-((1,3-dimethoxypropan-2-yl)oxy)ethyl methanesulfonate (Compound 17).

Step-6: Preparation of 2-((1,3-dimethoxypropan-2-yl)oxy)ethanamine (Compound 18)

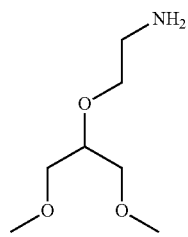

2-((1,3-Dimethoxypropan-2-yl)oxy)ethyl methanesulfonate (Compound 17) is reacted with aqueous ammonia (30%) for 16 hours. The resulting compound is extracted using DCM and the organic layer is concentrated to afford 2-((1,3-dimethoxypropan-2-yl)oxy)ethanamine (Compound 18).

Step-7: Preparation of 6-chloro-$N^3$-(2-((1,3-dimethoxypropan-2-yl)oxy)ethyl)-1,2,4-triazine-3,5-diamine (Compound 19)

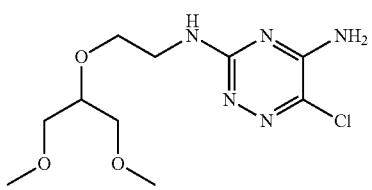 [SMILES: COCC(COC)OCCNc1nnc(Cl)c(N)n1]

A solution of 3,6-dichloro-1,2,4-triazin-5-amine (Compound 2), 2-((1,3-dimethoxypropan-2-yl)oxy)ethanamine (Compound 18) (1.5 eq) and NaHCO$_3$ (2 eq) in 1,4-dioxane is stirred for 18-20 hours at 85-90° C. After completion of the reaction, the crude product is purified by column chromatography to afford 6-chloro-$N^3$-(2-((1,3-dimethoxypropan-2-yl)oxy)ethyl)-1,2,4-triazine-3,5-diamine (Compound 19).

Step-8: Preparation of 6-(2,3-dichlorophenyl)-$N^3$-(2-((1,3-dimethoxypropan-2-yl)oxy)ethyl)-1,2,4-triazine-3,5-diamine (Compound 12)

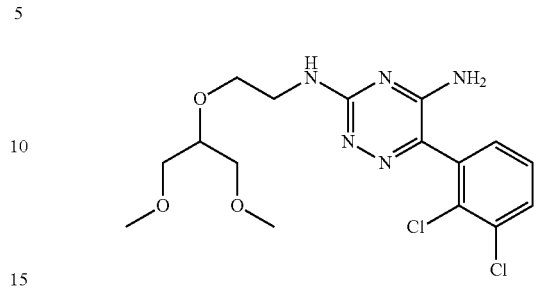

6-Chloro-$N^3$-(2-((1,3-dimethoxypropan-2-yl)oxy)ethyl)-1,2,4-triazine-3,5-diamine (Compound 19) is subjected to Suzuki coupling, with 2,3-dichlorophenyl boronic acid, using K$_2$HPO$_4$ as base and Pd(PPh$_3$)$_4$ as catalyst, in a dioxane/water medium at 85-90° C. The crude compound is purified by column chromatography to afford 6-(2,3-dichlorophenyl)-$N^3$-(2-((1,3-dimethoxypropan-2-yl)oxy)ethyl)-1,2,4-triazine-3,5-diamine (Compound 12). The free base form of the compound is subjected to 4M HCl in 2-propanol to afford the HCl salt (Compound 12).

Example 5

Preparation of Compound 20

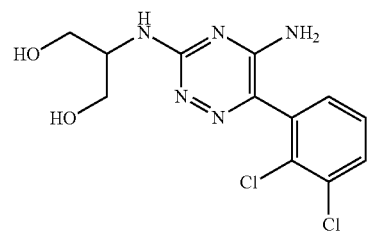 [SMILES: Nc1nc(NC(CO)CO)nnc1-c1cccc(Cl)c1Cl]

2-((5-Amino-6-(2,3-dichlorophenyl)-1,2,4-triazin-3-yl)amino)propane-1,3-diol (Compound 20)

2-((5-Amino-6-(2,3-dichlorophenyl)-1,2,4-triazin-3-yl)amino)propane-1,3-diol (Compound 20) was prepared according to the following steps.

Step 1: Preparation of 2-((5-amino-6-chloro-1,2,4-triazin-3-yl)amino)propane-1,3-diol (Compound 21)

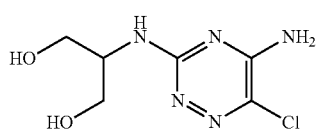 [SMILES: Nc1nc(NC(CO)CO)nnc1Cl]

3,6-Dichloro-1,2,4-triazin-5-amine (Compound 2) (3.00 g, 18.18 mmol) and 2-aminopropane-1,3-diol (2.98 g, 32.7 mmol) were dissolved in 30 mL of 1,4-dioxane. NaHCO$_3$ (3.51 g, 41.8 mmol) was added to the above reaction mixture and followed by 10-15 minutes of degassing. The reaction mixture was stirred at 80° C. for 8-10 hours. After completion of the reaction, the mixture was filtered (at 40-55° C.), and the organic layer was concentrated under vacuum to afford 2-((5-amino-6-chloro-1,2,4-triazin-3-yl)amino)propane-1,3-diol (Compound 21) (3.20 g, 80% yield).

Step 2: Preparation of 2-((5-amino-6-(2,3-dichlorophenyl)-1,2,4-triazin-3-yl)amino)propane-1,3-diol (Compound 20)

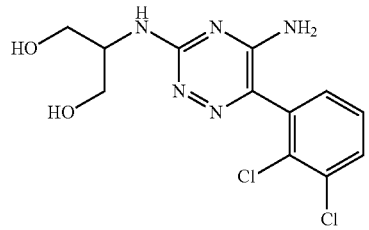 [SMILES: Nc1nc(NC(CO)CO)nnc1-c1cccc(Cl)c1Cl]

2-((5-Amino-6-chloro-1,2,4-triazin-3-yl)amino)propane-1,3-diol (Compound 21) (3.20 g, 14.57 mmol) and (2,3-dichlorophenyl)boronic acid (6.12 g, 32.1 mmol) were dissolved in 32 mL of 1,4-dioxane. Pd(PPh$_3$)$_4$ (1.684 g, 1.457 mmol), K$_2$HPO$_4$ (5.58 g, 32.1 mmol) and 10 mL of DI water were added to the above reaction mixture followed by 10-15 minutes of degassing. The degassed reaction mixture was stirred at 85-90° C. for 4-6 hours. After completion of the reaction, the reaction mass was concentrated and to it 10 mL of DI water and 20 mL EtOAc, were added. The pH was then adjusted to 1-2 with aqueous HCl and the reaction mass was filtered through a celite bed. The organic layer was separated and the aqueous layer was washed with EtOAc (2×10 mL). The pH of the aqueous layer was adjusted to 8-9 (using aqueous KOH) and it was stirred for one hour. The precipitated compound was filtered, washed with water (10 mL), and was dried under vacuum to afford 2-((5-amino-6-(2,3-dichlorophenyl)-1,2,4-triazin-3-yl)amino)propane-1,3-diol (Compound 20) (1.30 g, 27% yield) as a pale yellow solid. $^1$H NMR (500 MHz, DMSO-d$_6$): δ 7.70 (d, 1H), 7.45 (t, 1H), 7.35 (d, 1H), 5.80-7.30 (br s, 3H), 4.55-4.7 (t, 2H), 3.85-4.00 (br s, 1H), 3.50-3.60 (m, 4H); MS (ESI) for C$_{12}$H$_{13}$Cl$_2$N$_5$O$_2$: 330.04 (MH$^+$). The free base was dissolved in 4M hydrochloric acid in 2-propanol. The mixture was concentrated to afford the product as the hydrochloride salt.

Example 6

Preparation of Compound 22

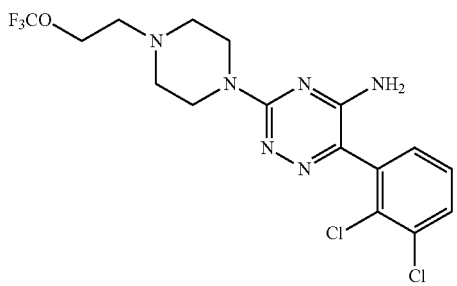 [SMILES: Nc1nc(N2CCN(CCOC(F)(F)F)CC2)nnc1-c1cccc(Cl)c1Cl]

6-(2,3-Dichlorophenyl)-3-(4-(2-(trifluoromethoxy)ethyl)piperazin-1-yl)-1,2,4-triazin-5-amine (Compound 22)

6-(2,3-Dichlorophenyl)-3-(4-(2-(trifluoromethoxy)ethyl)piperazin-1-yl)-1,2,4-triazin-5-amine (Compound 22) is prepared in accordance with the following steps. Although the results associated with this approach were not satisfactory when carried out, the general procedure described in this example is believed to be nonetheless helpful as optimization of this procedure should result in a more acceptable result.

Step-1: Preparation of tert-butyl 4-(2-hydroxyethyl)piperazine-1-carboxylate (Compound 23)

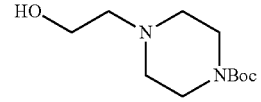

tert-Butyl piperazine-1-carboxylate (1 eq) is reacted with bromoethanol (1 eq) in DMF as solvent and K$_2$CO$_3$ as base (1 eq) at 60-65° C. for 18-20 hours. The crude product is purified by column chromatography to afford tert-butyl 4-(2-hydroxyethyl)piperazine-1-carboxylate (Compound 23).

Step-2: Preparation of tert-butyl 4-(2-(((methylthio)carbonothioyl)oxy)ethyl)piperazine-1-carboxylate (Compound 24)

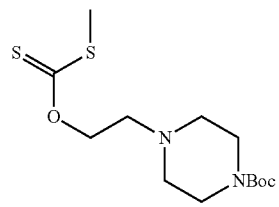 [SMILES: CSC(=S)OCCN1CCN(C(=O)OC(C)(C)C)CC1]

tert-Butyl 4-(2-hydroxyethyl)piperazine-1-carboxylate (Compound 23) is reacted with carbondisulfide (1 eq) in the presence of NaH (1 eq) as base, in THF solvent (at 5-15° C.). After one hour, methyl iodide (1 eq) is added at 5-10° C. and the reaction is stirred for one hour at 20-25° C. After completion of the reaction, the crude product is purified by column chromatography to afford tert-butyl 4-(2-(((methylthio)carbonothioyl)oxy)ethyl)piperazine-1-carboxylate (Compound 24).

Step-3: Preparation of 1-(2-(trifluoromethoxy)ethyl)piperazine (Compound 25)

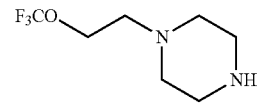

To a suspension of 1,3-dibromo-5,5-dimehtylhydantoin (3 eq) in dichloromethane is added HF-pyridine (40 eq) (at −78° C.), and then, slowly, tert-butyl 4-(2-(((methylthio) carbonothioyl)oxy)ethyl)piperazine-1-carboxylate (Compound 24) (1 eq) is added at the same temperature. The reaction mixture is stirred at −78° C. for one hour and is subsequently warmed to 0° C. and stirred for two hours. After completion of reaction, the crude product is purified by column chromatography to afford 1-(2-(trifluoromethoxy) ethyl)piperazine (Compound 25).

Step-4: Preparation of 6-chloro-3-(4-(2-(trifluoromethoxy)ethyl)piperazin-1-yl)-1,2,4-triazin-5-amine (Compound 26)

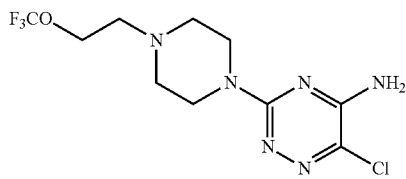 [SMILES: Nc1nc(N2CCN(CCOC(F)(F)F)CC2)nnc1Cl]

A solution of 3,6-dichloro-1,2,4-triazin-5-amine (Compound 2), 1-(2-(trifluoromethoxy)ethyl)piperazine (Compound 25) (1.5 eq) and NaHCO₃ (2 eq) in 1,4-dioxane is stirred for 18-20 hours at 85-90° C. After completion of reaction, the crude product is purified by column chromatography to afford the 6-chloro-3-(4-(2-(trifluoromethoxy) ethyl)piperazin-1-yl)-1,2,4-triazin-5-amine (Compound 26).

Step-5: Preparation of 6-(2,3-dichlorophenyl)-3-(4-(2-(trifluoromethoxy)ethyl)piperazin-1-yl)-1,2,4-triazin-5-amine (Compound 22)

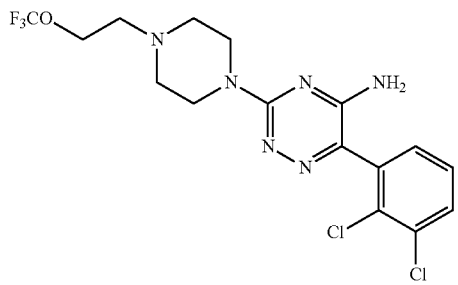

6-Chloro-3-(4-(2-(trifluoromethoxy)ethyl)piperazin-1-yl)-1,2,4-triazin-5-amine (Compound 26) is coupled to 2,3-dichlorophenyl boronic acid under Suzuki conditions, using K₂HPO₄ as base and Pd(PPh₃)₄ as catalyst in a dioxane/water medium at 85-90° C. The crude product is purified by column chromatography to afford 6-(2,3-dichlorophenyl)-3-(4-(2-(trifluoromethoxy)ethyl)piperazin-1-yl)-1,2,4-triazin-5-amine (Compound 22). The free base form of the compound is subjected to 4M HCl in 2-propanol to obtain the HCl salt of Compound 22.

Example 6A

Additional Approach for the Preparation of Compound 22

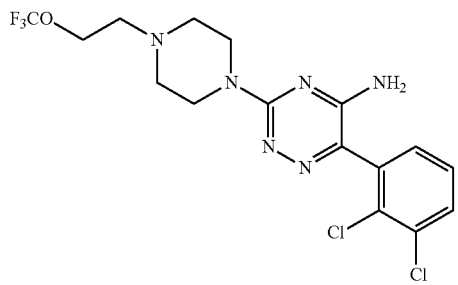 [SMILES: Nc1nc(N2CCN(CCOC(F)(F)F)CC2)nnc1-c1cccc(Cl)c1Cl]

6-(2,3-Dichlorophenyl)-3-(4-(2-(trifluoromethoxy)ethyl)piperazin-1-yl)-1,2,4-triazin-5-amine (Compound 22)

6-(2,3-Dichlorophenyl)-3-(4-(2-(trifluoromethoxy)ethyl) piperazin-1-yl)-1,2,4-triazin-5-amine (Coumpound 22) was prepared in accordance with the following steps.

Step 1: Preparation of 5-amino-6-chloro-3-N-(4-N-Boc-piperazinyl)amino-1,2,4-triazine. Schematically, the preparation of 5-amino-6-chloro-3-N-(4-N-Boc-piperazinyl) amino-1,2,4-triazine was carried out as indicated immediately below.

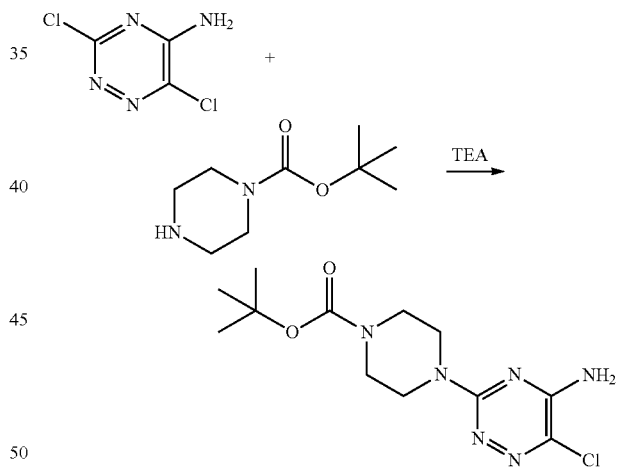

A vial was charged with 5-amino-3,6-dichloro-1,2,4-triazine (466 mg, 2.82 mmol) and triethylamine (1.0 mL, 7.17 mmol), and t-Boc-piperazine (0.5675 g, 2.96 mmol) in dioxane. The mixture was heated at 95° C. for 1.5 hours using a microwave. The mixture was cooled to room temperature, filtered and the white solid was washed with ethyl acetate. The organic solution was concentrated. The residue was purified with flash column chromatography on silica gel using 1-10% methanol/dichloromethane to afford 872.4 mg product as solid in 98% yield. ¹H NMR (500 MHz, Chloroform-d) δ 5.38 (br, 2H), 3.76-3.68 (m, 4H), 3.44 (dd, J=6.3, 3.9 Hz, 4H), 1.42 (s, 9H). LC-MS: 315.0 (MH⁺/z).

Step 2: Preparation of 3-N-piperazin-1-yl lamotrigine (Compound 79). Schematically, the preparation of 3-N-piperazin-1-yl lamotrigine was carried out as indicated immediately below.

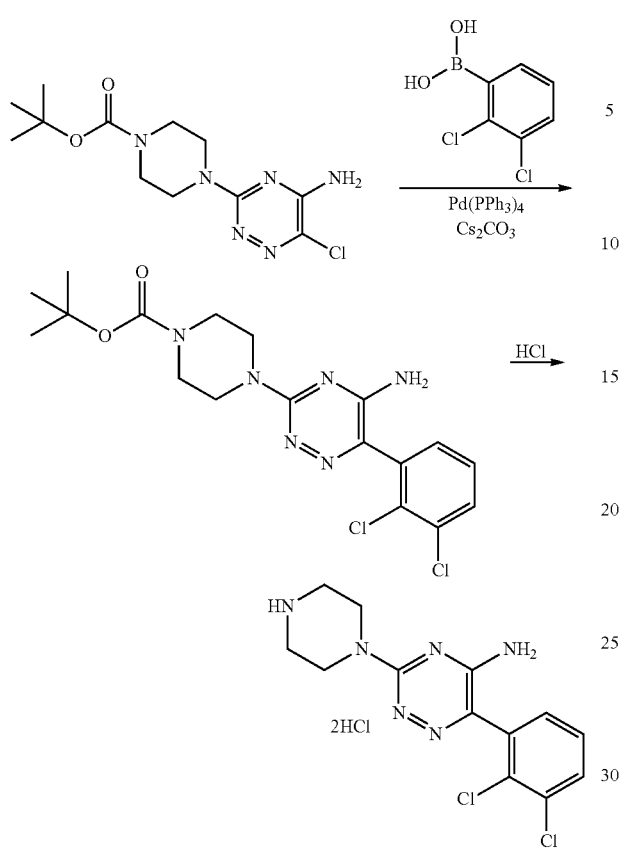

A mixture of (2,3-dichlorophenyl)boronic acid (355.4 g, 1.86 mmol), 5-amino-6-chloro-3-(4-N-BOC-piperazin-1-yl)amino-1,2,4-triazine (302.4 mg, 0.96 mmol) and cesium carbonate (1.0591 g, 3.22 mmol) was dissolved in dioxane/water (10 mL/2 mL), followed by addition of tetrakis(triphenylphosphine)palladium (112.6 mg, 0.097 mmol). The mixture was purged with nitrogen for a few minutes. The mixture was heated to 90° C. over 30 minutes, and kept at 90° C. for 5.5 hours. The mixture was cooled to room temperature and concentrated to remove the organic solvent. The residue was dissolved in water and extracted with dichloromethane (3×40 mL). The combined organic solution was dried over anhydrous sodium sulfate, filtered and the filtrate was concentrated. The residue was purified with flash column chromatography on silica gel using 1-10% methanol/dichloromethane. The product was purified again with flash column chromatography on silica gel using 30-55% ethyl acetate/hexane to afford intermediate (222.5 mg, 55%).

The intermediate (222.5 mg) was dissolved in 1.5 mL of methanol and 0.5 mL of 4 N hydrochloride in dioxane was added. The mixture was stirred at room temperature for 4 hours and 40 minutes. More of 4 N hydrochloride in dioxane (0.3 mL) was added. The mixture was stirred at room temperature for 17.5 hours. The mixture was concentrated to remove the solvents. The residue was dried under high vacuum to afford the final product as HCl salt (216.1 mg). $^1$H NMR (500 MHz, DMSO-$d_6$) δ 9.61 (s, 2H), 8.99 (br, 1H), 8.07 (br, 1H), 7.84 (d, J=7.9 Hz, 1H), 7.54 (t, J=7.9 Hz, 1H), 7.48 (d, J=7.6 Hz, 1H), 4.04 (s, 4H), 3.265 (s, 4H). LC-MS: 325.0 (MH$^+$/z).

The HCl salt (68.3 mg) was mixed with saturated potassium carbonate solution and extracted with dichloromethane (3×20 mL). The combined organic solution was washed with brine, dried over anhydrous soldium sulfate, and concentrated to afford the product as a free base (47.6 mg). $^1$H NMR (500 MHz, Chloroform-d) δ 7.55 (dd, J=2.0 Hz and 8.0 Hz, 1H), 7.37-7.31 (m, 2H), 4.69 (br, 2H), 3.86 (m, 4H), 2.95 (t, J=5.0 Hz, 4H). LC-MS: 325.0 (MH$^+$/z).

Step 3: Preparation of 6-(2,3-dichlorophenyl)-3-(4-(2-(trifluoromethoxy)ethyl)piperazin-1-yl)-1,2,4-triazin-5-amine (Compound 22). Schematically, the preparation of Compound 22 was carried out as indicated immediately below.

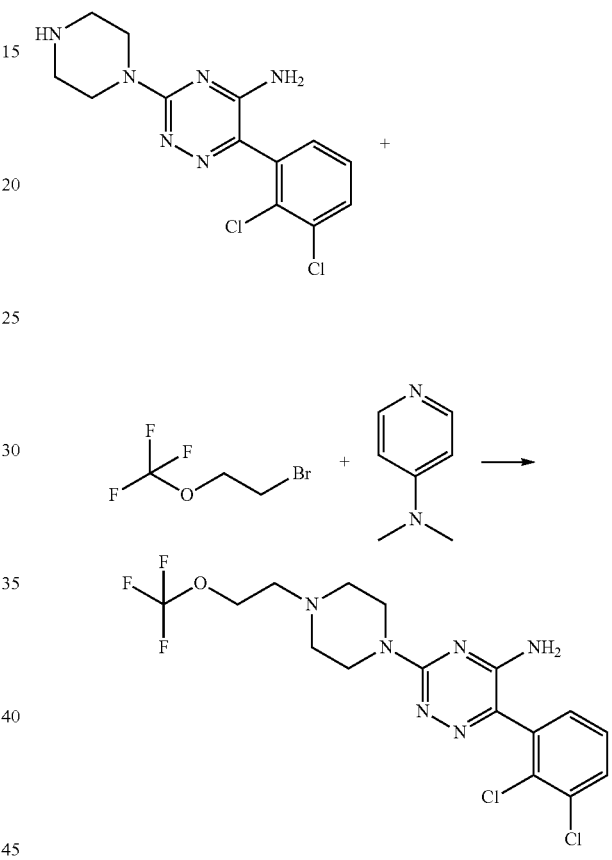

6-(2,3-dichlorophenyl)-3-(piperazin-1-yl)-1,2,4-triazin-5-amine (Compound 79) (100 mg, 0.308 mmol), 1-bromo-2-(trifluoromethoxy)ethane (59.3 mg, 0.308 mmol), and N,N-dimethylaminopyridine (37.6 mg, 0.308 mmol) were dissolved in dioxane (5 ml). The solution was heated at 105° C. on microwave reactor for 3 h. LC-MS analysis indicated the starting material was consumed completely. Solids were filtered off and filtrate was concentrated on Rotavap under reduced pressure. The resulting residue was loaded to a samplet and subject to flash chromatography on Biotage by using a gradient of 0-5% MeOH with DCM. Fractions containing desired product were collected, combined, and concentrated. After drying under high vacuo, product was afforded as white powder (24 mg, 95.2% purity, 18% yield). $^1$H-NMR (500 MHz, CDCl$_3$) δ 7.60 (1H, dd, $J_1$=5.0 Hz, $J_2$=2.0 Hz), 7.36 (2H, m), 4.79 (2H, bs), 4.14 (2H, t, J=5.5 Hz), 3.93 (4H, bs), 2.77 (2H, t, J=5.5 Hz), 2.63 (4H, t, J=5.0 Hz). LC-MS [ESI-MH$^+$]: m/z 437.

Example 7

Preparation of Compound 27

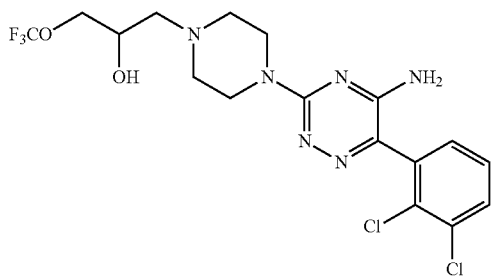 [SMILES: Nc1nc(N2CCN(CC(O)COC(F)(F)F)CC2)nnc1-c1cccc(Cl)c1Cl]

1-(4-(5-Amino-6-(2,3-dichlorophenyl)-1,2,4-triazin-3-yl)piperazin-1-yl)-3-(trifluoromethoxy)propan-2-ol (Compound 27)

1-(4-(5-Amino-6-(2,3-dichlorophenyl)-1,2,4-triazin-3-yl)piperazin-1-yl)-3-(trifluoromethoxy)propan-2-ol (Compound 27) was prepared according to the following steps.

Step 1: Preparation of 2-(benzyloxy)-3-(trifluoromethoxy)propan-1-ol (Compound 28)

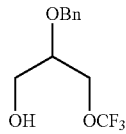

2-(Benzyloxy)propan-1,3-diol (25 g, 137 mmol), 1-trifluoromethyl-1,2-benziodoxol-3(1H)-one (4.34 g, 13.7 mmol) and bis(1,1,1-trifluoro-N-(trifluoromethyl)sulfonyl)methylsulfonamido)zinc (4.29 g, 6.85 mmol) were added to a round bottom flask containing 25 mL of chloroform. The reaction mixture was stired at 30-32° C. for 20 hours under nitrogen atmosphere. The reaction was monitored by $^{19}$F NMR. After completion of the reaction, the mixture was concentrated and the crude product obtained was purified by column chromatography (using ethyl acetate/hexane as eluant) giving 2-(benzyloxy)-3-(trifluoromethoxy)propan-1-ol (Compound 28) (2.0 g, 58% yield).

Step 2: Preparation of 2-(benzyloxy)-3-(trifluoromethoxy)propyl methanesulfonate (Compound 29)

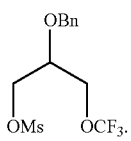

2-(Benzyloxy)-3-(trifluoromethoxy)propan-1-ol (Compound 28) (2.1 g, 8.4 mmol) was dissolved in 20 mL of dichloromethane, in a round bottom flask. To this was added triethylamine (1.189 g, 11.7 mmol) under a nitrogen atmosphere. The reaction was cooled to 0-5° C. and then methanesulfonyl chloride (1.154 g, 10.0 mmol) was added drop wise to the reaction using an addition funnel, maintaining the reaction temperature at 5-10° C. Post addition, the reaction was stirred at 20-25° C. for two hours. After completion of reaction, 10% aqueous ammonium chloride (30 ml) was added to the reaction and it was stirred for five minutes. The organic layer was separated and washed with saturated sodium bicarbonate solution (20 mL) and water (10 mL) respectively. The organic layer was dried over anhydrous sodium sulfate and concentrated to obtain the crude product which was purified by column chromatography (eluent ethyl acetate/hexane mixture) to give 2-(benzyloxy)-3-(trifluoromethoxy)propyl methanesulfonate (Compound 29) (2.0 g, 72.7% yield).

Step 3: Preparation of 1-(2-(benzyloxy)-3-(trifluoromethoxy)propyl)piperazine (Compound 30)

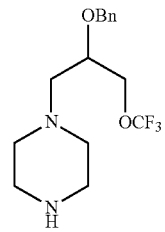

2-(Benzyloxy)-3-(trifluoromethoxy)propyl methanesulfonate (Compound 29) (0.650 g, 1.98 mmol), piperazine (1.705 g, 19.8 mmol) and $K_2CO_3$ (1.368 g, 9.90 mmol) were added to a round bottom flask containing 25 mL of dimethylformamide under a nitrogen atmosphere. The reaction mixture was stirred at 60-65° C. for six hours. The reaction progress was monitored by HPLC and after completion of reaction, the reaction mixture was cooled to 20-25° C. and filtered through sintered funnel to remove salts. The filtrate was concentrated under vacuum to obtain the crude product, which was purified by column chromatography (using dichloromethane/methanol as eluent) to give 1-(2-(benzyloxy)-3-(trifluoromethoxy)propyl)piperazine (Compound 30). (0.33 g, 52% yield).

Step-4: Preparation of 1-(piperazine-1-yl)-3-(trifluoromethoxy)propan-2-ol (Compound 31)

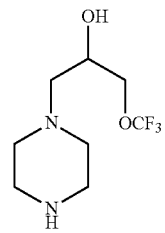

1-(2-(Benzyloxy)-3-(trifluoromethoxy)propyl)piperazine (Compound 30) (0.33 g, 1.03 mmol) and 50% wet Pd/C (0.07 g, 10% w/w) were added to a round bottom flask containing 25 mL of methanol and subjected to hydrogenation, for 20 hours. After completion, the reaction was filtered through a celite bed, and the filtrate was concentrated to give 1-(piperazine-1-yl)-3-(trifluoromethoxy)propan-2-ol (Compound 31) (0.18 g, 76.7% yield).

Step-5: Preparation of 1-(4-(5-amino-6-chloro-1,2,4-triazin-3-yl)piperazin-1-yl)-3-(trifluoromethoxy)propan-2-ol (Compound 32)

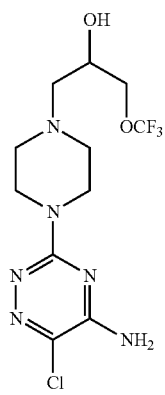

3,6-Dichloro-1,2,4-triazin-5-amine (0.108 g, 0.657 mmol), 1-(piperazine-1-yl)-3-(trifluoromethoxy)propan-2-ol (Compound 31) (0.18 g, 0.789 mmol) and sodium bicarbonate (0.083 g, 0.986 mmol) were added to a round bottom flask containing 10 mL of 1,4-dioxane, and equipped with a condenser and calcium chloride guard tube. Nitrogen was purged into the reaction mixture for 10-15 minutes and the reaction mass was heated under stirring at 80-85° C. for 5-6 hours. After completion of the reaction, the reaction mass was allowed to reach room temperature and was then filtered to remove salts. The filtrate was concentrated under vacuum. The obtained residue (crude) was purified by column chromatography (using dichloromethane/methanol as an eluent) to give 1-(4-(5-amino-6-chloro-1,2,4-triazin-3-yl)piperazin-1-yl)-3-(trifluoromethoxy)propan-2-ol (Compound 32) (78 mg, 33% yield).

Step-6: Preparation of 1-(4-(5-amino-6-(2,3-dichlorophenyl)-1,2,4-triazin-3-yl)piperazin-1-yl)-3-(trifluoromethoxy)propan-2-ol (Compound 27)

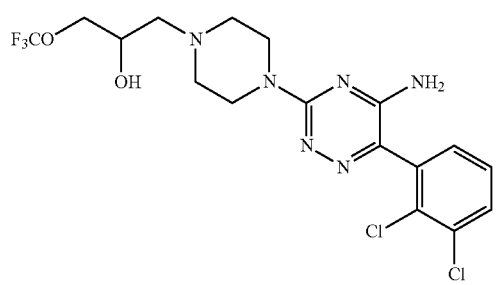 [SMILES: Nc1nc(N2CCN(CC(O)COC(F)(F)F)CC2)nnc1-c1cccc(Cl)c1Cl]

1-(4-(5-amino-6-chloro-1,2,4-triazin-3-yl)piperazin-1-yl)-3-(trifluoromethoxy)propan-2-ol (Compound 32) (78 mg, 0.219 mmol) and (2,3-dichlorophenyl)boronic acid (104 mg, 0.547 mmol) were dissolved in 10 mL of 1,4-dioxane. Pd(PPh$_3$)$_4$ (18 mg, 0.015 mmol), K$_2$HPO$_4$ (76 mg, 0.437 mmol) and 5 mL of water were added to the above reaction mixture. The reaction mixture was degassed for 10-15 minutes and then stirred under heating (at 85-90° C.) for 4-6 hours. After completion of the reaction, the reaction mixture was allowed to attain room temperature and was filtered through celite bed. The filtrate was concentrated under vacuum to remove the organic solvent. To the remaining crude, 10 mL of water was added and the product was extracted into dichloromethane (3×10 mL). The dichloromethane solution was concentrated and the crude thus obtained was purified by preparative thin layer chromatography to give 1-(4-(5-amino-6-(2,3-dichlorophenyl)-1,2,4-triazin-3-yl)piperazin-1-yl)-3-(trifluoromethoxy)propan-2-ol (Compound 27) (18 mg, 18% yield). $^1$H NMR (500 MHz, CDCl$_3$): δ 7.60 (m, 1H), 7.38 (m, 2H), 4.05 (m, 4H), 3.85-3.95 (m, 4H), 3.6-3.7 (m 1H), 2.75 (m, 2H), 2.5-2.6 (m, 4H); $^{19}$F NMR: δ−60.954 (s, OCF$_3$); MS (ESI) for C$_{17}$H$_{19}$Cl$_2$F$_3$N$_6$O$_2$: 467.05 (M$^+$). The free base was dissolved in 4M hydrochloride in 2-propanol (2 mL) and stirred for one hour. The mixture was concentrated and product was precipitated by addition of MTBE. The precipitated product was filtered and the cake was dried to afford pale yellow solid as hydrochloride salt (15 mg). $^1$H NMR (500 MHz, DMSO-d$_6$): δ 7.80 (m, 1H), 7.52 (m, 1H), 7.39 (m, 1H), 4.70-4.50 (m, 2H), 4.40-4.30 (m, 1H), 4.20-4.05 (m, 2H), 3.60-3.32 (m, 4H), 3.30-3.15 (m 4H); $^{19}$F NMR: δ−58.929 (s, OCF$_3$).

Example 7A

Additional Approach for the Preparation of Compound 27

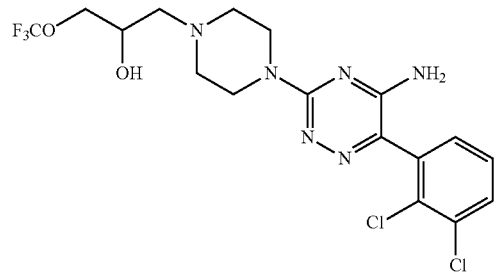 [SMILES: Nc1nc(N2CCN(CC(O)COC(F)(F)F)CC2)nnc1-c1cccc(Cl)c1Cl]

1-(4-(5-Amino-6-(2,3-dichlorophenyl)-1,2,4-triazin-3-yl)piperazin-1-yl)-3-(trifluoromethoxy)propan-2-ol (Compound 27)

1-(4-(5-Amino-6-(2,3-dichlorophenyl)-1,2,4-triazin-3-yl)piperazin-1-yl)-3-(trifluoromethoxy)propan-2-ol (Compound 27) can also be prepared in accordance with the following steps.

Step-1: Preparation of 2-(benzyloxy)-3-(trityloxy)propan-1-ol (Compound 33)

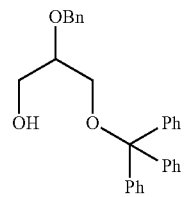 [SMILES: OCC(COC(c1ccccc1)(c1ccccc1)c1ccccc1)OCc1ccccc1]

2-(Benzyloxy)propane-1,3-diol is reacted with 0.7 eq of trityl chloride in DCM as solvent and triethylamine (1 eq) as base. After completion of reaction, the crude product is purified by column chromatography to afford 2-(benzyloxy)-3-(trityloxy)propan-1-ol (Compound 33).

Step-2: Preparation of 2-(benzyloxy)-3-(trityloxy)propyl methanesulfonate (Compound 34)

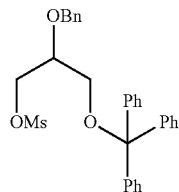

2-(Benzyloxy)-3-(trityloxy)propan-1-ol (Compound 33) is reacted with methanesulfonyl chloride (1 eq) in DCM as solvent and triethylamine (1.2 eq) as base to afford 2-(benzyloxy)-3-(trityloxy)propyl methanesulfonate (Compound 34).

Step-3: Preparation of benzyl 4-(2-(benzyloxy)-3-(trityloxy)propyl)piperazine-1-carboxylate (Compound 35)

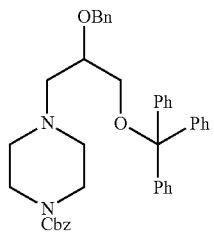 [SMILES: O=C(OCc1ccccc1)N1CCN(CC(COC(c2ccccc2)(c2ccccc2)c2ccccc2)OCc2ccccc2)CC1]

Benzyl piperazine-1-carboxylate (1 eq) is reacted with 2-(benzyloxy)-3-(trityloxy)propyl methanesulfonate (Compound 34) (1 eq) in DMF solvent and K$_2$CO$_3$ as base (1 eq) at 60-65° C. for 18-20 hours. The resulting crude product is purified by column chromatography to afford benzyl 4-(2-(benzyloxy)-3-(trityloxy)propyl)piperazine-1-carboxylate (Compound 35).

Step-4: Preparation of benzyl 4-(2-(benzyloxy)-3-hydroxypropyl)piperazine-1-carboxylate (Compound 36)

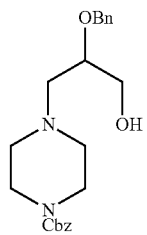 [SMILES: O=C(OCc1ccccc1)N1CCN(CC(CO)OCc2ccccc2)CC1]

Selective trityl deprotection of benzyl 4-(2-(benzyloxy)-3-(trityloxy)propyl)piperazine-1-carboxylate (35) is carried out at pH ~3 using aqueous HCl. Crude compound resulting from the reaction is purified by column chromatograph to yield benzyl 4-(2-(benzyloxy)-3-hydroxypropyl)piperazine-1-carboxylate (Compound 36).

Step-5: Preparation of benzyl 4-(2-(benzyloxy)-3-(((methylthio)carbonothioyl)oxy)propyl)piperazine-1-carboxylate (Compound 37)

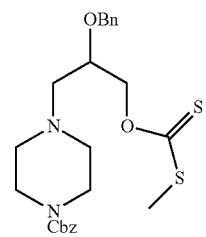 [SMILES: CSC(=S)OCC(CN1CCN(C(=O)OCc2ccccc2)CC1)OCc1ccccc1]

Benzyl 4-(2-(benzyloxy)-3-hydroxypropyl)piperazine-1-carboxylate (Compound 36) is reacted with carbondisulfide (1 eq) in the presence of NaH (1 eq) as base in THF solvent at 5-15° C. After one hour, to the reaction mixture is added methyl iodide (1 eq) at 5-10° C. and the reaction mixture is stirred for one hour at 20-25° C. After completion of the reaction, the crude product is purified by column chromatography to afford the benzyl 4-(2-(benzyloxy)-3-(((methylthio)carbonothioyl)oxy)propyl)piperazine-1-carboxylate (Compound 37).

Step-6: Preparation of benzyl 4-(2-(benzyloxy)-3-(trifluoromethoxy)propyl)piperazine-1-carboxylate (Compound 38)

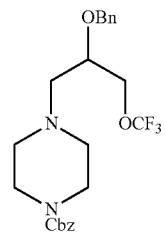

To a suspension of 1,3-dibromo-5,5-dimethylhydantoin (3 eq) in dichloromethane is added HF-pyridine (40 eq) at −78° C., followed by the slow addition of benzyl 4-(2-(benzyloxy)-3-(((methylthio)carbonothioyl)oxy)propyl)piperazine-1-carboxylate (Compound 37) (1 eq) at the same temperature. The reaction mixture is stirred at −78° C. for one hour and subsequently is warmed to 0° C. and stirred at the same temperature for two hours. After completion of the reaction, the crude product is purified by column chromatography to afford benzyl 4-(2-(benzyloxy)-3-(trifluoromethoxy)propyl)piperazine-1-carboxylate (Compound 38).

Step-7: Preparation of 1-(piperazin-1-yl)-3-(trifluoromethoxy)propan-2-ol (Compound 31)

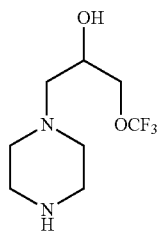

Benzyl 4-(2-(benzyloxy)-3-(trifluoromethoxy)propyl)piperazine-1-carboxylate (Compound 38) is subjected to hydrogenation reaction conditions using Pd/C in a $H_2$ atmosphere to afford 1-(piperazin-1-yl)-3-(trifluoromethoxy)propan-2-ol (Compound 31).

Step-8: Preparation of 1-(4-(5-amino-6-chloro-1,2,4-triazin-3-yl)piperazin-1-yl)-3-(trifluoromethoxy)propan-2-ol (Compound 32)

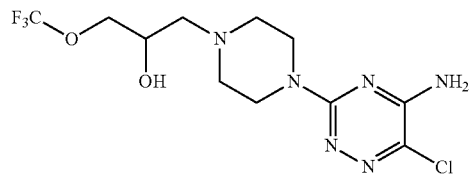 [SMILES: Nc1nc(N2CCN(CC(O)COC(F)(F)F)CC2)nnc1Cl]

3,6-Dichloro-1,2,4-triazin-5-amine (Compound 2), 1-(piperazin-1-yl)-3-(trifluoromethoxy)propan-2-ol (Compound 31) (1.5 eq) and $NaHCO_3$ (2 eq) are added to a 1,4-dioxane solution and the reaction is carried out for 18-20 hours at 85-90° C. After completion of the reaction, the crude product is purified by column chromatography to afford 1-(4-(5-amino-6-chloro-1,2,4-triazin-3-yl)piperazin-1-yl)-3-(trifluoromethoxy)propan-2-ol (Compound 32).

Step-9: Preparation of 1-(4-(5-amino-6-(2,3-dichlorophenyl)-1,2,4-triazin-3-yl)piperazin-1-yl)-3-(trifluoromethoxy)propan-2-ol (Compound 27)

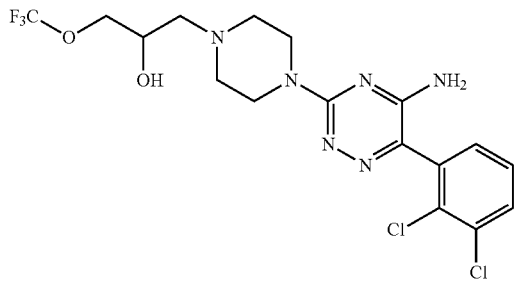 [SMILES: Nc1nc(N2CCN(CC(O)COC(F)(F)F)CC2)nnc1-c1cccc(Cl)c1Cl]

1-(4-(5-Amino-6-chloro-1,2,4-triazin-3-yl)piperazin-1-yl)-3-(trifluoromethoxy)propan-2-ol (Compound 32) is subjected to Suzuki coupling reaction with 2,3-dichlorophenyl boronic acid using $K_2HPO_4$ as base and $Pd(PPh_3)_4$ as catalyst in a dioxane/water medium at 85-90° C. The crude compound thus obtained is purified by column chromatography to afford 1-(4-(5-amino-6-(2,3-dichlorophenyl)-1,2,4-triazin-3-yl)piperazin-1-yl)-3-(trifluoromethoxy)propan-2-ol (Compound 27). The free base of the compound is subjected to 4M HCl in 2-propanol to obtain the HCl salt of Compound 27.

Example 8

Preparation of Compound 39

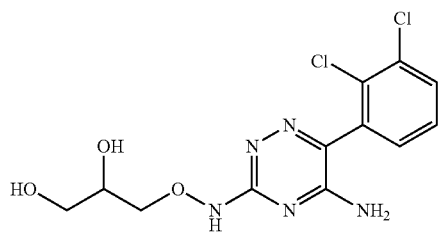 [SMILES: Nc1nc(NOCC(O)CO)nnc1-c1cccc(Cl)c1Cl]

3-(45-Amino-6-(2,3-dichlorophenyl)-1,2,4-triazin-3-yl)amino)oxy)propane-1,2-diol (Compound 39)

3-(((5-Amino-6-(2,3-dichlorophenyl)-1,2,4-triazin-3-yl)amino)oxy)propane-1,2-diol (Compound 39) is prepared in accordance with the following steps.

Step-1: Preparation of 2-(2,3-dihydroxypropoxy)isoindoline-1,3-dione (Compound 40)

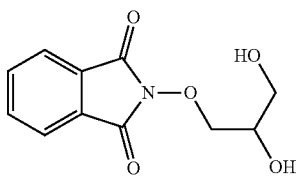 [SMILES: O=C1c2ccccc2C(=O)N1OCC(O)CO]

N-Hydroxy-phthalimide is reacted with 3-bromo-propane-1,2-diol in the presence of $K_2CO_3$ as base in DMF solvent, the crude compound is then purified by column chromatography to afford 2-(2,3-dihydroxypropoxy)isoindoline-1,3-dione (Compound 40).

Step-2: Preparation of 3-(aminooxy)propane-1,2-diol (Compound 41)

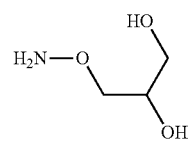

2-(2,3-Dihydroxypropoxy)isoindoline-1,3-dione (Compound 40) is subjected to hydrazine hydrate in ethanol and the reaction mixture is heated at reflux temperature for four hours. The crude compound is purified by column chromatography to afford 3-(aminooxy)propane-1,2-diol (Compound 41).

Step-3: Preparation of 3-(((5-amino-6-chloro-1,2,4-triazin-3-yl)amino)oxy)propane-1,2-diol (Compound 42)

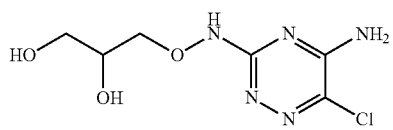 [SMILES: Nc1nc(NOCC(O)CO)nnc1Cl]

A solution of 3,6-dichloro-1,2,4-triazin-5-amine (Compound 2), 3-(aminooxy)propane-1,2-diol (Compound 41) (1.5 eq) and NaHCO$_3$ (2 eq) in 1,4-dioxane is stirred for 18-20 hours at 85-90° C. After completion of the reaction, the crude product is purified by column chromatography to afford 3-(((5-amino-6-chloro-1,2,4-triazin-3-yl)amino)oxy)propane-1,2-diol (Compound 42).

Step-4: Preparation of 3-(((5-amino-6-(2,3-dichlorophenyl)-1,2,4-triazin-3-yl)amino)oxy)propane-1,2-diol (Compound 39)

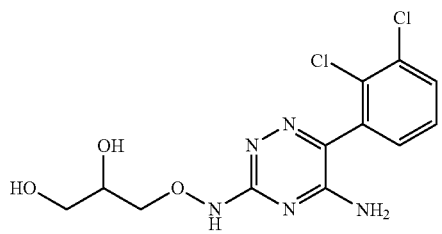 [SMILES: Nc1nc(NOCC(O)CO)nnc1-c1cccc(Cl)c1Cl]

3-(((5-Amino-6-chloro-1,2,4-triazin-3-yl)amino)oxy)propane-1,2-diol (Compound 42) is coupled to 2,3-dichlorophenyl boronic acid under Suzuki conditions, using K$_2$HPO$_4$ as base and Pd(PPh$_3$)$_4$ as catalyst in a dioxane/water medium at 85-90° C. The crude product is purified by column chromatography to afford 3-(45-amino-6-(2,3-dichlorophenyl)-1,2,4-triazin-3-yl)amino)oxy)propane-1,2-diol (Compound 39). The free base form of the compound is subjected to 4M HCl in 2-propanol to obtain the HCl salt of the compound (Compound 39).

Example 9

Preparation of Compound 43

4-((5-Amino-6-(2,3-dichlorophenyl)-1,2,4-triazin-3-yl)amino)-1-methoxybutan-2-ol (Compound 43)

4-((5-Amino-6-(2,3-dichlorophenyl)-1,2,4-triazin-3-yl)amino)-1-methoxybutan-2-ol (Compound 43) is prepared in accordance with the following steps.

Step-1: Preparation of 4-((5-amino-6-chloro-1,2,4-triazin-3-yl)amino)-1-methoxybutan-2-ol (Compound 44)

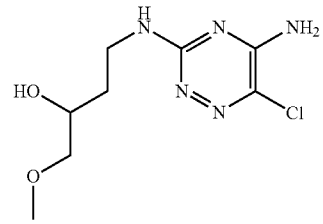

A mixture of 3,6-dichloro-1,2,4-triazin-5-amine (Compound 2), 4-amino-1-methoxybutan-2-ol (1.5 eq) and NaHCO$_3$ (2 eq) in 1,4-dioxane is stirred for 18-20 hours at 85-90° C. After completion of the reaction, the crude product is purified by column chromatography to afford 4-((5-amino-6-chloro-1,2,4-triazin-3-yl)amino)-1-methoxybutan-2-ol (Compound 44).

Step-2: Preparation of 4-((5-amino-6-(2,3-dichlorophenyl)-1,2,4-triazin-3-yl)amino)-1-methoxybutan-2-ol (Compound 43)

4-((5-Amino-6-chloro-1,2,4-triazin-3-yl)amino)-1-methoxybutan-2-ol (Compound 44) is coupled to 2,3-dichlorophenyl boronic acid under Suzuki conditions, using K$_2$HPO$_4$ as base and Pd(PPh$_3$)$_4$ as catalyst in a dioxane/water medium at 85-90° C. The crude product is purified by column chromatography to afford 4-((5-amino-6-(2,3-dichlorophenyl)-1,2,4-triazin-3-yl)amino)-1-methoxybutan-2-ol (Compound 43). The free base form of the compound is subjected to 4M HCl in 2-propanol to obtain the HCl salt of the compound (Compound 43).

Example 10

Preparation of Compound 45

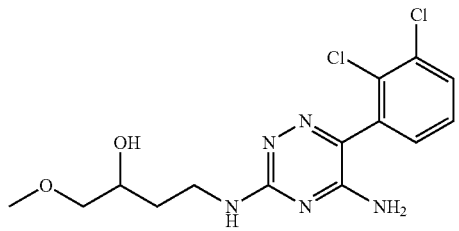 [SMILES: COCC(O)CCNc1nnc(-c2cccc(Cl)c2Cl)c(N)n1]

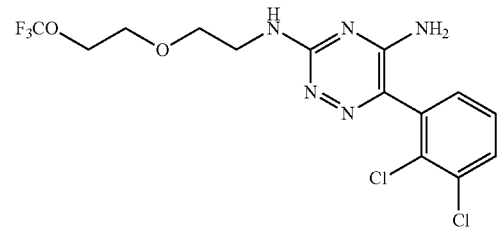 [SMILES: Nc1nc(NCCOCCOC(F)(F)F)nnc1-c1cccc(Cl)c1Cl]

6-(2,3-Dichlorophenyl)-N³-(2-(2-(trifluoromethoxy)ethoxy)ethyl)-1,2,4-triazine-3,5-diamine (Compound 45)

6-(2,3-Dichlorophenyl)-N³-(2-(2-(trifluoromethoxy)ethoxy)ethyl)-1,2,4-triazine-3,5-diamine (Compound 45) was prepared according to the following steps.

Step 1: Preparation of 6-chloro-N³-(2-(2-(trifluoromethoxy)ethoxy)ethyl)-1,2,4-triazine-3,5-diamine (Compound 46)

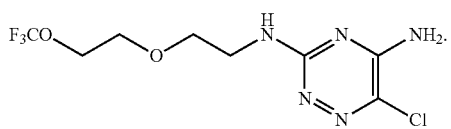 [SMILES: Nc1nc(NCCOCCOC(F)(F)F)nnc1Cl]

3,6-Dichloro-1,2,4-triazin-5-amine (Compound 2) (54.3 mg, 0.329 mmol) and 2-(2-(trifluoromethoxy)ethoxy)ethanamine (798 mg, 4.60 mmol) were added to a round bottom flask, containing 8 mL of 1,4-dioxane. Sodium bicarbonate (414 mg, 4.93 mmol) was added to the above reaction mixture and the mixture was degassed for 10-15 minutes. The reaction mixture was stirred under heating at 80-85° C. for 8-10 hours. After completion of the reaction, the mixture was allowed to attain room temp (20-25° C.) and was thereafter filtered to remove salts. The filtrate was concentrated under vacuum and the crude thus obtained was purified by column chromatography (using dichloromethane/methanol as eluant) to give 6-chloro-N³-(2-(2-(trifluoromethoxy)ethoxy)ethyl)-1,2,4-triazine-3,5-diamine (Compound 46) (540 mg, 54% yield).

Step 2: Preparation of 6-(2,3-dichlorophenyl)-N³-(2-(2-(trifluoromethoxy)ethoxy)ethyl)-1,2,4-triazine-3,5-diamine (Compound 45)

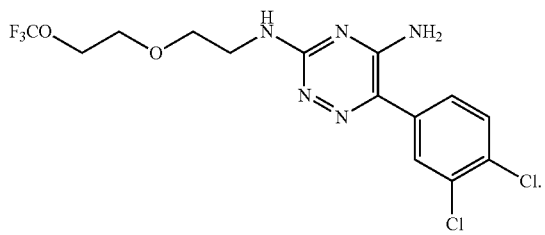 [SMILES: Nc1nc(NCCOCCOC(F)(F)F)nnc1-c1ccc(Cl)c(Cl)c1]

6-Chloro-N³-(2-(2-(trifluoromethoxy)ethoxy)ethyl)-1,2,4-triazine-3,5-diamine (Compound 46) (200 mg, 0.66 mmol) and (2,3-dichlorophenyl)boronic acid (253 mg, 1.32 mmol) were dissolved in 12 mL of 1,4-dioxane. Tetrakis(triphenylphosphine)palladium (0) (77 mg, 0.066 mmol), dipotassium phosphate (230 mg, 1.32 mmol) and 3 ml of water were added to the above reaction mixture and degassed for 10-15 minutes. The reaction mixture was stirred under heating at 85-90° C. for 4-6 hours (maintaining nitrogen atmosphere all through). After completion of the reaction, the reaction mass was allowed to attain room temperature, and then filtered through a celite bed. The filtrate was concentrated under vacuum to remove the organic solvent. To the crude remaining, 10 mL of water was added and the product was extracted into dichloromethane (3×10 mL). The dichloromethane solution was concentrated and the crude thus obtained was purified by column chromatography (using dichloromethane/methanol eluent) to give 6-(2,3-dichlorophenyl)-N³-(2-(2-(trifluoromethoxy)ethoxy)ethyl)-1,2,4-triazine-3,5-diamine (Compound 45). (41 mg, 15% yield). $^1$H NMR (500 MHz, CDCl$_3$): δ 7.85 (m, 1H), 7.45 (m, 1H), 7.35 (m, 1H), 4.21 (m, 2H), 3.73 (m, 2H), 3.58 (m 2H), 3.48 (m, 2H); $^{19}$F NMR: δ−58.806 (s, OCF$_3$); MS (ESI) for C$_{14}$H$_{14}$Cl$_2$F$_3$N$_5$O$_2$: 412.06 (M$^+$). The free base was dissolved in 4M hydrochloride in 2-propanol (2 mL) and was stirred for one hour. The mixture was concentrated and product was precipitated by addition of methyl tert-butylether. The obtained solid was filtered and dried to afford an off-white product as the hydrochloride salt (40 mg). $^1$H NMR (500 MHz, DMSO-d$_6$+D$_2$O): δ 7.72 (m, 1H), 7.60-7.45 (m, 2H), 4.18 (m, 2H), 3.76 (m, 2H), 3.65 (m 2H), 3.55 (m, 2H); $^{19}$F NMR: δ−58.828 (s, OCF$_3$).

Example 11

Sodium Channel Blockage of Test Compounds

The potency of test compounds (e.g., compounds prepared in accordance with Examples 1-9 and 13-25) to block Na+ channels is measured electrophysiologically using isolated rat dorsal root ganglion cells in vitro. Currents are measured using the whole-cell variant of the patch clamp method. I$_{Na}$ is elicited by a pulse to −20 mV from a holding potential of −120 mV or −70 mV to measure blockade at the inactivated state (pulse duration of 40 ms), Peak inward current is measured for I$_{Na}$. Pacing rates of 0.1, 3 and Hz are examined. Increasing concentrations of test compounds are added to the cells in a cumulative manner to generate a concentration-response relationship which is utilized to calculate the IC$_{50}$.

Example 12

Neuropathic Pain Model

The efficacy of test compounds (e.g., compounds prepared in accordance with Examples 1-9 and 13-25) in reducing mechanical allodynia is assessed in the chronic constriction injury model in rats. Male SD rats are briefly anesthetized under pentobarbital anesthesia and surgery is performed following the Bennett model of sciatic nerve ligation where the left sciatic nerve is loosely ligated with four chromic gut sutures. 7-14 days post-surgery, rats that are clearly allodynic were randomized to treatment groups (n−10 rats/group). Mechanical allodynia is evaluated using the von Frey up-down method, 30 minutes before and at 1 and 2 hr after a single dose of test dose or Gabapentin. Aminobenzotriazole (100 mg/kg p.o.) is dosed orally 16-24 hours prior to treatment with test compounds.

Example 13

Preparation of Compound 47

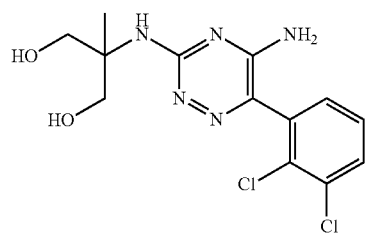 [SMILES: CC(CO)(CO)Nc1nnc(-c2cccc(Cl)c2Cl)c(N)n1]

2-((5-Amino-6-(2,3-dichlorophenyl)-1,2,4-triazin-3-yl)amino)-2-methylpropane-1,3-diol (Compound 47)

2-((5-Amino-6-(2,3-dichlorophenyl)-1,2,4-triazin-3-yl)amino)-2-methylpropane-1,3-diol (Compound 47) was prepared according to the following steps.

Step 1: Preparation of 2-((5-amino-6-chloro-1,2,4-triazin-3-yl)amino)-2-methylpropane-1,3-diol (Compound 48)

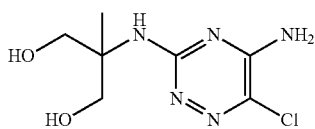

3,6-Dichloro-1,2,4-triazin-5-amine (2.00 g, 12.12 mmol) and 2-amino-2-methylpropane-1,3-diol (1.53 g, 14.55 mmol), Dioxane (30 mL) and sodium bicarbonate (2.04 g, 24.25 mmol) were added to a round bottom flask. Nitrogen gas was purged into the reaction mixture for 10-15 minutes and the reaction mass was heated under stirring at 120-125° C. for 20 hours. After completion of the reaction, the reaction mass was cooled to room temperature and filtered to remove salts. The filtrate dioxane solution was concentrated under vacuum to obtain the crude, which was purified by column chromatography (using DCM/Methanol as eluent) to give 2-((5-amino-6-chloro-1,2,4-triazin-3-yl)amino)-2-methylpropane-1,3-diol (Compound 48) (0.80 g, 28.20% yield).

Step 2: Preparation of 2-((5-amino-6-(2,3-dichlorophenyl)-1,2,4-triazin-3-yl)amino)-2-methylpropane-1,3-diol (Compound 47)

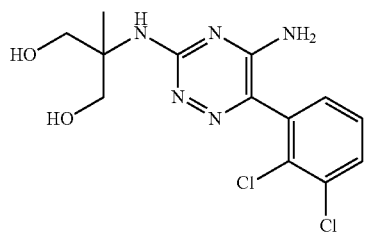 [SMILES: CC(CO)(CO)Nc1nnc(-c2cccc(Cl)c2Cl)c(N)n1]

2-((5-Amino-6-chloro-1,2,4-triazin-3-yl)amino)-2-methylpropane-1,3-diol (Compound 48) (0.80 g, 3.42 mmol) and (2,3-dichlorophenyl)boronic acid (1.11 g, 5.82 mmol) were dissolved in 16 mL of 1,4-dioxane. Pd(PPh$_3$)$_4$ (0.396 g, 0.342 mmol), K$_2$HPO$_4$ (1.193 g, 6.85 mmol) and 10 mL of DI water were added to the above reaction mixture. The reaction mixture was degassed for 10-15 minutes and then stirred 90° C. for 4-6 hours. After completion of the reaction, the reaction mass was allowed to attain room temperature. The cooled reaction mass was filtered through a celite bed and the filtrate was concentrated under vacuum. To the crude thus obtained, 20 mL of water was added and the product was extracted into DCM (3×20 mL). The DCM solution was concentrated, dried and the crude product was purified by column chromatography to give 2-((5-amino-6-(2,3-dichlorophenyl)-1,2,4-triazin-3-yl)amino)-2-methylpropane-1,3-diol (Compound 47) (0.50 g, 42.4% yield). The free base (130 mg) was dissolved in 4M hydrochloride in 2-propanol and stirred for one hour. The mixture was concentrated to afford a pale yellow solid as the hydrochloride salt (140 mg). $^1$H NMR (500 MHz, DMSO-d$_6$+D$_2$O): δ 7.85 (d, 1H), 7.60-7.50 (m, 2H), 3.55-3.65 (br s, 4H), 1.35-1.40 (s, 3H); MS (ESI) for C$_{13}$H$_{15}$Cl$_2$N$_5$O$_2$: 344.05 (MH$^+$).

Example 14

Preparation of Compound 49

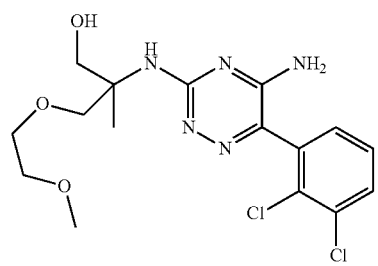 [SMILES: COCCOCC(C)(CO)Nc1nnc(-c2cccc(Cl)c2Cl)c(N)n1]

2-((5-Amino-6-(2,3-dichlorophenyl)-1,2,4-triazin-3-yl)amino)-3-(2-methoxyethoxy)-2-methylpropan-1-ol (Compound 49)

2-((5-Amino-6-(2,3-dichlorophenyl)-1,2,4-triazin-3-yl)amino)-3-(2-methoxyethoxy)-2-methylpropan-1-ol (Compound 49) was prepared according to the following steps.

Step 1: Preparation 2-((5-amino-6-chloro-1,2,4-triazin-3-yl)amino)-3-(2-methoxyethoxy)-2-methylpropan-1-ol (Compound 50)

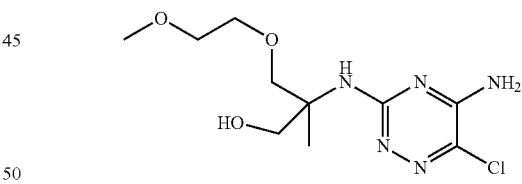

3,6-Dichloro-1,2,4-triazin-5-amine (0.50 g, 3.03 mmol) and 2-amino-3-(2-methoxyethoxy)-2-methylpropan-1-ol (0.72 g, 4.39 mmol), N,N-diisopropylethylamine (1.96 g, 15.15 mmol) and 5 mL of DMSO were added to round bottom flask. The resulting reaction mixture was stirred under heating at 125° C. for 20 hours. At the end of reaction time, the reaction mixture was allowed to attain room temperature and 10 mL water was added to it. The product was extracted using DCM (3×20 mL). The crude product obtained upon evaporation of DCM was purified by column chromatography (using DCM/Methanol as eluent) affording 2-((5-amino-6-chloro-1,2,4-triazin-3-yl)amino)-3-(2-methoxyethoxy)-2-methylpropan-1-ol (Compound 50) (0.35 g, 39.60% yield).

Step 2: Preparation of 2-((5-amino-6-(2,3-dichlorophenyl)-1,2,4-triazin-3-yl)amino)-3-(2-methoxyethoxy)-2-methylpropan-1-ol (Compound 49)

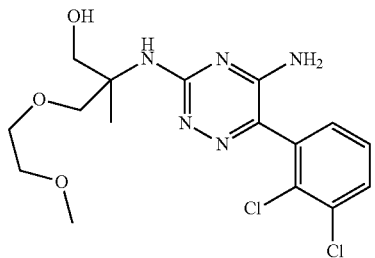 [SMILES: COCCOCC(C)(CO)Nc1nnc(-c2cccc(Cl)c2Cl)c(N)n1]

2-((5-Amino-6-chloro-1,2,4-triazin-3-yl)amino)-3-(2-methoxyethoxy)-2-methylpropan-1-ol (Compound 50) (0.35 g, 1.20 mmol) and (2,3-dichlorophenyl)boronic acid (0.389 g, 2.04 mmol) were dissolved in 10 mL of 1,4-dioxane. Pd(PPh$_3$)$_4$ (0.139 g, 0.12 mmol), K$_2$HPO$_4$ (0.418 g, 2.399 mmol) and 5 mL of DI were added to the above reaction mixture. The reaction mixture was degassed for 10-15 minutes and then stirred under heating (at 85-90° C.) for 4 hours. After completion of the reaction, reaction mass was allowed to cool to room temperature. The reaction mixture was filtered through a celite bed and concentrated under vacuum. To the residue, 20 mL of water was added and the product was extracted into DCM (3×20 mL). The DCM solution was concentrated and the crude thus obtained was purified by column chromatography to give 2-((5-amino-6-(2,3-dichlorophenyl)-1,2,4-triazin-3-yl)amino)-3-(2-methoxyethoxy)-2-methylpropan-1-ol (Compound 3) (0.140 g, 29% yield). $^1$H NMR (500 MHz, DMSO-d$_6$): δ 7.70 (d, 1H), 7.45 (m, 1H), 7.35 (d, 1H), 6.15-7.30 (br s, 2H), 5.90-6.00 (s, 1H), 5.05-5.20 (s, 1H), 3.65-3.75 (d, 1H), 3.80-3.40 (m, 8H), 3.20-3.30 (s, 3H), 1.30-1.35 (s, 3H); MS (ESI) for C$_{16}$H$_{21}$Cl$_2$N$_5$O$_3$: 402.08 (MH$^+$). The free base was dissolved in 4M hydrochloride in 2-propanol and stirred for one hour. The mixture was concentrated to afford pale yellow solid as hydrochloride salt (65 mg).

Example 15

Preparation of Compound 51

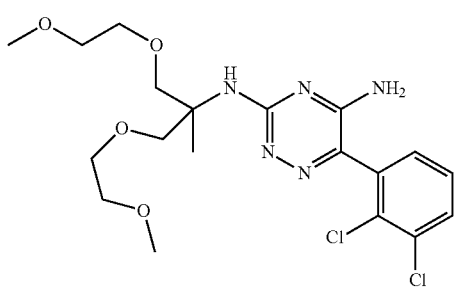 [SMILES: COCCOCC(C)(COCCOC)Nc1nnc(-c2cccc(Cl)c2Cl)c(N)n1]

6-(2,3-Dichlorophenyl)-N3-(7-methyl-2,5,9,12-tetraoxatridecan-7-yl)-1,2,4-triazine-3,5-diamine (Compound 51)

6-(2,3-Dichlorophenyl)-N$^3$-(7-methyl-2,5,9,12-tetraoxatridecan-7-yl)-1,2,4-triazine-3,5-diamine (Compound 51) was prepared according to the following steps.

Step 1: Preparation of 6-chloro-N$^3$-(7-methyl-2,5,9,12-tetraoxatridecan-7-yl)-1,2,4-triazine-3,5-diamine (Compound 52)

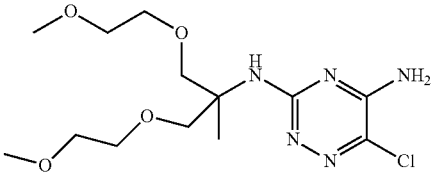 [SMILES: COCCOCC(C)(COCCOC)Nc1nnc(Cl)c(N)n1]

3,6-Dichloro-1,2,4-triazin-5-amine (0.50 g, 3.03 mmol) and 7-methyl-2,5,9,12-tetraoxatridecan-7-amine (0.805 g, 3.64 mmol), N,N-diisopropylethylamine (1.958 g, 15.15 mmol) and 5 mL of DMSO were added to round bottom flask. The resulting reaction mixture was stirred under heating at 125° C. for 20 hours. After completion of the reaction, the reaction mixture was cooled to room temperature and 20 mL water was added to it. The product was extracted using DCM (3×20 mL). The crude product obtained upon evaporation of DCM was purified by column chromatography (using DCM/Methanol as eluent) affording 6-chloro-N$^3$-(7-methyl-2,5,9,12-tetraoxatridecan-7-yl)-1,2,4-triazine-3,5-diamine (Compound 52) (0.5 g, 47.2% yield).

Step 2: Preparation of 6-(2,3-dichlorophenyl)-N$^3$-(7-methyl-2,5,9,12-tetraoxatridecan-7-yl)-1,2,4-triazine-3,5-diamine (Compound 51)

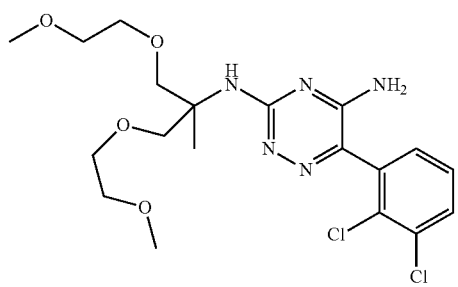 [SMILES: COCCOCC(C)(COCCOC)Nc1nnc(-c2cccc(Cl)c2Cl)c(N)n1]

6-Chloro-N3-(7-methyl-2,5,9,12-tetraoxatridecan-7-yl)-1,2,4-triazine-3,5-diamine (Compound 52) (0.5 g, 1.429 mmol) and (2,3-dichlorophenyl)boronic acid (0.464 g, 2.43 mmol) were dissolved in 10 mL of 1,4-dioxane. Pd(PPh$_3$)$_4$ (0.083 g, 0.071 mmol), K$_2$HPO$_4$ (0.498 g, 2.86 mmol) and 5 mL of DI water were added to the above reaction mixture. The reaction mixture was degassed for 10-15 minutes and then stirred under heating (at 85-90° C.) for 4 hours. After completion of the reaction, the reaction mass was allowed to attain room temperature. The reaction mixture was filtered through a celite bed and the filtrate was concentrated under vacuum. To the residue 20 mL of water was added and the product extracted into DCM (3×20 mL). The DCM solution was concentrated and the crude upon purification by column chromatography (using DCM/Methanol as eluent) yielded 6-(2,3-dichlorophenyl)-N³-(7-methyl-2,5,9,12-tetraoxatridecan-7-yl)-1,2,4-triazine-3,5-diamine (Compound 51) (0.140 g, 21.28% yield). ¹H NMR (500 MHz, CDCl₃): δ 7.50-7.60 (d, 1H), 7.30-7.40 (m, 2H), 5.65-5.85 (br s, 1H), 4.90-4.60 (s, 2H), 3.85-3.90 (m, 2H), 3.80-3.50 (m, 10H), 3.45-3.30 (s, 6H), 1.40-1.30 (s, 3H); MS (ESI) for $C_{19}H_{27}Cl_2N_5O_4$: 460.16 (MH⁺). The free base was dissolved in 4M hydrochloride in 2-propanol and stirred for one hour. The mixture was concentrated to afford pale yellow solid as hydrochloride salt (35 mg).

Example 16

Preparation of Compound 53

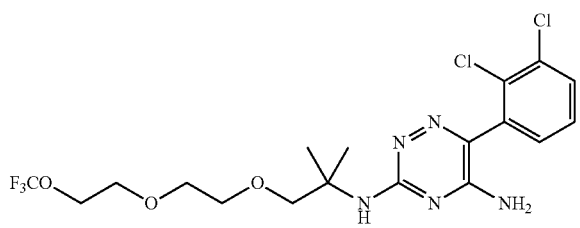 [SMILES: CC(C)(COCCOCCOC(F)(F)F)Nc1nnc(-c2cccc(Cl)c2Cl)c(N)n1]

6-(2,3-Dichlorophenyl)-N3-(2-methyl-1-(2-(2-(trifluoromethoxy)ethoxy)ethoxy)propan-2-yl)-1,2,4-triazine-3,5-diamine (Compound 53)

6-(2,3-Dichlorophenyl)-N³-(2-methyl-1-(2-(2-(trifluoromethoxy)ethoxy)ethoxy)propan-2-yl)-1,2,4-triazine-3,5-diamine (Compound 53) was prepared according to the following steps.

Step 1: Preparation of 6-chloro-N³-(2-methyl-1-(2-(2-(trifluoromethoxy)ethoxy)ethoxy)propan-2-yl)-1,2,4-triazine-3,5-diamine (Compound 54)

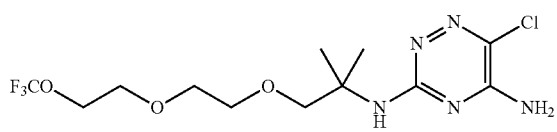 [SMILES: CC(C)(COCCOCCOC(F)(F)F)Nc1nnc(Cl)c(N)n1]

3,6-Dichloro-1,2,4-triazin-5-amine (70 mg 0.424 mmol) and 2-methyl-1-(2-(2-(trifluoromethoxy)ethoxy)ethoxy)propan-2-amine (500 mg, 2.039 mol), N,N-diisopropylethylamine (5 mL) and 2 mL of 1,4-dioxane were added to a round bottom flask. The reaction mixture was degassed for 10-15 minutes and stirred under heating at 80° C. for 3 days. After completion of the reaction, the reaction mass was allowed to cool to room temperature (25° C.). The reaction mass was concentrated under vacuum, and the crude compound upon purification by column chromatography yielded 6-chloro-N³-(2-methyl-1-(2-(2-(trifluoromethoxy)ethoxy)ethoxy)propan-2-yl)-1,2,4-triazine-3,5-diamine (Compound 54). (130 mg, 81% yield).

Step 2: Preparation of 6-(2,3-dichlorophenyl)-N³-(2-methyl-1-(2-(2-(trifluoromethoxy)ethoxy)ethoxy)propan-2-yl)-1,2,4-triazine-3,5-diamine (Compound 53)

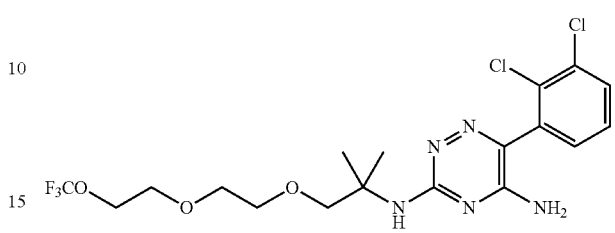

6-Chloro-N³-(2-methyl-1-(2-(2-(trifluoromethoxy)ethoxy) ethoxy) propan-2-yl)-1,2,4-triazine-3,5-diamine (Compound 54) (240 mg, 0.642 mmol) and (2,3-dichlorophenyl)boronic acid (208 mg, 1.092 mmol) were dissolved in 8 mL of 1,4-dioxane. Pd(PPh₃)₄ (37 mg, 0.0328 mmol), K₂HPO₄ (246 mg, 1.413 mmol) and 4 mL of DI water were added to the above reaction mixture. The reaction mixture was degassed for 10-15 minutes and then stirred under heating (at 85-90° C.) for 4 hours. After completion of the reaction, the reaction mass was cooled to room temperature and was filtered through a celite bed. The filtrate was concentrated under vacuum, and to the residue 20 mL of water was added and the product was extracted into DCM (3×20 mL). The DCM solution was concentrated and the crude upon purification by column chromatography (using MTBE/Hexane as eluent) yielded 6-(2,3-dichlorophenyl)-N³-(2-methyl-1-(2-(2-(trifluoromethoxy)ethoxy)ethoxy) propan-2-yl)-1,2,4-triazine-3,5-diamine (Compound 53) (45 mg, 14.4% yield). The free base was dissolved in 4M hydrochloride in 2-propanol and stirred for one hour. The mixture was concentrated to afford a pale brown solid as the hydrochloride salt (50 mg). ¹H NMR (500 MHz, CDCl₃+ D₂O): δ 7.60 (d, 1H), 7.40-7.30 (m, 2H), 4.10 (m, 2H), 3.80 (m, 2H), 3.70 (m, 4H), 3.60 (s, 2H), and 1.60-1.50 (s, 6H). MS (ESI) for $C_{18}H_{22}Cl_2F_3N_5O_3$: 484.12 (MH⁺).

Example 17

Preparation of Compound 55

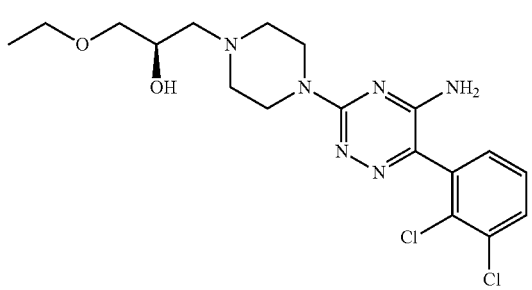 [SMILES: CCOC[C@H](O)CN1CCN(c2nnc(-c3cccc(Cl)c3Cl)c(N)n2)CC1]

(R)-1-(4-(5-Amino-6-(2,3-dichlorophenyl)-1,2,4-triazin-3-yl)piperazin-1-yl)-3-ethoxypropan-2-ol (Compound 55)

(R)-1-(4-(5-amino-6-(2,3-dichlorophenyl)-1,2,4-triazin-3-yl)piperazin-1-yl)-3-ethoxypropan-2-ol (Compound 55) was prepared according to the following steps.

Step 1: Preparation of (R)-1-(4-(5-amino-6-chloro-1,2,4-triazin-3-yl)piperazin-1-yl)-3-ethoxypropan-2-ol (Compound 56)

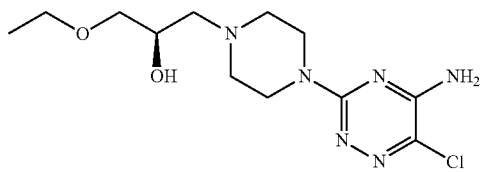 [SMILES: CCOC[C@H](O)CN1CCN(c2nnc(Cl)c(N)n2)CC1]

3,6-Dichloro-1,2,4-triazin-5-amine ((1000 mg, 6.13 mmol) and (R)-1-ethoxy-3-(piperazin-1-yl)propan-2-ol (1500 mg, 7.973 mol), 1,4-dioxane (20 mL) and sodium bicarbonate (1000 mg 12.16 mmol) were added to a round bottom flask. Nitrogen gas was purged into the reaction mixture for 10-15 minutes, following which the reaction mass was stirred at 80-85° C. for 8 hours (under an inert atmosphere). After completion of the reaction, the reaction mass was allowed to come to room temperature and it was filtered to remove salts. The filtrate was concentrated under vacuum and MTBE (10 mL) was added to residue with stirring for 30 minutes, which afforded a solid product. Upon filtering and drying, the obtained product was (R)-1-(4-(5-amino-6-chloro-1,2,4-triazin-3-yl)piperazin-1-yl)-3-ethoxypropan-2-ol (Compound 56) (1300 mg, 67% yield).

Step 2: Preparation of (R)-1-(4-(5-amino-6-(2,3-dichlorophenyl)-1,2,4-triazin-3-yl)piperazin-1-yl)-3-ethoxy propan-2-ol (Compound 55)

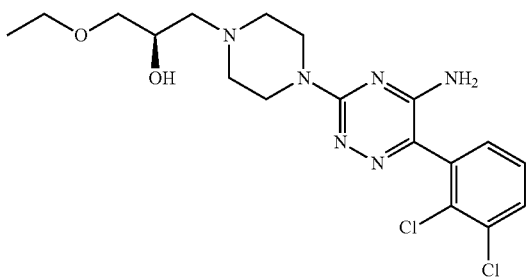 [SMILES: CCOC[C@H](O)CN1CCN(c2nnc(-c3cccc(Cl)c3Cl)c(N)n2)CC1]

(R)-1-(4-(5-Amino-6-chloro-1,2,4-triazin-3-yl)piperazin-1-yl)-3-ethoxy propan-2-ol (Compound 56) (600 mg, 1.894 mmol) and (2,3-dichlorophenyl)boronic acid (976 mg, 5.11 mmol) were dissolved in 10 mL of 1,4-dioxane. Pd(PPh$_3$)$_4$ (109 mg, 0.095 mmol), K$_2$HPO$_4$ (726 mg, 1.14 mmol) and 4 mL of DI water were added to the above reaction mixture. The reaction mixture was degassed for 10-15 minutes and then stirred under heating (at 85-90° C.) for 4 hours. After completion of the reaction, the reaction mass was cooled to room temperature and filtered through a celite bed. The filtrate was concentrated under vacuum whereupon 20 mL of water was then added to the residue. The product was extracted into DCM (3×20 mL). The DCM solution was concentrated and the crude compound upon purification by column chromatography (using DCM/methanol as eluent) yielded (R)-1-(4-(5-amino-6-(2,3-dichlorophenyl)-1,2,4-triazin-3-yl)piperazin-1-yl)-3-ethoxypropan-2-ol (Compound 55) (250 mg, 30.9% yeild). $^1$H NMR (500 MHz, CDCl$_3$): δ 7.60 (d, 1H), 7.45-7.30 (m, 2H), 4.70 (br s, 2H) 4.0-3.8 (m, 5H), 3.60-3.40 (m, 4H), 2.80-2.70 (m, 2H), 2.60-2.45 (m, 2H), 2.30 (m, 1H) and 1.30-1.20 (t, 3H). MS (ESI) for C$_{18}$H$_{22}$Cl$_2$F$_3$N$_5$O$_3$: 427.12 (MH$^+$). The free base was dissolved in 4M hydrochloride in 2-propanol and stirred for one hour. The mixture was concentrated to afford off white solid as hydrochloride salt (250 mg).

Example 18

Preparation of Compound 57

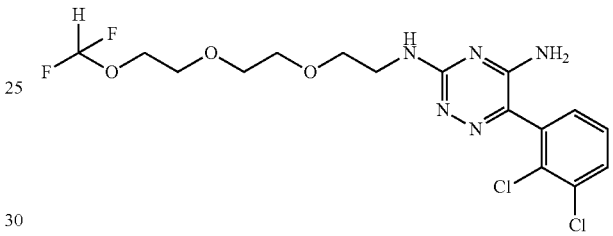

6-(2,3-Dichlorophenyl)-N$^3$-(2-(2-(2-(difluoromethoxy)ethoxy)ethoxy)ethyl)-1,2,4-triazine-3,5-diamine (Compound 57)

6-(2,3-Dichlorophenyl)-N$^3$-(2-(2-(2-(difluoromethoxy)ethoxy)ethoxy)ethyl)-1,2,4-triazine-3,5-diamine (Compound 57) was prepared according to the following steps.

Step 1: Preparation of 6-chloro-N$^3$-(2-(2-(2-(difluoromethoxy)ethoxy)ethoxy)ethyl)-1,2,4-triazine-3,5-diamine (Compound 58)

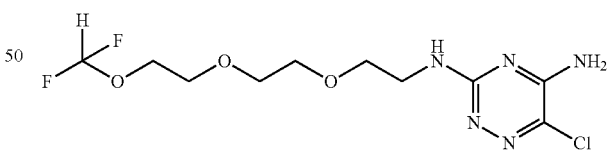

To a solution of 2-(2-(2-(difluoromethoxy)ethoxy)ethoxy) ethanamine (720 mg, 3.6 mmol) in 1,4-dioxane (10 mL) was added 5-amino-3,6-dichloro-triazine (500 mg, 3.0 mmol). The reaction mixture was then charged with sodium bicarbonate (500 mg, 6.0 mmol). The reaction mixture was stirred at 90° C. for 8 hours. Ethyl acetate (10 mL) was added into the reaction mixture. The suspension was passed through a celite bed and the filtrate was evaporated to obtain the crude product. The crude upon purification by flash chromatography yielded 6-chloro-N$^3$-(2-(2-(2-(difluoromethoxy)ethoxy) ethoxy)ethyl)-1,2,4-triazine-3,5-diamine (Compound 58) (0.7 g, 70% yield).

Step 2: Preparation of 6-(2,3-dichlorophenyl)-N³-(2-(2-(2-(difluoromethoxy)ethoxy)ethoxy)ethyl)-1,2,4-triazine-3,5-diamine (Compound 57)

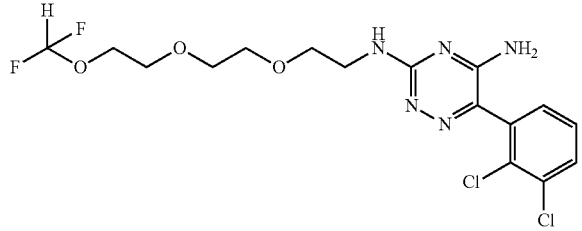 [SMILES: Nc1nc(NCCOCCOCCOC(F)F)nnc1-c1cccc(Cl)c1Cl]

A suspension of 6-chloro-N³-(2-(2-(2-(difluoromethoxy)ethoxy)ethoxy)ethyl)-1,2,4-triazine-3,5-diamine (Compound 58) (700 mg, 2.1 mmol), (2,3-dichlorophenyl)boronic acid (690 mg, 3.6 mmmol), and K₂HPO₄ (820 mg, 4.7 mmol) in 1,4-dioxane: water (2:1, 15 mL) was purged with nitrogen gas for 15 minutes. The reaction mixture was charged with Pd(PPh₃)₄ (250 mg, 0.21 mmol) and heated to 90° C. for 3 hours. Ethyl acetate (10 mL) was added into the reaction mixture. The suspension was passed through a celite bed and the filtrate was concentrated under vacuum. The crude upon purification by flash chromatography yielded 6-(2,3-dichlorophenyl)-N³-(2-(2-(2-(difluoromethoxy)ethoxy)ethoxy)ethyl)-1,2,4-triazine-3,5-diamine (Compound 57) (150 mg, 17% yield). ¹H NMR (500 MHz, CDCl₃): δ 7.57 (dd, 1H), 7.36 (dd, 1H), 7.32-7.35 (m, 1H), 6.24 (t, 1H), 6.21 (bs, 1H), 4.94 (bs, 2H), 4.00 (t, 2H), 3.68-3.72 (m, 10H). 19F NMR (CDCl₃): -82.3 ppm. MS (ESI) for $C_{16}H_{19}Cl_2F_2N_5O_3$: 438 (MH⁺). The free base (150 mg) was dissolved in 2 mL of 4N hydrochloride in 2-propanol. The mixture was concentrated to afford product as hydrochloride salt.

Example 19

Preparation of Compound 59

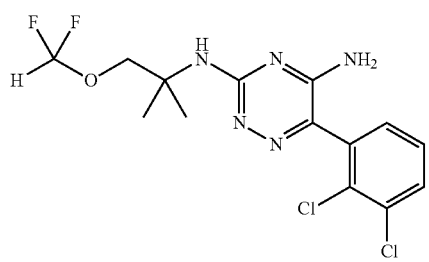 [SMILES: CC(C)(COC(F)F)Nc1nnc(-c2cccc(Cl)c2Cl)c(N)n1]

6-(2,3-Dichlorophenyl)-N³-(1-(difluoromethoxy)-2-methylpropan-2-yl)-1,2,4-triazine-3,5-diamine (Compound 59)

6-(2,3-Dichlorophenyl)-N³-(1-(difluoromethoxy)-2-methylpropan-2-yl)-1,2,4-triazine-3,5-diamine (Compound 59) was prepared according to the following steps.

Step-1: Preparation of 6-chloro-N³-(1-(difluoromethoxy)-2-methylpropan-2-yl)-1,2,4-triazine-3,5-diamine (Compound 60)

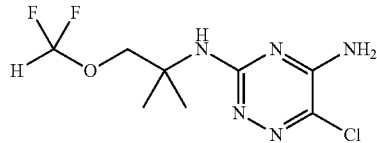 [SMILES: CC(C)(COC(F)F)Nc1nnc(Cl)c(N)n1]

To a solution of 1-(difluoromethoxy)-2-methylpropan-2-amine (400 mg, 2.8 mmol) in DMSO (10 mL) was added 5-amino-3,6-dichloro-triazine (120 mg, 0.7 mmol). The reaction mixture was then charged with DIPEA (0.6 mL, 3.6 mmol) and was stirred at 120° C. for 18 hours. After completion of the reaction, the reaction mixture was concentrated. The crude thus obtained was dissolved in 10 mL of ethyl acetate and was washed sequentially with water (2×50 mL) and brine (30 mL). The ethyl acetate layer was dried over sodium sulfate and concentrated to afford 6-chloro-N³-(1-(difluoromethoxy)-2-methylpropan-2-yl)-1,2,4-triazine-3,5-diamine (Compound 60) (200 mg, 99% yield).

Step 2: Preparation of 6-(2,3-dichlorophenyl)-N³-(1-(difluoromethoxy)-2-methylpropan-2-yl)-1,2,4-triazine-3,5-diamine (Compound 59)

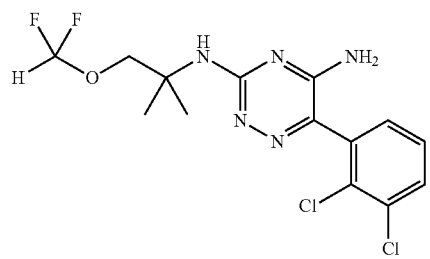 [SMILES: CC(C)(COC(F)F)Nc1nnc(-c2cccc(Cl)c2Cl)c(N)n1]

A suspension of 6-chloro-N³-(1-(difluoromethoxy)-2-methylpropan-2-yl)-1,2,4-triazine-3,5-diamine (Compound 60) (700 mg, 2.1 mmol), (2,3-dichlorophenyl)boronic acid (690 mg, 3.6 mmol), and K₂HPO₄ (820 mg, 4.7 mmol) in 1,4-dioxane:water (2:1, 15 mL) was purged with nitrogen gas for 15 minutes. The reaction mixture was charged with Pd(PPh₃)₄ (250 mg, 0.21 mmol) and heated to 90° C. for 3 hours. After completion of the reaction, 10 mL of ethyl acetate was added into the reaction mixture and it was filtered through a celite bed. The crude obtained, upon evaporation of the solvent, was purified by flash chromatography affording 6-(2,3-dichlorophenyl)-N3-(2-(2-(2-(difluoromethoxy)ethoxy)ethoxy)ethyl)-1,2,4-triazine-3,5-diamine (Compound 59) (150 mg, 17% yield). ¹H NMR (500 MHz, CDCl₃): δ 7.57 (dd, 1H), 7.37 (dd, 1H), 7.33-7.38 (m, 1H), 6.24 (t, 1H), 6.09 (bs, 1H), 4.85 (bs, 2H), 4.14 (s, 2H), 1.49 (s, 6H). ¹⁹F NMR (CDCl₃): -82.4 ppm. MS (ESI) for $C_{14}H_{15}Cl_2F_2N_5O$: 378 (MH⁺). The free base (150 mg) was dissolved in 2 mL of 4N hydrochloride in 2-propanol. The mixture was concentrated to afford product as hydrochloride salt.

Example 20

Preparation of Compound 61

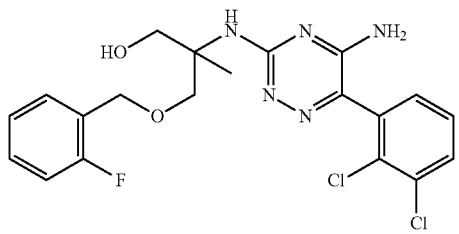 [SMILES: CC(CO)(COCc1ccccc1F)Nc1nnc(-c2cccc(Cl)c2Cl)c(N)n1]

2-((5-Amino-6-(2,3-dichlorophenyl)-1,2,4-triazin-3-yl)amino)-3-((2-fluorobenzyl)oxy)-2-methylpropan-1-ol (Compound 61)

2-((5-Amino-6-(2,3-dichlorophenyl)-1,2,4-triazin-3-yl)amino)-3-((2-fluorobenzyl)oxy)-2-methylpropan-1-ol (compound 61) was prepared according to the following steps.

Step 1: Preparation of 2-((5-amino-6-chloro-1,2,4-triazin-3-yl)amino)-3-((2-fluorobenzyl)oxy)-2-methylpropan-1-ol (Compound 62)

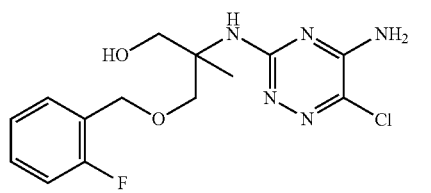 [SMILES: CC(CO)(COCc1ccccc1F)Nc1nnc(Cl)c(N)n1]

To a solution of 2-amino-3-((2-fluorobenzyl)oxy)-2-methylpropan-1-ol (510 mg, 2.4 mmol) in DMSO (2 mL) was added 5-amino-3,6-dichloro-triazine (200 mg, 1.2 mmol). The reaction mixture was then charged with DIPEA (1 mL, 6.0 mmol) and was stirred at 120° C. for 18 hours. The reaction mixture was concentrated and the crude upon purification by flash chromatography yielded 2-((5-amino-6-chloro-1,2,4-triazin-3-yl)amino)-3-((2-fluorobenzyl)oxy)-2-methylpropan-1-ol (Compound 62) (0.2 g, 48% yield).

Step 2: Preparation of 2-((5-amino-6-(2,3-dichlorophenyl)-1,2,4-triazin-3-yl)amino)-3-((2-fluorobenzyl)oxy)-2-methylpropan-1-ol (compound 61)

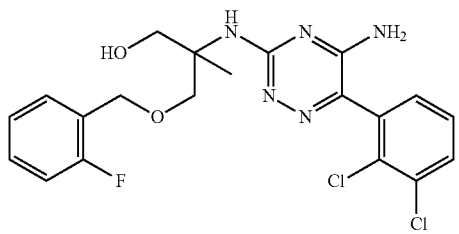 [SMILES: CC(CO)(COCc1ccccc1F)Nc1nnc(-c2cccc(Cl)c2Cl)c(N)n1]

A suspension of 2-((5-amino-6-chloro-1,2,4-triazin-3-yl)amino)-3-((2-fluorobenzyl)oxy)-2-methylpropan-1-ol (Compound 62) (200 mg, 0.5 mmol), (2,3-dichlorophenyl)boronic acid (190 mg, 1.0 mmol), and cesium carbonate (420 mg, 1.3 mmol) in 1,4-dioxane:water (2:1, 15 mL) was purged with nitrogen gas for 15 minutes. The reaction mixture was charged with Pd(PPh$_3$)$_4$ (34 mg, 0.03 mmol) and heated to 90° C. for 6 hours. Ethyl acetate (10 mL) was added into the reaction mixture. The suspension was passed through a plug of celite and the filtrate was concentrated under vacuum to afford the crude product. Crude upon purification by flash chromatography yielded 2-((5-amino-6-(2,3-dichlorophenyl)-1,2,4-triazin-3-yl)amino)-3-((2-fluorobenzyl)oxy)-2-methylpropan-1-ol (Compound 61) (50 mg, 19% yield). $^1$H NMR (500 MHz, CDCl$_3$): δ 7.59 (dd, 1H), 7.34-7.38 (m, 3H), 7.22-7.24 (m, 1H), 7.09 (t, 1H), 7.01 (t, 1H), 5.6 (bs, 1H), 4.8 (bs, 2H), 4.64 (s, 2H), 3.82-3.84 (m, 1H), 3.65-3.71 (m, 4H), 1.43 (s, 3H). $^{19}$F NMR (CDCl$_3$): δ −118. MS (ESI) for C$_{21}$H$_{20}$Cl$_2$FN$_5$O$_2$: 452 (MH$^+$). The free base (50 mg) was dissolved in 2 mL of 4N hydrochloride in 2-propanol. The mixture was concentrated to afford product as hydrochloride salt.

Example 21

Preparation of Compound 63

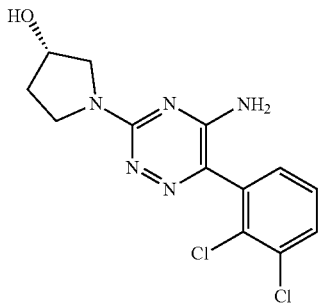 [SMILES: Nc1nc(N2CC[C@H](O)C2)nnc1-c1cccc(Cl)c1Cl]

(S)-1-(5-Amino-6-(2,3-dichlorophenyl)-1,2,4-triazin-3-yl)pyrrolidin-3-ol (Compound 63)

(S)-1-(5-Amino-6-(2,3-dichlorophenyl)-1,2,4-triazin-3-yl)pyrrolidin-3-ol, (Compound 63) was prepared according to the following steps.

Step 1: Preparation of (S)-1-(5-amino-6-chloro-1,2,4-triazin-3-yl)pyrrolidin-3-ol (Compound 64)

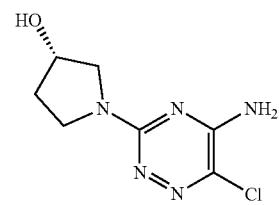 [SMILES: Nc1nc(N2CC[C@H](O)C2)nnc1Cl]

To a solution of (S)-pyrrolidin-3-ol (400 mg, 4.6 mmol) in DMSO (2 mL) were added 5-amino-3,6-dichloro-triazine (660 mg, 4.0 mmol) and sodium bicarbonate (670 mg, 8.0 mmol). The reaction mixture was stirred at 120° C. for 18 hours. Upon attaining completion, the reaction mass was diluted with 10 mL of water. The precipitated product was filtered, washed with ethyl acetate (2×20 mL), and was dried under vacuum affording (S)-1-(5-amino-6-chloro-1,2,4-triazin-3-yl)pyrrolidin-3-ol (Compound 64) (430 mg, 49% yield).

Step 2: Preparation of (S)-1-(5-amino-6-(2,3-dichlorophenyl)-1,2,4-triazin-3-yl)pyrrolidin-3-ol (Compound 63)

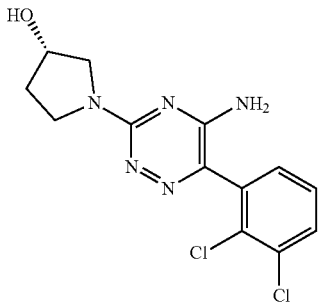 [SMILES: Nc1nc(N2CC[C@H](O)C2)nnc1-c1cccc(Cl)c1Cl]

A suspension of (S)-1-(5-amino-6-chloro-1,2,4-triazin-3-yl)pyrrolidin-3-ol (Compound 64) (430 mg, 1.9 mmol), (2,3-dichlorophenyl)boronic acid (647 mg, 3.4 mmol), and $K_2HPO_4$ (764 mg, 4.4 mmol) in 1,4-dioxane:water (2:1, 6 mL) was purged with nitrogen gas for 15 minutes. The reaction mixture was charged with $Pd(PPh_3)_4$ (230 mg, 0.2 mmol) and heated to 90° C. for 3 hours. Ethyl acetate (10 mL) was added into the reaction mixture. The suspension was passed through a plug of celite. The crude thus obtained, after evaporation of the solvent, was purified by flash chromatography yielding (S)-1-(5-amino-6-(2,3-dichlorophenyl)-1,2,4-triazin-3-yl)pyrrolidin-3-ol (Compound 63) (120 mg, 18% yield). $^1H$ NMR (500 MHz, $CDCl_3$): δ 7.70 (dd, 1H), 7.44 (t, 1H), 7.35 (dd, 1H), 6.7 (bs, 2H), 4.95 (d, 1H), 4.36 (bs, 1H), 3.50-3.54 (m 4H), 1.95-2.00 (m, 1H), 1.88-1.95 (m, 1H). MS (ESI) for $C_{13}H_{13}Cl_2N_5O$: 326 ($MH^+$). The free base (120 mg) was dissolved in 2 mL of 4N hydrochloride in 2-propanol. The mixture was concentrated to afford product as hydrochloride salt.

Example 22

Preparation of Compound 65

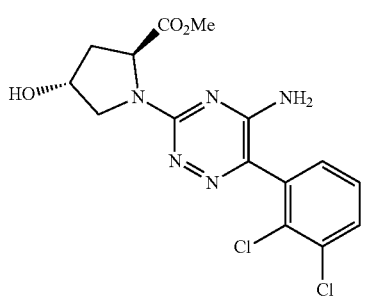 [SMILES: COC(=O)[C@@H]1C[C@@H](O)CN1c1nnc(-c2cccc(Cl)c2Cl)c(N)n1]

(2S,4R)-Methyl 1-(5-amino-6-(2,3-dichlorophenyl)-1,2,4-triazin-3-yl)-4-hydroxypyrrolidine-2-carboxylate (Compound 65)

(2S,4R)-Methyl 1-(5-amino-6-(2,3-dichlorophenyl)-1,2,4-triazin-3-yl)-4-hydroxypyrrolidine-2-carboxylate (Compound 65) was prepared according to the following steps.

Step 1: Preparation of (2S,4R)-methyl 1-(5-amino-6-chloro-1,2,4-triazin-3-yl)-4-hydroxypyrrolidine-2-carboxylate (Compound 66)

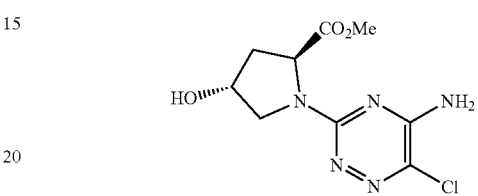

To a solution of (2S,4R)-methyl 4-hydroxypyrrolidine-2-carboxylate (1.3 g, 7.2 mmol) in DMSO (2 mL) were added 5-amino-3,6-dichloro-triazine (700 mg, 4.2 mmol) and triethylamine (3.8 mL, 38.2 mmol). The reaction mixture was stirred at 120° C. for 18 hours. Excess triethylamine was removed by evaporation under vacuum and the crude upon purification by flash chromatography yielded (2S,4R)-methyl 1-(5-amino-6-chloro-1,2,4-triazin-3-yl)-4-hydroxypyrrolidine-2-carboxylate (Compound 66) (500 mg, 43% yield).

Step 2: Preparation of (2S,4R)-methyl 1-(5-amino-6-(2,3-dichlorophenyl)-1,2,4-triazin-3-yl)-4-hydroxypyrrolidine-2-carboxylate, hydrochloride salt (compound 65)

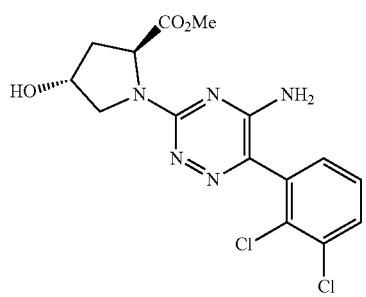 [SMILES: COC(=O)[C@@H]1C[C@@H](O)CN1c1nnc(-c2cccc(Cl)c2Cl)c(N)n1]

A suspension of (2S,4R)-methyl 1-(5-amino-6-chloro-1,2,4-triazin-3-yl)-4-hydroxypyrrolidine-2-carboxylate (Compound 66) (200 mg, 0.7 mmol), (2,3-dichlorophenyl)boronic acid (230 mg, 1.2 mmol), and cesium carbonate (520 mg, 1.6 mmol) in 1,4-dioxane:water (2:1, 6 mL) was purged with nitrogen gas for 15 minutes. The reaction mixture was charged with $Pd(PPh_3)_4$ (40 mg, 0.05 mmol) and heated to 90° C. for 3 hours. Upon attaining completion, 10 mL ethyl acetate was added into the reaction mixture. The suspension was passed through a plug of celite. The crude obtained, after evaporation of the solvent, was purified by flash chromatography yielding (2S,4R)-methyl 1-(5-amino-6-(2,3-dichlorophenyl)-1,2,4-triazin-3-yl)-4-hydroxypyrrolidine-2-carboxylate (Compound 65) (100 mg, 35% yield). $^1H$ NMR (500 MHz, CDCl$_3$): δ 7.66 (dd, 1H), 7.42 (t, 1H), 7.34 (d, 1H), 4.85 (bs, 2H), 4.65 (bs, 1H), 4.60 (s, 1H), 4.54 (bs, 1H), 3.82 (bs, 2H), 3.73 (s, 3H), 2.36 (bs, 1H), 2.17 (s, 1H). MS (ESI) for C$_{15}$H$_{15}$Cl$_2$N$_5$O$_3$: 384 (MH$^+$). The free base (100 mg) was dissolved in 2 mL of 4N hydrochloride in 2-propanol. The mixture was concentrated to afford product as hydrochloride salt.

Example 23

Preparation of Compound 67

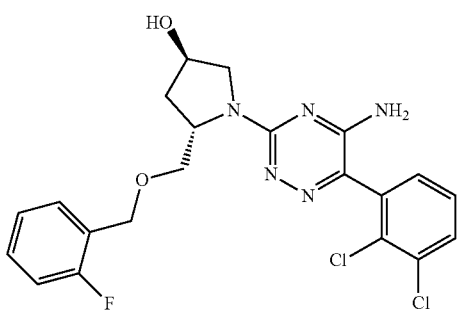 [SMILES: Nc1nc(N2C[C@H](O)C[C@H]2COCc2ccccc2F)nnc1-c1cccc(Cl)c1Cl]

(3R,5S)-1-(5-Amino-6-(2,3-dichlorophenyl)-1,2,4-triazin-3-yl)-5-(((2-fluorobenzyl)oxy)methyl)pyrrolidin-3-ol (Compound 67)

(3R,5S)-1-(5-Amino-6-(2,3-dichlorophenyl)-1,2,4-triazin-3-yl)-5-(((2-fluorobenzyl)oxy)methyl)pyrrolidin-3-ol (Compound 67) was prepared according to the following steps.

Step 1: Preparation of (3R,5S)-1-(5-amino-6-chloro-1,2,4-triazin-3-yl)-5-(((2-fluorobenzyl)oxy)methyl)pyrrolidin-3-ol (Compound 68)

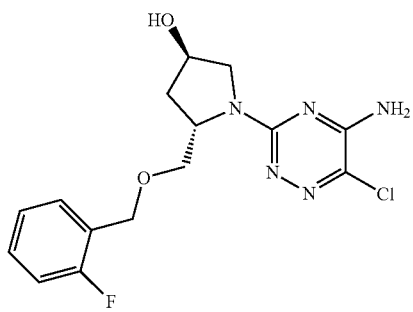 [SMILES: Nc1nc(N2C[C@H](O)C[C@H]2COCc2ccccc2F)nnc1Cl]

To a solution of (3R,5S)-5-(((2-fluorobenzyl)oxy)methyl)pyrrolidin-3-ol (300 mg, 1.3 mmol) in DMSO (2 mL) were added 5-amino-3,6-dichloro-triazine (150 mg, 0.9 mmol) and triethylamine (1.0 mL, 7.2 mmol). The reaction mixture was stirred at 120° C. for 4 hours. The reaction mixture was evaporated to remove excess triethylamine. The residue was taken in 30 mL of ethyl acetate, washed sequentially with water (2×10 mL) and brine (10 mL). The ethyl acetate layer was dried over sodium sulfate, concentrated under vacuum to afford the crude product. The crude upon purification by flash chromatography yielded (3R,5S)-1-(5-amino-6-chloro-1,2,4-triazin-3-yl)-5-(((2-fluorobenzyl)oxy)methyl)pyrrolidin-3-ol (Compound 68) (250 mg, 78% yield).

Step 2: Preparation of (3R,5S)-1-(5-amino-6-(2,3-dichlorophenyl)-1,2,4-triazin-3-yl)-5-(((2-fluorobenzyl)oxy)methyl)pyrrolidin-3-ol (Compound 67)

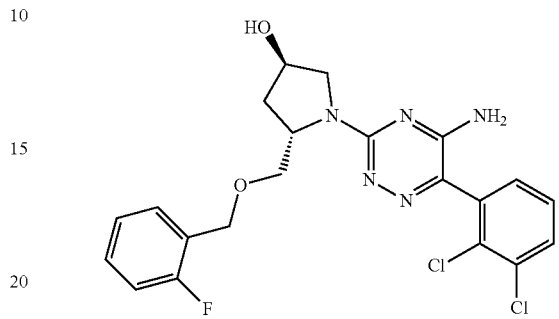

A suspension of (3R,5S)-1-(5-amino-6-chloro-1,2,4-triazin-3-yl)-5-(((2-fluorobenzyl)oxy)methyl)pyrrolidin-3-ol (Compound 68) (250 mg, 0.7 mmol), (2,3-dichlorophenyl)boronic acid (230 mg, 1.2 mmol), and cesium carbonate (500 mg, 1.5 mmol) in 1,4-dioxane:water (2:1, 6 mL) was purged with nitrogen gas for 15 minutes. The reaction mixture was charged with Pd(PPh$_3$)$_4$ (40 mg, 0.05 mmol) and heated to 90° C. for 3 hours. Ethyl acetate (10 mL) was added into the reaction mixture. The suspension was passed through a plug of celite. The crude, generated after evaporation of the solvent, was purified by flash chromatography yielding (3R,5S)-1-(5-amino-6-(2,3-dichlorophenyl)-1,2,4-triazin-3-yl)-5-(((2-fluorobenzyl)oxy)-methyl)pyrrolidin-3-ol (Compound 67) (60 mg, 18% yield). $^1$H NMR (500 MHz, CDCl$_3$): δ 7.59 (dd, 1H), 7.34-7.38 (m, 3H), 7.22-7.24 (m, 1H), 7.09 (t, 1H), 7.01 (t, 1H), 4.67-4.69 (m, 4H), 4.58-4.59 (m, 3H), 3.78-3.86 (m, 4H), 2.37-2.42 (m, 1H), 2.13-2.18 (m, 1H). $^{19}$F NMR (470 MHz, CDCl$_3$): δ −118. MS (ESI) for C$_{21}$H$_{20}$Cl$_2$FN$_5$O$_2$: 464 (MH$^+$). The free base (60 mg) was dissolved in 2 mL of 4N hydrochloride in 2-propanol. The mixture was concentrated to afford product as hydrochloride salt.

Example 24

Preparation of Compound 69

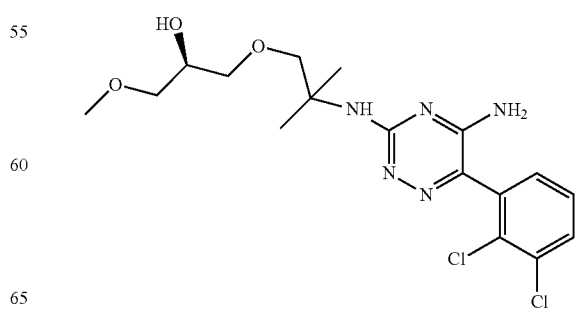

(R)-1-(2-((5-Amino-6-(2,3-dichlorophenyl)-1,2,4-triazin-3-yl)amino)-2-methylpropoxy)-3-methoxypropan-2-ol (Compound 69)

(R)-1-(2-((5-Amino-6-(2,3-dichlorophenyl)-1,2,4-triazin-3-yl)amino)-2-methylpropoxy)-3-methoxypropan-2-ol (Compound 69) is prepared in accordance with the following steps.

Step-1: Preparation of (R)-1-(2-((5-amino-6-chloro-1,2,4-triazin-3-yl)amino)-2-methylpropoxy)-3-methoxypropan-2-ol (Compound 70)

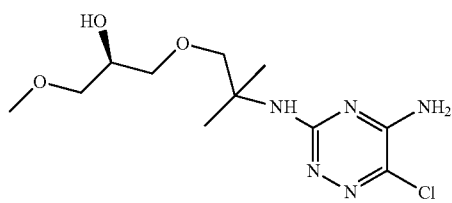 [SMILES: COC[C@@H](O)COCC(C)(C)Nc1nnc(Cl)c(N)n1]

3,6-Dichloro-1,2,4-triazin-5-amine (1.00 eq), (R)-1-(2-amino-2-methylpropoxy)-3-methoxypropan-2-ol (1.5 eq) and sodium bicarbonate (2 eq) are added to a 1,4-dioxane solution and degassed for 5-10 minutes; the reaction is then carried out for 18-20 hours at 85-90° C. After completion of the reaction, the crude product is purified by column chromatography to afford (R)-1-(2-((5-amino-6-chloro-1,2,4-triazin-3-yl)amino)-2-methylpropoxy)-3-methoxypropan-2-ol (Compound 70).

Step-2: Preparation of (R)-1-(2-((5-amino-6-(2,3-dichlorophenyl)-1,2,4-triazin-3-yl)amino)-2-methylpropoxy)-3-methoxypropan-2-ol (Compound 69)

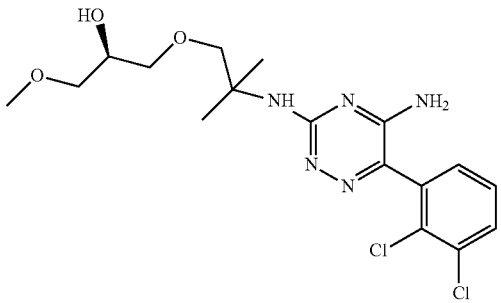 [SMILES: COC[C@@H](O)COCC(C)(C)Nc1nnc(-c2cccc(Cl)c2Cl)c(N)n1]

(R)-1-(2-((5-Amino-6-chloro-1,2,4-triazin-3-yl)amino)-2-methylpropoxy)-3-methoxypropan-2-ol (Compound 70) is subjected to Suzuki coupling reaction with (2,3-dichlorophenyl)boronic acid using $K_2HPO_4$ as base and $Pd(PPh_3)_4$ as catalyst in a mixture of dioxane/water at 85-90° C. The crude obtained, after routine work-up, upon purification by column chromatography affords (R)-1-(2-((5-amino-6-(2,3-dichlorophenyl)-1,2,4-triazin-3-yl)amino)-2-methylpropoxy)-3-methoxypropan-2-ol (Compound 69). The free base of the compound is subjected to 4M HCl in 2-propanol to obtain the HCl salt of Compound 69.

Example 25

Preparation of Compound 71

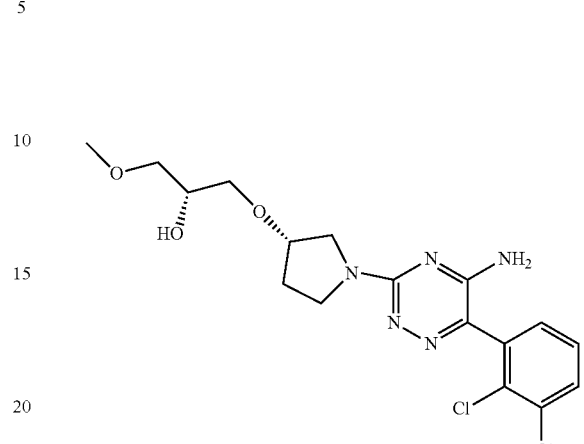

(R)-1-(((S)-1-(5-Amino-6-(2,3-dichlorophenyl)-1,2,4-trazin-3-yl)pyrrolidin-3-yl)oxy)-3-methoxypropan-2-ol (Compound 71)

(R)-1-(((S)-1-(5-Amino-6-(2,3-dichlorophenyl)-1,2,4-triazin-3-yl)pyrrolidin-3-yl)oxy)-3-methoxypropan-2-ol (Compound 71) is prepared in accordance with the following steps.

Step-1: Preparation of (R)-1-(((S)-1-(5-Amino-6-chloro-1,2,4-triazin-3-yl)pyrrolidin-3-yl)oxy)-3-methoxypropan-2-ol (Compound 72)

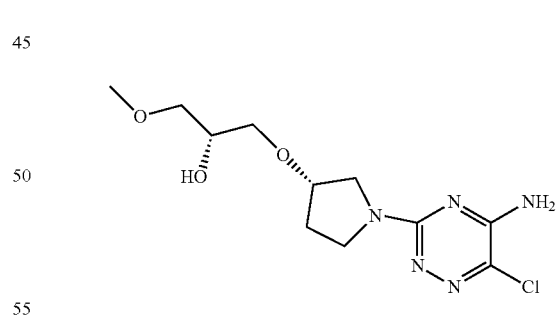

3,6-Dichloro-1,2,4-triazin-5-amine (1.00 eq), (R)-1-methoxy-3-((S)-pyrrolidin-3-yloxy)propan-2-ol (1.5 eq) and sodium bicarbonate (2 eq) are added to 1,4-dioxane and degassed for 5-10 minutes. The reaction is performed by stirring at 85-90° C. for 18-20 hours. After completion of the reaction, a routine work-up affords crude which upon purification by column chromatography affords (R)-1-(((S)-1-(5-amino-6-chloro-1,2,4-triazin-3-yl)pyrrolidin-3-yl)oxy)-3-methoxypropan-2-ol (Compound 72).

Step-2: Preparation of (R)-1-(((S)-1-(5-amino-6-(2,3-dichlorophenyl)-1,2,4-triazin-3-yl)pyrrolidin-3-yl)oxy)-3-methoxypropan-2-ol (Compound 71)

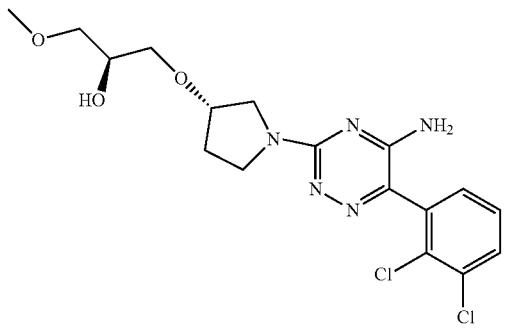 [SMILES: COC[C@H](O)CO[C@H]1CCN(c2nnc(-c3cccc(Cl)c3Cl)c(N)n2)C1]

(R)-1-(((S)-1-(5-Amino-6-chloro-1,2,4-triazin-3-yl)pyrrolidin-3-yl)oxy)-3-methoxypropan-2-ol (Compound 72) is subjected to a Suzuki coupling reaction with (2,3-dichlorophenyl)boronic acid using $K_2HPO_4$ as a base and $Pd(PPh_3)_4$ as a catalyst in a dioxane/water mixture, at 85-90° C. The crude compound thus obtained is purified by column chromatography to afford (R)-1-(((S)-1-(5-amino-6-(2,3-dichlorophenyl)-1,2,4-triazin-3-yl)pyrrolidin-3-yl)oxy)-3-methoxypropan-2-ol (Compound 71). The free base of the compound is subjected to 4M HCl in 2-propanol to obtain the HCl salt of Compound 71.

Example 26

Preparation of Compound 73

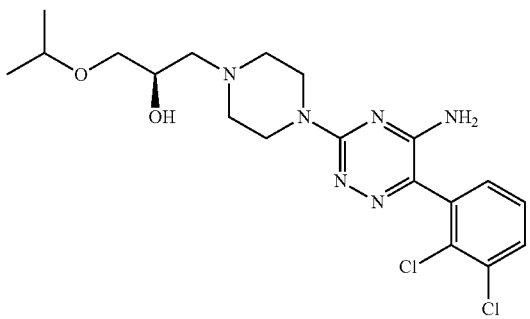 [SMILES: CC(C)OC[C@H](O)CN1CCN(c2nnc(-c3cccc(Cl)c3Cl)c(N)n2)CC1]

(R)-1-(4-(5-Amino-6-(2,3-dichlorophenyl)-1,2,4-triazin-3-yl)piperazin-1-yl)-3-isopropoxypropan-2-ol (Compound 73)

(R)-1-(4-(5-amino-6-(2,3-dichlorophenyl)-1,2,4-triazin-3-yl)piperazin-1-yl)-3-isopropoxy-propan-2-ol (Compound 73) was prepared in accordance with the following steps.

Step-1: Preparation of (R)-1-(4-(5-amino-6-chloro-1,2,4-triazin-3-yl)piperazin-1-yl)-3-isopropoxy-propan-2-ol (Compound 74)

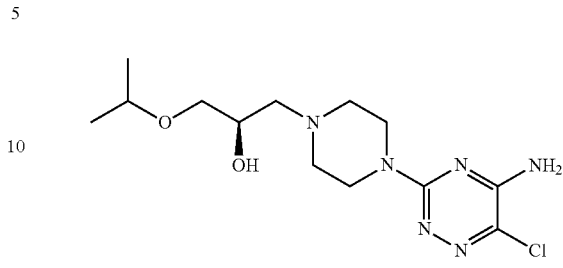

To a solution of (R)-1-isopropoxy-3-(piperazin-1-yl)propan-2-ol (2.45 g, 12.12 mmol) in 1,4-dioxane (10 mL) was added 5-amino-3,6-dichloro-triazine (2.0 g, 12.12 mmol). The reaction mixture was then charged with sodium bicarbonate (3.06 mL, 36.4 mmol). The reaction mixture was stirred at 90° C. for 5 hours. Evaporation of the solvent and purification of the residue by flash chromatography yielded (R)-1-(4-(5-amino-6-chloro-1,2,4-triazin-3-yl)piperazin-1-yl)-3-isopropoxy-propan-2-ol (Compound 74) (1.5 g, 37.8% yield).

Step-2: Preparation of (R)-1-(4-(5-amino-6-(2,3-dichlorophenyl)-1,2,4-triazin-3-yl)piperazin-1-yl)-3-isopropoxy-propan-2-ol (Compound 73)

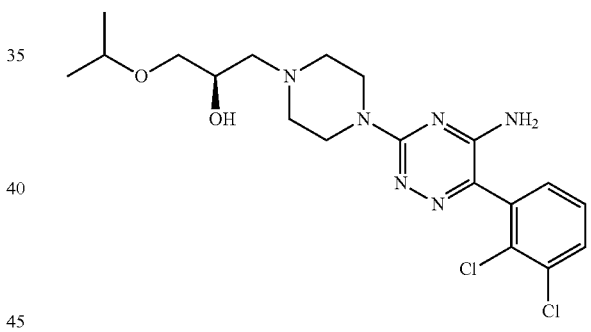

A suspension of (R)-1-(4-(5-amino-6-chloro-1,2,4-triazin-3-yl)piperazin-1-yl)-3-isopropoxy-propan-2-ol (Compound 74) (570 mg, 1.7 mmol), (2,3-dichlorophenyl)boronic acid (1.2 g, 6.4 mmol), and cesium carbonate (1.2 g, 3.79 mmol) in 1,4-dioxane:water (2:1, 6 mL) was purged with nitrogen gas for 15 minutes. The reaction mixture was charged with $Pd(PPh_3)_4$ (100 mg, 0.09 mmol) and heated to 90° C. for 3 hours. Ethyl acetate (10 mL) was added into the reaction mixture. The suspension was passed through a plug of celite. The resulting crude, after evaporation of the solvent, was purified by flash chromatography and yielded (R)-1-(4-(5-amino-6-(2,3-dichlorophenyl)-1,2,4-triazin-3-yl)piperazin-1-yl)-3-isopropoxy-propan-2-ol (Compound 73) (260 mg, 38% yield). $^1$H NMR (500 MHz, CDCl$_3$): δ 7.59 (dd, 1H), 7.30-7.4 (m, 2H), 4.70 (bs, 2H), 3.85-3.95 (m, 5H), 3.59-3.65 (m, 1H), 3.39-3.49 (ABq, 2H), 3.25 (bs, 1H), 2.69-2.75 (m, 2H), 2.51-2.59 (m, 3H), 2.45 (dd, 1H), 1.19 (d, 6H). MS (ESI) for $C_{19}H_{26}Cl_2N_6O_2$: 442 (MH$^+$). The free base (160 mg) was dissolved in 2 mL of 4N hydrochloride in 2-propanol. The mixture was concentrated to afford product as hydrochloride salt.

Example 27

Preparation of Compound 75

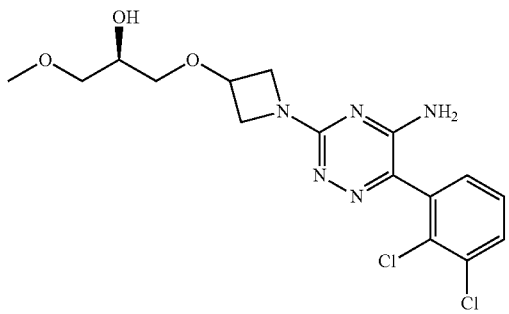 [SMILES: COC[C@@H](O)COC1CN(c2nnc(-c3cccc(Cl)c3Cl)c(N)n2)C1]

(R)-1-((1-(5-Amino-6-(2,3-dichlorophenyl)-1,2,4-trazin-3-yl)azetidin-3-yl)oxy)-3-methoxypropan-2-ol (Compound 75)

(R)-1-((1-(5-amino-6-(2,3-dichlorophenyl)-1,2,4-triazin-3-yl)azetidin-3-yl)oxy)-3-methoxypropan-2-ol (Compound 75) is prepared according to the following steps

Step 1: Preparation of (R)-1-((1-(5-amino-6-chloro-1,2,4-triazin-3-yl)azetidin-3-yl)oxy)-3-methoxypropan-2-ol (Compound 76)

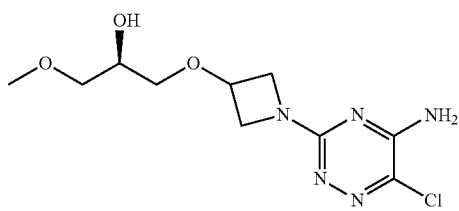 [SMILES: COC[C@@H](O)COC1CN(c2nnc(Cl)c(N)n2)C1]

(R)-1-((1-(5-amino-6-chloro-1,2,4-triazin-3-yl)azetidin-3-yl)oxy)-3-methoxypropan-2-ol Chemical Formula: $C_{10}H_{16}ClN_5O_3$ Molecular Weight: 289.719

To a solution of (R)-1-(azetidin-3-yloxy)-3-methoxypropan-2-ol (1.0 equiv.) in 1,4-dioxane (10 mL) is added 5-amino-3,6-dichloro-triazine (1.0 equiv.). The reaction mixture is then charged with sodium bicarbonate (3.0 equiv) and stirred at 90° C. Evaporation of the solvent and purification of the residue by flash chromatography affords (R)-1-((1-(5-amino-6-chloro-1,2,4-triazin-3-yl)azetidin-3-yl)oxy)-3-methoxypropan-2-ol (Compound 76).

Step-2: Preparation of (R)-1-((1-(5-amino-6-(2,3-dichlorophenyl)-1,2,4-triazin-3-yl)azetidin-3-yl)oxy)-3-methoxypropan-2-ol (Compound 75)

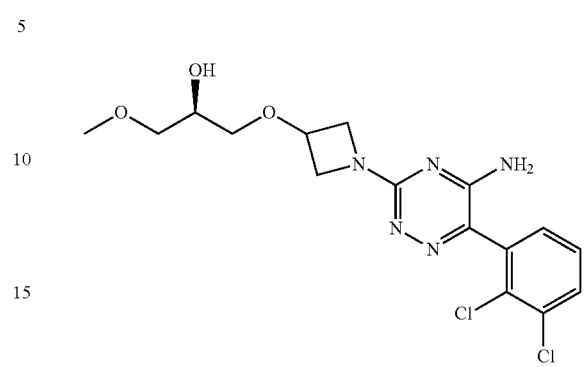

To a suspension of (R)-1-((1-(5-amino-6-chloro-1,2,4-triazin-3-yl)azetidin-3-yl)oxy)-3-methoxypropan-2-ol (Compound 76) (1.0 equiv.), (2,3-dichlorophenyl)boronic acid (1.7 equiv.), and cesium carbonate (3.3 equiv.) in 1,4-dioxane:water is added Pd(PPh$_3$)$_4$ (0.05 equiv.) and heated to 90° C. The crude produced after evaporation of the solvent and purification by flash chromatography affords (R)-1-((1-(5-amino-6-(2,3-dichlorophenyl)-1,2,4-triazin-3-yl)azetidin-3-yl)oxy)-3-methoxypropan-2-ol, (Compound 75). The free base is dissolved in 2 mL of 4N hydrochloride in 2-propanol. The mixture is concentrated to afford product as hydrochloride salt.

Example 28

Preparation of Compound 77

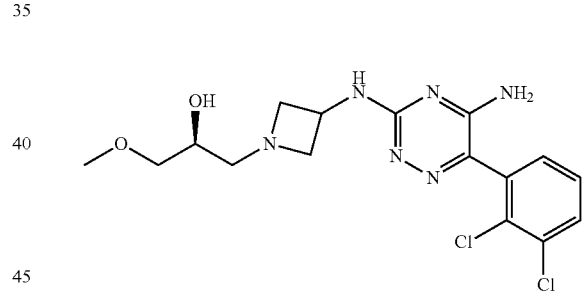

(S)-1-(3-((5-amino-6-(2,3-dichlorophenyl)-1,2,4-trazin-3-yl)amino)azetidin-1-yl)-3-methoxypropan-2-ol (Compound 77)

(S)-1-(3-((5-amino-6-(2,3-dichlorophenyl)-1,2,4-triazin-3-yl)amino)azetidin-1-yl)-3-methoxypropan-2-ol (Compound 77) is prepared according to the following steps.

Step 1: Preparation of (S)-1-(3-((5-amino-6-chloro-1,2,4-triazin-3-yl)amino)azetidin-1-yl)-3-methoxypropan-2-ol (Compound 78)

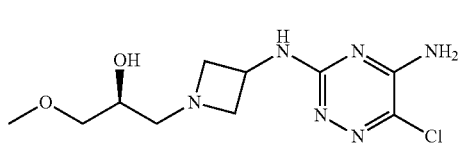 [SMILES: COC[C@@H](O)CN1CC(Nc2nnc(Cl)c(N)n2)C1]

To a solution of (S)-1-(3-aminoazetidin-1-yl)-3-methoxypropan-2-ol (1.0 equiv.) in 1,4-dioxane (10 mL) is added 5-amino-3,6-dichloro-triazine (1.0 equiv.). The reaction mixture is then charged with sodium bicarbonate (3.0 equiv) and stirred at 90° C. Evaporation of the solvent and purification of the residue by flash chromatography affords (S)-1-(3-((5-amino-6-chloro-1,2,4-triazin-3-yl)amino)azetidin-1-yl)-3-methoxypropan-2-ol (Compound 78).

Step-2: Preparation of (S)-1-(3-((5-amino-6-(2,3-dichlorophenyl)-1,2,4-triazin-3-yl)amino)azetidin-1-yl)-3-methoxypropan-2-ol (Compound 77)

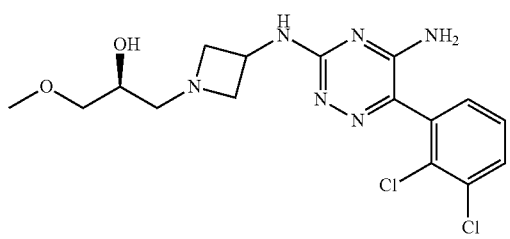 [SMILES: COC[C@@H](O)CN1CC(Nc2nnc(-c3cccc(Cl)c3Cl)c(N)n2)C1]

To a suspension of (S)-1-(3-((5-amino-6-chloro-1,2,4-triazin-3-yl)amino)azetidin-1-yl)-3-methoxypropan-2-ol (Compound 78) (1.0 equiv.), (2,3-dichlorophenyl)boronic acid (1.7 equiv.), and cesium carbonate (3.3 equiv.) in 1,4-dioxane:water is added Pd(PPh$_3$)$_4$ (0.05 equiv.) and heated to 90° C. The crude after evaporation of the solvent upon purification by flash chromatography affords (S)-1-(3-((5-amino-6-(2,3-dichlorophenyl)-1,2,4-triazin-3-yl)amino)azetidin-1-yl)-3-methoxypropan-2-ol (Compound 77).

Example 29

Preparation of Compound 78

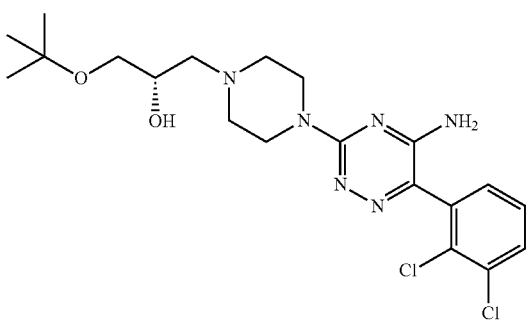 [SMILES: CC(C)(C)OC[C@@H](O)CN1CCN(c2nnc(-c3cccc(Cl)c3Cl)c(N)n2)CC1]

Preparation of (2S)-1-{4-[5-Amino-6-(2,3-dichlorophenyl)-1,2,4-triazin-3-yl]piperazin-1-yl}-3-tert-butoxypropan-2-ol (Compound 78)

2-(tert-butoxymethyl)oxirane (45.9 mg, 0.352 mmol) was added to a suspension of 6-(2,3-Dichlorophenyl)-3-(piperazin-1-yl)-1,2,4-triazin-5-amine (Compound 79) (46 mg, 0.141 mmol) in ethanol (0.4 mL). The resulting mixture was heated in a microwave oven at 120° C. for 30 minutes. The solvent was removed under reduced pressure and the crude product was purified by flash chromatography (90:10 dichloromethane/methanol) to afford (2S)-1-{4-[5-Amino-6-(2,3-dichlorophenyl)-1,2,4-triazin-3-yl]piperazin-1-yl}-3-tert-butoxypropan-2-ol (Compound 78) (31 mg, 48.1%) as an off white foam. $^1$H NMR (500 MHz, Chloroform-d): δ 7.57 (dt, J=1.5, 7.50 Hz, 1H), 7.40-7.29 (m, 2H), 4.84 (bs, 2H), 3.90 (m, 5H), 3.45-3.35 (m, 2H), 2.71 (dt, J=5.0, 10.7 Hz, 2H), 2.54 (m, 2H), 2.50 (ddd, J=1.2, 4.1, 12.4 Hz, 1H), 1.21 (s, 9H). MS (EI) for C$_{20}$H$_{28}$Cl$_2$N$_6$O$_2$: 455 (MH$^+$).

Example 30

Preparation of Compound 80

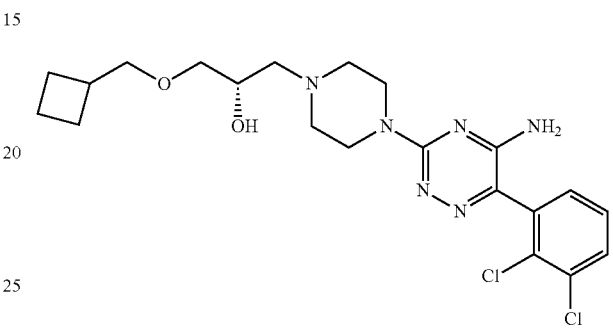

Preparation of (2S)-1-{4-[5-Amino-6-(2,3-dichlorophenyl)-1,2,4-triazin-3-yl]piperazin-1-yl}-3-(cyclobutylmethoxy)propan-2-ol (Compound 80)

2S)-1-{4-[5-Amino-6-(2,3-dichlorophenyl)-1,2,4-triazin-3-yl]piperazin-1-yl}-3-(cyclobutylmethoxy)propan-2-ol (Compound 80) was prepared according to the following steps.

Step 1: Preparation of 6-(2,3-Dichlorophenyl)-3-{4-[(2S)-oxiran-2-ylmethyl]piperazin-1-yl}-1,2,4-triazin-5-amine (Compound 81)

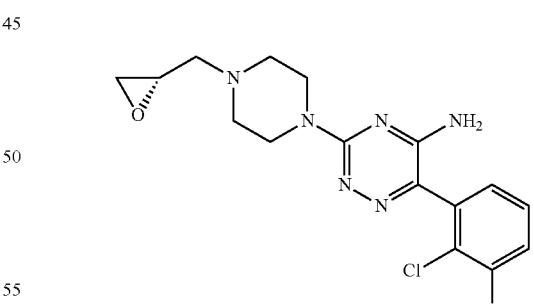

(S)-2-(chloromethyl)oxirane (0.263 mL, 3.37 mmol) was added to a suspension of 6-(2,3-Dichlorophenyl)-3-(piperazin-1-yl)-1,2,4-triazin-5-amine (Compound 79) (995 mg, 3.06 mmol) in ethanol (15 mL). The resulting mixture was stirred at room temperature for 33 hours and the solvent was removed under reduced pressure. The residue was purified by flash chromatography (90:10 dichloromethane/methanol), suspended in tetrahydrofurane (10 mL) and treated with 4M sodium hydroxide (0.467 mL, 1.867 mmol). The resulting solution was stirred at room temperature for 4 hours. Water was added and the solvent was removed under reduced pressure. The residue was dissolved in dichloromethane (100 mL) and washed with sodium chloride saturated solution (50 mL). The organic layer was dried over anhydrous magnesium sulfate and the solvent was removed under reduced pressure to yield 6-(2,3-Dichlorophenyl)-3-{4-[(2S)-oxiran-2-ylmethyl]piperazin-1-yl}-1,2,4-triazin-5-amine (Compound 81) (0.66 g, 93%) as a light yellow foam that was used without further purification. $^1$H NMR (500 MHz, Chloroform-d): δ 7.58 (dd, J=2.06, 7.6 Hz, 1H), 7.41-7.32 (m, 2H), 4.78 (bs, 2H), 3.95 (d, J=5.3 Hz, 4H), 3.18 (dq, J=3.2, 6.9 Hz, 1H), 2.89-2.80 (m, 2H), 2.73 (dt, J=5.1, 10.7 Hz, 2H), 2.62 (dt, J=5.2, 10.9 Hz, 2H), 2.54 (dd, J=2.7, 5.0 Hz, 1H), 2.34 (dd, J=6.9, 13.3 Hz, 1H). MS (EI) for $C_{16}H_{18}Cl_2N_6O$: 381 (MH$^+$).

Step 2: Preparation of (2S)-1-{4-[5-Amino-6-(2,3-dichlorophenyl)-1,2,4-triazin-3-yl]piperazin-1-yl}-3-(cyclobutylmethoxy)propan-2-ol (Compound 80)

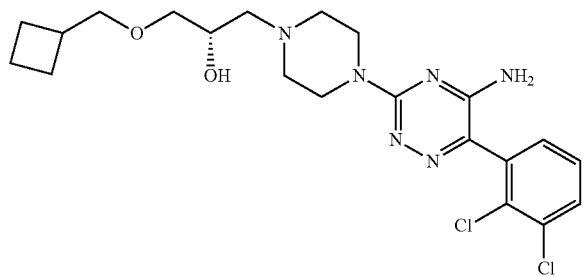 [SMILES: Nc1nc(N2CCN(C[C@H](O)COCC3CCC3)CC2)nnc1-c1cccc(Cl)c1Cl]

A mixture of 6-(2,3-Dichlorophenyl)-3-{4-[(2S)-oxiran-2-ylmethyl]piperazin-1-yl}-1,2,4-triazin-5-amine (Compound 89) (60 mg, 0.157 mmol), cyclobutylmethanol (0.3 mL, 3.56 mmol) and 50% sodium hydroxide (13 µL, 0.157 mmol) was heated in a microwave oven at 120° C. for 30 minutes. Excess of cyclobutylmethanol was removed under reduced pressure and the crude product was purified by reverse phase preparative HPLC using a Phenomenex Gemini, 10 □m, C18, 150×21.2 mm column at a flow rate of 20 mL/min and mobile phases of 85% water, 15% acetonitrile (with 10 mM NH4OH) and 45% water, 55% acetonitrile (with 10 mM NH4OH) to afford (2S)-1-{4-[5-Amino-6-(2,3-dichlorophenyl)-1,2,4-triazin-3-yl]piperazin-1-yl}-3-(cyclobutylmethoxy)propan-2-ol (Compound 80) (4.2 mg, 5.17%) as a white solid. $^1$H NMR (500 MHz, Chloroform-d): δ 7.59 (dd, J=7.5, 2.2 Hz, 1H), 7.42-7.33 (m, 2H), 4.76 (bs, 2H), 3.99 (m, 5H), 3.54-3.43 (m, 4H), 2.78 (m, 2H), 2.60 (td, J=13.2, 11.8, 6.2 Hz, 4H), 2.51 (m, 1H), 2.13-2.02 (m, 2H), 2.00-1.87 (m, 2H), 1.80-1.69 (m, 3H). MS (EI) for $C_{21}H_{28}Cl_2N_6O_2$: 467 (MH$^+$).

The free base was dissolved in acetonitrile and treated with 1N hydrochloric acid in ethyl ether (50 µL). Solvents were removed under reduced pressure to generate the hydrochloride salt of the tittle compound as a white solid.

Example 31

Preparation of Compound 83

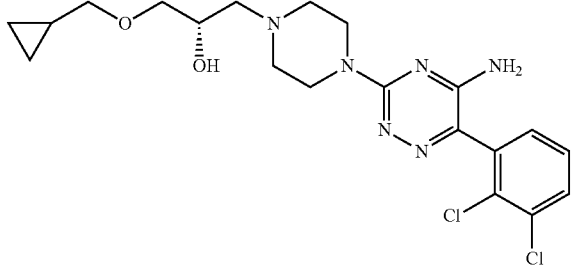 [SMILES: Nc1nc(N2CCN(C[C@H](O)COCC3CC3)CC2)nnc1-c1cccc(Cl)c1Cl]

Preparation of (2S)-1-{4-[5-Amino-6-(2,3-dichlorophenyl)-1,2,4-triazin-3-yl]piperazin-1-yl}-3-(cyclopropylmethoxy)propan-2-ol (Compound 83)

The title compound was prepared following the same method as for Example 30, but using cyclopropylmethanol. From 60 mg of 6-(2,3-dichlorophenyl)-3-{4-[(2S)-oxiran-2-ylmethyl]piperazin-1-yl}-1,2,4-triazin-5-amine (Compound 81), 9.0 mg of (2S)-1-{4-[5-Amino-6-(2,3-dichlorophenyl)-1,2,4-triazin-3-yl]piperazin-1-yl}-3-(cyclopropylmethoxy)propan-2-ol (Compound 83) were obtained as a white solid (11% yield). $^1$H NMR (500 MHz, Chloroform-d): δ 7.58 (dd, J=2.1, 7.5 Hz, 1H), 7.41-7.32 (m, 2H), 4.78 (bs, 2H), 4.00 (ddd, J=3.3, 5.1, 10.2 Hz, 1H), 4.00-3.89 (m, 4H), 3.55 (dd, J=4.1, 9.9 Hz, 1H), 3.49 (dd, J=5.7, 9.9 Hz, 1H), 3.35 (d, J=6.9 Hz, 2H), 2.75 (dt, J=5.0, 10.7 Hz, 2H), 2.56 (tt, J=5.8, 10.8 Hz, 3H), 2.48 (dd, J=3.6, 12.5 Hz, 1H), 1.80 (bs, 1H), 1.15-1.03 (m, 1H), 0.59-0.52 (m, 2H), 0.26-0.19 (m, 2H). MS (EI) for $C_{20}H_{26}Cl_2N_6O_2$: 453 (MH$^+$).

The free base was dissolved in acetonitrile and treated with 1N hydrochloric acid in ethyl ether (100 µL). Solvents were removed under reduced pressure to generate the hydrochloride salt of the tittle compound as a white solid.

Example 32

Preparation of Compound 84

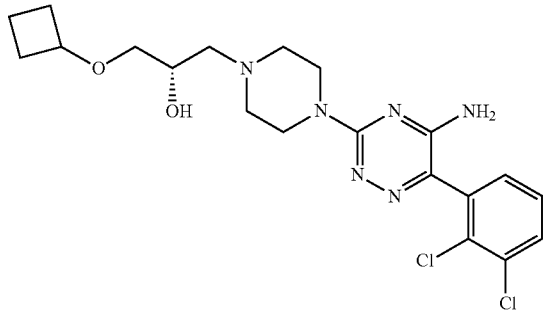 [SMILES: Nc1nc(N2CCN(C[C@H](O)COC3CCC3)CC2)nnc1-c1cccc(Cl)c1Cl]

Preparation of (2S)-1-{4-[5-Amino-6-(2,3-dichloro-phenyl)-1,2,4-triazin-3-yl]piperazin-1-yl}-3-(cy-clobutyloxy)propan-2-ol (Compound 84)

The title compound was prepared following the same method as for Example 30, but using cyclobutanol. From 103 mg of 6-(2,3-dichlorophenyl)-3-{4-[(2S)-oxiran-2-ylm-ethyl]piperazin-1-yl}-1,2,4-triazin-5-amine (Compound 81), 45 mg of (2S)-1-{4-[5-Amino-6-(2,3-dichlorophenyl)-1,2,4-triazin-3-yl]piperazin-1-yl}-3-(cyclobutyloxy)propan-2-ol (Compound 84) were obtained as a white solid (32% yield). $^1$H NMR (500 MHz, Chloroform-d): δ 7.59 (dd, J=2.1, 7.5 Hz, 1H), 7.42-7.33 (m, 2H), 4.78 (bs, 2H), 4.03-3.91 (m, 1H), 3.92 (m, 5H), 3.46-3.31 (m, 2H), 2.78-2.70 (m, 2H), 2.55 (ddd, J=3.9, 7.7, 13.3 Hz, 3H), 2.46 (dd, J=3.6, 12.5 Hz, 1H), 2.28-2.18 (m, 2H), 2.03-1.89 (m, 2H), 1.77-1.66 (m, 2H), 1.52 (qt, J=8.0, 10.53 Hz, 1H). MS (EI) for $C_{20}H_{26}Cl_2N_6O_2$: 453 (MH$^+$).

The free base was dissolved in acetonitrile and treated with 1N hydrochloric acid in ethyl ether (0.7 mL). Solvents were removed under reduced pressure to generate the hydrochloride salt of the tittle compound as a white solid.

Example 33

Preparation of Compound 85

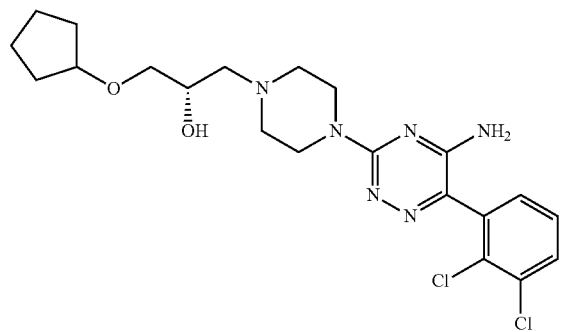 [SMILES: Nc1nc(N2CCN(C[C@H](O)COC3CCCC3)CC2)nnc1-c1cccc(Cl)c1Cl]

Preparation of (2S)-1-{4-[5-Amino-6-(2,3-dichloro-phenyl)-1,2,4-triazin-3-yl]piperazin-1-yl}-3-(cyclo-pentyloxy)propan-2-ol (Compound 85)

The title compound was prepared following the same method as for Example 30, but using cyclopentanol. From 99 mg of 6-(2,3-dichlorophenyl)-3-{4-[(2S)-oxiran-2-ylm-ethyl]piperazin-1-yl}-1,2,4-triazin-5-amine (Compound 81), 4.3 mg of (2S)-1-{4-[5-Amino-6-(2,3-dichlorophenyl)-1,2,4-triazin-3-yl]piperazin-1-yl}-3-(cyclopentyloxy)pro-pan-2-ol (Compound 85) were obtained as a white solid (3.3% yield). $^1$H NMR (500 MHz, Chloroform-d) δ 7.59 (dd, J=2.1, 7.6 Hz, 1H), 7.42-7.32 (m, 2H), 4.75 (bs, 2H), 3.95 (dq, J=2.4, 3.1, 5.7 Hz, 1H), 3.93 (m, 5H), 3.50-3.38 (m, 2H), 2.74 (dt, J=5.0, 10.7 Hz, 2H), 2.66-2.50 (m, 2H), 2.51-2.43 (m, 2H), 1.79-1.63 (m, 7H), 1.58-1.52 (m, 2H). MS (EI) for $C_{21}H_{28}Cl_2N_6O_2$: 467 (MH$^+$).

Example 34

Preparation of Compound 86

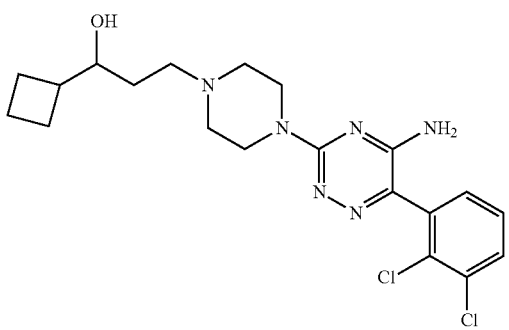 [SMILES: Nc1nc(N2CCN(CCC(O)C3CCC3)CC2)nnc1-c1cccc(Cl)c1Cl]

Preparation of 3-(4-(5-amino-6-(2,3-dichlorophe-nyl)-1,2,4-triazin-3-yl)piperazin-1-yl)-1-cyclobutyl-propan-1-ol The following is a general scheme useful for the preparation of 3-(4-(5-amino-6-(2,3-dichlorophenyl)-1,2,4-tri-azin-3-yl)piperazin-1-yl)-1-alkylylpropan-1-ols (exempli-fied for the cyclobutylpropan-1-ol shown above):

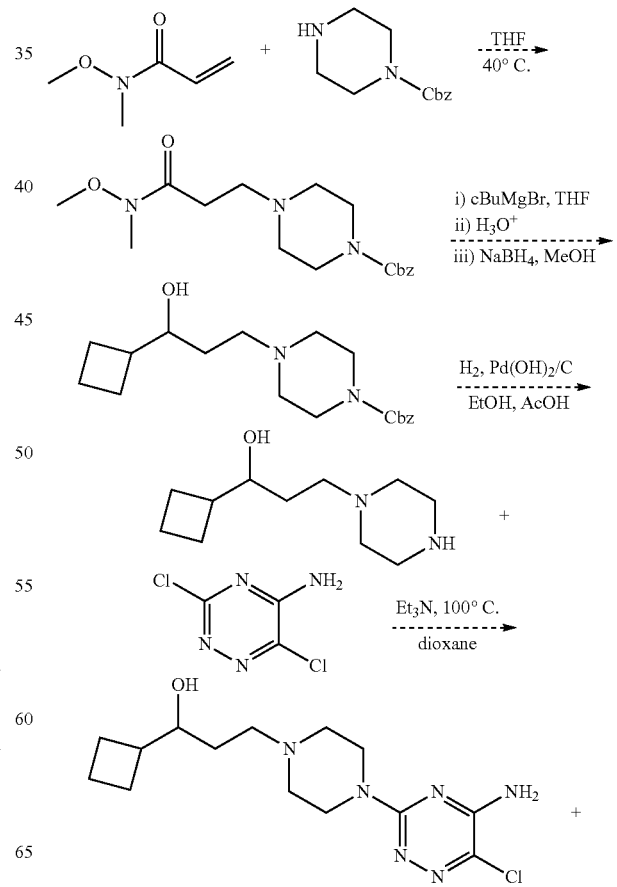

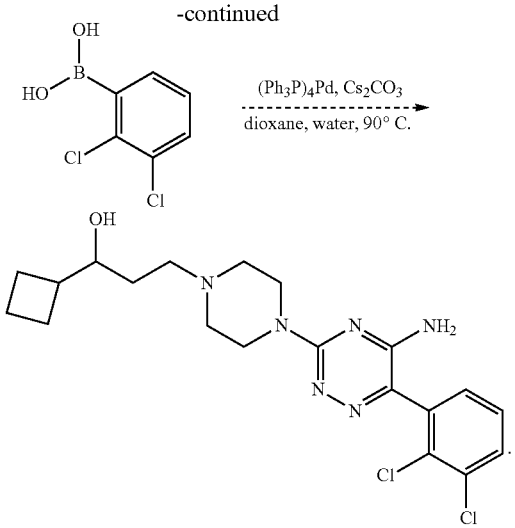

Step 1: Preparation of benzyl 4-(3-(methoxy(methyl)amino)-3-oxopropyl)piperazine-1-carboxylate is as follows.

A 100 mL flask is charged with N-methoxy-N-methylacrylamide (0.576 g, 5 mmol), dry tetrahydrofuran (20 mL) and benzyl piperazine-1-carboxylate (1.211 g, 5.50 mmol), and the mixture heated at 40° C. for 16 hours to afford a solution of benzyl 4-(3-(methoxy(methyl)amino)-3-oxopropyl)piperazine-1-carboxylate (1.677 g, 5.00 mmol) in tetrahydrofuran (10 mL), which is carried forward directly to the next step.

Step 2: Preparation of benzyl 4-(3-cyclobutyl-3-oxopropyl)piperazine-1-carboxylate is carried out as follows.

A solution of benzyl 4-(3-(methoxy(methyl)amino)-3-oxopropyl)piperazine-1-carboxylate (1.677 g, 5.00 mmol) in tetrahydrofuran (20 mL) is cooled to 0° C., whereupon a solution of cyclobutylmagnesium bromide, 0.5 M in tetrahydrofuran (15.0 mL, 7.50 mmol) is added dropwise. After consumption of starting Weinreb amide, the mixture is quenched with saturated ammonium chloride (10 mL), and partitioned between ethyl acetate (100 mL), and water (50 mL). The organic layer is washed with 0.5 M sodium dihydrogen phosphate (2×30 mL), 1 M sodium bicarbonate (20 mL), dried (sodium sulfate) and concentrated to afford crude benzyl 4-(3-cyclobutyl-3-oxopropyl)piperazine-1-carboxylate (assumed 5.00 mmol), which may be carried forward to the next step without further purification.

Step 3: Preparation of benzyl 4-(3-cyclobutyl-3-hydroxypropyl)piperazine-1-carboxylate is carried out as set forth below.

The crude benzyl 4-(3-cyclobutyl-3-oxopropyl)piperazine-1-carboxylate (assumed 5.00 mmol) is taken up in methanol (20 mL), and treated with sodium borohydride (0.95 g, 25 mmol) at room temperature for the appropriate time. After the reaction is complete, the mixture is partitioned between ethyl acetate (100 mL) and 1 M sodium carbonate (50 mL), and the organic layer is dried (sodium sulfate), filtered and concentrated. Purification by chromatography on silica may be expected to afford benzyl 4-(3-cyclobutyl-3-hydroxypropyl)piperazine-1-carboxylate.

Step 4: Preparation of 1-cyclobutyl-3-(piperazin-1-yl)propan-1-ol is as described below.

A solution of benzyl 4-(3-cyclobutyl-3-hydroxypropyl)piperazine-1-carboxylate (0.66 g, 2.0 mmol) and acetic acid (0.23 mL, 4.00 mmol) in ethanol (20 mL) is added to 10% palladium hydroxide on carbon (0.14 g, 0.10 mmol), and the mixture hydrogenated at room temperature for sufficient time to remove the carboxybenzyl group. The mixture is filtered and concentrated to afford crude 1-cyclobutyl-3-(piperazin-1-yl)propan-1-ol (assumed 2.00 mmol) which is carried forward to the next step without further purification.

Step 5: Preparation of 3-(4-(5-amino-6-chloro-1,2,4-triazin-3-yl)piperazin-1-yl)-1-cyclobutylpropan-1-ol is described below.

A 25 mL flask is charged with 1-cyclobutyl-3-(piperazin-1-yl)propan-1-ol, bis acetate salt (0.190 g, 0.60 mmol) and 3,6-dichloro-1,2,4-triazin-5-amine (0.082 g, 0.50 mmol), dry 1,4-dioxane (1 mL) and triethylamine (0.21 mL, 1.50 mmol), and the mixture heated in a microwave vial at 120° C. for 45 min. The mixture is concentrated and the residue partitioned between dichloromethane (50 mL) and 1 M sodium carbonate (25 mL). The organic layer is dried (sodium sulfate), filtered and concentrated to afford crude 3-(4-(5-amino-6-chloro-1,2,4-triazin-3-yl)piperazin-1-yl)-1-cyclobutylpropan-1-ol (assumed 0.50 mmol), which might be carried forward to the next step without further purification.

Step 6: Preparation of 3-(4-(5-amino-6-(2,3-dichlorophenyl)-1,2,4-triazin-3-yl)piperazin-1-yl)-1-cyclobutylpropan-1-ol is as follows.

A 20 mL septumed screw-capped vial is charged with tetrakis(triphenylphosphine)-palladium (116 mg, 0.10 mmol), capped with a septum, and purged with nitrogen, whereupon solutions of 3-(4-(5-amino-6-chloro-1,2,4-triazin-3-yl)piperazin-1-yl)-1-cyclobutylpropan-1-ol (assumed 0.50 mmol) in nitrogen sparged dioxane (7 mL) and (2,3-dichlorophenyl)boronic acid (191 mg, 1.00 mmol) and cesium carbonate (505 mg, 1.55 mmol) in nitrogen-sparged water (2.3 mL) are added, and the stirred mixture heated in a heat block at 90° C. for the appropriate time to consume the chlorotriazine. The mixture is concentrated and chromatographed to afford 3-(4-(5-amino-6-(2,3-dichlorophenyl)-1,2,4-triazin-3-yl)piperazin-1-yl)-1-cyclobutylpropan-1-ol.

Example 35

Preparation of Compound 87

Preparation of 6-(2,3-dichlorophenyl)-3-(4-(2,2,2-trifluoroethyl)piperazin-1-yl)-1,2,4-triazin-5-amine (Compound 87)

Compound 87

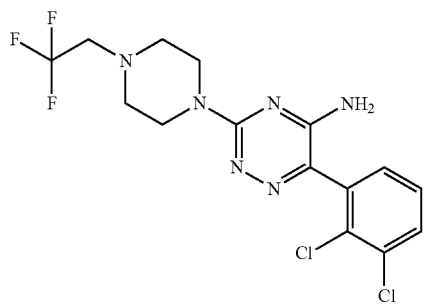

Preparation of 2,2,2-trifluoroethyl methanesulfonate: To an approximately 0.2 M solution of 2,2,2-trifluoroethanol (2 mL, 27.4 mmol) in DCM (100 mL) containing 20% excess TEA (2.25 mL, 32.9 mmol) at 0-10° C. was added a 10% excess mesyl chloride (1.5 ml, 0.961 mmol) over a period of 5-10 min. Stirring for an additional 10-15 min completed the reaction. The reaction mixture was transferred to a separatory funnel with the addition of more DCM. The mixture was extracted by cold 10% hydrochloric acid, saturated sodium bicarbonate solution and brine. Drying the solution followed by removal of solvent gave product as clear oil. $^1$H-NMR (500 MHz, DMSO-$d_6$) δ 3.362 (3H, s), 4.945 (2H, q, J=8.5 Hz).

Preparation of 6-(2,3-dichlorophenyl)-3-(4-(2,2,2-trifluoroethyl)piperazin-1-yl)-1,2,4-triazin-5-amine: 6-(2,3-Dichlorophenyl)-3-(piperazin-1-yl)-1,2,4-triazin-5-amine (50 mg, 0.154 mmol), 2,2,2-trifluoroethyl methanesulfonate (110 mg, 0.615 mmol) and triethylamine (86 μL) were dissolved in dioxane (3 mL). The mixture was heated at 200° C. for 6 h. Solvent was removed and residue was subject to flash column chromatography to give a product as white solid (10 mg, 99% purity, 16% yield). LC-MS [ESI-MH$^+$]: m/z 407; $^1$H-NMR (500 MHz, DMSO-$d_6$) δ 2.687 (4H, t, J=8.5 Hz), 3.239 (2H, q, J=10.0 Hz), 3.738 (4H, m), 6.510-6.800 (1H, br), 7.358 (1H, dd, $J_1$=1.5 Hz, $J_2$=8.0 Hz), 7.448 (1H, t, J=2.5 Hz), 7.710 (1H, dd, $J_1$=1.5 Hz, $J_2$=8.0 Hz).

The product was dissolved in methanol and 4 equiv. HCl aqueous solution was added. Methanol was removed under reduced pressure. The remaining solution was frozen and lyophilized for 2 days to afford hydrochloride salt.

Example 36

Preparation of Compound 88

Preparation of 6-(2,3-dichlorophenyl)-3-(4-(2-(trifluoromethoxy)ethyl)piperazin-1-yl)-1,2,4-triazin-5-amine (Compound 88)

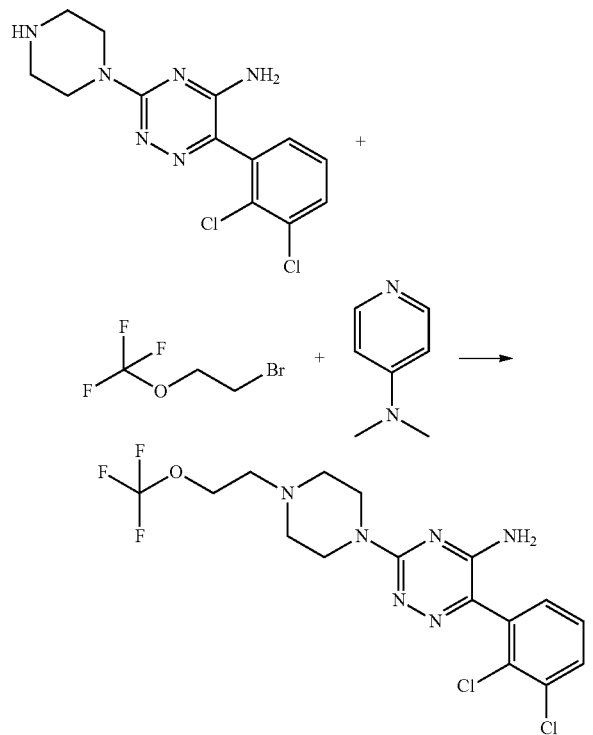

6-(2,3-dichlorophenyl)-3-(piperazin-1-yl)-1,2,4-triazin-5-amine (100 mg, 0.308 mmol), 1-bromo-2-(trifluoromethoxy)ethane (59.3 mg, 0.308 mmol), and N,N-dimethylpyridine (37.6 mg, 0.308 mmol) were dissolved in dioxane (5 mL). The solution was heated at 105° C. on microwave reactor for 3 h. Solids were filtered off and filtrate was concentrated on Rotavap under reduced pressure. The resulting residue was purified by silica gel column. Fractions containing desired product were collected, combined, and concentrated. After drying under high vacuo, product was afforded as white powder (24 mg, 95.2% purity, 18% yield). LC-MS [ESI-MH$^+$]: m/z 437. $^1$H-NMR (500 MHz, CDCl$_3$) δ 2.63 (4H, t, J=5.0 Hz), 2.77 (2H, t, J=5.5 Hz), 3.93 (4H, bs), 4.14 (2H, t, J=5.5 Hz), 4.79 (2H, bs), 7.36 (2H, m), 7.60 (1H, dd, $J_1$=5.0 Hz, $J_2$=2.0 Hz).

The product was dissolved in methanol and 4 equiv. HCl aqueous solution was added. Methanol was removed under reduced pressure. The remaining solution was frozen and lyophilized for 2 days to afford hydrochloride salt.

Example 37

Preparation of Compound 89

Preparation of 2-(4-(5-amino-6-(2,3-dichlorophenyl)-1,2,4-triazin-3-yl)piperazin-1-yl)propan-1-ol (Compound 89)

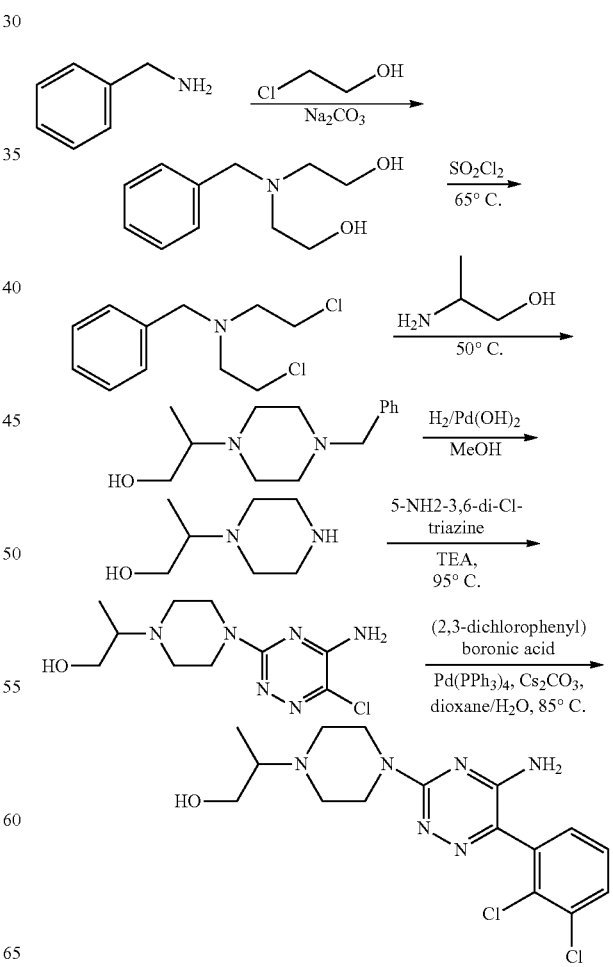

Preparation of 2,2-(benzylimino)diethanol: Benzyl amine (5.09 mL, 46.7 mmol) and 2-chloroethanol (9.38 mL, 140 mmol) were added together in a 250-mL flask. A solid sodium carbonate (7.42 g, 70 mmol) was added following with water (2 mL). The reaction was heating up in an oil bath to 112° C. for 3 hrs. The reaction mixture was cool down and co-evaporated with MeOH (30 mL×3). The residue was then dissolved in DCM and filtrated. The remaining residue was washed with DCM 3 times. The combined DCM was concentrated under reduced pressure and gave an oil-like product (4.78 g, 53% yield) after high vacuo drying. LC-MS (ESI, MH$^+$) 196.2; $^1$H NMR (500 MHz, CDCl$_3$) δ 2.74 (4H, t, J=5.0 Hz), 3.65 (4H, t, J=5.0 Hz), 3.72 (2H, s), 7.28-7.37 (5H, m).

Preparation of bis-(2-chloro-ethyl)-(4-benzyl)-amine: 2,2-(Benzylimino)diethanol (2.78 g, 14.2 mmol) was dissolved in DCM (10 mL) in a 100-mL flask. Thionyl chloride (3.63 mL, 49.8 mmol) was added slowly in several portions. The reaction was continued for overnight at ambient temperature to completion. The reaction was work up with saturated NaCl solution and extracted with DCM 50 (mL×3). The extracted DCM solution was dried over Na$_2$SO$_4$, filtrated, and concentrated under the reduced pressure. The residue was solidified to give a product (2.64 g, 80% yield) after high vacuo drying. $^1$H NMR (500 MHz, CDCl$_3$) δ 2.94 (4H, t, J=7.0 Hz), 3.52 (4H, t, J=7.0 Hz), 3.76 (2H, s), 7.28-7.36 (5H, m).

Preparation 2-(4-benzylpiperazin-1-yl)propan-1-ol: The bis-(2-chloro-ethyl)-(4-benzyl)-amine (1.01 g, 4.35 mmol) was dissolved in EtOH (40 mL) in a 250-mL flask. 2-Amino-propan-1-ol (347 mL, 4.35 mmol) and triethylamine (1.27 mL, 9.14 mmol) were added and the reaction was kept at 40° C. in an oil bath. After 24 hrs, the temperature was increased to 50° C. and the reaction was kept for another 24 hrs to complete. The reaction was quenched with saturated NH$_4$Cl solution and extracted with DCM (30 mL×3). The combined DCM solution was washed with NaCl saturated solution and dried over Na$_2$SO$_4$. After filtration, the solution was concentrated under the reduced pressure. The residue was purified by silica gel column to give a colorless product (252 mg, 25% yield) after the solvent was evaporated. The product solidified after high vacuo. LC-MS (ESI, MH$^+$) 235.4; $^1$H NMR (500 MHz, CDCl$_3$) δ 0.92 (3H, d, J=6.5 Hz), 2.45-2.58 (6H, b), 2.67-2.78 (2H, m), 2.78-2.85 (1H, m), 3.31 (1H, t, J=10.5 Hz), 3.42 (1H, dd, J=5.0, 10.5 Hz), 3.52 (2H, s), 7.26-7.33 (5H, m).

Preparation of 2-(piperazin-1-yl)propan-1-ol: To a solution of 2-(4-benzylpiperazin-1-yl)propan-1-ol (287 mg, 1.225 mmol) in methanol (10 mL) was added Pd(OH)$_2$/C (20% wt, 38 mg). The mixture was stirred vigorously under H$_2$ atmosphere for 15 h. LC-MS analysis indicated the starting material was consumed completely. Solids were filtered off and filtrate was concentrated on Rotavap under reduced pressure. The resulting residue (173 mg) was used directly for next step reaction without further purification. LC-MS [ESI-MH$^+$]: m/z 145. $^1$H-NMR (500 MHz, CDCl$_3$) δ 1.212 (3H, d, J=6.5 Hz), 2.534 (2H, m), 2.840 (2H, m), 2.868 (1H, m), 2.984 (2H, m), 3.047 (2H, m), 3.309 (1H, m), 3.430 (1H, m).

Preparation of 2-(4-(5-amino-6-chloro-1,2,4-triazin-3-yl)piperazin-1-yl)propan-1-ol: 2-(Piperazin-1-yl)propan-1-ol (171 mg, 1.185 mmol), 3,6-dichloro-1,2,4-triazin-5-amine (170 mg, 1.03 mmol) and triethylamine (0.402 ml, 2.89 mmol) were dissolved in p-dioxane (5 mL). The solution was heated at 95° C. on microwave reactor for 3 h. Solids were filtered off and filtrate was concentrated under reduced pressure. The resulting residue was subject to flash column chromatography. Yield product as yellowish solids (200 mg, 64% yield). LC-MS [ESI-MH$^+$]: m/z 273; $^1$H-NMR (500 MHz, DMSO-d$_6$) δ 1.253 (3H, d, J=6.5 Hz), 3.143 (2H, m), 3.376 (2H, m), 3.483 (2H, m), 3.606 (1H, m), 3.751 (1H, m), 4.578 (2H, d, J=13.0 Hz), 5.505 (1H, s), 7.480 (1H, br), 7.996 (1H, br).

Preparation of 2-(4-(5-amino-6-(2,3-dichlorophenyl)-1,2,4-triazin-3-yl)piperazin-1-yl)propan-1-ol: 2-(4-(5-amino-6-chloro-1,2,4-triazin-3-yl)piperazin-1-yl)propan-1-ol (80 mg, 0.293 mmol), 2,3-dichlorophenyl)boronic acid (84 mg, 0.44 mmol), cesium carbonate (191 mg, 0.587 mmol) were dissolved in 2 mL degassed p-dioxane/H$_2$O (v/v 3:1) and tetrakis(triphenylphosphine)palladium (85 mg, 0.073 mmol) was added under nitrogen atmosphere. The reaction mixture was stirred at 85° C. for 3 hours. Solids were filtered off and filtrate was concentrated under reduced pressure. The residue was subject to flash column chromatography to give a product as yellow solid (52 mg, 96.5% purity, 45.0% yield). LC-MS [ESI-MH$^+$]: m/z 383; $^1$H-NMR (500 MHz, DMSO-d$_6$) δ 0.945 (3H, d, J=6.5 Hz), 2.550 (4H, m), 2.610 (1H, m), 3.702 (4H, br), 4.026 (1H, m), 4.340 (1H, dd, J$_1$=4.5 Hz, J$_2$=6.5 Hz). 6.450-7.100 (1H, br), 7.358 (1H, dd, J$_1$=1.5 Hz, J$_2$=8.0 Hz), 7.448 (1H, t, J=2.5 Hz), 7.710 (1H, dd, J$_1$=1.5 Hz, J$_2$=8.0 Hz).

The product was dissolved in methanol and 4 equiv. HCl aqueous solution was added. Methanol was removed under reduced pressure. The remaining solution was frozen and lyophilized for 2 days to afford hydrochloride salt.

Example 38

Preparation of Compound 90

Preparation of 2-(4-(5-amino-6-(2,3-dichlorophenyl)-1,2,4-triazin-3-yl)piperazin-1-yl)-2-methylpropan-1-ol (Compound 90)

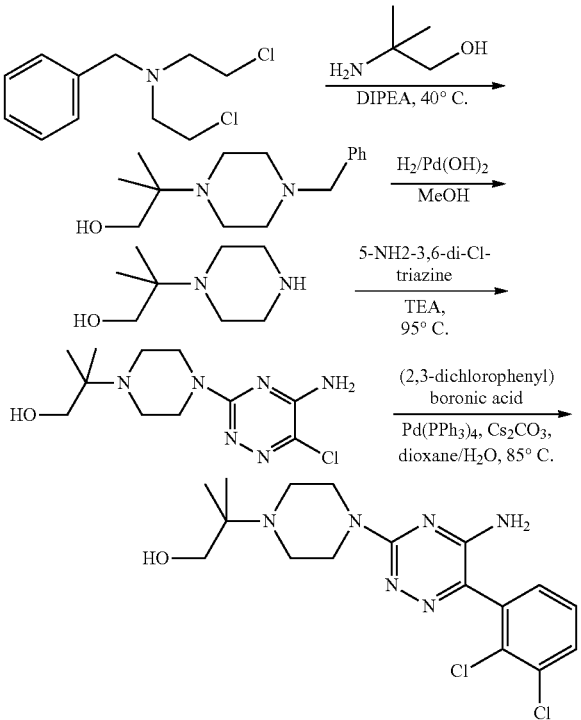

Preparation of 2-(4-benzylpiperazin-1-yl)-2-methylpropan-1-ol: The bis-(2-chloro-ethyl)-(4-benyl)-amine (1.83 g, 7.88 mmol) was dissolved in EtOH (75 mL) in a 250-mL flask. 2-Amino-2-methylpropan-1-ol (752 mL, 7.88 mmol) was added and the reaction was kept at 40° C. in an oil bath over 60 hrs. The reaction was quenched with saturated NH$_4$Cl solution and extracted with DCM (40 mL×3). The combined DCM solution was washed with NaCl saturated solution and dried over Na$_2$SO$_4$. After filtration, the solution was concentrated under the reduced pressure. The residue was purified on silica gel column to give a solidified product (503 mg, 26% yield) after evaporate the solvent and high vacuo drying. LC-MS (ESI, MH$^+$) 249.3; $^1$H NMR (500 MHz, CDCl$_3$) δ 1.03 (6H, s), 2.40-2.65 (8H, b), 3.32 (2H, s), 3.50 (2H, s), 7.25-7.32 (5H, m).

Preparation of 2-methyl-2-(piperazin-1-yl)propan-1-ol: To a solution of 2-(4-benzylpiperazin-1-yl)-2-methylpropan-1-ol (240 mg, 0.966 mmol) in methanol (10 mL) was added Pd(OH)$_2$/C (20% wt, 27 mg). The mixture was stirred vigorously under H$_2$ atmosphere for 15 h. LC-MS analysis indicated the starting material was consumed completely. Solids were filtered off and filtrate was concentrated on Rotavap under reduced pressure. The resulting residue (140 mg) was used directly for next step reaction without further purification. LC-MS [ESI-MH$^+$]: m/z 159.

Preparation of 2-(4-(5-amino-6-chloro-1,2,4-triazin-3-yl)piperazin-1-yl)-2-methyl-propan-1-ol: 2-Methyl-2-(piperazin-1-yl)propan-1-ol (140 mg, 0.885 mmol), 3,6-dichloro-1,2,4-triazin-5-amine (127 mg, 0.769 mmol) and triethylamine (0.32 ml, 2.31 mmol) were dissolved in dioxane (5 mL). The solution was heated at 95° C. on microwave reactor for 3 h. Solids were filtered off and filtrate was concentrated under reduced pressure. The resulting residue was subject to flash column chromatography to give a product as yellowish solids (124 mg, 56.2% yield). LC-MS [ESI-MH$^+$]: m/z 287; $^1$H-NMR (500 MHz, DMSO-d$_6$) δ 0.943 (6H, s), 2.568 (4H, t, J=5.0 Hz), 3.283 (2H, d, J=5.5 Hz), 3.595 (4H, t, J=5.0 Hz), 4.298 (1H, t, J=5.0 Hz), 7.302 (1H, br), 7.766 (1H, br).

Preparation of 2-(4-(5-amino-6-(2,3-dichlorophenyl)-1,2,4-triazin-3-yl)piperazin-1-yl)-2-methylpropan-1-ol: 2-(4-(5-Amino-6-chloro-1,2,4-triazin-3-yl)piperazin-1-yl)-2-methyl-propan-1-ol (120 mg, 0.418 mmol), (2,3-dichlorophenyl)boronic acid (120 mg, 0.628 mmol), cesium carbonate (273 mg, 0.837 mmol) were dissolved in 2 mL degassed p-dioxane/H$_2$O (v/v 3:1) and tetrakis(triphenylphosphine)palladium (121 mg, 0.105 mmol) was added under nitrogen atmosphere. The reaction mixture was stirred at 85° C. for 3 hours. LC-MS analysis indicated the reaction was complete. Solids were filtered off and filtrate was concentrated under reduced pressure. The residue was subject to flash column chromatography to give a product as white solid (60 mg, 95.5% purity, 32.0% yield). LC-MS [ESI-MH$^+$]: m/z 397; $^1$H-NMR (500 MHz, DMSO-d6) δ 0.945 (6H, s), 2.550 (4H, m), 2.610 (1H, m), 3.493 (1H, m), 3.702 (4H, br), 6.450-7.100 (1H, br), 7.358 (1H, dd, J$_1$=1.5 Hz, J$_2$=8.0 Hz), 7.448 (1H, t, J=2.5 Hz), 7.710 (1H, dd, J$_1$=1.5 Hz, J$_2$=8.0 Hz).

The product was dissolved in methanol and 4 equiv. HCl aqueous solution was added. Methanol was removed under reduced pressure. The remaining solution was frozen and lyophilized for 2 days to afford hydrochloride salt.

Example 39

Preparation of Compound 91

Preparation of (S)-1-((5-amino-6-(2,3-dichlorophenyl)-1,2,4-triazin-3-yl)amino)-3-(2,2,2-trifluoroethoxy)propan-2-ol (Compound 91)

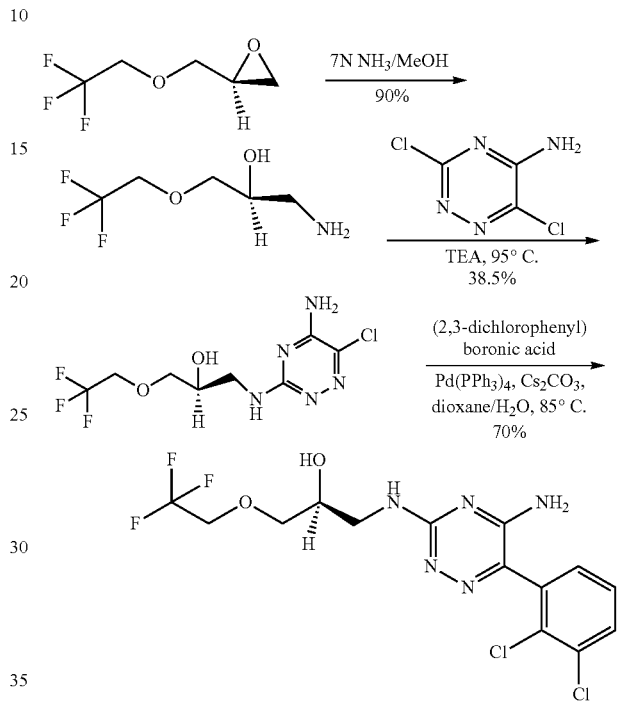

Preparation of (S)-1-amino-3-(2,2,2-trifluoroethoxy)propan-2-ol: (S)-2-((2,2,2-Trifluoroethoxy)methyl)oxirane (184 mg, 1.176 mmol) in THF (15 mL) was dropwise added to 7N ammonia in MeOH (1.7 ml, 11.8 mmol) in 1 h by a syringe pump. Then the mixture was stirred at ambient temperature for 2 days. Solvent was stripped off under reduced vacuum to give a liquid residue (184 mg, 90% yield). $^1$H-NMR (500 MHz, CDCl$_3$) δ 2.755 (1H, dd, J$_1$=7.5 Hz, J$_2$=17.5 Hz), 2.887 (1H, dd, J$_1$=4.0 Hz, J$_2$=13.0 Hz), 3.626 (1H, m), 3.709 (1H, m), 3.762 (1H, m), 3.901 (2H, q, J$_1$=8.5 Hz).

Preparation of (S)-1-((5-amino-6-chloro-1,2,4-triazin-3-yl)amino)-3-(2,2,2-trifluoroethoxy)propan-2-ol: (S)-1-Amino-3-(2,2,2-trifluoroethoxy)propan-2-ol (100 mg, 0.678 mmol), 3,6-dichloro-1,2,4-triazin-5-amine (286 mg, 1.733 mmol) and triethylamine (225 µL, 1.617 mmol) were dissolved in p-dioxane (5 mL). The solution was heated at 95° C. on microwave reactor for 3 h. Solids were filtered off and filtrate was concentrated under reduced pressure. The resulting residue was subject to flash column chromatography to give a product as yellowish solids (67 mg, 38.5% yield). LC-MS [ESI-MH$^+$]: m/z 302; $^1$H-NMR (500 MHz, CDCl$_3$) δ 3.502 (1H, m), 3.690 (oct, J$_1$=6.0 Hz, J$_2$=10.0 Hz, J$_3$=31.0 Hz), 3.906 (2H, q, J=9.0 Hz), 4.050 (1H, m), 5.513 (2H, br).

Preparation of (S)-1-((5-amino-6-(2,3-dichlorophenyl)-1,2,4-triazin-3-yl)amino)-3-(2,2,2-trifluoroethoxy)propan-2-ol: (S)-1-((5-Amino-6-chloro-1,2,4-triazin-3-yl)amino)-3-(2,2,2-trifluoroethoxy)propan-2-ol (67 mg, 0.222 mmol), (2,3-dichlorophenyl)boronic acid (85 mg, 0.444 mmol), cesium carbonate (145 mg, 0.444 mmol) were dissolved in 2 mL degassed p-dioxane/H₂O (v/v 3:1) and tetrakis(triphenylphosphine)palladium (121 mg, 0.105 mmol) was added under nitrogen atmosphere. The reaction mixture was stirred at 85° C. for 3 hours. LC-MS analysis indicated the reaction was completed. Solids were filtered off and filtrate was concentrated under reduced pressure. The residue was subject to flash column chromatography to give a product as white solids (70 mg, 95.3%, 76% yield). LC-MS [ESI-MH⁺]: m/z 412; ¹H-NMR (500 MHz, CDCl₃) δ 3.641 (1H, br), 3.709 (3H, m), 3.923 (2H, q, J=8.0 Hz), 4.115 (1H, m), 5.3-6.2 (1H, br), 7.400 (2H, m), 7.650 (1H, m).

The product was dissolved in methanol and 4 equiv. HCl aqueous solution was added. Methanol was removed under reduced pressure. The remaining solution was frozen and lyophilized for 2 days to afford hydrochloride salt.

Example 40

Preparation of Compound 92

Preparation of 3-(4-(5-amino-6-(2,3-dichlorophenyl)-1,2,4-triazin-3-yl)piperazin-1-yl)propane-1,2-diol (Compound 92)

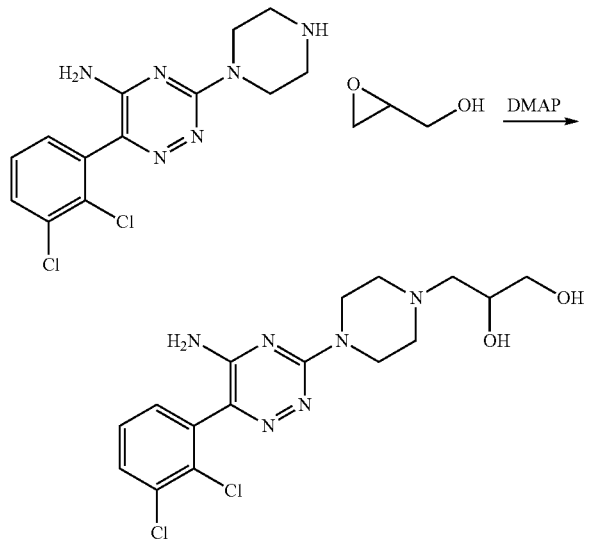

In a 50-mL flask, 6-(2,3-dichlorophenyl)-3-(piperazin-1-yl)-1,2,4-triazin-5-amine (101 mg, 0.311 mmol) was added in dioxane (1.5 mL). The oxirano-2-ylmethanol (0.206 mL, 3.11 mmol) and DMAP (7.61 mg, 0.062 mmol) were added. The reaction was heated up to 110° C. in an oil bath for 3 hrs. The solution was evaporated and the residue was purified by silica gel column. The product fractions were combined and solvent was evaporated to give an oil-like product (46.2 mg, 37% yield). RP-HPLC (betasil C18, 0.5 mL/min, 10-100% ACN in 10 min) 3.97 min (with purity 93.5%); LC-MS (ESI, MH⁺) 400.2; ¹H NMR (500 MHz, CDCl₃) δ 2.41-2.45 (1H, m), 2.54-2.56 (2H, m), 2.66 (1H, t, J=10.0 Hz), 2.75-2.78 (2H, m), 3.53-3.56 (1H, m), 3.76-3.82 (1H, m), 3.89-3.97 (5H, bm), 4.80 (2H, s), 7.35-7.39 (2H, m), 9.58-7.60 (1H, m).

The free base was dissolved in diluted HCl/MeOH (0.125 M) and stirried for 15 min before it was evaporated. The dried HCl salt was then re-dissolved in deionized water. After filtration, the clear water solution was cool down to freeze, and lyophilization to give the off-white solid product as hydrochloride salt.

Preparation of 2-((2-((5-amino-6-(2,3-dichlorophenyl)-1,2,4-triazin-3-yl)amino)ethyl)-sulfonyl)ethanol

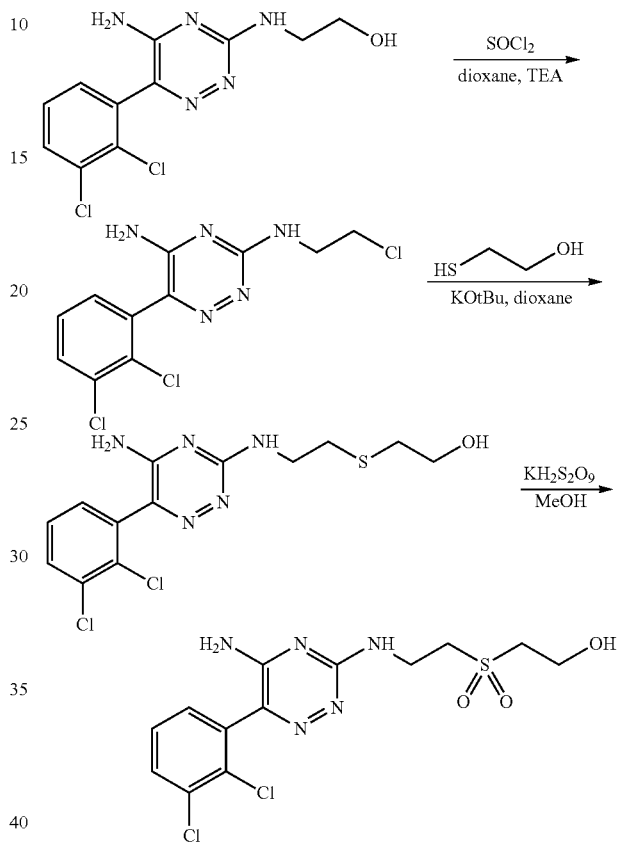

Preparation of N-3-(2-chloroethyl)-6-(2,3-dichlorophenyl)-1,2,4-triazine-3,5-diamine: In a 100-mL flask, 2-((5-amino-6-(2,3-dichlorophenyl)-1,2,4-triazin-3-yl)-amino) ethanol (504 mg, 1.68 mmol) was dissolved in dioxane (35 mL). Thionyl chloride (367 mL, 5.04 mmol) was added following by TEA (0.773 mL, 5.55 mmol). The reaction was let it going overnight before it was quenched with NH₄Cl saturated solution and extracted with DCM 50 (mL×3). The extracted DCM solution was dried over Na₂SO₄, filtrated, and concentrated under the reduced pressure. The residue solidified to give a product (475 mg, 89% yield) after high vacuo drying. RP-HPLC (betasil C18, 0.5 mL/min, 10-100% ACN in 10 min) 5.50 min; LC-MS (ESI, MH⁺) 319.6; ¹H NMR (500 MHz, CDCl₃) δ 1.33 (2H, d, J=6.5 Hz), 3.66-3.70 (2H, m), 7.45-7.48 (2H, m), 7.72-7.74 (2H, m).

Preparation of 2-((2-((5-amino-6-(2,3-dichlorophenyl)-1,2,4-triazin-3-yl)amino)ethyl)thio)ethanol: In a 100-mL flask, N-3-(2-chloroethyl)-6-(2,3-dichlorophenyl)-1,2,4-triazine-3,5-diamine (80 mg, 0.250 mmol) was dissolved in BuOH (1.8 mL). 2-mercaptoethanol (140 μL, 2.0 mmol) was added together with KOtBu (2.0 mL, 1M). The reaction mixture was heated up to 50° C. and completed in 40 min by LC-MS. The reaction was stopped by mixing with saturated NH₄Cl (80 mL) and extracted with DCM (30 mL×3). The combined DCM solution was dried over $Na_2SO_4$, filtrated, and concentrated under the pressure to give a product (32 mg, 36% yield). RP-HPLC (betasil C18, 0.5 mL/min, 10-100% ACN in 10 min) 5.15 min; LC-MS (ESI, MH$^+$) 360.0; $^1$H NMR (500 MHz, CDCl$_3$) δ 2.82-2.86 (2H, m), 2.89-2.92 (2H, t, J=6.0 Hz), 3.82 (2H, t, J=6.0 Hz), 3.94 (2H, t, J=5.5 Hz), 7.37-7.39 (2H, m), 7.59-7.61 (1H, m).

Preparation of 2-((2-((5-amino-6-(2,3-dichlorophenyl)-1,2,4-triazin-3-yl)amino)ethyl)sulfonyl)ethanol: 2-((2-((5-Amino-6-(2,3-dichlorophenyl)-1,2,4-triazin-3-yl)amino)ethyl)thio)ethanol (286 mg, 0.794 mmol) was dissolved in MeOH (5 mL) in 100-mL flask. Oxone (1.46 g, 2.38 mmol) was added and the reaction was kept at room temperature for overnight. The residue was dissolved in saturated NH$_4$Cl solution and extracted with DCM (20 mL×3). The combined DCM solution was dried over $Na_2SO_4$ and after filtration, it was concentrated under the pressure. The residue was purified on a silica gel column to give a product (70 mg, 22.5% yield). RP-HPLC (betasil C18, 0.5 mL/min, 10-100% ACN in 10 min) 6.72 min; LC-MS (ESI, MH$^+$) 392.0; $^1$H NMR (500 MHz, D$_2$O) δ 3.16 (1H, t, J=1.5 Hz), 3.21 (2H, t, J=9.5 Hz), 3.42 (2H, t, J=6.5 Hz), 3.83-3.86 (4H, m), 7.28-7.34 (2H, m), 7.59-7.61 (1H, m).

Example 41

Preparation of Compound 93

Preparation of 2-((2-((5-amino-6-(2,3-dichlorophenyl)-1,2,4-triazin-3-yl)amino)propyl)sulfonyl)ethanol (Compound 93)

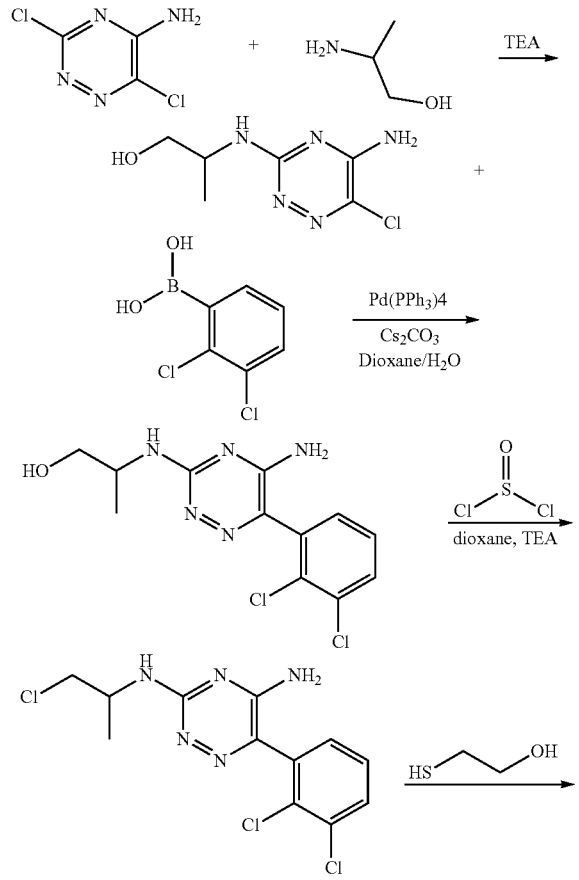

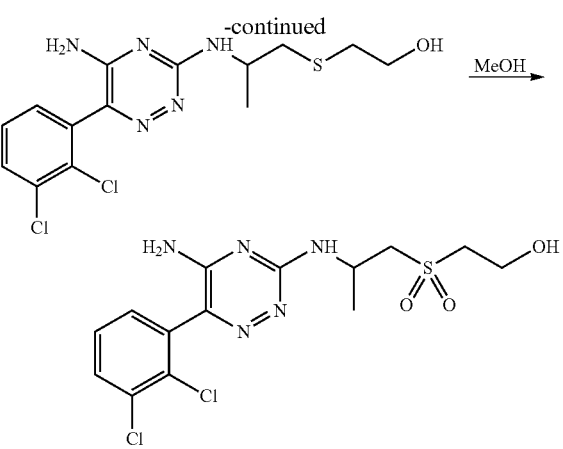

Preparation of 2-((5-amino-6-chloro-1,2,4-triazin-3-yl)amino)propan-1-ol: 5-Amino-3,6-dichloro-1,2,4-triazine (1.5 g, 9.09 mmol) was dissolved in dioxane (60 mL) at room temperature. Triethylamine (1.9 mL, 13.6 mmol) was added, followed by addition of 2-aminopropan-1-ol (1.37 g, 18.2 mmol). The resulting mixture was stirred at 95° C. for overnight. After overnight reaction, the mixture was cooled down to room temperature, filtered, and the organic solution was concentrated. The residue was purified on silica gel column to afford a solid product (1.93 g). LC-MS (ESI, MH$^+$) 413; HPLC: >85%

Preparation of 2-((5-amino-6-(2,3-dichlorophenyl)-1,2,4-triazin-3-yl)amino)propan-1-ol: (2,3-dichlorophenyl)boronic acid (1.93 g, 10.1 mmol), 2-((5-amino-6-chloro-1,2,4-triazin-3-yl)amino)propan-1-ol (1.37 g, 6.73 mmol), cesium carbonate (4.38 g, 13.5 mmol) were dissolved in 150 mL degassed mixture of dioxane/H$_2$O (3:1) and tetrakis(triphenylphosphine) palladium (1.49 g, 1.68 mmol) was added under nitrogen atmosphere. The reaction mixture was stirred at 85° C. for 4 hours. Insoluble was filtered and solvent was evaporated to dryness at 50° C. The residue was purified on silica gel column to afford a solid product (1.54 g, 73% yield). RP-HPLC (betasil C18, 0.5 mL/min, 10-100% ACN in 10 min) 4.57 min (with purity 97.4%); LC-MS (ESI, MH$^+$) 314; $^1$H NMR (500 MHz, CDCl$_3$) δ 1.29-1.31 (2H, d), 3.49-3.68 (1H, m), 3.80-3.83 (1H, m), 4.17 (1H, bs), 4.92 (2H, br), 7.36-7.38 (2H, m), 7.57-7.60 (1H, m).

Preparation of N3-(1-chloropropan-2-yl)-6-(2,3-dichlorophenyl)-1,2,4-triazine-3,5-diamine: 2-((5-amino-6-(2,3-dichlorophenyl)-1,2,4-triazin-3-yl)amino)propan-1-ol (150 mg, 0.478 mmol) was dissolved in 15 mL of dioxane. Thionyl chloride (0.135 mL, 1.43 mmol) was added slowly and the reaction was stirred at room temperature for 30 min. Triethylamine (0.20 mL, 1.57 mmol) was added. The reaction mixture was stirred at room temperature for overnight. Solvent was evaporated. Residue was dissolved in 60 mL of dichloromethane and 5 mL of methanol, washed with saturated NH$_4$Cl (10 ml×3). Dichloromethane solution was dried over anhydrous sodium sulfate, concentrated, and solvent was evaporated to dryness to afford 150 mg of solid product. RP-HPLC (betasil C18, 0.5 mL/min, 10-100% ACN in 10 min) 5.89 min (with purity 87.3%); LC-MS (ESI, MH$^+$) 332.

Preparation of 2-((2-((5-amino-6-(2,3-dichlorophenyl)-1,2,4-triazin-3-yl)amino)propyl)thio)ethanol: N3-(1-chloropropan-2-yl)-6-(2,3-dichlorophenyl)-1,2,4-triazine-3,5-diamine (150 mg, 0.451 mmol)) was dissolved in 4 mL of 1.0 N potassium tert-butoxide solution. 2-Mercaptoethanol (0.253 mL) was added. The reaction mixture was heated at 50° C. for 2.5 hrs using microwave reactor. Reaction mixture was mixed with sat MH₄Cl (50 mL), was extracted with dichloromethane (20 mL×3). Combined dichloromethane was dried with anhydrous MgSO₄, filtered, and solvent was evaporated to dryness. The residue was purified on silica gel to afford 30 mg product as solid. LC-MS (ESI, MH⁺) 374.

Preparation of 2-((2-((5-amino-6-(2,3-dichlorophenyl)-1,2,4-triazin-3-yl)amino)propyl)sulfonyl)ethanol: 2-((2-((5-amino-6-(2,3-dichlorophenyl)-1,2,4-triazin-3-yl)amino)propyl)thio)ethanol (30 mg, 0.08 mmol) was dissolved in 5 mL of mixture methanol-deionized water. Oxone monopersulfate compound (73.9 mg, 0.24 mmol) was added. The mixture was stirred at room temperature for overnight. Solvent was concentrated. The residue was purified with on silica gel to afford product (14 mg). LC-MS (ESI, MH⁺) 406.

Preparation of 2-((2-((5-amino-6-(2,3-dichlorophenyl)-1,2,4-triazin-3-yl)amino)propyl)sulfonyl)ethanol.HCl salt: 2-((2-((5-amino-6-(2,3-dichlorophenyl)-1,2,4-triazin-3-yl)amino)propyl)sulfonyl)ethanol (14 mg) was dissolved in 15 mL of 0.5N HCl aqueous. The aqueous was dried by lyophlization to afford 15 mg of 2-((2-((5-amino-6-(2,3-dichlorophenyl)-1,2,4-triazin-3-yl)amino)propyl)sulfonyl) ethanol as hydrochloride salt. RP-HPLC (betasil C18, 0.5 mL/min, 10-100% ACN in 10 min) 4.81 min (with purity 98.4%); LC-MS (ESI, MH⁺) 406; ¹H NMR (500 MHz, D₂O) δ 1.42-1.44 (2H, d), 3.48-3.67 (4H, m), 3.80-3.89 (1H, m), 4.03-4.10 (2H, m), 7.43-7.50 (2H, m), 7.76-7.78 (1H, dd).

Example 42

Preparation of Compound 94

Preparation of (R)-1-(4-(5-amino-6-(2,3-dichlorophenyl)-1,2,4-triazin-3-yl)-piperazin-1-yl)-3-(2,2,2-trifluoroethoxy)-propan-2-ol (Compound 94)

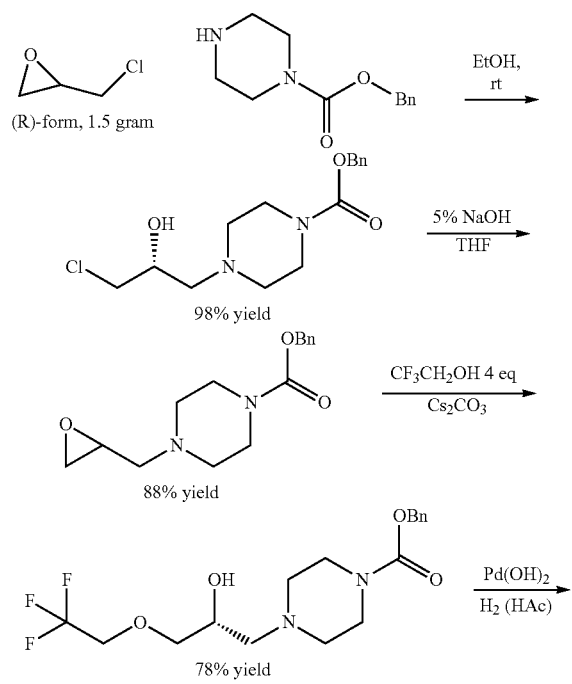

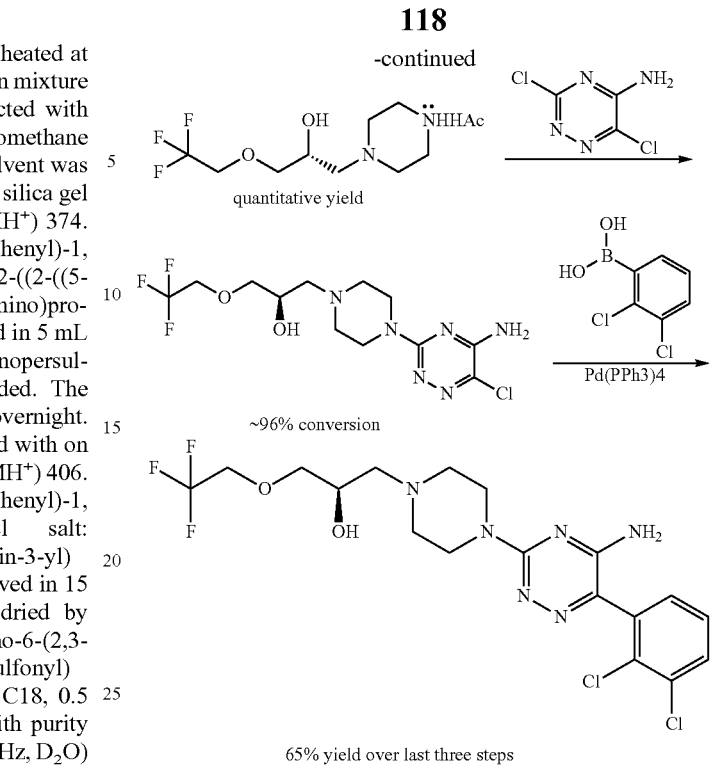

Preparation of (R)-benzyl-4-(3-chloro-2-hydroxypropyl)-piperazine-1-carboxylate: 1-Z-Piperazine (2.21 mL, 11.44 mmol) was dissolved in EtOH (48 mL) at room temperature in a 250-mL flask. (R)-epichlorohydrin (1.26 mL, 16.02 mmol) was added. The reaction was kept at ambient temperature for overnight and then with elevated temperature at 50° C. for another 5 hrs. The ethanol solution was evaporated and the residue was dissolved in saturated NH₄Cl solution and extracted with DCM (50 mL×3). The combined DCM phase was washed with saturated NaCl solution before it was dried over Na₂SO₄. After filtration, the solution was concentrated under the reduced pressure. The residue was dried overnight to give an oil-like product (3.52 grams, 98% yield). No further purification was applied. RP-HPLC (betasil C18, 0.5 mL/min, 10-100% ACN in 10 min) ELSD signal 4.52 min; LC-MS (ESI, MH⁺) 313.2; ¹H NMR (500 MHz, CDCl₃) δ 2.45 (2H, bs), 2.53 (2H, d, J=7.0 Hz), 2.63 (2H, bs), 3.51-3.64 (6H, m), 3.94-3.99 (1H, m), 5.15 (2H, s), 7.33-7.39 (5H, m).

Preparation of (R)-benzyl-4-(oxiran-2-ylmethyl)-piperazine-1-carboxylate: The above residue (3.52 g, 11.25 mmol) was dissolved in THF (30 mL) in a 250-mL flask. A NaOH solution was prepared using 4.0 gram of solid NaOH dissolving in water (50 mL). After cool down to room temperature, this basic solution was added to the above THF solution with vigorously stirring. LC-MS indicated the reaction was completed in 20 min. The above basic solution was then diluted with NH₄Cl saturated solution (150 mL) and extracted with DCM (50 mL×3). The combined DCM phase was washed with saturated NaCl solution (80 mL) and carefully dried over Na₂SO₄. After filtration, the solution was concentrated under the reduced pressure. The residue was set up for high vacuo for overnight and gave 2.73 grams (88%) of epoxide product. No further purification was applied. RP-HPLC (betasil C18, 0.5 mL/min, 10-100% ACN in 10 min) ELSD signal 4.14 min; LC-MS (ESI, MH⁺) 277.2; ¹H NMR (500 MHz, CDCl₃) δ 2.28 (1H, dd, J=13.0, 7.0 Hz), 2.49 (2H, bs), 2.51 (1H, dd, J=5.0, 3.0 Hz), 2.57-2.62 (2H, m), 2.78-2.82 (2H, m), 3.10-3.13 (1H, m), 3.57 (4H, 6s), 5.15 (2H, s), 7.33-7.40 (5H, m).

Preparation of (R)-benzyl-4-(2-hydroxy-3-(2,2,2-trifluoroethoxy)-propyl)-piperazine-carboxylate: The above epoxide product (2.29 g, 8.27 mmol) was dissolved in DMF (42 mL) in a 250-mL flask. Trifluoroethanol (1.89 mL, 24.8 mmol) and cesium carbonate (1.62 g, 4.96 mmol) were added. The reaction was set up at 100° C. for the 1" hours and more trifluoroethanol (630 µL) was added before the temperature was increased to 110° C. for 3 hrs. After cool down, the solution was quenched with saturated NH$_4$Cl (150 mL) and extraction with DCM (50 mL×3). The combined DCM phase was washed with saturated NaCl solution (80 mL) before it was dried over Na$_2$SO$_4$. After filtration, the solution was concentration under the reduced pressure. The DMF solvent was evaporated and the residue was further dried under high vacuo for overnight. The residue was then re-dissolved in DCM and purified on silica gel column. After high vacuo for overnight, an oil-like product (2.44 g, 78% yield) was obtained. -HPLC (betasil C18, 0.5 mL/min, 10-100% ACN in 10 min) ELSD signal 5.78 min; LC-MS (ESI, MH$^+$) 377.2; $^1$H NMR (500 MHz, CDCl$_3$) δ 2.42 (1H, dd, J=12.5, 4.0 Hz), 2.43 (2H, bs), 2.52 (1H, dd, J=12.5, 10.0 Hz), 2.63 (2H, bs), 3.51-3.55 (4H, m), 3.63 (1H, dd, J=10.0, 5.0 Hz), 3.72 (1H, dd, J=5.0, 3.5 Hz), 3.90-3.97 (3H, m), 5.15 (2H, s), 7.34-7.39 (5H, m).

Preparation of (R)-1-(piperazin-1-yl)-3-(2,2,2-trifluoroethoxy)-propan-2-ol.HAc: The above Cbz-protected product (2.44 g, 6.48 mmol) was dissolved in ethanol (65 mL) in a 250-mL flask. Acetic acid (742 µL, 12.97 mmol) was added. The flask was purged with N$_2$ once before Pd(OH)$_2$ catalysis (244 mg, 20% wt) was added. A H$_2$ balloon was prepared with a three way joint. The reaction system was exchanged with H$_2$ twice before the reaction started with vigorously stirring. The deprotection completed in 30 min with gravity filtration and the catalyst residue was washed with MeOH 3 times. The combined alcohol solution was evaporated under reduced pressure and an oil-like product 2.2 gram (quantitative yield) was obtained after overnight high vacuo drying. RP-HPLC (betasil C18, 0.5 mL/min, 10-100% ACN in 10 min) ELSD signal 1.26 min; LC-MS (ESI, MH$^+$) not available; $^1$H NMR (500 MHz, D$_2$O) δ 1.89 (3H, s, HAc), 2.57 (2H, d, J=6.0 Hz), 2.80-2.83 (4H, 6 m), 3.25 (4H, t, J=5.0 Hz), 3.63 (1H, dd, J=10.5, 6.0 Hz)), 3.73 (1H, dd, J=10.5, 3.5 Hz), 4.03 (2H, q, J=9.0 Hz), 4.04 (1H, m).

Preparation of (R)-1-(4-(5-amino-6-chloro-1,2,4-triazin-3-yl)-piperazin-1-yl)-3-(2,2,2-trifluoroethoxy)propan-2-ol: The above HAc salt product was dissolved in dioxane (7 mL) in a 100-mL flask. 3,6-dichloro-1,2,4-triazine-5-amine (324 mg, 1.96 mmol) and TEA (684 µL, 4.91 mmol) were added to the reaction solution. The reaction was set up at 85° C. and LC-MS indicated the completeness of reaction in two hours. The reaction residue was evaporated and overnight high vauco drying before next step reaction. RP-HPLC (betasil C18, 0.5 mL/min, 10-100% ACN in 10 min) 5.78 min; LC-MS (ESI, MH$^+$) 377.2; $^1$H NMR (500 MHz, CDCl$_3$) δ 2.42 (1H, dd, J=12.5, 4.0 Hz), 2.43 (2H, bs), 2.52 (1H, dd, J=12.5, 10.0 Hz), 2.63 (2H, bs), 3.51-3.55 (4H, m), 3.63 (1H, dd, J=10.0, 5.0 Hz), 3.72 (1H, dd, J=5.0, 3.5 Hz), 3.90-3.97 (3H, m), 5.15 (2H, s), 7.34-7.39 (5H, m).

Preparation of (R)-1-(4-(5-amino-6-(2,3-dichlorophenyl)-1,2,4-triazin-3-yl)-piperazin-1-yl)-3-(2,2,2-trifluoroethoxy)-propan-2-ol: The above residue (1.55 g, 4.18 mmol) was suspended in a mixture solution of dioxane (65 mL) and water (15 mL) in the original 250-mL flask. (2,3-Dichlorophenyl)-boronic acid (997 mg, 5.23 mmol) and cesium carbonate (2.48 g, 7.53 mmol) were added to the reaction solution. After purged with N$_2$ once, the tetrakis(triphenylphosphine)palladium catalyst (966 mg, 0.836 mmol) was added with another 2 min vacuo bubbling before the reaction was started warm up to 85° C. in oil bath. Reaction in 3 hrs before the solution was evaporated under reduce pressure and the residue was then dissolved in methanol and azotropic evaporation 3 times until it looks dry. High vauco drying the residue overnight before it was dissolved in methanol 5 mL and filtration. The residue was washed with methanol (3 mL×2). The solution was evaporated and the residue was purified on silica gel column. The product fractions were combined and the solvent was evaporated and high vacuo gives the off-white product 869 mg (43.2% yield). RP-HPLC (betasil C18, 0.5 mL/min, 10-100% ACN in 10 min) 4.82 min (with purity 98.2%); LC-MS (ESI, MH$^+$) 481.0; $^1$H NMR (500 MHz, CDCl$_3$) δ 2.45 (1H, dd, J=12.0, 3.0 Hz), 2.52-2.58 (3H, m), 2.72-2.74 (2H, m), 3.64 (1H, dd, J=10.0, 5.0 Hz), 3.73 (1H, dd, J=10.0, 3.5 Hz), 3.91-3.97 (7H, m), 4.86 (2H, bs), 7.34-7.38 (2H, m), 7.56-7.58 (1H, m). The chiral column: CHIRALCEL OD-H (Lot No. ODH0CD-SA010); Column Size: 0.46 cm (I.D)×15 cm (L); Mobile Phase: n-Hexane/Ethanol=90/10 (v/v); Flow rate: 1.0 mL/min; Injection: 10 µL; Detection: UV 220 nm; Column Temp: 35° C.; Program: Isocratic. The product enantiomeric purity 89.1% ee.

Preparation of (R)-1-(4-(5-amino-6-(2,3-dichlorophenyl)-1,2,4-triazin-3-yl)-piperazin-1-yl)-3-(2,2,2-trifluoroethoxy)-propan-2-ol. 2HCl: The above purified product (1.56 g, 3.24 mmol) was dissolved in methanol (30 mL) in a 500-mL flask. The HCl/methanol (1.25M, 13 mL, 16.2 mmol) was diluted with methanol (100 mL) and was added to the above solution. After stirring for 5 min, the methanol was slowly evaporated under the reduce pressure. The residue was high vacuo dried before it was redissolved in deionized water (160 mL). The cloudy solution was vacuo filtrated before it was freeze. It was then lyophilized over 5 days before the off-white solid product (1.67 g, 93% yield) was obtained. RP-HPLC (betasil C18, 0.5 mL/min, 10-100% ACN in 10 min) 4.83 min; LC-MS (ESI, MH$^+$) 481.0; $^1$H NMR (500 MHz, CDCl$_3$) δ 3.21-3.26 (2H, m), 3.0-3.8 (6H, bs), 3.62 (1H, dd, J=10.5, 5.0 Hz), 3.68 (1H, dd, J=10.5, 4.5 Hz), 3.90-3.98 (3H, m), 4.21-4.25 (2H, m), 7.30 (1H, d, J=7.5 Hz), 7.35 (1H, t, J=7.5 Hz), 7.62 (1H, d, J=8.0 Hz).

The S-form HCl salt product (Compound 95) was prepared using a similar strategy. The spectra of the product is identical to the R-form product.

Example 43

Preparation of Compound 96

Preparation of (R)-1-(4-(5-amino-6-(2,3-dichlorophenyl)-1,2,4-triazin-3-yl)piperazin-1-yl)-3-methoxypropan-2-ol (Compound 96)

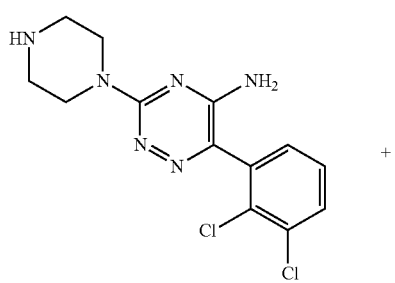

121

-continued

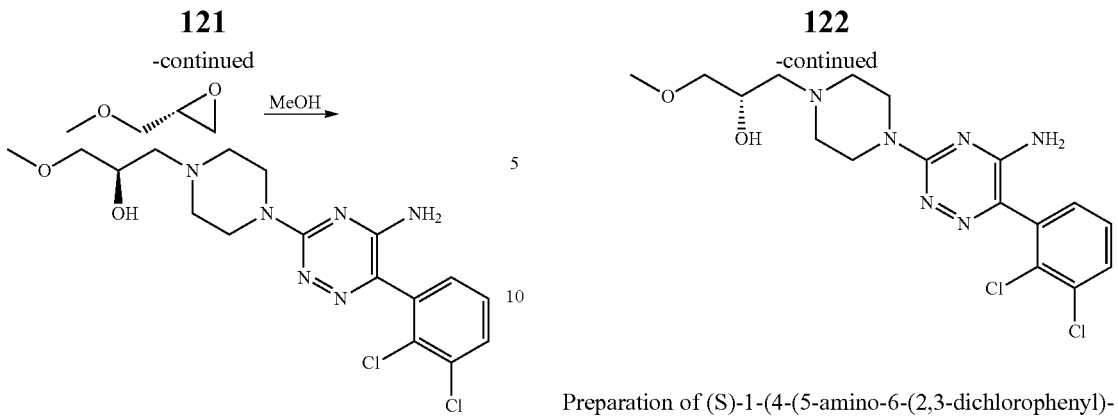

Preparation of (R)-1-(4-(5-amino-6-(2,3-dichlorophenyl)-1,2,4-triazin-3-yl)piperazin-1-yl)-3-methoxypropan-2-ol:
Piperazine-lamotrigine (100 mg), (R)-(−)-Glycidyl methyl ether (54 mg) were dissolved in 1.5 mL of methanol. The reaction was carried on microwave reactor at 90° C. for 60 minutes. A sample was checked by LC-MS and showed the reaction was completed. The reaction mixture was concentrated and purified on silica gel column. Fractions were combined to give product (75 mg) after overnight vacuo. LC-MS (ESI, MH$^+$) 413; HPLC: >97%

The above product was dissolved in 10 mL methanol, 0.8 mL of 1.25M HCl in methanol was added. The mixture was stirred at ambient temperature for 10 min. Solvent was evaporated to dryness; the residue was dissolved in 10 mL of deionized water. The solution was filtrated before it was freeze and lyophilized for two days to give the final hydrochloride salts: 80 mg. RP-HPLC (betasil C18, 0.5 mL/min, 10-100% ACN in 10 min) 4.33 min (with purity 97.4%); LC-MS (ESI, MH$^+$, free base) 413; $^1$H NMR (500 MHz, D$_2$) δ 3.34-3.36 (2H, m), 3.38 (3H, s), 3.40-3.59 (8H, m, bs), 4.29-4.33 (1H, m), 7.43-7.51 (2H, m), 7.76-7.78 (1H, dd).

Example 44

Preparation of Compound 97

Preparation of (S)-1-(4-(5-amino-6-(2,3-dichlorophenyl)-1,2,4-triazin-3-yl)piperazin-1-yl)-3-methoxypropan-2-ol (Compound 97)

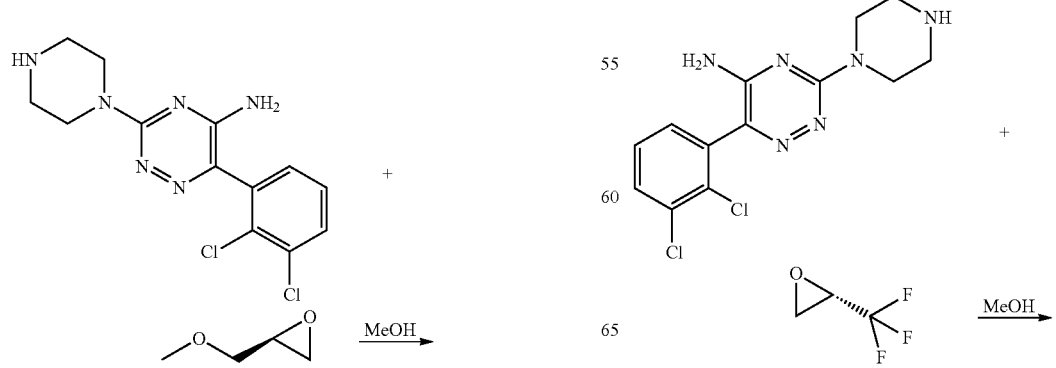

122

-continued

Preparation of (S)-1-(4-(5-amino-6-(2,3-dichlorophenyl)-1,2,4-triazin-3-yl)piperazin-1-yl)-3-methoxypropan-2-ol:
Piperazine-lamotrigine (1.3 g), (R)-(−)-Glycidyl methyl ether (704 mg) were dissolved in 15 mL of methanol. The reaction was carried on microwave reactor at 90° C. for 60 minutes. A sample was checked by LC-MS and showed the reaction was completed. The reaction mixture was concentrated and purified on silica gel column to obtain 694 mg of product. LC-MS (ESI, MH$^+$) 413; HPLC: >95%

The above product was dissolved in 70 mL methanol, 6.7 mL of 1.25M HCl in methanol was added. The mixture was stirred at ambient temperature for 10 min. Solvent was evaporated to dryness, residue was dissolved in 20 mL of deionized water. The solution was filtrated before it was freeze and was lyophilized for two days to give the final hydrochloride salts: 725 mg. RP-HPLC (betasil C18, 0.5 mL/min, 10-100% ACN in 10 min) 4.27 min (with purity 95.9%); LC-MS (ESI, MH$^+$) 413; $^1$H NMR (500 MHz, D$_2$) δ 3.34-3.36 (2H, m), 3.38 (3H, s), 3.40-3.59 (8H, m), 4.29-4.33 (1H, m), 7.43-7.51 (2H, m), 7.76-7.78 (1H, dd).

Example 45

Preparation of Compound 98

Preparation of (S)-1-(4-(5-amino-6-(2,3-dichlorophenyl)-1,2,4-triazin-3-yl)piperazin-1-yl)-3-methoxypropan-2-ol (Compound 98)

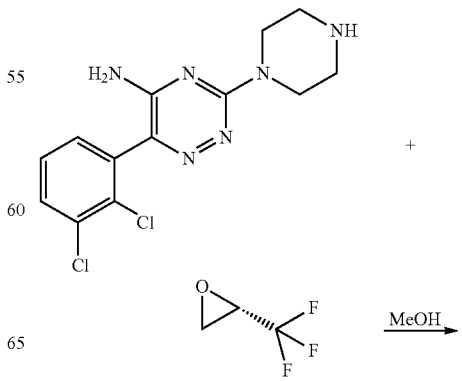

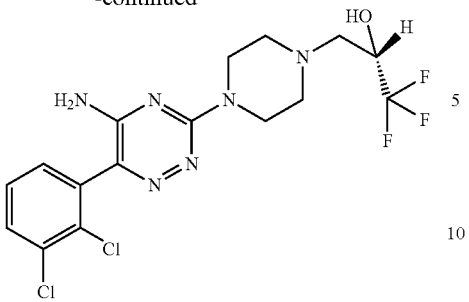

Preparation of (S)-1-(4-(5-amino-6-(2,3-dichlorophenyl)-1,2,4-triazin-3-yl)piperazin-1-yl)-3-methoxypropan-2-ol: Piperazine-lamotrigine (750 mg, Comppound 79), (S)-(–)-3,3,3-Trifluoro-1,2-epoxypropane (465 mg) were dissolved in 10 mL of methanol. The reaction was carried on microwave reactor at 95° C. for 45 minutes. A sample was checked by LC-MS and showed the reaction was completed. The reaction mixture was concentrated and purified on silica gel column to give 667 mg of product. LC-MS (ESI, MH$^+$) 437; $^1$H NMR (500 MHz, CDCl$_3$) δ 2.73-2.85 (6H, m), 4.01 (4H, bs), 4.22 (1H, bs), 4.76 (2H, m), 7.34-7.36 (2H, m), 7.56-7.59 (1H, m).

The above product (667 mg) was dissolved in 60 mL methanol, 6.1 mL of 1.25M HCl in methanol was added. The mixture was stirred at ambient temperature for 10 min. Solvent was evaporated to dryness, residue was dissolved in 34 mL of deionized water (about 20% wt). The solution was filtrated before it was freeze and was lyophilized for two days to give the final HCl salts: 719 mg. RP-HPLC (betasil C18, 0.5 mL/min, 10-100% ACN in 10 min) 4.60 min (with purity 95.8%); LC-MS (ESI, MH$^+$, free base) 437; $^1$H NMR (500 MHz, D$_2$) δ 3.50-3.62 (6H, m), 4.13 (4H, bs), 4.72-4.7 (1H, m), 7.43-7.51 (2H, m), 7.76-7.78 (1H, m).

Example 46

Preparation of Compound 99

Preparation of 6-(2,3-dichlorophenyl)-3-(3-(2,2,2-trifluoroethoxy)azetidin-1-yl)-1,2,4-triazin-5-amine.HCl salt (Compound 99)

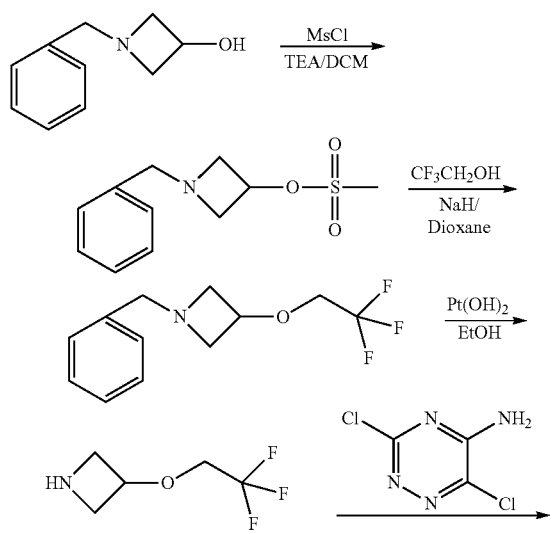

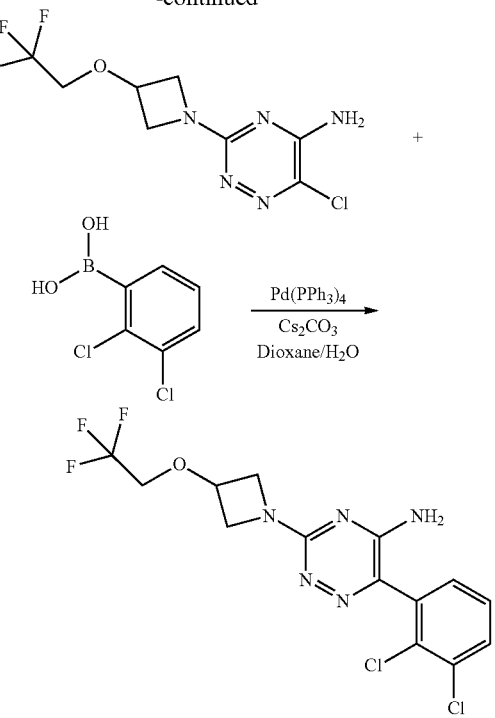

Preparation of 1-benzylazetidin-3-yl methanesulfonate: 1-Benzylazetidin-3-ol (1.0 g, 6.13 mmol) and triethylamine (1.7 mL, 12.25 mmol) were dissolved in 100 ml of DCM. Methanesulfonyl chloride (0.50 ml, 6.43 mmol) was added, the mixture was stirred at room temperature for overnight. After overnight reaction, the mixture was washed with 15 mL of saturated NH$_4$Cl aqueous solution, dried with MgSO$_4$, filtered, and solvent was evaporated to dryness to afford product (1.47 g). LC-MS (ESI, MH$^+$) 242; $^1$H NMR (500 MHz, CDCl$_3$) δ 3.01 (3H, s), 3.23-3.27 (2H, dd), 3.67 (2H, s), 3.66-3.74 (2H, dd), 5.07-5.12 (1H, m), 7.25-7.34 (5H, m).

Preparation of 1-benzyl-3-(2,2,2-trifluoroethoxy)azetidine: 2,2,2-Trifluoroethanol (3.06 g, 30.6 mmol) was dissolved in 50 mL of dioxane. NaH (0.735 mg, 18.4 mmol) was added to the 2,2,2-trifluoroethanol solution and stirred for 30 minutes. To the mixture of 2,2,2-trifluoroethanol and NaH, 1-benzylazetidin-3-yl methanesulfonate (1.47 g, 6.12 mmol) was added and stirred at 80° C. under nitrogen atmosphere for 4 hours. After cooling to room temperature, insoluble was filtered and solvent was evaporated to dryness at 50° C. The residue was purified on silica gel column to afford 0.82 g product as liquid in 56% yield. LC-MS (ESI, MH$^+$) 246; $^1$H NMR (500 MHz, CDCl$_3$) δ 3.07 (2H, s), 3.69 (4H, br), 3.37-3.83 (2H, q), 4.27-4.33 (1H, m), 7.28-7.44 (5H, m)

Preparation of 3-(2,2,2-trifluoroethoxy)azetidine: 1-Benzyl-3-(2,2,2-trifluoroethoxy)azetidine (620 mg) was dissolved in 62 mL of ethanol, Pt(OH)$_2$ (62 mg) and acetic acid (0.15 mL) were added to ethanol solution. The mixture was hydrogenated using hydrogen balloon for 2 days. After filtration, solvent was evaporated to dryness and the residue was dried in vacuum to obtain product (395 mg) as liquid. While the LC-MS showed that 1-benzyl-3-(2,2,2-trifluoroethoxy)azetidine was not detected, the product will be used directly for next reaction.

Preparation of 6-chloro-3-(3-(2,2,2-trifluoroethoxy)azetidin-1-yl)-1,2,4-triazin-5-amine: A vial was charged with 3,6-dichloro-1,2,4-triazin-5-amine (135 mg, 0.816 mmol) and triethylamine (0.34 mL, 2.45 mmol), 3-(2,2,2-trifluoroethoxy)azetidine in 4 mL of dioxane. The mixture was heated at 95° C. for 3 hours using microwave reactor. Solvent was evaporated to dryness, residue was used for next step reaction without purification. LC-MS (ESI, MH+) 284

Preparation of 6-(2,3-dichlorophenyl)-3-(3-(2,2,2-trifluoroethoxy)azetidin-1-yl)-1,2,4-triazin-5-amine.HCl salt: (2,3-dichlorophenyl) boronic acid (234 mg, 1.24 mmol), 6-chloro-3-(3-(2,2,2-trifluoroethoxy)azetidin-1-yl)-1,2,4-triazin-5-amine (231 mg, 0.82 mmol), cesium carbonate (532 mg, 1.63 mmol) were dissolved in 20 mL degassed mixture of dioxane/H$_2$O (3:1) and tetrakis (triphenylphosphine)palladium (236 mg, 0.21 mmol) was added under nitrogen atmosphere. The reaction mixture was stirred at 85° C. for one hour. Insoluble was filtered and solvent was evaporated to dryness at 50° C. The residue was purified on silica gel to afford product (204 mg) as solid. The product was further purified by dissolving in 30 mL of 0.5 N HCl aqueous and 10 mL of dichloromethane, after separation, aqueous was washed with dichloromethane (10 ml×2), then HCl aqueous was lyophilized for overnight to afford product (120 mg) as hydrochloride salt. RP-HPLC (betasil C18, 0.5 mL/min, 10-100% ACN in 10 min) 6.24 min (with purity 99.3%); LC-MS (ESI, MH+) 394; $^1$H NMR (500 MHz, D$_2$) δ 3.98-4.04 (2H, q), 4.14-4.18 (2H, dd), 4.45-4.49 (2H, dd), 4.67-4.68 (1H, m), 7.33-7.40 (2H, m), 7.66-7.68 (1H, dd).

Example 47

Preparation of Compound 100

Synthesis of 3-N-mPEG$_3$-lamotrigine-d$_3$ (Compound 100)

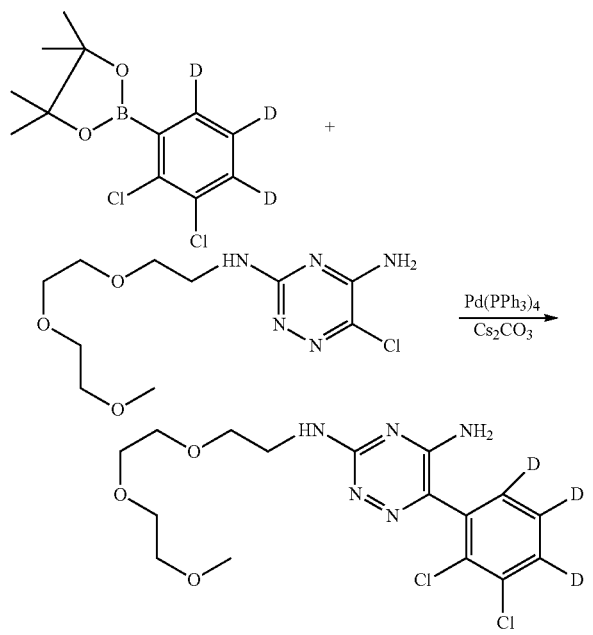

Synthesis of 5-amino-3,6-dichloro-1,2,4-triazine

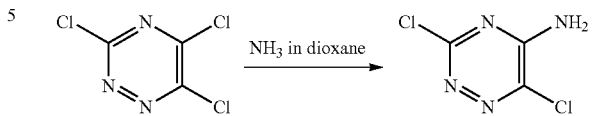

3,5,6-Trichloro-1,2,4-triazine (4.6114 g, 24.28 mmol) was dissolved in THF (100 mL) at room temperature. And then triethylamine (5.0 mL, 35.9 mmol) was added. The mixture was cooled to 0° C., ammonia in dioxane (0.5 M, 51 mL, 25.5 mmol) was added. The mixture was stirred at 0° C. for 30 min, at room temperature for 5 h. The mixture was filtered to remove the solid. The solid was washed with ethyl acetate. The combined organic solution was concentrated. The crude mixture was mixed with about 50 mL of ethyl acetate and warmed up, and then cooled to room temperature. The solid was collected and washed with ether to afford the first partial product. The solution was concentrated to remove all of solvents. The residue was mixed with about 5 ml of ethyl acetate, the solid was collected and dried. The solution was purified with flash column chromatography on silica gel using 35-100% ethyl acetate/hexanes to afford 3rd part of solid. The total of product was 3.8998 g and the yield was 97%. LC-MS: 165.1 (MH+/z).

Synthesis of 2-(2,3-dichloro-phenyl-4,5,6-d$_3$)-4,4,5, 5-tetramethyl-1,3,2-dioxaborolane

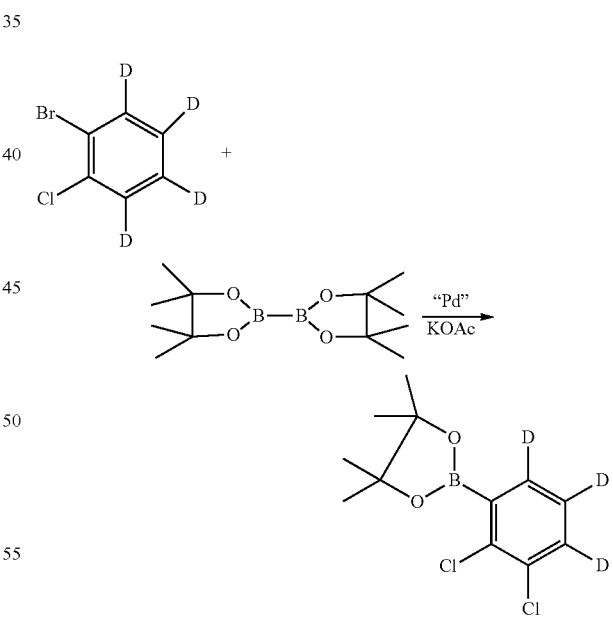

A mixture of 1,2-dichloro-3-bromobenzene-d$_3$ (0.3535 g, 1.53 mmol), bis(pinacolato)diboron (0.590 g, 2.30 mmol), and potassium acetate (0.4649 g, 4.74 mmol) in anhydrous DMSO (14 mL) was stirred at room temperature. And then 1,1'-[bis(bis-phenylphosphino) ferrocene]dichloropalladium (II) (0.057 g, 0.078 mmol) was added. The mixture was degassed with nitrogen, stirred at 95° C. for 3 h. The mixture was cooled to room temperature and added into water (150 mL). The mixture was extracted with ethyl acetate (3×50 mL). The combined organic solution was washed with saturated sodium chloride solution (100 mL), dried over anhydrous sodium sulfate, and concentrated. The crude material was purified with flash column chromatography on silica gel with 1-10% ethyl acetate/hexane to afford 0.241 g of product as solid with slight green color in 57% yield.

Synthesis of 5-amino-6-chloro-3-mPEG$_3$-amino-1,2,4-triazine

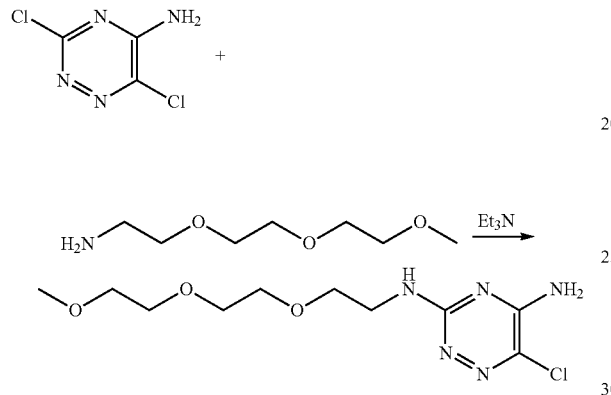

5-Amino-3,5-dichloro-1,2,4-triazine (1.460 g, 8.85 mmol) was dissolved in dioxane (30 mL) at room temperature. Triethylamine (2.7 mL, 19.37 mmol) was added, followed by addition of mPEG$_3$-NH$_2$ (1.9812 g, 12.14 mmol). The resulting mixture was stirred at 95° C. for 7 h. The mixture was cooled to room temperature, filtered to remove the white solid and the solid was washed with ethyl acetate. The combined organic solution was concentrated and purified with flash column chromatography on silica gel (1-10% methanol/dichloromethane) to afford 2.1236 g of product as solid. The yield was 82%.

$^1$H-NMR (500 MHz, CDCl$_3$): 3.691-3.654 (m, 6H, 3CH$_2$), 3.625-3.594 (m, 6H, 3CH$_2$), 3.436 (s, 3H, CH$_3$). LC-MS: 292.1 (MH$^+$/z).

Synthesis of 3-N-mPEG$_3$-lamotrigine-d$_3$: A mixture of 2-(2,3-dichloro-phenyl-4,5,6-d$_3$)-4,4,5,5-tetramethyl-1,3,2-dioxaborolane (241 mg, 0.87 mmol), 5-amino-6-chloro-3-mPEG$_3$-amino-1,2,4-triazine (0.2527 g, 0.87 mmol), cesium carbonate (0.630 g, 1.91 mmol) and tetrakis(triphenylphosphine)palladium (54.1 mg, 0.047 mmol) in dioxane/water (9 mL/3 mL) was purged with nitrogen and then heated at 95° C. for 22 h. The mixture was concentrated under reduced pressure to remove the organic solvent. The residue was mixed with brine, extracted with dichloromethane (2×100 mL). The combined organic solution was washed with brine, dried over anhydrous sodium sulfate, concentrated. The crude mixture was purified with column chromatography on silica gel using 1-10% methanol/ethyl acetate to afford 138.8 mg of product. The yield was 43%. $^1$H-NMR (500 MHz, DMSO-d$_6$): 6.90 (br, 3H), 3.56-3.50 (m, 8H, 4CH$_2$), 3.46-3.43 (m, 4H, 2CH$_2$), 3.24 (s, 3H, CH$_3$). LC-MS: 405.2 (MH$^+$/z).

Example 48

Preparation of Compound 101

Synthesis of 5-hydroxy lamotrigine (Compound 101)

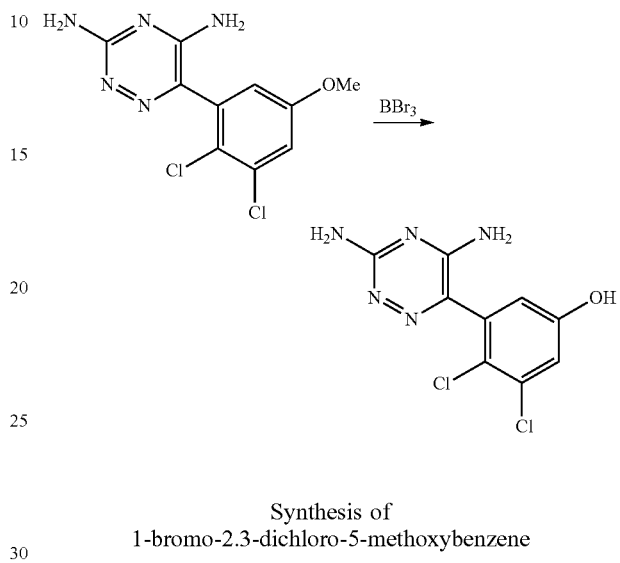

Synthesis of 1-bromo-2,3-dichloro-5-methoxybenzene

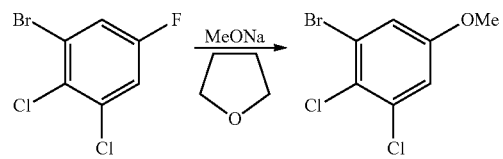

1-Bromo-2,3-dichloro-5-fluorobenzene (1.0401 g, 4.27 mmol) was dissolved in toluene (30 mL), and then the solvent was removed under reduced pressure. The residue was dried under high vacuum for a few minutes. Anhydrous THF (15 mL) was added to dissolve the starting material. And then sodium methanoxide (0.9873 g, 17.36 mmol) was added. The mixture was heated at 75° C. for 4.5 h, cooled to room temperature. The mixture was quenched with saturated ammonium chloride solution, concentrated to remove THF. The remaining mixture was extracted with ethyl acetate (4×150 mL). The organic solution was washed with brine, dried over anhydrous sodium sulfate, concentrated to dryness to afford 1.0188 g of product as white solid in 93% yield. $^1$H-NMR (500 MHz, CDCl$_3$): 7.109 (d, J=3.0 Hz, 1H), 6.988 (d, J=3.0 Hz, 1H), 3.786 (s, 3H).

Synthesis of 2-(2,3-dichloro-5-methoxyphenyl)-4,4,5,5-tetramethyl-1,3,2-dioxaborolane

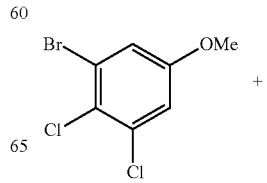

-continued

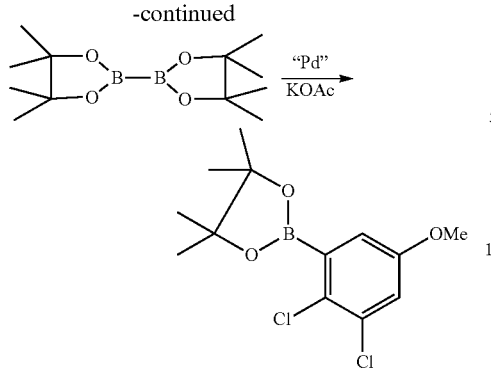

A mixture of 1-bromo-2,3-dichloro-5-methoxybenzene (9.3601 g, 36.6 mmol), bis (pinacolato)diboron (13.3339 g, 52.0 mmol), potassium acetate (10.7268 g, 109 mmol) and 1,1'-[bis(bisphenylphosphino)ferrocene]dichloropalladium (II) (1.32 g, 1.804 mmol) in anhydrous DMSO (100 mL) was stirred at 95° C. for 5.5 h. The mixture was cooled to room temperature and poured into ice. The mixture was extracted with ethyl acetate (3×200 mL). The combined organic solution was washed with saturated sodium chloride solution (3×150 mL), dried over anhydrous sodium sulfate, and concentrated. The residue was purified with flash column chromatography on silica gel by using ethyl acetate/hexane to afford 9.6970 g of product in 88% yield. $^1$H-NMR (500 MHz, CDCl$_3$): 7.092 (d, J=3.0 Hz, 1H), 7.050 (d, J=3.0 Hz, 1H), 3.794 (s, 3H), 1.368 (s, 9H).

Synthesis of 5-hydroxy lamotrigine: 5-Methoxy-lamotrigine (80.6 mg, 0.282 mmol) was mixed with anhydrous dichloromethane (15 mL) at room temperature, and then 0.85 mL of boron tribromide solution 1.0 M in dichloromethane (0.85 mmol) was added. The resulting mixture was stirred at room temperature for 1.5 h. More of boron tribromide solution (0.7 mL) was added. The mixture was stirred at room temperature for 19 h. More of boron tribromide solution (2.4 mL) was added. The mixture was stirred at room temperature for 4 h. More of boron tribromide solution (1.0 mL) was added. The mixture was stirred for 20 h. The mixture was quenched with methanol. The mixture was concentrated to remove all of organic solvents. The remaining mixture was extracted with dichloromethane (3×30 mL). The aqueous solution was collected and lyophilized. The residue was stirred in ammonia (~3 mL) for 18 h. A few drops of methanol were added. The mixture was stirred for 15 min. The mixture was concentrated to remove all of solvents. The material was purified with flash column chromatography on silica gel using 1-30% methanol/dichloro methane. The fractions were collected and concentrated. About 25 mg of material was obtained. The material was dissolved in ~5 mL of THF, ethylenediamine (0.85 mL, 12.74 mmol) was added. A white suspension was obtained. The mixture was stirred at room temperature for 3 h, concentrated to remove all of solvents. The material was purified with flash column chromatography on silica gel using 1-30% methanol/dichloromethane. The fractions were collected and concentrated to afford 20.8 mg of product as white solid. $^1$H-NMR (500 MHz, DMSO-d$_6$): 10.231 (s, 1H), 7.048 (s, 1H), 6.714 (s, 1H), 6.397 (s, 2H). LC-MS: 272.0 (MH$^+$/z).

Example 49

Preparation of Compound 102

Synthesis of 3-N-piperazinyl-5'-O-mPEG$_3$-lamotrigine (Compound 102)

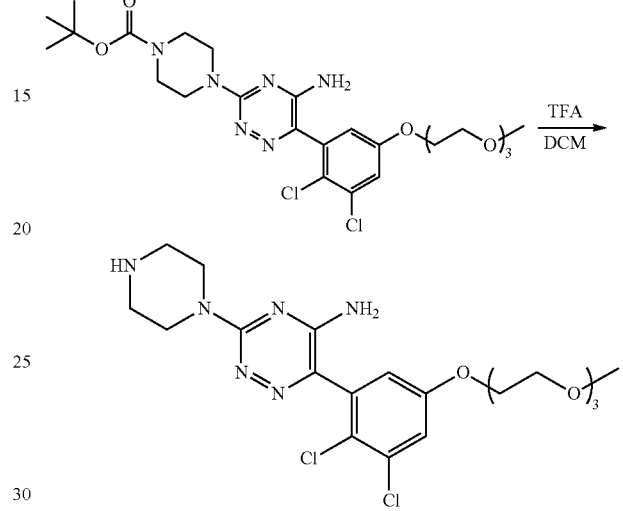

Synthesis of 3-N-piperazinyl-5'-O-mPEG$_3$-lamotrigine: 3-N-(4-Boc-piperazinyl)-5'-O-mPEG$_3$-lamotrigine (112.6 mg) dissolved in dichloromethane (5 mL), trifluoroacetic acid (3 mL) was added. The mixture was stirred at room temperature for 5.5 h. The mixture was diluted with dichloromethane, washed with saturated potassium carbonate, brine, dried over anhydrous sodium sulfate, concentrated. The residue was purified with NH-column using 0-10% methanol/dichloromethane as solvents to afford product (75 mg). $^1$H NMR (500 MHz, Chloroform-d) δ 7.138 (d, J=3.0 Hz, 1H, Ar—H), 6.920 (d, J=3.0 Hz, 1H, Ar—H), 5.279 (br, 2H, NH$_2$), 4.111 (t, J=4.5 Hz, 2H, CH$_2$), 3.853 (br, 4H, 2 CH$_2$), 3.817 (t, J=5.0 Hz, 2H, CH$_2$), 3.698-3.680 (m, 2H, 2CH$_2$), 3.648-3.603 (m, 4H, 2CH$_2$), 3.526-3.507 (m, 2H, CH$_2$), 3.352 (s, 3H, CH$_3$), 2.946 (t, 4H, J=5.0 Hz, 2CH$_2$). LC-MS: 487.0 (MH$^+$/z).

Preparation of reactants was carried out as follows.

Synthesis of 5-amino-6-chloro-3-N-(4-N-Boc-piperazinyl)amino-1,2,4-triazine

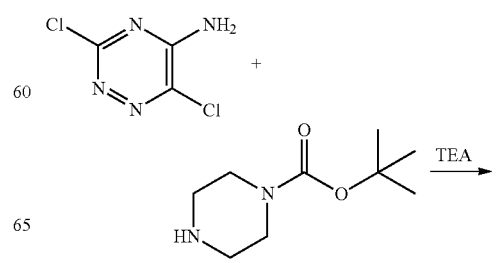

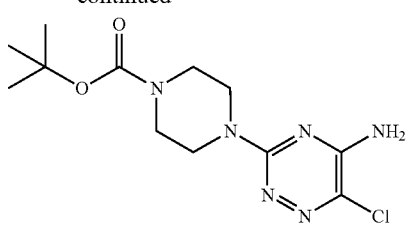

A vial was charged with 5-amino-3,6-dichloro-1,2,4-triazine (466 mg, 2.82 mmol) and triethylamine (1.0 mL, 7.17 mmol), t-Boc-piperazine (0.5675 g, 2.96 mmol) in dioxane. The mixture was heated at 95° C. for 1.5 h using microwave. The mixture was cooled to room temperature, filtered and the white solid was washed with ethyl acetate. The organic solution was concentrated. The residue was purified with flash column chromatography on silica gel using 1-10% methanol/dichloromethane to afford 872.4 mg product as solid in 98% yield. $^1$H NMR (500 MHz, Chloroform-d) δ 5.38 (br, 2H), 3.76-3.68 (m, 4H), 3.44 (dd, J=6.3, 3.9 Hz, 4H), 1.42 (s, 9H). LC-MS: 315.0 (MH$^+$/z).

Synthesis of
1-bromo-5-O-mPEG$_3$-2,3-dichlorobenzene

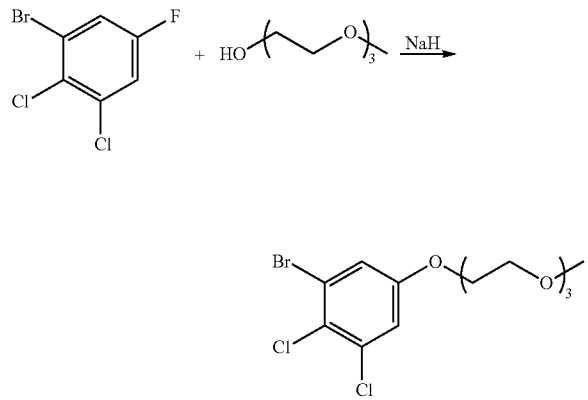

1-Bromo-2,3-dichloro-5-fluorobenzene (1.4618 g, 5.99 mmol) and mPEG$_3$-OH (1.1097 g, 6.76 mmol) was mixed with toluene (25 mL) and removed the solvent. The remaining material was dried under high vacuum for a few minutes. The mixture was dissolved in anhydrous THF (20 mL). 60% Sodium hydride (0.3549 g, 8.87 mmol) was added. The resulting mixture was heated at 75° C. for 3 h. The mixture was cooled to room temperature. Saturated ammonium chloride aqueous solution was added to quench the reaction. The mixture was concentrated to remove the organic solvent. The remaining mixture was extracted with dichloromethane (3×20 mL). The combined organic solution was washed with brine, dried over anhydrous sodium sulfate, concentrated. The residue was purified with biotage flash column using 15-100% ethyl acetate/hexane to afford the product (2.057 g, yield: 88%). $^1$H NMR (500 MHz, Chloroform-d) δ 7.17 (d, J=2.9 Hz, 1H), 7.05 (d, J=2.8 Hz, 1H), 4.16-4.07 (m, 2H), 3.89-3.83 (m, 2H), 3.77-3.65 (m, 6H), 3.60-3.55 (m, 2H), 3.41 (s, 3H).

Synthesis of 2-(2,3-dichloro-5-O-mPEG$_3$-phenyl)-4,4,5,5-tetramethyl-1,3,2-dioxaborolane

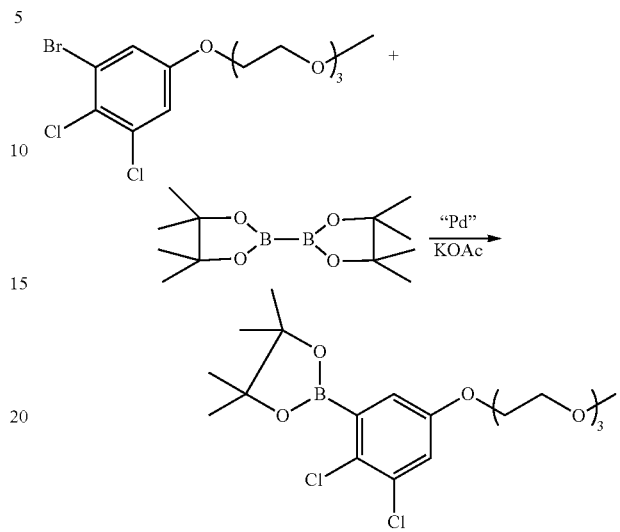

A mixture of 1-bromo-2,3-dichloro-5-O-mPEG$_3$-benzene (1.7749 g, 4.57 mmol), bis(pinacolato)diboron (1.7712 g, 6.91 mmol), potassium acetate (1.420 g, 14.47 mmol) and 1,1'-[bis(diphenylphosphino)ferrocene]dichloropalladium (II) (0.1737 g, 0.24 mmol) in anhydrous DMSO (30 mL) was degassed with nitrogen, stirred at 95° C. for 5 h. The mixture was cooled to room temperature and poured into ice. The mixture was extracted with ethyl acetate (3×50 mL). The combined organic solution was washed with saturated sodium chloride solution (50 mL), dried over anhydrous sodium sulfate, and concentrated. The residue was separated with flash column chromatography on silica gel using ethyl acetate/hexane to afford product (1.8639 g, yield: 94%). $^1$H NMR (500 MHz, Chloroform-d) δ 7.103 (d, J=3.0 Hz, 1H), 7.06 (d, J=3.0 Hz, 1H), 4.14-4.05 (m, 2H), 3.82 (m, 2H), 3.73-3.69 (m, 2H), 3.66-3.62 (m, 4H), 3.54-3.52 (m, 2H), 3.36 (s, 3H), 1.34 (s, 9H).

Synthesis of 3-N-(4-Boc-piperazinyl)-5-O-mPEG$_3$-lamotrigine

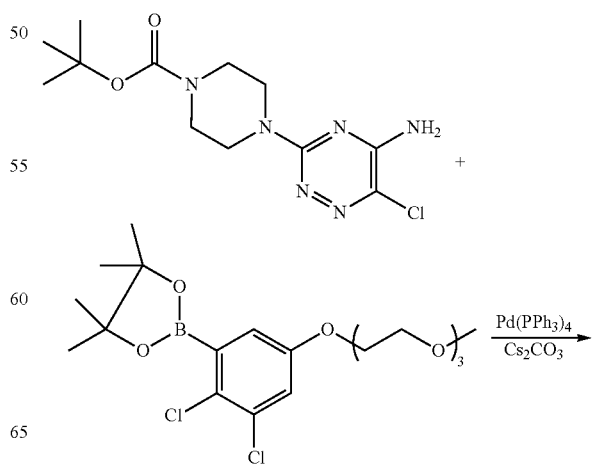

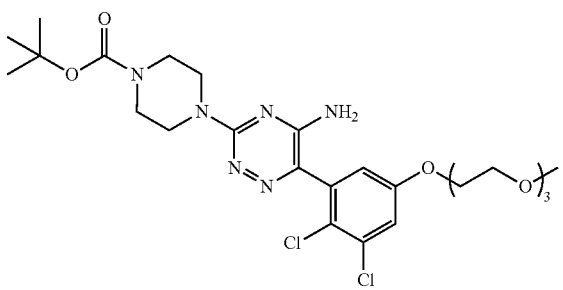

A mixture of 2-(2,3-dichloro-5-O-mPEG$_3$-phenyl)-4,4,5,5-tetramethyl-1,3,2-dioxaborolane (664.8 g, 1.53 mmol), the 3-(N-Boc-piperazinyl)amino-5-amino-6-chloro-1,2,4-triazine (287.9 mg, 0.92 mmol) was dissolved in dioxane (10 mL). A solution of cesium carbonate (831.3 mg, 2.53 mmol) in water (2 mL) was added. And then tetrakis(triphenylphosphine)palladium (56.3 mg, 0.053 mmol) was added. The mixture was purged with nitrogen for a few minutes. The mixture was heated at 85° C. for 4 h 15 min using microwave. The mixture was concentrated under reduced pressure to dryness. The residue was mixed with water, extracted with dichloromethane (4×20 mL). The organic solution was concentrated. The residue was purified with flash column chromatography to afford the product (178.2 mg, yield: 33%). $^1$H NMR (500 MHz, Chloroform-d) δ 7.14 (d, J=2.9 Hz, 1H), 6.91 (d, J=2.9 Hz, 1H), 4.82 (br, 2H), 4.11 (dd, J=5.7, 3.6 Hz, 2H), 3.84-3.80 (m, 6H), 3.71-3.58 (m, 6H), 3.51 (q, J=5.2 Hz, 6H), 3.35 (s, 3H), 1.47 (s, 9H). LC-MS: 315.0 (MH$^+$/z).

Example 50

Preparation of Compound 103

Synthesis of 3-N-(4'-N-mPEG$_3$-piperazinyl) lamotrigine (Compound 103)

Synthesis of N-mPEG$_3$-piperazine

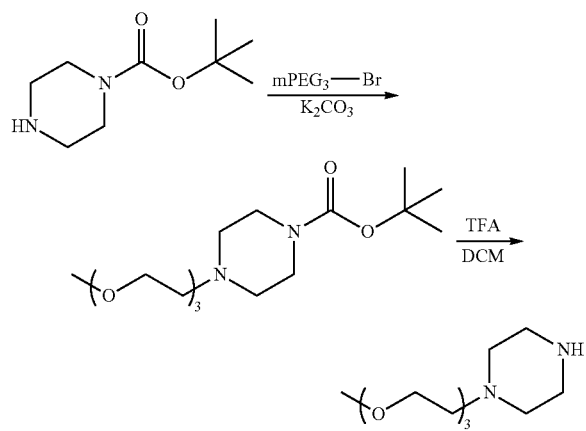

A solution of potassium carbonate (2.2957 g, 16.61 mmol) in water (3 mL) was added to a mixture of t-Boc-piperazine (0.9837 g, 5.12 mmol) and mPEG$_3$-Br (1.3123 g, 5.78 mmol) in a vial. The resulting mixture was heated at 120° C. for 1.5 h by using microwave. The mixture was diluted with water, extracted with dichloromethane (3×30 mL). The combined organic solution was washed with brine, dried over brine, concentrated. The residue was dried under high vacuum to afford 1-N-t-Boc-4-N-mPEG$_3$-piperazine. $^1$H NMR (500 MHz, Chloroform-d) δ 3.64-3.58 (m, 8H), 3.53-3.51 (m, 2H), 3.41 (m, 4H), 3.34 (s, 3H), 2.57 (t, J=5.8 Hz, 2H), 2.43-2.41 (m, 4H), 1.44 (s, 9H).

1-N-t-Boc-4-N-mPEG$_3$-piperazine was dissolved in dichloromethane (10 mL), and trifluoroacetic acid (6 mL) was added. The mixture was stirred at room temperature for 23 h. The mixture was concentrated to remove all of solvents. The residue was dried under high vacuum. The residue was dissolved in dichloromethane, washed with saturated aqueous potassium carbonate, dried over anhydrous sodium sulfate, concentrated. Only 209 mg of product was isolated. Sodium chloride was added to the aqueous solution to saturate the mixture, and then extracted with dichloromethane again. The combined organic solution was dried over anhydrous sodium sulfate, concentrated to afford product (1.1578 g, yield: 97%). $^1$H NMR (500 MHz, Chloroform-d) δ 3.60-3.55 (m, 8H), 3.51-3.49 (m, 2H), 3.33 (s, 3H), 2.84 (t, J=4.8 Hz, 6H), 2.53 (t, J=6.0 Hz, 23H), 2.42 (br, 4H).

Synthesis of 5-amino-6-chloro-3-(4'-N-mPEG$_4$-piperazinyl)amino-1,2,4-triazine

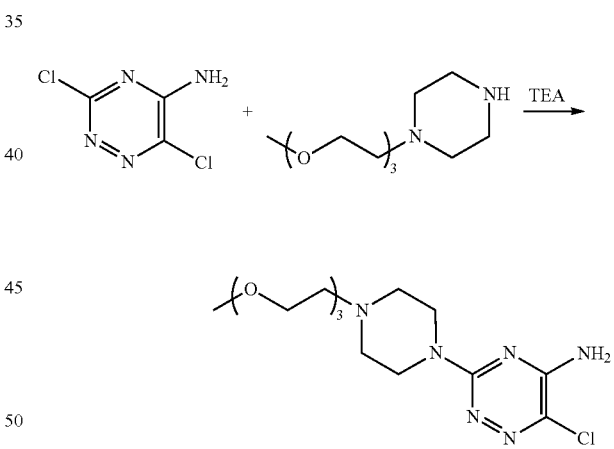

A vial was charged with 5-amino-3,6-dichloro-1,2,4-triazine (658.8 mg, 3.99 mmol) and triethylamine (2.5 mL, 17.94 mmol), N-mPEG$_3$-piperazine (0.9471 g, 4.08 mmol) in dioxane (7.5 mL). The mixture was heated at 95° C. for 1.5 h using microwave. The mixture was cooled to room temperature, filtered and the white solid was washed with dichloromethane. The organic solution was concentrated. The residue was purified with flash column chromatography on silica gel using 1-10% methanol/dichloromethane to afford product (1.2111 g, Yield: 84%). $^1$H NMR (500 MHz, Chloroform-d) δ 5.18 (br, 2H), 3.80 (br, 4H), 3.65-3.62 (m, 8H), 3.54-3.52 (m, 2H), 3.36 (s, 3H), 2.63 (s, 2H), 2.55 (br, 2H), 2.55 (br, 4H). LC-MS: 361.2 (MH$^+$/z).

135

Synthesis of 3-N-(4'-N-mPEG$_3$-piperazinyl) lamotrigine (Compound 103)

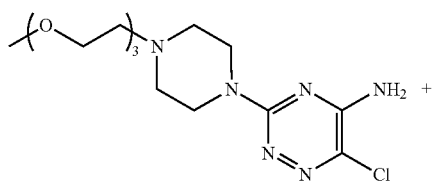

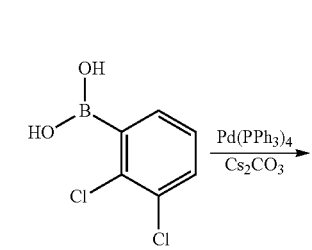

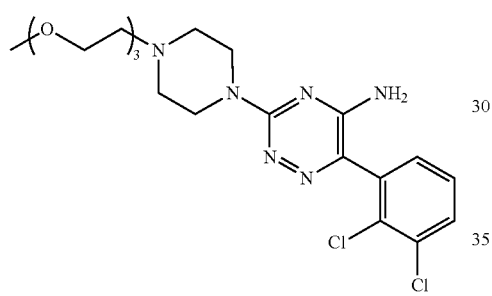

5-Amino-6-chloro-3-(N-mPEG$_3$-piperazinyl)amino-1,2,4-triazine (239.3 mg, 0.66 mmol) was dissolved in dioxane (15 mL). (2,3-Dichlorophenyl)boronic acid (242.6 mg, 1.27 mmol) and cesium carbonate (691.7 mg, 2.10 mmol) were added. And then water (5 mL) was added. The mixture was degassed with nitrogen, tetrakis(triphenylphosphine)palladium (42.2 mg, 0.037 mmol) was added. The mixture was purged with nitrogen for a few minutes, and then heated to 85° C. during 55 min, and kept at 85° C. for 1 h. The mixture was concentrated under reduced pressure to dryness. The residue was mixed with water, extracted with dichloromethane (4×20 mL). The organic solution was concentrated. The residue was purified with flash column chromatography on silica gel to afford product (135.7 mg, Yield: 43%). $^1$H NMR (500 MHz, Chloroform-d) δ 7.546 (dd, J=1.5 and 7.5 Hz, 1H, Ar—H), 7.351 (m, 2H, Ar—H), 4.689 (br, 2H, NH$_2$), 3.891 (br, 4H, 2 CH$_2$), 3.666-3.625 (m, 8H, 4CH$_2$), 3.545-3.527 (m, 2H, CH$_2$), 3.367 (s, 3H, CH$_3$), 2.637 (t, J=6.0 Hz, 2H, CH$_2$), 2.578 (t, J=5.0 Hz, 4H, 2CH$_2$). LC-MS: 471.0 (MH$^+$/z).

Some of product was dissolved in dichloromethane (3 mL), 2 N hydrochloride in ether (1.5 mL) was added to afford white solid. Acetonitrile (3 mL) was added to get cloud mixture, methanol (3 mL) was added to result in a clear solution. The mixture was concentrated to remove all of solvents and dried under high vacuum to afford 94.8 mg of product as HCl salt. LC-MS: 471.0 (MH$^+$/z).

136

Example 51

Preparation of Compound 104

Synthesis of 3-N-(4'-N-mPEG$_3$-piperazinyl) 5-fluoro lamotrigine (Compound 104)

Synthesis of 1-N-Boc-4-N-mPEG$_3$-CM-piperazine

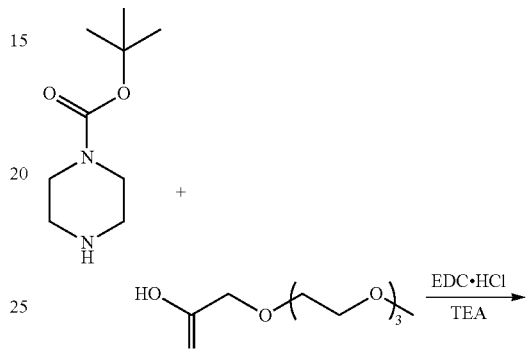

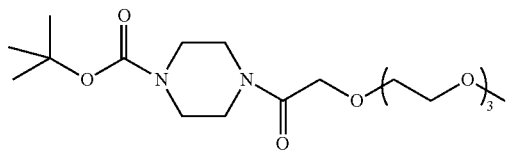

T-Boc-piperazine (1.1369 g, 6.10 mmol) and 2,5,8,11-tetraoxatridecan-13-oic acid (1.09 g, 4.90 mmol) were dissolved in dichloromethane (10 mL). Triethylamine (3.0 mL, 21.52 mmol) was added, followed by addition of N-(3-dimethylaminopropyl)-N'-ethylcarbodiimide hydrochloride (1.6310 g, 8.51 mmol). More of dichloromethane (20 mL) was added to get a solution. The resulting mixture was stirred at room temperature for 24 h. The reaction was taken up in 30 mL of dichloromethane, washed with brine and dried over anhydrous sodium sulfate. Solvent was removed by rotavap. The residue was purified on column chromatography on silica gel to afford product as colorless oil (1.0463 g, Yield: 55%). $^1$H NMR (500 MHz, Chloroform-d) δ 4.19 (s, 2H), 3.67-3.61 (m, 10H), 3.55-3.51 (m, 4H), 3.49-3.40 (m, 6H), 3.55 (s, 3H), 1.45 (s, 9H).

Synthesis of 2-(2,3-dichloro-5-fluoro-phenyl)-4,4,5,5-tetramethyl-1,3,2-dioxaborolane

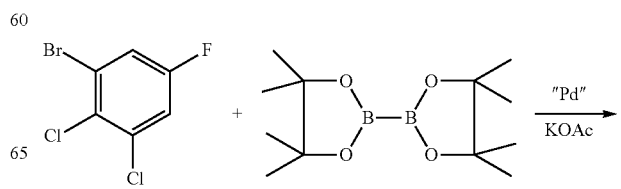

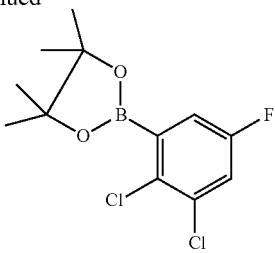

A mixture of 1-bromo-2,3-dichloro-5-fluorobenzene (3.1304 g, 12.94 mmol), bis(pinacolato)diboron (5.7397 g, 22.38 mmol), potassium acetate (3.9788 g, 40.1 mmol) in DMSO (60 mL) was stirred at room temperature for about 30 min. The mixture was degassed with nitrogen for a few minutes and 1,1'-[bis(diphenylphosphino)ferrocene]dichloro-palladium (II) (0.7953 g, 1.09 mmol) was added. The mixture was degassed again with nitrogen, was heated to 80° C. with stirring and kept at 80° C. for 4 h 20 min. The mixture was cooled to room temperature and poured into ice. The mixture was extracted with ethyl acetate (3×150 mL). The combined organic solution was washed with saturated sodium chloride solution (150 mL), dried over anhydrous sodium sulfate, and concentrated. The residue was separated with flash column chromatography on silica gel using ethyl acetate/hexane to afford product as white solid (2.6156 g, Yield: 70%). $^1$H NMR (500 MHz, Chloroform-d) δ 7.070 (d, J=3.0 Hz, 1H), 7.029 (d, J=3.0 Hz, 1H), 1.238 (s, 12H).

Synthesis of 3-N-(4'-N-mPEG$_3$-piperazinyl) 5-fluoro lamotrigine

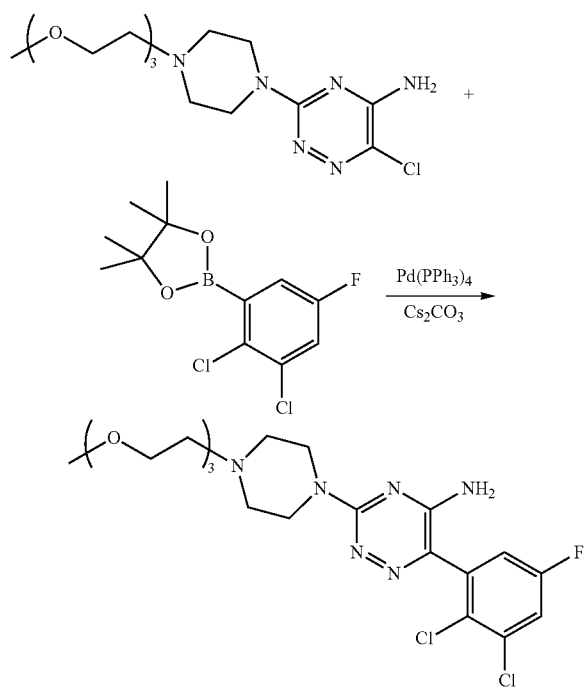

5-Amino-6-chloro 3-(N-mPEG$_3$-piperazinyl)amino-1,2,4-triazine (320 mg, 0.89 mmol) was dissolved in dioxane (15 mL). (2,3-Dichloro-5-fluorophenyl)-4,4,5,5-tetramethyl-1,3,2-dioxaborolane (355.1 mg, 1.22 mmol) was added. Cesium carbonate (904.3 mg, 2.75 mmol) in water (5 mL) was added. The mixture was degassed with nitrogen, Tetrakis (triphenylphosphine)palladium (58.8 mg, 0.05 mmol) was added. The mixture was purged with nitrogen for a few minutes, and then heated to 85° C. during 0.5 h, and kept at 85° C. for 3 h. The mixture was concentrated under reduced pressure to dryness. The residue was mixed with water, extracted with dichloromethane (4×20 mL). The organic solution was concentrated. The residue was purified with biotage on silica gel using 4-7% methanol/dichloromethane to afford product (73.8 mg, Yield: 17%). $^1$H-NMR (500 MHz, CDCl$_3$): 7.317 (dd, J=3.0 and 8.0 Hz, 1H, Ar—H), 7.129 (dd, J=3.0 and 8.0 Hz, 1H, Ar—H), 4.686 (br, 2H, NH$_2$), 3.893 (br, 4H, 2CH$_2$), 3.664-3.625 (m, 8H, 4CH$_2$), 3.545-3.527 (m, 2H, CH$_2$), 3.368 (s, 3H, CH$_3$), 2.636 (t, J=6.0 Hz, 2H, CH$_2$), 2.578 (t, J=5.0 Hz, 4H, 2CH$_2$). LC-MS: 489.0 (MH$^+$/z).

The product (60 mg) was dissolved in dichloromethane (3 mL), 2 M hydrochloride in ether (2 mL) was added, methanol (1 mL) was added to dissolve and afford a clean solution. The mixture was concentrated to remove all of solvents and dried under high vacuum to the product as HCl salt. LC-MS: 489.0 (MH$^+$/z).

Example 52

Preparation of Compound 105

Synthesis of 3-N-mPEG$_2$-CM-piperazinyl lamotrigine (Compound 105)

Synthesis of tert-butyl 4-(2-(2-(2-methoxyethoxy)ethoxy) acetyl)piperazine-1-carboxylate

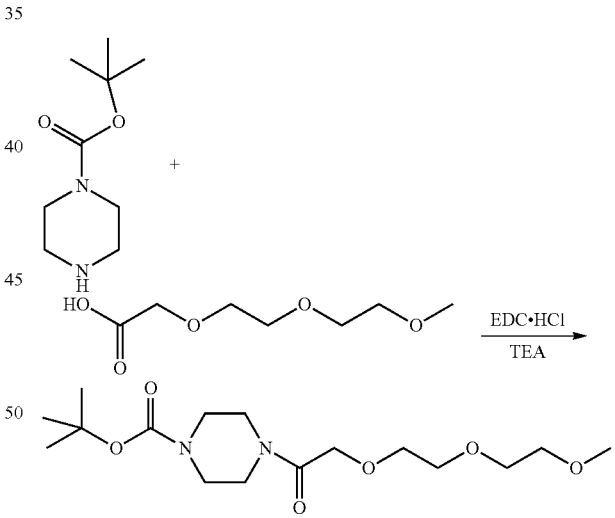

T-Boc-piperazine (1.5837 g, 8.50 mmol) and mPEG$_2$-CM (1.55 mL, 10.10 mmol) were dissolved in dichloromethane (100 mL). Triethylamine (3.5 mL, 25.10 mmol) was added, followed by addition of N-(3-dimethylaminopropyl)-N'-ethylcarbodiimide hydrochloride (3.0889 g, 16.11 mmol). The resulting mixture was stirred at room temperature for 24 h. The reaction was washed with brine and dried over anhydrous sodium sulfate. Solvent was removed by rotavap. The residue was purified with column chromatography on silica gel using 0-10% methanol/dichloromethane to afford product as oil (2.4095 g, Yield: 82%). $^1$H NMR (500 MHz, Chloroform-d) δ 4.20 (s, 2H), 3.69-3.64 (m, 4H), 3.62-3.61

(m, 2H), 3.57-3.54 (m, 2H), 3.53-3.51 (m, 2H), 3.49-3.48 (m, 2H), 3.43-3.38 (m, 4H), 3.36 (s, 3H), 1.45 (s, 9H).

Synthesis of 2-(2-(2-methoxyethoxy)ethoxy)-1-(piperazin-1-yl)ethanone

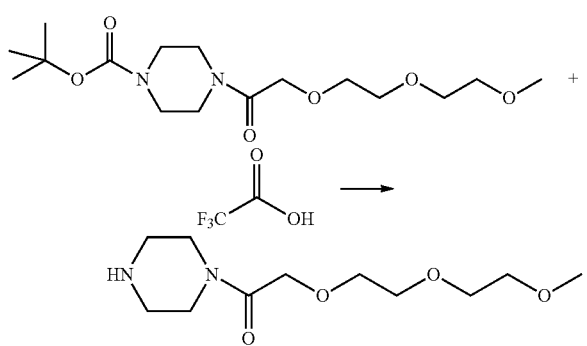

N-Boc-N'-2-(2-(2-methoxyethoxy)ethoxy)acetyl piperazine (4.5095 g, 6.96 mmol) was dissolved in dichloromethane (15 mL), and trifluoroacetic acid (6 mL) was added. The mixture was stirred at room temperature for 2 h. The mixture was quenched with saturated aqueous potassium carbonate, brine was added. The organic solution was separated. The aqueous the aqueous solution was saturated with sodium chloride and extracted with dichloromethane. The combined organic solution dried over anhydrous sodium sulfate, concentrated to afford product (1.1992 g, Yield: 70%). $^1$H NMR (500 MHz, Chloroform-d) δ 4.19 (s, 2H), 3.70-3.65 (m, 4H), 3.63-3.61 (m, 2H), 3.57 (t, J=3.0 Hz, 2H), 3.54-3.52 (m, 2H), 3.48 (t, J=3.0 Hz, 2H), 3.36 (s, 3H), 2.86-2.83 (m, 4H).

Synthesis of 5-amino-3-N-(4-mPEG$_2$-CM piperazinyl)-6-chloro-1,2,4-triazine

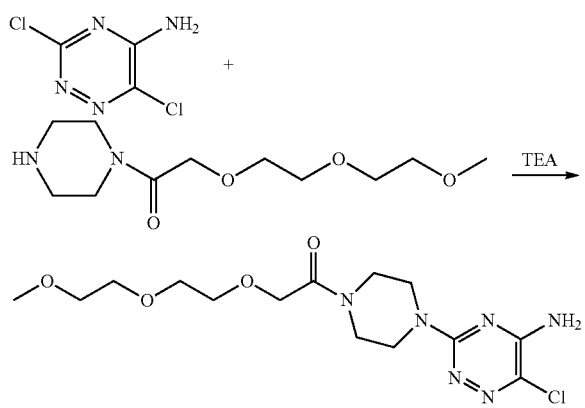

A vial was charged with 5-amino-3,6-dichloro-1,2,4-triazine (586.3 mg, 3.55 mmol) and triethylamine (1.5 mL, 10.76 mmol), 2-(2-(2-methoxyethoxy)ethoxy)-1-(piperazin-1-yl)ethanone (0.898 g, 3.65 mmol) in dioxane (8.0 mL). The mixture was heated at 95° C. for 1.5 h using microwave. The mixture was cooled to room temperature, filtered and the white solid was washed with dichloromethane. The organic solution was concentrated. The residue was dissolved in dichloromethane (50 mL), washed with water. The aqueous solution was extracted with dichloromethane (30 ml). The combined organic solution was dried over anhydrous sodium sulfate, concentrated. The residue was purified with flash column chromatography on silica gel using 1-10% methanol/dichloromethane to afford product (1.0453 g, Yield: 78%). $^1$H NMR (500 MHz, Chloroform-d) δ 5.24 (br, 2H), 4.24 (s, 2H), 3.84 (t, J=3.0 Hz, 2H), 3.77 (t, J=3.0 Hz, 2H), 3.71-3.69 (m, 2H), 3.67-3.64 (m, 4H), 3.63-3.61 (m, 2H), 3.59 (t, J=3.0 Hz, 2H), 3.54-3.52 (m, 2H), 3.35 (s, 3H). LC-MS: 375.0 (MH$^+$/z).

Synthesis of 3-N-mPEG$_2$-CM-piperazinyl lamotrigine

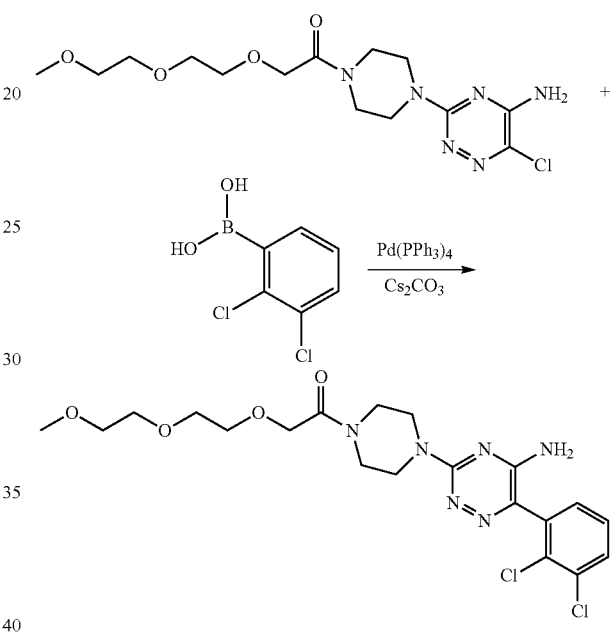

5-Amino-6-chloro-3-(N-mPEG$_2$-CM-piperazinyl)-1,2,4-triazine (354.5 mg, 0.95 mmol) was dissolved in dioxane (18 mL). (2,3-Dichlorophenyl)boronic acid (489 mg, 2.56 mmol) and cesium carbonate (1.2194 mg, 3.71 mmol) were added. And then water (5 mL) was added. The mixture was sonicated and degassed with nitrogen, tetrakis(triphenylphosphine)palladium (60.5 mg, 0.05 mmol) was added. The mixture was purged with nitrogen for a few minutes, and then heated to 85° C. during 25 min, and kept at 85° C. for 22 h. More of the palladium catalyst (52 mg) was added. The mixture was stirred at 85° C. for 2 h 20 min. More of the palladium catalyst (56.6 mg) was added. The mixture was stirred at 85° C. for 4.5 h. More of the palladium catalyst (65 mg) was added. The mixture was stirred at 85° C. for 1.5 h. The mixture was concentrated under reduced pressure to dryness. The residue was mixed with water, extracted with dichloromethane (4×20 mL). The organic solution was concentrated. The residue was purified with flask column chromatography on silica gel using methanol/dichloromethane to afford product (86.9 mg, Yield: 19%). $^1$H NMR (500 MHz, Chloroform-d) δ 7.56 (dd, J=7.0, 2.5 Hz, 1H), 7.36-7.32 (m, 2H), 4.75 (br, 2H), 4.26 (s, 2H), 3.94 (s, 2H), 3.87 (m, 2H), 3.72-3.67 (m, 6H), 3.64-3.62 (m, 4H), 3.54-3.52 (m, 2H), 3.36 (s, 3H). LC-MS: 485.0 (MH$^+$/z).

47.1 mg of product was mixed with 2 mL of acetonitrile and 2 mL of dichloromethane. Methanol (3 mL) was added.

2 N Hydrochloride in ether (1 mL) was added to result in a clean solution. The mixture was concentrated to remove all of solvents and dried under high vacuum to afford product as HCl salt (49.7 mg).

Example 53

Preparation of Compound 106

Synthesis of 3-N-mPEG$_2$-CM-piperazinyl 5'-fluoro lamotrigine (Compound 106)

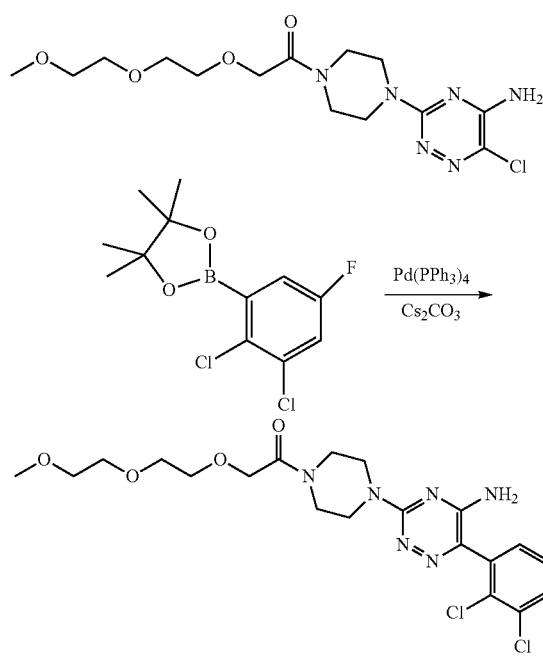

5-Amino-6-chloro-3-(N-mPEG$_2$-CM-piperazinyl)-1,2,4-triazine (200.4 mg, 0.54 mmol) and (2,3-dichloro-5-fluorophenyl)-4,4,5,5-tetramethyl-1,3,2-dioxaborolane (225 mg, 0.77 mmol) were mixed in dioxane (15 mL), sonicated for a few minutes. Cesium carbonate (657.5 mg, 2.00 mmol) in water (5 mL) was added. The mixture was degassed with nitrogen, tetrakis(triphenyl phosphine)palladium (56.1 mg, 0.05 mmol) was added. The mixture was purged with nitrogen for a few minutes, and stirred at room temperature for 40 min, at 85° C. for 16 h. More of the palladium catalyst (77 mg) was added. The mixture was stirred at 85° C. for 1 h 45 min. More of the palladium catalyst (97 mg) was added. The mixture was stirred at 85° C. for 1 h. The mixture was concentrated under reduced pressure to dryness. The residue was mixed with water, extracted with dichloromethane (4×20 mL). The organic solution was concentrated. The residue was purified with column chromatography on silica gel using methanol/dichloromethane to afford crude product, which was dissolved in dichloromethane and hexane was added. The mixture was cooled to 0° C. and centrifuged to afford white solid as product (45.5 mg, Yield: 17%). $^1$H NMR (500 MHz, Chloroform-d) δ 7.33 (dd, J=8.0, 2.5 Hz, 1H), 7.11 (dd, J=8.0, 2.5 Hz, 1H), 4.82 (br, 2H), 4.25 (s, 4H), 3.94 (t, J=5.3 Hz, 2H), 3.87 (d, J=5.6 Hz, 2H), 3.72-3.68 (m, 6H), 3.64-3.62 (m, 4H), 3.54-3.52 (m, 2H), 3.35 (s, 3H). LC-MS: 503.0 (MH$^+$/z).

7.6 mg of product was dissolved in methanol (1 mL), 0.5 mL of 2 N hydrochloride in ether was added. The mixture was concentrated to remove the solvents and dried under high vacuum to product as HCl salt (4.7 mg). LC-MS: 503.0 (MH$^+$/z).

Example 54

Preparation of Compound 107

Synthesis of 3-N-(4'-N-mPEG$_2$-CM piperidinyl) lamotrigine (Compound 107)

Synthesis of tert-Butyl (1-(2-(2-(2-methoxyethoxy)ethoxy)acetyl)piperidin-4-yl) carbamate

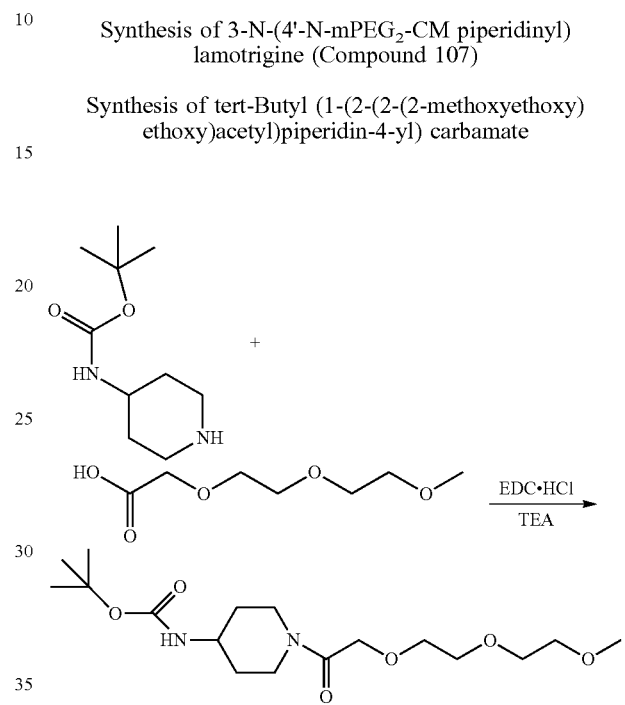

4-Boc amino-piperadine (2.2842 g, 10.95 mmol) and mPEG$_2$-CM (2.0 mL, 13.03 mmol) were dissolved in dichloromethane (60 mL). Triethylamine (4.0 mL, 28.70 mmol) was added, followed by addition of N-(3-dimethylaminopropyl)-N'-ethylcarbodiimide hydrochloride (3.5165 g, 18.34 mmol). The resulting mixture was stirred at room temperature for 22 h. More of N-(3-dimethylaminopropyl)-N'-ethylcarbodiimide hydrochloride (0.408 g) was added. The mixture was stirred at room temperature for 4.5 h. The reaction was washed with brine and dried over anhydrous sodium sulfate. Solvent was removed by rotavap. The residue was purified with column chromatography on silica gel using 0-10% methanol/dichloromethane to afford product as oil (2.3017 g, Yield: 58%). $^1$H NMR (500 MHz, Chloroform-d) δ 4.57 (s, 1H), 4.46-4.43 (m, 1H), 4.25 (d, J=13.5 Hz, 1H), 4.12 (d, J=13.5 Hz, 1H), 3.92-3.89 (m, 1H), 3.74-3.61 (m, 7H), 3.57-3.51 (m, 2H), 3.37 (s, 3H), 3.07 (t, J=12.0 Hz, 1H), 2.73 (t, J=12 Hz, 1H), 1.96 (d, J=6 Hz, 2H), 1.43 (s, 9H), 1.37 (m, 1H), 1.31-1.21 (m, 1H).

Synthesis of 1-(4-aminopiperidin-1-yl)-2-(2-(2-methoxyethoxy)ethoxy)ethanone

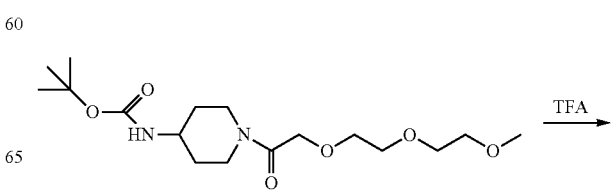

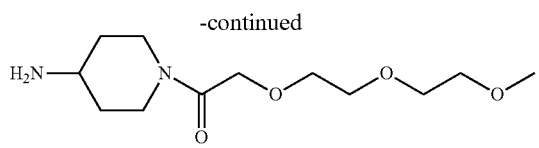

Tert-Butyl (1-(2-(2-(2-methoxyethoxy)ethoxy)acetyl)piperidin-4-yl) carbamate (2.3017 g, 6.39 mmol) was dissolved in dichloromethane (30 mL). Trifluoroacetic acid (6.0 mL) was added. The resulting mixture was stirred at room temperature for 3 h. The mixture was concentrated and dried under high vacuum for 30 min. The residue was dissolved in methanol, and passed through a column with AGO AG MP-1 and AG-2 strong anion exchange resin. The solution was concentrated to afford product as free base (1.6744 g, Yield: 99%). $^1$H NMR (500 MHz, Chloroform-d) δ 4.42 (m, 1H), 4.23-4.14 (m, 2H), 3.89-3.86 (m, 1H), 3.73-3.66 (m, 4H), 3.63-3.61 (m, 2H), 3.54-3.52 (m, 2H), 3.47 (s, 1H), 3.36 (s, 3H), 3.04-2.99 (m, 1H), 2.92-2.86 (m, 1H), 2.73-2.68 (m, 1H), 1.84-1.82 (m, 1H), 1.29-1.18 (m, 3H).

Synthesis of 5-amino-6-chloro-3-N-(1-(2-(2-(2-methoxyethoxy)ethoxy)acetyl) piperidin-4-yl) amino-1,2,4-triazine

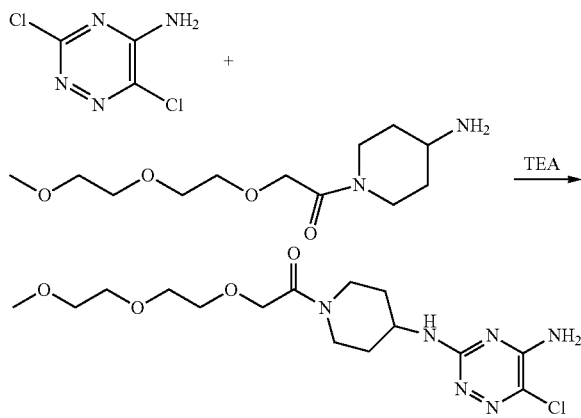

A vial was charged with 5-amino-3,6-dichloro-1,2,4-triazine (321.9 mg, 1.95 mmol) and triethylamine (0.3 mL, 2.152 mmol), 1-(4-aminopiperidin-1-yl)-2-(2-(2-methoxyethoxy) ethoxy)ethanone (0.5219 g, 2.01 mmol) in dioxane (10.0 mL). The mixture was heated at 95° C. for 1.5 h using microwave. More of triethylamine (0.7 mL, 5.02 mmol) was added. The mixture was heated again at 95° C. for 1.5 h. More of triethylamine (0.5 mL) was added. The mixture was heated at 95° C. for 45 min. The mixture was cooled to room temperature, was concentrated to remove the solvent. The residue was dissolved in dichloromethane (50 mL), washed with saturated potassium carbonate. The aqueous solution was extracted with dichloromethane (40 ml). The combined organic solution was washed with brine, dried over anhydrous sodium sulfate, concentrated. The residue was purified with flash column chromatography on silica gel using 1-10% methanol/dichloromethane to afford product (176.5 mg, Yield: 23%). $^1$H NMR (500 MHz, Chloroform-d) δ 5.24 (s, 2H), 5.00 (br, 1H), 4.45 (d, J=13.5 Hz, 1H), 4.26 (d, J=13.4 Hz, 1H), 4.14 (d, J=13.4 Hz, 1H), 4.01 (s, 1H), 3.93 (d, J=13.7 Hz, 1H), 3.74-3.57 (m, 6H), 3.57-3.50 (m, 2H), 3.36 (s, 3H), 3.14 (t, J=12.1 Hz, 1H), 2.82 (t, J=12.6 Hz, 1H), 2.11-2.04 (m, 2H), 1.48 (m, 1H), 1.37 (m, 1H). LC-MS: 389.2 (MH$^+$/z).

Synthesis of 3-N-(4'-N-mPEG$_2$-CM piperidinyl) lamotrigine

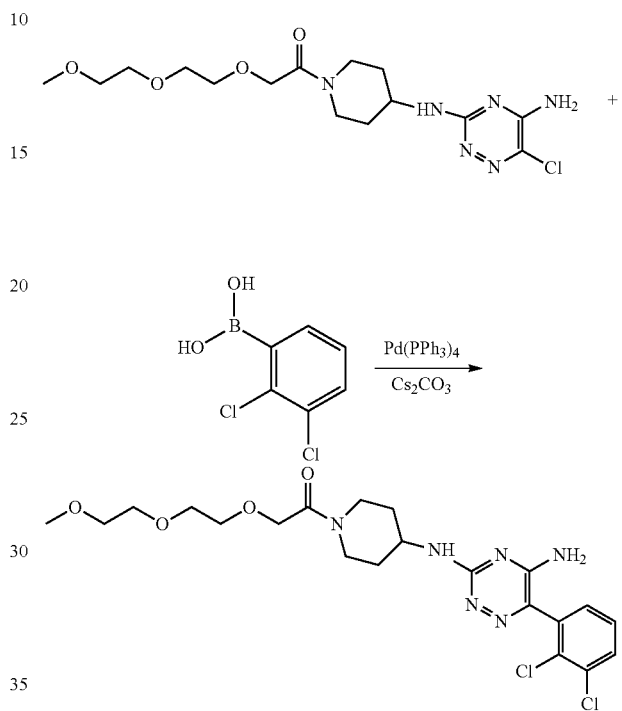

5-Amino-6-chloro-3-N-(1-(2-(2-(2-methoxyethoxy)ethoxy)acetyl)piperidin-4-yl)amino-1,2,4-triazine (172 mg, 0.442 mmol) was dissolved in dioxane (10 mL). (2,3-Dichlorophenyl)boronic acid (191 mg, 1.00 mmol) and cesium carbonate (517.8 mg, 1.57 mmol) were added. And then water (2.5 mL) was added. Tetrakis(triphenylphosphine)palladium (128 mg, 0.12 mmol) was added. The mixture was purged with nitrogen for a few minutes, and then heated to 85° C. during 40 min, and kept at 85° C. for 4 h. The mixture was concentrated under reduced pressure to dryness. The residue was mixed with water, extracted with dichloromethane (4×20 mL). The organic solution was concentrated. The residue was purified with reverse column chromatography on C-18 column using 15% acetonitrile/water to afford product (38.5 mg, Yield: 17.5%). $^1$H NMR (500 MHz, Chloroform-d) δ 7.533 (dd, J=3.0 Hz and 6.5 Hz, 1H), 7.328-7.237 (m, 2H), 4.985 (br, 2H), 4.403 (d, J=12.5 Hz, 1H), 4.174 (q, 2H), 3.896 (d, J=13.5 Hz, 1H), 3.691-3.591 (m, 6H), 3.522-3.505 (m, 2H), 3.332 (s, 3H), 3.143 (t, J=11.5 Hz, 1H), 2.841 (t, J=11.5 Hz, 1H), 2.084 (br, 2H), 1.553-1.511 (m, 1H), 1.454-1.385 (m, 1H), 1.290-1.190 (m, 1H), 0.850-0.803 (m, 1H). LC-MS: 449.0 (MH$^+$/z).

The product (21.6 mg) was dissolved in dichloromethane (5 mL), 0.5 mL of 2N hydrochloride in ether was added. A few drops of acetonitrile were added to afford a clear solution, concentrated to remove all of solvents. The residue was dried under high vacuum to afford the product as HCl salt (22 mg). LC-MS: 449.0 (MH$^+$/z).

Example 55

Preparation of Compound 108

Synthesis of 3-N-(1-N-mPEG₃-piperidin-4-yl) lamotrigine (Compound 108)

Synthesis of 1-(2-(2-(2-methoxyethoxy)ethoxy)ethyl)piperidin-4-amine

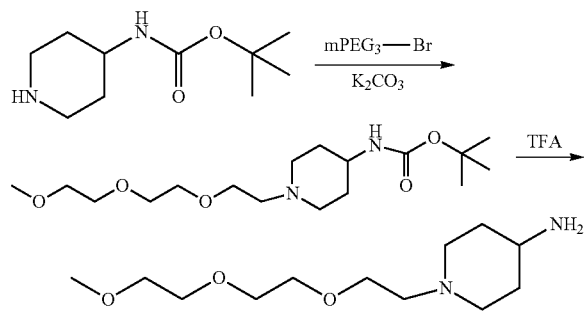

A solution of potassium carbonate (2.9903 g, 21.41 mmol) in water (3.5 mL) was added to a mixture of 4-Boc-amino-piperadine (1.5010 g, 7.19 mmol) and mPEG₃-Br (1.8364 g, 8.09 mmol) in a vial. The resulting mixture was heated at 120° C. for 1.5 h by using microwave. The mixture was diluted with water, extracted with dichloromethane (3×30 mL). The combined organic solution was washed with brine, dried over anhydrous sodium sulfate, concentrated. The residue was dried under high vacuum to afford tert-butyl (1-(2-(2-(2-methoxyethoxy) ethoxy)ethyl) piperidin-4-yl) carbamate. ¹H NMR (500 MHz, Chloroform-d) δ 4.39 (br, 1H), 3.62-3.56 (m, 8H), 3.53-3.52 (m, 2H), 3.43 (br, 1H), 3.36 (s, 3H), 2.84 (d, J=12.4 Hz, 2H), 2.55 (t, J=6.0 Hz, 2H), 2.10 (t, J=11.5 Hz, 2H), 1.89 (d, J=10.5 Hz, 2H), 1.42 (s, 11H).

Tert-Butyl (1-(2-(2-(2-methoxyethoxy)ethoxy)ethyl)piperidin-4-yl) carbamate was dissolved in dichloromethane (35 mL), and trifluoroacetic acid (7 mL) was added. The mixture was stirred at room temperature for 4 h. More of trifluoroacetic acid (0.45 mL) was added. The mixture was stirred at RT for 1.5 h. The mixture was concentrated to remove all of solvents. The residue was dried under high vacuum. The residue was dissolved in methanol, and passed through a column with AG® 1 AG MP-1 and AG-2 strong anion exchange resin. The solution was concentrated to afford product as free base in quantitative yield. ¹H NMR (500 MHz, Chloroform-d) δ 3.63-3.61 (m, 8H), 3.54-3.47 (m, 2H), 3.34 (s, 3H), 2.98 (d, J=11.6 Hz, 1H), 2.75 (m, 1H), 2.65 (t, J=5.9 Hz, 1H), 2.18 (m, 1H), 1.85 (m, 1H), 1.48 (m, 1H).

Synthesis of 5-amino-6-chloro-3-N-(1-(2-(2-(2-methoxyethoxy)ethoxy)ethyl) piperidin-4-yl)amino-1,2,4-triazine

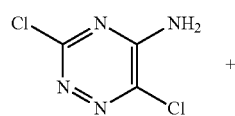

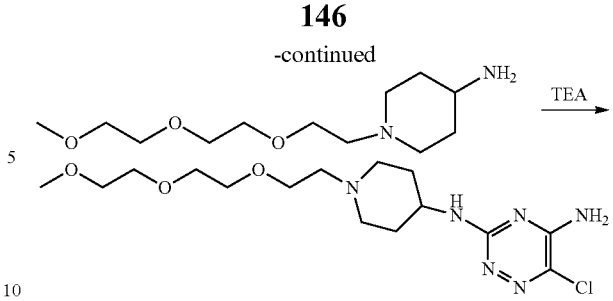

A vial was charged with 5-amino-3,6-dichloro-1,2,4-triazine (700.2 mg, 4.24 mmol) and triethylamine (1.5 mL, 10.76 mmol), 1-(2-(2-(2-methoxyethoxy)ethoxy)piperidin-4-amine (1.0633 g, 4.32 mmol) in dioxane (10.0 mL). The mixture was heated at 95° C. for 1.5 h using microwave. The mixture was cooled to room temperature, was concentrated to remove the solvent. The residue was dissolved in dichloromethane (50 mL), washed with water. The aqueous solution was extracted with dichloromethane (30 ml). The combined organic solution was dried over anhydrous sodium sulfate, concentrated. The residue was purified with flash column chromatography on silica gel using 1-10% methanol/dichloromethane and 15% methanol/dichloromethane to afford product as solid (429.5 mg, 27%). ¹H NMR (500 MHz, Chloroform-d) δ 5.26 (s, 2H), 4.90 (br, 1H), 3.84 (br, 1H), 3.61 (m, 8H), 3.53-3.51 (m, 2H), 3.34 (s, 3H), 2.96 (m, 2H), 2.65 (m, 2H), 2.29 (m, 2H), 2.01 (m, 2H), 1.52 (m, 2H). LC-MS: 375.2 (MH⁺/z).

Synthesis of 3-N-(1-N-mPEG₃-piperidin-4-yl) lamotrigine

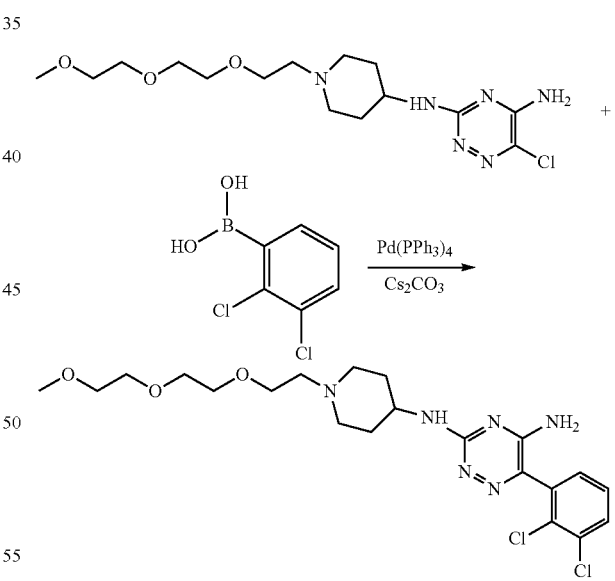

5-Amino-6-chloro-3-(1-N-mPEG₃-piperidin-4-yl)amino-1,2,4-triazine (189.9 mg, 0.51 mmol) was dissolved in dioxane (10 mL). (2,3-Dichlorophenyl)boronic acid (262.6 mg, 1.38 mmol) and cesium carbonate (699.6 mg, 2.13 mmol) were added. And then water (2.5 mL) was added. Tetrakis(triphenylphosphine)palladium (160.6 mg, 0.14 mmol) was added. The mixture was purged with nitrogen for a few minutes, and then heated to 85° C. during 40 min, and kept at 85° C. for 3.5 h. The mixture was concentrated under reduced pressure to dryness. The residue was mixed with water, extracted with dichloromethane (4×20 mL). The organic solution was concentrated. The residue was purified with column chromatography on silica gel using 1-10% methanol/dichloromethane to afford product (166.2 mg, Yield: 68%). $^1$H NMR (500 MHz, Chloroform-d) δ 7.551 (dd, J=2.0 Hz and 7.5 Hz, 1H), 7.362-7.308 (m, 1H), 4.735 (br, 2H), 3.920 (br, 1H), 3.648-3.609 (m, 10H), 3.545-3.526 (m, 2H), 3.362 (s, 3H), 2.914 (br, 2H), 2.604 (br, 2H), 2.245 (br, 2H), 2.058 (br, 2H), 1.611 (m, 3H). LC-MS: 485.0 (MH$^+$/z).

Product (100.2 mg) was dissolved in a mixture of acetonitrile (3 mL)/dichloromethane (3 mL), about 1 mL of 2 N hydrochloride in ether was added. The mixture was concentrated to remove all of solvents, dried under high vacuum to afford product as HCl salt (94.6 mg). LC-MS: 485.0 (MH$^+$/z).

Example 56

Preparation of Compound 109

Synthesis of 3-N-(4'-N-mPEG$_2$-CM piperidinyl) 5'-fluoro lamotrigine (Compound 109)

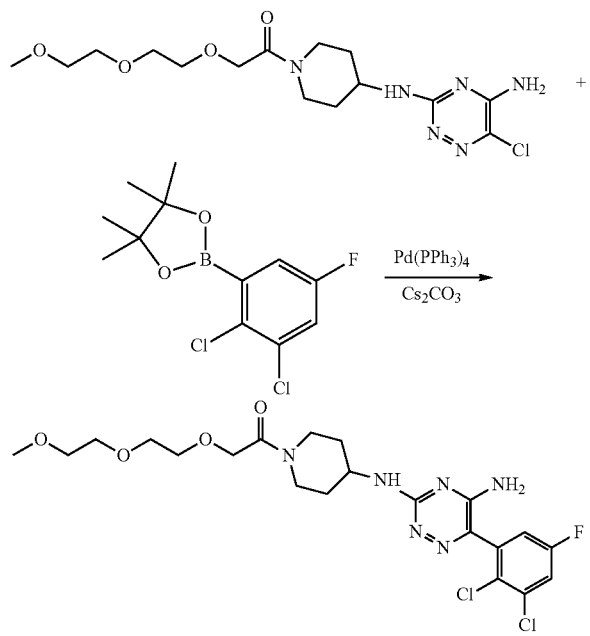

5-Amino-6-chloro-3-N-(1-(2-(2-(2-methoxyethoxy)ethoxy)acetyl)piperidin-4-yl)amino-1,2,4-triazine (176 mg, 0.45 mmol) was dissolved in dioxane (10 mL). Pinacol (2,3-dichloro-5-fluorophenyl)boronic ester (308.5 mg, 1.06 mmol) and cesium carbonate (561.2 mg, 1.71 mmol) were added. And then water (2.5 mL) was added. Tetrakis(triphenylphosphine)palladium (114.5 mg, 0.10 mmol) was added. The mixture was purged with nitrogen for a few minutes, and then heated to 85° C. during 25 min, and kept at 85° C. for 2.5 h. The mixture was concentrated under reduced pressure to dryness. The residue was mixed with water, extracted with dichloromethane (4×20 mL). The organic solution was concentrated. The residue was purified with column chromatography on silica gel using 1-10% methanol/dichloromethane to afford product (113.4 mg, Yield: 48%). $^1$H-NMR (500 MHz, Methanol-d$_4$) δ 7.541 (dd, J=3.0 Hz and 8.0 Hz, 1H), 7.224 (dd, J=3.0 Hz and 8.0 Hz, 1H), 4.90 (br, 2H), 4.434 (d, J=13.0 Hz, 1H), 4.32 (d, J=13.9 Hz, 1H), 4.23 (d, J=13.8 Hz, 1H), 4.101-4.058 (m, 1H), 3.951 (d, J=14.3 Hz, 1H), 3.708-3.676 (m, 4H), 3.644-3.625 (m, 2H), 3.556-3.538 (m, 2H), 3.360 (s, 3H), 3.207 (t, J=12.5 Hz, 1H), 2.882 (t, J=11.5 Hz, 1H), 2.078 (t, J=13.5 Hz, 2H), 1.618-1.548 (m, 1H), 1.519-1.442 (m, 1H). LC-MS: 517.0 (MH$^+$/z).

The product (~41 mg) was mixed with acetonitrile (3 mL). Methanol (5 mL) was added and warmed up to afford a clear solution. 2N Hydrochloride in ether (1 mL) was added. The mixture was concentrated to remove the solvents and dried under high vacuum to afford product as HCl salt (42.5 mg).

Example 57

Preparation of Compound 110

Synthesis of 3-N-(1-N-mPEG$_3$-piperidin-4-yl) 5'-fluoro lamotrigine (Compound 110)

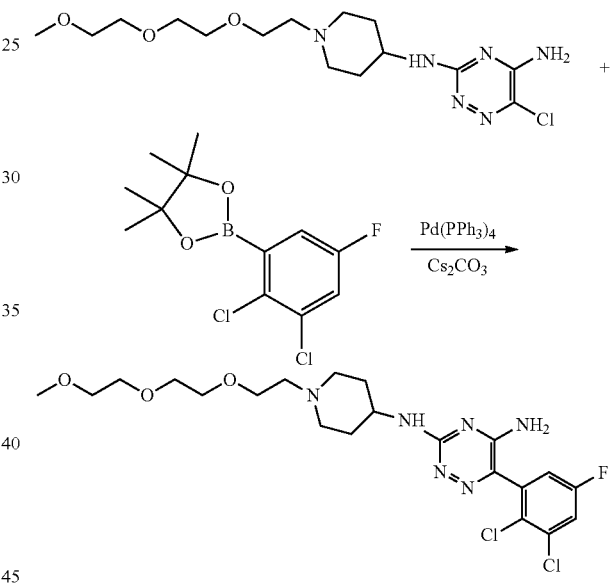

5-Amino-6-chloro-3-(1-N-mPEG$_3$-piperidin-4-yl)amino-1,2,4-triazine (156 mg, 0.42 mmol) was dissolved in dioxane (10 mL). Pinacol (2,3-dichloro-5-fluorophenyl)boronic ester (278.8 mg, 0.96 mmol) and cesium carbonate (523.4 mg, 1.59 mmol) were added. And then water (2.5 mL) was added. Tetrakis(triphenylphosphine)palladium (126.7 mg, 0.11 mmol) was added. The mixture was purged with nitrogen for a few minutes, and then heated to 85° C. during 25 min, and kept at 85° C. for 2 h. The mixture was concentrated under reduced pressure to dryness. The residue was mixed with water, extracted with dichloromethane (4×20 mL). The organic solution was concentrated. The residue was purified with column chromatography on silica gel using 1-10% methanol/dichloromethane to afford product (121.9 mg, Yield: 58%). $^1$H NMR (500 MHz, Chloroform-d) δ 7.314 (dd, J=3.0 Hz and 8.0 Hz, 1H), 7.123 (dd, J=3.0 Hz and 8.0 Hz, 1H), 4.922 (br, 2H), 3.920 (br, 1H), 3.674-3.646 (m, 2H), 3.620-3.602 (m, 6H), 3.529-3.510 (m, 2H), 3.344 (s, 3H), 3.012 (br, 2H), 2.692 (br, 2H), 2.359 (br, 2H), 2.079 (br, 2H), 1.735-1.716 (m, 2H). LC-MS: 503.0 (MH$^+$/z).

Example 58

Preparation of Compound 111

Synthesis of 3-N-(4-N-mPEG₃-3,5-dimethylpiperazinyl) lamotrigine (Compound 111)

Synthesis of 1-N-mPEG₃-2,6-dimethylpiperazine

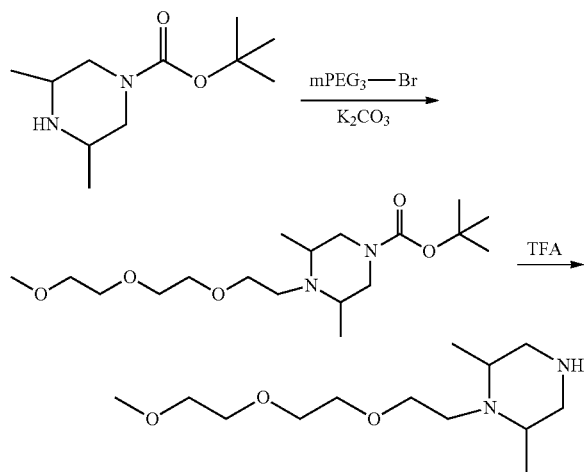

A solution of potassium carbonate (1.4370 g, 10.40 mmol) in water (3 mL) was added to a mixture of 1-N-t-Boc-3,5-dimethyl piperazine (0.6882 g, 3.21 mmol) and mPEG₃-Br (0.8872 g, 3.91 mmol) in a vial. The resulting mixture was heated at 120° C. for 1.5 h by using microwave. The mixture was diluted with water, extracted with dichloromethane (3×30 mL). The combined organic solution was washed with brine, dried over brine, concentrated. The residue was dried under high vacuum. The residue was separated with flash column chromatography on silica gel column using 1-5% methanol/dichloromethane, and NH-column using 0-5% methanol/dichloromethane to afford the intermediate.

The intermediate was dissolved in dichloromethane (8 mL), and trifluoroacetic acid (5 mL) was added. The mixture was stirred at room temperature for 6 h. Water was added. The organic solution was removed and the aqueous solution was washed again with dichloromethane. The aqueous solution was treated with 1N sodium hydroxide solution until a basic solution was obtained, sodium chloride was added to saturate the aqueous solution, extracted with dichloromethane (5×20 mL). The combined organic solution was dried over anhydrous sodium sulfate, concentrated to afford a oil as final product (175.4 mg). ¹H NMR (500 MHz, Chloroform-d) δ 3.635-3.575 (m, 6H), 3.540-3.490 (m, 4H), 3.360 (s, 3H), 2.880 (t, J=7.5 Hz, 2H), 2.816 (d, J=11.0 Hz, 2H), 2.546-2.486 (m, 2H), 2.449 (t, J=11.5 Hz, 2H), 1.035 (d, J=6.0 Hz, 6H).

The product was mixed with acetonitrile (3 mL) and dichloromethane (3 mL). 1.5 mL of 2 N hydrochloride in ether was added. The mixture was concentrated to remove all of solvents and dried under high vacuum to afford the product as HCl salt (119.1 mg).

Synthesis of 5-amino-6-chloro-3-N-(4-mPEG₃-3,5-dimethylpiperazinyl)amino-1,2,4-triazine

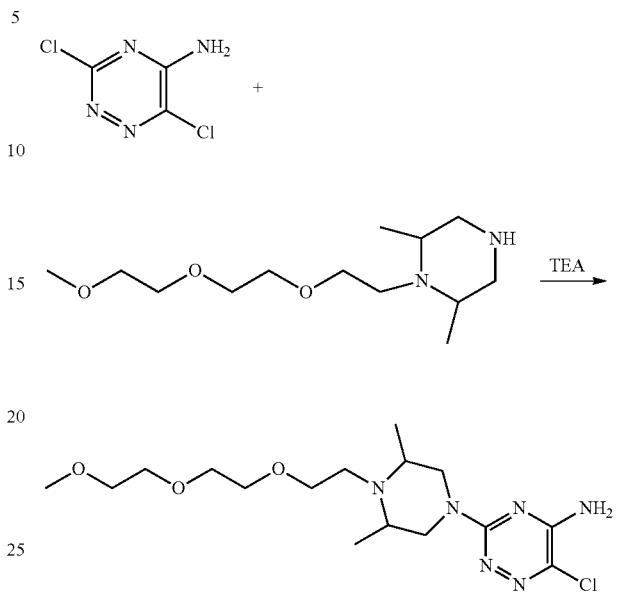

A vial was charged with 5-amino-3,6-dichloro-1,2,4-triazine (114.4 mg, 0.69 mmol) and triethylamine (0.4 mL, 2.87 mmol), 1-N-mPEG₃-2,6-dimethylpiperazine (0.1742 g, 0.67 mmol) in dioxane (2.5 mL). The mixture was heated at 95° C. for 1.5 h using microwave. The mixture was cooled to room temperature, filtered and the white solid was washed with dichloromethane. The organic solution was concentrated. The residue was dissolved in dichloromethane, washed with saturated potassium carbonate, dried over anhydrous sodium sulfate, concentrated. The residue was purified with flash column chromatography on silica gel using ethyl acetate and 0-10% methanol/ethyl acetate to afford product as oil (226.8 mg, Yield: 87%). ¹H NMR (500 MHz, Chloroform-d) δ 5.257 (s, 2H), 4.412 (br, 2H), 3.595-3.547 (m, 6H), 3.509-3.467 (m, 4H), 3.334 (s, 3H), 2.898 (t, J=7.5 Hz, 2H), 2.654-2.584 (m, 4H), 1.112 (d, J=5.5 Hz, 6H). LC-MS: 389.2 (MH⁺/z).

Synthesis of 3-N-(4-N-mPEG₃-3,5-dimethylpiperazinyl) lamotrigine

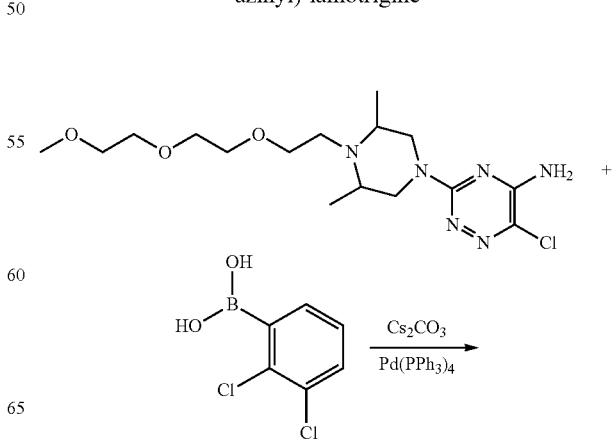

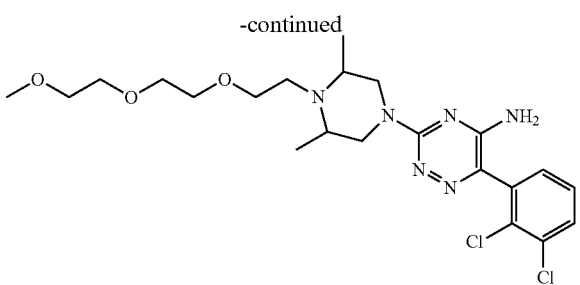

5-amino-6-chloro-3-N-(4-mPEG₃-3,5-dimethylpiperazinyl)amino-1,2,4-triazine (226.8 mg, 0.66 mmol) was dissolved in dioxane (15 mL). (2,3-Dichlorophenyl)boronic acid (265.3 mg, 1.39 mmol) and cesium carbonate (739.3 mg, 2.25 mmol) were added. And then water (5 mL) was added. The mixture was degassed with nitrogen, tetrakis(triphenylphosphine)palladium (86 mg, 0.074 mmol) was added. The mixture was purged with nitrogen for a few minutes, and then heated to 90° C. during 55 min, and kept at 90° C. for 4 h 10 min. The mixture was concentrated under reduced pressure to dryness. The residue was mixed with water, extracted with dichloromethane (4×20 mL). The organic solution was concentrated. The residue was purified with flash column chromatography on silica gel using 30-100% ethyl acetate/hexane and 1-10% methanol/ethyl acetate to afford product as solid (215.3 mg, Yield: 74%).

Take 0.115 g of product to dissolve in methanol (1.0 mL), 0.5 mL of 2 N hydrochloride in ether was added. The mixture was concentrated to remove the solvents and dried under high vacuum to afford the product as HCl salt (135.4 mg). ¹H NMR (500 MHz, Chloroform-d) δ 7.543 (dd, J=2.0 Hz and 8.0 Hz, 1H), 7.355-7.300 (m, 2H), 4.681 (s, 2H), 4.588 (br, 2H), 3.616-3.590 (m, 6H), 3.532-3.514 (m, 4H), 3.353 (s, 3H), 2.946 (t, J=6.5 Hz, 2H), 2.697 (m, 4H), 1.163 (d, J=3.0 Hz, 6H). LC-MS: 499.2 (MH⁺/z).

Example 59

Preparation of Compounds 112 and 164

Synthesis of 4-O-mPEG₃-lamotrigine

Synthesis of 6-chloro-3,5-diamino-1,2,4-triazine

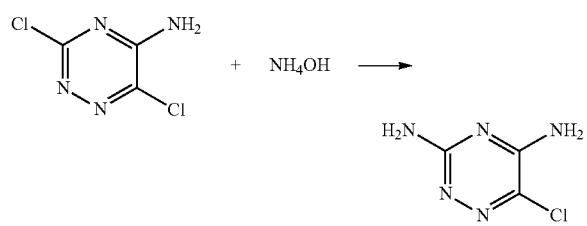

A vial was placed 5-amino-3,6-trichloro-1,2,4-triazine (1.5805 g, 8.57 mmol). THF was added to dissolve the yellow solid. 10 mL of ammonium hydroxide was added. The mixture was stirred at 0° C. for a few min. The vial was heated at 95° C. using microwave for 1 h. The mixture was cooled to room temperature, concentrated to remove the organic solvent. The remaining mixture was filtrated and washed with water. The yellow solid was collected and dried to afford product (1.6221 g, Yield: 69%). ¹H NMR (500 MHz, DMSO-d₆) δ 7.622 (br, 2H), 7.113 (br, 2H). ¹³C-NMR (500 MHz, DMSO-d₆) δ 162.06, 153.10, 132.66.

Synthesis of 4-methoxy lamotrigine

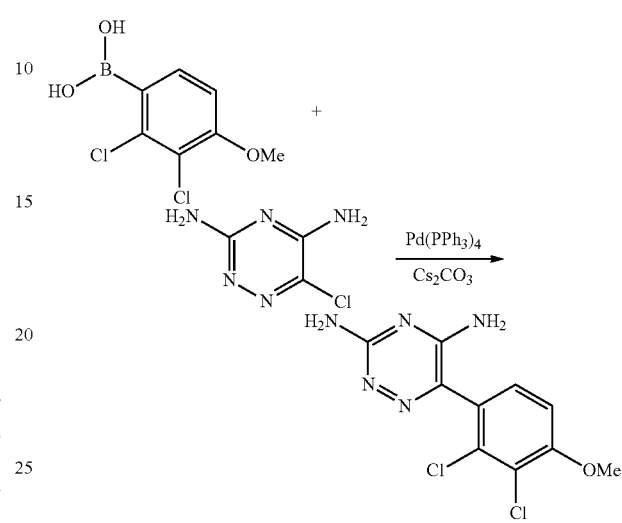

A mixture of (2,3-dichloro-4-methoxyphenyl) boronic acid (323.8 mg, 1.44 mmol), 3,5-diamino-6-chloro-1,2,4-triazine (170 mg, 1.17 mmol), cesium carbonate (989.4 mg, 3.01 mmol) and tetrakis(triphenylphosphine)palladium (100.4 mg, 0.09 mmol) in dioxane/water (10 mL/2 mL) was heated at 85° C. for 6.5 h. The mixture was concentrated under reduced pressure to dryness. The residue was mixed with water, and dichloromethane. The mixture was filtered and washed with dichloromethane. The solid was collected to afford product (331.5 mg, Yield: 99%) ¹H NMR (500 MHz, DMSO-d₆) δ 7.324 (d, J=6.0 Hz, 1H), 7.237 (d, J=6.0 Hz, 1H), 6.59 (br, 1H), 6.366 (br, 3H), 3.934 (s, 3H). LC-MS: 286.0 (MH⁺/z).

Synthesis of 4-hydroxy lamotrigine

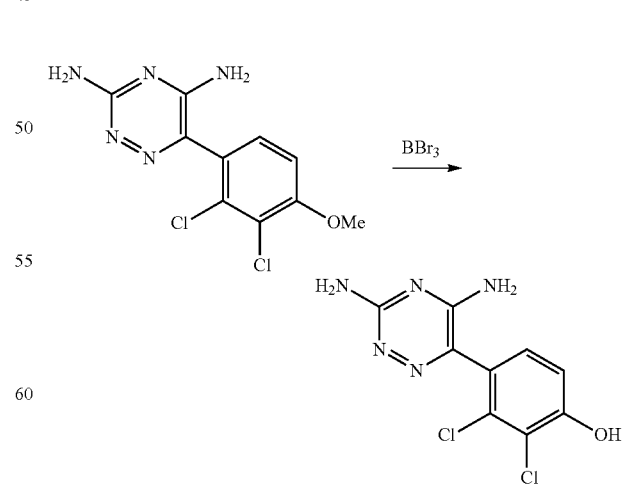

Compound 164

4-Methoxy-lamotrigine (290.5 mg, 1.02 mmol) was mixed with anhydrous dichloromethane (15 mL) at room temperature, and then 5 mL of boron tribromide solution 1.0 M in dichloromethane (5 mmol) was added. The resulting mixture was stirred at room temperature for 5.5 h. More of boron tribromide solution (5 mL) was added. The mixture was stirred at room temperature for 17 h. More of boron tribromide solution (2 mL) was added. The mixture was stirred at room temperature for 5 h. The mixture was quenched by slow addition of methanol. The mixture was concentrated to remove all of organic solvents. The remaining mixture was mixed with ammonia (~20 mL) and stirred at room temperature for 17.5 h. The mixture was concentrated to remove all of solvents. The material was purified with flash column chromatography on silica gel using 1-30% methanol/dichloromethane to afford product as slight powder (122.7 mg, Yield: 44%). $^1$H NMR (500 MHz, DMSO-$d_6$) δ 10.794 (s, 1H), 7.141 (d, J=8.5 Hz, 1H), 7.021 (d, J=8.5 Hz, 1H), 6.401 (s, 2H). LC-MS: 270.1 (MH$^+$/z).

Synthesis of 4-O-mPEG$_3$-lamotrigine (Compound 112)

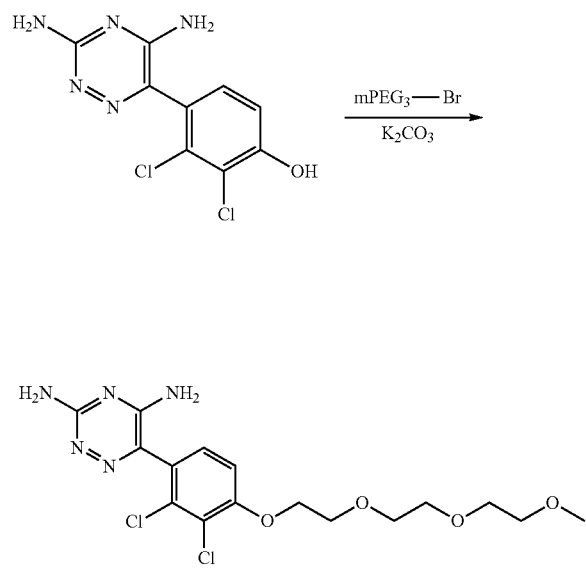

The mixture of 4-hydroxy-lamotrigine (68.2 mg, 0.25 mmol), mPEG$_3$-Br (68.5 mg, 0.30 mmol) and potassium carbonate (125.6 mg, 0.91 mmol) in DMF (5 ml) was stirred at 65° C. for 6 h. Water was added to quench the reaction. The mixture was extracted with ethyl acetate (2×60 mL). The combined organic solution was washed with brine, dried over anhydrous sodium sulfate, concentrated. The residue was purified with flash column chromatography on silica gel using 1-10% methanol/dichloromethane to afford product as white solid (65.1 mg, Yield: 62%).

$^1$H NMR (500 MHz, Methanol-$d_4$) δ 7.312 (d, J=8.5 Hz, 1H), 7.206 (d, J=8.5 Hz, 1H), 4.308-4.290 (m, 2H), 3.936-3.918 (m, 2H), 3.774-3.756 (m, 2H), 3.677-3.636 (m, 4H), 3.541 (dd, J=5.6, 3.7 Hz, 2H), 3.307 (s, 3H). LC-MS: 418.0 (MH$^+$/z).

Example 60

Preparation of Compound 113

Synthesis of 3-N-(4-N,N-methyl-mPEG$_3$-amino) piperidin-1-yl) lamotrigine (Compound 113)

Synthesis of 1-N-Boc-4-(N,N-methyl-mPEG$_3$)amino piperidine

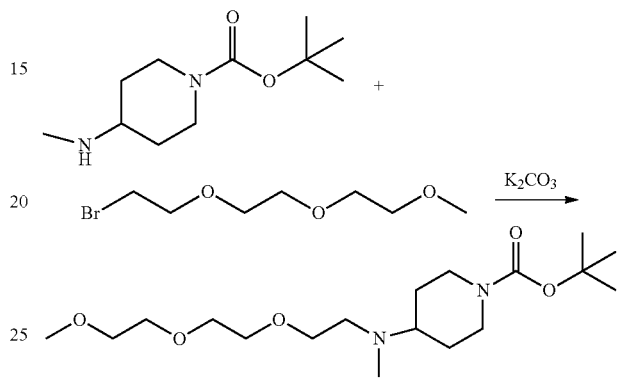

A mixture of 1-N-t-Boc-4-methylamino piperidine (1.0458 g, 4.88 mmol) and mPEG$_3$-Br (1.2490 g, 5.50 mmol) and potassium carbonate (1.8871 g, 13.65 mmol) in water (2.0 mL) in a vial was heated at 120° C. for 1.5 h by using microwave. The mixture was diluted with water, extracted with dichloromethane (3×30 mL). The combined organic solution was washed with brine, dried over anhydrous sodium sulfate, concentrated. The residue was dried under high vacuum. The residue was separated with flash column chromatography on silica gel using 1-5% methanol in dichloromethane to afford product (1.2531 g) as oil in 78% yield. $^1$H NMR (500 MHz, Chloroform-d) δ 4.11 (s, 2H), 3.65-3.56 (m, 6H), 3.55-3.49 (m, 4H), 3.35 (s, 3H), 2.63 (br, 2H), 2.62 (t, J=6.2 Hz, 2H), 2.49 (m, 1H), 2.27 (s, 3H), 1.70 (d, J=12.7 Hz, 2H), 1.42 (s, 9H), 1.44-1.30 (m, 2H). MS for $C_{18}H_{36}N_2O_5$: 361.2 (MH$^+$).

Synthesis of 4-(N,N-methyl-mPEG$_3$)amino piperidine

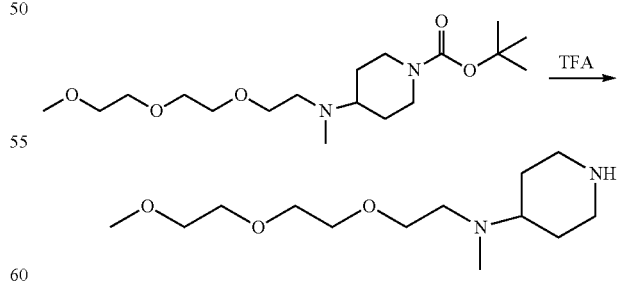

1-Boc-4-(N,N-methyl-mPEG$_3$)amino piperidine (1.2531 g, 3.48 mmol) was dissolved in dichloromethane (10 mL). Trifluoroacetic acid (3 mL) was added. The resulting mixture was stirred at room temperature for 4 h. The mixture was concentrated to remove the solvent. The residue was dissolved in dichloromethane, treated with aqueous potassium hydroxide until the aqueous solution was basic. Some brine was added. The organic solution was separated and the aqueous solution was extracted with dichloromethane (2×30 mL). The combined organic solution was dried over anhydrous sodium sulfate, concentrated to afford the product (774 mg) in 86% yield. $^1$H NMR (500 MHz, Chloroform-d) δ 3.67-3.55 (m, 6H), 3.55-3.48 (m, 4H), 3.34 (s, 3H), 3.09 (dt, J=11.9, 2.5 Hz, 2H), 2.63 (t, J=6.3 Hz, 2H), 2.51 (dt, J=12, 2.5 Hz, 2H), 2.46-2.37 (m, 1H), 2.26 (s, 3H), 1.76-1.68 (m, 2H), 1.35 (qd, J=12.2, 4.0 Hz, 2H).

Synthesis of 5-amino-6-chloro-3-(4-(N,N-methyl (mPEG$_3$) amino)piperidin-1-yl)-1,2,4-triazine

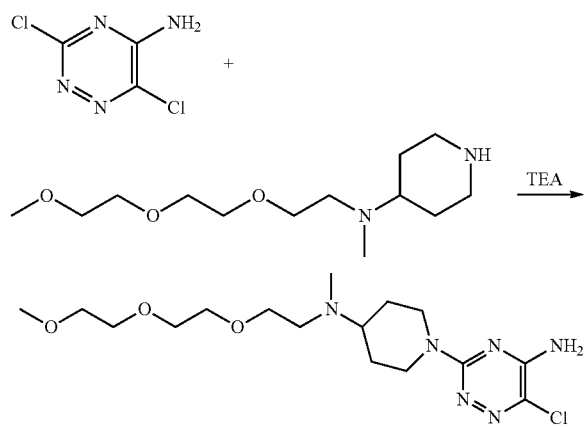

A vial was charged with 5-amino-3,6-dichloro-1,2,4-triazine (471.0 mg, 2.85 mmol), triethylamine (1.5 mL, 10.76 mmol), 4-(N,N-methyl-mPEG$_3$) amino piperidine (774.0 mg, 2.97 mmol) in dioxane (10 mL). The mixture was heated at 95° C. for 1.5 h using microwave. The mixture was cooled to room temperature and transferred into a flask with dichloromethane, concentrated to remove the solvents. The residue was mixed with brine, extracted with dichloromethane (3×40 mL). The combined organic solution was dried over anhydrous sodium sulfate, concentrated. The residue was separated with flash column chromatography on silica gel using 1-10% methanol in dichloromethane to afford the product (1.0055 g) in 91%. $^1$H NMR (500 MHz, Chloroform-d) δ 5.18 (s, 2H), 4.74 (d, J=13.2 Hz, 2H), 3.66-3.59 (m, 6H), 3.58-3.50 (m, 4H), 3.36 (s, 3H), 2.81 (td, J=12.9, 2.5 Hz, 2H), 2.67 (br, 3H), 2.30 (s, 3H), 1.83 (d, J=12.5 Hz, 2H), 1.45 (qd, J=12.3, 4.3 Hz, 2H). MS for C$_{16}$H$_{29}$ClN$_6$O$_3$: 389.2 (MH$^+$).

Synthesis of 3-N-(4-N,N-methyl-mPEG$_3$-amino) piperidin-1-yl) lamotrigine (Compound 113)

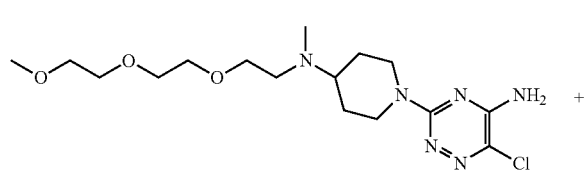

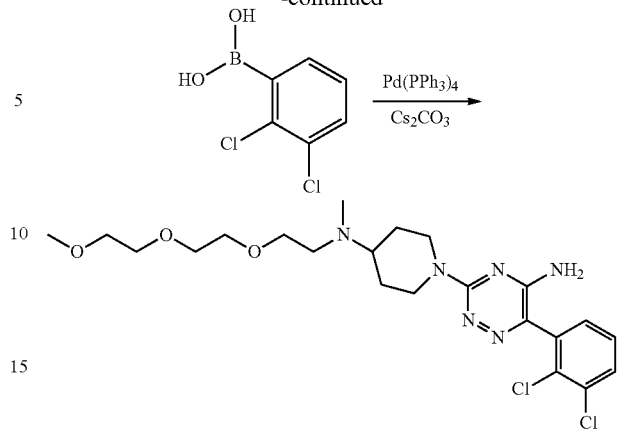

(2,3-Dichlorophenyl)boronic acid (476.8 mg, 2.499 mmol) and 5-amino-6-chloro-3-(4-(N,N-methyl (mPEG$_3$) amino)piperidin-1-yl)-1,2,4-triazine (349.7 mg, 0.899 mmol) was dissolved in water/dioxane (5/15 mL). Cesium carbonate (1.0573 g, 3.21 mmol) was added. The mixture was degassed with nitrogen, tetrakis(triphenylphosphine) palladium (99.7 mg, 0.086 mmol) was added. The mixture was purged with nitrogen for a few minutes, and then heated to 90° C. during 15 min, and kept at 90° C. for 4 h. The mixture was concentrated under reduced pressure to dryness. The residue was mixed with brine, extracted with dichloromethane (4×20 mL). The organic solution was concentrated. The residue was purified with column chromatography using 1-5% methanol in dichloromethane to afford product (244.6 mg) in 55% yield. $^1$H NMR (500 MHz, Chloroform-d) δ 7.54 (dd, J=8.3, 1.8 Hz, 1H), 7.38-7.28 (m, 2H), 4.90 (d, J=13.0 Hz, 2H), 4.67 (s, 2H), 3.62 (q, J=3.4, 2.8 Hz, 8H), 3.53 (dd, J=5.7, 3.7 Hz, 2H), 3.36 (s, 3H), 2.86 (t, J=12.9 Hz, 2H), 2.71 (br, 3H), 2.33 (s, 3H), 1.87 (d, J=12.5 Hz, 2H), 1.55-1.48 (m, 2H). MS for C$_{22}$H$_{32}$Cl$_2$N$_6$O$_3$: 499.2 (MH$^+$).

3-N-(4-N,N-Methyl-mPEG$_3$-amino)piperidin-1-yl) lamotrigine (218 mg) was dissolved in dichloromethane (~6 mL), 2.0 M HCl in ether (1 mL) was added to result in a white suspension. Methanol (~2 mL) was added to afford a clear solution. The solution was concentrated to remove all of solvents. The residue was dried under high vacuum to afford the product as HCl salt.

Example 61

Preparation of Compound 114

Synthesis of 2-Me-lamotrigine (Compound 114)

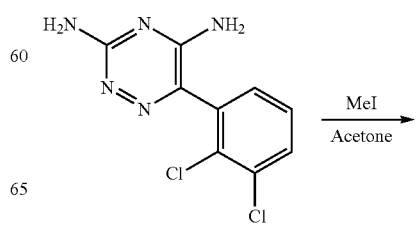

-continued

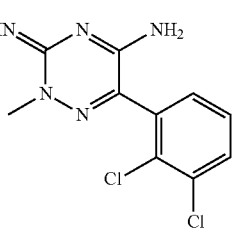

Lamotrigine (281.3 mg, 1.08 mmol) was dissolved in acetone (30 mL) at room temperature. Iodomethane (0.3 mL, 3.10 mmol) was added. The resulting mixture was stirred at room temperature for 23.5 h. After the reaction completed based on LC-MS, the reaction mixture was filtrated and washed with acetone. About 225 mg white solid was obtained, the solution was concentrated to afford a yellow solid. Both solids were combined and dried under high vacuum. The solid was stirred with ammonia (25 mL) for 4 h. The mixture was filtered and washed with water. The solid was lyophilized overnight to result in 227.2 mg of product. $^1$H NMR (500 MHz, Chloroform-d) δ 7.58 (dd, J=8.0, 1.6 Hz, 1H), 7.37-7.28 (m, 2H), 3.67 (s, 3H). LC-MS: 270.0 (MH$^+$/z).

About 15 mg of product (0.05 mmol) was dissolved in methanol (~5 mL). Methanesulfonic acid (20 μL, 0.3 mmol) was added. The mixture was concentrated to remove all of solvent and dried under high vacuum. $^1$H NMR (500 MHz, DMSO-d$_6$) δ 9.22 (s, 1H), 8.84 (br, 1H), 8.32 (br, 1H), 8.26 (s, 1H), 7.96 (d, J=8.0, 1.2 Hz, 1H), 7.69-7.58 (m, 2H), 3.85 (s, 3H). LC-MS: 270.0 (MH$^+$/z).

In one or more embodiments, the compounds of the invention are as described herein with the provisio that the compounds do not include Compound 114.

Example 62

Preparation of Compound 115

Synthesis of 3-N-piperidin-4-yl lamotrigine (Compound 115)

Synthesis of 5-amino-3,6-dichloro-1,2,4-triazine

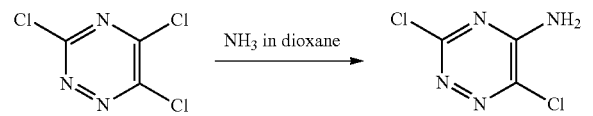

3,5,6-Trichloro-1,2,4-triazine (4.6114 g, 24.28 mmol) was dissolved in THF (100 mL) at room temperature. And then triethylamine (5.0 mL, 35.9 mmol) was added. The mixture was cooled to 0° C., ammonia in dioxane (0.5 M, 51 mL, 25.5 mmol) was added. The mixture was stirred at 0° C. for 30 min, at room temperature for 5 h. The mixture was filtered to remove the solid. The solid was washed with ethyl acetate. The combined organic solution was concentrated. The crude mixture was mixed with about 50 mL of ethyl acetate and warmed up, and then cooled to room temperature. The solid was collected and washed with ether to afford the first partial product. The solution was concentrated to remove all of solvents. The residue was mixed with about 5 ml of ethyl acetate, the solid was collected and dried. The solution was purified with flash column chromatography on silica gel using 35-100% ethyl acetate/hexanes to afford 3rd part of solid. The total of product was 3.8998 g and the yield was 97%. LC-MS: 165.1 (MH$^+$/z).

Synthesis of 5-amino-6-chloro-3-(1-N-tert-Boc-piperidin-4-yl)amino-1,2,4-triazine

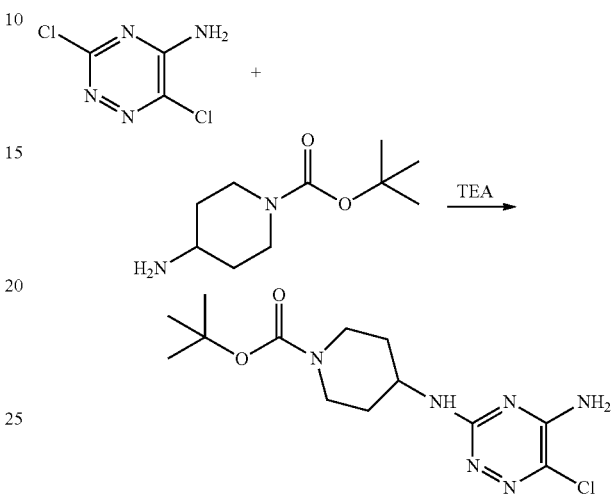

A flask was charged with 5-amino-3,6-dichloro-1,2,4-triazine (1.2659 g, 7.67 mmol) and 4-amino-1-t-Boc-piperidine (1.5894 g, 7.70 mmol) in dioxane (50 mL). Triethylamine (3.0 mL, 21.52 mmol) was added, the mixture was heated to 95° C. within 15 min and kept at 95° C. for 2 h, at 100° C. for 3.5 h. The mixture was cooled to room temperature, filtered and the white solid was washed with ethyl acetate. The organic solution was concentrated. The residue was purified with flash column chromatography on silica gel using 1-10% methanol/dichloromethane to afford product (998 mg, Yield: 40%). $^1$H NMR (500 MHz, Chloroform-d) δ 5.252 (br, 2H), 4.909 (br, 1H), 4.024-3.914 (m, 3H), 2.895 (m, 3H), 2.010-1.989 (m, 2H), 1.444 (s, 9H), 1.398-1.315 (m, 2H). LC-MS: 329.0 (MH$^+$/z).

Synthesis of 3-N-piperidin-4-yl lamotrigine (Compound 115)

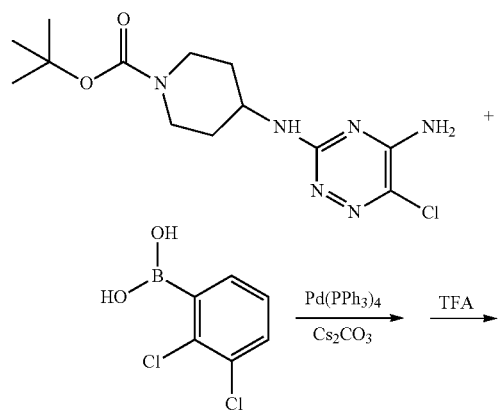

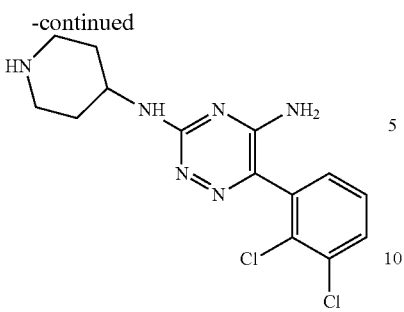

Tert-Butyl 4-((5-amino-6-chloro-1,2,4-triazin-3-yl)amino)piperidine-1-carboxylate (250 mg, 0.76 mmol), (2,3-dichlorophenyl)boronic acid (392.9 mg, 2.06 mmol) and cesium carbonate (703.2 mg, 2.14 mmol) was dissolved in dioxane/water (10 mL/2.5 mL). Tetrakis(triphenyl phosphine)palladium (284.2 mg, 0.25 mmol) was added. The mixture was purged with nitrogen for a few minutes, and then heated to 85° C. during 25 min, and kept at 85° C. for 3.5 h. The mixture was concentrated under reduced pressure to dryness. The residue was mixed with water, extracted with dichloromethane (4×20 mL). The organic solution was concentrated. The residue was purified with column chromatography on silica gel using 1-10% methanol/dichloromethane to afford product (162.5 mg, Yield: 49%).

The product was dissolved in dichloromethane (5 mL), about 2 mL of trifluoroacetic acid was added. The mixture was stirred at room temperature for 6.5 h. The mixture was concentrated to remove the solvents. The residue was dissolved in dichloromethane (20 mL), washed with saturated potassium carbonate, brine, dried over anhydrous sodium sulfate, concentrated. The residue was purified with NH-column using 1-15% methanol/dichloromethane and recrystallized with methanol/dichloromethane/hexane to afford product (54 mg). $^1$H-NMR (500 MHz, CDCl$_3$): 7.553 (d, J=2.0 Hz and 8.0 Hz, 1H), 7.367-7.310 (m, 2H), 4.713 (br, 2H), 3.960 (br, 2H), 3.115 (t, J=3.5 Hz, 1H), 3.089 (t, J=3.5 Hz, 1H), 2.755-2.702 (m, 2H), 2.082 (m, 2H), 1.454-1.386 (m, 2H). LC-MS: 339.0 (MH$^+$/z).

Example 63

Preparation of Compound 79

Synthesis of 3-N-piperazin-1-yl lamotrigine (Compound 79)

Synthesis of 5-amino-6-chloro-3-N-(4-N-Boc-piperazinyl)amino-1,2,4-triazine

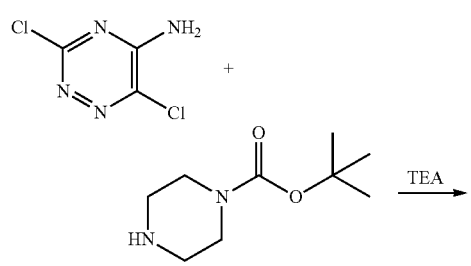

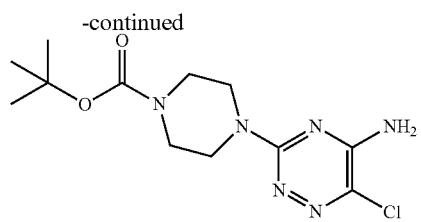

A vial was charged with 5-amino-3,6-dichloro-1,2,4-triazine (466 mg, 2.82 mmol) and triethylamine (1.0 mL, 7.17 mmol), t-Boc-piperazine (0.5675 g, 2.96 mmol) in dioxane. The mixture was heated at 95° C. for 1.5 hours using microwave. The mixture was cooled to room temperature, filtered and the white solid was washed with ethyl acetate. The organic solution was concentrated. The residue was purified with flash column chromatography on silica gel using 1-10% methanol/dichloromethane to afford 872.4 mg product as solid in 98% yield. $^1$H NMR (500 MHz, Chloroform-d) δ 5.38 (br, 2H), 3.76-3.68 (m, 4H), 3.44 (dd, J=6.3, 3.9 Hz, 4H), 1.42 (s, 9H). LC-MS: 315.0 (MH$^+$/z).

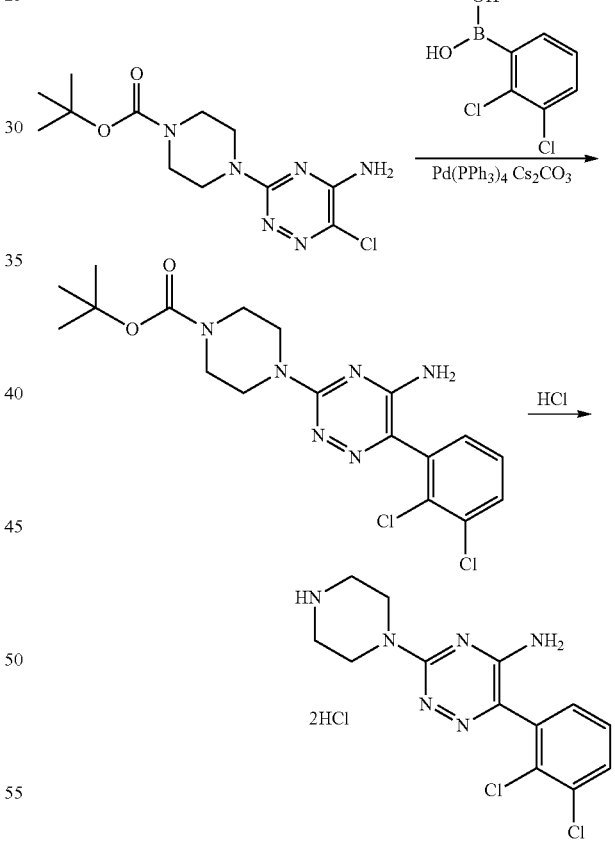

A mixture of (2,3-dichlorophenyl)boronic acid (355.4 g, 1.86 mmol), 5-amino-6-chloro-3-(4-N-BOC-piperazin-1-yl)amino-1,2,4-triazine (302.4 mg, 0.96 mmol) and cesium carbonate (1.0591 g, 3.22 mmol) was dissolved in dioxane/water (10 mL/2 mL). And then tetrakis(triphenylphosphine)palladium (112.6 mg, 0.097 mmol) was added. The mixture was purged with nitrogen for a few minutes. The mixture was heated to 90° C. during 30 min, and kept at 90° C. for 5.5 h. The mixture was cooled to room temperature, concentrated to remove the organic solvent. The residue was dissolved in water and extracted with dichloromethane (3×40 mL). The combined organic solution was dried over anhydrous sodium sulfate, concentrated. The residue was separated with flash column chromatography on silica gel using 1-10% methanol/dichloromethane. The product was purified again with flash column chromatography on silica gel using 30-55% ethyl acetate/hexane to afford intermediate (222.5 mg, 55%).

The intermediate (222.5 mg) was dissolved in 1.5 mL of methanol, 0.5 mL of 4 N hydrochloride in dioxane was added. The mixture was stirred at room temperature for 4 h 40 min. More of 4 N hydrochloride in dioxane (0.3 mL) was added. The mixture was stirred at room temperature for 17.5 h. The mixture was concentrated to remove the solvents. The residue was dried under high vacuum to afford final product as HCl salt (216.1 mg). $^1$H NMR (500 MHz, DMSO-$d_6$) δ 9.61 (s, 2H), 8.99 (br, 1H), 8.07 (br, 1H), 7.84 (d, J=7.9 Hz, 1H), 7.54 (t, J=7.9 Hz, 1H), 7.48 (d, J=7.6 Hz, 1H), 4.04 (s, 4H), 3.265 (s, 4H). LC-MS: 325.0 (MH$^+$/z).

68.3 mg of HCl salt was mixed with saturated potassium carbonate solution, extracted with dichloromethane (3×20 mL). The combined organic solution was washed with brine, dried over anhydrous sodium sulfate, concentrated to afford the product as free base (47.6 mg). $^1$H NMR (500 MHz, Chloroform-d) δ 7.551 (dd, J=2.0 Hz and 8.0 Hz, 1H), 7.367-7.308 (m, 2H), 4.689 (br, 2H), 3.862 (m, 4H), 2.954 (t, J=5.0 Hz, 4H). LC-MS: 325.0 (MH$^+$/z).

Example 64

Preparation of Compound 117

Synthesis of 3-N-piperazin-1-yl 5-fluoro lamotrigine (Compound 117)

Synthesis of 2-(2,3-dichloro-5-fluoro-phenyl)-4,4,5,5-tetramethyl-1,3,2-dioxaborolane

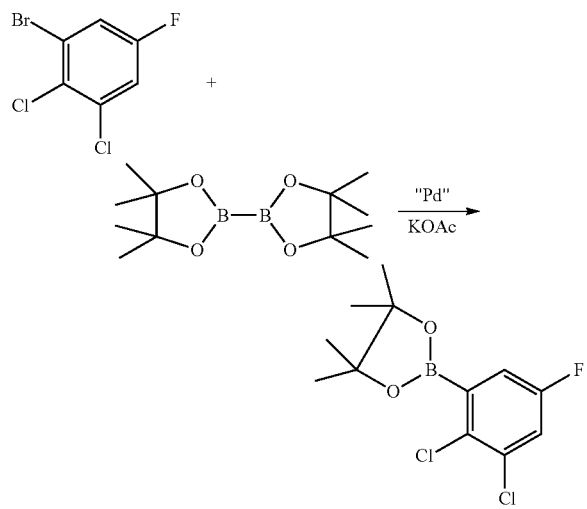

A mixture of 1-bromo-2,3-dichloro-5-fluorobenzene (3.1304 g, 12.94 mmol), bis(pinacolato)diboron (5.7397 g, 22.38 mmol), potassium acetate (3.9788 g, 40.1 mmol) in DMSO (60 mL) was stirred at room temperature for about 30 min. The mixture was degassed with nitrogen for a few minutes and 1,1'-[bis(diphenylphosphino)ferrocene]dichloropalladium (II) (0.7953 g, 1.09 mmol) was added. The mixture was degassed again with nitrogen, was heated to 80° C. with stirring and kept at 80° C. for 4 h 20 min. The mixture was cooled to room temperature and poured into ice. The mixture was extracted with ethyl acetate (3×150 mL). The combined organic solution was washed with saturated sodium chloride solution (150 mL), dried over anhydrous sodium sulfate, and concentrated. The residue was separated with flash column chromatography on silica gel using ethyl acetate/hexane to afford product as white solid (2.6156 g, Yield: 70%). $^1$H NMR (500 MHz, Chloroform-d) δ 7.070 (d, J=3.0 Hz, 1H), 7.029 (d, J=3.0 Hz, 1H), 1.238 (s, 12H).

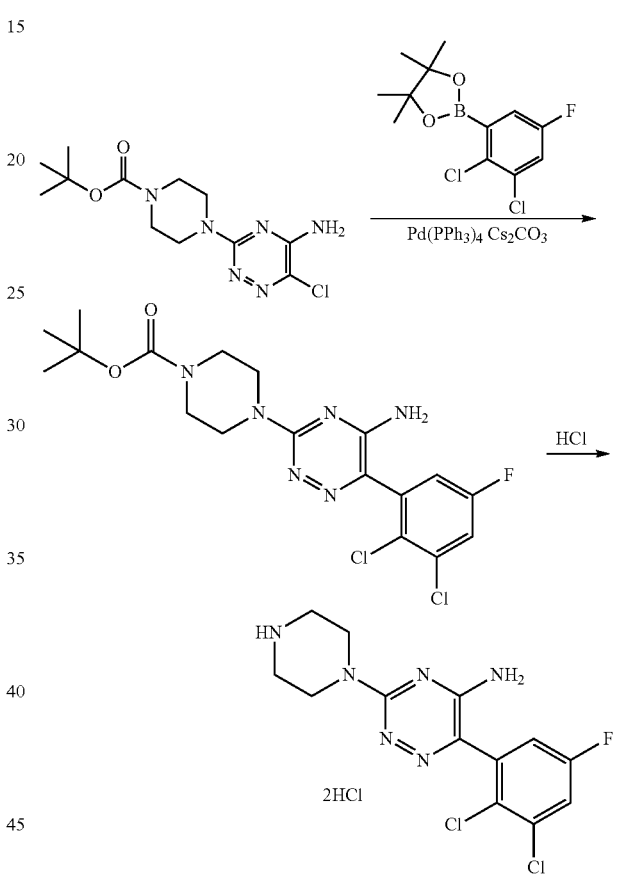

A mixture of 2-(2,3-dichloro-5-fluorophenyl)-4,4,5,5-tetramethyl-1,3,2-dioxaborolane (313.7 g, 1.08 mmol), 3-(4-N-Boc-piperazin-1-yl)amino-5-amino-6-chloro-1,2,4-triazine (228.2 mg, 0.73 mmol) and cesium carbonate (0.7863 g, 2.39 mmol) was dissolved in dioxane/water (10/2 mL). And then tetrakis(triphenylphosphine)palladium (89.5 mg, 0.078 mmol) was added. The mixture was purged with nitrogen for a few minutes. The mixture was heated to 90° C., and kept at 90° C. for 5.5 h. The mixture was cooled to room temperature, concentrated to remove the organic solvent. The residue was dissolved in water and extracted with dichloromethane (3×40 mL). The combined organic solution was dried over anhydrous sodium sulfate, concentrated. The residue was separated with flash column chromatography on silica gel using 30-55% ethyl acetate/hexane to afford the intermediate (154.3 mg, Yield: 48%) and starting material (59.1 mg, recovery: 26%).

The intermediate (149.2 mg) was dissolved in 1.5 mL of methanol, 0.5 mL of 4N hydrochloride in dioxane was added. The mixture was stirred at room temperature for 4 h 35 min. More of 4 N hydrochloride in dioxane (0.2 mL) was added. The mixture was stirred at r.t. for 1 h. The mixture was concentrated to remove the solvents. The residue was dried under high vacuum to afford final product as HCl salt (161.4 mg). $^1$H NMR (500 MHz, Methanol-$d_4$) δ 7.704 (dd, J=3.0 Hz and 8.0 Hz, 1H), 7.383 (dd, J=3.0 Hz and 8.0 Hz, 1H), 4.12 (m, 4H), 3.465 (t, J=5.0 Hz, 4H). LC-MS: 343.0 (MH$^+$/z).

Example 65

Preparation of Compound 118

Synthesis of 3-N-(3',5'-dimethylpiperazin-1-yl) lamotrigine (Compound 118) (Stereochemistry as Shown in the Schematic)

Synthesis of 5-amino-3-(3,5-dimethylpiperazin-1-yl) amino-1,2-4-triazine

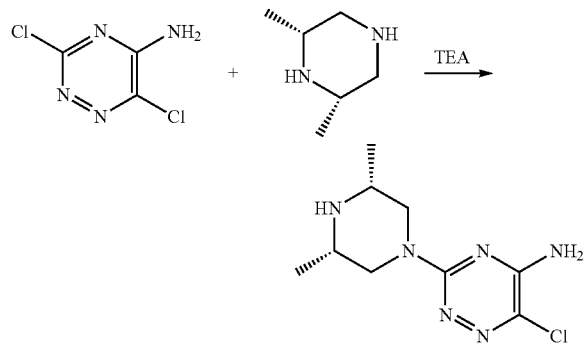

A vial was charged with 5-amino-3,6-dichloro-1,2,4-triazine (495.1 mg, 4.25 mmol) and triethylamine (1.5 mL, 10.76 mmol), 2,6-dimethylpiperazine (0.7054 g, 4.28 mmol) in dioxane (11 mL). The mixture was heated at 95° C. for 1.5 h using microwave. The mixture was cooled to room temperature, filtered and the white solid was washed with dichloromethane. The organic solution was concentrated. The residue was dissolved in dichloromethane, washed with saturated potassium carbonate, dried over anhydrous sodium sulfate, concentrated. The residue was purified with flash column chromatography on silica gel using ethyl acetate and 0-10% methanol/ethyl acetate to afford product as solid (0.8916 g, yield: 86%). $^1$H NMR (500 MHz, Chloroform-d) δ 5.168 (br, 2H), 4.550 (d, J=12.5 Hz, 2H), 2.859-2.800 (m, 2H), 2.432 (d, J=13.2 Hz, 1H), 2.406 (d, J=10.5 Hz, 1H), 1.094 (d, J=6.5 Hz, 6H). LC-MS: 243.0 (MH$^+$/z).

Synthesis of 3-N-(3',5'-dimethylpiperazin-1-yl) lamotrigine (Compound 118)

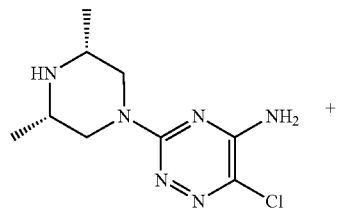

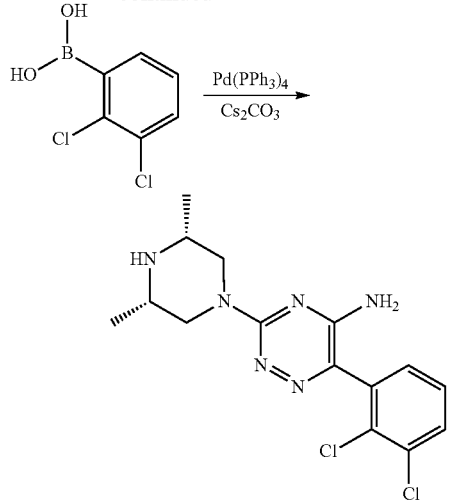

5-Amino-6-chloro-3-(3,5-dimethylpiperazin-1-yl)amino-1,2-4-triazine (287 mg, 1.182 mmol), (2,3-dichlorophenyl) boronic acid (520.1 mg, 2.73 mmol and cesium carbonate (1.3013 g, 3.95 mmol) were added. And then water (5 mL) was added. The mixture was degassed with nitrogen, tetrakis (triphenylphosphine)palladium (121.5 mg, 0.105 mmol) was added. The mixture was purged with nitrogen for a few minutes, and then heated to 90° C. during 55 min, and kept at 90° C. for 4 h 15 min. The mixture was concentrated under reduced pressure to dryness. The residue was mixed with brine, extracted with dichloromethane (4×20 mL). The organic solution was concentrated. The residue was purified with flash column chromatography on silica gel using 1-10% methanol/dichloromethane. The product was purified again with reverse column chromatography using 10-50% acetonitrile/water to afford the product (123.2 mg, Yield: 30%). $^1$H NMR (500 MHz, Chloroform-d) δ 7.550 (dd, J=2.0 Hz and 7.5 Hz, 1H), 7.366-7.307 (m, 2H), 4.685 (m, 4H), 2.927-2.875 (m, 2H), 2.488 (t, J=12.0 Hz, 2H), 1.133 (d, J=6.0 Hz, 6H). LC-MS: 353.0 (MH$^+$/z).

62.2 mg of product was dissolved into 1.5 mL of methanol. 0.4 mL of 2 N hydrochloride solution in ether was added. The mixture was concentrated to dryness. The residue was dried under high vacuum to afford the product as HCl salt (65.2 mg).

Example 66

Preparation of Compound 119

Synthesis of 3-N-(3',5'-dimethylpiperazin-1-yl) 5'-fluoro lamotrigine (Compound 119) (Stereochemistry as Shown in the Schematic)

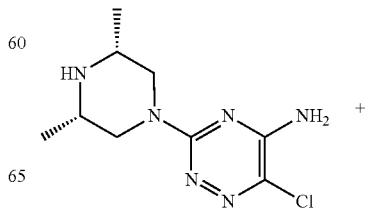

165

-continued

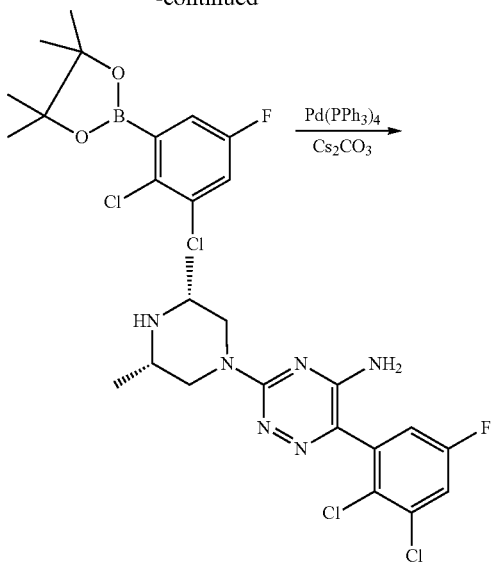

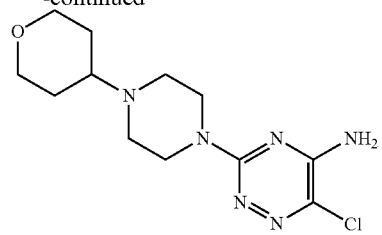

5-Amino-6-chloro-3-(3,5-dimethylpiperazinyl)amino-1,2,4-triazine (179.5 mg, 0.74 mmol) was dissolved in dioxane (15 mL). 2-(2,3-dichloro-5-fluorophenyl)-4,4,5,5-tetramethyl-1,3,2-dioxaborolane (420.6 mg, 1.446 mmol) and cesium carbonate (781.4 g, 2.37 mmol) were added. And then water (5 mL) was added. The mixture was degassed with nitrogen, tetrakis(triphenylphosphine)palladium (103.5 mg, 0.09 mmol) was added. The mixture was purged with nitrogen for a few minutes, and then heated to 90° C. during 15 min, and kept at 90° C. for 5 h. The mixture was concentrated under reduced pressure to dryness. The residue was mixed with brine, extracted with dichloromethane (4×20 mL). The organic solution was concentrated. The residue was purified with reverse column chromatography using 10-50% acetonitrile/water to afford product as white solid (98.3 mg, Yield: 36%). $^1$H NMR (500 MHz, Chloroform-d) δ 7.317 (dd, J=3.0 Hz and 7.5 Hz, 1H), 7.131 (dd, J=3.0 Hz and 8.0 Hz, 1H), 4.696 (m, 4H), 2.922-2.883 (m, 2H), 2.496 (t, J=11.5 Hz, 2H), 1.134 (d, J=6.0 Hz, 6H). LC-MS: 371.0 (MH$^+$/z).

Take 38.9 mg of product to dissolve in methanol (2 mL), add 2 N hydrogen chloride solution in ether (0.5 mL), and then concentrate to remove all of solvents. The residue was dried under high vacuum to afford the product as HCl salt (426 mg). LC-MS: 371.0 (MH$^+$/z).

Example 67

Preparation of Compound 120

Synthesis of 3-N-(4-(tetrahydro-2H-pyran-4-yl)piperazin-1-yl) lamotrigine di HCl (Compound 120)

Synthesis of 5-amino-6-chloro-3-(4-(tetrahydro-2H-pyran-4-yl)piperazin-1-yl)-1,2,4-triazine

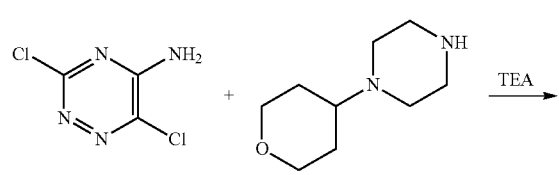

166

-continued

A vial was charged with 5-amino-3,6-dichloro-1,2,4-triazine (1.0521 g, 6.38 mmol), triethylamine (4.0 mL, 28.7 mmol), 1-(tetrahydro-2H-pyran-4-yl)piperazine 2HCl (1.6973 g, 6.63 mmol) in dioxane (10 mL). The mixture was heated at 95° C. for 1.5 h. The mixture was cooled to room temperature and transferred into a flask with dichloromethane, concentrated to remove the solvents. The residue was mixed with aqueous potassium carbonate, extracted with dichloromethane (3×60 mL). The aqueous mixture was filtered to collect the solid. The solid was dried under high vacuum to afford first batch of product (222 mg). The combined organic solution was concentrated. The residue was dissolved in warm dichloromethane, cooled to room temperature. The solid was collected and washed with dichloromethane to afford another batch of product (1.6048 g). The total yield was 99%. $^1$H NMR (500 MHz, Chloroform-d) δ 5.14 (s, 2H), 3.99 (dd, J=11.3, 4.3 Hz, 2H), 3.76 (t, J=5.1 Hz, 4H), 3.34 (td, J=11.9, 1.9 Hz, 2H), 2.59-2.53 (m, 4H), 2.42 (tt, J=11.4, 3.8 Hz, 1H), 1.75-1.72 (m, 2H), 1.62-1.53 (m, 2H). MS for $C_{12}H_{19}ClN_6O$: 299.0 (MH$^+$).

Synthesis of 3-N-(4-(tetrahydro-2H-pyran-4-yl)piperazin-1-yl) lamotrigine di HCl (Compound 120)

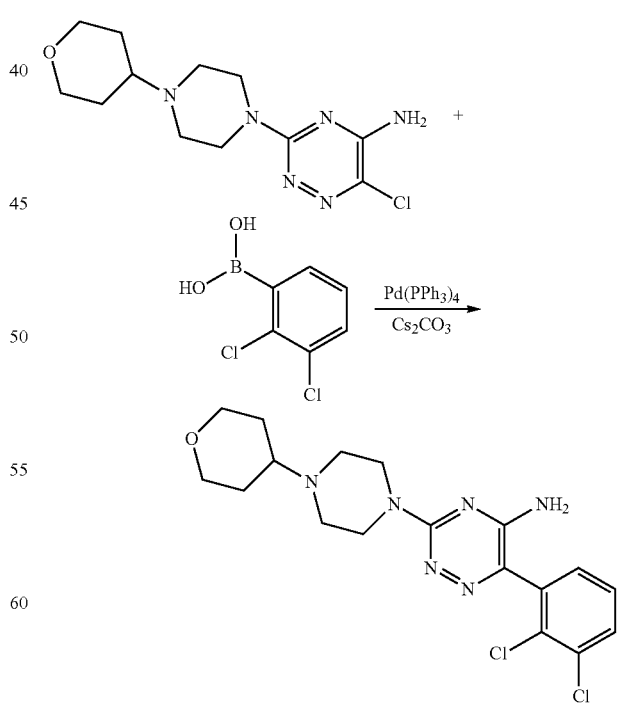

(2,3-Dichlorophenyl)boronic acid (737.8 mg, 3.87 mmol) and 5-amino-6-chloro-3-(4-(tetrahydro-2H-pyran-4-yl)piperazin-1-yl)-1,2,4-triazine (399.8 mg, 1.338 mmol) was dissolved in water/dioxane (5/15 mL). Cesium carbonate (1.4146 g, 4.30 mmol) was added. The mixture was degassed with nitrogen, tetrakis(triphenylphosphine)palladium (161.8 mg, 0.140 mmol) was added. The mixture was purged with nitrogen for a few minutes, and then heated to 90° C. during 15 min, and kept at 90° C. for 5 h. The mixture was concentrated under reduced pressure to dryness. The residue was purified with flash column chromatography on silica gel using 3-10% methanol in dichloromethane (52.1 mg). $^1$H NMR (500 MHz, Chloroform-d) δ 7.55 (dd, J=7.6, 2.1 Hz, 1H), 7.38-7.29 (m, 2H), 4.69 (s, 2H), 4.03 (dd, J=11.4, 4.5 Hz, 2H), 3.89 (s, 4H), 3.38 (td, J=11.9, 1.9 Hz, 2H), 2.66-2.55 (m, 4H), 2.47 (m, 1H), 1.78 (d, J=12.5 Hz, 2H), 1.61 (td, J=12.2, 4.5 Hz, 2H). MS for $C_{18}H_{22}Cl_2N_6O$: 409.0 (MH$^+$). The product was dissolve in dichloromethane (~3 mL)/methanol (~2 mL), 2.0 M HCl in ether (1 mL) was added. The solution was concentrated to remove all of solvents. The residue was dried under high vacuum to afford the product as HCl salt. MS for $C_{18}H_{22}Cl_2N_6O$: 409.0 (MH$^+$).

Example 68

Preparation of Compound 121

Synthesis of 3-N-(4-(piperidin-4-yl)piperazin-1-yl) lamotrigine 3HCl salt (Compound 121)

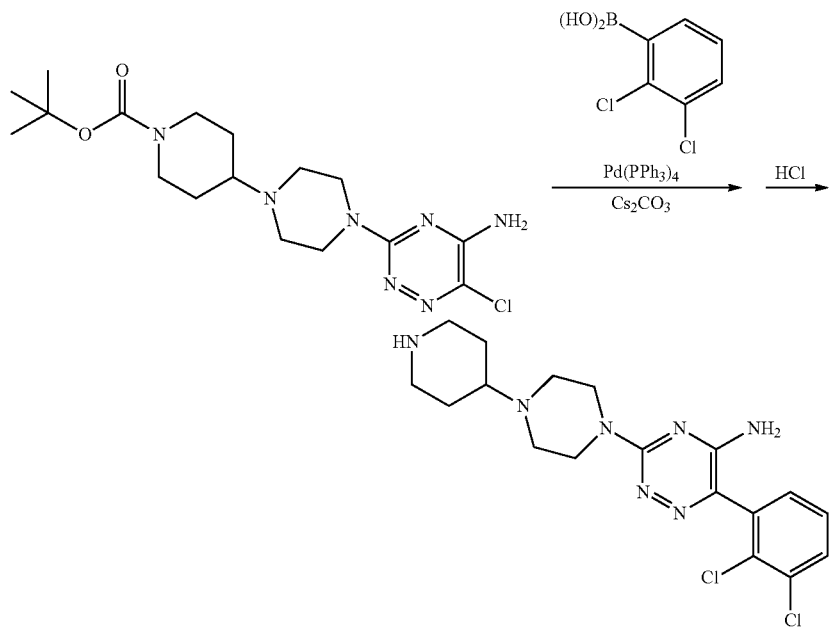

(2,3-Dichlorophenyl)boronic acid (515.2 mg, 2.70 mmol) and 3-amino-6-chloro-3-(1-Boc-piperidin-4-yl) piperazin-1-yl)-1,2,4-triazine (326.4 mg, 0.820 mmol) was dissolved in water/dioxane (5/15 mL). Cesium carbonate (1.0435 g, 3.17 mmol) was added. The mixture was degassed with nitrogen, tetrakis(triphenylphosphine)palladium (143.8 mg, 0.124 mmol) was added. The mixture was purged with nitrogen for a few minutes, and then heated to 90° C. during 15 min, and kept at 90° C. for 3 h. The mixture was concentrated under reduced pressure to dryness. The residue was mixed with brine, extracted with dichloromethane (2×20 mL). The organic solution was concentrated. The residue was purified with flash column chromatography on silica gel using 1-5% methanol/dichloromethane to afford 3-N-(1-Boc-(piperidin-4-yl)piperazin-1-yl) lamotrigine (320.8 mg) in 77% yield. $^1$H NMR (500 MHz, Chloroform-d) δ 7.58-7.49 (m, 1H), 7.42-7.29 (m, 2H), 4.69 (s, 2H), 4.14 (br, 2H), 3.88 (s, 4H), 2.70 (s, 2H), 2.62 (t, J=5.1 Hz, 4H), 2.42 (m, 1H), 1.81 (d, J=11.0 Hz, 2H), 1.43 (s, 9H), 1.41 (m, 2H). MS for $C_{23}H_{31}Cl_2N_7O_2$: 508.2 (MH$^+$).

3-N-(1-Boc-(piperidin-4-yl)piperazin-1-yl) lamotrigine (78 mg, 0.153 mmol) was dissolved in methanol (0.5 mL), 4.0 M HCl in dioxane (1.5 mL) was added. The mixture was stirred at room temperature for 6 h. The mixture was concentrated to remove all of solvents to afford 3-N-(4-(piperidin-4-yl)piperazin-1-yl) lamotrigine HCl salt as white solid (76.9 mg) in 97% yield. $^1$H NMR (500 MHz, Deuterium Oxide) δ 7.77 (dd, J=8.0, 1.5 Hz, 1H), 7.52-7.42 (m, 2H), 4.10 (br, 4H), 3.66 (d, J=12.8 Hz, 3H), 3.52 (s, 4H), 3.13 (t, J=12.7 Hz, 2H), 2.47 (d, J=13.5 Hz, 2H), 1.99 (qd, J=13.2, 4.1 Hz, 2H). MS for $C_{18}H_{23}Cl_2N_7$: 408.0 (MH$^+$).

3-N-(4-(piperidin-4-yl)piperazin-1-yl) lamotrigine HCl salt (26.2 mg) was mixed with dichloromethane, washed with aqueous potassium carbonate. The organic solution was separated and the aqueous solution was extracted with dichloromethane. The organic solutions were combined and washed with brine, dried over anhydrous sodium sulfate, concentrated to afford the product as free base. $^1$H NMR (500 MHz, Chloroform-d) δ 7.55 (dd, J=7.7, 2.0 Hz, 1H), 7.38-7.28 (m, 2H), 4.69 (s, 2H), 3.89 (s, 4H), 3.16 (d, J=12.2 Hz, 2H), 2.67-2.56 (m, 6H), 2.39 (ddt, J=11.4, 7.0, 3.5 Hz, 1H), 1.84 (d, J=12.5 Hz, 2H), 1.44 (qd, J=12.2, 4.0 Hz, 2H).

Example 69

Preparation of Compound 122

Synthesis of (R)-5-amino-3-N-[3-(hydroxymethyl)piperazin-1-yl] lamotrigine diHCl (Compound 122)

Synthesis of (R)-5-amino-6-chloro-3-[4-Boc-3-(hydroxymethyl)piperazin-1-yl] 1,2,4-triazine

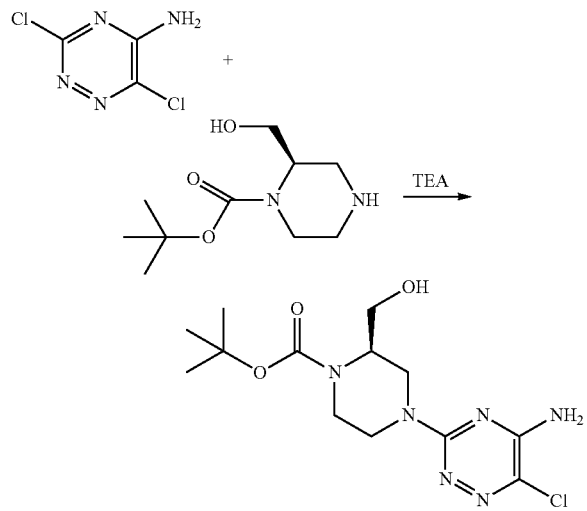

A vial was charged with 5-amino-3,6-dichloro-1,2,4-triazine (573.3 mg, 3.47 mmol), triethylamine (1.5 mL, 10.76 mmol), (R)-tert-butyl 2-(hydroxymethyl)piperazine-1-carboxylate (791.3 mg, 3.55 mmol) in dioxane (10 mL). The mixture was heated at 95° C. for 1.5 h using microwave. More of (R)-tert-butyl 2-(hydroxymethyl)piperazine-1-carboxylate (69.4 mg) was added. The mixture was heated at 95° C. for another 1 h using microwave. The mixture was cooled to room temperature and transferred into a flask with dichloromethane, concentrated to remove the solvents. The residue was mixed with saturated potassium carbonate solution, extracted with dichloromethane (3×40 mL). The combined organic solution was dried over anhydrous sodium sulfate, concentrated. The residue was mixed with small amount of dichloromethane, filtered to collect the white solid as first batch of product (649.6 mg). The solution was concentrated and the residue was separated with flash column chromatography on silica gel using 1-5% methanol in dichloromethane to afford another batch of product (174.3 mg). The total yield was 69%. $^1$H NMR (500 MHz, Chloroform-d) δ 5.32 (s, 2H), 4.71 (br, 1H), 4.47 (d, J=12.5 Hz, 1H), 4.24 (s, 1H), 3.90 (s, 1H), 3.54 (s, 1H), 3.44 (s, 1H), 3.15 (d, J=14.0 Hz, 1H), 3.05 (t, J=12.0 Hz, 1H), 2.95 (s, 1H), 1.45 (s, 9H). MS for $C_{13}H_{21}ClN_6O_3$: 345.0 (MH$^+$).

Synthesis of (R)-5-amino-3-N-[3-(hydroxymethyl)piperazin-1-yl] lamotrigine diHCl

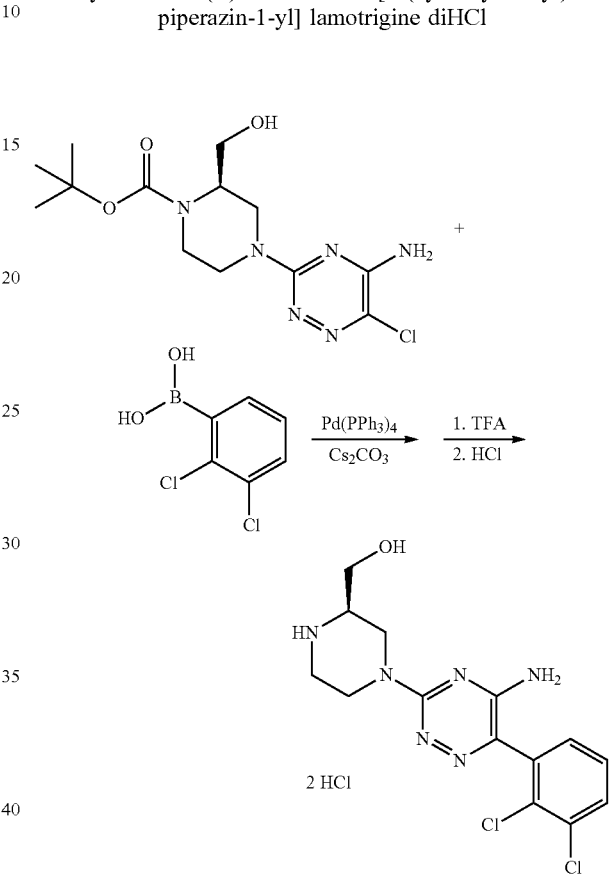

(2,3-Dichlorophenyl)boronic acid (632.8 mg, 3.32 mmol) and (R)-5-amino-6-chloro-3-[4-Boc-3-(hydroxymethyl)piperazin-1-yl] 1,2,4-triazine (369.0 mg, 1.07 mmol) was dissolved in water/dioxane (5/15 mL). Cesium carbonate (1.3661 g, 4.15 mmol) was added. The mixture was degassed with nitrogen, tetrakis(triphenylphosphine)palladium (144.3 mg, 0.125 mmol) was added. The mixture was purged with nitrogen for a few minutes, and then heated to 90° C. during 15 min, and kept at 90° C. for 4 h. More of catalyst (51.8 mg) was added. The mixture was stirred at 90° C. for 2 h. The mixture was concentrated under reduced pressure to dryness. The residue dissolved in dichloromethane, washed with brine, dried over anhydrous sodium sulfate, concentrated. The residue was dissolved on methanol (5 mL). Ammonium hydroxide (10 mL) was added. The mixture was stirred at room temperature for 20 h. The mixture was concentrated to remove all of solvents. The residue was separated with NH-column by using 0-10% methanol in dichloromethane to afford (R)-5-amino-3-[4-Boc-3-(hydroxymethyl)piperazin-1-yl] lamotrigine (160 mg) in 33% yield. MS for $C_{19}H_{24}Cl_2N_6O_3$: 455.0 (MH$^+$).

(R)-5-amino-3-[4-Boc-3-(hydroxymethyl)piperazin-1-yl] lamotrigine (160 mg, 0.351 mmol) was dissolved in dichloromethane (10 mL). Trifluoro acetic acid (2.0 mL) was added. The mixture was stirred at room temperature for 2 h. The mixture was concentrated to remove the solvents. The residue was dried under vacuum for a few minutes. The residue was dissolved in dichloromethane, washed with 5% sodium bicarbonate aqueous solution. The organic solution was separated and the aqueous solution was extracted with dichloromethane (2×30 mL). The combined organic solution was dried with anhydrous sodium sulfate, concentrated to afford the product as solid (99.9 mg). $^1$H NMR (500 MHz, Methanol-$d_4$) δ 7.66 (dd, J=8.0, 1.6 Hz, 1H), 7.43 (t, J=7.8 Hz, 1H), 7.37 (dd, J=7.6, 1.6 Hz, 1H), 4.66 (dt, J=12.7, 2.0 Hz, 1H), 4.61-4.54 (m, 1H), 3.58 (qd, J=11.0, 5.7 Hz, 2H), 3.35 (s, 2H), 3.09 (dt, J=11.4, 2.3 Hz, 1H), 3.09-3.00 (m, 1H), 2.83 (tt, J=10.7, 2.6 Hz, 2H), 2.77 (dd, J=12.7, 10.4 Hz, 1H). MS for $C_{16}H_{16}Cl_2N_6O$: 355.0 (MH$^+$).

35.5 mg of product as free base was dissolved in methanol (2.0 mL), 2.0 M HCl (0.5 mL) in ether was added. The resulting mixture was concentrated to remove all of solvents. The residue was dried under high vacuum to afford the product as HCl salt.

Example 70

Preparation of Compound 123

Synthesis of (R)-5-amino-3-N-[3-(hydroxymethyl) piperazin-1-yl] 5'-fluoro lamotrigine di HCl salt (Compound 123)

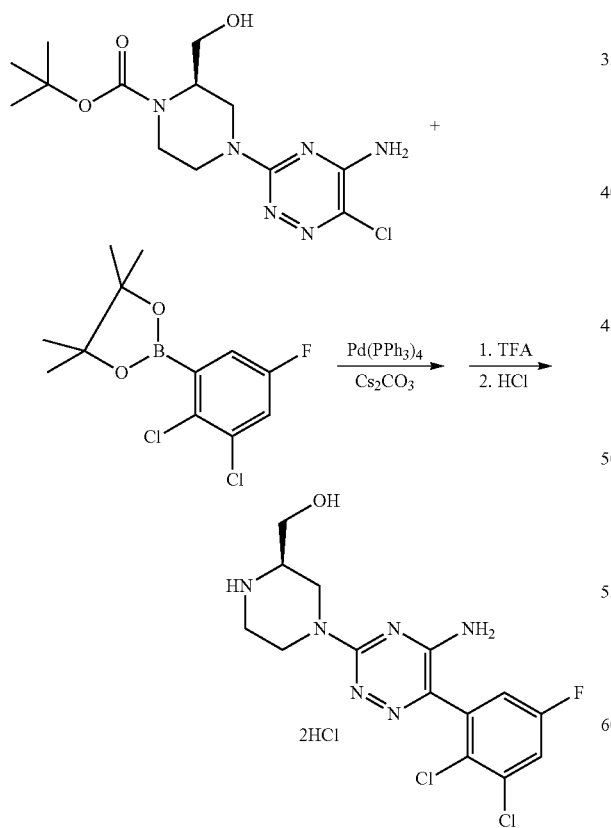

2-(2,3-Dichloro-5-fluorophenyl)-4,4,5,5-tetramethyl-1,3,2-dioxaborolane (387.7 mg, 1.333 mmol) and (R)-5-amino-6-chloro-3-[4-Boc-3-(hydroxymethyl)piperazin-1-yl] 1,2,4-triazine (240.3 mg, 0.697 mmol) was dissolved in water/dioxane (5/15 mL). Cesium carbonate (780.4 mg, 2.371 mmol) were added. The mixture was degassed with nitrogen, tetrakis(triphenylphosphine)palladium (144.1 mg, 0.125 mmol) was added. The mixture was purged with nitrogen for a few minutes, and stirred at 90° C. for 4.5 h. The mixture was concentrated under reduced pressure to dryness. The residue dissolved in dichloromethane, washed with brine, dried over anhydrous sodium sulfate, concentrated. The residue was purified with column chromatography on silica gel to afford (R)-5-amino-3-[4-Boc-3-(hydroxymethyl)piperazin-1-yl] 5'-fluoro lamotrigine (166.7 mg) in 51% yield. MS for $C_{19}H_{23}Cl_2FN_6O_3$: 473.0 (MH$^+$).

(R)-5-amino-3-[4-Boc-3-(hydroxymethyl)piperazin-1-yl] 5'-fluoro lamotrigine (166.7 mg) (95 mg, 0.2 mmol) was dissolved in dichloromethane (3 mL), trifluroacetic acid (1 mL) was added. The mixture was stirred at room temperature for 2 h. The mixture was concentrated to remove all of solvent. The residue was dried. The residue was mixed with dichloromethane, aqueous sodium bicarbonate solution was added. The organic solution was separated and the aqueous solution was saturated with sodium chloride, extracted with dichloromethane. The combined organic solution was dried over anhydrous sodium sulfate, concentrated to afford the product as free base (59 mg) in 79% yield. $^1$H NMR (500 MHz, Methanol-$d_4$) δ 7.55 (dd, J=8.2, 3.0 Hz, 1H), 7.23 (dd, J=8.2, 2.9 Hz, 1H), 4.71-4.64 (m, 1H), 4.59 (d, J=13.1 Hz, 1H), 3.65-3.52 (m, 2H), 3.08 (ddd, J=27.4, 13.3, 3.0 Hz, 2H), 2.89-2.75 (m, 3H). MS for $C_{14}H_{15}Cl_2FN_6O$: 373.0 (MH$^+$).

54 mg of the product as free based was dissolved in methanol (1.5 mL), 2 N HCl (0.5 mL) in ether was added. The mixture was concentrated to remove all of solvents. The residue was dried under high vacuum to afford the product was HCl salt (55.4 mg).

Example 71

Preparation of Compound 124

Synthesis of 5-amino-3-[3-(s)-(hydroxymethyl)piperazin-1-yl] lamotrigine (Compound 124)

Synthesis of (S)-5-amino-6-chloro-3-[4-Boc-3-(hydroxymethyl)piperazin-1-yl] 1,2,4-triazine

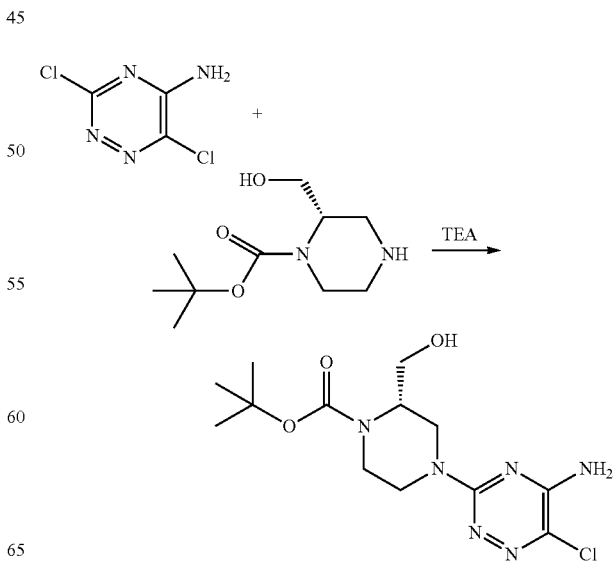

A vial was charged with 5-amino-3,6-dichloro-1,2,4-triazine (589.6 mg, 3.57 mmol), triethylamine (1.5 mL, 10.76 mmol), (S)-tert-butyl 2-(hydroxymethyl)piperazine-1-carboxylate (890 mg, 3.99 mmol) in dioxane (12 mL). The mixture was heated at 95° C. for 1.5 h using microwave. The mixture was cooled to room temperature and transferred into a flask with dichloromethane, concentrated to remove the solvents. The residue was mixed with saturated potassium carbonate, extracted with dichloromethane (3×40 mL). The combined organic solution was dried over anhydrous sodium sulfate, concentrated. The residue was separated with flash column chromatography on silica gel using 1-5% methanol in dichloromethane to afford the product (955.7 mg) in 78%. $^1$H NMR (500 MHz, Chloroform-d) δ 5.30 (s, 2H), 4.69 (br, 1H), 4.45 (d, J=12.3 Hz, 1H), 4.21 (s, 1H), 3.88 (s, 1H), 3.52 (s, 1H), 3.42 (s, 1H), 3.13 (d, J=14.2 Hz, 1H), 3.02 (t, J=12.0 Hz, 1H), 2.93 (s, 1H), 1.43 (s, 9H). MS for $C_{13}H_{21}ClN_6O_3$: 345.2 (MH$^+$).

Synthesis of 5-amino-3-[3-(s)-(hydroxymethyl)piperazin-1-yl] lamotrigine (Compound 124)

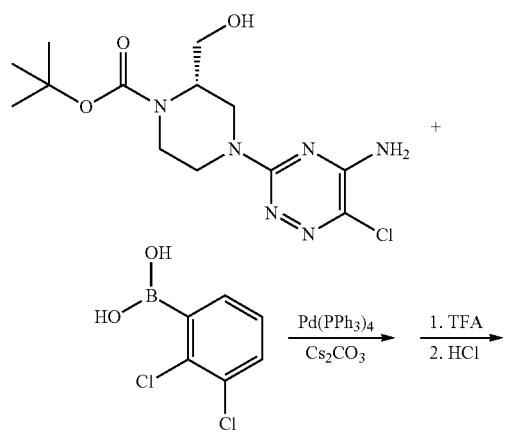

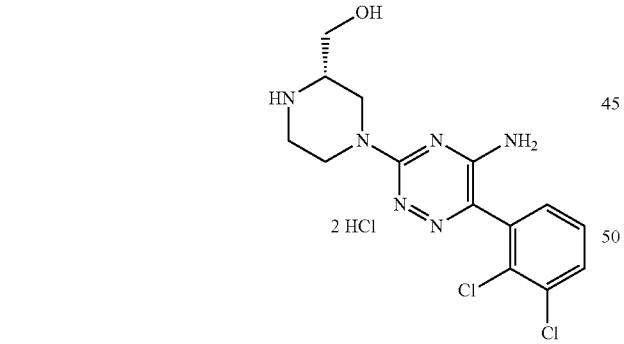

(2,3-Dichlorophenyl)boronic acid (363.1 mg, 1.903 mmol) and 5-amino-6-chloro-3-[4-Boc-3-(s)-(hydroxymethyl)piperazin-1-yl] 1,2,4-triazine (215.6 mg, 0.625 mmol) was dissolved in water/dioxane (5/15 mL). Cesium carbonate (733.6 mg, 2.229 mmol) were added. The mixture was degassed with nitrogen, tetrakis(triphenylphosphine)palladium (139.6 mg, 0.121 mmol) was added. The mixture was purged with nitrogen for a few minutes, and then heated to 90° C. during 10 min, and kept at 90° C. for 4 h. The mixture was concentrated under reduced pressure to dryness. The residue dissolved in dichloromethane, washed with brine, dried over anhydrous sodium sulfate, concentrated. The residue was dissolved in methanol (5 mL), ammonium hydroxide (20 mL) was added to afford a white suspension. The mixture was stirred at r. t. for 4 h. The mixture was concentrated to remove all of solvents. The residue was separated with NH-column using 0-10% methanol in dichloromethane to afford 5-amino-3-[4-Boc-3-(s)-(hydroxymethyl)piperazin-1-yl] lamotrigine (205.5 mg) in 72% yield. MS for $C_{19}H_{24}Cl_2N_6O_3$: 455.0 (MH$^+$).

(s)-5-Amino-3-[4-Boc-3-(hydroxymethyl)piperazin-1-yl] lamotrigine (140.9 mg, 0.31 mmol) was dissolved in dichloromethane (3 mL). Trifluoroacetic acid (1 mL) was added. The mixture was stirred at room temperature for 2 h. The mixture was concentrated to remove the solvents. The residue was dried. The residue was mixed with dichloromethane, aqueous sodium bicarbonate solution was added. The organic solution was separated and the aqueous solution was saturated with sodium chloride, extracted with dichloromethane. The combined organic solution was dried over anhydrous sodium sulfate, concentrated to afford 5-amino-3-[3-(s)-(hydroxymethyl)piperazin-1-yl] lamotrigine as free base (83.6 mg) in 76% yield. $^1$H NMR (500 MHz, Methanol-d$_4$) δ 7.66 (dd, J=8.0, 1.6 Hz, 1H), 7.43 (t, J=7.8 Hz, 1H), 7.37 (dd, J=7.6, 1.6 Hz, 1H), 4.70 4.63 (m, 1H), 4.59 (d, J=12.9 Hz, 1H), 3.65-3.52 (m, 2H), 3.14-3.01 (m, 2H), 2.89-2.75 (m, 3H). MS for $C_{14}H_{16}Cl_2N_6O$: 355.0 (MH$^+$).

5-Amino-3-[3-(s)-(hydroxymethyl)piperazin-1-yl] lamotrigine (63.5 mg) was dissolved in methanol (3 mL), filtrated through 0.2 μm filter, 2 N HCl (1.0 mL) in ether was added. The mixture was concentrated to remove all of solvents. The residue was dried under high vacuum to afford the product as HCl salt in quantitative yield. MS for $C_{14}H_{16}Cl_2N_6O$: 355.0 (MH$^+$).

Example 72

Preparation of Compound 125

Synthesis of 5-amino-3-[3-(s)-(hydroxymethyl)piperazin-1-yl] 5'-fluoro lamotrigine (Compound 125)

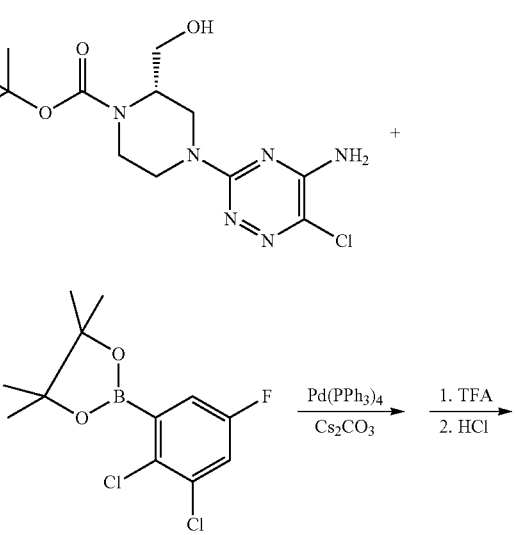

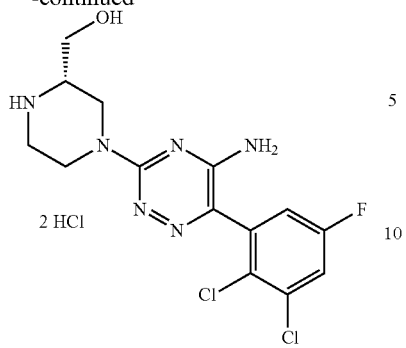

2-(2,3-Dichloro-5-fluorophenyl)-4,4,5,5-tetramethyl-1,3,2-dioxaborolane (349. 7 mg, 1.202 mmol) and 5-amino-6-chloro-3-[4-Boc-3-(s)-(hydroxymethyl)piperazin-1-yl] 1,2,4-triazine (227.1 mg, 0.659 mmol) was dissolved in water/dioxane (5/15 mL). Cesium carbonate (752.5 mg, 2.286 mmol) were added. The mixture was degassed with nitrogen, tetrakis(triphenylphosphine)palladium (100.2 mg, 0.087 mmol) was added. The mixture was purged with nitrogen for a few minutes, and then heated to 90° C. during 5 min, and kept at 90° C. for 4 h 35 min. More of catalyst (51.7 mg) was added. The mixture was stirred at 90° C. for 18 h. The mixture was concentrated under reduced pressure to dryness. The residue dissolved in dichloromethane, washed with brine, dried over anhydrous sodium sulfate, concentrated. The residue was purified to result in 5-amino-3-[4-Boc-3-(s)-(hydroxymethyl)piperazin-1-yl] 5'-fluoro lamotrigine (144.5 mg) in 46% yield. MS for $C_{19}H_{23}Cl_2FN_6O_3$: 473.0 (MH$^+$).

5-Amino-3-[4-Boc-3-(s)-(hydroxymethyl)piperazin-1-yl] 5'-fluoro lamotrigine (81 mg) was dissolved in dichloromethane (3 mL). Trifluoroacetic acid (~1 mL) was added. The resulting mixture was stirred at room temperature for 1 h 10 min. The mixture was concentrated to remove all of solvents. The residue was dried. The residue was mixed with dichloromethane, aqueous sodium bicarbonate solution was added. The organic solution was separated and the aqueous solution was saturated with sodium chloride, extracted with dichloromethane. The combined organic solution was dried over anhydrous sodium sulfate, concentrated to afford 5-amino-3-[3-(s)-(hydroxymethyl)piperazin-1-yl] 5'-fluoro lamotrigine as free base (54.6 mg). $^1$H NMR (500 MHz, Methanol-$d_4$) δ 7.55 (ddt, J=8.2, 3.0, 0.9 Hz, 1H), 7.23 (ddt, J=8.2, 2.9, 1.0 Hz, 1H), 4.68 (dd, J=12.7, 2.1 Hz, 1H), 4.60 (d, J=13.1 Hz, 1H), 3.66-3.53 (m, 2H), 3.16-3.03 (m, 2H), 2.93-2.77 (m, 3H). MS for $C_{14}H_{15}Cl_2FN_6O$: 373 (MH$^+$).

5-Amino-3-[3-(s)-(hydroxymethyl)piperazin-1-yl] 5'-fluoro lamotrigine (48.5 mg) was dissolved in methanol (1.5 mL) and acetonitrile (1 mL). 2.0 M HCl in ether (0.5 mL) was added. The mixture was sonicated and filtered through 0.2 μm filter. The mixture was concentrated to remove all of solvents to afford 5-amino-3-[3-(s)-(hydroxymethyl)piperazin-1-yl] 5'-fluoro lamotrigine as HCl salt. MS for $C_{14}H_{15}Cl_2FN_6O$: 373 (MH$^+$).

Example 73

Preparation of Compound 126

Synthesis of 5-amino-3-N-(3-amino azetidinyl) lamotrigine diHCl salt (Compound 126)

Synthesis of 5-amino-6-chloro-3-N-(3-N-Boc-amino azetidinyl)-1,2,4-triazine

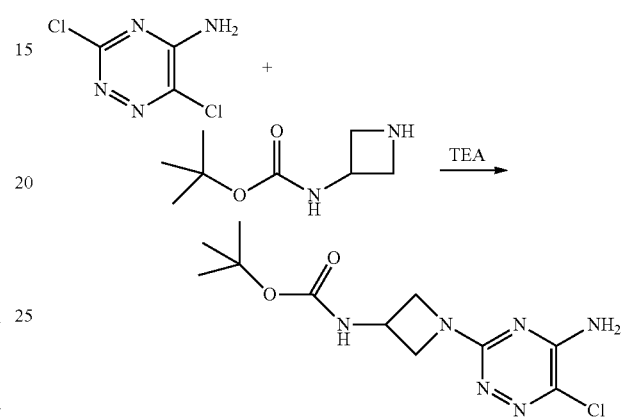

A vial was charged with 5-amino-3,6-dichloro-1,2,4-triazine (643.1 mg, 3.90 mmol), triethylamine (1.5 mL, 10.76 mmol), 3-N-Boc-amino-azetidine (698.6 mg, 3.98 mmol) in dioxane (10 mL). The mixture was heated at 90° C. for 1.5 h using microwave. More of 3-N-Boc-amino-azetidine (56.2 mg, 0.32 mmol) was added. The mixture was heated at 90° C. for another 45 min. The mixture was concentrated to remove the solvent. The residue was mixed with dichloromethane and aqueous sodium bicarbonate. The organic solution was separated and the aqueous solution was extracted with dichloromethane (2×30 mL). The combined organic solution was dried over anhydrous sodium sulfate, concentrated to afford white solid as product in quantitative yield. $^1$H NMR (500 MHz, Chloroform-d) δ 5.25 (s, 2H), 4.97 (s, 1H), 4.59 (s, 1H), 4.41 (t, J=8.0 Hz, 2H), 3.90 (dd, J=9.6, 5.2 Hz, 2H), 1.42 (s, 9H). MS for $C_{11}H_{17}ClN_6O_2$: 301 (MH$^+$).

Synthesis of 5-amino-3-N-(3-N-Boc-amino azetidinyl) lamotrigine

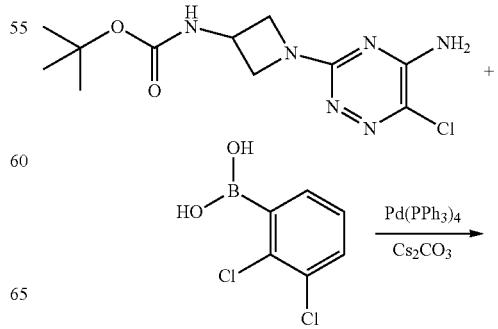

-continued

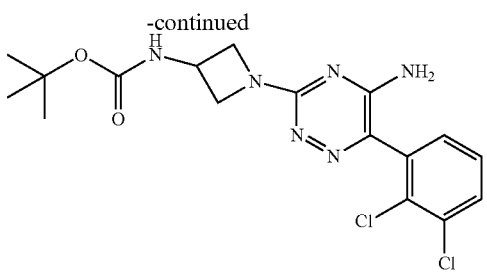

(2,3-Dichlorophenyl)boronic acid (1.2234 g, 6.41 mmol), 5-amino-6-chlorom-3-N-(3-N-Boc-amino azetidinyl)-1,2,4-triazine (886.4 mg, 0.664 mmol) and cesium carbonate (3.6613 g, 11.12 mmol) was dissolved in water/dioxane (6.5/20 mL). The mixture was degassed with nitrogen, tetrakis(triphenylphosphine)palladium (482.2 mg, 0.417 mmol) was added. The mixture was purged with nitrogen for a few minutes, and stirred at 90° C. for 4.5 h. The mixture was concentrated to remove organic solvents. The residue was dissolved in dichloromethane (60 mL). Water (10 mL) was added and brine (100 mL) was added. The organic solution was separated and the aqueous solution was extracted with dichloromethane (2×70 mL). The combined organic solution was dried over anhydrous sodium sulfate, concentrated. The residue was purified with flash column chromatography on silica gel to afford product (419.3 mg) in 35% yield. $^1$H NMR (500 MHz, Chloroform-d) δ 7.59-7.49 (m, 1H), 7.36-7.27 (m, 2H), 4.99 (s, 1H), 4.75 (s, 2H), 4.64 (s, 1H), 4.50 (s, 2H), 3.98 (dd, J=9.9, 5.1 Hz, 2H), 1.44 (s, 9H). MS for $C_{17}H_{20}Cl_2N_6O_2$: 411.0 (MH$^+$).

Synthesis of 5-amino-3-N-(3-amino azetidinyl) lamotrigine diHCl salt: (Compound 73)

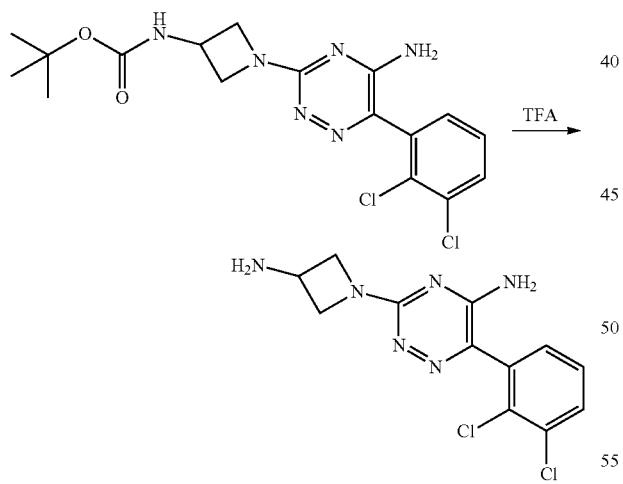

5-Amino-3-N-(3-N-Boc-amino azetidinyl) lamotrigine (418 mg, 1.016 mmol) was dissolved in dichloromethane (12 mL). Trifluoroacetic acid (2.0 mL) was added. The resulting mixture was stirred at room temperature for 5 h 50 min. The mixture was concentrated to remove all of solvents. The residue was dried under high vacuum for a few minutes. The residue was mixed with aqueous sodium bicarbonate, saturated with sodium chloride, extracted with dichloromethane. The organic solution was separated and the aqueous solution was extracted with dichloromethane.

The combined organic solution was dried over anhydrous sodium sulfate, concentrated to afford product as white solid (296 mg) in 94% yield. $^1$H NMR (500 MHz, Chloroform-d) δ 7.55 (dd, J=7.3, 2.4 Hz, 1H), 7.37-7.27 (m, 3H), 4.73 (s, 3H), 4.45 (t, J=8.3 Hz, 3H), 4.03-3.94 (m, 1H), 3.84 (dd, J=9.4, 5.2 Hz, 3H), 3.47 (s, 1H), 1.23 (s, 2H). MS for $C_{12}H_{12}Cl_2N_6$: 311.0 (MH$^+$).

5-Amino-3-N-amino azetidinyl lamotrigine (49 mg, 0.157 mmol) was dissolved in methanol to afford a clear solution. 2.0 M HCl in ether (0.4 mL, 0.8 mmol) was added. The mixture was concentrated to remove all of solvents to afford product as HCl salt. MS for $C_{12}H_{12}Cl_2N_6$: 311.0 (MH$^+$).

Example 74

Preparation of Compound 127

Synthesis of (R)-7-(5-amino-6-(2,3-dichlorophenyl)-1,2,4-triazin-3-yl)tetrahydro-1H-oxazolo[3,4-a]pyrazin-3(5H)-one (Compound 127)

Synthesis of (R)-7-(5-amino-6-chloro-1,2,4-triazin-3-yl)tetrahydro-1H-oxazolo[3,4-a]pyrazin-3(5H)-one

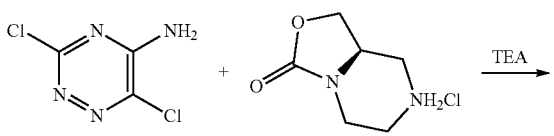

A vial was charged with 5-amino-3,6-dichloro-1,2,4-triazine (457.7 mg, 2.77 mmol), triethylamine (2.0 mL, 14.35 mmol), (R)-hexahydro-oxazolo[3,4-a]pyrazin-3-one HCl (551.8 mg, 3.09 mmol) in dioxane (10 mL). The mixture was heated at 90° C. for 1.5 h using microwave, 120° C. for 60 min. The mixture was concentrated to remove all of solvent. The residue was dissolved in dichloromethane, washed with aqueous sodium bicarbonate solution. The aqueous solution was extracted with dichloromethane (2×30 mL). The combined organic solution was washed with brine, dried over anhydrous sodium sulfate, concentrated. The red residue was mixed with small amount of dichloromethane (~10 mL), warmed up and cooled to room temperature. The solid was collected as product (296.4 mg). $^1$H NMR (500 MHz, Chloroform-d) δ 5.24 (br, 2H), 4.95-4.88 (m, 1H), 4.70 (d, J=12.4 Hz, 1H), 4.44 (t, J=8.6 Hz, 1H), 3.99 (dd, J=9.0, 5.5 Hz, 1H), 3.89-3.82 (m, 2H), 3.06 (td, J=12.7, 3.7 Hz, 1H), 2.93 (td, J=12.8, 3.7 Hz, 1H), 2.81 (dd, J=13.0, 11.1 Hz, 1H). MS for $C_9H_{11}ClN_6O_2$: 271.0 (MH$^+$).

179

Synthesis of (R)-7-(5-amino-6-(2,3-dichlorophenyl)-1,2,4-triazin-3-yl)tetrahydro-1H-oxazolo[3,4-a]pyrazin-3(5H)-one (Compound 127)

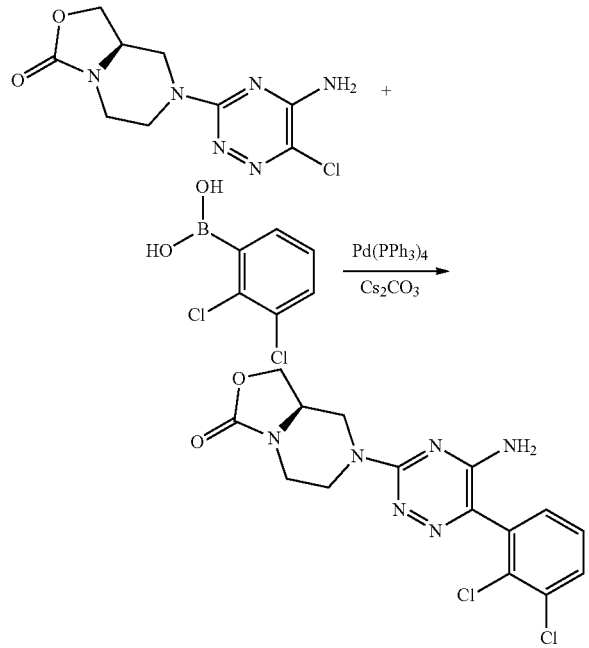

(2,3-Dichlorophenyl)boronic acid (285.2 mg, 1.495 mmol) and (R)-7-(5-amino-6-chloro-1,2,4-triazin-3-yl)tetrahydro-1H-oxazolo[3,4-a]pyrazin-3(5H)-one (179. 6 mg, 0.664 mmol) was dissolved in water/dioxane (5/15 mL). Cesium carbonate (722.5 mg, 2.195 mmol) were added. The mixture was degassed with nitrogen, tetrakis(triphenylphosphine)palladium (120.2 mg, 0.104 mmol) was added. The mixture was purged with nitrogen for a few minutes, and stirred at 90° C. for 5 h. The mixture was concentrated to remove organic solvents. The residue was dissolved in dichloromethane (30 mL). Water (10 mL) was added and brine (40 mL) was added. The organic solution was separated and the aqueous solution was extracted with dichloromethane (2×50 mL). The combined organic solution was dried over anhydrous sodium sulfate, concentrated. The residue was purified with flash column chromatography on silica gel using 30-100% ethyl acetate/hexane to afford product as white solid (155.8 mg) in 62% yield. $^1$H NMR (500 MHz, Chloroform-d) δ 7.60-7.53 (m, 1H), 7.37-7.29 (m, 2H), 5.07 (d, J=12.7 Hz, 1H), 4.85 (d, J=13.7 Hz, 1H), 4.77 (s, 2H), 4.45 (dd, J=8.9, 8.2 Hz, 1H), 4.01 (dd, J=9.0, 5.6 Hz, 1H), 3.95-3.84 (m, 2H), 3.11 (td, J=12.8, 3.7 Hz, 1H), 2.96 (td, J=12.8, 3.7 Hz, 1H), 2.84 (dd, J=13.0, 11.0 Hz, 1H). MS for $C_{15}H_{14}Cl_2N_6O_2$: 381.0 (MH$^+$).

(R)-7-(5-amino-6-(2,3-dichlorophenyl)-1,2,4-triazin-3-yl)tetrahydro-1H-oxazolo[3,4-a]pyrazin-3(5H)-one (88.6 mg, 0.232 mmol) was dissolved in a mixture of methanol, acetonitrile and dichloromethane to afford a clear solution. 2.0 M HCl in ether (0.6 mL, 1.2 mmol) was added. The mixture was concentrated to remove all of solvents to afford product as HCl salt.

180

Example 75

Preparation of Compound 128

Synthesis of (S)-7-(5-amino-6-(2,3-dichlorophenyl)-1,2,4-triazin-3-yl)tetrahydro-1H-oxazolo[3,4-a]pyrazin-3(5H)-one HCl salt (Compound 128)

Synthesis of (S)-7-(5-amino-6-chloro-1,2,4-triazin-3-yl)tetrahydro-1H-oxazolo[3,4-a]pyrazin-3(5H)-one

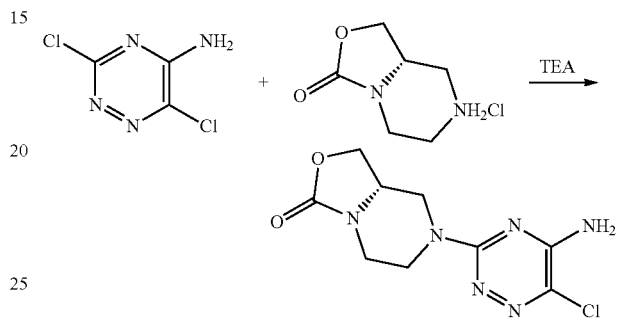

A vial was charged with 5-amino-3,6-dichloro-1,2,4-triazine (458.3 mg, 2.78 mmol), triethylamine (2.0 mL, 14.35 mmol), (s)-hexahydro-oxazolo[3,4-a]pyrazin-3-one HCl (561.8 mg, 3.05 mmol) in dioxane (10 mL). The mixture was heated at 120° C. for 60 min using microwave. The mixture was concentrated to remove all of solvent. The residue was dissolved in dichloromethane, washed with aqueous sodium bicarbonate solution. The aqueous solution was extracted with dichloromethane (5×30 mL). The combined organic solution was washed with brine, dried over anhydrous sodium sulfate, concentrated to afford product (720.8 mg) in 96% yield. $^1$H NMR (500 MHz, Chloroform-d) δ 5.27 (s, 2H), 4.92 (d, J=10.4 Hz, 1H), 4.71 (d, J=12.7 Hz, 1H), 4.45 (t, J=8.6 Hz, 1H), 3.99 (dd, J=9.0, 5.5 Hz, 1H), 3.89-3.80 (m, 2H), 3.06 (td, J=12.7, 3.7 Hz, 1H), 2.93 (td, J=12.8, 3.7 Hz, 1H), 2.81 (dd, J=13.0, 11.1 Hz, 1H). MS for $C_9H_{11}ClN_6O_2$: 271.0 (MH$^+$).

Synthesis of (S)-7-(5-amino-6-(2,3-dichlorophenyl)-1,2,4-triazin-3-yl)tetrahydro-1H-oxazolo[3,4-a]pyrazin-3(5H)-one HCl salt (Compound 128)

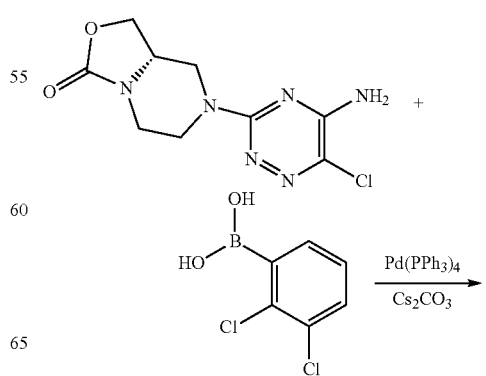

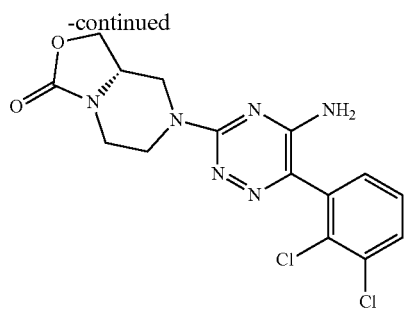

(2,3-Dichlorophenyl)boronic acid (225.6 mg, 1.182 mmol) and (S)-7-(5-amino-6-chloro-1,2,4-triazin-3-yl)tetrahydro-1H-oxazolo[3,4-a]pyrazin-3(5H)-one (164.8 mg, 0.609 mmol) and cesium carbonate (701.2 mg, 2.131 mmol) were dissolved in water/dioxane (5/15 mL). The mixture was degassed with nitrogen, tetrakis(triphenylphosphine) palladium (115.9 mg, 0.100 mmol) was added. The mixture was purged with nitrogen for a few minutes, and stirred at 90° C. for 4 h. The mixture was concentrated to remove organic solvents. The residue was dissolved in dichloromethane (30 mL). Water (10 mL) was added and brine (40 mL) was added. The organic solution was separated and the aqueous solution was extracted with dichloromethane (2×50 mL). The combined organic solution was dried over anhydrous sodium sulfate, concentrated. The residue was purified with flash column chromatography on silica gel to afford slight yellow solid (104.8 mg) as product in 45% yield. $^1$H NMR (500 MHz, Chloroform-d) δ 7.58 (dd, J=5.7, 3.9 Hz, 1H), 7.38-7.31 (m, 2H), 5.08 (d, J=12.5 Hz, 1H), 4.86 (d, J=13.6 Hz, 1H), 4.79 (s, 2H), 4.47 (t, J=8.6 Hz, 1H), 4.02 (dd, J=9.0, 5.6 Hz, 1H), 3.96-3.85 (m, 2H), 3.12 (td, J=12.7, 3.7 Hz, 1H), 2.98 (td, J=12.8, 3.7 Hz, 1H), 2.85 (dd, J=13.0, 11.0 Hz, 1H). MS for $C_{15}H_{14}Cl_2N_6O_2$: 381.0 (MH$^+$).

(R)-7-(5-amino-6-(2,3-dichlorophenyl)-1,2,4-triazin-3-yl)tetrahydro-1H-oxazolo[3,4-a]pyrazin-3(5H)-one (77.6 mg, 0.204 mmol) was dissolved in a mixture of methanol, acetonitrile and dichloromethane to afford a clear solution. 2.0 M HCl in ether (0.6 mL, 1.2 mmol) was added. The mixture was concentrated to remove all of solvents to afford product as HCl salt (78.7 mg) in 93% yield. MS for $C_{15}H_{14}Cl_2N_6O_2$: 381.0 (MH$^+$).

Example 76

Preparation of Compound 129

Synthesis of 3-N-(3-hydroxyazetin-1-yl) lamotrigine

Synthesis of 1-(5-amino-6-chloro-1,2,4-triazin-3-yl)azetidin-3-ol

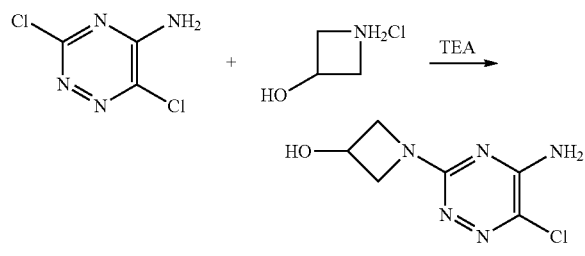

A vial was charged with 5-amino-3,6-dichloro-1,2,4-triazine (871.3 mg, 5.28 mmol), triethylamine (2.6 mL, 18.65 mmol), 3-hydroxyazetidine hydrochloride (656.3 mg, 5.81 mmol) in dioxane (10 mL). The mixture was heated at 90° C. for 1.5 h using microwave, 120° C. for 1 h. The mixture was mixed with water. Aqueous sodium bicarbonate solution was added until the solution is basic. Dichloromethane was added and sonicated for a few minutes. The mixture was filtered and the solid was washed with acetone, ether and dried under high vacuum to afford product (624 mg) in 59% yield. $^1$H NMR (500 MHz, Methanol-d$_4$) δ 4.64 (tt, J=6.7, 4.4 Hz, 1H), 4.29 (ddd, J=9.7, 6.6, 1.2 Hz, 2H), 3.86 (ddd, J=9.6, 4.4, 1.2 Hz, 2H).

Synthesis of 3-N-(3-hydroxyazetin-1-yl) lamotrigine (Compound 129)

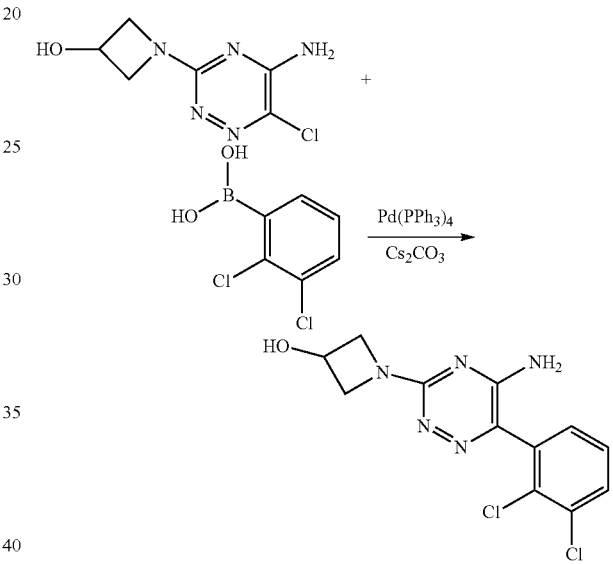

(2,3-Dichlorophenyl)boronic acid (0.934 g, 4.89 mmol), 1-(5-amino-6-chloro-1,2,4-triazin-3-yl)azetidin-3-ol (457.7 mg, 2.27 mmol) and cesium carbonate (2.2244 g, 6.76 mmol) was dissolved in water/dioxane (5/15 mL). The mixture was degassed with nitrogen, tetrakis(triphenylphosphine)palladium (315.1 mg, 0.273 mmol) was added. The mixture was purged with nitrogen for a few minutes, and stirred at 90° C. for 5 h. The mixture was concentrated to remove organic solvents. The residue was mixed with a mixture of dichloromethane and water, sonicated for a few minutes. The mixture was filtered and the solid was washed with dichloromethane and dried under high vacuum to afford product (560.0 mg) in 79% yield. $^1$H NMR (500 MHz, Methanol-d$_4$) δ 7.67 (dd, J=8.1, 1.6 Hz, 1H), 7.43 (t, J=7.8 Hz, 1H), 7.36 (dd, J=7.7, 1.6 Hz, 1H), 4.69 (tt, J=6.6, 4.4 Hz, 1H), 4.37 (ddd, J=9.5, 6.6, 1.2 Hz, 2H), 3.94 (ddd, J=9.5, 4.4, 1.2 Hz, 2H). MS for $C_{12}H_{11}Cl_2N_5O$: 312.0 (MH$^+$).

To a suspension of 3-N-(3-hydroxyazetin-1-yl) lamotrigine (46.9 mg, 0.150 mmol) in methanol (6 mL), acetonitrile (3 mL), acetone (3 mL) was added 2.0 M HCl in ether (0.4 mL, 0.8 mmol). The mixture was concentrated to remove all of solvents to afford product as HCl salt. $^1$H NMR (500 MHz, Methanol-d$_4$) δ 9.07 (s, 1H), 8.19 (s, 1H), 7.77 (dd, J=7.9, 1.7 Hz, 1H), 7.52-7.42 (m, 2H), 4.78 (tt, J=6.7, 4.3 Hz, 1H), 4.53 (ddd, J=10.1, 6.7, 1.4 Hz, 2H), 4.08 (ddd, J=10.1, 4.3, 1.4 Hz, 2H). MS for $C_{12}H_{11}Cl_2N_5O$: 312.0 (MH$^+$).

Example 77

Preparation of Compound 130

Synthesis of (R)-8-(5-amino-6-(2,3-dichlorophenyl)-1,2,4-triazin-3-yl)hexahydropyrazino[2,1-c][1,4]oxazin-4(3H)-one HCl salt (Compound 130)

Synthesis of (R)-8-(5-amino-6-chloro-1,2,4-triazin-3-yl)hexahydropyrazino[2,1-c][1,4]oxazin-4(3H)-one

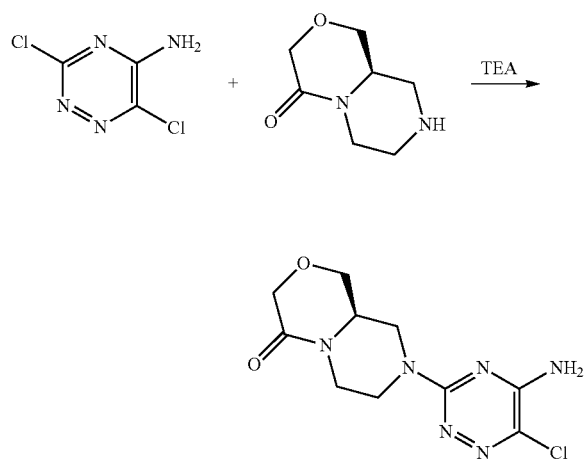

A vial was charged with 5-amino-3,6-dichloro-1,2,4-triazine (331 mg, 2.006 mmol), triethylamine (1.8 mL, 12.91 mmol), (R)-hexahydropyrazino[2,1-c][1,4]oxazin-4(3H)-one Hexahydrochloride (465.5 mg, 2.102 mmol) in dioxane (10 mL). The mixture was heated at 120 degree for 1.5 h using microwave. The mixture was concentrated to remove all of solvent. The residue was dissolved in dichloromethane, washed with aqueous sodium bicarbonate solution. The aqueous solution was extracted with dichloromethane (2×30 mL). The combined organic solution was washed with brine, dried over anhydrous sodium sulfate, concentrated. The residue was mixed with small amount of dichloromethane, warmed up and cooled to r.t. The mixture was filtered and the solid was washed with small amount of dichloromethane. The solid was collected and dried under high vacuum (242.8 mg). The solution was collected and purified with flash column chromatography on silica gel using 1-5% methanol in dichloromethane to afford another part of product (179.6 mg). The total yield was 74%. $^1$H NMR (500 MHz, Chloroform-d) δ 5.29 (s, 2H), 4.74-4.60 (m, 3H), 4.24-4.12 (m, 2H), 4.04 (q, J=8.0 Hz, 1H), 3.65-3.55 (m, 2H), 2.96 (ddd, J=13.8, 12.2, 3.6 Hz, 1H), 2.85-2.71 (m, 2H). MS for $C_{10}H_{13}ClN_6O_2$: 285.0 (MH$^+$).

Synthesis of (R)-8-(5-amino-6-(2,3-dichlorophenyl)-1,2,4-triazin-3-yl)hexahydropyrazino[2,1-c][1,4]oxazin-4(3H)-one HCl salt (Compound 130)

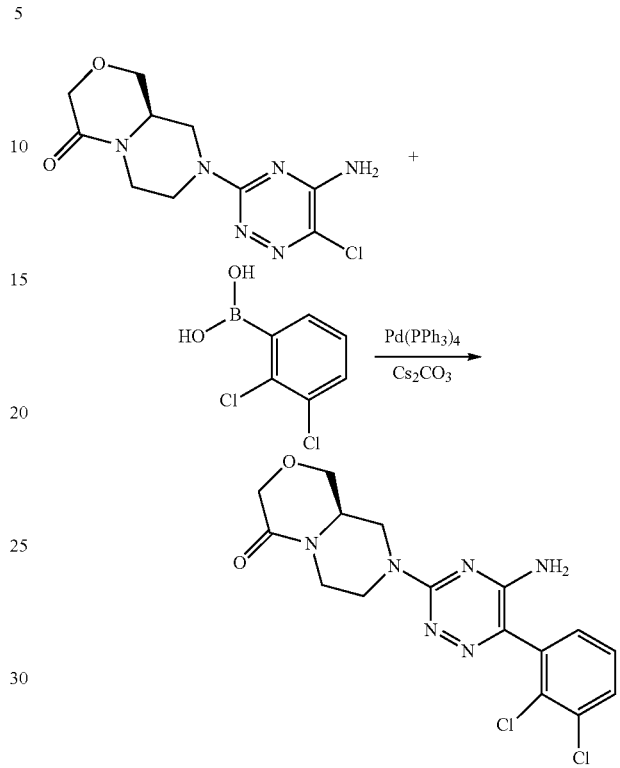

(2,3-Dichlorophenyl)boronic acid (0.3392 g, 1.778 mmol), (R)-8-(5-amino-6-chloro-1,2,4-triazin-3-yl)hexahydropyrazino[2,1-c][1,4]oxazin-4(3H)-one (244.1 mg, 0.857 mmol) and cesium carbonate (0.8478 g, 2.58 mmol) was dissolved in water/dioxane (5/15 mL). The mixture was degassed with nitrogen, tetrakis(triphenylphosphine)palladium (158.4 mg, 0.137 mmol) was added. The mixture was purged with nitrogen for a few minutes, and stirred at 90° C. for 5 h. The mixture was concentrated to remove organic solvents. The residue was mixed with brine, extracted with dichloromethane (3×50 mL). The combined organic solution was dried over anhydrous sodium sulfate, concentrated. The residue was purified with flash column chromatography on silica gel using 30-100% ethyl acetate in hexane to afford yellow solid as product (290.1 mg) in 86% yield. $^1$H NMR (500 MHz, Chloroform-d) δ 7.57 (dd, J=6.3, 3.3 Hz, 1H), 7.35 (q, J=3.8, 3.2 Hz, 2H), 4.90-4.82 (m, 2H), 4.79 (s, 2H), 4.71-4.64 (m, 1H), 4.24-4.16 (m, 2H), 4.12-4.02 (m, 2H), 3.70-3.58 (m, 2H), 3.01 (td, J=12.9, 3.4 Hz, 1H), 2.89-2.77 (m, 2H). MS for $C_{16}H_{16}Cl_2N_6O_2$: 395.0 (MH$^+$).

To a solution of (R)-8-(5-amino-6-(2,3-dichlorophenyl)-1,2,4-triazin-3-yl)hexahydro-pyrazino[2,1-c][1,4]oxazin-4(3H)-one (62.1 mg, 0.157 mmol) in methanol (3 mL) was added 2.0 M HCl in ether (0.4 mL, 0.8 mmol). The mixture was concentrated to remove all of solvents to afford product as HCl salt (57.2 mg, white solid, yield: 84%). $^1$H NMR (500 MHz, Methanol-d$_4$) δ 7.79 (dd, J=7.9, 1.8 Hz, 1H), 7.55-7.44 (m, 2H), 4.58 (dt, J=13.5, 3.4 Hz, 1H), 4.41 (br, 2H), 4.20 (s, 2H), 4.11 (dd, J=12.2, 4.5 Hz, 1H), 3.92-3.82 (m, 1H), 3.81-3.71 (m, 1H), 3.45-3.37 (m, 1H), 3.28-3.30 (m, 1H), 3.08 (ddd, J=14.5, 11.4, 3.6 Hz, 1H).

Example 78

Preparation of Compound 131

Synthesis of (S)-6-(2,3-dichlorophenyl)-3-(hexahydropyrazino[2,1-c][1,4]oxazin-8(1H)-yl)-1,2,4-triazin-5-amine di HCl salt (Compound 131)

Synthesis of (R)-8-(5-amino-6-chloro-1,2,4-triazin-3-yl)hexahydropyrazino[2,1-c][1,4]oxazin-4(3H)-one

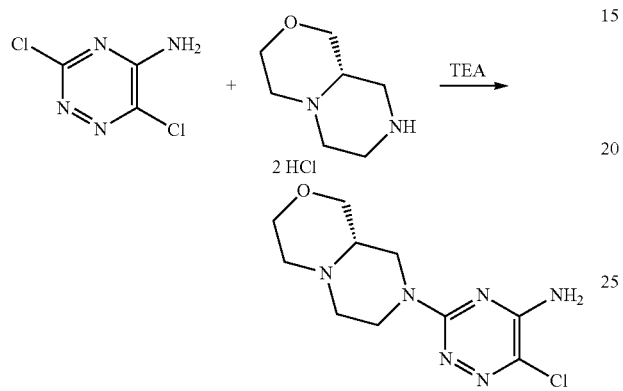

A vial was charged with 5-amino-3,6-dichloro-1,2,4-triazine (358.7 mg, 2.174 mmol), triethylamine (1.8 mL, 12.91 mmol), (S)-octahydropyrazino[2,1-c][1,4]oxazine dihydrochloride (504.1 mg, 2.296 mmol) in dioxane (10 mL). The mixture was heated at 120° C. for 1.5 h using microwave. The mixture was concentrated to remove all of solvent. The residue was dissolved in dichloromethane, washed with aqueous sodium bicarbonate solution. The aqueous solution was extracted with dichloromethane (2×30 mL). The combined organic solution was washed with brine, dried over anhydrous sodium sulfate, concentrated. The residue was purified with flash column chromatography on silica gel using 1-5% methanol in dichloromethane to afford slightly pink solid (0.5041 g) in 86% yield. $^1$H NMR (500 MHz, Chloroform-d) δ 5.20 (s, 2H), 4.60 (d, J=13.3 Hz, 1H), 4.44 (d, J=12.8 Hz, 1H), 3.85 (dd, J=11.4, 3.3 Hz, 1H), 3.76 (dd, J=11.1, 3.1 Hz, 1H), 3.71 (t, J=11.5 Hz, 1H), 3.28 (t, J=10.6 Hz, 1H), 3.08 (t, J=12.4 Hz, 1H), 2.79 (d, J=11.4 Hz, 1H), 2.68 (d, J=11.6 Hz, 1H), 2.57 (t, J=12.0 Hz, 1H), 2.38 (t, J=11.0 Hz, 1H), 2.28 (t, J=12.4 Hz, 1H), 2.23 (s, 1H). MS for $C_{10}H_{15}ClN_6O$: 271.0 (MH$^+$).

Synthesis of (S)-6-(2,3-dichlorophenyl)-3-(hexahydropyrazino[2,1-c][1,4]oxazin-8(1H)-yl)-1,2,4-triazin-5-amine di HCl salt (Compound 131)

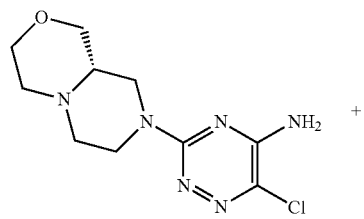

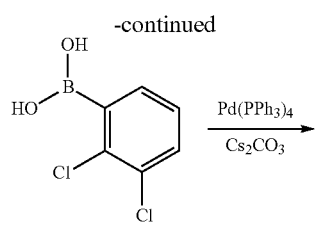

(2,3-Dichlorophenyl)boronic acid (0.450.4 g, 2.360 mmol), (S)-6-chloro-3-(hexahydropyrazino[2,1-c][1,4]oxazin-8(1H)-yl)-1,2,4-triazin-5-amine (282.3 mg, 1.043 mmol) and cesium carbonate (1.1547 g, 3.51 mmol) was dissolved in water/dioxane (5/15 mL). The mixture was degassed with nitrogen, tetrakis(triphenylphosphine)palladium (178.5 mg, 0.154 mmol) was added. The mixture was purged with nitrogen for a few minutes, and stirred at 90° C. for 4 h 45 min. The mixture was concentrated to remove organic solvents. The residue was mixed with brine, extracted with dichloromethane (3×50 mL). The combined organic solution was dried over anhydrous sodium sulfate, concentrated. The residue was purified with flash column chromatography on silica gel using 30-100% ethyl acetate in hexane and 10% methanol in ethyl acetate to afford a yellow solid (376.8 mg) in 95% yield. $^1$H NMR (500 MHz, Chloroform-d) δ 7.55 (dd, J=7.4, 2.3 Hz, 1H), 7.38-7.29 (m, 2H), 4.77 (s, 1H), 4.72 (s, 2H), 4.59 (d, J=12.6 Hz, 1H), 3.87 (dd, J=11.4, 3.3 Hz, 1H), 3.79 (dd, J=11.1, 3.1 Hz, 1H), 3.73 (td, J=11.5, 2.4 Hz, 1H), 3.32 (t, J=11.1, 10.2 Hz, 1H), 3.14 (td, J=12.7, 3.2 Hz, 1H), 2.87-2.80 (m, 1H), 2.71 (d, J=11.7 Hz, 1H), 2.63 (dd, J=12.8, 10.9 Hz, 1H), 2.46-2.23 (m, 3H). MS for $C_{16}H_{18}Cl_2N_6O$: 381.0 (MH$^+$).

To a solution of (S)-6-(2,3-dichlorophenyl)-3-(hexahydropyrazino[2,1-c][1,4]oxazin-8(1H)-yl)-1,2,4-triazin-5-amine (76.1 mg, 0.20 mmol) in methanol (3 mL) was added 2.0 M HCl in ether (0.4 mL, 0.8 mmol). The mixture was concentrated to remove all of solvents to afford product as HCl salt (73.5 mg, white solid) in 94% yield. $^1$H NMR (500 MHz, Methanol-$d_4$) δ 7.80 (dd, J=7.9, 1.8 Hz, 1H), 7.53-7.47 (m, 2H), 4.63 (br, 2H), 4.10 (d, J=12.4 Hz, 2H), 4.01 (t, J=12.6 Hz, 2H), 3.77-3.64 (m, 4H), 3.57-3.52 (s, 1H), 3.46-3.37 (m, 2H).

Example 79

Preparation of Compound 132

Synthesis of 3-N-(azetidin-3-yl) lamatrogine 2HCl salt (Compound 132)

Synthesis of 5-amino-3-(1-Boc-azetidin-3-yl)amino-6-chloro-1,2,4-triazine

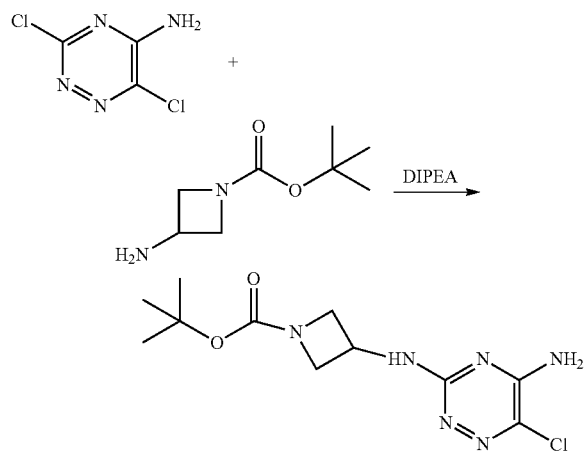

A vial was charged with 5-amino-3,6-dichloro-1,2,4-triazine (899.5 mg, 5.45 mmol), diisopropylethylamine (2.0 mL, 11.48 mmol), 3-amino-1-N-Boc azetidine (1.1452 g, 6.45 mmol) in dioxane (15 mL). The mixture was heated at 120° C. for 3 h using microwave. More of diisopropylethylamine (0.5 mL) and 3-amino-1-N-Boc azetidine (256 mg) were added. The mixture was heated at 120° C. for another 2 h. The mixture was concentrated to remove all of solvent. The residue was dissolved in dichloromethane, washed with aq. sodium bicarbonate solution. The organic solution was separated. The aqueous solution was mixed with brine, extracted with dichloromethane (2×35 mL). The combined organic solution was dried over anhydrous sodium sulfate, concentrated to afford a residue. The residue was mixed with small amount of dichloromethane, warmed up and cooled down to room temperature. The mixture was filtered and the solid was washed with dichloromethane and ether. The solid was collected and dried to afford first batch of product (897.1 mg). The solution was concentrated to remove all of solvents. The residue was purified with flash column chromatography on silica gel using 1-5% methanol in dichloromethane (266.8 mg). The total yield was 71%. $^1$H NMR (500 MHz, Chloroform-d) δ 5.28 (br, 2H), 4.60 (s, 1H), 4.31-4.23 (t, J=9.0 Hz, 2H), 3.77 (dd, J=9.4, 5.2 Hz, 2H), 1.43 (s, 9H). MS for $C_{11}H_{17}ClN_6O_2$: 301.0 (MH$^+$).

Synthesis of 3-N-(1-Boc-azetidin-3-yl) lamotrigine

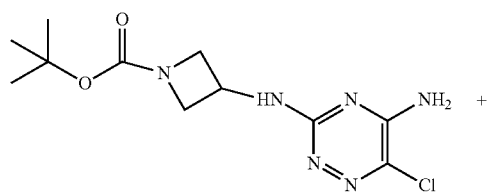

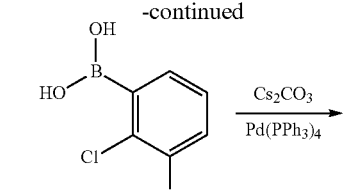

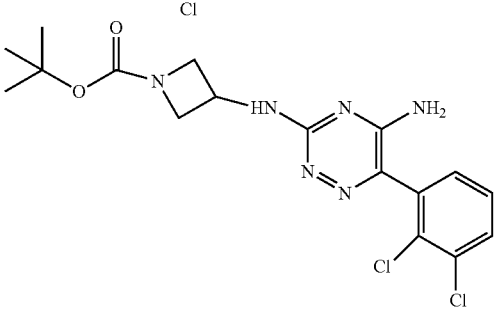

(2,3-Dichlorophenyl)boronic acid (231.4 mg, 1.213 mmol), 5-amino-3-(1-Boc-azetidin-3-yl)amino-6-chloro-1,2,4-triazine (173 mg, 0.575 mmol) and cesium carbonate (579.5 mg, 1.761 mmol) was dissolved in water/dioxane (5/15 mL). The mixture was degassed with nitrogen, tetrakis(triphenylphosphine)palladium (117 mg, 0.101 mmol) was added. The mixture was purged with nitrogen for a few minutes, and stirred at 90° C. for 6 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 30-100% ethyl acetate/hexane and 30-60% acetone/hexane to afford product as yellowish solid (94.9 mg) in 40% yield. $^1$H NMR (500 MHz, Chloroform-d) δ 7.56 (dd, J=6.7, 3.0 Hz, 1H), 7.36-7.31 (m, 2H), 4.81 (s, 2H), 4.70 (s, 1H), 4.29 (t, J=8.4 Hz, 2H), 3.84 (dd, J=9.2, 5.2 Hz, 2H), 1.42 (s, 9H). MS for $C_{17}H_{20}Cl_2N_6O_2$: 411.0 (MH$^+$).

Synthesis of 3-N-(azetidin-3-yl) lamatrogine 2HCl salt (Compound 132)

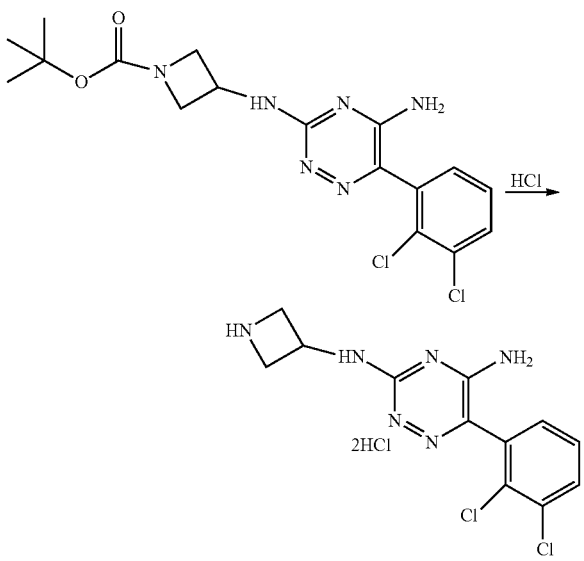

3-N-(1-Boc-azetidin-3-yl) lamotrigine (94.9 mg, 0.231 mmol) was dissolved in methanol (1 mL). 4 N HCl in dioxane (0.5 mL) at room temperature was added. The solution was stirred at room temperature for 5 h. The mixture was concentrated to remove all of solvent to afford product as HCl salt (62.2 mg) in 94% yield. $^1$H NMR (500 MHz, Methanol-$d_4$) δ 7.79 (dd, J=7.9, 1.7 Hz, 1H), 7.55-7.44 (m, 2H), 5.02-4.89 (m, 1H), 4.45-4.41 (m, 2H), 4.39-4.35 (m, 2H). MS for $C_{12}H_{12}Cl_2N_6$: 311.0 (MH$^+$).

Example 80-A

Preparation of Compound 165

Synthesis of 3-N-(3-hydroxy-3-trifluoromethyl)azetidinyl lamotrigine (Compound 165)

Synthesis of 5-amino-6-chloro-3-N-(3-Hydroxy-3-trifluoromethyl)azetidinyl 1,2,4-triazine

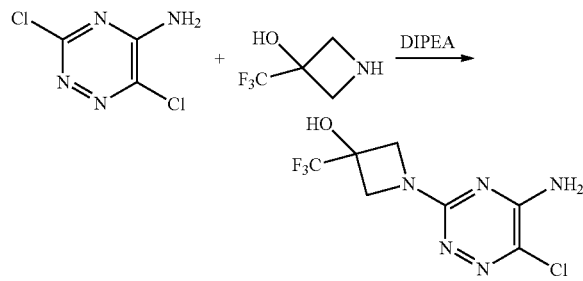

A vial was charged with 5-amino-3,6-dichloro-1,2,4-triazine (290.27 mg, 1.759 mmol), diisopropylethylamine (1.5 mL, 8.61 mmol), 3-(trifluoromethyl)azetidin-3-ol HCl salt (371.5 mg, 2.093 mmol) in dioxane (3 mL). The mixture was heated at 120° C. for 30 min using microwave. The mixture was concentrated to remove all of solvents. The residue was dissolved in dichloromethane, washed with aqueous sodium bicarbonate solution. Some brine was added. The organic solution was separated. The organic mixture was filtered and washed with dichloromethane to collect the white solid as product. The aqueous solution was saturated with sodium chloride, extracted with dichloromethane. The combined organic solution was concentrated to afford a residue. The residue was dissolved into a small of amount of warm dichloromethane, cooled. The solid was collected and washed with dichloromethane to afford second batch of product. The total yield was quantitative. $^1$H NMR (500 MHz, Methanol-$d_4$) δ 4.30 (d, J=10.0 Hz, 2H), 4.02 (d, J=10.1 Hz, 2H). MS for $C_7H_7ClF_3N_5O$: 270.0 (MH$^+$).

Synthesis of 3-N-(3-hydroxy-3-trifluoromethyl)azetidinyl lamotrigine (Compound 165)

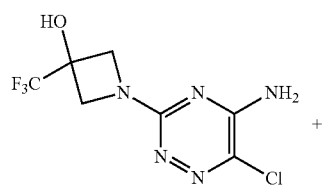

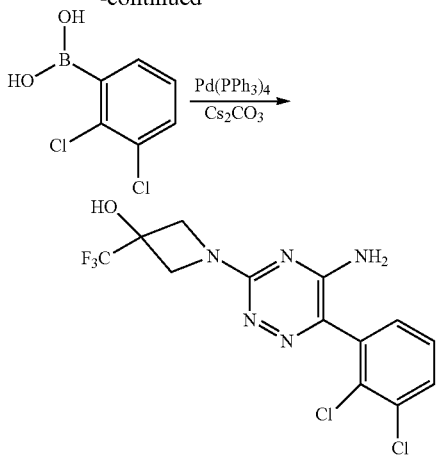

(2,3-Dichlorophenyl)boronic acid (249.8 mg, 1.309 mmol), 1-(5-amino-6-chloro-1,2,4-triazin-3-yl)-3-(trifluoromethyl)azetidin-3-ol (200.8 mg, 0.745 mmol) and cesium carbonate (782.8 mg, 2.379 mmol) was dissolved in water/dioxane (5/15 mL). The mixture was degassed with nitrogen, tetrakis(triphenylphosphine)palladium (148.3 mg, 0.128 mmol) was added. The mixture was purged with nitrogen for a few minutes, and stirred at 90° C. for 2.5 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 1-10% methanol in dichloromethane. The product was mixed with small amount of dichloromethane, warmed up, cooled and filtrated. The solid was collected to afford the final product (98.6 mg) in 35% yield. $^1$H NMR (500 MHz, Methanol-$d_4$) δ 7.68 (dd, J=8.0, 1.5 Hz, 1H), 7.44 (t, J=7.8 Hz, 1H), 7.37 (dd, J=7.6, 1.5 Hz, 1H), 4.38 (d, J=10.1 Hz, 2H), 4.10 (d, J=10.1 Hz, 2H). MS for $C_{13}H_{10}Cl_2F_3N_5O$: 380.0 (MH$^+$).

62.4 mg of free base was dissolved into methanol (0.5 mL), added 4N HCl in dioxane (1 mL) was added. The mixture was stirred for a few minutes and then concentrated to dryness to afford the product as HCl salt. $^1$H NMR (500 MHz, Methanol-$d_4$) δ 7.78 (dd, J=7.9, 1.7 Hz, 1H), 7.54-7.43 (m, 2H), 4.57 (d, J=10.5 Hz, 2H), 4.30 (d, J=10.6 Hz, 2H).

Example 80-B

Preparation of Compound 133

Synthesis of 3-N-(4-hydroxy-4-trifluoromethyl)piperidinyl lamotrigine (Compound 133)

Synthesis of 1-(5-amino-6-chloro-1,2,4-triazin-3-yl)-4-(trifluoromethyl)piperidin-4-ol

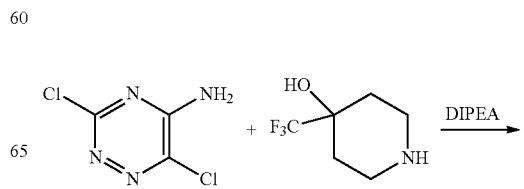

-continued

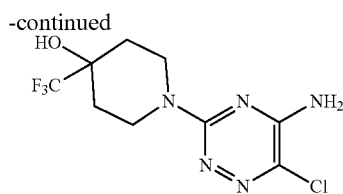

A vial was charged with 5-amino-3,6-dichloro-1,2,4-triazine (203.4 mg, 1.233 mmol), diisopropylethylamine (1.5 mL, 8.61 mmol), 4-(trifluoromethyl)piperidin-4-ol HCl (268.6 mg, 1.306 mmol) in dioxane (3 mL). The mixture was heated at 120° C. for 65 min using microwave. The mixture was concentrated to remove all of solvent. The residue was dissolved in dichloromethane, washed with aqueous sodium bicarbonate solution. The organic solution was separated. The aqueous solution was mixed with brine, extracted with dichloromethane (2×35 mL). The combined organic solution was dried over anhydrous sodium sulfate, concentrated to afford a residue. The residue was purified with flash column chromatography on silica using 1-10% methanol in dichloromethane (273.4 mg) in 75% yield. $^1$H NMR (500 MHz, Chloroform-d) δ 4.57 (d, J=13.5 Hz, 2H), 3.35 (s, 1H), 3.21-3.15 (m, 2H), 1.77-1.74 (m, 2H). MS for $C_9H_{11}ClF_3N_5O$: 298.0 (MH$^+$).

Synthesis of 3-N-(4-hydroxy-4-trifluoromethyl)piperidinyl lamotrigine (Compound 133)

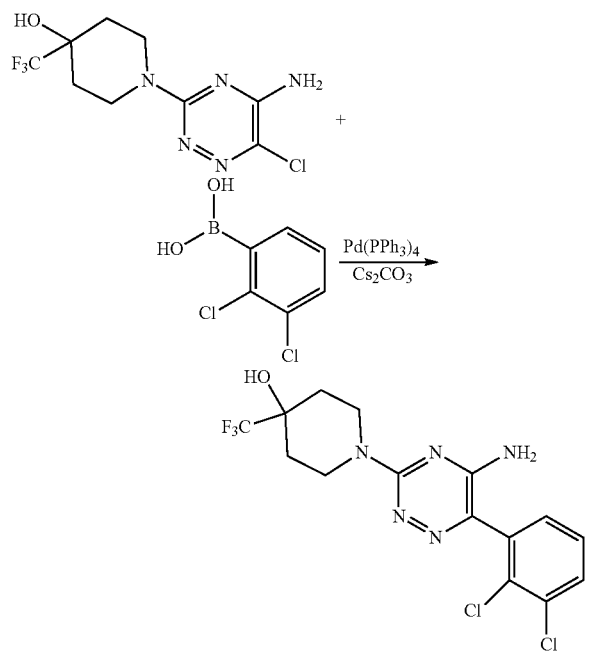

(2,3-Dichlorophenyl)boronic acid (228.6 mg, 1.198 mmol), 1-(5-amino-6-chloro-1,2,4-triazin-3-yl)-4-(trifluoromethyl)piperidin-4-ol (224 mg, 0.753 mmol) and cesium carbonate (725.3 mg, 2.204 mmol) was dissolved in water/dioxane (5/15 mL). The mixture was degassed with nitrogen, tetrakis(triphenylphosphine)palladium (127.5 mg, 0.110 mmol) was added. The mixture was purged with nitrogen for a few minutes, and stirred at 90° C. for 2 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 30-100% ethyl acetate/hexane. The product was dissolved in warm dichloromethane, cooled, filtered. The white solid was collected to afford product (161.7 mg) in 53% yield. $^1$H NMR (500 MHz, Chloroform-d) δ 7.55 (dd, J=7.6, 2.0 Hz, 1H), 7.38-7.26 (m, 2H), 4.82 (d, J=13.4 Hz, 2H), 4.71 (s, 2H), 3.24 (td, J=13.1, 2.8 Hz, 2H), 1.96 (s, 1H), 1.89 (td, J=13.1, 4.6 Hz, 2H), 1.80 (d, J=2.5 Hz, 1H), 1.77 (s, 1H). MS for $C_{15}H_{14}Cl_2F_3N_5O$: 408.1 (MH$^+$).

112.6 mg of free base was dissolved in methanol (~2 mL), 4 N HCl in dioxane (1 mL) was added. The mixture was stirred for a few minutes, and then concentrated to dryness and dried under high vacuum to afford product as HCl salt. $^1$H NMR (500 MHz, Methanol-d$_4$) δ 7.68 (dd, J=7.8, 1.7 Hz, 1H), 7.44-7.34 (m, 2H), 4.34 (br, 2H), 3.56 (s, 6H), 3.40 (m, 2H), 1.92-1.78 (m, 4H). MS for $C_{15}H_{14}Cl_2F_3N_5O$: 408.1 (MH$^+$).

Example 81

Preparation of Compound 134

Synthesis of (S)-1-((S)-4-(5-amino-6-(2,3-dichlorophenyl)-1,2,4-triazin-3-yl)-2-(hydroxymethyl)piperazin-1-yl)-3-methoxypropan-2-ol (Compound 134)

Synthesis of (S)-tert-butyl 4-((S)-2-hydroxy-3-methoxypropyl)-3-(hydroxymethyl)piperazine-1-carboxylate

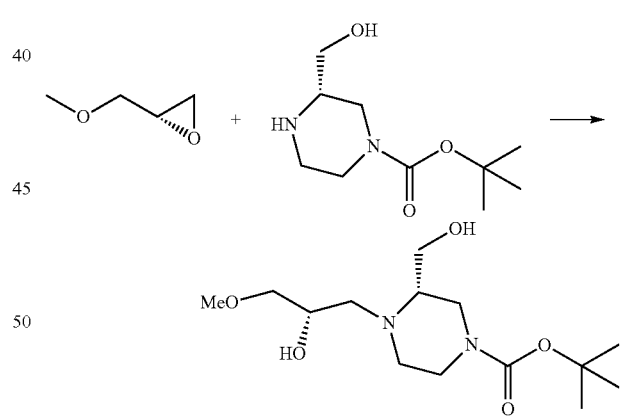

A vial was charged with (S)-tert-butyl 3-(hydroxymethyl)piperazine-1-carboxylate (321.4 mg, 1.441 mmol) and (S)-2-(methoxymethyl)oxirane (162.4 mg, 1.788 mmol) in ethanol (2.5 mL). The mixture was heated at 120° C. for 30 min using microwave. The mixture was cooled to room temperature, concentrated to remove all of solvent. The residue was purified with flash column chromatography on silica gel using 1-10% methanol in dichloromethane to afford the final product as colorless oil (379.3 mg) in 86% yield. $^1$H NMR (500 MHz, Chloroform-d) δ 3.88 (m, 1H), 3.82 (m, 1H), 3.66 (dd, J=13, 3 Hz, 1H), 3.64 (br, 1H), 3.50-3.47 (m, 2H), 3.41 (dd, J=9.7, 3.8 Hz, 1H), 3.37 (s, 3H), 3.30 (dd, J=9.7, 6.2 Hz, 1H), 3.25 (br, 1H), 2.90 (br, 1H), 2.80 (t, J=11.5 Hz, 2H), 2.46 (br, 1H), 2.35 (m, 2H), 1.43 (s, 9H). MS for $C_{14}H_{28}N_2O_5$: 305.2 (MH$^+$).

Synthesis of (S)-1-((S)-2-(hydroxymethyl)piperazin-1-yl)-3-methoxypropan-2-ol 2HCl salt

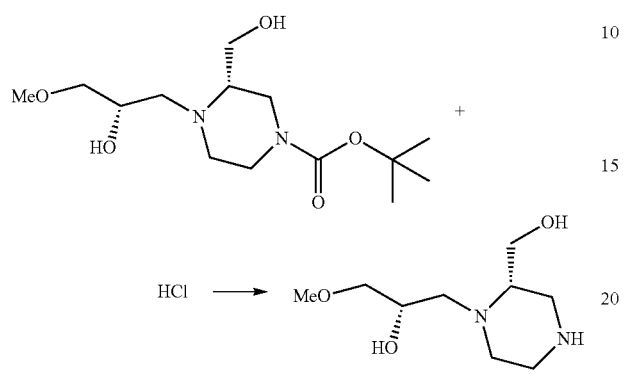

(S)-Tert-butyl 4-((S)-2-hydroxy-3-methoxypropyl)-3-(hydroxymethyl)piperazine-1-carboxylate (0.3793 g, 1.245 mmol) was dissolved in ethanol (4 mL). 4 N HCl in dioxane (1.5 mL) was added. The mixture was stirred at room temperature for 1 h. More of 4 N HCl in dioxane (1.5 mL) was added. The mixture was stirred at r.t. for 3 h. The mixture was concentrated to remove the solvents. The residue was dried under high vacuum to afford white solid in quantitative yield. $^1$H NMR (500 MHz, Methanol-d$_4$) δ 4.24 (dq, J=9.6, 4.9 Hz, 1H), 4.13 (dd, J=12.9, 3.5 Hz, 1H), 3.97 (dt, J=14.1, 3.4 Hz, 1H), 3.84 (d, J=10.6 Hz, 1H), 3.77-3.68 (m, 4H), 3.66 (s, 3H), 3.62-3.49 (s, 4H), 3.45-3.42 (m, 2H), 3.40 (s, 3H).

Synthesis of (S)-1-((S)-4-(5-amino-6-chloro-1,2,4-triazin-3-yl)-2-(hydroxymethyl)piperazin-1-yl)-3-methoxypropan-2-ol

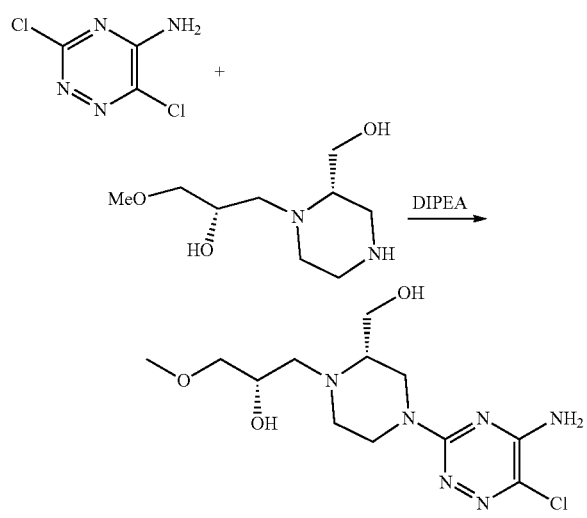

A mixture of 5-amino-3,6-dichloro-1,2,4-triazine (191.7 mg, 1.38 mmol), diisopropylethylamine (2.5 mL, 14.35 mmol), (S)-tert-butyl 2-(3-(hydroxymethyl)piperazin-1-yl) acetate diHCl (~344 mg, 1.24 mmol) in dioxane (10 mL) was heated at 95° C. for 2 h 20 min. The mixture was concentrated to remove all of solvents. The residue was dissolved in dichloromethane, washed with aqueous sodium bicarbonate solution. The organic solution was separated. The aqueous solution was mixed with brine, extracted with dichloromethane (2×35 mL). The combined organic solution was dried over anhydrous sodium sulfate, concentrated to afford a residue. The residue was purified with flash column chromatography on silica using 1-10% methanol in dichloromethane to afford product (69.5 mg) in 18% yield. MS for $C_{12}H_{21}ClN_6O_3$: 330 (MH$^+$).

Synthesis of (S)-1-((S)-4-(5-amino-6-(2,3-dichlorophenyl)-1,2,4-triazin-3-yl)-2-(hydroxymethyl)piperazin-1-yl)-3-methoxypropan-2-ol (Compound 134)

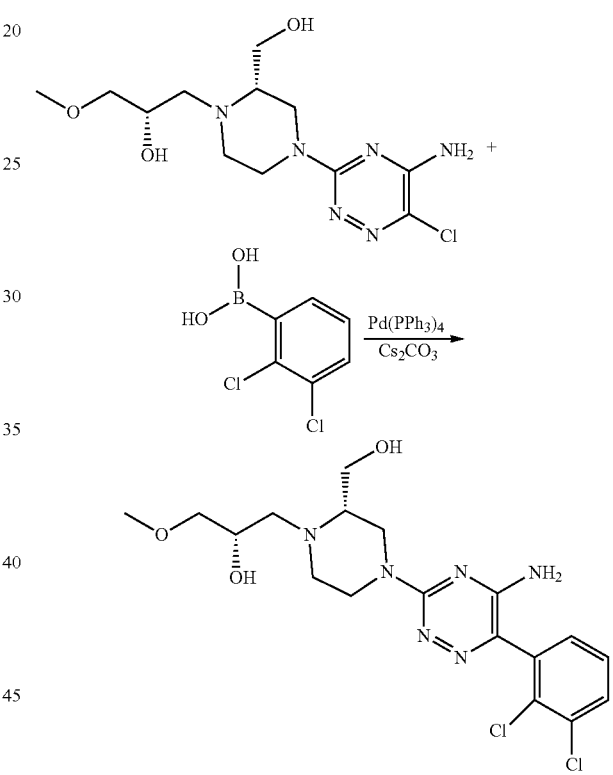

(2,3-Dichlorophenyl)boronic acid (94.6 mg, 0.496 mmol), (S)-1-((S)-4-(5-amino-6-chloro-1,2,4-triazin-3-yl)-2-(hydroxymethyl)piperazin-1-yl)-3-methoxypropan-2-ol (69 mg, 0.207 mmol) and cesium carbonate (231.1 mg, 0.702 mmol) was dissolved in water/dioxane (3/10 mL). The mixture was degassed with nitrogen, tetrakis(triphenylphosphine)palladium (72.2 mg, 0.062 mmol) was added. The mixture was purged with nitrogen for a few minutes, and stirred at 90° C. for 17.5 h. The mixture was concentrated to remove organic solvents. The residue was mixed with brine, extracted with dichloromethane (3×50 mL). The combined organic solution was dried over anhydrous sodium sulfate, concentrated. The residue was purified with flash column chromatography on silica gel using methanol in dichloromethane to afford product (54.9 mg) in 60% yield. $^1$H NMR (500 MHz, Chloroform-d) δ 7.53 (dd, J=7.5, 2.1 Hz, 1H), 7.36-7.26 (m, 2H), 4.94 (br, 2H), 4.17 (d, J=11.4 Hz, 2H), 3.92 (ddt, J=9.6, 6.7, 3.6 Hz, 1H), 3.81 (dd, J=11.9, 5.6

Hz, 1H), 3.69-3.50 (m, 3H), 3.41 (dd, J=9.9, 4.1 Hz, 1H), 3.35 (s, 3H), 3.34-3.31 (m, 1H), 3.05-2.97 (m, 1H), 2.81 (dd, J=13.5, 9.6 Hz, 1H), 2.62 (br, 1H), 2.52-2.41 (m, 2H). MS for $C_{18}H_{24}Cl_2N_6O_3$: 443.0 (MH+).

41.6 mg of product was dissolved in methanol (~2 mL), 4 N HCl in dioxane (1 mL) was added. The mixture was concentrated to remove all of solvents and dried under high vacuum to afford the HCl salt. $^1$H NMR (500 MHz, Methanol-$d_4$) δ 7.80 (dd, J=7.9, 1.7 Hz, 2H), 7.55-7.45 (m, 2H), 4.57 (br, 2H), 4.25 (s, 1H), 4.11 (d, J=11.5 Hz, 1H), 3.90 (m, 1H), 3.84-3.79 (m, 2H), 3.77-3.71 (m, 2H), 3.68-3.66 (m, 5H), 3.61-3.57 (m, 2H), 3.54-3.51 (m, 1H), 3.47-3.44 (m, 1H), 3.41 (s, 3H). MS for $C_{18}H_{24}Cl_2N_6O_3$: 443.0 (MH+).

Example 82

Preparation of Compound 135

Synthesis of (s)-5-N-(3-(hydroxymethyl)piperazinyl lamotrigine diHCl (Compound 135)

Synthesis of (S)-tert-butyl 4-(5-amino-6-chloro-1,2,4-triazin-3-yl)-3-(hydroxymethyl)piperazine-1-carboxylate

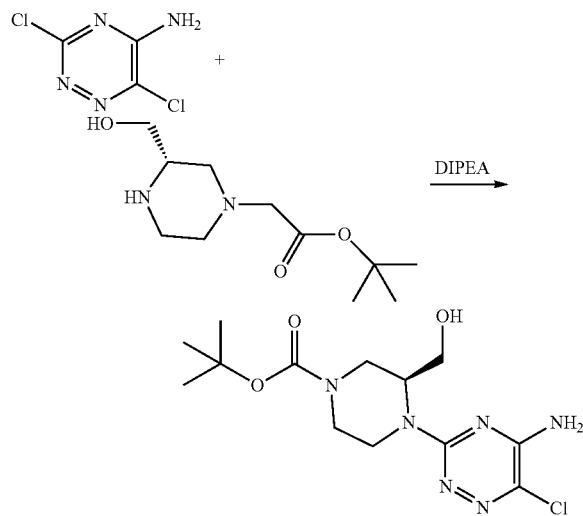

A vial was charged with 5-amino-3,6-dichloro-1,2,4-triazine (253.3 mg, 1.535 mmol), diisopropylethylamine (2.0 mL, 11.48 mmol), (S)-tert-butyl 2-(3-(hydroxymethyl)piperazin-1-yl)acetate (410.9 mg, 1.731 mmol) in dioxane (2 mL). The mixture was heated at 120° C. for 5 h using microwave. The mixture was concentrated to remove all of solvent. The residue was dissolved in dichloromethane, washed with aqueous sodium bicarbonate solution. The organic solution was separated. The aqueous solution was mixed with brine, extracted with dichloromethane (2×35 mL). The combined organic solution was dried over anhydrous sodium sulfate, concentrated to afford a residue. The residue was dissolved into small amount of dichloromethane, filtered. The solid was collected the first batch of product. The solution was purified with flash column chromatography on silica using 1-10% methanol in dichloromethane to afford another batch of product. The product was slight yellow solid (343 mg) and the yield was 65%. $^1$H NMR (500 MHz, Chloroform-d) δ 5.26 (br, 2H), 4.76 (s, 1H), 4.43 (d, J=13.3 Hz, 1H), 4.23-3.92 (s, 2H), 3.65 (m, 2H), 3.16-2.90 (s, 4H), 1.47 (s, 9H). MS for $C_{13}H_{21}ClN_6O_3$: 345.0 (MH+).

Synthesis of (s)-5-N-(4-N-t-Boc-3-(hydroxymethyl)piperazinyl lamotrigine

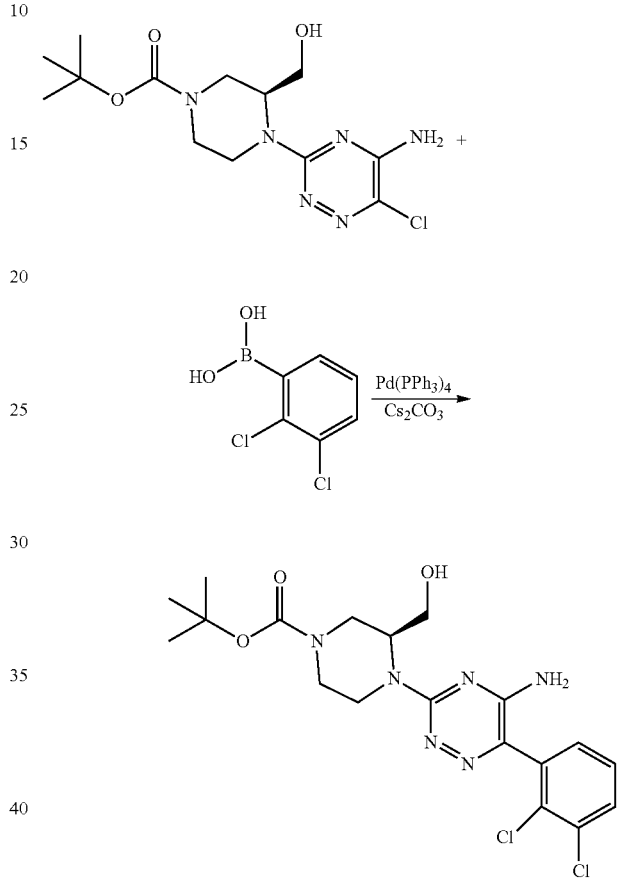

(2,3-Dichlorophenyl)boronic acid (187.1 mg, 0.981 mmol), (S)-tert-butyl 4-(5-amino-6-chloro-1,2,4-triazin-3-yl)-3-(hydroxymethyl)piperazine-1-carboxylate (156 mg, 0.452 mmol) and cesium carbonate (485.3 mg, 1.475 mmol) was dissolved in water/dioxane (3/10 mL). The mixture was degassed with nitrogen, Tetrakis(triphenylphosphine)palladium (107.5 mg, 0.093 mmol) was added. The mixture was purged with nitrogen for a few minutes, and stirred at 90° C. for 3 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 1-10% methanol in dichloromethane to afford slight yellow solid as product (126.5 mg) in 61% yield. $^1$H NMR (500 MHz, Chloroform-d) δ 7.56 (dd, J=6.6, 3.1 Hz, 1H), 7.37-7.29 (m, 2H), 4.90 (br, 1H), 4.79 (s, 2H), 4.57 (br, 1H), 4.23-3.98 (s, 2H), 3.73 (br, 2H), 3.24 (s, 2H), 3.09 (s, 2H), 1.48 (s, 9H). MS for $C_{19}H_{24}Cl_2N_6O_3$: 455.0 (MH+).

Synthesis of (s)-5-N-(3-(hydroxymethyl)piperazinyl lamotrigine diHCl (Compound 135)

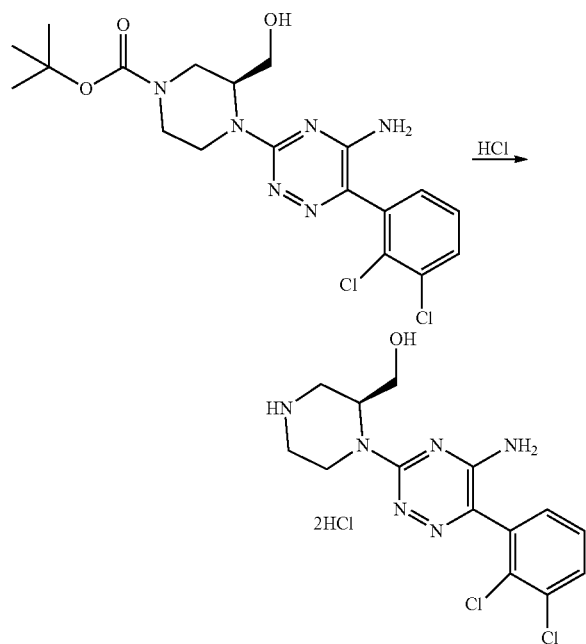

(S)-Tert-butyl 4-(5-amino-6-(2,3-dichlorophenyl)-1,2,4-triazin-3-yl)-3-(hydroxymethyl) piperazine-1-carboxylate (64.3 mg, 0.141 mmol) was dissolved in methanol (2 mL), 4N HCl in dioxane (0.75 mL, 3.0 mmol) was added. The mixture was stirred at room temperature for 1 h 50 min. The mixture was concentrated to remove all of solvents to afford the product as HCl salt in white powder (53 mg) in 88% yield. $^1$H NMR (500 MHz, Methanol-$d_4$) δ 7.80 (dd, J=7.8, 1.9 Hz, 1H), 7.55-7.46 (m, 2H), 4.62 (br, 1H), 4.09 (m, 1H), 4.01 (dd, J=11.2, 4.1 Hz, 1H), 3.85 (br, 1H), 3.77-3.73 (m, 1H), 3.68-3.65 (m, 1H), 3.60-3.57 (m, 1H), 3.50-3.45 (m, 1H), 3.35 (m, 1H). MS for $C_{14}H_{16}Cl_2N_6O$: 355.0 (MH$^+$).

Example 83

Preparation of Compound 136

Synthesis of 1-((S)-4-(5-amino-6-(2,3-dichlorophenyl)-1,2,4-triazin-3-yl)-2-(hydroxymethyl)piperazin-1-yl)-3-(tert-butoxy)propan-2-ol (Compound 136)

Synthesis of (3S)-tert-butyl 4-(3-(tert-butoxy)-2-hydroxypropyl)-3-(hydroxymethyl)piperazine-1-carboxylate

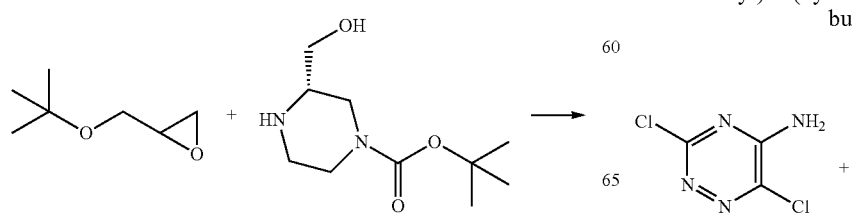

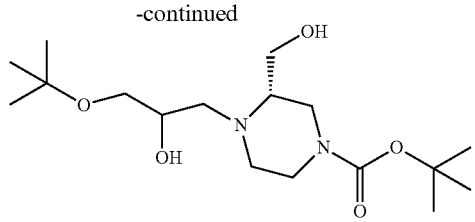

A vial was charged with (S)-tert-butyl 3-(hydroxymethyl) piperazine-1-carboxylate (367.3 mg, 1.647 mmol) and 2-(tert-butoxymethyl)oxirane (243.3 mg, 1.850 mmol) in ethanol (3 mL). The mixture was heated at 120° C. for 30 min using microwave. The mixture was cooled to room temperature, concentrated to remove all of solvents. The residue was purified with flash column chromatography on silica gel using 1-10% methanol in dichloromethane to afford the final product as colorless oil (497.5 mg) in 87% yield. $^1$H NMR (500 MHz, Chloroform-d) δ 3.86-3.80 (m, 2H), 3.71-3.68 (m, 1H), 3.53-3.41 (m, 2H), 3.40-3.35 (m, 2H), 3.24 (dd, J=9.1, 6.6 Hz, 1H), 3.10 (br, 1H), 2.91 (m, 1H), 2.83-2.75 (m, 1H), 2.48 (dd, J=13.1, 7.6 Hz, 2H), 2.39-2.30 (m, 1H), 1.44 (s, 9H), 1.18, 1.17 (2s, 9H). MS for $C_{17}H_{34}N_2O_5$: 347.2 (MH$^+$).

Synthesis of 1-(tert-butoxy)-3-((S)-2-(hydroxymethyl)piperazin-1-yl)propan-2-ol di HCl salt

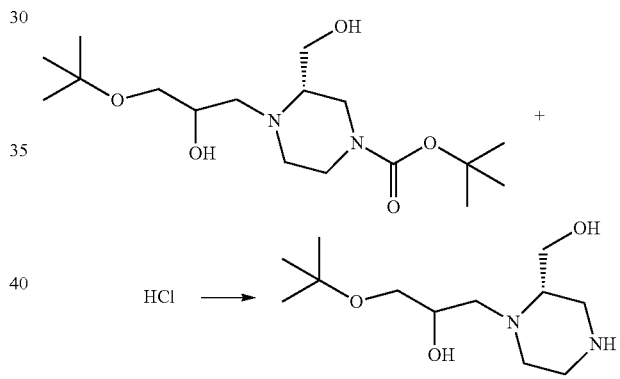

(3S)-Tert-butyl 4-(3-(tert-butoxy)-2-hydroxypropyl)-3-(hydroxymethyl)piperazine-1-carboxylate (0.4975 g, 1.434 mmol) was dissolved in ethanol (2.5 mL). 4 N HCl in dioxane (3 mL) was added. The mixture was stirred at r.t. for 2 h. The mixture was concentrated to remove all of solvents. The residue was dried under high vacuum for overnight to afford product quantitative yield. $^1$H NMR (500 MHz, Methanol-$d_4$) δ 4.20-4.12 (m, 2H), 4.08-3.92 (m, 2H), 3.88-3.82 (m, 1H), 3.78-3.61 (m, 9H), 3.58-3.45 (m, 5H), 3.41-3.36 (m, 1H), 1.23 (s, 9H). MS for $C_{12}H_{26}N_2O_3$: 247.2 (MH$^+$).

Synthesis of 1-((S)-4-(5-amino-6-chloro-1,2,4-triazin-3-yl)-2-(hydroxymethyl)piperazin-1-yl)-3-(tert-butoxy)propan-2-ol

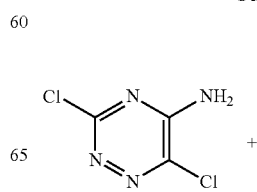

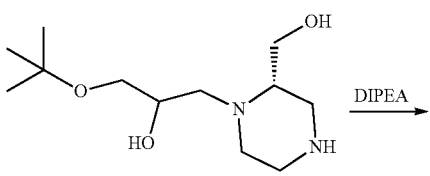

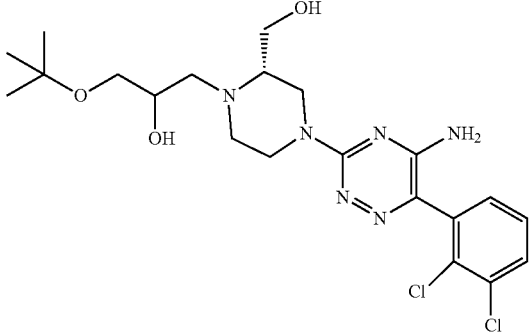

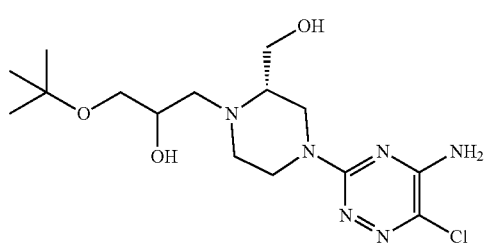

A mixture of 5-amino-3,6-dichloro-1,2,4-triazine (226.7 mg, 1.374 mmol), diisopropyl-ethylamine (2.5 mL, 14.35 mmol), 1-(tert-butoxy)-3-((S)-2-(hydroxymethyl)piperazin-1-yl)propan-2-ol 2HCl (~349 mg, 1.43 mmol) in dioxane (10 mL) was heated at 90° C. for 3.5 h. The mixture was concentrated to remove all of solvents. The residue was dissolved in dichloromethane, washed with aqueous sodium bicarbonate solution. The organic solution was separated. The aqueous solution was mixed with brine, extracted with dichloromethane (2×35 mL). The combined organic solution was dried over anhydrous sodium sulfate, concentrated to afford a residue. The residue was purified with flash column chromatography on silica using 1-10% methanol in dichloromethane to afford product in quantitative yield. $^1$H NMR (500 MHz, Chloroform-d) δ 5.26 (m, 2H), 4.15 (d, J=12.1 Hz, 1H), 3.85 (m, 3H), 3.78-3.70 (m, 1H), 3.65-3.53 (m, 2H), 3.46-3.52 (m, 2H), 3.28-3.25 (m, 1H), 3.00 (m, 1H), 2.87-2.73 (m, 2H), 2.61-2.37 (m, 3H), 1.18, 1.17 (2s, 9H). MS for $C_{15}H_{27}ClN_6O_3$: 375.2 (MH$^+$).

Synthesis of 1-((S)-4-(5-amino-6-(2,3-dichlorophenyl)-1,2,4-triazin-3-yl)-2-(hydroxy-ethyl)piperazin-1-yl)-3-(tert-butoxy)propan-2-ol (Compound 136)

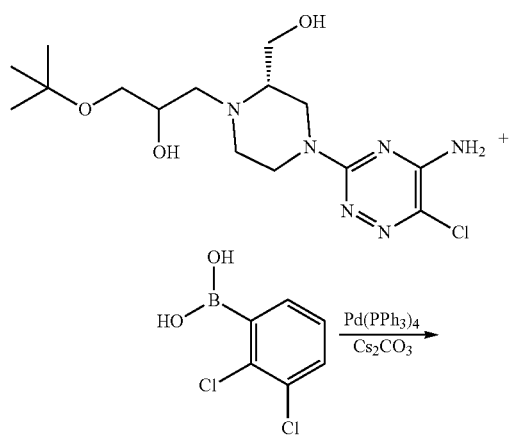

(2,3-Dichlorophenyl)boronic acid (218.7 mg, 1.146 mmol), 1-((S)-4-(5-amino-6-chloro-1,2,4-triazin-3-yl)-2-(hydroxymethyl)piperazin-1-yl)-3-(tert-butoxy)propan-2-ol (229.5 mg, 0.612 mmol) and cesium carbonate (596.5 mg, 1.812 mmol) was dissolved in water/dioxane (3/10 mL). The mixture was degassed with nitrogen, tetrakis(triphenylphosphine)palladium (138.7 mg, 0.120 mmol) was added. The mixture was purged with nitrogen for a few minutes, and stirred at 90° C. for 5 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 30-100% ethyl acetate in hexane. The product was dissolved in warm dichloromethane, cooled, filtered. The solution was collected and purified with flash column chromatography on silica gel using 1-10% methanol in dichloromethane to afford the product yellow solid (121.3 mg) in 41%. $^1$H NMR (500 MHz, Chloroform-d) δ 7.56-7.54 (m, 1H), 7.36-7.31 (m, 2H), 4.74 (d, J=11.6 Hz, 2H), 4.24 (d, J=13.7 Hz, 1H), 3.94-3.77 (m, 4H), 3.61-3.52 (m, 2H), 3.45-3.38 (m, 2H), 3.28 (dd, J=9.0, 6.6 Hz, 1H), 3.03 (d, J=11.7 Hz, 1H), 2.87-2.77 (m, 2H), 2.64-2.62 (m, 1H), 2.56-2.50 (m, 1H), 2.41 (d, J=13.7 Hz, 1H), 1.18, 1.19 (2s, 9H). MS for $C_{21}H_{30}Cl_2N_6O_3$: 485.2 (MH$^+$).

Example 84

Preparation of Compound 137

Synthesis of 3-N-[(4-N-2,3-di-hydroxy-propanyl)-(s)-3-hydroxymethyl)] piperazinyl-lamotrigine di HCl salt (Compound 137)

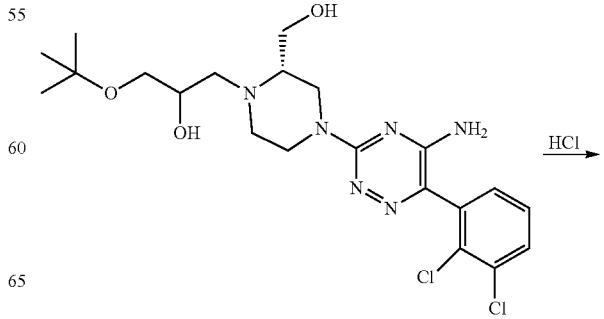

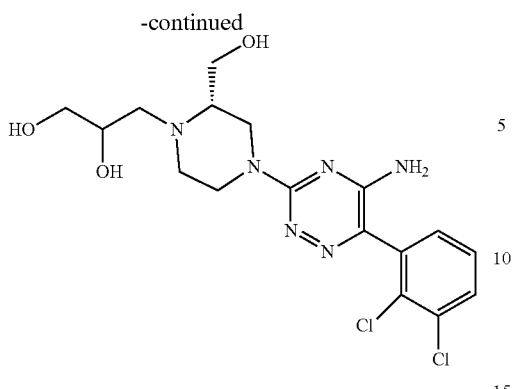

1-((S)-4-(5-amino-6-(2,3-dichlorophenyl)-1,2,4-triazin-3-yl)-2-(hydroxymethyl) piperazin-1-yl)-3-(tert-butoxy)propan-2-ol (63.8 mg, 0.131 mmol) was dissolved into methanol (2 mL), 4 N HCl in dioxane (4 mL) was added. The mixture was stirred at room temperature until LC-MS showed the reaction completed. The mixture was concentrated to remove the solvents. The residue was dried under high vacuum to afford the product as HCl salt in quantitative yield (slight yellow foam). $^1$H NMR (500 MHz, Methanol-$d_4$) δ 7.80 (dd, J=7.8, 1.8 Hz, 1H), 7.54-7.48 (m, 2H), 4.57 (br, 2H), 4.23-4.12 (m, 2H), 4.0 (br, 1H), 3.93-3.90 (m, 1H), 3.88-3.82 (m, 3H), 3.77-3.73 (m, 2H), 3.68-3.63 (m, 6H), 3.61-3.58 (m, 3H), 3.56-3.50 (m, 1H).). MS for $C_{17}H_{22}Cl_2N_6O_3$: 429.0 (MH$^+$).

Example 85

Preparation of Compound 138

Synthesis of (S)-1-((S)-4-(5-amino-6-(2,3-dichlorophenyl)-1,2,4-triazin-3-yl)-3-(hydroxymethyl)piperazin-1-yl)-3-methoxypropan-2-ol (Compound 138)

Synthesis of (S)-tert-butyl 4-((S)-2-hydroxy-3-methoxypropyl)-2-(hydroxymethyl)piperazine-1-carboxylate

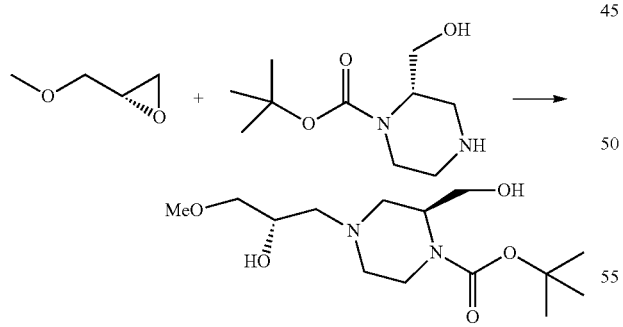

A mixture of (S)-tert-butyl 2-(hydroxymethyl)piperazine-1-carboxylate (602.7 mg, 2.79 mmol) and (S)-2-methoxyoxirane (308.9 mg, 3.4 mmol) in ethanol (10 mL) was heated at 120° C. for 30 min using microwave. The mixture was concentrated to dryness. The residue was purified with flash column chromatography on silica gel using 1-10% methanol in dichloromethane to afford a oil as the product (794.6 mg) in 94% yield. $^1$H NMR (500 MHz, Chloroform-d) δ 4.11 (br, 1H), 3.93-3.80 (m, 2H), 3.41 (dd, J=9.7, 3.7 Hz, 1H), 3.36 (s, 3H), 3.33 (dd, J=9.7, 6.0 Hz, 1H), 3.25 (br, 2H), 3.06 (d, J=11.6 Hz, 1H), 2.89 (br, 2H), 2.79 (d, J=11.2 Hz, 1H), 2.47 (dd, J=12.7, 9.1 Hz, 1H), 2.49-2.33 (m, 1H), 2.30-2.21 (m, 2H), 1.43 (s, 9H). MS for $C_{14}H_{28}N_2O_5$: 305.2 (MH$^+$).

Synthesis of (S)-1-((S)-3-(hydroxymethyl)piperazin-1-yl)-3-methoxypropan-2-ol 2HCl salt

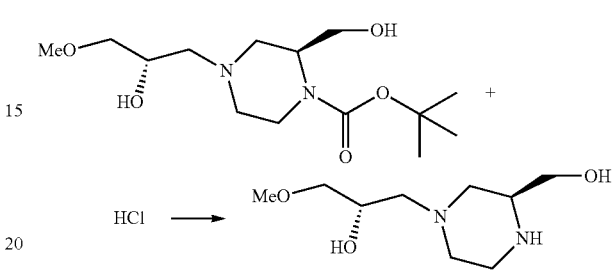

(S)-Tert-butyl 4-((S)-2-hydroxy-3-methoxypropyl)-2-(hydroxymethyl)piperazine-1-carboxylate (794 mg, 2.61 mmol) was dissolved in ethanol (6 mL), 4 N HCl in dioxane (2.9 mL) was added. The mixture was stirred at room temperature for 4.5 h. More of 4 N HCl in dioxane (1 mL) was added. The mixture was stirred at room temperature for 18 h. The mixture was concentrated to remove all of solvents to afford white solid as product in 98% yield. $^1$H NMR (500 MHz, Methanol-$d_4$) δ 4.26 (br, 1H), 3.97-3.82 (m, 2H), 3.78-3.71 (m, 2H), 3.66 (s, 1H), 3.61-3.54 (m, 2H), 3.52-3.41 (m, 4H), 3.39 (s, 3H), 3.37-3.33 (m, 1H).

Synthesis of (S)-1-((S)-4-(5-amino-6-chloro-1,2,4-triazin-3-yl)-3-(hydroxymethyl)piperazin-1-yl)-3-methoxypropan-2-ol

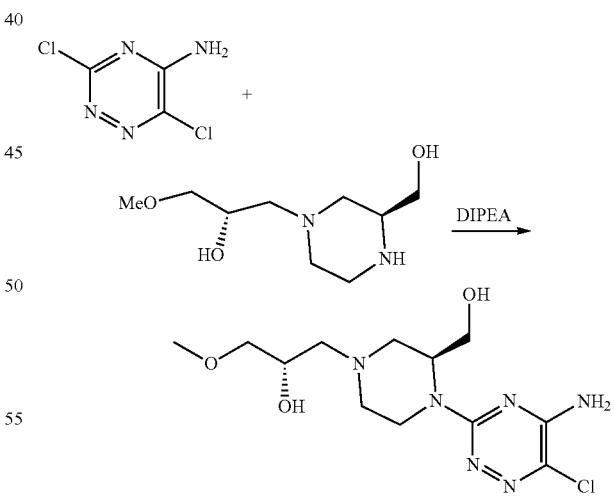

A mixture of 5-amino-3,6-dichloro-1,2,4-triazine (250.2 mg, 1.517 mmol), diisopropylethylamine (2.0 mL, 11.48 mmol), (S)-1-((S)-3-(hydroxymethyl)piperazin-1-yl)-3-methoxypropan-2-ol 2HCl (~500 mg, 1.804 mmol) in dioxane (7 mL) was heated at 150° C. for 4 h. The mixture was concentrated to remove all of solvents. The residue was dissolved in dichloromethane, washed with aq. sodium bicarbonate solution. The organic solution was separated.

The aqueous solution was saturated with sodium chloride, extracted with dichloromethane (2×35 mL). The combined organic solution was dried over anhydrous sodium sulfate, concentrated to afford a residue. The residue was purified with flash column chromatography on silica using 1-10% methanol in dichloromethane to afford product (169.9 mg) in 37% yield. $^1$H NMR (500 MHz, Methanol-d$_4$) δ 4.62 (br, 1H), 4.38 (d, J=13.1 Hz, 1H), 3.97-3.88 (m, 2H), 3.70 (dd, J=10.5, 5.6 Hz, 1H), 3.46 (dd, J=9.9, 4.1 Hz, 1H), 3.42-3.33 (m, 1H), 3.37 (s, 3H), 3.19 (br, 2H), 2.95 (d, J=11.2 Hz, 1H), 2.43 (br, 2H), 2.21 (d, J=10.9 Hz, 2H). MS for $C_{12}H_{21}ClN_6O_3$: 354.2 (MH$^+$).

Synthesis of (S)-1-((S)-4-(5-amino-6-(2,3-dichlorophenyl)-1,2,4-triazin-3-yl)-3-(hydroxymethyl)piperazin-1-yl)-3-methoxypropan-2-ol (Compound 138)

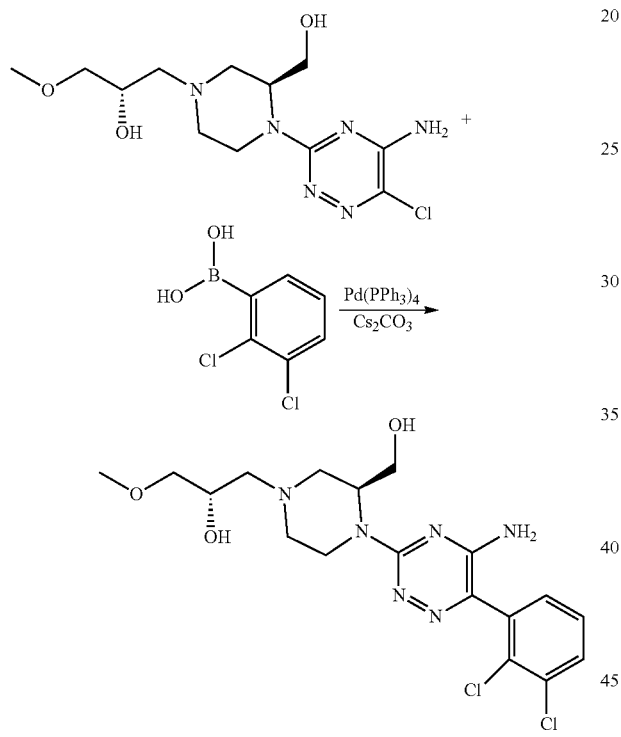

(2,3-Dichlorophenyl)boronic acid (162.5 mg, 0.852 mmol), (S)-1-((S)-4-(5-amino-6-chloro-1,2,4-triazin-3-yl)-3-(hydroxymethyl)piperazin-1-yl)-3-methoxypropan-2-ol (156.4 mg, 0.470 mmol) and cesium carbonate (485.4 mg, 1.475 mmol) was dissolved in water/dioxane (3/10 mL). The mixture was degassed with nitrogen, tetrakis(triphenylphosphine)palladium (100.8 mg, 0.087 mmol) was added. The mixture was purged with nitrogen for a few minutes, and stirred at 90° C. for 3 h. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 30-100% ethyl acetate/hexane. The product was dissolved in warm dichloromethane, cooled, filtered. The solution was collect and purified with flash column chromatography on silica gel using 1-10% methanol in dichloromethane to afford the product (141.5 mg) in 68% yield. $^1$H NMR (500 MHz, Chloroform-d) δ 7.56 (dd, J=7.3, 2.3 Hz, 1H), 7.39-7.29 (m, 2H), 4.91 (br, 1H), 4.75 (s, 2H), 4.63 (br, 1H), 4.04-3.92 (m, 3H), 3.47-3.42 (m, 3H), 3.39 (s, 3H), 3.40-3.36 (m, 1H), 3.19 (d, J=11.7 Hz, 1H), 3.07 (br, 1H), 2.94 (d, J=11.4 Hz, 1H), 2.52 (dd, J=12.6, 9.0 Hz, 1H), 2.42-2.32 (m, 3H). MS for $C_{18}H_{24}Cl_2N_6O_3$: 443.0 (MH$^+$).

54.1 mg of product was dissolved in methanol (~1 mL), 4 N HCl in dioxane (1 mL) was added. The mixture was concentrated to remove all of solvents and dried under high vacuum to product as HCl salt in quantitative yield. $^1$H NMR (500 MHz, Methanol-d$_4$) δ 7.80 (dd, J=7.7, 2.0 Hz, 1H), 7.56-7.46 (m, 2H), 4.27 (m, 1H), 4.17-4.09 (m, 1H), 3.81-3.78 (m, 1H), 3.69-3.64 (m, 7H), 3.59-3.54 (m, 1H), 3.50-3.44 (m, 2H), 3.43-3.39 (m, 4H), 3.37-3.35 (m, 2H). MS for $C_{18}H_{24}Cl_2N_6O_3$: 443.0 (MH$^+$).

Example 86

Preparation of Compound 139

Synthesis of 1-((S)-4-(5-amino-6-(2,3-dichlorophenyl)-1,2,4-triazin-3-yl)-3-(hydroxymethyl)piperazin-1-yl)-3-(tert-butoxy)propan-2-ol (Compound 139)

Synthesis of (2S)-tert-butyl 4-(3-(tert-butoxy)-2-hydroxypropyl)-2-(hydroxymethyl)piperazine-1-carboxylate

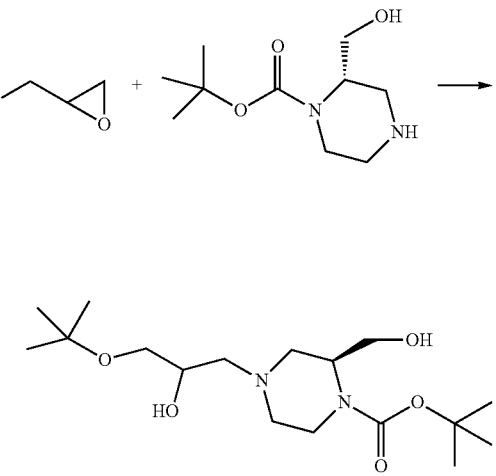

A mixture of (S)-tert-butyl 2-(hydroxymethyl)piperazine-1-carboxylate (850.9 mg, 3.93 mmol) and 2-(tert-butoxymethyl)oxirane (850 mg, 6.46 mmol) in ethanol (10 mL) was heated at 120° C. for 30 min using microwave. The mixture was concentrated to dryness. The residue was purified with flash column chromatography on silica gel using 1-10% methanol in dichloromethane to afford a oil as the product in quantitative yield. $^1$H NMR (500 MHz, Chloroform-d) δ 4.09 (s, 1H), 3.84 (m, 3H), 3.38 (dt, J=9.0, 3.7 Hz, 1H), 3.28 (m, 3H), 3.04 (dd, J=24.2, 11.7 Hz, 1H), 2.88-2.80 (m, 2H), 2.48-2.32 (m, 3H), 2.26-2.21 (m, 1H), 2.13-2.08 (m, 1H), 1.44 (s, 9H), 1.17 (d, 9H). MS for $C_{17}H_{34}N_2O_5$: 347.2 (MH$^+$).

Synthesis of 1-(tert-butoxy)-3-((S)-3-(hydroxymethyl)piperazin-1-yl)propan-2-ol di HCl

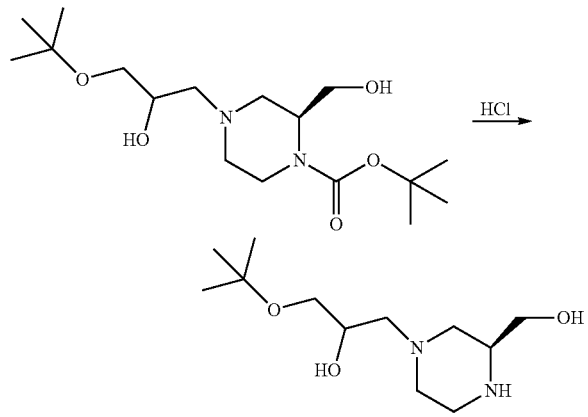

(S)-Tert-butyl 4-((S)-2-hydroxy-3-methoxypropyl)-2-(hydroxymethyl)piperazine-1-carboxylate (1.057 g, 3.05 mmol) was dissolved in ethanol (5 mL), 4 N HCl in dioxane (6 mL) was added. The mixture was stirred at room temperature for 3 h. The mixture was concentrated to remove all of solvents. The residue was dried under high vacuum to afford the product (911.9 mg) in 94% yield. MS for $C_{12}H_{26}N_2O_3$: 247.2 (MH+).

Synthesis of 1-((S)-4-(5-amino-6-chloro-1,2,4-triazin-3-yl)-3-(hydroxymethyl)piperazin-1-yl)-3-(tert-butoxy)propan-2-ol

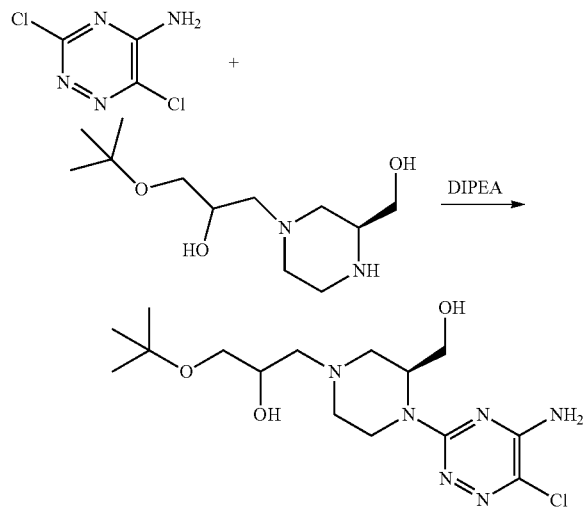

A mixture of 5-amino-3,6-dichloro-1,2,4-triazine (251.5 mg, 1.524 mmol), diisopropylethylamine (2.0 mL, 11.48 mmol), (1-(tert-butoxy)-3-((S)-3-(hydroxymethyl) piperazin-1-yl)propan-2-ol di HCl (~530 mg, 1.660 mmol) in dioxane (7 mL) was heated at 150 degree for 4 h. The mixture was concentrated to remove all of solvent. The residue was dissolved in dichloromethane, washed with aqueous sodium bicarbonate solution. The organic solution was separated. The aqueous solution was saturated with sodium chloride, extracted with dichloromethane (2×35 mL). The combined organic solution was dried over anhydrous sodium sulfate, concentrated to afford a residue. The residue was purified with flash column chromatography on silica using 1-10% methanol in dichloromethane to afford product (229.9 mg) in 40% yield. $^1$H NMR (500 MHz, Chloroform-d) δ 5.26 (br, 2H), 4.72 (s, 1H), 4.46 (d, J=13.4 Hz, 1H), 4.02-3.83 (m, 3H), 3.42-3.36 (m, 2H), 3.34-3.29 (m, 1H), 3.15 (ddt, J=24.8, 11.8, 2.0 Hz, 1H), 2.96 (ddt, J=22.3, 11.4, 2.0 Hz, 1H), 2.52-2.36 (m, 3H), 2.31 (m, 1H), 2.29-2.15 (m, 1H), 1.18 (d, 9H). MS for $C_{15}H_{27}ClN_6O_3$: 375.2 (MH+).

Synthesis of 1-((S)-4-(5-amino-6-(2,3-dichlorophenyl)-1,2,4-triazin-3-yl)-3-(hydroxymethyl)piperazin-1-yl)-3-(tert-butoxy)propan-2-ol (Compound 139)

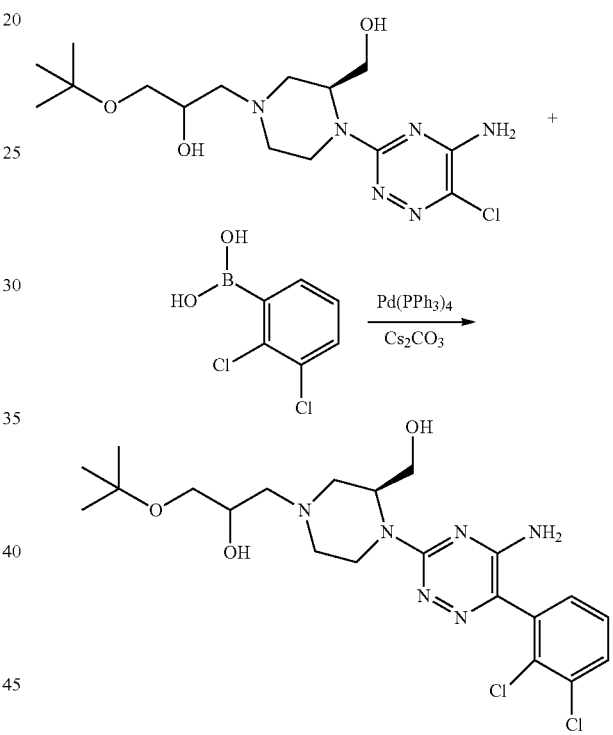

(2,3-Dichlorophenyl)boronic acid (217.9 mg, 1.142 mmol), 1-((S)-4-(5-amino-6-chloro-1,2,4-triazin-3-yl)-3-(hydroxymethyl)piperazin-1-yl)-3-(tert-butoxy)propan-2-ol (228 mg, 0.608 mmol) and cesium carbonate (626.7 mg, 1.904 mmol) was dissolved in water/dioxane (3.5/10 mL). The mixture was degassed with nitrogen, tetrakis(triphenylphosphine)palladium (135.7 mg, 0.117 mmol) was added. The mixture was purged with nitrogen for a few minutes, and stirred at 90° C. for 3.5 h using microwave. The mixture was concentrated to remove organic solvents. The residue was mixed with brine, extracted with dichloromethane (3×50 mL). The combined organic solution was dried over anhydrous sodium sulfate, concentrated. The residue was purified twice with flash column chromatography on silica gel using 1-10% methanol in dichloromethane to afford the product (223.1 mg) in 76% yield. $^1$H NMR (500 MHz, Chloroform-d) δ 7.56 (dd, J=7.4, 2.1 Hz, 1H), 7.40-7.28 (m, 2H), 4.90 (br, 1H), 4.75 (s, 2H), 4.63 (br, 1H), 4.05-3.95 (m, 2H), 3.90 (m, 1H), 3.51-3.40 (m, 2H), 3.35-3.31 (m, 1H), 3.18 (dd, J=27.4, 11.7 Hz, 1H), 3.00 (dd, J=23.9, 11.5 Hz, 1H), 2.56-2.32 (m, 4H), 2.23 (td, J=11.9, 3.7 Hz, 1H), 1.19 (d, 9H). MS for $C_{21}H_{30}Cl_2N_6O_3$: 485.2 (MH$^+$).

Example 87

Preparation of Compound 140

Synthesis of 3-((S)-4-(5-amino-6-(2,3-dichlorophenyl)-1,2,4-triazin-3-yl)-3-(hydroxymethyl)piperazin-1-yl)propane-1,2-diol di HCl salt (Compound 140)

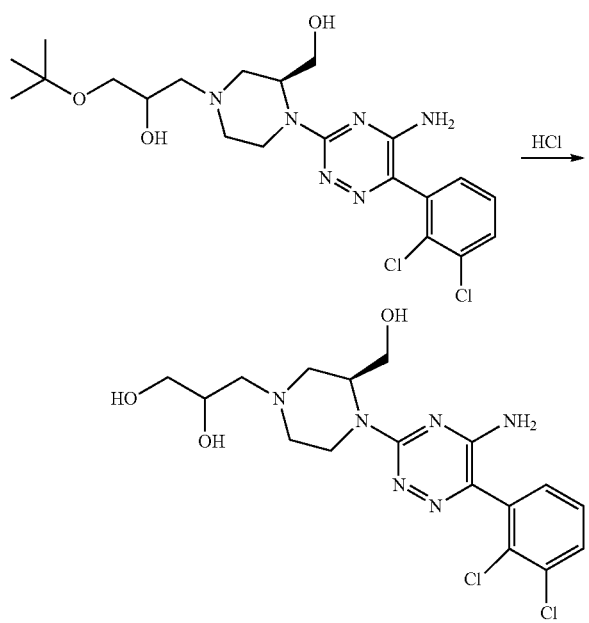

(1-((S)-4-(5-Amino-6-(2,3-dichlorophenyl)-1,2,4-triazin-3-yl)-3-(hydroxymethyl) piperazin-1-yl)-3-(tert-butoxy) propan-2-ol (85.5 mg, 0.176 mmol) was stirred in 4 N HCl in dioxane (2 mL) for 65 h. The mixture was concentrated to remove all of solvents. The residue was dried under high vacuum to afford the product as HCl salt in quantitative yield. $^1$H NMR (500 MHz, Methanol-d$_4$) δ 7.83-7.79 (m, 1H), 7.56-7.49 (m, 2H), 4.19-3.73 (m, 6H), 3.68-3.57 (m, 11H), 3.52-3.32 (m, 4H). MS for $C_{17}H_{22}Cl_2N_6O_3$: 429.0 (MH$^+$).

Example 88

Preparation of Compound 141

Synthesis of 6-(2,3-dichlorophenyl)-3-(4,7-diazaspiro[2.5]octan-4-yl)-1,2,4-triazin-5-amine (Compound 41)

Synthesis of tert-butyl 4-(5-amino-6-chloro-1,2,4-triazin-3-yl)-4,7-diazaspiro[2.5]octane-7-carboxylate

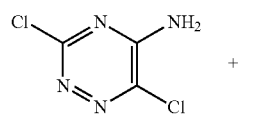 +

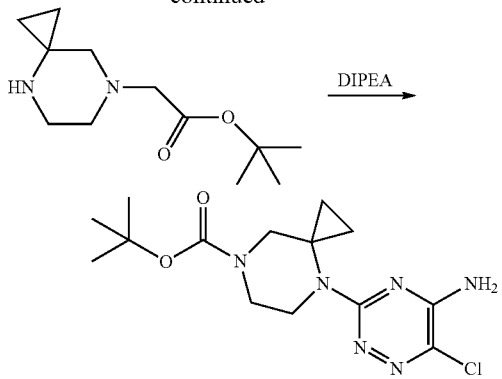

A vial was charged with 5-amino-3,6-dichloro-1,2,4-triazine (108.5 mg, 0.658 mmol), diisopropylethylamine (0.5 mL, 2.87 mmol), tert-butyl 2-(4,7-diazaspiro[2.5]octan-7-yl)acetate (154.8 mg, 0.650 mmol) in dioxane (2.5 mL). The mixture was heated at 155° C. for 9.5 h using microwave. The mixture was concentrated to remove all of solvent. The residue was dissolved in dichloromethane, washed with aqueous sodium bicarbonate solution. The organic solution was separated. The aqueous solution was mixed with brine, extracted with dichloromethane (2×35 mL). The combined organic solution was dried over anhydrous sulfate, concentrated to afford a residue. The residue was purified with flash column chromatography on silica using 1-10% methanol in dichloromethane to afford product (118.3 mg) in 53% yield. $^1$H NMR (500 MHz, Chloroform-d) δ 5.24 (s, 2H), 3.91 (t, J=4.5 Hz, 2H), 3.42 (m, 2H), 3.33 (s, 2H), 1.43 (s, 9H), 0.96 (m, 4H). MS for $C_{14}H_{21}ClN_6O_2$: 341.2 (MH$^+$).

Synthesis of tert-butyl 4-(5-amino-6-(2,3-dichlorophenyl)-1,2,4-triazin-3-yl)-4,7-diazaspiro[2.5]octane-7-carboxylate

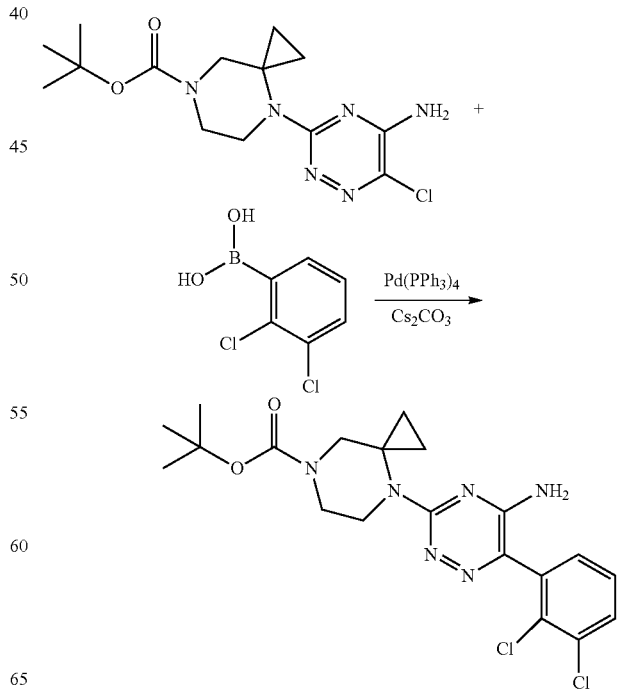

(2,3-Dichlorophenyl)boronic acid (678 mg, 3.55 mmol), tert-butyl 4-(5-amino-6-chloro-1,2,4-triazin-3-yl)-4,7-diazaspiro[2.5]octane-7-carboxylate (600 mg, 1.76 mmol) and cesium carbonate (1.8595 g, 6.56 mmol) was dissolved in water/dioxane (6/20 mL). The mixture was degassed with nitrogen, tetrakis(triphenylphosphine)palladium (294 mg, 0.255 mmol) was added. The mixture was purged with nitrogen for a few minutes, and stirred at 90° C. for 4.5 h. The mixture was concentrated to remove organic solvents. The residue was mixed with brine, extracted with dichloromethane (3×80 mL). The combined organic solution was dried over anhydrous sodium sulfate, concentrated. The residue was purified twice with flash column chromatography on silica gel using 1-10 methanol/dichloromethane, 30-100% ethyl acetate/hexane to afford product (611.5 mg) in 77% yield. $^1$H NMR (500 MHz, Chloroform-d) δ 7.56 (dd, J=7.9, 1.7 Hz, 1H), 7.41-7.30 (m, 2H), 4.76 (s, 2H), 4.01 (s, 2H), 3.50 (s, 2H), 3.40 (s, 2H), 1.45 (s, 9H), 1.07 (s, 2H), 0.97 (s, 2H). MS for $C_{20}H_{24}Cl_2N_6O_2$: 451.0 (MH$^+$).

Synthesis of 6-(2,3-dichlorophenyl)-3-(4,7-diazaspiro[2.5]octan-4-yl)-1,2,4-triazin-5-amine (Compound 141)

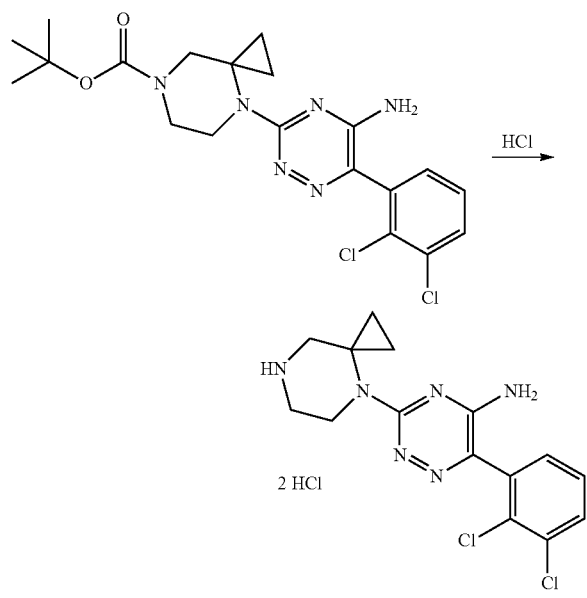

Tert-butyl 4-(5-amino-6-(2,3-dichlorophenyl)-1,2,4-triazin-3-yl)-4,7-diazaspiro[2.5]octane-7-carboxylate (611.5 mg, 1.355 mmol) was dissolved in methanol (1.0 mL), 4N HCl in dioxane (3.0 mL) was added. The mixture was stirred at room temperature for 4 h 40 min. The mixture was concentrated to remove the solvents. The residue was dried under high vacuum to afford white powder. 59.4 mg of product was kept as HCl salt. The other was dissolved in water, saturated potassium bicarbonate solution was added, and then extracted with dichloromethane (3×25 mL). The combined organic solution was washed with brine, dried over anhydrous sodium sulfate, concentrated to afford the product as free base (410.4 mg). $^1$H NMR (500 MHz, Chloroform-d) δ 7.56 (dd, J=7.9, 1.7 Hz, 1H), 7.40-7.38 (m, 1H), 7.33 (t, J=7.5 Hz, 1H), 4.73 (s, 2H), 4.04 (s, 2H), 2.94 (t, J=5.0 Hz, 2H), 2.84 (s, 2H), 1.10 (s, 2H), 0.91 (s, 2H). MS for $C_{15}H_{16}Cl_2N_6$: 351.0 (MH$^+$).

Example 89

Preparation of Compound 142

Synthesis of 6-(2,3-dichlorophenyl)-3-(2,2-dimethylpiperazin-1-yl)-1,2,4-triazin-5-amine di HCl salt (Compound 142)

Synthesis of tert-butyl 4-(5-amino-6-chloro-1,2,4-triazin-3-yl)-3,3-dimethylpiperazine-1-carboxylate

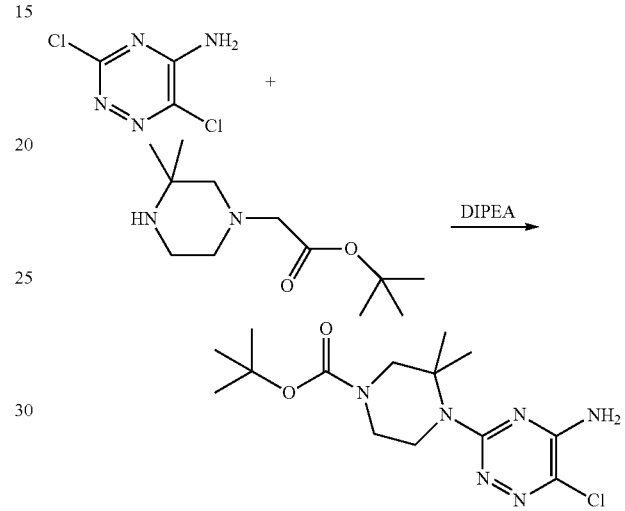

A vial was charged with 5-amino-3,6-dichloro-1,2,4-triazine (736 mg, 4.46 mmol), diisopropylethylamine (2.0 mL, 11.48 mmol), tert-butyl 2-(3,3-dimethylpiperazin-1-yl)acetate (1.0875 g, 4.52 mmol) in dioxane (8 mL). The mixture was heated at 155° C. for 12 h using microwave. The mixture was concentrated to remove all of solvent. The residue was treated with saturated sodium bicarbonate solution, extracted with dichloromethane (4×50 mL). The combined organic solution was washed with brine, dried over anhydrous sodium sulfate, concentrated. The residue was separated with flash column chromatography on silica gel using 1-10% methanol in dichloromethane, and 30-100% ethyl acetate/Hexane to afford product (201.8 mg) in 13% yield. $^1$H NMR (500 MHz, Chloroform-d) δ 5.12 (s, 2H), 4.06-4.02 (m, 2H), 3.52-3.46 (m, 2H), 1.50 (s, 6H), 1.44 (s, 9H). MS for $C_{14}H_{23}ClN_6O_2$: 343.2 (MH$^+$).

Synthesis of tert-butyl 4-(5-amino-6-(2,3-dichlorophenyl)-1,2,4-triazin-3-yl)-3,3-dimethylpiperazine-1-carboxylate

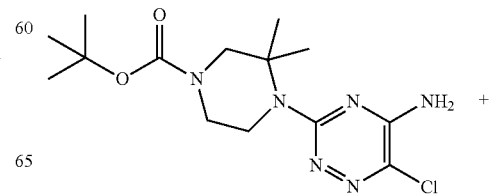

-continued

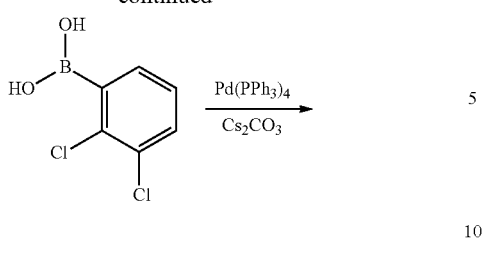

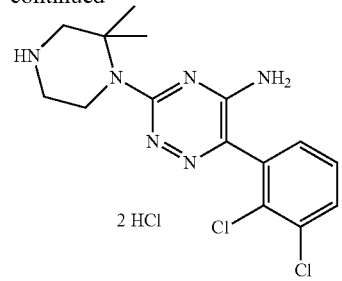

2 HCl

Tert-butyl 4-(5-amino-6-(2,3-dichlorophenyl)-1,2,4-triazin-3-yl)-3,3-dimethylpiperazine-1-carboxylate (158 mg, 0.349 mmol) was dissolved in methanol (1 mL), 4 N HCl in dioxane (0.6 mL) was added. The mixture was stirred at room temperature for 5 h. The mixture was concentrated to remove the solvents. The residue was dried under high vacuum to afford white powder as HCl salt (132.4 mg). The yield was 89%. $^1$H NMR (500 MHz, Methanol-d$_4$) δ 7.79 (dd, J=7.8, 1.9 Hz, 1H), 7.55-7.42 (m, 2H), 4.01-3.95 (m, 2H), 3.60 (t, J=5.6 Hz, 2H), 3.46 (s, 2H), 3.35 (s, 2H), 1.80 (s, 6H). MS for $C_{15}H_{18}Cl_2N_6$: 353.0 (MH$^+$).

Example 90

Preparation of Compound 143

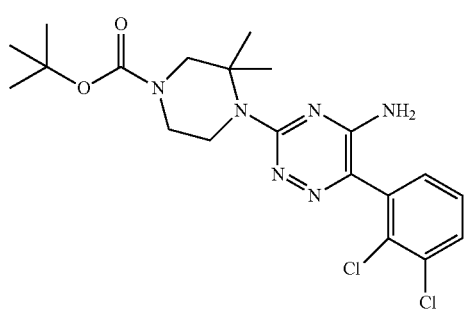

(2,3-dichlorophenyl)boronic acid (174.1 mg, 0.912 mmol), tert-butyl 4-(5-amino-6-chloro-1,2,4-triazin-3-yl)-3,3-dimethylpiperazine-1-carboxylate (179 mg, 0.522 mmol) and cesium carbonate (0.520 g, 1.58 mmol) was dissolved in water/dioxane (2/7 mL). The mixture was degassed with nitrogen, tetrakis(triphenylphosphine)palladium (136.5 mg, 0.118 mmol) was added. The mixture was purged with nitrogen for a few minutes, and stirred at 90° C. for 2 h. The mixture was concentrated to remove organic solvents. The residue was mixed with brine, extracted with dichloromethane (3×80 mL). The combined organic solution was dried over anhydrous sodium sulfate, concentrated. The residue was purified with flash column chromatography on silica gel using 1-10% methanol/dichloromethane, 30-70% ethyl acetate/hexane to afford product (158.3 mg) in 67% yield. $^1$H NMR (500 MHz, Chloroform-d) δ 7.55-7.53 (m, 1H), 7.37-7.30 (m, 2H), 4.66 (s, 2H), 4.18-4.15 (m, 2H), 3.56-3.51 (m, 4H), 1.58 (d, J=2.5 Hz, 6H), 1.46 (s, 9H). MS for $C_{20}H_{26}Cl_2N_6O_2$: 453.2 (MH$^+$).

Synthesis of 6-(2,3-dichlorophenyl)-3-(2,2-dimethylpiperazin-1-yl)-1,2,4-triazin-5-amine di HCl salt (Compound 142)

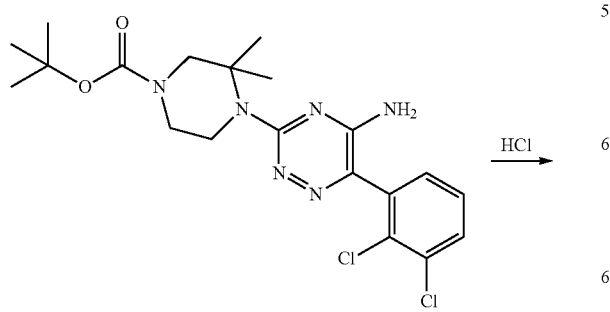

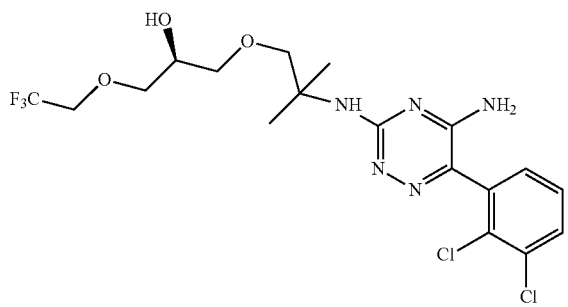 [SMILES: CC(C)(COC[C@H](O)COCC(F)(F)F)Nc1nnc(-c2cccc(Cl)c2Cl)c(N)n1]

(S)-1-(2-((5-amino-6-(2,3-dichlorophenyl)-1,2,4-triazin-3-yl)amino)-2-methylpropoxy)-3-(2,2,2-trifluoroethoxy)propan-2-ol (Compound 143)

Compound 143, (S)-1-(2-((5-amino-6-(2,3-dichlorophenyl)-1,2,4-triazin-3-yl)amino)-2-methylpropoxy)-3-(2,2,2-trifluoroethoxy)propan-2-ol, is prepared as follows.

Step-1: Preparation of (S)-1-(2-((5-amino-6-chloro-1,2,4-triazin-3-yl)amino)-2-methylpropoxy)-3-(2,2,2-trifluoroethoxy)propan-2-ol

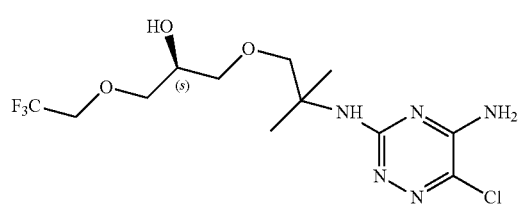 [SMILES: CC(C)(COC[C@H](O)COCC(F)(F)F)Nc1nnc(Cl)c(N)n1]

3,6-Dichloro-1,2,4-triazin-5-amine (1.00 eq.), (S)-1-(2-amino-2-methylpropoxy)-3-(2,2,2-trifluoroethoxy)propan-2-ol (1.5 eq.) and NaHCO₃ (2 eq.) are added to a 1,4-dioxane solution and degassed, for 5-10 min. The reaction mixture was stirred at 85° C. for 12 h. After completion of the reaction, the crude product is purified by column chromatography to afford (S)-1-(2-((5-amino-6-chloro-1,2,4-triazin-3-yl)amino)-2-methylpropoxy)-3-(2,2,2-trifluoroethoxy)propan-2-ol.

Step-2: Preparation of (S)-1-(2-((5-amino-6-(2,3-dichlorophenyl)-1,2,4-triazin-3-yl)amino)-2-methylpropoxy)-3-(2,2,2-trifluoroethoxy)propan-2-ol (Compound 143)

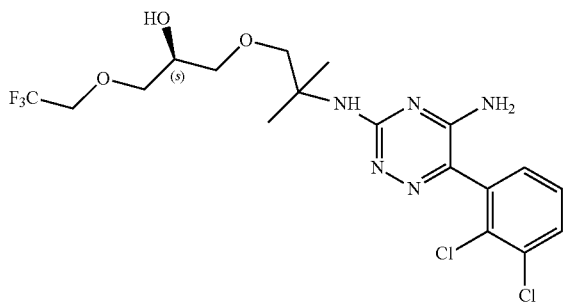 [SMILES: CC(C)(COC[C@H](O)COCC(F)(F)F)Nc1nnc(-c2cccc(Cl)c2Cl)c(N)n1]

To a suspension of (S)-1-(2-((5-amino-6-chloro-1,2,4-triazin-3-yl)amino)-2-methylpropoxy)-3-(2,2,2-trifluoroethoxy)propan-2-ol (Compound 5) (1.0 eq.), (2,3-dichlorophenyl)boronic acid (1.7 eq.), cesium carbonate (3.3 eq.) in 1,4-dioxane:water (2:1) is added Pd(PPh₃)₄ (0.05 eq.) and heated to 90° C. for 8 h. Crude after evaporation of the solvent upon purification by flash chromatography affords (S)-1-(2-((5-amino-6-(2,3-dichlorophenyl)-1,2,4-triazin-3-yl)amino)-2-methylpropoxy)-3-(2,2,2-trifluoroethoxy)propan-2-ol (Compound 143). The free base is dissolved in 2 mL of 4N hydrochloride in 2-propanol. The mixture is concentrated under vacuum to afford product as hydrochloride salt.

Example 91

Preparation of Compound 144

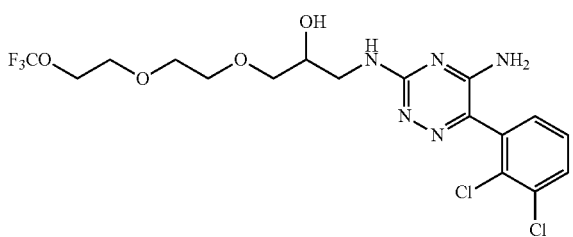 [SMILES: Nc1nc(NCC(O)COCCOCCOC(F)(F)F)nnc1-c1cccc(Cl)c1Cl]

1-((5-amino-6-(2,3-dichlorophenyl)-1,2,4-triazin-3-yl)amino)-3-(2-(2-(trifluoromethoxy)-ethoxy)ethoxy)propan-2-ol (Compound 144)

1-((5-amino-6-(2,3-dichlorophenyl)-1,2,4-triazin-3-yl)amino)-3-(2-(2-(trifluoromethoxy)-ethoxy)ethoxy)propan-2-ol (compound 6) is prepared according to the following steps:

Step 1: Preparation of 1-((5-amino-6-chloro-1,2,4-triazin-3-yl)amino)-3-(2-(2-(trifluoromethoxy)-ethoxy)ethoxy)propan-2-ol

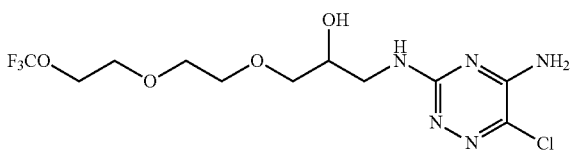 [SMILES: Nc1nc(NCC(O)COCCOCCOC(F)(F)F)nnc1Cl]

To a solution of 1-amino-3-(2-(2-(trifluoromethoxy)ethoxy)ethoxy)propan-2-ol (1.0 equiv.) in 1,4-dioxane (10 mL) is added 5-amino-3,6-dichloro-triazine (1.0 eq.). Reaction mixture is then charged with sodium bicarbonate (3.0 eq.) and stirred at 90° C. for 12 h. Evaporation of the solvent and purification of the residue by flash chromatography yields (1-((5-amino-6-chloro-1,2,4-triazin-3-yl)amino)-3-(2-(2-(trifluoromethoxy)-ethoxy)ethoxy)propan-2-ol.

Step-2: Preparation of 1-((5-amino-6-(2,3-dichlorophenyl)-1,2,4-triazin-3-yl)amino)-3-(2-(2-(trifluoromethoxy)-ethoxy)ethoxy)propan-2-ol (Compound 144)

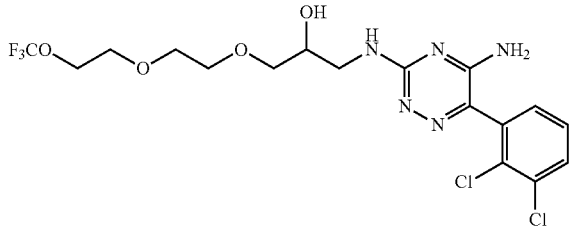 [SMILES: Nc1nc(NCC(O)COCCOCCOC(F)(F)F)nnc1-c1cccc(Cl)c1Cl]

To a suspension of (1-((5-amino-6-chloro-1,2,4-triazin-3-yl)amino)-3-(2-(2-(trifluoromethoxy)-ethoxy)ethoxy)propan-2-ol (compound 7) (1.0 eq.), (2,3-dichlorophenyl)boronic acid (1.7 eq.), cesium carbonate (3.3 equiv.) in 1,4-dioxane:water (2:1) is added Pd(PPh₃)₄ (0.05 eq.) and heated to 90° C. for 6 h. Crude after evaporation of the solvent is purified by flash chromatography to afford 1-((5-amino-6-(2,3-dichlorophenyl)-1,2,4-triazin-3-yl)amino)-3-(2-(2-(trifluoromethoxy)-ethoxy)ethoxy)propan-2-ol (compound 144). The free base is dissolved in 2 mL of 4N hydrochloride in 2-propanol. The mixture is concentrated under vacuum to afford product as hydrochloride salt.

Example 92

Preparation of Compound 145

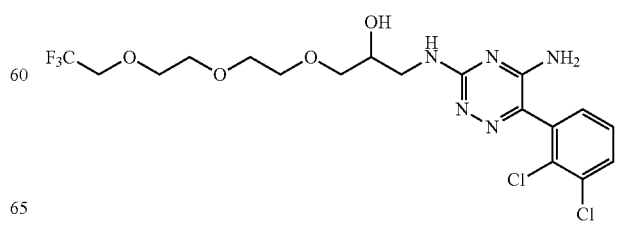

1-((5-amino-6-(2,3-dichlorophenyl)-1,2,4-triazin-3-yl)amino)-3-(2-(2-(2,2,2-trifluoroethoxy)-ethoxy)ethoxy)propan-2-ol (Compound 145)

1-((5-amino-6-(2,3-dichlorophenyl)-1,2,4-triazin-3-yl)amino)-3-(2-(2-(2,2,2-trifluoroethoxy)-ethoxy)ethoxy)propan-2-ol (compound 145) is prepared according to the following steps:

Step 1: Preparation of 1-((5-amino-6-chloro-1,2,4-triazin-3-yl)amino)-3-(2-(2-(2,2,2-trifluoroethoxy)-ethoxy)ethoxy)propan-2-ol

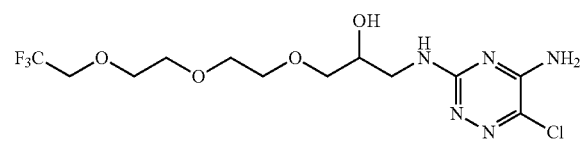 [SMILES: Nc1nc(NCC(O)COCCOCCOCC(F)(F)F)nnc1Cl]

To a solution of 1-amino-3-(2-(2-(2,2,2-trifluoroethoxy)ethoxy)ethoxy)propan-2-ol (1.0 eq.) in 1,4-dioxane (10 mL) is added 5-amino-3,6-dichloro-triazine (1.0 eq.). Reaction mixture is then charged with sodium bicarbonate (3.0 eq.) and stirred at 90° C. for 10 h. Evaporation of the solvent and purification of the residue by flash chromatography yields 1-((5-amino-6-chloro-1,2,4-triazin-3-yl)amino)-3-(2-(2-(2,2,2-trifluoroethoxy)-ethoxy)ethoxy)propan-2-ol.

Step-2: Preparation of 1-((5-amino-6-(2,3-dichlorophenyl)-1,2,4-triazin-3-yl)amino)-3-(2-(2-(2,2,2-trifluoroethoxy)-ethoxy)ethoxy)propan-2-ol (Compound 145)

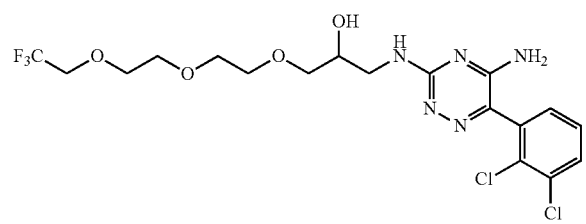 [SMILES: Nc1nc(NCC(O)COCCOCCOCC(F)(F)F)nnc1-c1cccc(Cl)c1Cl]

To a suspension of (1-((5-amino-6-chloro-1,2,4-triazin-3-yl)amino)-3-(2-(2-(2,2,2-trifluoroethoxy)ethoxy)ethoxy)propan-2-ol (1.0 eq.), (2,3-dichlorophenyl) boronic acid (1.7 eq.), cesium carbonate (3.3 eq.) in 1,4-dioxane:water (2:1) is added Pd(PPh$_3$)$_4$ (0.05 eq.) and heated to 90° C. Crude after evaporation of the solvent is purified by flash chromatography and yields 1-((5-amino-6-(2,3-dichlorophenyl)-1,2,4-triazin-3-yl)amino)-3-(2-(2-(2,2,2-trifluoroethoxy)-ethoxy)ethoxy)propan-2-ol. The free base is dissolved in 2 mL of 4N hydrochloride in 2-propanol. The mixture is concentrated under vacuum to afford product as hydrochloride salt.

Example 93

Preparation of Compound 146

The synthesis of (S)-3-((2-((5-amino-6-(2,3-dichlorophenyl)-1,2,4-triazin-3-yl)amino)ethyl)amino)-1,1,1-trifluoropropan-2-ol (Compound 146)

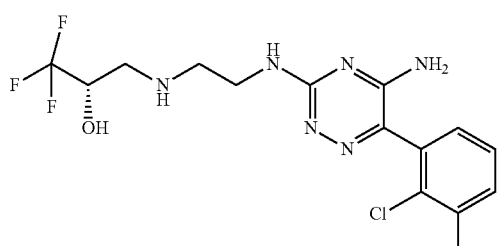

Step 1. The synthesis of (S)-tert-butyl (2-((3,3,3-trifluoro-2-hydroxypropyl)amino)ethyl)carbamate is as Follows

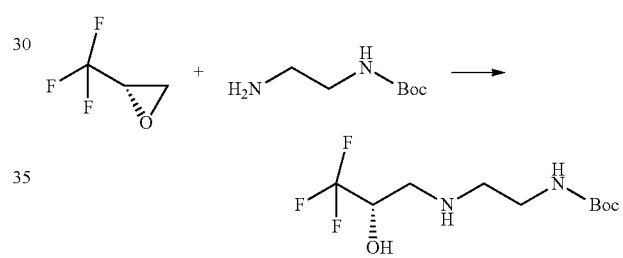

N-Boc-ethylenediamine (4 g, 25 mmol) and (S)-2-(trifluoromethyl)oxirane (3.36 g, 30 mmol) are dissolved in methanol (50 mL). The solution is stirred at 90° C. for 1.5 hours. The solvent is evaporated at reduced pressure. The obtained crude (6.8 g) is used for next step without further purification.

Step 2. The synthesis of (S)-3-((2-aminoethyl)amino)-1,1,1-trifluoropropan-2-ol

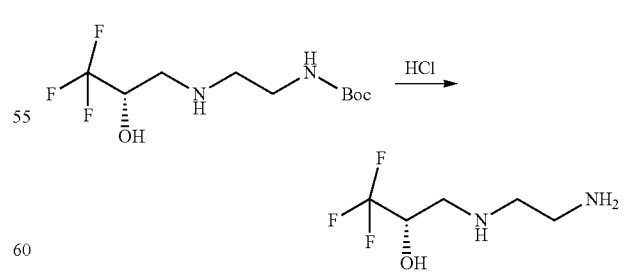

The (S)-tert-butyl (2-((3,3,3-trifluoro-2-hydroxypropyl)amino)ethyl)carbamate crude (6.8 g) is dissolved in methanol (20 mL), in which HCl in methanol (2N, 60 mL) is added at room temperature. The solution is stirred at room temperature for 2 hours. The solvent is evaporated at reduced pressure. The obtained crude is washed with saturated NaHCO₃ solution (50 mL) and extracted with DCM (50 mL×3). The organic phase is combined, dried off by anhydrous Na2SO₄, and evaporated to afford (S)-3-((2-aminoethyl)amino)-1,1,1-trifluoropropan-2-ol crude (4.4 g), which is used for next step without further purification.

Step 3. The synthesis of (S)-3-((2-((5-amino-6-chloro-1,2,4-triazin-3-yl)amino)ethyl)amino)-1,1,1-trifluoropropan-2-ol

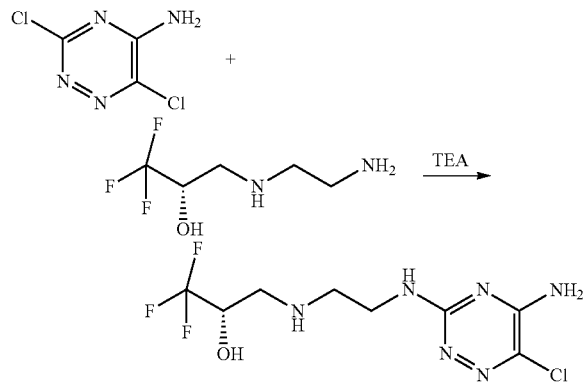

(S)-3-((2-aminoethyl)amino)-1,1,1-trifluoropropan-2-ol (4.3 g, 25 mmol) and 3,6-dichloro-1,2,4-triazin-5-amine (4.53 g, 27.5 mmol) are dissolved in anhydrous dioxane (14 mL). TEA (4.4 mL, 31.6 mmol) is added into solution. The reaction solution is heated at 95° C. for 1 hour. The mixture is cooled to room temperature and white precipitate is observed. The mixture is filtered to collect the solution. The solution is concentrated to remove the solvents. The residue is used for next step without further purification.

Step 4. (S)-3-((2-((5-amino-6-(2,3-dichlorophenyl)-1,2,4-triazin-3-yl)amino)ethyl)amino)-1,1,1-trifluoropropan-2-ol

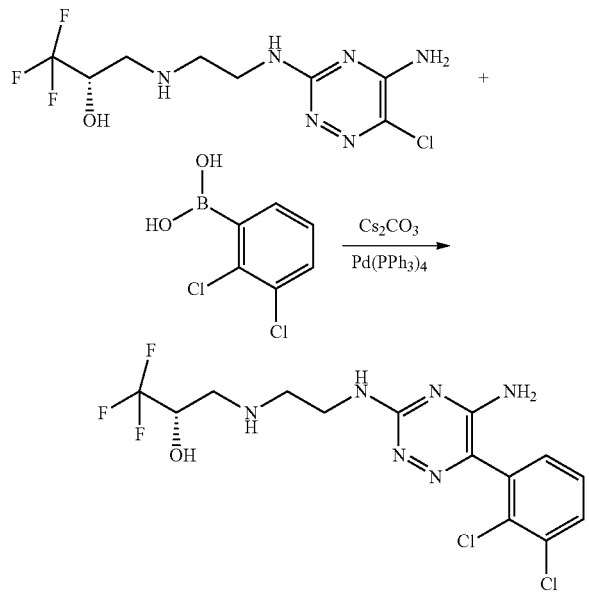

(2,3-dichlorophenyl)boronic acid (5.25 g, 27.5 mmol), (S)-3-((2-((5-amino-6-chloro-1,2,4-triazin-3-yl)amino)ethyl)amino)-1,1,1-trifluoropropan-2-ol (7.52 g, 25 mmol), and cesium carbonate (16.29 g, 50 mmol) are added in mixture of water and dioxane (50 mL and 150 mL, respectively). After the mixture is degassed and filled with nitrogen, tetrakis(triphenylphosphine)palladium (5.78 g, 5 mmol) is added. The mixture is purged with nitrogen again for a few minutes, and stirred at 85° C. for 4 hours. The mixture is cooled to room temperature. Yellow precipitation is formed. The mixture is filtered and the solid is washed with dioxane. The solution is collected and concentrated to remove organic solvents.

The residue is mixed with brine (150 mL) and extracted with DCM (3×50 mL). The combined organic solution is dried over anhydrous Na₂SO₄ and concentrated. The residue is purified with flash column chromatography using MeOH/DCM (0-10%) to afford product (S)-3-((2-((5-amino-6-(2,3-dichlorophenyl)-1,2,4-triazin-3-yl)amino)ethyl)amino)-1,1,1-trifluoropropan-2-ol (4.9 g, 11.92 mmol, over all yield 47.7%).

Example 94

Preparation of Compound 147

The synthesis of (S)-3-((2-((5-amino-6-(2,3-dichlorophenyl)-1,2,4-triazin-3-yl)(methyl)amino)ethyl)amino)-1,1,1-trifluoropropan-2-ol

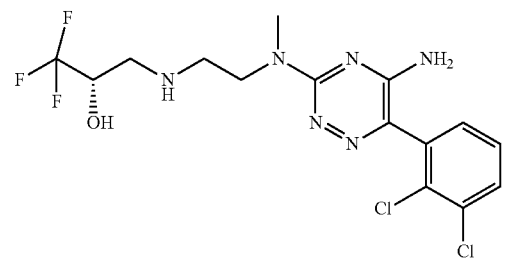 [SMILES: CN(CCNC[C@H](O)C(F)(F)F)c1nnc(-c2cccc(Cl)c2Cl)c(N)n1]

The synthesis of (S)-3-((2-((5-amino-6-(2,3-dichlorophenyl)-1,2,4-triazin-3-yl)(methyl)amino)ethyl)amino)-1,1,1-trifluoropropan-2-ol is performed following the above procedure by using N-Boc-N-methylethylenediamine as starting material:

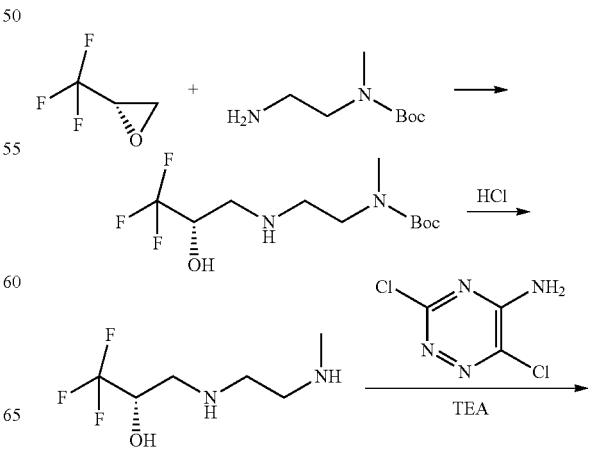

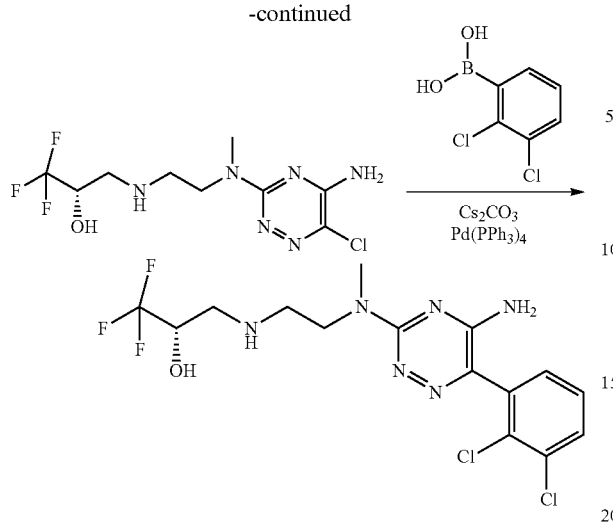

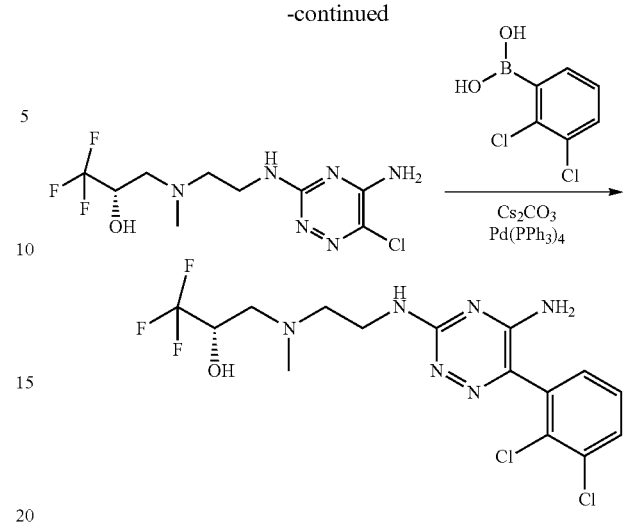

Example 95

Preparation of Compound 148

The synthesis of (S)-3-((2-((5-amino-6-(2,3-dichlorophenyl)-1,2,4-triazin-3-yl)amino)ethyl)(methyl)amino)-1,1,1-trifluoropropan-2-ol

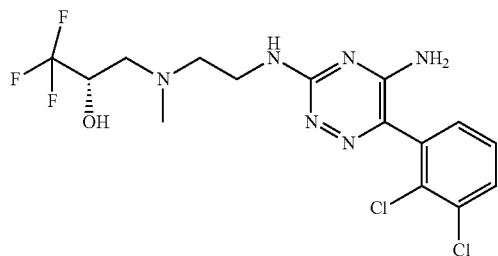 [SMILES: CN(CCNc1nnc(-c2cccc(Cl)c2Cl)c(N)n1)C[C@H](O)C(F)(F)F]

The synthesis of (S)-3-((2-((5-amino-6-(2,3-dichlorophenyl)-1,2,4-triazin-3-yl)amino)ethyl)(methyl)amino)-1,1,1-trifluoropropan-2-ol is performed following the above procedure by using tert-Butyl 2-(methylamino)ethylcarbamate as starting material.

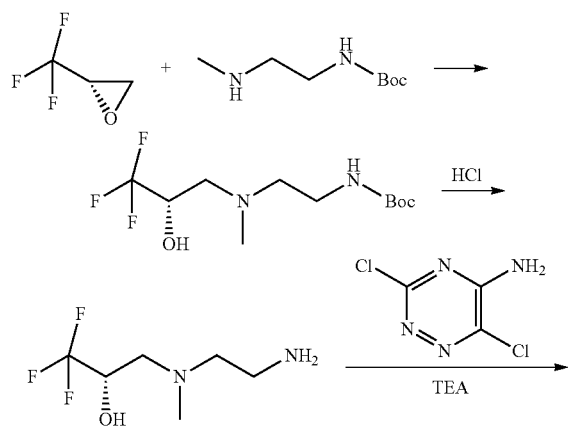

Example 96

Preparation of Compound 149

The synthesis of (S)-3-((2-((5-amino-6-(2,3-dichlorophenyl)-1,2,4-triazin-3-yl)(methyl)amino)ethyl)(methyl)amino)-1,1,1-trifluoropropan-2-ol

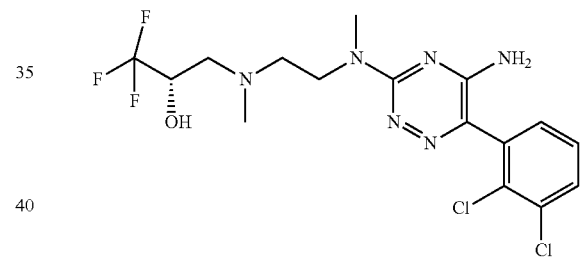

The synthesis of (S)-3-((2-((5-amino-6-(2,3-dichlorophenyl)-1,2,4-triazin-3-yl)(methyl)amino)ethyl)(methyl)amino)-1,1,1-trifluoropropan-2-ol is performed following the above procedure by using tert-butyl methyl(2-(methylamino)ethyl)carbamate as starting material.

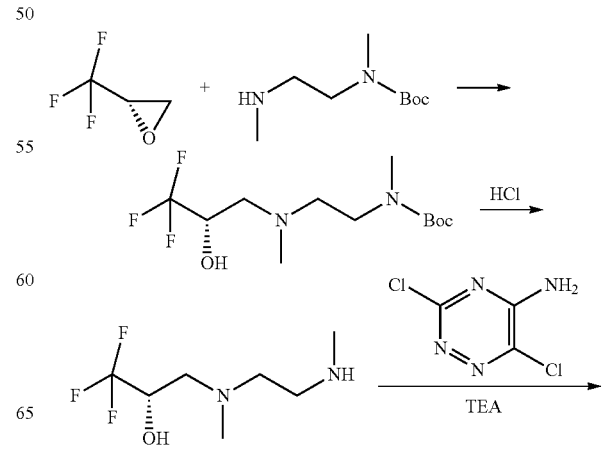

221
-continued

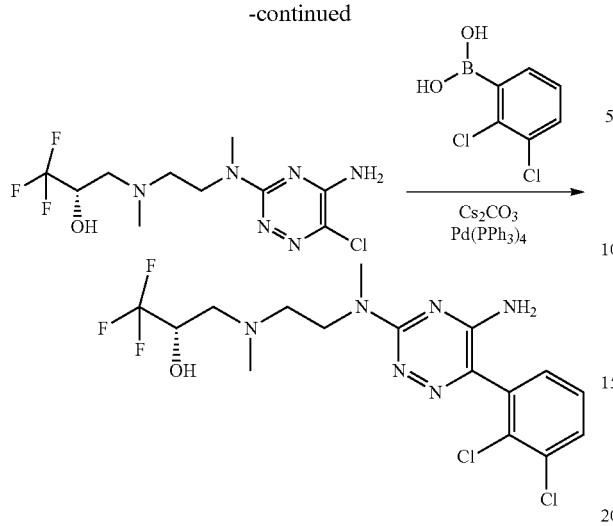

Example 97

Preparation of Compound 150

The synthesis of (R)-3-((2-((5-amino-6-(2,3-dichlorophenyl)-1,2,4-triazin-3-yl)amino)ethyl)amino)-1,1,1-trifluoropropan-2-ol

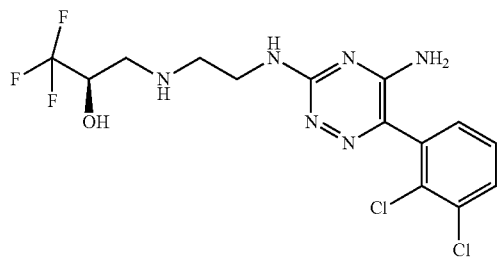 [SMILES: Nc1nc(NCCNC[C@@H](O)C(F)(F)F)nnc1-c1cccc(Cl)c1Cl]

The synthesis of (R)-3-((2-((5-amino-6-(2,3-dichlorophenyl)-1,2,4-triazin-3-yl)amino)ethyl)amino)-1,1,1-trifluoropropan-2-ol is performed following the above procedure by using (R)-2-(trifluoromethyl)oxirane and N-Boc-ethylenediamine as starting material:

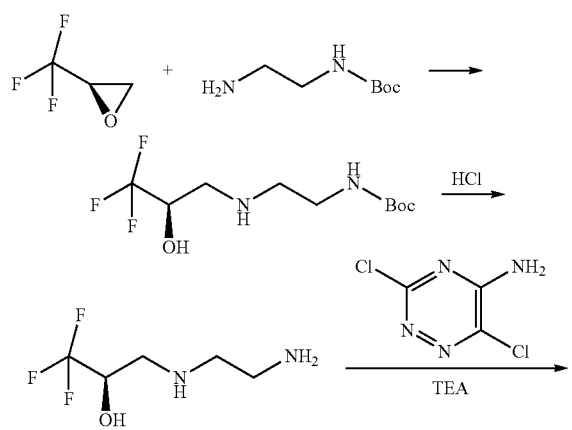

222
-continued

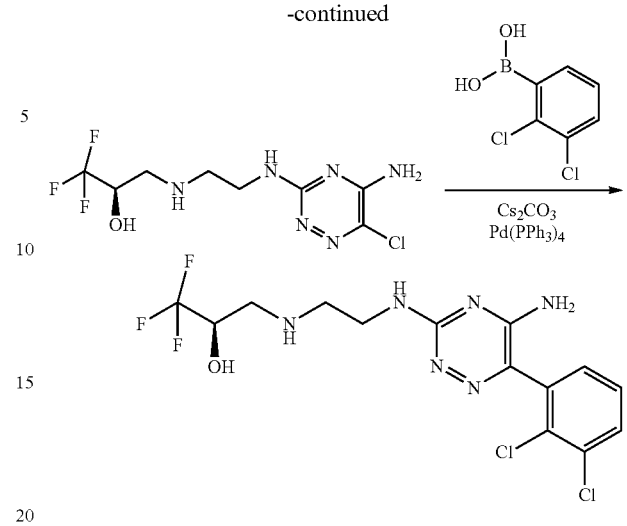

Example 98

Preparation of Compound 151

The synthesis of (R)-3-((2-((5-amino-6-(2,3-dichlorophenyl)-1,2,4-triazin-3-yl)(methyl)amino)ethyl)amino)-1,1,1-trifluoropropan-2-ol (Compound 151)

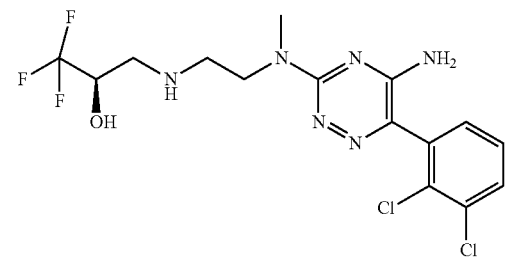 [SMILES: CN(CCNC[C@@H](O)C(F)(F)F)c1nnc(-c2cccc(Cl)c2Cl)c(N)n1]

The synthesis of (R)-3-((2-((5-amino-6-(2,3-dichlorophenyl)-1,2,4-triazin-3-yl)(methyl)amino)ethyl)amino)-1,1,1-trifluoropropan-2-ol is performed following the above procedure by using N-Boc-N-methylethylenediamine as starting material.

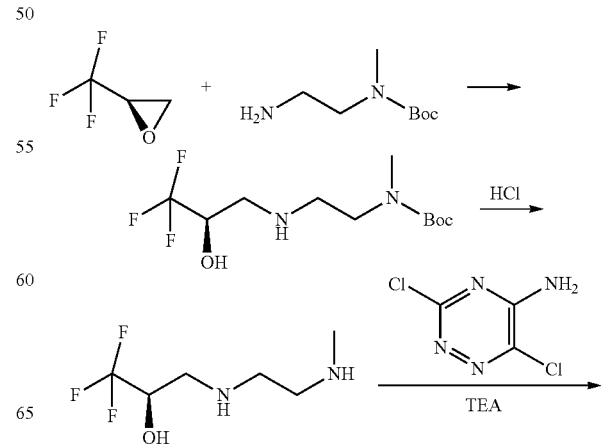

223
-continued

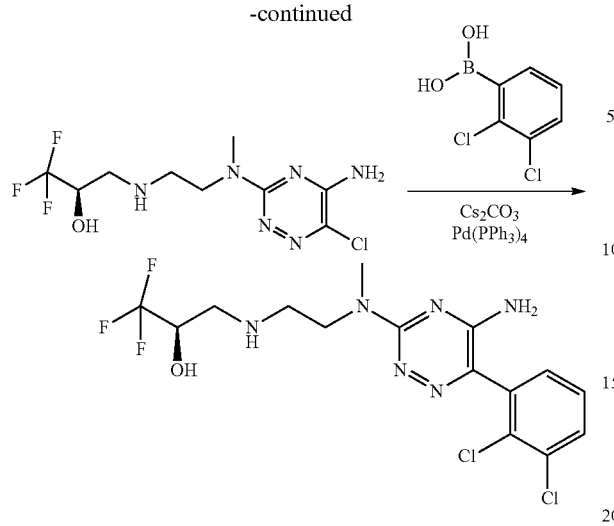

Example 99

Preparation of Compound 152

The synthesis of (R)-3-((2-((5-amino-6-(2,3-dichlorophenyl)-1,2,4-triazin-3-yl)amino)ethyl)(methyl)amino)-1,1,1-trifluoropropan-2-ol

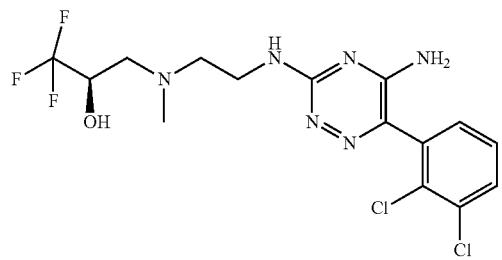 [SMILES: CN(CCNc1nnc(-c2cccc(Cl)c2Cl)c(N)n1)C[C@@H](O)C(F)(F)F]

The synthesis of (R)-3-((2-((5-amino-6-(2,3-dichlorophenyl)-1,2,4-triazin-3-yl)amino)ethyl)(methyl)amino)-1,1,1-trifluoropropan-2-ol is performed following the above procedure by using tert-Butyl 2-(methylamino)ethylcarbamate as starting material.

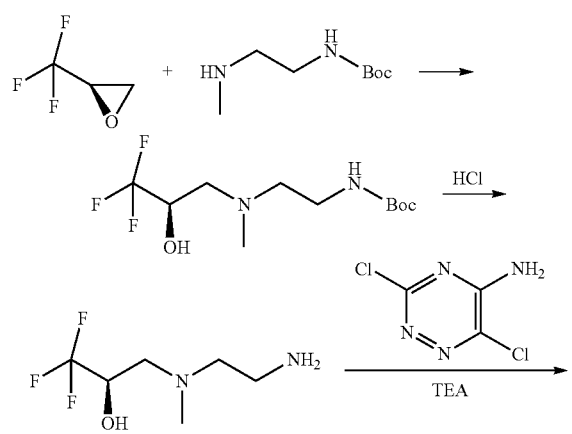

224
-continued

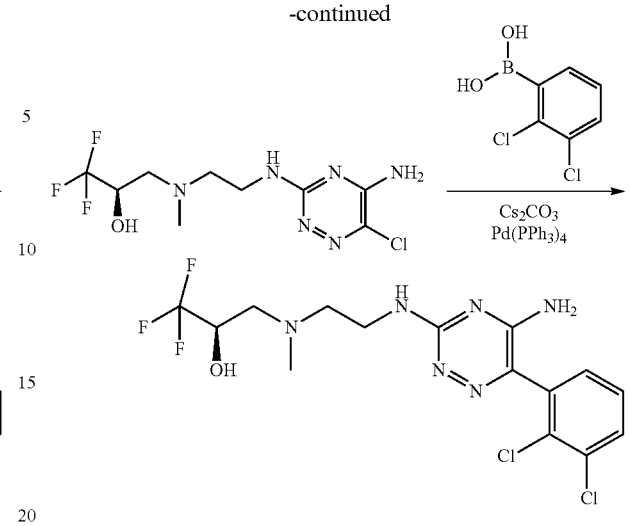

Example 100

Preparation of Compound 154

The synthesis of (R)-3-((2-((5-amino-6-(2,3-dichlorophenyl)-1,2,4-triazin-3-yl)(methyl)amino)ethyl)(methyl)amino)-1,1,1-trifluoropropan-2-ol

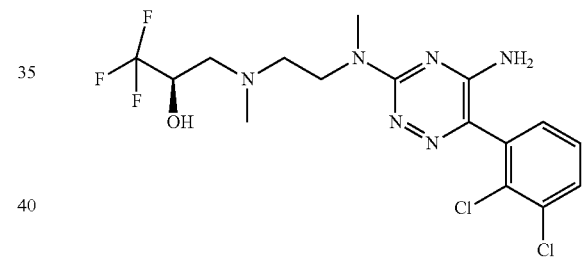

The synthesis of (R)-3-((2-((5-amino-6-(2,3-dichlorophenyl)-1,2,4-triazin-3-yl)(methyl)amino)ethyl)(methyl)amino)-1,1,1-trifluoropropan-2-ol is carried out following the above procedure by using tert-butyl methyl(2-(methylamino)ethyl)carbamateethylcarbamate as starting material.

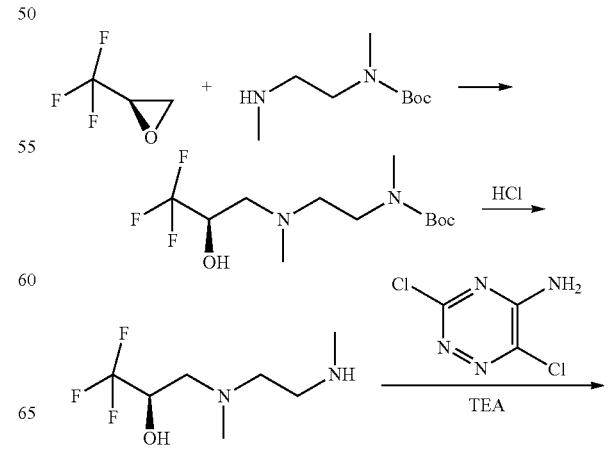

225
-continued

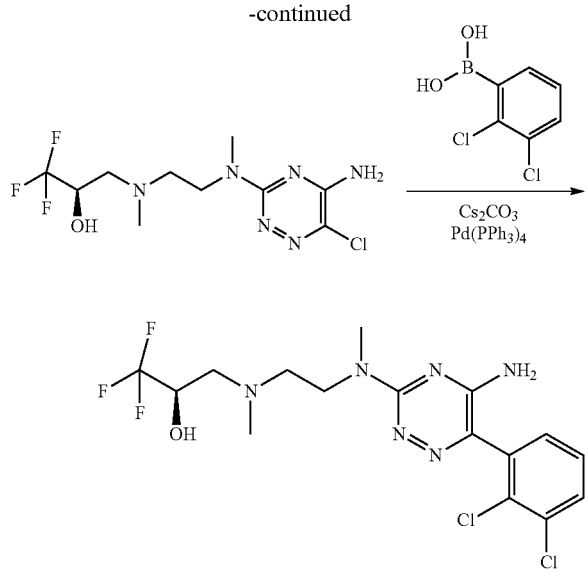
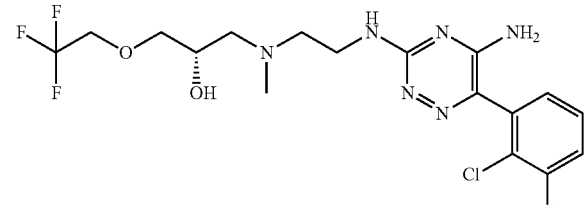

226

Example 101

Preparation of Compound 155

The synthesis of (S)-1-((2-((5-amino-6-(2,3-dichlorophenyl)-1,2,4-triazin-3-yl)amino)ethyl)(methyl)amino)-3-(2,2,2-trifluoroethoxy)propan-2-ol The synthesis of (S)-1-((2-((5-amino-6-(2,3-dichlorophenyl)-1,2,4-triazin-3-yl)amino)ethyl)(methyl)amino)-3-(2,2,2-trifluoroethoxy)propan-2-ol is carried out as set forth below using (S)-epichlorohydrin and tert-butyl (2-(methylamino)ethyl)carbamate as starting materials.

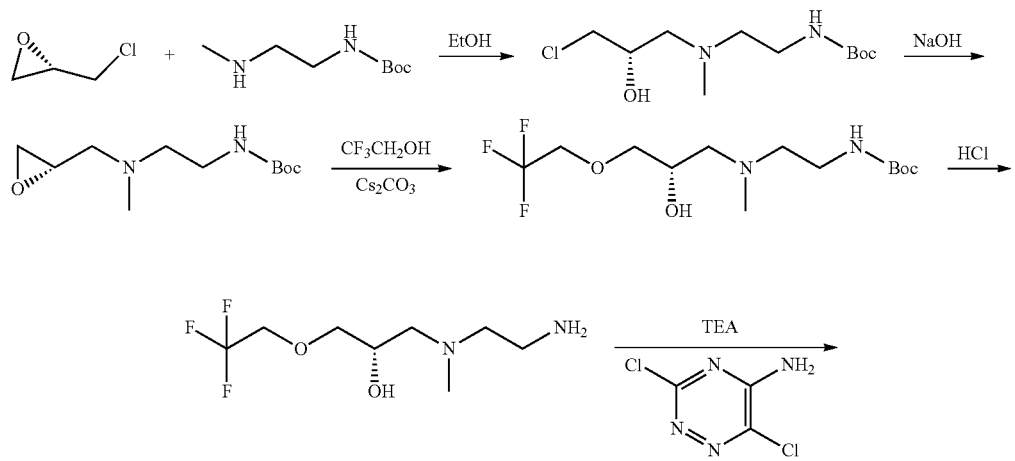

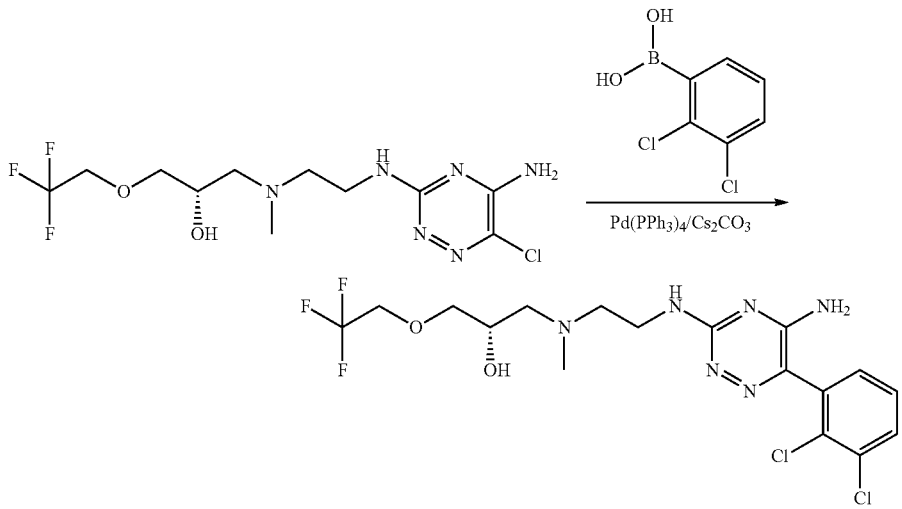

Example 102

Preparation of Compound 156

The synthesis of (S)-1-((2-((5-amino-6-(2,3-dichlorophenyl)-1,2,4-triazin-3-yl)(methyl)amino)ethyl)(methyl)amino)-3-(2,2,2-trifluoroethoxy)propan-2-ol

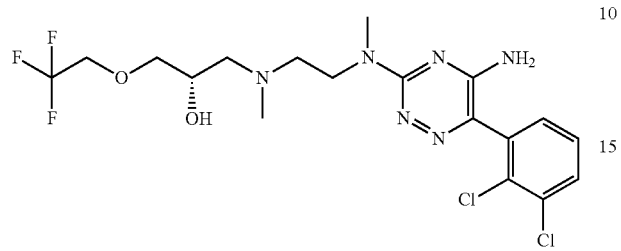

The synthesis of (S)-1-((2-((5-amino-6-(2,3-dichlorophenyl)-1,2,4-triazin-3-yl)(methyl)amino)ethyl)(methyl)amino)-3-(2,2,2-trifluoroethoxy)propan-2-ol is performed following the synthetic methodology shown below using (S)-epichlorohydrin and tert-butyl methyl(2-(methylamino)ethyl)carbamate as starting materials.

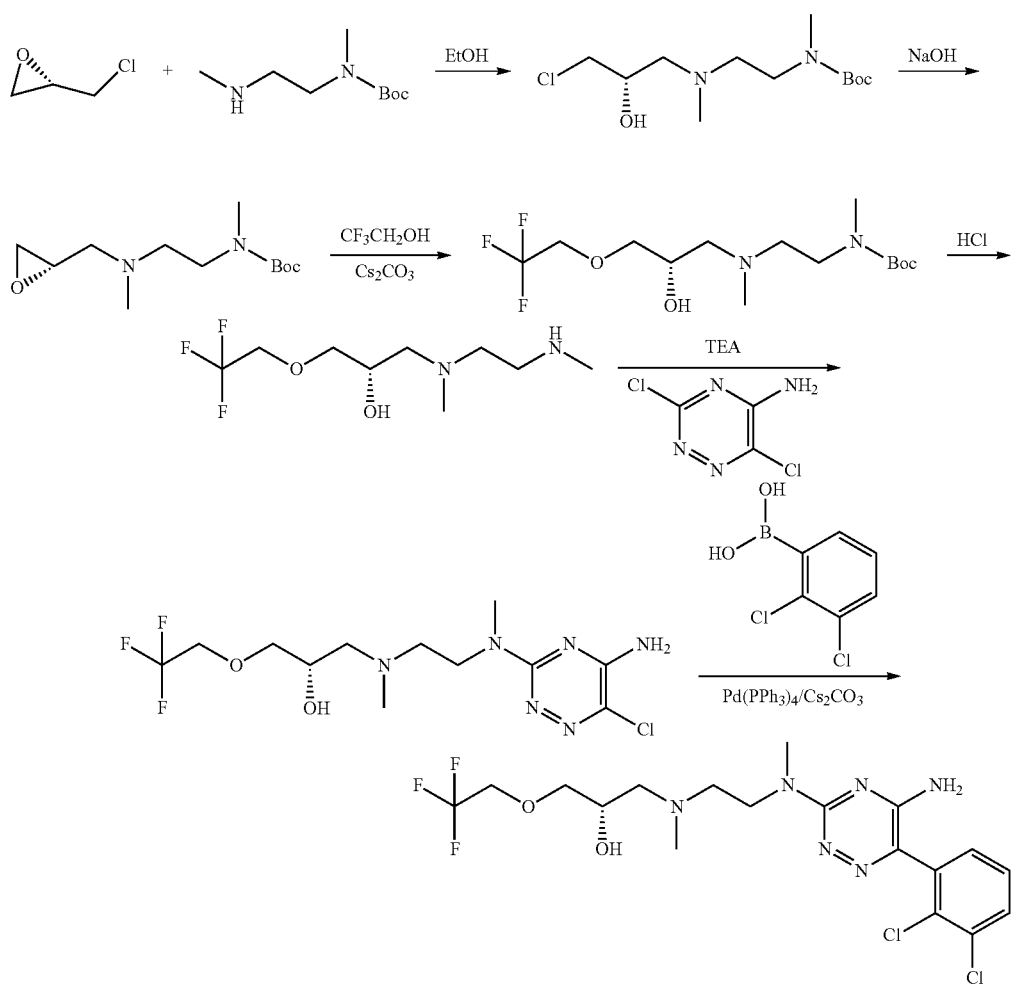

Example 103

Preparation of Compound 157

The synthesis of (R)-1-((2-((5-amino-6-(2,3-dichlorophenyl)-1,2,4-triazin-3-yl)amino)ethyl)(methyl)amino)-3-(2,2,2-trifluoroethoxy)propan-2-ol

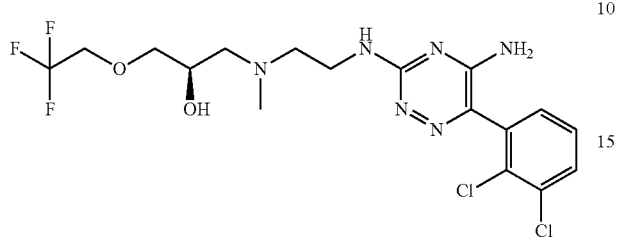

The synthesis of (R)-1-((2-((5-amino-6-(2,3-dichlorophenyl)-1,2,4-triazin-3-yl)amino)ethyl)(methyl)amino)-3-(2,2,2-trifluoroethoxy)propan-2-ol is conducted following the synthetic methodology shown below using (R)-epichlorohydrin and tert-butyl (2-(methylamino)ethyl)carbamate as starting materials.

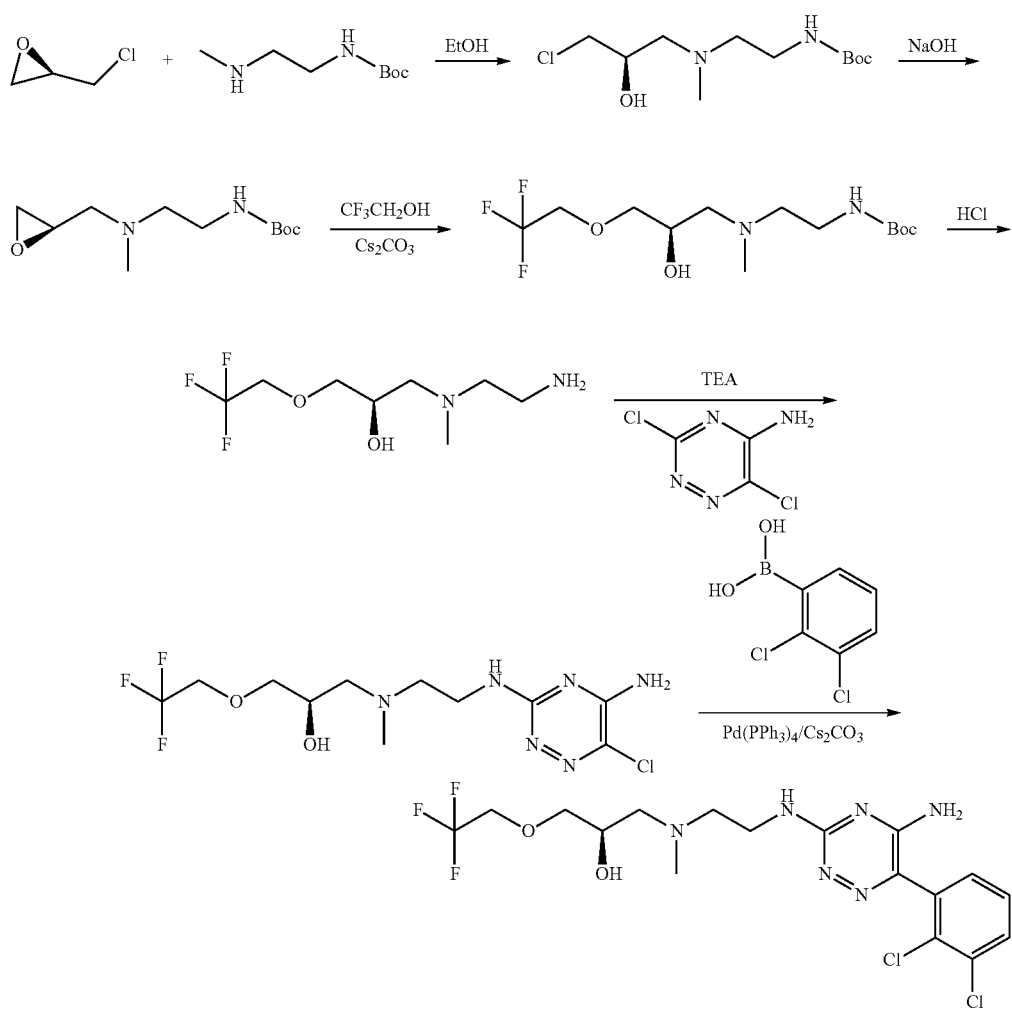

Example 104

Preparation of Compound 158

The synthesis of (R)-1-((2-((5-amino-6-(2,3-dichlorophenyl)-1,2,4-triazin-3-yl)(methyl)amino)ethyl)(methyl)amino)-3-(2,2,2-trifluoroethoxy)propan-2-ol (Compound 158)

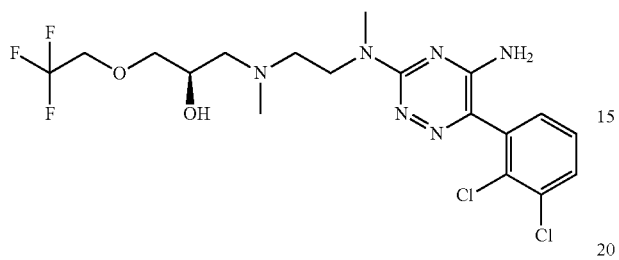

The synthesis of (R)-1-((2-((5-amino-6-(2,3-dichlorophenyl)-1,2,4-triazin-3-yl)(methyl)amino)ethyl)(methyl)amino)-3-(2,2,2-trifluoroethoxy)propan-2-ol is performed following the synthetic methodology shown below using (R)-epichlorohydrin and tert-butyl methyl(2-(methylamino)ethyl)carbamate as starting materials.

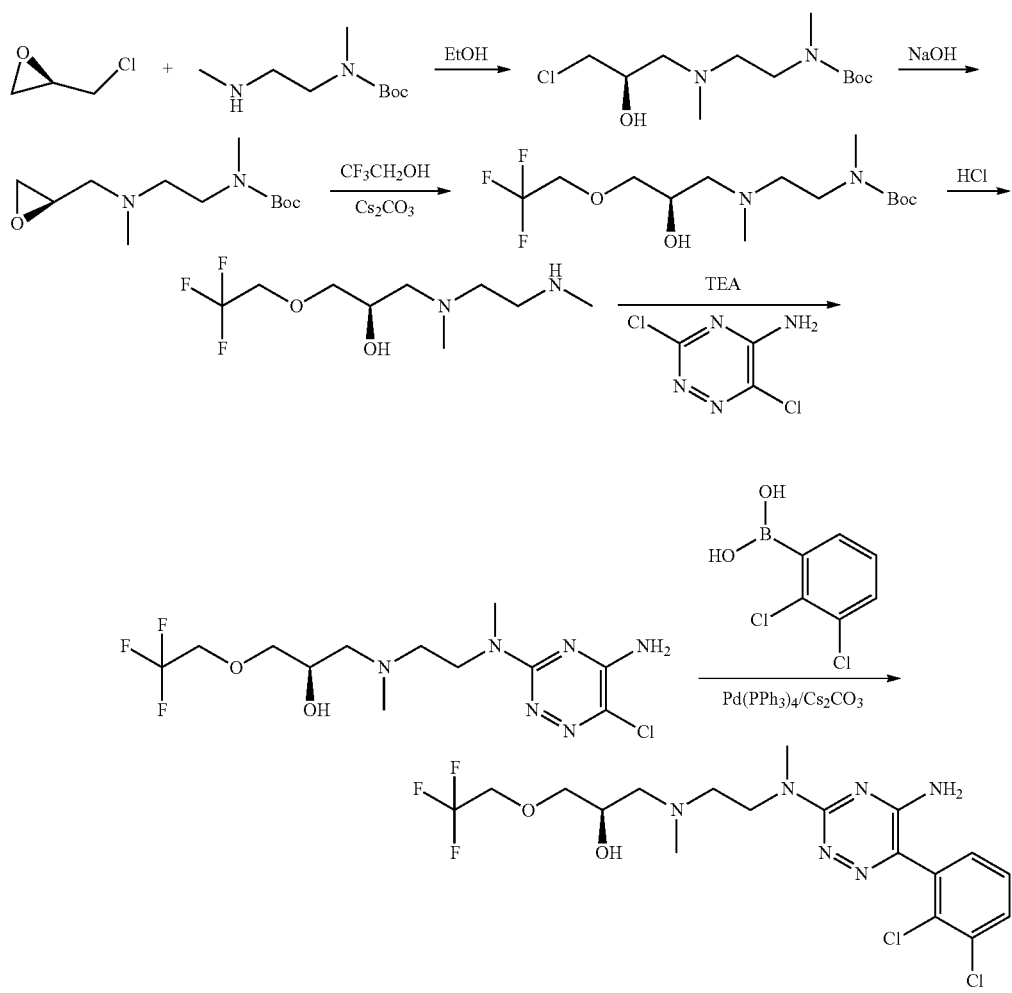

Example 105

Preparation of Compound 159

Preparation of (S)-1-(((R)-1-(5-amino-6-(2,3-dichlorophenyl)-1,2,4-triazin-3-yl)pyrrolidin-3-yl)amino)-3-methoxypropan-2-ol, hydrochloride salt (Compound 159)

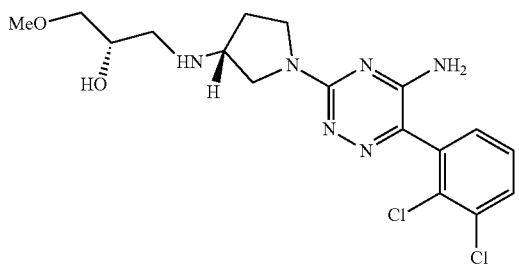 [SMILES: COC[C@@H](O)CN[C@@H]1CCN(c2nnc(-c3cccc(Cl)c3Cl)c(N)n2)C1]

(S)-1-(((R)-1-(5-amino-6-(2,3-dichlorophenyl)-1,2,4-triazin-3-yl)pyrrolidin-3-yl)amino)-3-methoxypropan-2-ol was prepared according to the following steps.

Step 1: Preparation of (R)-tert-butyl (1-(5-amino-6-chloro-1,2,4-triazin-3-yl)pyrrolidin-3-yl)carbamate: A 0.5-2 mL microwave vial was charged with (R)-tert-butyl pyrrolidin-3-ylcarbamate, hydrochloride (0.145 g, 0.65 mmol), 3,6-dichloro-1,2,4-triazin-5-amine (0.082 g, 0.50 mmol), dry 1,4-dioxane (1 mL) and triethylamine (0.21 mL, 1.50 mmol), and the mixture heated in a microwave vial at 120° C. for 45 min. The mixture was carried forward to the next step without further purification. MS (EI) for $C_{13}H_{21}ClN_6O_2$: 329.2 (MH+).

Step 2: Preparation of (R)-3-(3-aminopyrrolidin-1-yl)-6-chloro-1,2,4-triazin-5-amine: The crude reaction mixture from the last step was diluted with methanol (2 mL) and 4 M HCl in dioxane (2.5 mL), and the resultant solution aged at RT for 5 min, before warming to 60° C. The mixture was removed from the heat after 20 min, concentrated to dryness, and the residue partitioned between CHCl3/IPA (3:1, 3×5 mL) and 2 M sodium carbonate (5 mL). The combined organic layers were dried (sodium sulfate), filtered and concentrated to a yellow oil (crude 109 mg), which was carried forward to the next step without further purification. MS (EI) for $C_7H_{11}ClN_6$: 215.0 (MH+).

Step 3: Preparation of (S)-1-(((R)-1-(5-amino-6-chloro-1,2,4-triazin-3-yl)pyrrolidin-3-yl)amino)-3-methoxypropan-2-ol: A suspension of (R)-3-(3-aminopyrrolidin-1-yl)-6-chloro-1,2,4-triazin-5-amine (107 mg, 0.50 mmol) and (S)-2-(methoxymethyl)oxirane (0.045 mL, 0.50 mmol) in dry Ethanol (3 mL) was heated to 60° C., whereupon it dissolved. Neat (S)-2-(methoxymethyl)oxirane (0.045 mL, 0.50 mmol) was added and the mixture heated at 60° C. for 18 h. Additional (S)-2-(methoxymethypoxirane (0.023 mL, 0.25 mmol) was added after 16.5 h. The mixture was evaporated from toluene (10 mL) to afford a brown oil (crude 171 mg), which was used in the next step without further purification. MS (EI) for $C_{11}H_{19}ClN_6O_2$: 303.1 (MH+).

Step 4: Preparation of (S)-1-(((R)-1-(5-amino-6-(2,3-dichlorophenyl)-1,2,4-triazin-3-yl)pyrrolidin-3-yl)amino)-3-methoxypropan-2-ol: A 20 mL septumed screw-capped vial was charged with tetrakis(triphenylphosphine)palladium (116 mg, 0.10 mmol), capped with a septum, and purged with nitrogen, whereupon solutions of (S)-1-(((R)-1-(5-amino-6-chloro-1,2,4-triazin-3-yl)pyrrolidin-3-yl)amino)-3-methoxypropan-2-ol (171 mg, assumed 0.50 mmol) in nitrogen sparged dioxane (7 mL) and (2,3-dichlorophenyl)boronic acid (191 mg, 1.00 mmol) and cesium carbonate (505 mg, 1.55 mmol) in nitrogen-sparged water (2.3 mL) were added, and the stirred yellow suspension heated in a heat block at 90° C. for 1.3 h. The cooled mixture was partitioned between toluene (7 mL) and 2 M sodium hydroxide (3 mL), and the aqueous layer extracted with further toluene (7 mL). The combined organic layers were extracted with 2 M H2SO4 (3 mL, 2×2 mL). The combined acid extracts were basified to pH >12 with 4 M sodium hydroxide, and extracted with 1,2-DCE (2×mL). The combined DCE layers were dried (sodium sulfate), filtered and concentrated. Reverse phase prep HPLC (2 injections; eluting with 15-35% acetonitrile in 10 mM aqueous ammonium formate on a 150×21.2 mm i.d., 10 um Gemini C18 column) afforded, after freebasing with 1 M sodium hydroxide/dichloromethane, (S)-1-(((R)-1-(5-amino-6-(2,3-dichlorophenyl)-1,2,4-triazin-3-yl)pyrrolidin-3-yl)amino)-3-methoxypropan-2-ol as a pale cream solid (49 mg, 23% over 4 steps). $^1$H NMR (500 MHz, DMSO-$d_6$) δ 7.71 (dd, J=8.1, 1.5 Hz, 1H), 7.45 (t, J=7.8 Hz, 1H), 7.35 (dd, J=7.7, 1.6 Hz, 1H), 6.74 (s, 2H), 4.75 (d, J=4.9 Hz, 1H), 3.70-3.62 (m, 2H), 3.62-3.44 (m, 2H), 3.34-3.23 (m, 2H), 3.28 (dd, J=9.5, 5.6 Hz, 2H), 3.25 (s, 3H), 2.60 (dd, J=11.7, 4.3 Hz, 1H), 2.07 (dq, J=12.7, 6.4, 5.5 Hz, 1H), 1.82 (br s, 1H), 1.78 (dq, J=12.7, 6.4, 5.3 Hz, 1H); MS (EI) for $C_{17}H_{22}Cl_2N_6O_2$: 413.0 (MH+).

The free base (47 mg) was dissolved in acetonitrile (2 mL), treated with 4 M HCl in dioxane (300 uL), concentrated to dryness. The residue was dissolved in acetonitrile/water (10:1), and concentrated under centrifugal evaporation to afford the dihydrochloride salt as a very pale orange glass.

Example 106

Preparation of Compound 160

Preparation of (S)-1-(((1-(5-amino-6-(2,3-dichlorophenyl)-1,2,4-triazin-3-yl)azetidin-3-yl)methyl)(methyl)amino)-3-methoxypropan-2-ol, hydrochloride salt (Compound 160)

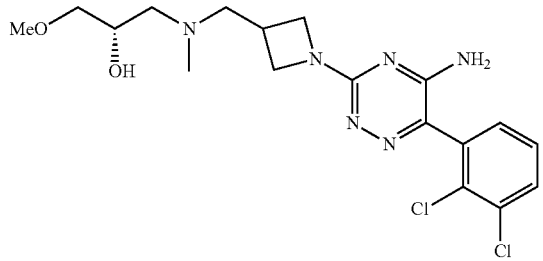 [SMILES: COC[C@@H](O)CN(C)CC1CN(c2nnc(-c3cccc(Cl)c3Cl)c(N)n2)C1]

(S)-1-(((1-(5-amino-6-(2,3-dichlorophenyl)-1,2,4-triazin-3-yl)azetidin-3-yl)methyl)(methyl)amino)-3-methoxypropan-2-ol was prepared according to the following steps.

Step 1: Preparation of tert-butyl ((1-(5-amino-6-chloro-1,2,4-triazin-3-yl)azetidin-3-yl)methyl)(methyl)carbamate: As described for Example 105 above, tert-butyl (azetidin-3-ylmethyl)(methyl)carbamate (0.110 g, 0.55 mmol) and 3,6-dichloro-1,2,4-triazin-5-amine (0.082 g, 0.50 mmol) were coupled to afford crude tert-butyl ((1-(5-amino-6-chloro-1,2,4-triazin-3-yl)azetidin-3-yl)methyl)(methyl)carbamate (assumed 0.50 mmol), which was carried forward to the next step without further purification.

Step 2: Preparation of 6-chloro-3-(3-((methylamino)methyl)azetidin-1-yl)-1,2,4-triazin-5-amine: As described for Example 105 above, tert-butyl ((1-(5-amino-6-chloro-1,2,4-triazin-3-yl)azetidin-3-yl)methyl)(methyl)carbamate (assumed 0.50 mmol) was treated with 4 M HCl in dioxane (2.5 mL, 10 mmol) to afford crude 6-chloro-3-(3-((methylamino)methyl)azetidin-1-yl)-1,2,4-triazin-5-amine (137 mg, assumed 0.50 mmol), which was carried forward to the next step without further purification.

Step 3: Preparation of (S)-1-(((1-(5-amino-6-chloro-1,2,4-triazin-3-yl)azetidin-3-yl)methyl)(methyl)amino)-3-methoxypropan-2-ol: As described for Example 105 above, 6-chloro-3-(3-((methylamino)methyl)azetidin-1-yl)-1,2,4-triazin-5-amine (137 mg, assumed 0.50 mmol) and (S)-2-(methoxymethyl)oxirane (0.058 mL, 0.65 mmol) were coupled to afford crude (S)-1-(((1-(5-amino-6-chloro-1,2,4-triazin-3-yl)azetidin-3-yl)methyl)(methyl)amino)-3-methoxypropan-2-ol (assumed 0.50 mmol), which was carried forward to the next step without further purification.

Step 4: Preparation of (S)-1-(((1-(5-amino-6-(2,3-dichlorophenyl)-1,2,4-triazin-3-yl)azetidin-3-yl)methyl)(methyl)amino)-3-methoxypropan-2-ol: As described for Example 105 above, crude (S)-1-(((1-(5-amino-6-chloro-1,2,4-triazin-3-yl)azetidin-3-yl)methyl)(methyl)amino)-3-methoxypropan-2-ol (assumed 0.50 mmol) and (2,3-di-chlorophenyl)boronic acid (191 mg, 1.00 mmol) were coupled to afford, after reverse phase prep HPLC purifycation (2 injections; eluting with 30-45% acetonitrile in 10 mM aqueous ammonium hydroxide on a 150×21.2 mm i.d., 10 um Gemini C18 column), (S)-1-(((1-(5-amino-6-(2,3-dichlorophenyl)-1,2,4-triazin-3-yl)azetidin-3-yl)methyl)(methyl)amino)-3-methoxypropan-2-ol as a colorless solid (45 mg, 21% over 4 steps). $^1$H NMR (500 MHz, CDCl$_3$) δ 7.56 (dd, J=7.4, 2.3 Hz, 1H), 7.38-7.30 (m, 2H), 5.01 (s, 2H), 4.33-4.25 (m, 2H), 3.86 (ddd, J=7.0, 5.0, 2.3 Hz, 3H), 3.44 (dd, J=9.9, 3.9 Hz, 1H), 3.39 (s, 3H), 3.37 (dd, J=9.9, 5.6 Hz, 1H), 3.33 (s, 1H), 2.95 (ddt, J=9.9, 7.6, 3.9 Hz, 1H), 2.81 (dd, J=12.5, 7.8 Hz, 1H), 2.71 (dd, J=12.5, 7.3 Hz, 1H), 2.49 (dd, J=12.5, 9.7 Hz, 1H), 2.39 (dd, J=12.5, 3.8 Hz, 1H), 2.30 (s, 3H); MS (EI) for C$_{18}$H$_{24}$Cl$_2$N$_6$O$_2$: 427.2 (MH$^+$).

The free base (45 mg) was dissolved in acetonitrile (2 mL), treated with 4 M HCl in dioxane (265 uL), concentrated to dryness. The residue was dissolved in acetonitrile/water (10:1), and concentrated under centrifugal evaporation to afford the dihydrochloride salt as a very pale yellow solid foam.

Example 107

Preparation of Compound 161

Preparation of (2S)-1-(6-(5-amino-6-(2,3-dichlorophenyl)-1,2,4-triazin-3-yl)-1,6-diazaspiro[3.5]nonan-1-yl)-3-methoxypropan-2-ol, hydrochloride salt (Compound 161)

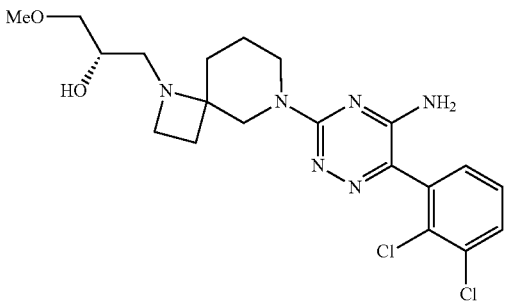 [SMILES: COC[C@@H](O)CN1CCC12CCCN(c1nnc(-c3cccc(Cl)c3Cl)c(N)n1)C2]

(2S)-1-(6-(5-amino-6-(2,3-dichlorophenyl)-1,2,4-triazin-3-yl)-1,6-diazaspiro[3.5]nonan-1-yl)-3-methoxypropan-2-ol was prepared according to the following steps.

Step 1: Preparation of tert-butyl 6-(5-amino-6-chloro-1,2,4-triazin-3-yl)-2,6-diazaspiro[3.5]nonane-2-carboxylate: As described for Example 105 above, tert-butyl 2,6-diazaspiro[3.5]nonane-2-carboxylate, hemioxalate (0.166 g, 0.53 mmol) and 3,6-dichloro-1,2,4-triazin-5-amine (0.082 g, 0.50 mmol) were coupled to afford crude tert-butyl 6-(5-amino-6-chloro-1,2,4-triazin-3-yl)-2,6-diazaspiro[3.5]nonane-2-carboxylate (assumed 0.50 mmol), which was carried forward to the next step without further purification.

Step 2: Preparation of 6-chloro-3-(2,6-diazaspiro[3.5]nonan-6-yl)-1,2,4-triazin-5-amine: As described for Example 105 above, tert-butyl 6-(5-amino-6-chloro-1,2,4-triazin-3-yl)-2,6-diazaspiro[3.5]nonane-2-carboxylate (assumed 0.50 mmol) was treated with 4 M HCl in dioxane (2.5 mL, 10 mmol) to afford crude 6-chloro-3-(2,6-diazaspiro[3.5]nonan-6-yl)-1,2,4-triazin-5-amine (129 mg, assumed 0.50 mmol), which was carried forward to the next step without further purification.

Step 3: Preparation of (2S)-1-(6-(5-amino-6-chloro-1,2,4-triazin-3-yl)-1,6-diazaspiro[3.5]nonan-1-yl)-3-methoxypropan-2-ol: As described for Example 105 above, 6-chloro-3-(2,6-diazaspiro[3.5]nonan-6-yl)-1,2,4-triazin-5-amine (129 mg, assumed 0.50 mmol), and (S)-2-(methoxymethyl)oxirane (0.058 mL, 0.65 mmol) were coupled to afford crude (2S)-1-(6-(5-amino-6-chloro-1,2,4-triazin-3-yl)-1,6-di azaspiro [3.5] nonan-1-yl)-3-methoxypropan-2-ol (assumed 0.50 mmol), which was carried forward to the next step without further purification.

Step 4: Preparation of (2S)-1-(6-(5-amino-6-(2,3-dichlorophenyl)-1,2,4-triazin-3-yl)-1,6-diazaspiro[3.5]nonan-1-yl)-3-methoxypropan-2-ol: As described for Example 105 above, crude (2S)-1-(6-(5-amino-6-chloro-1,2,4-triazin-3-yl)-1,6-diazaspiro[3.5]nonan-1-yl)-3-methoxypropan-2-ol (assumed 0.50 mmol) and (2,3-dichlorophenyl)boronic acid (191 mg, 1.00 mmol) were coupled to afford, after reverse phase prep HPLC purification (2 injections; eluting with 25-40% acetonitrile in 10 mM aqueous ammonium hydroxide on a 150×21.2 mm i.d., 10 um Gemini C18 column), (2S)-1-(6-(5-amino-6-(2,3-dichlorophenyl)-1,2,4-triazin-3-yl)-1,6-diazaspiro[3.5]nonan-1-yl)-3-methoxypropan-2-ol as a pale yellow solid (12 mg, 5% over 4 steps). $^1$H NMR (500 MHz, CDCl$_3$) δ 7.57 (dd, J=7.9, 1.7 Hz, 1H), 7.39 (dd, J=7.7, 1.7 Hz, 1H), 7.35 (t, J=7.7 Hz, 1H), 5.03 (s, 2H), 3.96 (s, 2H), 3.82 (s, 2H), 3.72 (dq, J=9.1, 4.4 Hz, 1H), 3.38 (s, 3H), 3.43-3.30 (m, 2H), 3.24 (dd, J=22.9, 7.3 Hz, 2H), 3.01 (d, J=7.3 Hz, 1H), 2.92 (d, J=7.2 Hz, 1H), 2.59 (dd, J=12.0, 8.8 Hz, 1H), 2.51 (dd, J=12.0, 3.6 Hz, 1H), 1.82 (t, J=5.9 Hz, 2H), 1.62 (t, J=6.0 Hz, 2H); MS (EI) for C$_{20}$H$_{26}$Cl$_2$N$_6$O$_2$: 453.2 (MH$^+$).

The free base (11 mg) was dissolved in acetonitrile (2 mL), treated with 4 M HCl in dioxane (50 uL), concentrated to dryness. The residue was dissolved in acetonitrile/water (10:1), and concentrated under centrifugal evaporation to afford the dihydrochloride salt as a very pale yellow solid foam.

Example 108

Preparation of Compound 162

Preparation of (2S)-1-((1-(5-amino-6-(2,3-dichlorophenyl)-1,2,4-triazin-3-yl)-3-methylpyrrolidin-3-yl)amino)-3-methoxypropan-2-ol, hydrochloride salt (Compound 162)

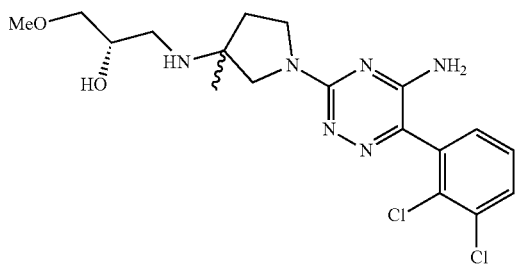 [SMILES: COC[C@@H](O)CNC1(C)CCN(c2nnc(-c3cccc(Cl)c3Cl)c(N)n2)C1]

of (2S)-1-((1-(5-amino-6-(2,3-dichlorophenyl)-1,2,4-triazin-3-yl)-3-methylpyrrolidin-3-yl)amino)-3-methoxypropan-2-ol was prepared according to the following steps.

Step 1: Preparation of tert-butyl (1-(5-amino-6-chloro-1,2,4-triazin-3-yl)-3-methylpyrrolidin-3-yl)carbamate: As described for Example 105 above, tert-butyl (3-methylpyrrolidin-3-yl)carbamate (0.260 g, 1.30 mmol), 3,6-dichloro-1,2,4-triazin-5-amine (0.165 g, 1.00 mmol), dry 1,4-Dioxane (1 mL) and triethylamine (0.42 mL, 3.00 mmol), were coupled to afford crude tert-butyl (1-(5-amino-6-chloro-1,2,4-triazin-3-yl)-3-methylpyrrolidin-3-yl)carbamate (assumed 1.00 mmol), which was carried forward to the next step without further purification.

Step 2: Preparation of 3-(3-amino-3-methylpyrrolidin-1-yl)-6-chloro-1,2,4-triazin-5-amine: As described for Example 105 above, tert-butyl (1-(5-amino-6-chloro-1,2,4-triazin-3-yl)-3-methylpyrrolidin-3-yl)carbamate (assumed 1.00 mmol), was treated with 4 M HCl in dioxane (5 mL, 20 mmol) to afford crude 3-(3-amino-3-methylpyrrolidin-1-yl)-6-chloro-1,2,4-triazin-5-amine (243 mg, assumed 1.00 mmol), which was carried forward to the next step without further purification.

Step 3: Preparation of (2S)-1-((1-(5-amino-6-chloro-1,2,4-triazin-3-yl)-3-methylpyrrolidin-3-yl)amino)-3-methoxypropan-2-ol: As described for Example 105 above, 3-(3-amino-3-methylpyrrolidin-1-yl)-6-chloro-1,2,4-triazin-5-amine (243 mg, assumed 1.00 mmol) and (S)-2-(methoxymethy)oxirane (0.099 mL, 1.1 mmol) were coupled to afford crude (2S)-1-((1-(5-amino-6-chloro-1,2,4-triazin-3-yl)-3-methylpyrrolidin-3-yl)amino)-3-methoxypropan-2-ol (assumed 1.00 mmol), which was carried forward to the next step without further purification. MS (EI) for C$_{12}$H$_{21}$ClN$_6$O$_2$: 317.2 (MH$^+$).

Step 4: Preparation of (2S)-1-((1-(5-amino-6-(2,3-dichlorophenyl)-1,2,4-triazin-3-yl)-3-methylpyrrolidin-3-yl)amino)-3-methoxypropan-2-ol: As described for Example 105 above, crude ((2S)-1-((1-(5-amino-6-chloro-1,2,4-triazin-3-yl)-3-methylpyrrolidin-3-yl)amino)-3-methoxypropan-2-ol (assumed 1.00 mmol), and (2,3-dichlorophenyl) boronic acid (382 mg, 2.00 mmol) were coupled to afford, after reverse phase prep HPLC purification (3 injections; eluting with 15-35% acetonitrile in 10 mM aqueous ammonium formate on a 150×21.2 mm i.d., 10 um Gemini C18 column), and freebasing with 1 M sodium hydroxide/dichloromethane, (2S)-1-((1-(5-amino-6-(2,3-dichlorophenyl)-1,2,4-triazin-3-yl)-3-methylpyrrolidin-3-yl)amino)-3-methoxypropan-2-ol (83 mg, 19% over 4 steps). $^1$H NMR (500 MHz, DMSO-d$_6$) δ 7.70 (dd, J=8.0, 1.5 Hz, 1H), 7.44 (t, J=7.8 Hz, 1H), 7.34 (dd, J=7.6, 1.5 Hz, 1H), 6.86 (s, 2H), 4.70 (dd, J=4.9, 1.9 Hz, 1H), 3.62-3.54 (m, 4H), 3.31 (dt, J=9.9, 5.0 Hz, 2H), 3.25 (ddd, J=9.4, 5.9, 3.5 Hz, 1H), 3.23 (2 singlets, 3H, diastereomers), 2.67-2.40 (m, 2H), 1.92 (d, J=7.4 Hz, 1H), 1.86-1.60 (m, 2H), 1.21 (s, 3H); MS (EI) for C$_{18}$H$_{24}$Cl$_2$N$_6$O$_2$: 427.2 (MH$^+$).

The free base (80 mg) was dissolved in acetonitrile (2 mL), treated with 4 M HCl in dioxane (470 uL), concentrated to dryness. The residue was dissolved in acetonitrile/water (10:1), and concentrated under centrifugal evaporation to afford the dihydrochloride salt as a light yellow-orange solid.

Example 109

Preparation of Compound 163

Preparation of (S)-1-((1-(5-amino-6-(2,3-dichlorophenyl)-1,2,4-triazin-3-yl)azetidin-3-yl)amino)-3-methoxypropan-2-ol, hydrochloride salt (Compound 163)

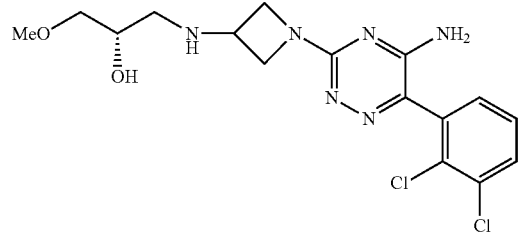 [SMILES: COC[C@@H](O)CNC1CN(c2nnc(-c3cccc(Cl)c3Cl)c(N)n2)C1]

(S)-1-((1-(5-amino-6-(2,3-dichlorophenyl)-1,2,4-triazin-3-yl)azetidin-3-yl)amino)-3-methoxypropan-2-ol was prepared according to the following steps.

Step 1: Preparation of tert-butyl (1-(5-amino-6-chloro-1,2,4-triazin-3-yl)azetidin-3-yl)carbamate: As described for Example 105 above, tert-butyl azetidin-3-ylcarbamate, HCl (0.136 g, 0.65 mmol), and 3,6-dichloro-1,2,4-triazin-5-amine (0.082 g, 0.50 mmol) were coupled to afford crude tert-butyl (1-(5-amino-6-chloro-1,2,4-triazin-3-yl)azetidin-3-yl)carbamate (assumed 0.50 mmol), which was carried forward to the next step without further purification.

Step 2: Preparation of 3-(3-aminoazetidin-1-yl)-6-chloro-1,2,4-triazin-5-amine: As described for Example 105 above, tert-butyl (1-(5-amino-6-chloro-1,2,4-triazin-3-yl)azetidin-3-yl)carbamate (assumed 0.50 mmol), was treated with 4 M HCl in dioxane (2.5 mL, 10 mmol) to afford crude 3-(3-aminoazetidin-1-yl)-6-chloro-1,2,4-triazin-5-amine (57 mg, assumed 0.28 mmol), which was carried forward to the next step without further purification.

Step 3: Preparation of (S)-1-((1-(5-amino-6-chloro-1,2,4-triazin-3-yl)azetidin-3-yl)amino)-3-methoxypropan-2-ol: As described for Example 105 above, crude 3-(3-aminoazetidin-1-yl)-6-chloro-1,2,4-triazin-5-amine (57 mg, assumed 0.28 mmol) and (S)-2-(methoxymethyl)oxirane (0.033 mL, 0.36 mmol) were coupled to afford (S)-1-((1-(5-amino-6-chloro-1,2,4-triazin-3-yl)azetidin-3-yl)amino)-3-methoxypropan-2-ol (90 mg, assumed 0.28 mmol), which was carried forward to the next step without further purification. MS (EI) for $C_{10}H_{17}ClN_6O_2$: 289.0 (MH$^+$).

Step 4: Preparation of (S)-1-((1-(5-amino-6-(2,3-dichlorophenyl)-1,2,4-triazin-3-yl)azetidin-3-yl)amino)-3-methoxypropan-2-ol: As described for Example 105 above, crude (S)-1-((1-(5-amino-6-chloro-1,2,4-triazin-3-yl)azetidin-3-yl)amino)-3-methoxypropan-2-ol (90 mg, assumed 0.28 mmol) and (2,3-dichlorophenyl)boronic acid (191 mg, 1.00 mmol) were coupled to afford, after reverse phase prep HPLC purification (2 injections; eluting with 15-35% acetonitrile in 10 mM aqueous ammonium formate on a 150×21.2 mm i.d., 10 um Gemini C18 column), and free-basing with 1 M sodium hydroxide/dichloromethane, (S)-1-((1-(5-amino-6-(2,3-dichlorophenyl)-1,2,4-triazin-3-yl)azetidin-3-yl)amino)-3-methoxypropan-2-ol as a film (8.6 mg, 4% over 4 steps). $^1$H NMR (500 MHz, CDCl$_3$) δ 7.58 (dd, J=7.3, 2.3 Hz, 1H), 7.38 (dd, J=7.7, 2.3 Hz, 1H), 7.35 (t, J=7.6 Hz, 1H), 4.96 (s, 2H), 4.41 (t, J=8.2 Hz, 2H), 3.96 (dt, J=9.3, 4.8 Hz, 2H), 3.89 (dq, J=10.2, 3.7 Hz, 1H), 3.82 (tt, J=7.0, 4.9 Hz, 1H), 3.47 (dd, J=9.7, 3.8 Hz, 1H), 3.42 (dd, J=9.7, 6.3 Hz, 1H), 3.41 (s, 3H), 2.77 (dd, J=12.1, 3.8 Hz, 1H), 2.70 (dd, J=12.1, 7.8 Hz, 1H), 2.18 (br s, 2H); MS (EI) for $C_{16}H_{20}Cl_2N_6O_2$: 399.0 (MH$^+$).

The freebase (8.6 mg) was dissolved in acetonitrile (2 mL), treated with 4 M HCl in dioxane (50 uL), concentrated to dryness. The residue was dissolved in acetonitrile/water (10:1), and concentrated under centrifugal evaporation to afford the dihydrochloride salt as a very pale yellow solid foam.

Example 110

Preparation of Compound 153

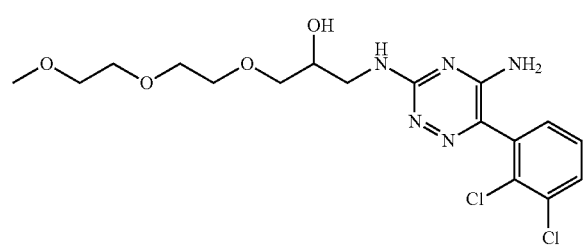 [SMILES: COCCOCCOCC(O)CNc1nnc(-c2cccc(Cl)c2Cl)c(N)n1]

1-((5-Amino-6-(2,3-dichlorophenyl)-1,2,4-triazin-3-yl)amino)-3-(2-(2-methoxyethoxy)ethoxy)propan-2-ol (Compound 153)

1-((A-amino-6-(2,3-dichlorophenyl)-1,2,4-triazin-3-yl)amino)-3-(2-(2-methoxyethoxy)ethoxy)propan-2-ol (Compound 1) was prepared according to the following steps.

Step 1: Preparation of 1-((5-amino-6-chloro-1,2,4-triazin-3-yl)amino)-3-(2-(2-methoxyethoxy)ethoxy)propan-2-ol

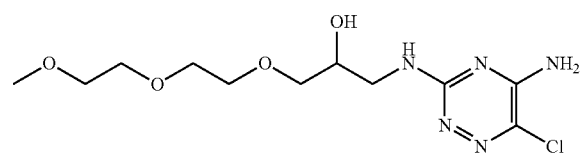 [SMILES: COCCOCCOCC(O)CNc1nnc(Cl)c(N)n1]

3,6-Dichloro-1,2,4-triazin-5-amine (500 mg, 3.03 mmol) and 1-amino-3-(2-(2-methoxyethoxy)ethoxy)propan-2-ol (703 mg, 3.64 mmol) were dissolved in 10 mL of 1,4-dioxane. Reaction mixture was then charged with sodium bicarbonate (382 mg, 4.55 mmol) and stirred at 90° C. for 10 h. Evaporation of the solvent and purification of the residue by column chromatography afforded 1-((5-amino-6-chloro-1,2,4-triazin-3-yl)amino)-3-(2-(2-methoxyethoxy)ethoxy)propan-2-ol (compound 2) (530 mg, 54.4% yield).

Step 2: Preparation of 1-((5-amino-6-(2,3-dichlorophenyl)-1,2,4-triazin-3-yl)amino)-3-(2-(2-methoxyethoxy)ethoxy)propan-2-ol (Compound 153)

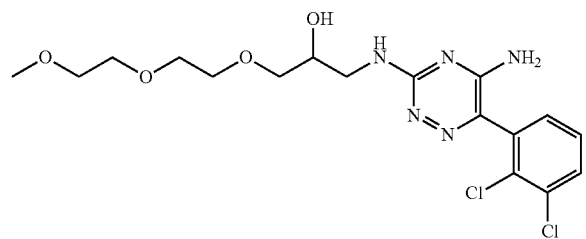 [SMILES: COCCOCCOCC(O)CNc1nnc(-c2cccc(Cl)c2Cl)c(N)n1]

1-((5-Amino-6-chloro-1,2,4-triazin-3-yl)amino)-3-(2-(2-methoxyethoxy)ethoxy)Propan-2-ol (530 mg, 1.647 mmol) and (2,3-dichlorophenyl)boronic acid (534 mg, 2.80 mmol) were dissolved in 20 mL of 1,4-dioxane. Pd(PPh$_3$)$_4$ (190 mg, 0.165 mmol), K$_2$HPO$_4$ (631 mg, 3.62 mmol) and 5 ml of DI water were added to the above reaction mixture and de gassed for 15 minutes. Then reaction mixture was stirred at 90° C. for 8 h. Crude after evaporation of the solvent upon purification by column chromatography yielded 1-((5-amino-6-(2,3-dichlorophenyl)-1,2,4-triazin-3-yl)amino)-3-(2-(2-methoxyethoxy)ethoxy)propan-2-ol (compound 1) as light yellow solid (310 mg, 43.5% yield). $^1$H NMR (500 MHz, CDCl$_3$): δ 7.70 (dd, 1H), 7.45 (t, 1H), 7.35 (d, 1H), 6.20-7.30 (bs, 3H), 4.80-5.30 (bs, 1H), 3.75-3.85 (m, 1H), 3.46-3.59 (m, 6H), 3.30-3.46 (m, 5H), 3.17-3.29 (bs, 4H); MS (ESI) for $C_{17}H_{23}Cl_2N_5O_4$: 432.3016 (MH$^+$). The free base was dissolved in 4M hydrochloride in 2-propanol. The mixture was concentrated under vacuum to afford product as hydrochloride salt.

Example 111

Preparation of Compound 166

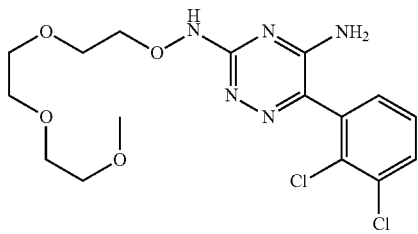 [SMILES: COCCOCCOCCONc1nnc(-c2cccc(Cl)c2Cl)c(N)n1]

6-(2,3-Dichlorophenyl)-3-((2-(2-(2-methoxyethoxy) ethoxy)ethoxy)amino)-1,2,4-triazin-5-amine (Compound 166)

6-(2,3-Dichlorophenyl)-3-((2-(2-(2-methoxyethoxy) ethoxy)ethoxy)amino)-1,2,4-triazin-5-amine was prepared according to the following steps.

Step 1: Preparation of 6-chloro-3-((2-(2-(2-methoxyethoxy)ethoxy)ethoxy)amino)-1,2,4-triazin-5-amine

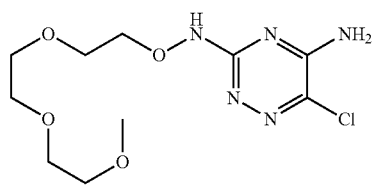 [SMILES: COCCOCCOCCONc1nnc(Cl)c(N)n1]

3,6-dichloro-1,2,4-triazin-5-amine (400 mg, 2.425 mmol) and O-(2-(2-(2-methoxyethoxy)ethoxy)ethyl)hydroxylamine (652 mg, 3.64 mmol) were dissolved in 10 mL of 1,4-dioxane. Reaction mixture is then charged with sodium bicarbonate (407 mg, 4.85 mmol) and stirred at 90° C. for 10 h. Reaction mixture was filtered to remove salt and evaporation of the solvent under vacuum gave crude product. Purification of the crude product by column chromatography yielded 6-chloro-3-((2-(2-(2-methoxyethoxy)ethoxy) ethoxy)amino)-1,2,4-triazin-5-amine (260 mg, 34.8% yield).

Step 2: Preparation of 6-(2,3-dichlorophenyl)-3-((2-(2-(2-methoxyethoxy)ethoxy)ethoxy)amino)-1,2,4-triazin-5-amine (Compound 166)

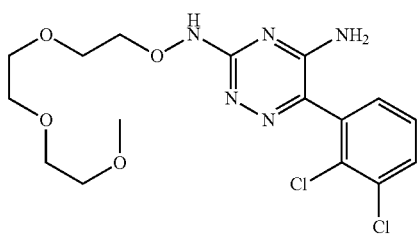 [SMILES: COCCOCCOCCONc1nnc(-c2cccc(Cl)c2Cl)c(N)n1]

6-Chloro-3-((2-(2-(2-methoxyethoxy)ethoxy)ethoxy) amino)-1,2,4-triazin-5-amine (260 mg, 0.845 mmol) and (2,3-dichlorophenyl)boronic acid (242 mg, 1.267 mmol) were dissolved in 10 mL of 1,4-dioxane. Pd(PPh$_3$)$_4$ (78 mg, 0.068 mmol), K$_2$HPO$_4$ (294 mg, 1.690 mmol) and 3 ml of DI water were added to the above reaction mixture and degassed for 15 minutes. Then the reaction mixture was stirred at 90° C. for 8 h. Crude after evaporation of the solvent upon purification by flash chromatography yielded 6-(2,3-dichlorophenyl)-3-((2-(2-(2-methoxyethoxy)ethoxy) ethoxy)amino)-1,2,4-triazin-5-amine (compound 166) as off white solid (60 mg, 16.98% yield). $^1$H NMR (500 MHz, DMSO-d$_6$): δ 7.70-7.80 (d, 1H), 7.40-7.50 (t, 1H), 7.30-7.40 (d, 1H), 6.45-7.10 (bs 2H), 6.35-6.45 (s, 1H), 3.96-4.06 (t, 2H), 3.65-3.70 (t, 2H), 3.55-3.60 (m, 2H), 3.49-3.55 (m, 4H), 3.42-3.47 (m, 2H), 3.23-3.26 (s, 3H); MS (ESI) for C$_{16}$H$_{21}$Cl$_2$N$_5$O$_4$: 418.2750 (MH$^+$). The free base was dissolved in 4M hydrochloride in 2-propanol. The mixture was concentrated under vacuum to afford product as hydrochloride salt.

Example 112

Preparation of Compound 167

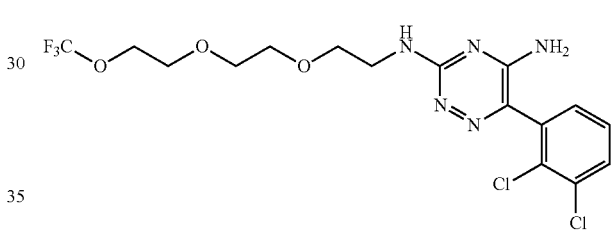

6-(2,3-Dichlorophenyl)-N$^3$-(2-(2-(2-(trifluoromethoxy)ethoxy)ethoxy)ethyl)-1,2,4-triazine-3,5-diamine (Compound 167)

6-(2,3-dichlorophenyl)-N$^3$-(2-(2-(2-(trifluoromethoxy) ethoxy)ethoxy)ethyl)-1,2,4-triazine-3,5-diamine (Compound 167) was prepared according to the following steps.

Step 1: Preparation of 6-chloro-N$^3$-(2-(2-(2-(trifluoromethoxy)ethoxy)ethoxy)ethyl)-1,2,4-triazine-3,5-diamine

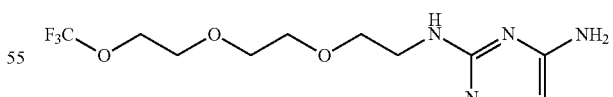

3,6-Dichloro-1,2,4-triazin-5-amine (54.3 mg, 3.29 mmol) and 2-(2-(2-(trifluoromethoxy)ethoxy)ethoxy)ethanamine (1000 mg, 4.60 mmol) were dissolved in 10 mL of 1,4-dioxane. Reaction mixture was then charged with sodium bicarbonate (414 mg, 4.93 mmol) and stirred at 90° C. for 10 h. Reaction mixture was filtered to remove salt and evaporation of the solvent under vacuum gave crude product. Purification of the crude product by column chromatography yielded 6-chloro-N³-(2-(2-(2-(trifluoromethoxy)ethoxy)ethoxy)ethyl)-1,2,4-triazine-3,5-diamine (960 mg, 86% yield).

Step 2: Preparation of 6-(3,4-dichlorophenyl)-N³-(2-(2-(2-(trifluoromethoxy)ethoxy)ethoxy)ethyl)-1,2,4-triazine-3,5-diamine (Compound 167)

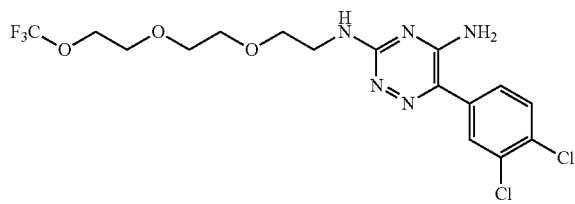 [SMILES: Nc1nc(NCCOCCOCCOC(F)(F)F)nnc1-c1ccc(Cl)c(Cl)c1]

6-chloro-N³-(2-(2-(2-(trifluoromethoxy)ethoxy)ethoxy)ethyl)-1,2,4-triazine-3,5-diamine (960 mg, 2.78 mmol) and (2,3-dichlorophenyl)boronic acid (901 mg, 4.72 mmol) were dissolved in 16 mL of 1,4-dioxane. Pd(PPh$_3$)$_4$ (321 mg, 0.278 mmol), K$_2$HPO$_4$ (1064 mg, 6.11 mmol) and 4 ml of DI water were added to the above reaction mixture and de gassed for 15 minutes. Then reaction mixture is stirred at 90° C. for 8 h. Crude after evaporation of the solvent upon purification by flash chromatography yielded 6-(3,4-dichlorophenyl)-N³-(2-(2-(2-(trifluoromethoxy)ethoxy)ethoxy)ethyl)-1,2,4-triazine-3,5-diamine (compound 167) as off white solid (90 mg, 7.11% yield). $^1$H NMR (500 MHz, DMSO): δ 7.65-7.72 (dd, 1H), 7.40-7.45 (t, 1H), 7.35-7.40 (d, 1H), 4.15-4.20 (m, 2H), 3.65-3.70 (m, 2H), 3.50-3.60 (m, 6H), 3.28-3.40 (m, 2H), 3.20-3.30 (m, 2H); MS (ESI) for C$_{16}$H$_{18}$Cl$_2$F$_3$N$_5$O$_3$: 456.07 (MH$^+$). The free base was dissolved in 4M hydrochloride in 2-propanol. The mixture was concentrated under vacuum to afford product as hydrochloride salt.

Example 113

Preparation of Compound 116

Preparation of 6-(2,3-dichlorophenyl)-N3-(2-morpholinoethyl)-1,2,4-triazine-3,5-diamine (Compound 116)

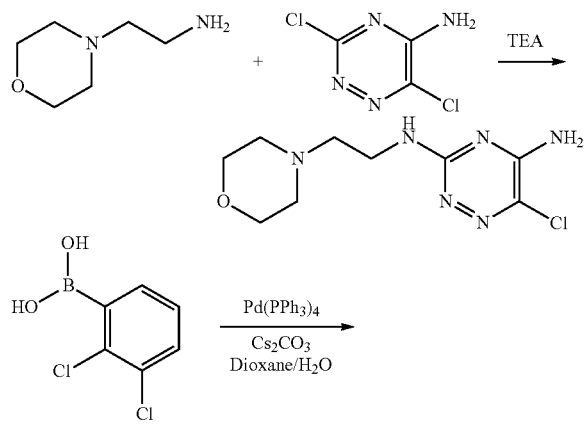

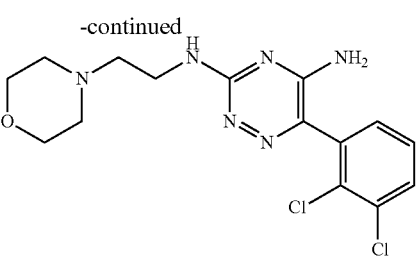

Preparation of 6-chloro-N3-(2-morpholinoethyl)-1,2,4-triazine-3,5-diamine: 5-Amino-3,6-dichloro-1,2,4-triazine (165 mg, 1.00 mmol) was dissolved in dioxane (10 mL) at room temperature. Et$_3$N (0.307 mL, 2.20 mmol) was added, followed by addition of 2-morpholinoethanamine (0.196 mL, 1.49 mmol). The resulting mixture was stirred at 95° C. for 4 hours. The reaction mixture was stirred at 95° C. for overnight. After cooling to ambient temperature, insoluble was filtrated and washed with 10 mL of ethyl acetate. Filtrate was concentrated at 50° C. with reduced pressure. Residue was mixed with 100 mL of DCM and stirred for 10 minutes. Insoluble was collected through filtration and washed with DCM (10 mL×2). The precipitate was dried in vacuum for overnight to give the desired product 111 mg (36% yield). LC-MS (ESI, MH$^+$) 259

Preparation of 6-(2,3-dichlorophenyl)-N3-(2-morpholinoethyl)-1,2,4-triazine-3,5-diamine: (2,3-dichlorophenyl)boronic acid (387.2 mg, 2.03 mmol), 6-chloro-N3-(2-morpholinoethyl)-1,2,4-triazine-3,5-diamine (350 mg, 1.35 mmol), cesium carbonate (882 mg, 2.71 mmol) were dissolved in 35 mL degassed dioxane/H$_2$O (3:1) and tetrakis (triphenylphosphine)palladium (392 mg, 0.338 mmol) was added under nitrogen atmosphere. The reaction mixture was stirred at 85° C. for 1 hour to completion. After cooling to ambient temperature, the solvent was evaporated to dryness. Residue was mixed with 60 mL of deionized water, pH was adjusted to 1.5 with 1.0 N HCl. Insoluble was dissolved in 20 mL of DCM for wash. Aqueous solution was washed with more DCM (20 mL×2). The pH of aqueous was adjusted to 9.5-10.0 with K$_2$CO$_3$. Insoluble was dissolved in 20 mL of DCM for extraction. Aqueous was extracted with more DCM (20 mL×3). Combined DCM extract was washed with 20 mL of saturated NaCl, dried with MgSO$_4$, filtered, and solvent was evaporated to dryness. The residue was purified on silica gel column to give the desired product 233 mg (22%). RP-HPLC (betasil C18, 0.5 mL/min, 10-100% ACN in 10 min) 4.50 min (with purity 99.8%); LC-MS (ESI, MH$^+$, free base) 369; $^1$H NMR (500 MHz, CDCl$_3$) δ 2.59-2.72 (6H, m), 3.61 (2H, br), 3.77-3.79 (4H, t), 4.84 (2H, br), 5.57-6.21 (1H, br), 7.36-7.40 (2H, m), 7.58-7.61 (1H, m).

Example 114

Preparation of Compound 168

Preparation of 6-(2,3-dichlorophenyl)-N3-(2-(2-(diethylamino)ethoxy)ethyl)-1,2,4-triazine-3,5-diamine (Compound 168)

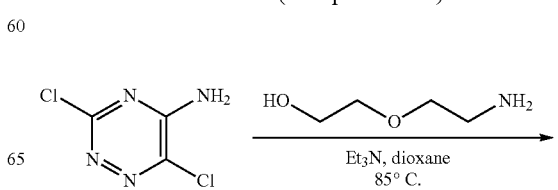

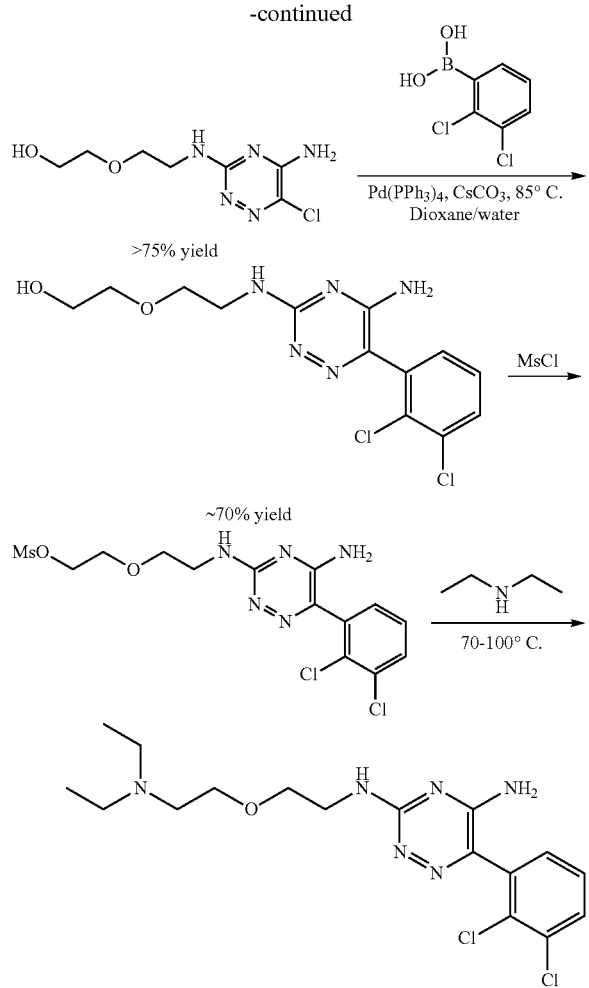

Preparation of 2-(2-((5-amino-6-chloro-1,2,4-triazin-3-yl)amino)ethoxy)ethanol: 3,6-dichloro-1,2,4-triazin-5-amine (510 mg, 3.09 mmol) was dissolved in dioxane (27 mL) at room temperature. Et₃N (646 µL, 4.64 mmol) was added, following by addition of 2-(2-aminoethoxy)ethanol (616 µL, 6.18 mmol). The resulting mixture was heated in oil-bath to 85° C. (external) and the reaction was kept at this temperature for 18 hrs. After cool down to room temperature, the upper clear solution was decanted to another round bottle flask. The remaining brownish oil was washed with small amount of dioxane and decanted one more time. The combined dioxane solution was evaporated to dryness and the residue was mixed in DCM. The product precipitation was obtained in DCM after the solution was set in refrigerator at 0° C. for 2 hrs. Insoluble solid product was collected through filtration and the product was carefully washed with DCM×2. A solid product was then obtained after high vacuo drying.

The DCM solution obtained from wash was combined with the above brownish residue and evaporated to dryness. The residue was dissolved in MeOH and transferred to Biotage samplet. The purification on silicone gel column was using a program 2-10% of MeOH/DCM in 20 CV. The product fractions were identified with TLC, hplc, and confirmed by LC-MS before product fractions were combined together. Rotary evaporate the solvent and high vacuo to give the product (600 mg, 83% yield). UPLC (Agilent extended C-18, 0.5 mL/min, 10-100% ACN in 5 min) 0.90 min; LC-MS (ESI, MH⁺) 234.0+235.0 (~35%); ¹H NMR (500 MHz, CDCl₃) δ 3.61-3.66 (4H, m), 3.68-3.74 (2H, m), 3.77-3.80 (2H, m), 5.47 (1H, bs), 5.77 (1H, bs).

Preparation of 2-(2-((5-amino-6-(2,3-dichlorophenyl)-1,2,4-triazin-3-yl)amino)ethoxy)ethanol: 2-(2-((5-amino-6-chloro-1,2,4-triazin-3-yl)amino)ethoxy)ethanol (196 mg, 0.837 mmol), 2,3-dichlorophenylboronic acid (200 mg, 1.05 mmol), cesium carbonate (496 mg, 1.51 mmol) were dissolved in a dioxane/water (3/1) mixture solution (20 mL). The solution was bubbled with N₂ gas for 3 min before Pd(PPh₃)₄ (203 mg, 0.176 mmol) was added and N₂ bubbling another 2 min before the reaction was heated up to 85° C. The reaction was monitored with HPLC and LC-MS to confirm the completeness in 2-3 hrs. The dioxane was then removed via rotary evaporation. The residue was dissolved in MeOH and loaded on Biotage samplet directly. The silicone gel column purification was using a program 2-10% MeOH/DCM in 20 CV. The product was well separated from other components and the fractions were confirmed with TLC, hplc, and LC-MS before the fractions were combined. A heavily oil-like product (152 mg, 53% yield) was obtained after high vauco drying. UPLC (Agilent extended C-18, 0.5 mL/min, 10-100% ACN in 5 min) 4.76 min; LC-MS (ESI, MH⁺) 344.0+346.0 (~70%); ¹H NMR (500 MHz, CDCl₃) δ 3.65-3.66 (2H, m), 3.74-3.79 (6H, m), 7.34-7.39 (2H, m), 7.58-7.60 (1H, m).

Preparation of 2-(2-((5-amino-6-(2,3-dichlorophenyl)-1,2,4-triazin-3-yl)amino)ethoxy)ethyl methanesulfonate: 2-(2-((5-amino-6-(2,3-dichlorophenyl)-1,2,4-triazin-3-yl)amino)ethoxy)ethanol (39.4 mg, 114 mmol) was dissolved in dioxane (2 mL) at ambient temperature with reaction concentration at about 0.05 M. MsCl (9.75 uL, 126 mmol) was added in one portion. With stirring, TEA (19 uL, 137 mmol) was dissolved in dioxane (1-2 mL) in a test tube and was added to the above mixture solution dropwise. After addition, the reaction was kept at room temperature for 30 min and hplc shows the completeness. If the starting material is remaining more than 5%, additional MsCl (based on the amount of remaining alcohol) and same equivalent of TEA were added to complete the reaction. Work up: The reaction was quenched by adding MeOH and mixture solution was evaporated to dryness. The residue was dissolved in NaHCO₃ and extracted with DCM×3 times. Aqueous phase was checked with LC-MS to confirm the completeness of extraction. The combined DCM solution was dried over Na₂SO₄ and after filtration; it was concentrated under reduced pressure. The residue was loaded on Biotage column and purified with 2-7% MeOH/DCM in 20 CV. The UV signal shows the product peak and a few more fractions as a tail. TLC and hplc confirmed the product before combine together and rotary evaporation to give a colorless solid product. High vacuo to give product (48 mg, 100% yield) and the final product was protected in N₂ and stored in refrigerator (or low temperature). UPLC (Agilent extended C-18, 0.5 mL/min, 10-100% ACN in 5 min) 5.40 min; LC-MS (ESI, MH⁺) 422.0+424.0 (65%); ¹H NMR (500 MHz, CDCl₃) δ 3.06 (3H, s), 3.70-3.74 (4H, m), 3.78-3.79 (2H, m), 4.36-4.38 (2H, m), 6.40 (1H, bs), 7.33-7.38 (2H, m), 7.56-7.58 (1H, m).

Preparation of 6-(2,3-dichlorophenyl)-N3-(2-(2-(diethylamino)ethoxy)ethyl)-1,2,4-triazine-3,5-diamine: 2-(2-((5-amino-6-(2,3-dichlorophenyl)-1,2,4-triazin-3-yl)amino)ethoxy)ethyl methanesulfonate (236 mg, 0.559 mmol) was dissolved in dioxane (10 mL). Diethyl amine (289 μL, 2.79 mmol) was added. The reaction was set up at 70° C. for 2 hrs before it heated to 100° C. for overnight. The conversion is about 44%. Another 289 uL of diethyl amine was added to continue the reaction for 60 hrs. The reaction was stopped by evaporate the solvent to dryness. The residue was dissolved in 10 mL 1N HCl and 10 mL Water with DCM extraction 10 mL×3. The combined DCM phase was evaporated and residue was purified on silica gel column to give the product 130 mg (58.3%) yield. RP-HPLC (betasil C18, 0.5 mL/min, 10-100% ACN in 10 min) 4.40 min (with purity 99.1%); LC-MS (ESI, MH+, free base) 399; $^1$H NMR (500 MHz, CDCl$_3$) δ 1.00-1.03 (6H, t), 2.55-2.60 (4H, q) 2.64-2.67 (2H, t), 3.57-3.60 (2H, t), 3.67 (4H, br), 5.14 (2H, br), 6.32 (1H, br), 7.31-7.37 (2H, m), 7.55-7.57 (1H, m).

Example 115

Preparation of Compound 169

Preparation of 6-(2,3-dichlorophenyl)-N3-(2-(2-(4-methylpiperazin-1-yl)ethoxy)ethyl)-1,2,4-triazine-3,5-diamine (Compound 169)

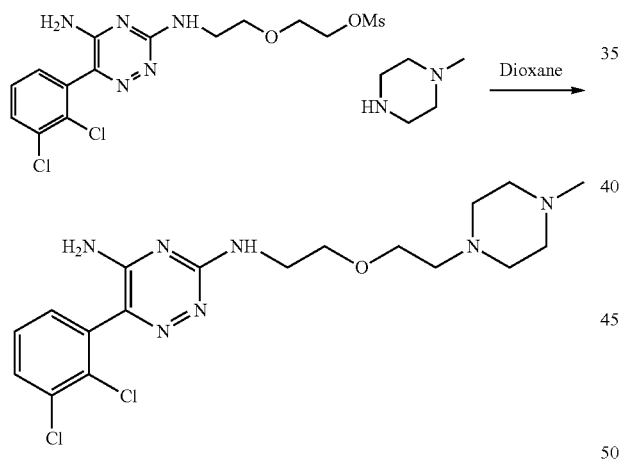

2-(2-((5-amino-6-(2,3-dichlorophenyl)-1,2,4-triazin-3-yl)amino)ethoxy)ethyl methanesulfonate (175 mg, 0.414 mmol) was dissolved in dioxane (8 mL) 1-methylpiperazine (230 μL, 2.07 mmol) was added. The reaction was set up at 100° C. for 16 hrs. The reaction was stopped by evaporate the solvent to dryness. The residue was dissolved in 10 mL 1N HCl and 10 mL water with DCM extraction 10 mL×3. The combined DCM phase was evaporated and residue was purified on silica gel column to give the product 130 mg (58.3%) yield. RP-HPLC (betasil C18, 0.5 mL/min, 10-100% ACN in 10 min) 4.02 min (with purity 96.8%); LC-MS (ESI, MH+, free base) 426; $^1$H NMR (500 MHz, CDCl$_3$) δ 2.27 (3H, s), 2.46-2.60 (10H, t), 3.61-3.64 (2H, t), 3.68 (4H, br), 5.05 (2H, br), 6.34 (1H, br), 7.33-7.39 (2H, m), 7.56-7.59 (1H, m).

Example 116

Preparation of Compound 170

Preparation of N-(2-(2-((5-amino-6-(2,3-dichlorophenyl)-1,2,4-triazin-3-yl)amino)ethoxy)ethyl)methanesulfonamide (Compound 170)

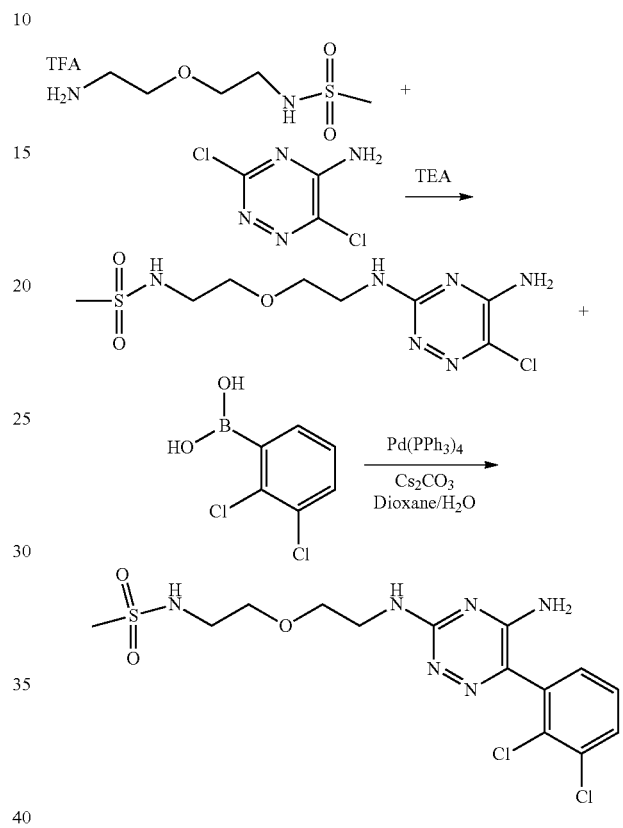

Preparation of N-(2-(2-((5-amino-6-chloro-1,2,4-triazin-3-yl)amino)ethoxy)ethyl)-methanesulfonamide: N-(2-(2-aminoethoxy)ethyl)methanesulfonamide (437 mg, 2.4 mmol) was dissolved in 15 mL of dioxane. TEA (1.67 mL, 12 mmol) and 5-amino-3,6-dichloro-1,2,4-triazine (200 mg, 1.2 mmol). The resulting mixture was stirred at 85° C. for overnight. After cooling to room temperature, the solvent was evaporated to dryness. The residue was purified on silica gel column to give the desired product 176 mg (24% yield).

Preparation of N-(2-(2-((5-amino-6-(2,3-dichlorophenyl)-1,2,4-triazin-3-yl)amino)ethoxy)ethyl)-methanesulfonamide: (2,3-Dichlorophenyl)boronic acid (162 mg, 850 mmol), N-(2-(2-((5-amino-6-chloro-1,2,4-triazin-3-yl)amino)ethoxy)ethyl)methanesulfinamide (176 mg, 566 mmol), cesium carbonate (369 mg, 1.13 mmol) were dissolved in 20 ml degassed diaxane/H$_2$O (3:1) and tetrakis (triphenylphosphine)palladium (164 mg, 142 mmol) was added under nitrogen atmosphere. The reaction mixture was stirred at 85° C. Dioxane 3 mL was added after 15 min at 85° C. A sample was checked by LC-MS after 2 hours reaction. Solvent was evaporated to dryness at 50° C., reduced pressure. Residue was dried in high vacuum for 2 hours. Residue was mixed with DCM/MeOH and loaded on 25 samplet, dried in vacuum for overnight. Silica gel column purification gives the desired product 165 mg (69.2% yield).

RP-HPLC (betasil C18, 0.5 mL/min, 10-100% ACN in 10 min) 4.72 min (with purity 97.7%); LC-MS (ESI, MH+, free base) 421; $^1$H NMR (500 MHz, CDCl$_3$) δ 3.01 (3H, s), 3.34-3.36 (2H, t), 3.66-3.71 (6H, m), 5.14 (2H, br), 5.57 (1H, br), 6.20-6.27 (1H, br), 7.36-7.40 (2H, m), 7.58-7.61 (1H, m).

Example 117

Preparation of Compound 171 and 172

Preparation of N3-(2-(2-(1H-tetrazol-1-yl)ethoxy) ethyl)-6-(2,3-dichlorophenyl)-1,2,4-triazine-3,5-diamine (Compound 171) and N3-(2-(2-(2H-tetrazol-2-yl)ethoxy)ethyl)-6-(2,3-dichlorophenyl)-1,2,4-triazine-3,5-diamine (Compound 172)

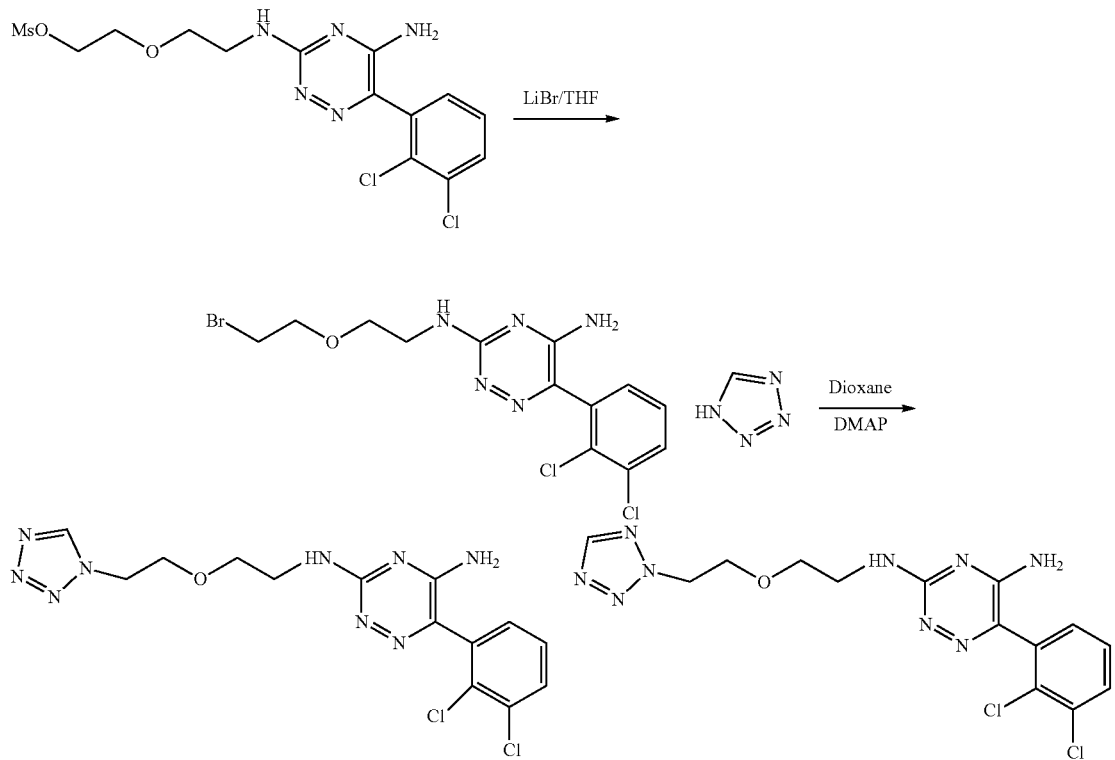

Preparation of N3-(2-(2-bromoethoxy)ethyl)-6-(2,3-dichlorophenyl)-1,2,4-triazine-3,5-diamine: 2-(2-((5-amino-6-(2,3-dichlorophenyl)-1,2,4-triazin-3-yl)amino)ethoxy) ethyl methanesulfonate (1.01 g, 2.37 mmol) was dissolved in 47 mL of THF. Lithium bromide (2.06 g, 23.7 mmol) was added. The reaction mixture was stirred at 60° C. for 2 hours. A sample was checked by LC-MS. The reaction was stopped after 3 hours at 60° C. After cooling to ambient temperature, the insoluble was filtered, washed with DCM, and the solvent was evaporated to dryness at reduced pressure. Residue was dissolved in 200 mL of DCM, washed with sat NaHCO$_3$ (2×30 ml). DCM layer was dried with MgSO$_4$, filtered and solvent was evaporated to dryness. Residue was dissolved in methanol and purified on silica gel column to give the desired product 608 mg (63.1% yield) after high vauco.

N3-(2-(2-bromoethoxy)ethyl)-6-(2,3-dichlorophenyl)-1,2,4-triazine-3,5-diamine: (300 mg, 0.737 mmol) was dissolved in dioxane (16 mL). 90 mg of DMAP (90 mg, 0.737 mmol) and 9 ml of 1H-tetrazole (51.6 mg, 0.737 mmol) were added. The reaction mixture was stirred at 102° C. under nitrogen atmosphere for 20 hrs. the solvent was evaporated and the residue was purified on silica gel column to give two product N3-(2-(2-(1H-tetrazol-1-yl)ethoxy)ethyl)-6-(2,3-dichlorophenyl)-1,2,4-triazine-3,5-diamine (40 mg, 13.7% yield) and N3-(2-(2-(2H-tetrazol-2-yl)ethoxy)ethyl)-6-(2,3-dichlorophenyl)-1,2,4-triazine-3,5-diamine (51 mg, 17.5% yield). RP-HPLC (betasil C18, 0.5 mL/min, 10-100% ACN in 10 min) 4.97 min (with purity 97.6%); LC-MS (ESI, MH+) 396; $^1$H NMR (500 MHz, CDCl$_3$) δ 3.66-3.72 (4H, m), 3.88-3.90 (2H, t), 4.63-4.66 (2H, t), 4.99 (2H, br), 5.93 (1H, br), 7.36-7.40 (2H, m), 7.58-7.80 (1H, m), 8.80 (1H, s); RP-HPLC (betasil C18, 0.5 mL/min, 10-100% ACN in 10 min) 4.95 min (with purity 99.6%); LC-MS (ESI, MH+) 396; $^1$H NMR (500 MHz, CDCl$_3$) δ 3.63-3.70 (4H, m), 4.05-4.08 (2H, t), 4.83-4.86 (2H, t), 5.10 (2H, br), 5.86 (1H, br), 7.32-7.39 (2H, m), 7.56-7.58 (1H, m), 8.52 (1H, s)

Example 118

Preparation of Compound 173

Preparation of 6-(2,3-dichlorophenyl)-N3-(2-(2-((2-methoxyethyl)amino)ethoxy)ethyl)-1,2,4-triazine-3,5-diamine (Compound 173)

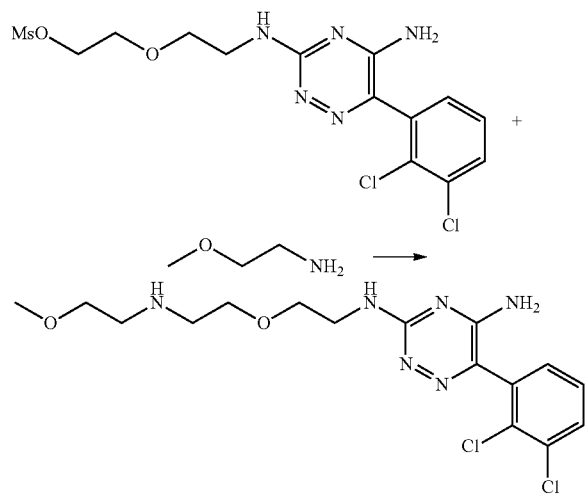

2-(2-((5-amino-6-(2,3-dichlorophenyl)-1,2,4-triazin-3-yl)amino)ethoxy)ethyl methanesulfonate (358 mg, 0.848 mmol) was mixed with 0.75 ml of 2-methoxyethanamine (737 µL, 8.48 mmol). The mixture was stirred at 80° C. under nitrogen atmosphere for overnight. Solvent was evaporated to dryness at reduced pressure. The residue was purified on silica gel column to give the product (110 mg, 32.3% yield). RP-HPLC (betasil C18, 0.5 mL/min, 10-100% ACN in 10 min) 4.53 min (with purity 95.7%); LC-MS (ESI, MH$^+$) 401; $^1$H NMR (500 MHz, CDCl$_3$) δ 2.83-2.88 (4H, m), 3.31 (3H, s), 3.50-3.53 (2H, t), 3.63-3.70 (6H, m), 5.02 (2H, br), 6.16 (1H, br), 7.35-7.39 (2H, m), 7.57-7.60 (1H, m).

Example 119

Preparation of Compound 174 and 175

Preparation of N3-(2-(2-aminoethoxy)ethyl)-6-(2,3-dichlorophenyl)-1,2,4-triazine-3,5-diamine (Compound 174) and N-(2-(2-((5-amino-6-(2,3-dichlorophenyl)-1,2,4-triazin-3-yl)amino)ethoxy)ethyl) acetamide (Compound 175)

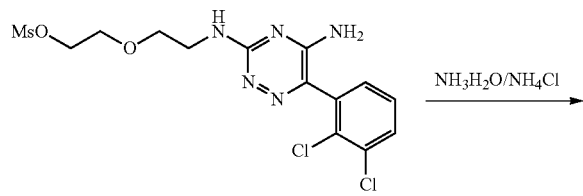

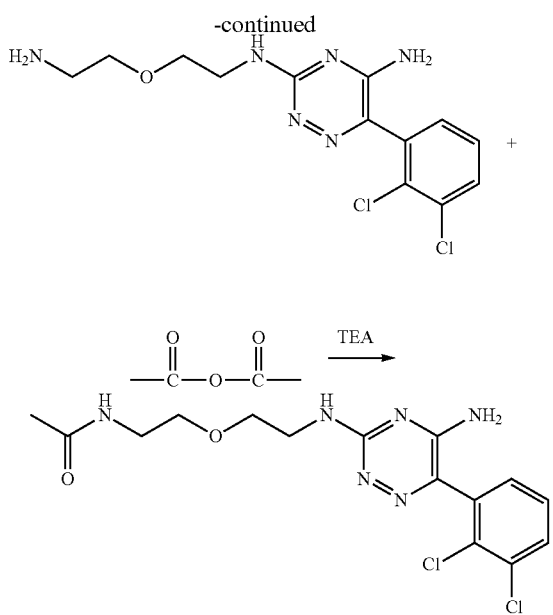

Preparation of N3-(2-(2-aminoethoxy)ethyl)-6-(2,3-dichlorophenyl)-1,2,4-triazine-3,5-diamine: 2-(2-((5-amino-6-(2,3-dichlorophenyl)-1,2,4-triazin-3-yl)amino)ethoxy) ethyl methanesulfonate (300 mg, 710 mmol) was mixed with 10 mL of ACN, 10 mL of ethanol, and 30 ml of MH$_3$H$_2$O, containing 3 g of NH$_4$Cl. The reaction mixture was stirred at ambient temperature for 48 hours. Solvent was evaporated to dryness at reduced pressure. Residue was mixed with 100 mL of ethanol and filtered. Combined ethanol was evaporated to dryness at reduced pressure. The product from residue was extracted with DCM (50 ml×2). Combined DCM was dried over with MgSO$_4$, filtered, and solvent was evaporated to dryness. Residue was dried in high vacuum for overnight to give a product (56 mg, 23% yield). RP-HPLC (betasil C18, 0.5 mL/min, 10-100% ACN in 10 min) 4.33 min (with purity 92.5%); LC-MS (ESI, MH$^+$) 343; $^1$H NMR (500 MHz, DMSO-d$_6$+D$_2$) δ 3.01 (2H, br), 3.58-3.65 (4H, m), 7.53-7.56 (2H, m), 7.84-7.87 (1H, m). The product was dissolved in 2 mL of 1.0 N HCl. Insoluble was filtered and filtrate was lyophilized for overnight to give the product hydrochloride salt.

Preparation of N-(2-(2-((5-amino-6-(2,3-dichlorophenyl)-1,2,4-triazin-3-yl)amino)ethoxy)ethyl)acetamide: N3-(2-(2-aminoethoxy)ethyl)-6-(2,3-dichlorophenyl)-1,2,4-triazine-3,5-diamine: (42 mg, 122 mmol) was dissolved in dioxane (5 mL), TEA (34.1 µL, 245 mmol) was added. Acetic anhydride (12.1 µL, 128 mmol) was added. The reaction solution was stirred at ambient temperature for 15 min. A sample was checked by LC-MS, showed the reaction was over. 20 µl of BuNH$_2$ was added to quench the excess of acetic anhydride. Solvent was evaporated to dryness at reduced pressure. Residue was purified on silica gel column to give the product (34 mg, 72.1% yield). RP-HPLC (betasil C18, 0.5 mL/min, 10-100% ACN in 10 min) 4.72 min (with purity 98.0%); LC-MS (ESI, MH$^+$) 385; $^1$H NMR (500 MHz, CDCl$_3$) δ 2.04 (3H, s), 2.10 (1H, s), 3.47-50 (2H, m), 3.58-3.61 (2H, t), 3.68 (4H, br), 5.10 (2H, br), 6.61 (1H, br), 7.30-7.39 (2H, m), 7.60-7.63 (1H, m).

Example 120

Preparation of Compound 176

Preparation of 6-(2,3-dichlorophenyl)-N3-(2-(2-(methylsulfonyl)ethoxy)ethyl)-1,2,4-triazine-3,5-diamine (Compound 176)

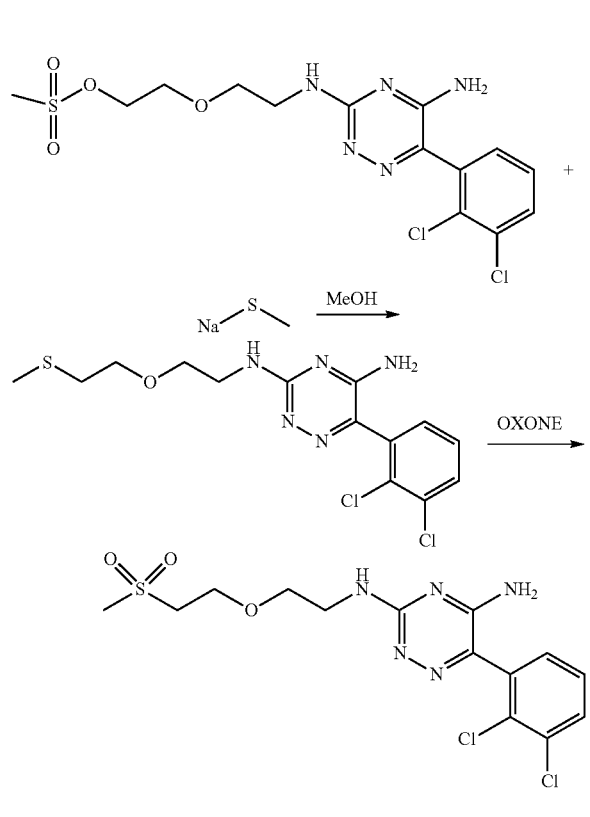

Preparation of 6-(2,3-dichlorophenyl)-N3-(2-(2-(methylthio)ethoxy)ethyl)-1,2,4-triazine-3,5-diamine: 2-(2-((5-Amino-6-(2,3-dichlorophenyl)-1,2,4-triazin-3-yl)amino)ethoxy)ethyl methanesulfonate (200 mg, 0.474 mmol) and sodium methanethiolate (100 mg, 1.42 mmol) were mixed in methanol (20 mL) and stirred at ambient temperature. The reaction solution was concentrated and the residue was subject to flash chromatography to give a product 72 mg (75% pure, 25% fragment). LC-MS [ESI-MH$^+$]: m/z 373.

Preparation of 6-(2,3-dichlorophenyl)-N3-(2-(2-(methylsulfonyl)ethoxy)ethyl)-1,2,4-triazine-3,5-diamine: The methylsulfide starting material (40 mg, 0.107 mmol, 75% purity) was dissolved in MeOH (4 mL). A solution of oxone in water (2 mL) was added to the above solution at 0° C. to form a suspension. The mixture was stirred at ambient temperature for overnight. 30% of sulfoxide and 70% sulfone were generated. Additional 20 mg of oxone was added. After 3 hrs, reaction was completed. The residue was subjected to reversed-phase chromatography. Desired fractions were collected and concentrated. Final water solution was lyophilized to dryness to give a product as white foaming powder (48 mg, 99% purity, 84% yield). LC-MS [ESI-MH$^+$]: m/z 406. $^1$H-NMR (DMSO-d$_6$) δ ppm: 3.063 (s, 3H), 3.351 (d, J=5.0 Hz, 2H), 3.676-3.751 (m, 4H), 3.981 (d, 2H), 6.372 (s, 1H), 7.355 (d, J=6.5 Hz, 1H), 7.442 (dd, J$_1$=8.0 Hz, J$_2$=7.5 Hz, 1H), 7.700 (d, J=6.5 Hz, 1H).

Example 121

Preparation of Compound 177

Preparation of 6-(2,3-dichlorophenyl)-N3-(3-(2-(2-methoxyethoxy)ethoxy)-2-methylpropyl)-1,2,4-triazine-3,5-diamine (Compound 177)

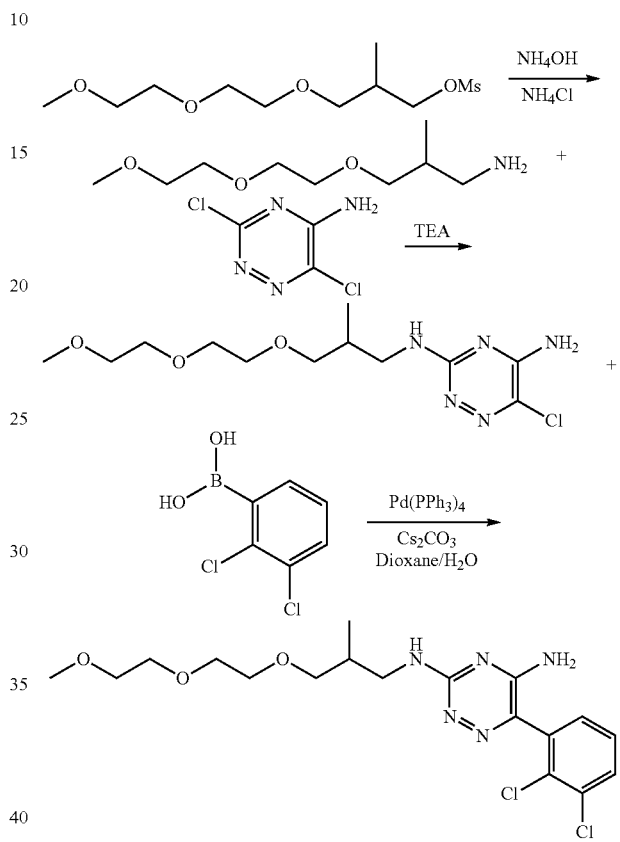

Preparation of 3-(2-(2-methoxyethoxy)ethoxy)-2-methylpropan-1-amine: 3-(2-(2-methoxyethoxy)ethoxy)-2-methylpropyl methanesulfonate (500 mg, 1.85 mmol) was mixed with 10 ml of ethanol, 50 ml of NH$_4$OH (containing 10% of NH$_4$Cl). The mixture was stirred at ambient temperature for 2 days. Solid NaCl was added to 15%. Desired product was extracted with DCM (30 ml×5). Combined DCM was dried with MgSO$_4$, filtered, and solvent was evaporated to dryness. Residue was dried in vacuum for overnight to give the product mixture 424 mg (>100% yield).

Preparation of 6-chloro-N3-(3-(2-(2-methoxyethoxy)ethoxy)-2-methylpropyl)-1,2,4-triazine-3,5-diamine: 3-(2-(2-methoxyethoxy)ethoxy)-2-methylpropan-1-amine (132 mg, 690 mmo) and 5-Amino-3,6-dichloro-1,2,4-triazine (114 mg, 0.69 mmol) were dissolved in dioxane (15 mL) at room temperature. Et$_3$N (0.192 mL, 1.38 mmol) was added. The resulting mixture was stirred at 95° C. under nitrogen atmosphere for overnight. After cooling to room temperature, the solvent was evaporated to dryness. The residue was purified on silica gel column to give the product 104 mg (47.1 yield).

Preparation of 6-(2,3-dichlorophenyl)-N3-(3-(2-(2-methoxyethoxy)ethoxy)-2-methylpropyl)-1,2,4-triazine-3,5-diamine: (2,3-dichlorophenyl)boronic acid (93 mg, 0.488 mmol), 6-chloro-N3-(3-(2-(2-methoxyethoxy)ethoxy)-2- methylpropyl)-1,2,4-triazine-3,5-diamine (104 mg, 0.325 mmol), cesium carbonate (212 mg, 0.650 mmol) were dissolved in 20 mL degassed diaxane/H2O (3:1) and tetrakis (triphenylphosphine)palladium (94 mg, 0.081 mmol) was added under nitrogen atmosphere. The reaction mixture was stirred at 85° C. Solvent was evaporated to dryness at 50° C., reduced pressure. Residue was purified on silica gel column to give the product 55 mg (39.3% yield). RP-HPLC (betasil C18, 0.5 mL/min, 10-100% ACN in 10 min) 6.02 min (with purity 96.3%); LC-MS (ESI, MH$^+$) 430; $^1$H NMR (500 MHz, CDCl$_3$) δ 1.00-1.03 (3H, d), 2.12 (1H, br), 3.34 (4H, br), 3.48-3.70 (8H, m), 3.71-3.74 (4H, m), 5.10 (2H, br), 6.61 (1H, br), 7.30-7.39 (2H, m), 7.60-7.62 (1H, m).

Example 122

Preparation of Compound 178

Preparation of 2-((2-(2-((5-amino-6-(2,3-dichlorophenyl)-1,2,4-triazin-3-yl)amino)ethoxy)ethyl)amino)acetic acid (Compound 178)

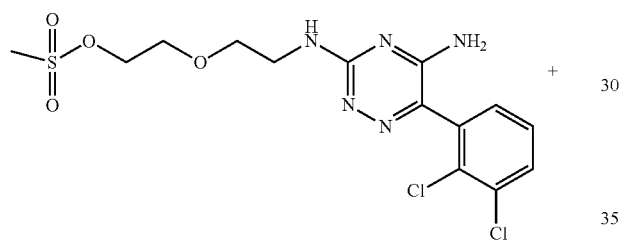

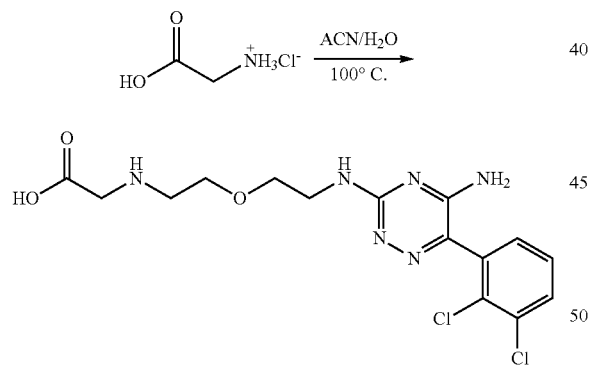

2-(2-((5-Amino-6-(2,3-dichlorophenyl)-1,2,4-triazin-3-yl)amino)ethoxy)ethyl methanesulfonate (100 mg, 0.237 mmol), glycine (356 mg, 4.74 mmol), and NaHCO3 (60 mg, 710 mmol) were dissolved in a 6 mL acetonitrile/water (1:1) solution. The mixture was heated over 100° C. in an oil bath for 2 days. After concentration, the product was purified on C18 column to yield product as white solid (36 mg, 96% purity, 37.9% yield). LC-MS [ESI-MH$^+$]: m/z 400. $^1$H NMR (DMSO-d$_6$) δ ppm: 7.698 (d, J=5.5 Hz, 1H), 7.441 (t, J=8 Hz, 1H), 7.352 (d, J=8 Hz, 1H), 7.20-6.35 (b, 2H), 4.640 (t, J=6.0 Hz, 1H), 4.534 (quintet, J$_1$=11 Hz, J$_2$=5.5 Hz, J$_3$=5.5 Hz, 1H), 4.396 (dd, J$_1$=5.5 Hz, J$_2$=6.5 Hz, 1H), 3.540-3.440 (m, 12H).

Example 123

Preparation of Compound 179

Preparation of (S)-2-((2-(2-((5-amino-6-(2,3-dichlorophenyl)-1,2,4-triazin-3-yl)amino)ethoxy)ethyl)amino)-3-methylbutanoic acid (Compound 179)

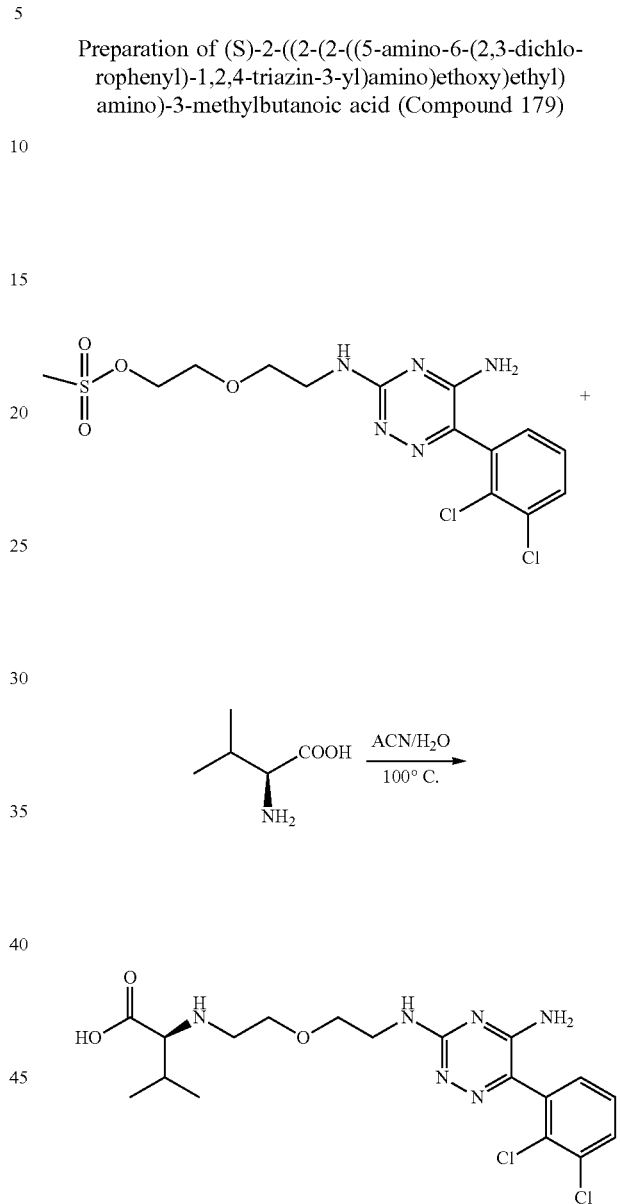

2-(2-((5-Amino-6-(2,3-dichlorophenyl)-1,2,4-triazin-3-yl)amino)ethoxy)ethyl methanesulfonate (100 mg, 0.059 mmol), L-valine (555 mg, 1.184 mmol) and sodium bicarbonate (60 mg, 0.178 mmol) were added into a mixture solvent of acetonitrile (5 mL) and deionized water (5 mL). The mixture was heated over 100° C. for overnight. Solvent was removed under reduced pressure. Residue was subjected to reversed phase purification to yield product as white solid (31 mg, 97% purity, 29.5% yield). LC-MS [ESI-MH$^+$]: m/z 443. $^1$H-NMR (DMSO-d$_6$) δ ppm: 7.689 (d, J=1.5 Hz, 1H), 7.437 (t, J=8 Hz, 1H), 7.357 (dd, J$_1$=1.5 Hz, J$_2$=7.5 Hz, 1H), 7.20-6.35 (b, 2H), 4.100-4.200 (b, 2H), 3.522-3.428 (m, 6H), 2.781 (t, J=6.0 Hz, 1H), 1.849 (m, 1H), 1.776 (s, 1H), 0.853 (d, J=7.0 Hz, 1H), 0.802 (d, J=6.5 Hz, 1H).

Example 124

Preparation of Compound 180

Preparation of 6-(2,3-dichlorophenyl)-N3-(10-((2-(2-methoxyethoxy)ethoxy)methyl)-2,5,8,11-tetraoxatridecan-13-yl)-1,2,4-triazine-3,5-diamine (Compound 180)

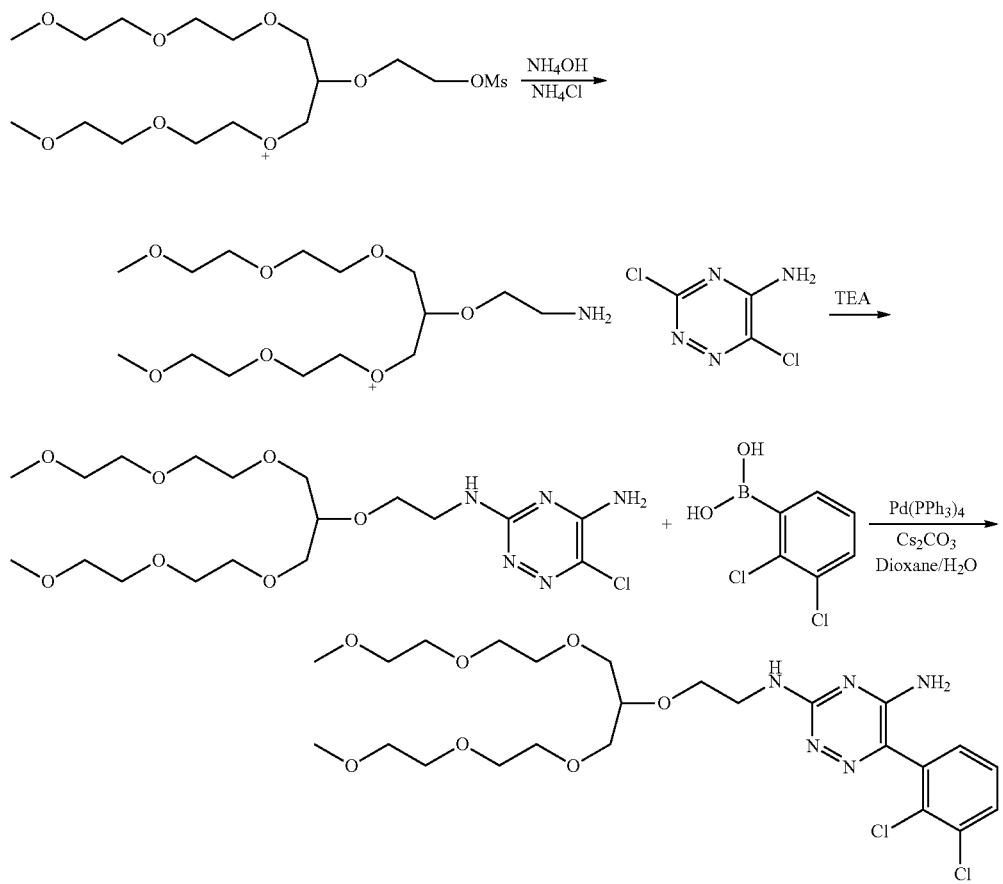

Preparation of 10-((2-(2-methoxyethoxy)ethoxy)methyl)-2,5,8,11-tetraoxatridecan-13-amine: 10-((2-(2-methoxyethoxy)ethoxy)methyl)-2,5,8,11-tetraoxatridecan-13-yl methanesulfonate (500 mg, 1.195 mmol) was mixed with 10 mL of ethanol, 75 mL of NH$_4$OH (containing 10% of NH$_4$Cl). The mixture was stirred at ambient temperature for 2 days. Solid NaCl (about 8 g) was added to solution and the desired product was extracted with DCM (30 mL×4). Combined DCM extract was dried with MgSO$_4$, filtered, and solvent was evaporated to dryness. Residue was dried in vacuum for overnight to give the product 387 mg (95% yield).

Preparation of 6-chloro-N3-(10-((2-(2-methoxyethoxy)ethoxy)methyl)-2,5,8,11-tetraoxatridecan-13-yl)-1,2,4-triazine-3,5-diamine: 10-((2-(2-methoxyethoxy)ethoxy)methyl)-2,5,8,11-tetraoxatridecan-13-amine (387 mg, 1.14 mmol) and 5-Amino-3,6-dichloro-1,2,4-triazine (157 mg, 0.95 mmol) were dissolved in dioxane (20 mL) at room temperature. Et$_3$N (0.265 mL, 1.9 mmol) was added. The resulting mixture was stirred at 95° C. under nitrogen atmosphere for overnight. Solvent was evaporated to dryness. The residue was purified on silica gel column to the product 353 mg (79% yield).

Preparation of 6-(2,3-dichlorophenyl)-N3-(10-((2-(2-methoxyethoxy)ethoxy)methyl)-2,5,8,11-tetraoxatridecan-13-yl)-1,2,4-triazine-3,5-diamine: (2,3-dichlorophenyl)boronic acid (216 mg, 1.132 mmol), 6-chloro-N3-(10-((2-(2-methoxyethoxy)ethoxy)methyl)-2,5,8,11-tetraoxatridecan-13-yl)-1,2,4-triazine-3,5-diamine (353 mg, 0.754 mmol), cesium carbonate (492 mg, 1.51 mmol) were dissolved in 30 mL degassed mixture of diaxane/H$_2$O (3:1) and tetrakis (triphenylphosphine)palladium (218 mg, 0.189 mmol) was added under nitrogen atmosphere. The reaction mixture was stirred at 85° C. for overnight. Solvent was evaporated to dryness at 50° C. under the reduced pressure. Residue was purified on silica gel column to give the product 286 mg (65.5% yield). RP-HPLC (betasil C18, 0.5 mL/min, 10-100% ACN in 10 min) 6.36 min (with purity 95.3%); LC-MS (ESI, MH$^+$) 578; $^1$H NMR (500 MHz, CDCl$_3$) δ 3.36 (6H, s), 3.54-3.80 (22H, m), 3.80 (1H, br), 3.84-3.86 (2H, t), 5.10 (2H, br), 6.61 (1H, br), 7.34-7.39 (2H, m), 7.56-7.60 (1H, m).

Example 125

Preparation of Compound 181

Preparation of 6-(2,3-dichlorophenyl)-N3-(2-(2-(2-(oxetan-3-yloxy)ethoxy)ethoxy)ethyl)-1,2,4-triazine-3,5-diamine (Compound 181)

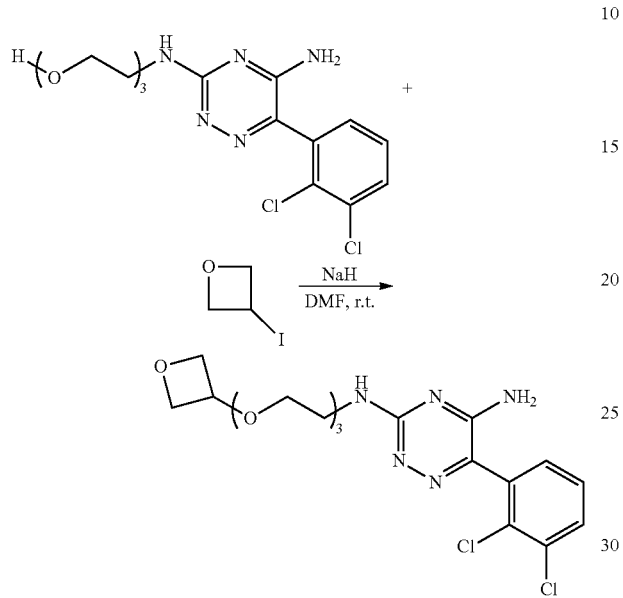

To a solution of 2-(2-(2-((5-amino-6-(2,3-dichlorophenyl)-1,2,4-triazin-3-yl)amino)ethoxy)ethoxy)ethanol (800 mg, 0.506 mmol) in DMF (20 mL) was added 3-iodo-oxetane (298 mg, 1.62 mmol). NaH (810 mg, 60% dispersion in mineral oil, 20.26 mmol) was added to the above solution. The mixture was stirred at ambient temperature for 1 h. Additional 300 mg and 400 mg of NaH (60% dispersion in mineral oil) were added consecutively. After 3 h, 27% conversion was observed. Solid was filtered off and washed with dioxane. Filtrate was concentrated on RotaVap under reduced pressure. The residue was purified on silica gel column to afford 50 mg product (5.6% yield) as light yellow solid (95.5% purity). LC-MS [ESI-MH$^+$]: m/z 444. $^1$H-NMR (DMSO-d$_6$) δ ppm: 7.698 (d, J=5.5 Hz, 1H), 7.441 (t, J=8 Hz, 1H), 7.352 (d, J=8 Hz, 1H), 7.20-6.35 (b, 2H), 4.640 (t, J=6.0 Hz, 1H), 4.534 (quintet, J$_1$=11 Hz, J$_2$=5.5 Hz, J$_3$=5.5 Hz, 1H), 4.396 (dd, J$_1$=5.5 Hz, J$_2$=6.5 Hz, 1H), 3.540-3.440 (m, 12H).

Example 126

Preparation of Compound 182

Preparation of 2-((5-amino-6-(2,3-dichlorophenyl)-1,2,4-triazin-3-yl)amino)propan-1-ol (Compound 182)

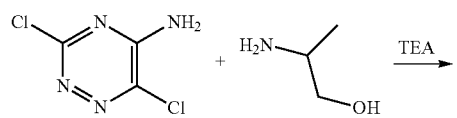

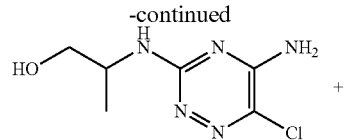

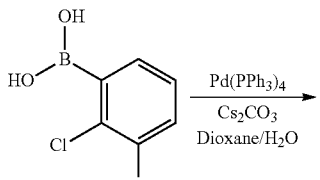

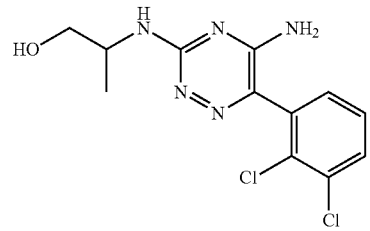

Preparation of 2-((5-amino-6-chloro-1,2,4-triazin-3-yl)amino)propan-1-ol: 5-Amino-3,6-dichloro-1,2,4-triazine (1.5 g, 9.09 mmol) was dissolved in dioxane (60 mL) at room temperature. Et$_3$N (1.9 mL, 13.64 mmol) was added, followed by addition of 2-aminopropan-1-ol (1.37 g, 18.2 mmol). The resulting mixture was stirred at 95° C. for overnight. Solvent was evaporated to dryness at reduced pressure. Residue was purified on silica gel column to give the product 1.93 g (>100% yield).

Preparation of 2-((5-amino-6-(2,3-dichlorophenyl)-1,2,4-triazin-3-yl)amino)propan-1-ol: (2,3-dichlorophenyl)boronic acid (1.93 g, 10.1 mmol), 2-((5-amino-6-chloro-1,2,4-triazin-3-yl)amino)propan-1-ol (1.37 g, 6.73 mmol), cesium carbonate (4.4 g, 13.5 mmol) were dissolved in 150 mL degassed mixture of dioxane/H$_2$O (3:1) and tetrakis(triphenylphosphine)palladium (1.94 g, 1.68 mmol) was added under nitrogen atmosphere. The reaction mixture was stirred at 85° C. for 4 hours. Insoluble was filtered and solvent was evaporated to dryness at 50° C., reduced pressure, residue was dried in vacuum for overnight and purified on silica gel column to give the product 1.54 g (72.9% yield) after high vacuo. RP-HPLC (betasil C18, 0.5 mL/min, 10-100% ACN in 10 min) 6.36 min (with purity 95.3%); LC-MS (ESI, MH$^+$) 578; $^1$H NMR (500 MHz, CDCl$_3$) δ 3.36 (6H, s), 3.54-3.80 (22H, m), 3.80 (1H, br), 3.84-3.86 (2H, t), 5.10 (2H, br), 6.61 (1H, br), 7.34-7.39 (2H, m), 7.56-7.60 (1H, m).

Example 127

Preparation of Compound 183

Preparation of 2-(2-((5-amino-6-(2,3-dichlorophenyl)-1,2,4-triazin-3-yl)amino)ethoxy)ethyl methyl carbonate (Compound 183)

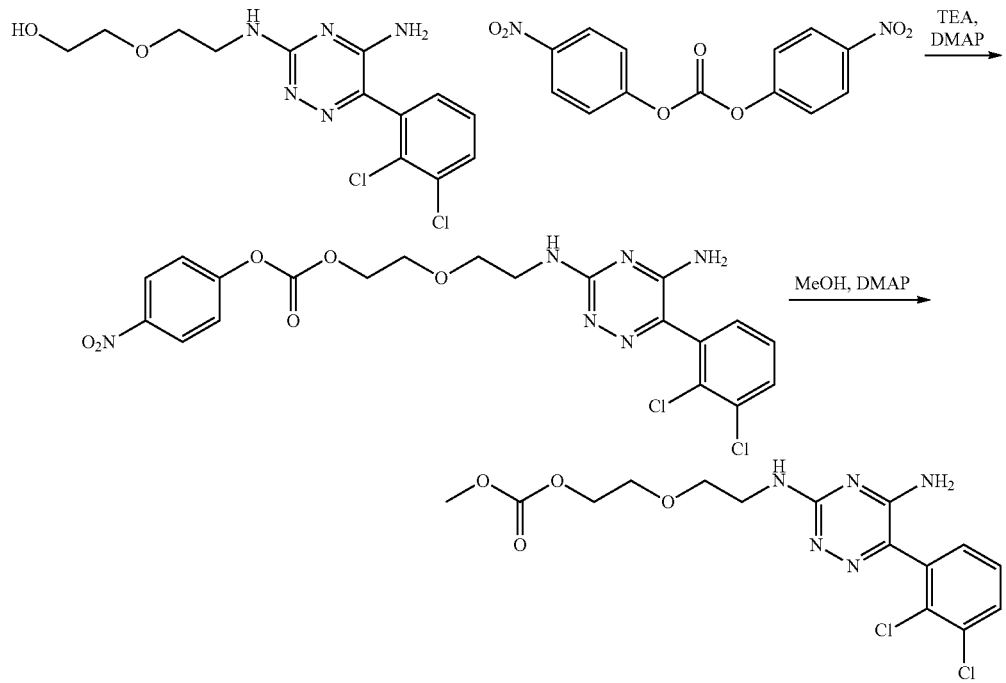

2-(2-((5-Amino-6-(2,3-dichlorophenyl)-1,2,4-triazin-3-yl)amino)ethoxy)ethanol (200 mg, 0.581 mmol), and bis(4-nitrophenyl) carbonate (194 mg, 0.639 mmol), DMAP (7.1 mg, 0.058 mmol), and TEA (50 μL, 360 mmol) were mixed in dioxane (20 mL). Solvent was removed and residue was dried over vacuum overnight, affording sticky yellow residue. The residue was dissolved in 30 mL DCM and washed with 0.1 N monobasic phosphate. DCM phase was dried over $Na_2SO_4$ and solid was filtered off. Concentration gave yellow foaming residue, which was further dried under high vacuo overnight. Yield product as yellow foaming solid (140 mg, 51% purity). The above product mixture (140 mg, 0.137 mmol), methanol (557 μL, 13.74 mmol), and DMAP (16.8 mg, 0.137 mmol) were mixed. The mixture was stirred under $N_2$ atmosphere at ambient temperature. Solvent was removed and the residue was subject to flash chromatography purification to yield product as off-white solid (40 mg, 96.8% purity, 52.5% yield). LC-MS [ESI-MH$^+$]: m/z 402. $^1$H-NMR (DMSO-$d_6$) δ ppm: 3.554 (t, J=4.5 Hz, 2H), 3.565 (s, 2H), 3.637 (t, J=4.5 Hz, 2H), 3.697 (s, 3H), 4.203 (t, J=4.5 Hz, 2H), 7.355 (d, J=6.5 Hz, 1H), 7.442 (dd, $J_1$=8.0 Hz, $J_2$=7.5 Hz, 1H), 7.700 (d, J=6.5 Hz, 1H).

Example 128

Preparation of Compound 184

Preparation of 6-(2,3-dichlorophenyl)-N3-(2-(2-(piperazin-1-yl)ethoxy)ethyl)-1,2,4-triazine-3,5-diamine.3HCl (Compound 184)

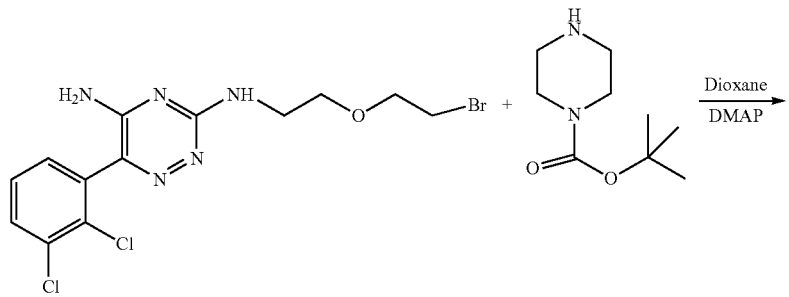

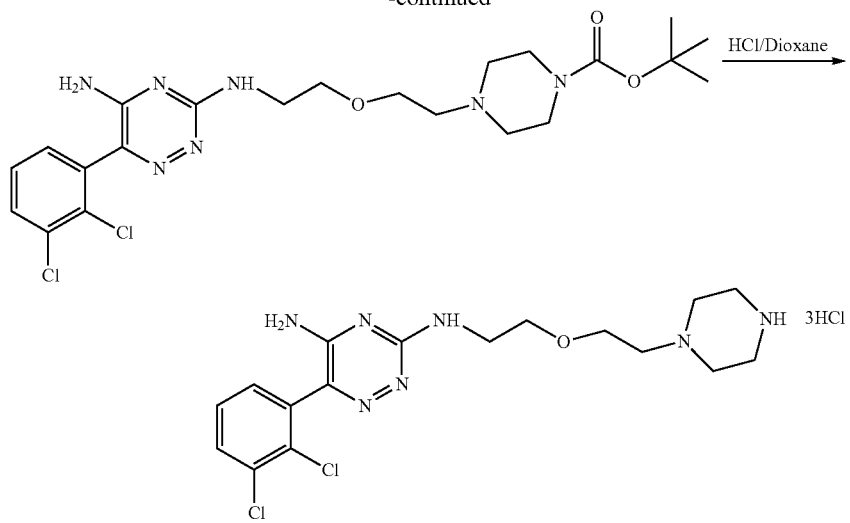

Preparation of tert-butyl 4-(2-(2-((5-amino-6-(2,3-dichlorophenyl)-1,2,4-triazin-3-yl)amino)ethoxy)ethyl)piperazine-1-carboxylate: N3-(2-(2-bromoethoxy)ethyl)-6-(2,3-dichlorophenyl)-1,2,4-triazine-3,5-diamine (50 mg, 123 mmol) was dissolved in 5 mL of dioxane. tert-Butyl piperazine-1-carboxylate (46 mg, 246 mmol) and DMAP (7.50 mg, 0.061 mmol) were added. The reaction mixture was stirred at 95° C. for overnight. The solvent was evaporated to dryness. The residue was purified on silica gel column to give product 38 mg (60.4% yield).

Preparation of 6-(2,3-dichlorophenyl)-N3-(2-(2-(piperazin-1-yl)ethoxy)ethyl)-1,2,4-triazine-3,5-diamine.3HCl: tert-Butyl 4-(2-(2-((5-amino-6-(2,3-dichlorophenyl)-1,2,4-triazin-3-yl)amino)ethoxy)ethyl)piperazine-1-carboxylate (61 mg, 0.119 mmo) was dissolved in 2 mL of Methanol and 2 ml of HCl (4M in dioxane) and stirred at ambient temperature for 1 hour. Solvent was evaporated to dryness, residue was dried in vacuum for overnight to give a product 60 mg (97% yield). RP-HPLC (betasil C18, 0.5 mL/min, 10-100% ACN in 10 min) 4.25 min (with purity 97.7%); LC-MS (ESI, MH$^+$) 412; $^1$H NMR (500 MHz, D$_2$) δ 3.57-3.66 (10H, m), 3.72-3.76 (4H, br), 3.92 (2H, br), 7.33-7.40 (2H, m), 7.66-7.68 (1H, m).

Example 129

Preparation of Compound 185

Preparation of 2-((5-amino-6-(2,3-dichlorophenyl)-1,2,4-triazin-3-yl)(methyl)amino)ethanol.HCl (Compound 185)

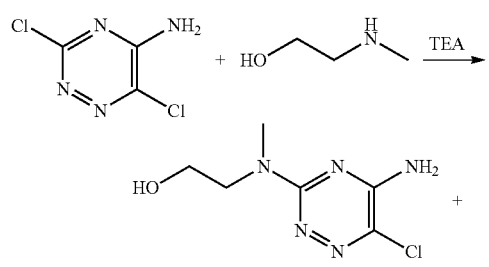

Preparation of 2-((5-amino-6-chloro-1,2,4-triazin-3-yl)(methyl)amino)ethanol: 5-Amino-3,6-dichloro-1,2,4-triazine (366 mg, 2.22 mmol) and 2-(methylamino)ethanol (213 μL, 2.66 mmol) were dissolved in dioxane (25 mL) at room temperature. Et$_3$N (0.62 mL, 4.44 mmol) was added. The mixture was stirred at 90° C. for overnight. Solvent was evaporated to dryness, residue was redissolved in DCM (20 mL), insoluble was collected and dried in vacuum for 3 hours to give the product 392 mg (87% yield).

Preparation of 2-((5-amino-6-(2,3-dichlorophenyl)-1,2,4-triazin-3-yl)(methyl)amino)ethanol: (2,3-dichlorophenyl)boronic acid (410 mg, 2.15 mmol), 2-((5-amino-6-chloro-1,2,4-triazin-3-yl)(methyl)amino)ethanol (292 mg, 1.43 mmol), cesium carbonate (934 mg, 2.87 mmol) were dissolved in 30 mL degassed dioxane/H$_2$O (3:1) and tetrakis (triphenylphosphine)palladium (934 mg, 2.87 mmol) was added under nitrogen atmosphere. The reaction mixture was stirred at 90° C. for 2 hours. Solvent was evaporated to dryness and residue was purified on silica gel column to give the desired product 320 mg (71% yield). RP-HPLC (betasil C18, 0.5 mL/min, 10-100% ACN in 10 min) 4.55 min (with purity 95.8%); LC-MS (ESI, MH$^+$) 314; $^1$H NMR (500 MHz, DMSO-d$_6$) δ 3.22 (3H, s), 3.66-3.72 (4H, m), 7.53-7.57 (2H, m), 7.84-7.87 (1H, m), 8.25 (1H, br), 9.23 (1H, br). The product was dissolved in 2 mL of 1.0 N HCl. Insoluble was filtered and filtrate was lyophilized for overnight to give the product hydrochloride salt.

Example 130

Preparation of Compound 186

Preparation of 6-(2,3-dichlorophenyl)-N3-(2-(2-((2-methoxyethyl)sulfonyl)ethoxy)ethyl)-1,2,4-triazine-3,5-diamine (Compound 186)

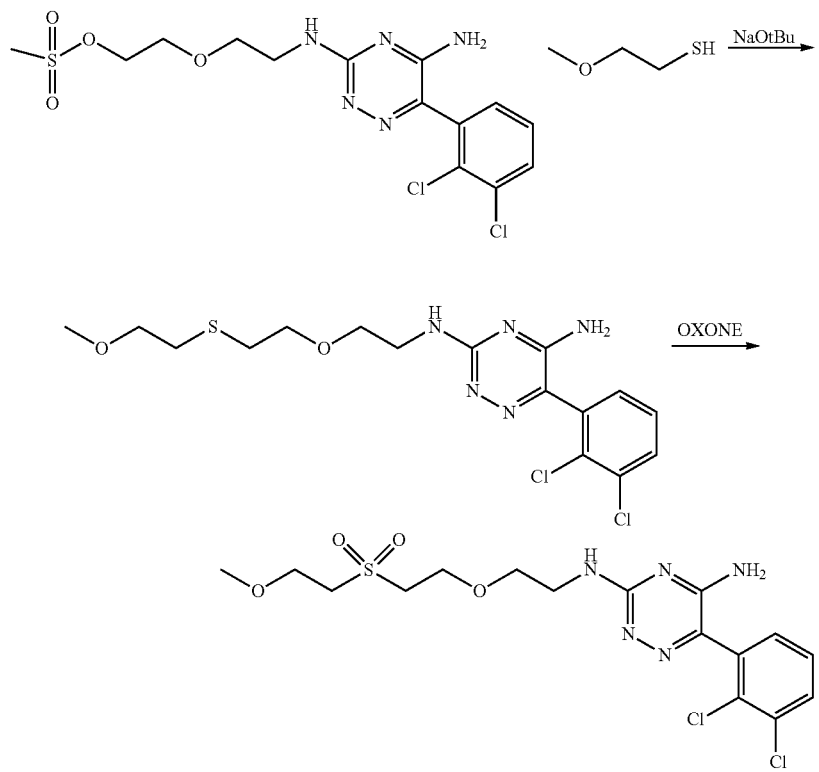

Preparation of 6-(2,3-dichlorophenyl)-N3-(2-(2-((2-methoxyethylthio)ethoxy)ethyl)-1,2,4-triazine-3,5-diamine: The solution of sodium 2-methoxythioethoxide (21.8 mg, 0.237 mmol) and KOtBu (0.237 mL, 1M, 0.237 mmol) in tBuOH were added to a solution of 2-(2-((5-Amino-6-(2,3-dichlorophenyl)-1,2,4-triazin-3-yl)amino)ethoxy)ethyl methanesulfonate (100 mg, 0.237 mmol) in DMF (1 mL). The mixture was stirred at RT under N$_2$ atmosphere. After 2 hrs, reaction was completed. Solvent was removed under reduced pressure. The residue was purified on silica gel column to yield 30 mg white solid (84% purity). LC-MS [ESI-MH$^+$]: m/z 418; $^1$H NMR (500 MHz, DMSO-d$_6$) δ ppm: 2.691 (t, J=6.5 Hz, 2H), 3.236 (s, 3H), 3.467 (m, 4H), 3.560 (m, 4H), 6.600-7.250 (b, 2H), 7.352 (q, J$_1$=1.5 Hz, J$_2$=7.5 Hz, 1H), 7.443 (t, J=6 Hz, 1H), 7.572 (d, J=6 Hz, 1H).

Preparation of 6-(2,3-dichlorophenyl)-N3-(2-(2-((2-methoxyethyl)sulfonyl)ethoxy)ethyl)-1,2,4-triazine-3,5-diamine: The 6-(2,3-dichlorophenyl)-N3-(2-(2-((2-methoxyethylthio)ethoxy)ethyl)-1,2,4-triazine-3,5-diamine (43 mg, 0.090 mmol, 88% purity) was dissolved in MeOH (1 mL). A solution of oxone (83 mg, 0.271 mmol) in water (1 mL) was added to the above solution at 0° C. to form a suspension. The mixture was stirred at room temperature for overnight. The product mixture was purified on silica gel column to give product as yellow solid (40 mg, 95% purity, 97.3% yield). LC-MS [ESI-MH$^+$]: m/z 450; $^1$H NMR (500 MHz, DMSO-d$_6$) δ ppm: 3.251 (s, 3H), 3.376 (m, 4H), 3.458 (b, 2H), 3.571 (t, J=6 Hz, 2H), 3.685 (t, J=6 Hz, 2H), 3.800 (t, J=6 Hz, 2H), 6.600-7.250 (b, 2H), 7.351 (q, J$_1$=1.5 Hz, J$_2$=7.5 Hz, 1H), 7.444 (t, J=6 Hz, 1H), 7.694 (d, J=6 Hz, 1H).

Example 131

Preparation of Compound 187

Preparation of 6-(2,3-dichlorophenyl)-N3-(2-(2-(methylsulfinyl)ethoxy)ethyl)-1,2,4-triazine-3,5-diamine (Compound 187)

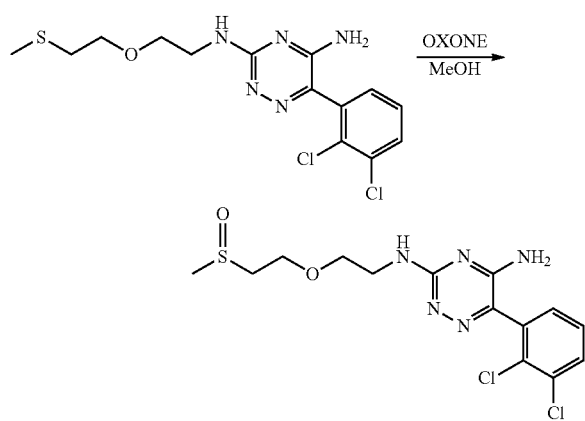

The 6-(2,3-dichlorophenyl)-N3-(2-(2-(methylthio)ethoxy)ethyl)-1,2,4-triazine-3,5-diamine (50 mg, 0.134 mmol, 96% purity) was dissolved in MeOH (1 mL). A solution of oxone (39.4 mg, 0.128 mmol) in water (1 mL) was added dropwise to the above solution at 0° C. to form a suspension. The addition was finished in half an hour. The mixture was stirred at 0° C. for 3 h. LC-MS analysis showed that the reaction to sulfoxide was completed. Solvent was removed under reduced pressure and residue was loaded to a silica gel column to give the product as light-yellow solid (50 mg, 96% purity, 100% yield). LC-MS [ESI-MH+]: m/z 390; $^1$H-NMR (DMSO-d$_6$) δ ppm: 2.564 (s, 3H), 2.848 (m, 1H), 3.038 (m, 1H), 3.164 (d, J=5.0 Hz, 2H), 3.453 (br, 2H), 3.571 (t, J=6.0 Hz, 2H), 3.777 (m, 2H), 4.108 (m, 1H), 6.500-7.300 (br, 2H), 7.355 (d, J=6.5 Hz, 1H), 7.442 (dd, J$_1$=8.0 Hz, J$_2$=7.5 Hz, 1H), 7.700 (d, J=6.5 Hz, 1H).

Example 132

Preparation of Compound 188

Preparation of 6-(2,3-dichlorophenyl)-N3-(1-(2-(2-methoxyethoxy)ethoxy)propan-2-yl)-1,2,4-triazine-3,5-diamine.HCl (Compound 188)

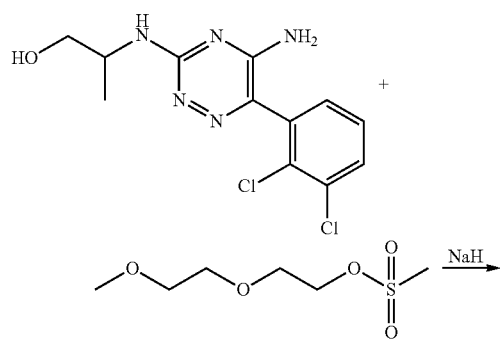

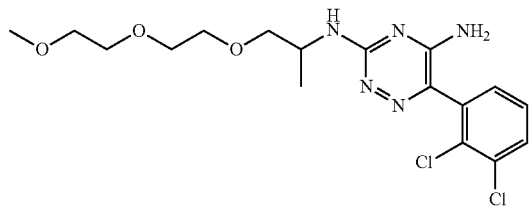

2-((5-amino-6-(2,3-dichlorophenyl)-1,2,4-triazin-3-yl)amino)propan-1-ol (198 mg, 0.631 mmol) was dissolved in 10 mL of dioxane. NaH (252 mg, 6.31 mmol) was added, then 3 mL of DMF was added. After stirring at ambient temperature for 10 min, 2-(2-methoxyethoxy)ethyl methanesulfonate (100 mg, 0.504 mmol) in 2 mL of dioxane was added. The mixture was stirred at 80° C. for 1.5 hours, and the residue was dissolved in 30 mL deionized water. Solid NaCl was added to 10% and pH was adjusted to about 11.0. Desired product was extracted with DCM (15 mL×3). Combined DCM was dried with MgSO$_4$, filtered and solvent was evaporated to dryness. Residue was dried in vacuum and purified on silica gel column to give the product 40 mg (15.2% yield). RP-HPLC (betasil C18, 0.5 mL/min, 10-100% ACN in 10 min) 5.60 min (with purity 90.4%); LC-MS (ESI, MH$^+$) 416; $^1$H NMR (500 MHz, DMSO-d$_6$) δ 1.18-1.20 (3H, d), 3.23 (3H, s), 3.42-3.57 (10H, m), 4.19 (1H, br) 7.53-7.57 (2H, m), 7.84-7.87 (1H, m), 8.25 (1H, br), 9.23 (1H, br). The product was dissolved in 2 mL of 1.0 N HCl. Insoluble was filtered and filtrate was lyophilized for overnight to give the product hydrochloride salt.

Example 133

Preparation of Compound 189

Preparation of 6-(2,3-dichlorophenyl)-N3-methyl-N3-(2-(methylamino)ethyl)-1,2,4-triazine-3,5-diamine (Compound 189)

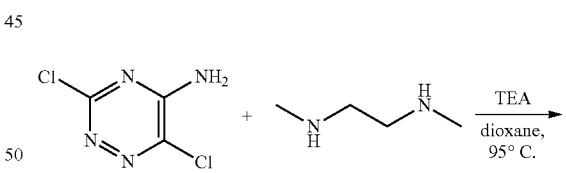

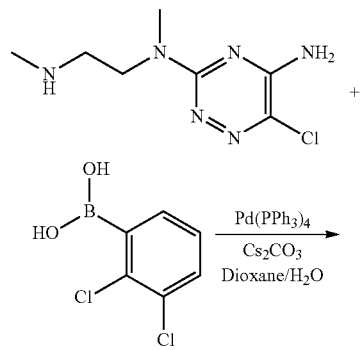

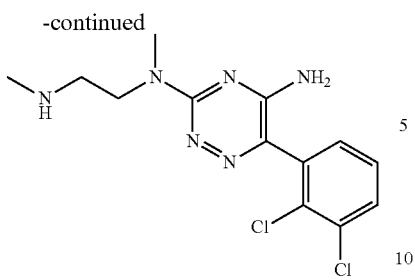

Preparation of 6-chloro-N3-methyl-N3-(2-(methylamino)ethyl)-1,2,4-triazine-3,5-diamine: 5-Amino-3,6-dichloro-1,2,4-triazine (200 mg, 1.212 mmol) was dissolved in dioxane (30 mL) at room temperature. Et₃N (0.17 mL, 1.21 mmol) was added, followed by addition of N1,N2-dimethylethane-1,2-diamine (1.28 g, 14.55 mmol) in 1 ml of dioxane. The resulting mixture was stirred at 95° C. for 1 hour. A sample was checked by LC-MS and showed the reaction was over. Solvent was evaporated to dryness, residue was mixed with 50 mL of hexane and liquid was decanted, precipitate was dried in high vacuum for overnight to give the product 338 mg (>100% yield).

Preparation of 6-(2,3-dichlorophenyl)-N3-methyl-N3-(2-(methylamino)ethyl)-1,2,4-triazine-3,5-diamine: (2,3-dichlorophenyl)boronic acid (347 mg, 1.82 mmol), 6-chloro-N3-methyl-N3-(2-(methylamino)ethyl)-1,2,4-triazine-3,5-diamine (1.212 mmol, 263 mmol), cesium carbonate (790 mg, 2.42 mmol) were dissolved in 30 mL degassed dioxane/H₂O (3:1) and tetrakis(triphenylphosphine)palladium (350 mg, 0.303 mmol) was added under nitrogen atmosphere. The reaction mixture was stirred at 85° C. for 1.5 hour. Solvent was evaporated to dryness at 50° C. under the reduced pressure. Residue was mixed with DCM/MeOH and insoluble was filtered and concentrated. Reside was purified on silica gel column to give product 277 mg (69.8% yield). RP-HPLC (betasil C18, 0.5 mL/min, 10-100% ACN in 10 min) 3.97 min (with purity 98.0%); LC-MS (ESI, MH⁺) 327; ¹H NMR (500 MHz, D₂) δ 2.77 (3H, s), 3.26 (3H, s), 3.38-3.41 (2H, t), 4.00-4.09 (2H, m), 7.45-7.52 (2H, m), 7.78-7.80 (1H, m). The was dissolved in 2 mL of DCM, 0.63 mL of 1.0 M HCl in diethyl ether was added. The mixture was stirred at r.t. for 1 hour. Solvent was evaporated to dryness and high vacuo to give the product as hydrochloride salt.

Example 134

Preparation of Compound 190

Preparation of N-(2-((5-amino-6-(2,3-dichlorophenyl)-1,2,4-triazin-3-yl)(methyl)amino)ethyl)-2-(2-methoxyethoxy)-N-methylacetamide (Compound 190)

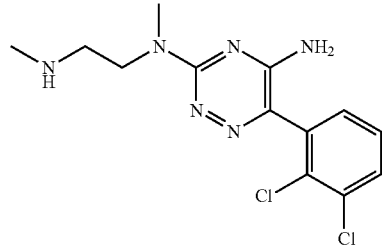

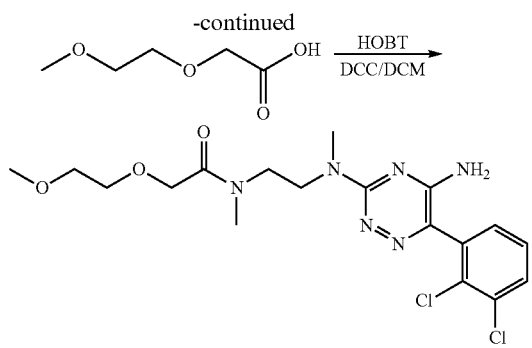

2-(2-Methoxyethoxy)acetic acid (44.3 mg, 0.330 mmol) and HOBT (37.2 mg, 0.275 mmol) were dissolved in 20 mL of anhydrous DCM. DCC (85 mg, 0.413 mmol) was added. The reaction mixture was stirred at ambient temperature for 30 minutes, then mixed with 90 mg of 6-(2,3-dichlorophenyl)-N3-methyl-N3-(2-(methylamino)ethyl)-1,2,4-triazine-3,5-diamine (90 mg, 0.275 mmol). The reaction mixture was stirred at ambient temperature under nitrogen atmosphere for overnight. Insoluble was filtered off and filtrate was concentrated at reduced pressure. Residue was dissolved in 20 ml of deionized water, pH was adjusted to 2.0 with 1.0 N HCl. Insoluble was filtered and aqueous was washed with DCM (20 mL×2). NaCl was added to make 15% and pH was readjusted to 12.3 with NaOH. Desired product was extracted with DCM (20 mL×4). Combined DCM extract was dried with MgSO4, filtered and solvent was evaporated to dryness. Residue was purified on silica gel column to give product 71 mg (58.2% yield). RP-HPLC (betasil C18, 0.5 mL/min, 10-100% ACN in 10 min) 4.85 min (with purity 99.8%); LC-MS (ESI, MH⁺, free base) 443; ¹H NMR (500 MHz, D₂) δ 3.00 (3H, s), 3.24 (3H, s), 3.34 (3H, s), 3.60-3.77 (6H, m), 3.77 (2H, br), 4.18-4.30 (2H, m), 7.45-7.52 (2H, m), 7.78-7.80 (1H, m). The product was dissolved in 1.0 N HCl. Insoluble was filtered and filtrate was lyophilized for overnight to give the product hydrochloride salt.

Example 135

Preparation of Compound 191

Preparation of 2-((2-(2-46-amino-5-(2,3-dichlorophenyl)pyrazin-2-yl)amino)ethoxy)ethyl)-(methyl)amino)acetamide (Compound 191)

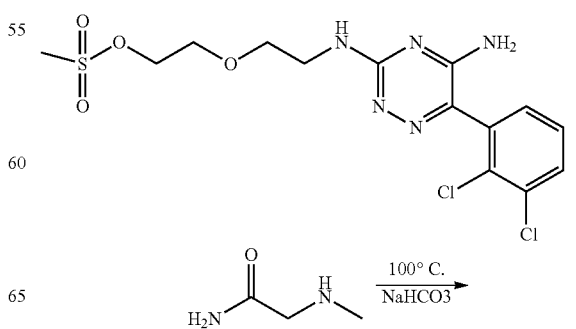

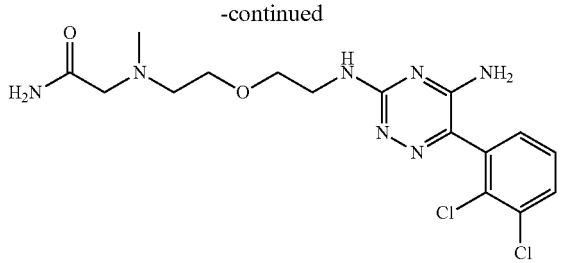

2-(2-((5-Amino-6-(2,3-dichlorophenyl)-1,2,4-triazin-3-yl)amino)ethoxy)ethyl methanesulfonate (190 mg, 73% purity, 0.328 mmol), N-methyl glycinamide (868 mg, 9.85 mmol) and sodium bicarbonate (83 mg, 0.985 mmol) were added to a mixture of acetonitrile (10 mL) and deionized water (10 mL). The mixture was heated over 100° C. overnight. The product mixture was purified on silica gel column to give product as white powder (32 mg, purity 94.5%, yield 23.6%). LC-MS [ESI-MH$^+$]: m/z 415. $^1$H-NMR (DMSO-$d_6$) δ ppm: 2.256 (s, 3H), 2.784 (br, 1H), 3.038 (m, 1H), 3.163 (d, J=5.0 Hz, 2H), 3.417 (br, 2H), 3.487 (m, 4H), 6.500-7.300 (br, 2H), 7.355 (d, J=6.5 Hz, 1H), 7.442 (dd, J$_1$=8.0 Hz, J$_2$=7.5 Hz, 1H), 7.700 (d, J=6.5 Hz, 1H).

Example 136

Preparation of Compound 192

Preparation of 2-(2-amino-2-oxoethoxy)-N-(2-((5-amino-6-(2,3-dichlorophenyl)-1,2,4-triazin-3-yl)(methyl)amino)ethyl)-N-methylacetamide (Compound 192)

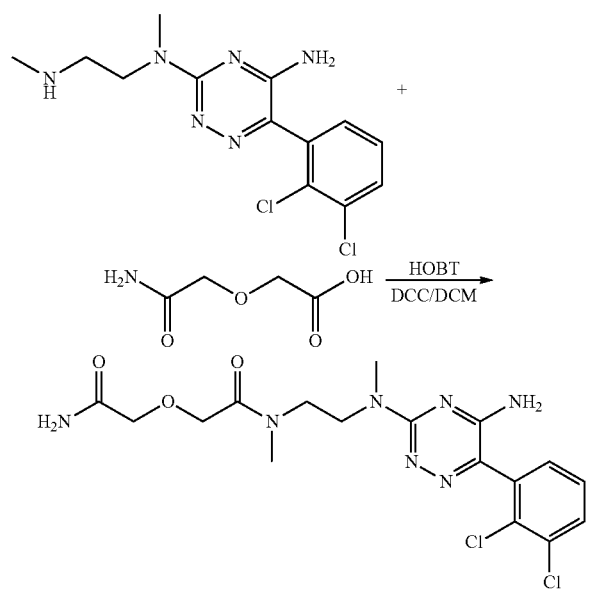

2-(2-Amino-2-oxoethoxy)acetic acid (43.9 mg, 0.330 mmol) and HOBT (24.8 mg, 18.3 mmol) were dissolved in anhydrous dioxane (15 mL), DCC (68.1 mg, 0.330 mmol) was added. The reaction mixture was stirred at ambient temperature for 30 minutes, then mixed with 6-(2,3-dichlorophenyl)-N3-methyl-N3-(2-(methylamino)ethyl)-1,2,4-triazine-3,5-diamine (60 mg, 0.183 mmol). The reaction mixture was stirred at ambient temperature under nitrogen atmosphere for overnight. Insoluble was filtered off and filtrate was concentrated at reduced pressure. Residue was dissolved in 20 mL of deionized water, pH was adjusted to 2.0 with 1.0 N HCl. Insoluble was filtered and aqueous was washed with DCM (20 ml×2). Solid NaCl was added to make 15% and pH was readjusted to 12.3 with NaOH. Desired product was extracted with DCM (20 mL×4). Combined DCM extraction was dried with MgSO$_4$, filtered, and solvent was evaporated to dryness. Residue was purified on silica gel column to give the product 48.2 mg (59.2% yield). RP-HPLC (betasil C18, 0.5 mL/min, 10-100% ACN in 10 min) 4.43 min (with purity 97.5%); LC-MS (ESI, MH$^+$) 442; $^1$H NMR (500 MHz, D$_2$) δ 2.96 (3H, s), 3.19 (3H, s), 3.57-3.75 (4H, m), 3.98.4.02 (2H, m), 4.23-4.30 (2H, m), 7.45-7.52 (2H, m), 7.78-7.80 (1H, m). The product was dissolved in 1.0 N HCl. Insoluble was filtered and filtrate was lyophilized for overnight to give the product hydrochloride salt.

Example 137

Preparation of Compound 193

Preparation of 6-(2,3-dichlorophenyl)-N3-(2-((2-(2-methoxyethoxy)ethyl)(methyl)amino)ethyl)-N3-methyl-1,2,4-triazine-3,5-diamine (Compound 193)

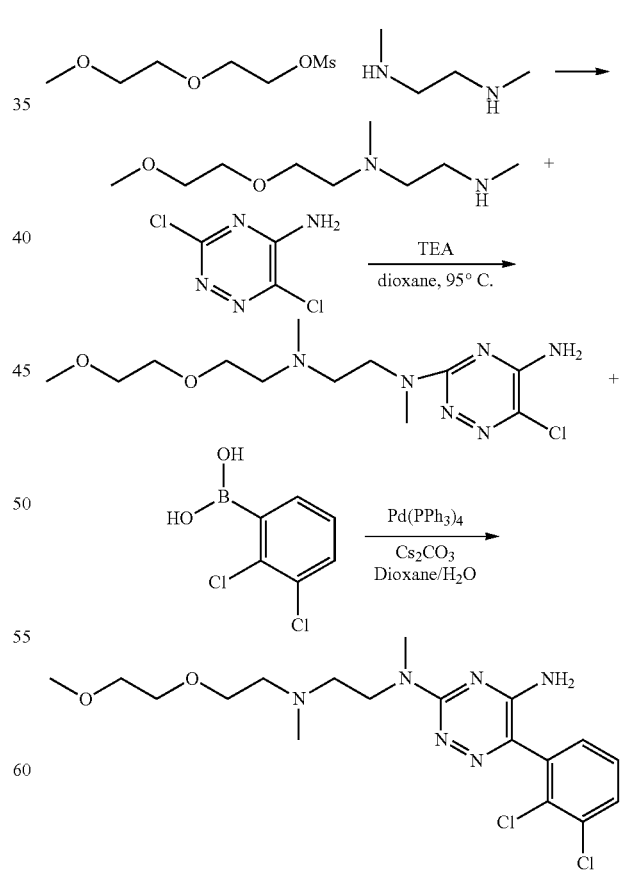

Preparation of N1-(2-(2-methoxyethoxy)ethyl)-N1,N2-dimethylethane-1,2-diamine: 2-(2-Methoxyethoxy)ethyl methanesulfonate (400 mg, 2.02 mmol) and 1.8 g of N1,N2-dimethylethane-1,2-diamine (1.8 g, 20.2 mmol) were dissolved in 20 mL of dioxane. The reaction mixture was stirred at 90° C. for overnight. Solvent was evaporated to dryness, residue was dried in high vacuum for overnight to give a product 380 mg (99% yield).

Preparation of 6-(2,3-dichlorophenyl)-N3-(2-((2-(2-methoxy-ethoxy)ethyl)(methyl)amino)ethyl)-N3-methyl-1,2,4-triazine-3,5-diamine: 5-Amino-3,6-dichloro-1,2,4-triazine (300 mg, 1.09 mmol) was dissolved in dioxane (30 ml) at room temperature. N1-(2-(2-methoxyethoxy)ethyl)-N1,N2-dimethylethane-1,2-diamine (380 mg, 2.0 mmol) and TEA (0.464 mL, 3.33 mmol) were added. The resulting mixture was stirred at 90° C. for overnight. The mixture directly goes to next step after adding 10 mL of deionized water. (2,3-Dichlorophenyl)boronic acid (429 mg, 2.25 mmol), cesium carbonate (0.98 mg, 3.00 mmol) were dissolved in mixture of 6-chloro-N3-(2-((2-(2-methoxyethoxy)ethyl)(methyl)amino)ethyl)-N3-methyl-1,2,4-triazine-3,5-diamine. The mixture was purged with $N_2$ for 10 min and tetrakis(triphenylphosphine)palladium (433 mg, 0.375 mmol) was added under nitrogen atmosphere. The reaction mixture was stirred at 90° C. for 1 hour. After cooling to room temperature, insoluble was filtered and filtrate was concentrated to dryness at 50° C., reduced pressure. Residue was dissolved in 50 mL of deionized water. pH was readjusted to 2.0 with 1.0 N HCl, washed with DCM (20 ml×3). Aqueous was checked by LC-MS, then adjusted to pH 12.5 with NaOH, NaCl was added to about 15%. and desired product was extracted with DCM (20 mL×4). Combined DCM was dried with $MgSO_4$, filtered and solvent was evaporated to dryness. Residue was purified on silica gel column to give the product 308 mg (47.8% yield) after high vauco drying. RP-HPLC (betasil C18, 0.5 mL/min, 10-100% ACN in 10 min) 4.41 min (with purity 96.6%); LC-MS (ESI, MH$^+$) 429; $^1$H NMR (500 MHz, $D_2$) δ 3.00 (3H, s), 3.26 (3H, s), 3.34 (3H, s), 3.58-3.70 (8H, m), 3.84-3.87 (2H, t), 4.15 (2H, br), 7.45-7.52 (2H, m), 7.78-7.80 (1H, m). The product was dissolved in 1.0 N HCl. Insoluble was filtered and filtrate was lyophilized for overnight to give the product hydrochloride salt.

Example 138

Preparation of Compound 194

Preparation of 2-((2-(2-((5-amino-6-(2,3-dichlorophenyl)-1,2,4-triazin-3-yl)amino)ethoxy)ethyl)amino)acetamide (Compound 194)

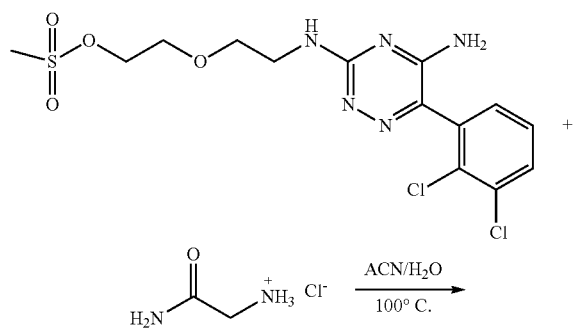

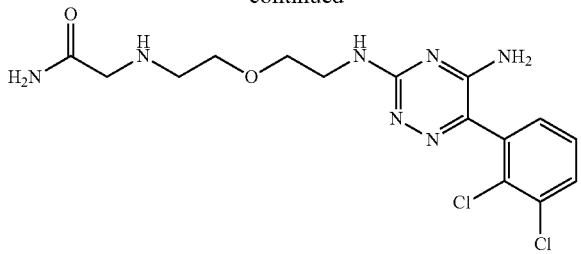

2-(2-((5-Amino-6-(2,3-dichlorophenyl)-1,2,4-triazin-3-yl)amino)ethoxy)ethyl methanesulfonate (220 mg, 0.260 mmol), 2-aminoacetamide hydrochloride (288 mg, 2.60 mmol) and sodium bicarbonate (1.09 g, 13.02 mmol) were added to a mixture of acetonitrile (20 mL) and deionized water (20 mL). The mixture was heated over 100° C. in an oil bath for overnight. The product mixture was purified on silica gel column to give product as white powder (14 mg, yield 13.4%). LC-MS [ESI-MH$^+$]: m/z 400; $^1$H-NMR (CDCl$_3$) δ ppm: 7.582 (m, 1H), 7.437 (t, J=8 Hz, 1H), 7.370 (m, 2H), 5.577 (br, 2H), 4.888 (br, 2H), 3.681 (br, 4H), 3.615 (t, J=5.0 Hz, 2H), 3.372 (s, 2H), 2.880 (t, J=5.0 Hz, 2H).

Example 139

Preparation of Compound 195

Preparation of 1-amino-3-((5-amino-6-(2,3-dichlorophenyl)-1,2,4-triazin-3-yl)amino)propan-2-ol.HCl (Compound 195)

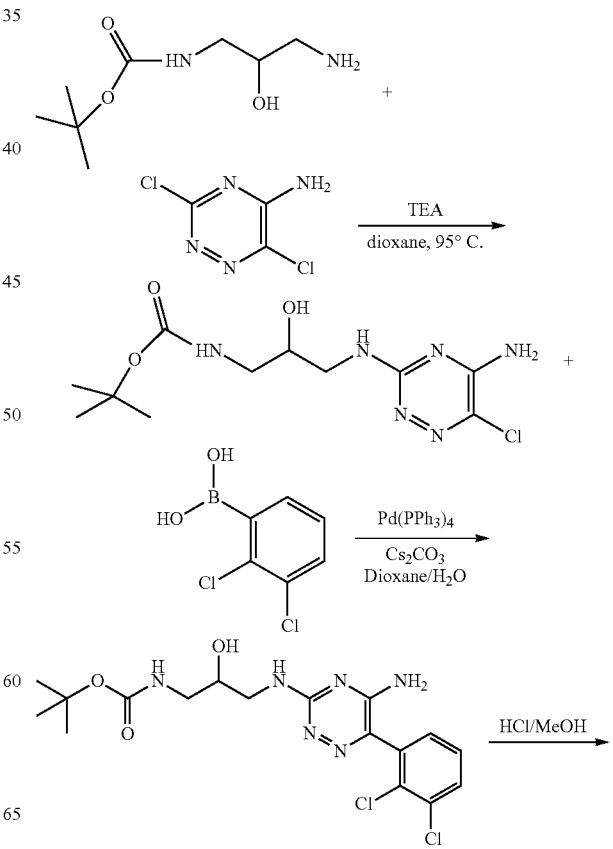

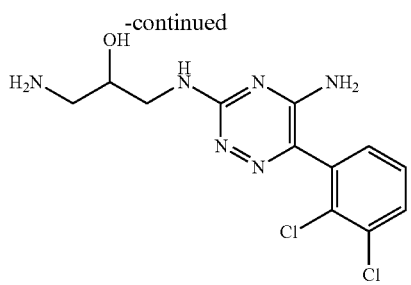

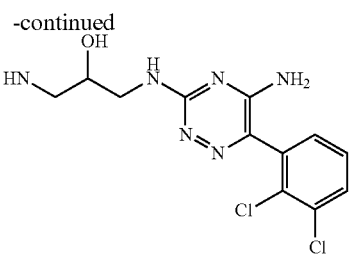

Preparation of tert-butyl (3-((5-amino-6-chloro-1,2,4-triazin-3-yl)amino)-2-hydroxypropyl)carbamate: 5-Amino-3,6-dichloro-1,2,4-triazine (300 mg, 1.82 mmol) was dissolved in dioxane (30 ml) at room temperature. tert-Butyl (3-amino-2-hydroxypropyl)carbamate (450 mg, 2.36 mmol) and TEA (507 μL, 3.64 mmol) were added. The resulting mixture was stirred at 90° C. for overnight. Insoluble was filtered and filtrate was concentrated at reduced pressure. Residue was purified on silica gel column product 474 mg (82% yield).

Preparation of 1-amino-3-((5-amino-6-(2,3-dichlorophenyl)-1,2,4-triazin-3-yl)amino)propan-2-ol: (2,3-dichlorophenyl)boronic acid (234 mg, 1.23 mmol), tert-butyl (3-((5-amino-6-chloro-1,2,4-triazin-3-yl)amino)-2-hydroxypropyl)carbamate (261 mg, 0.819 mmol), cesium carbonate (534 mg, 1.64 mmol) were dissolved in 30 mL degassed dioxane/H2O (3:1) and tetrakis(triphenylphosphine)palladium (237 mg, 0.205 mmol) was added under nitrogen atmosphere. The reaction mixture was stirred at 85° C. for 2 hours. Solvent was evaporated to dryness at 50° C. under the reduced pressure. Residue was purified on silica gel column to give product 243 mg (69.1% yield). The product was mixed with 15 mL of 4.0N HCl in dioxane and 5 ml of methanol, stirred at r.t. for 2 hour. Solvent was evaporated to dryness. Residue was dried in high vacuum overnight to give the final product as hydrochloride salt. RP-HPLC (betasil C18, 0.5 mL/min, 10-100% ACN in 10 min) 4.09 min (with purity 99.8%); LC-MS (ESI, MH$^+$) 329; $^1$H NMR (500 MHz, D$_2$) δ 2.87-2.93 (1H, m), 2.92-3.15 (1H, d), 3.52-3.70 (2H, m), 4.13 (1H, br), 7.45-7.52 (2H, m), 7.78-7.80 (1H, m).

Example 140

Preparation of Compound 196

Preparation of N-(3-((5-amino-6-(2,3-dichlorophenyl)-1,2,4-triazin-3-yl)amino)-2-hydroxypropyl)-2-(2-methoxyethoxy)acetamide (Compound 196)

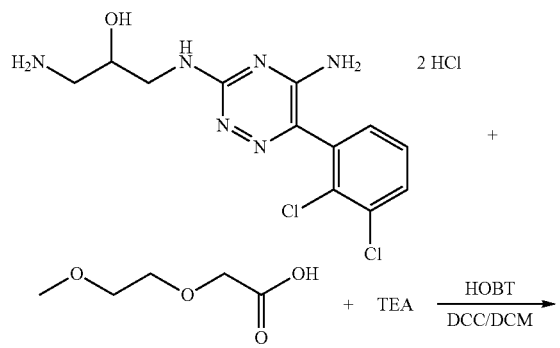

2-(2-Methoxyethoxy)acetic acid (48.9 mg, 0.365 mmol) and HOBT (40.1 mg, 0.304 mmol) were dissolved in 10 mL of anhydrous DCM. DCC (94 mg, 0.456 mmol) was added. The reaction mixture was stirred at ambient temperature for 30 minutes, then mixed with 1-amino-3-((5-amino-6-(2,3-dichlorophenyl)-1,2,4-triazin-3-yl)amino)propan-2-ol (100 mg, 0.304 mmol) and TEA (93 uL, 0.668 mmol) in 10 mL of anhydrous acetonitrile. The reaction mixture was stirred at ambient temperature under nitrogen atmosphere for 2 hours. A sample was checked by LC-MS, showed that reaction was over. Solvent was evaporated to dryness at reduced pressure, residue was dried in vacuum for overnight. Residue was dissolved in 15 mL of MeOH, 5 mL of 1.0 N NaOH was added, stirred at room temperature for 30 min. pH was readjusted to 2.0 with 1.0 N HCl. Insoluble was filtrated and filtrate was concentrated at reduced pressure to almost dryness. Residue was dissolved 20 ml of deionized water, pH was adjusted to 2.0 with 1.0 N HCl aqueous, washed with DCM (20 mL×2). Aqueous was adjusted to pH 12.5 with NaOH, stirred for 30 minutes. Solid NaCl was added to about 15%. and desired product was extracted with DCM (20 mL×4). Combined DCM was dried with MgSO$_4$, filtered and solvent was evaporated to dryness. Residue was dried in vacuum for overnight to give the final product 76 mg (56.2% yield). RP-HPLC (betasil C18, 0.5 mL/min, 10-100% ACN in 10 min) 4.86 min (with purity 96.9%); LC-MS (ESI, MH$^+$, free base) 445; $^1$H NMR (500 MHz, D$_2$) δ 3.22-3.27 (2H, m), 3.28 (3H, s), 3.34-3.44 (3H, m), 3.53-3.55 (2H, t) 3.62-3.64 (2H, t), 3.94 (1H, br), 3.98 (2H, s), 7.34-7.41 (2H, m), 7.66-7.69 (1H, m). The product was dissolved in 1.0 N HCl. Insoluble was filtered and filtrate was lyophilized for overnight to give the product hydrochloride salt.

Example 141

Preparation of Compound 197

Preparation of methyl 2-(2-(2-((5-amino-6-(2,3-dichlorophenyl)-1,2,4-triazin-3-yl)amino)ethoxy)ethoxy)acetate (Compound 197)

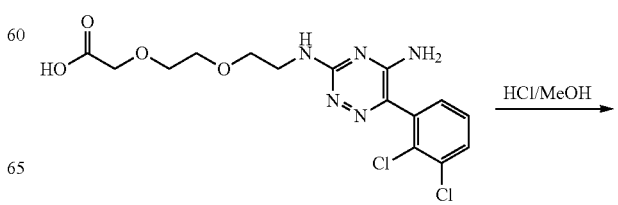

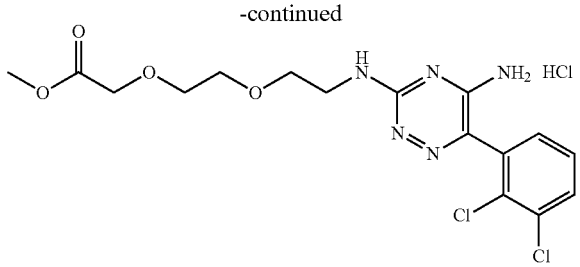

2-(2-(2-((5-Amino-6-(2,3-dichlorophenyl)-1,2,4-triazin-3-yl)amino)ethoxy)ethoxy)acetic (5 mg) was dissolved in 0.5 mL of MeOH, 0.07 mL of 1.0 M HCl in ether was added. The mixture was stirred at room temperature for 1 hour. Solvent was evaporated to dryness, residue was dried in high vacuum for overnight to give the product 5.0 mg (100% yield). RP-HPLC (betasil C18, 0.5 mL/min, 10-100% ACN in 10 min) 5.32 min (with purity 94.8%); LC-MS (ESI, MH$^+$) 416; $^1$H NMR: N/A Example 142

Preparation of Compound 198

Preparation of 2-(2-amino-2-oxoethoxy)-N-(3-((5-amino-6-(2,3-dichlorophenyl)-1,2,4-triazin-3-yl)amino)-2-hydroxypropyl)acetamide (Compound 198)

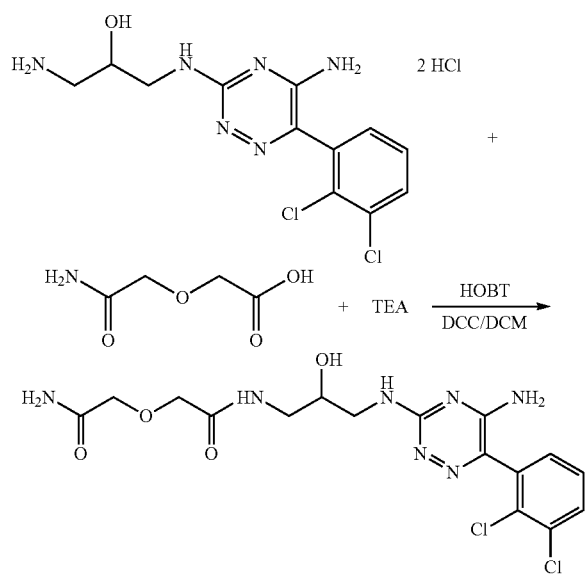

2-(2-Amino-2-oxoethoxy)acetic acid (58.2 mg, 0.437 mmol) and HOBT (49.2 mg, 0.365 mmol) were dissolved in 10 mL of anhydrous CAN. DCC (113 mg, 0.547 mmol) was added. The reaction mixture was stirred at ambient temperature for 30 minutes, then mixed with 1-amino-3-((5-amino-6-(2,3-dichlorophenyl)-1,2,4-triazin-3-yl)amino)propan-2-ol (120 mg, 0.365 mmol) and TEA (152 µL, 1.09 mmol) in 10 mL of anhydrous acetonitrile and 2 mL of DMF. The reaction mixture was stirred at ambient temperature under nitrogen atmosphere for overnight. Solvent was evaporated to dryness under the reduced pressure, residue was dried in vacuum for overnight. The residue was purified on silica gel column to give product 52 mg (32.1%).

RP-HPLC (betasil C18, 0.5 mL/min, 10-100% ACN in 10 min) 4.42 min (with purity 96.3%); LC-MS (ESI, MH$^+$) 444; $^1$H NMR (500 MHz, D$_2$) δ 3.22-3.27 (2H, m), 3.28 (3H, s), 3.34-3.44 (3H, m), 3.53-3.55 (2H, t), 3.62-3.64 (2H, t), 3.94 (1H, br), 3.98 (2H, s), 7.34-7.41 (2H, m), 7.66-7.69 (1H, m). The product was dissolved in 1.0 N HCl. Insoluble was filtered and filtrate was lyophilized for overnight to give the product hydrochloride salt.

Example 143

Preparation of Compound 199

Preparation of methyl 2-((2-(2-((5-amino-6-(2,3-dichlorophenyl)-1,2,4-triazin-3-yl)amino)ethoxy)ethyl)amino)acetate (Compound 199)

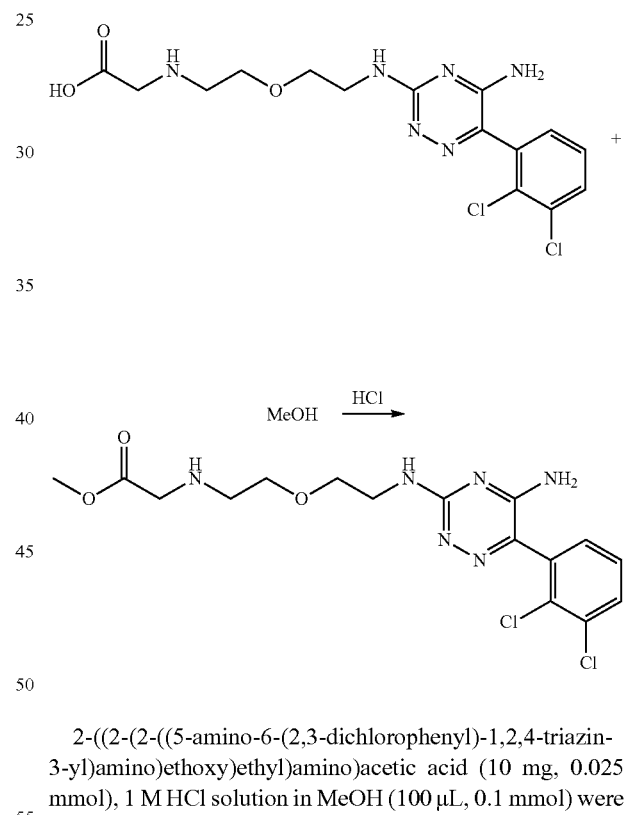

2-((2-(2-((5-amino-6-(2,3-dichlorophenyl)-1,2,4-triazin-3-yl)amino)ethoxy)ethyl)amino)acetic acid (10 mg, 0.025 mmol), 1 M HCl solution in MeOH (100 µL, 0.1 mmol) were added to anhydrous MeOH (5 mL). The solution was stirred under N$_2$ atmosphere at ambient temperature for 24 h. Then 10 µL concentrated H$_2$SO$_4$ was added. In a week, 80% conversion was afforded. Solvent was removed under reduced pressure. Residue was subject to flash chromatography. Yield product as white powder (10 mg, purity 92.0%, yield 97%). LC-MS [ESI-MH$^+$]: m/z 415; $^1$H-NMR (DMSO-d$_6$) □ ppm: 7.689 (d, J=1.5 Hz, 1H), 7.437 (t, J=8 Hz, 1H), 7.357 (dd, J$_1$=1.5 Hz, J$_2$=7.5 Hz, 1H), 7.20-6.35 (br, 2H), 3.617 (s, 3H), 3.510 (m, 3H), 3.462 (m, 2H), 3.369 (m, 3H), 2.671 (t, J=6.0 Hz, 2H).

Example 144

Preparation of Compound 200

Preparation of 2-(4-(5-amino-6-(2,3-dichlorophenyl)-1,2,4-triazin-3-yl)piperazin-1-yl)ethanol (Compound 200)

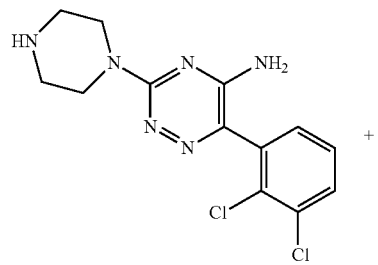

+

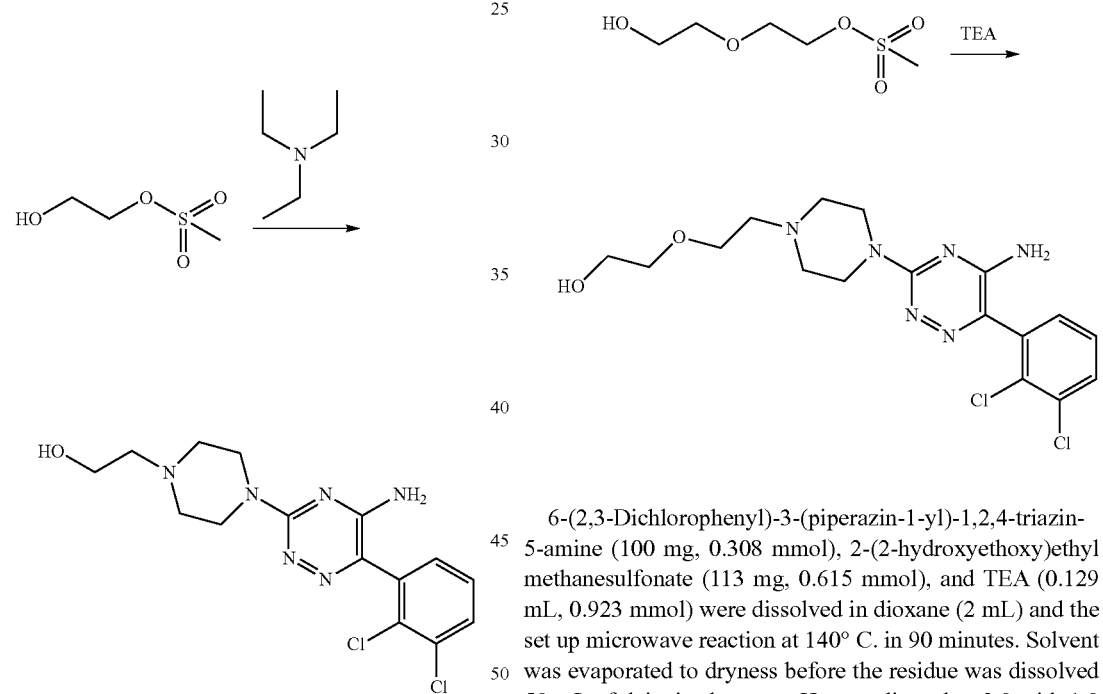

6-(2,3-Dichlorophenyl)-3-(piperazin-1-yl)-1,2,4-triazin-5-amine (50 mg, 0.154 mmol), 2-hydroxyethyl methanesulfonate (86 mg, 0.615 mmol), and TEA (0.13 mL, 0.923 mmol) were set up in a Microwave reaction in 1.5 ml of dioxane at 140° C. for 90 minutes. The product mixture was evaporated and the residue was purified on silica gel column to give product (20 mg, 35.2% yield). RP-HPLC (betasil C18, 0.5 mL/min, 10-100% ACN in 10 min) 4.11 min (with purity 96.8%); LC-MS (ESI, MH+) 369; $^1$H NMR (500 MHz, D$_2$) δ 3.38-3.40 (2H, t), 3.73 (8H, br), 3.94-3.97 (2H, t), 7.34-7.41 (2H, m), 7.66-7.69 (1H, m). The product was dissolved in 1.0 N HCl. Insoluble was filtered and filtrate was lyophilized for overnight to give the product hydrochloride salt.

Example 145

Preparation of Compound 201

Preparation of 2-(2-(4-(5-amino-6-(2,3-dichlorophenyl)-1,2,4-triazin-3-yl)piperazin-1-yl)ethoxy)ethanol (Compound 201)

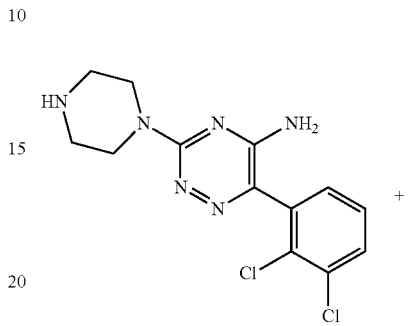

6-(2,3-Dichlorophenyl)-3-(piperazin-1-yl)-1,2,4-triazin-5-amine (100 mg, 0.308 mmol), 2-(2-hydroxyethoxy)ethyl methanesulfonate (113 mg, 0.615 mmol), and TEA (0.129 mL, 0.923 mmol) were dissolved in dioxane (2 mL) and the set up microwave reaction at 140° C. in 90 minutes. Solvent was evaporated to dryness before the residue was dissolved 50 mL of deionized water. pH was adjusted to 2.0 with 1.0 N HCl aqueous and then washed with DCM (20 mL×2). Aqueous was adjusted to pH 12.5 with NaOH and solid NaCl was added to about 15%. The desired product was extracted with DCM (20 mL×4). Combined DCM was dried with MgSO$_4$, filtered, and solvent was evaporated to dryness. Residue was purified on silica gel column to the product 60 mg (39.3% yield). RP-HPLC (betasil C18, 0.5 mL/min, 10-100% ACN in 10 min) 4.16 min (with purity 91.8%); LC-MS (ESI, MH+) 413; $^1$H NMR (500 MHz, D$_2$) δ 3.48-3.51 (2H, t), 3.52-3.88 (12H, m), 3.89-3.91 (2H, t), 7.44-7.51 (2H, m), 7.76-7.79 (1H, m). The product was dissolved in 1.0 N HCl. Insoluble was filtered and filtrate was lyophilized for overnight to give the product hydrochloride salt.

Example 146

Preparation of Compound 202

Preparation of 6-(2,3-dichlorophenyl)-3-(4-(2-(methylsulfonyl)ethyl)piperazin-1-yl)-1,2,4-triazin-5-amine (Compound 202)

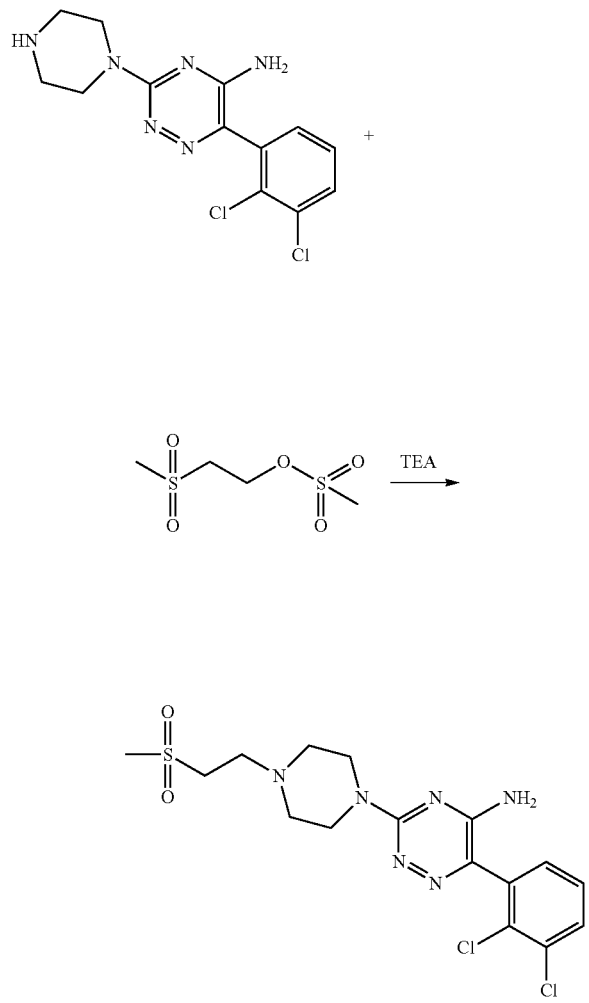

6-(2,3-Dichlorophenyl)-3-(piperazin-1-yl)-1,2,4-triazin-5-amine (100 mg, 0.308 mmol), 2-(methylsulfonyl)ethyl methanesulfonate (187 mg, 0.923 mmol), and TEA (0.17 mL, 1.23 mmol) were dissolved in dioxane (2 mL) and set up a microwave reaction at 140° C. in 90 minutes. Solvent was evaporated to dryness. Residue was purified on silica gel column to give a product 88 mg (66.3% yield). RP-HPLC (betasil C18, 0.5 mL/min, 10-100% ACN in 10 min) 4.34 min (with purity 93.6%); LC-MS (ESI, MH$^+$) 431; $^1$H NMR (500 MHz, D$_2$) δ 3.20 (3H, s), 3.51 (4H, br), 3.70-3.73 (2H, t), 3.82-3.85 (2H, t), 4.10 (4H, br), 7.44-7.51 (2H, m), 7.76-7.79 (1H, m). The product was dissolved in 1.0 N HCl. Insoluble was filtered and filtrate was lyophilized for overnight to give the product hydrochloride salt.

Example 147

Preparation of Compounds 203 and 204

Preparation of tert-butyl 2-(2-(4-(5-amino-6-(2,3-dichlorophenyl)-1,2,4-triazin-3-yl)piperazin-1-yl)ethoxy)acetate (Compound 203) and 2-(2-(4-(5-amino-6-(2,3-dichlorophenyl)-1,2,4-triazin-3-yl)piperazin-1-yl)ethoxy)acetic acid (Compound 204)

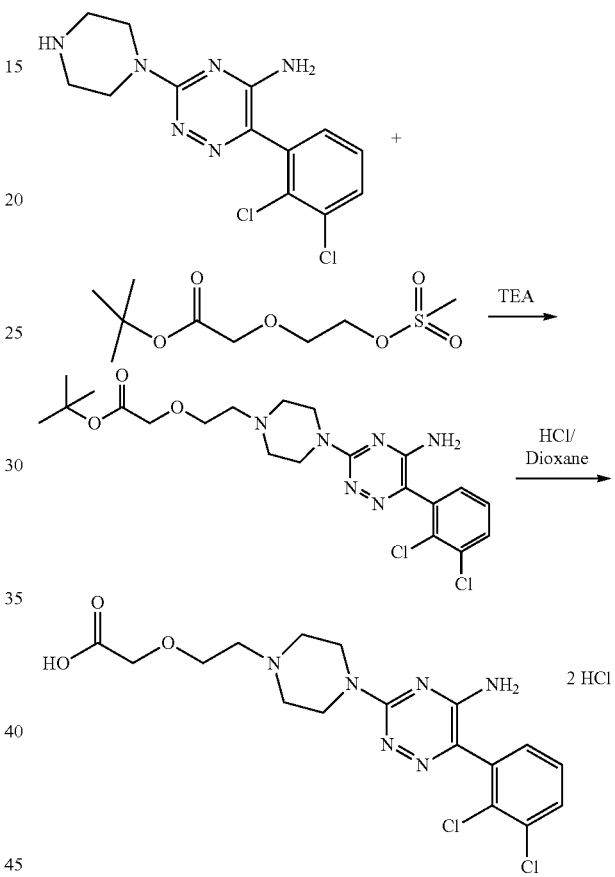

6-(2,3-Dichlorophenyl)-3-(piperazin-1-yl)-1,2,4-triazin-5-amine (70 mg, 0.215 mmol) was dissolved in dioxane (3 mL) at room temperature. Triethylamine (0.12 mL, 0.861 mmol) was added, followed by addition of tert-butyl 2-(2-((methylsulfonyl)oxy)ethoxy)acetate (109 mg. 0.431 mmol). The resulting mixture was stirred at 140° C. for 90 minutes. After reaction mixture was cooled to room temperature, the organic solution was concentrated. The residue was purified with flash column chromatography on silica gel using 1-10% methanol/dichloromethane to afford 48 mg product as solid. RP-HPLC (betasil C18, 0.5 mL/min, 10-100% ACN in 10 min) 5.36 min (with purity 92.4%); LC-MS (ESI, MH$^+$) 483; $^1$H NMR (500 MHz, D$_2$) δ 1.48 (9H, s), 3.51-3.54 (2H, t), 3.64 (8H, br), 3.94-3.96 (2H, t), 4.17 (2H, s), 7.44-7.51 (2H, m), 7.76-7.79 (1H, m).

tert-Butyl 2-(2-(4-(5-amino-6-(2,3-dichlorophenyl)-1,2,4-triazin-3-yl)piperazin-1-yl)ethoxy)-acetate was mixed with 5 mL of 1.0 N HCl, stirred at room temperature for overnight. Solvent was evaporated to dryness and residue was dried in high vacuum for overnight to give the final product. RP-HPLC (betasil C18, 0.5 mL/min, 10-100% ACN in 10 min) 4.10 min (with purity 87.3%); LC-MS (ESI, MH+, free base) 427; ¹H NMR (500 MHz, D$_2$) δ 3.47-3.50 (2H, t), 3.12-4.10 (8H, br), 3.92-3.95 (2H, t), 4.13 (2H, s), 7.44-7.51 (2H, m), 7.76-7.79 (1H, m).

Example 148

Preparation of Compound 205

Preparation of 2-((5-amino-6-(2,3-dichlorophenyl)-1,2,4-triazin-3-yl)amino)-2-methylpropanal (Compound 205)

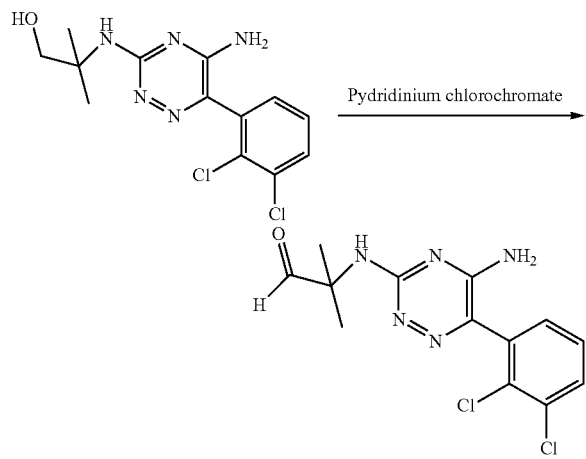

2-((5-amino-6-(2,3-dichlorophenyl)-1,2,4-triazin-3-yl)amino)-2-methylpropan-1-ol (46 mg, 0.140 mmol) was dissolved in 10 mL of dichloromethane. Pyridinium chlorochromate (750 mg, 3.48 mmol) was added. The mixture was stirred at room temperature for overnight. The residue was purified on silica gel column to give the desired product 20 mg (43.7%). RP-HPLC (betasil C18, 0.5 mL/min, 10-100% ACN in 10 min) 4.94 min (with purity 99.0%); LC-MS (ESI, MH+) 326; ¹H NMR (500 MHz, CD$_3$OD) δ 1.34 (6H, s), 5.47 (1H, s), 7.38-7.40 (2H, m), 7.65-7.68 (1H, m).

Example 149

Preparation of Compound 206

Preparation of 2-((5-amino-6-(2,3-dichlorophenyl)-1,2,4-triazin-3-yl)amino)-2-methylpropanoic acid (Compound 206)

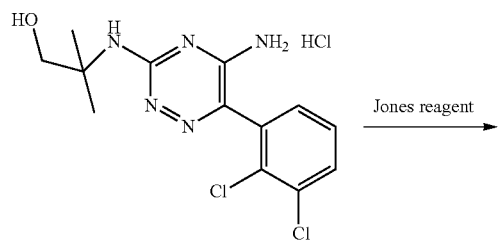

Jones reagent

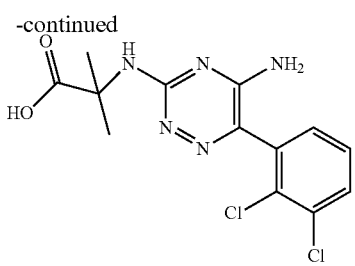

2-((5-amino-6-(2,3-dichlorophenyl)-1,2,4-triazin-3-yl)amino)-2-methylpropan-1-ol HCl salt (20 mg, 0.055 mmol) was dissolved in 0.5 mL of deionized water and 1 mL of 2.0 M Jones reagent. The mixture was set at microwave reactor at 90° C. for 60 minutes. 20 mL of deionized water was added and solid NaHCO$_3$ was added slowly to the aqueous until pH researched to 7.0. The mixture was concentrated to dryness at 50° C., reduced pressure. The residue was dried in vacuum for 30 min., then mixed with methanol (20 mL×3), insoluble was filtered. The process was repeated again, then residue was dried in vacuum for overnight. Residue was mixed with 5 mL of deionized water, insoluble was filtered and filtrate was lyophilized for overnight to afford 10 mg as yellowish solid with 53.6% of yield. RP-HPLC (betasil C18, 0.5 mL/min, 10-100% ACN in 10 min) 4.83 min (with purity 88.6%); LC-MS (ESI, MH+) 342; ¹H NMR (500 MHz, D$_2$) δ 1.48-1.49 (6H, d), 7.36-7.45 (2H, m), 7.67-7.70 (1H, m).

Example 150

Preparation of Compound 207

Preparation of (S)-1-(4-(5-amino-6-(2,3-dichlorophenyl)-1,2,4-triazin-3-yl)piperazin-1-yl)-3-chloropropan-2-ol (Compound 207)

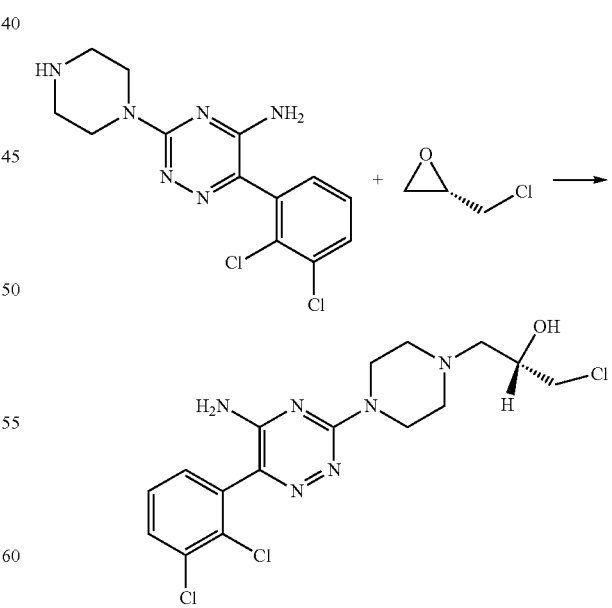

6-(2,3-Dichlorophenyl)-3-(piperazin-1-yl)-1,2,4-triazin-5-amine (509 mg, 1.565 mmol) and (S)-2-(chloromethyl)oxirane were dissolved in EtOH (200 proof, 4 mL). The solution was stirred under N$_2$ atmosphere at ambient temperature. After 2 days, the mixture turned into brown color. Solvent was removed under reduced pressure and solid residue was subject to flash chromatography. Yield product as yellowish solids (360 mg, purity 91%, yield 50.1%). LC-MS [ESI-MH$^+$]: m/z 417; $^1$H-NMR (CDCl$_3$) δ ppm: 7.577 (m, 1H), 7.375 (m, 2H), 4.763 (br, 2H), 4.037 (m, 1H), 3.935 (br, 4H), 3.624 (m, 3H), 2.765 (m, 2H), 2.652 (m, 4H). The product was dissolved in methanol and 4 equiv. HCl aqueous solution was added. Methanol was removed under reduced pressure. The remaining solution was frozen and lyophilized for 2 days to afford hydrochloride salt.

Example 151

Preparation of Compound 208

Preparation of 1-(4-(5-amino-6-(2,3-dichlorophenyl)-1,2,4-triazin-3-yl)piperazin-1-yl)-3-(4-(2',3'-dichloro-[1,1'-biphenyl]-4-yl)piperazin-1-yl)propan-2-ol (Compound 208)

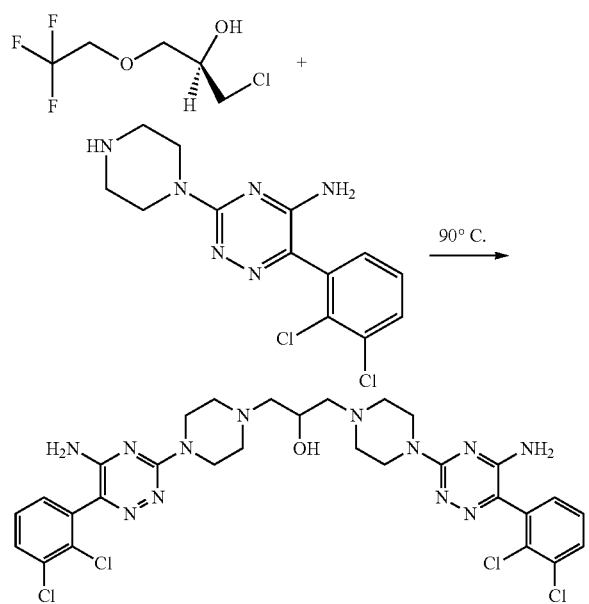

6-(2,3-Dichlorophenyl)-3-(piperazin-1-yl)-1,2,4-triazin-5-amine (0.5 g, 1.538 mmol), (R)-1-chloro-3-(2,2,2-trifluoroethoxy)propan-2-ol (2.96 g, 15.38 mmol) and pyridine (0.1 mL) were dissolved in anhydrous MeOH (2 mL). The solution was heated at 90° C. for 15 h. Solvent was removed under reduced pressure. The resulting residue was subject to flash chromatography. Yield product as white solids (77 mg, purity 98.0%, yield 7.1%).

LC-MS [ESI-MH$^+$]: m/z 705; $^1$H-NMR (CDCl$_3$) δ ppm: 7.577 (m, 2H), 7.375 (m, 4H), 4.754 (br, 4H), 4.116 (br, 1H), 3.980 (br, 8H), 3.499 (s, 2H), 2.770 (br, 4H), 2.683 (br, 4H), 2.526 (br, 4H). The product was dissolved in methanol and 4 equiv. HCl aqueous solution was added. Methanol was removed under reduced pressure. The remaining solution was frozen and lyophilized for 2 days to afford hydrochloride salt.

Example 152

Preparation of Compound 209

Preparation of 6-(2,3-dichlorophenyl)-N3-(2-(2-(2-isopropoxyethoxy)ethoxy)ethyl)-1,2,4-triazine-3,5-diamine (Compound 209)

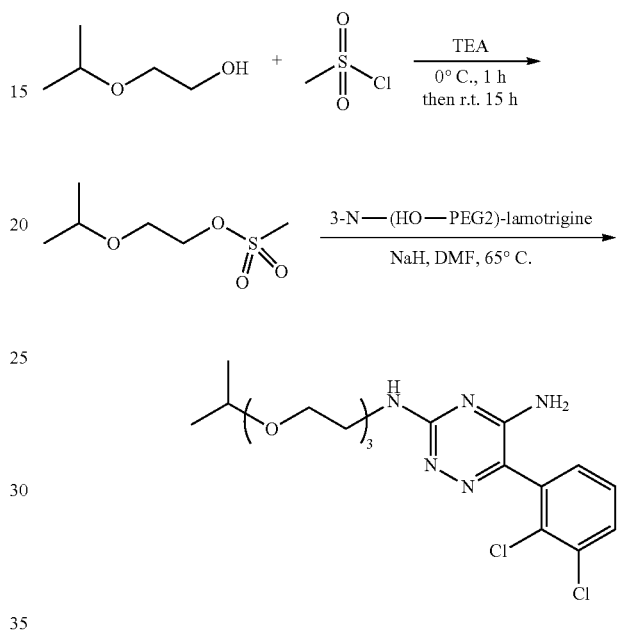

Preparation of 2-isopropoxyethyl methanesulfonate: 2-Isopropoxyethanol (2 g, 19.20 mmol) and TEA (4.82 mL, 34.6 mmol) were mixed in DCM (20 mL). Methanesulfonyl chloride (2.23 mL, 28.8 mmol) was added slowly. The mixture was stirred at ambient temperature. Solid was filtered off. Filtrate was concentrated under reduced pressure. Resulting residue was azetropically distilled with toluene 2 time. The residue was dried under high vacuum overnight. Hexane was added into the flask and the mixture was refluxed to extract mesylate product. The extraction was repeated 3 time, generating 500 mL solution. Solvent was removed and resulting residue was dried over vacuo overnight. Yield product as brown oil (2.8 g, yield 80%). $^1$H NMR (DMSO-d$_6$) δ ppm: 4.27 (t, J=4.5 Hz, 2H)), 3.598 (m, 3H), 3.174 (s, 3H), 1.094 (d, J=6 Hz, 6H).

Preparation of 6-(2,3-dichlorophenyl)-N3-(2-(2-(2-isopropoxyethoxy)ethoxy)ethyl)-1,2,4-triazine-3,5-diamine: To a solution of 2-(2-((5-amino-6-(2,3-dichlorophenyl)-1,2,4-triazin-3-yl)amino)ethoxy)ethanol (200 mg, 0.58 mmol) in DMF (5 mL) was added 2-isopropoxyethyl methanesulfonate (106 mg, 0.58 mmol). NaH (349 mg, 60% dispersion in mineral oil, 8.72 mmol) was added to the above solution. The mixture was heated over 65° C. in an oil bath. Solvent was removed under reduced pressure. Resulting residue was subject to chromatography purification to give product as white solid (25 mg, 90% purity, 10% yield). LC-MS [ESI-MH$^+$]: m/z 430. $^1$H-NMR (DMSO-d$_6$) δ ppm: 7.698 (d, J=5.5 Hz, 1H), 7.441 (t, J=7.5 Hz, 1H), 7.352 (d, J=7.5 Hz, 1H), 7.20-6.35 (b, 2H), 3.540 (m, 7H), 3.480 (d, J=4.0 Hz, 1H), 4.444 (m, 4H), 1.067 (d, J=6.5 Hz, 6H).

Example 153

Preparation of Compound 210

Preparation of 2,2'-((5-amino-6-(2,3-dichlorophenyl)-1,2,4-triazin-3-yl)azanediyl)diethanol (Compound 210)

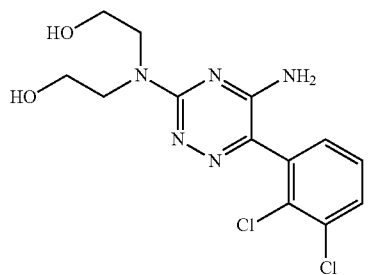 [SMILES: Nc1nc(N(CCO)CCO)nnc1-c1cccc(Cl)c1Cl]

A solution of 2,2'-azanediyldiethanol (1.402 g, 13.33 mmol), 3,6-dichloro-1,2,4-triazin-5-amine (2 g, 12.12 mmol) and triethylamine (5.07 ml, 36.4 mmol) was stirred at 95° C. under nitrogen for two hours. LCMS showed the completion of reaction. The reaction was cooled to room temperature. To the reaction mixture were added (2,3-dichlorophenyl)boronic acid (2.78 g, 14.54 mmol), and cesium carbonate (11.85 g, 36.4 mmol) followed by water (10.00 ml). The mixture was degassed under nitrogen for ten minutes before Tetrakis (2.80 g, 2.424 mmol) was added in. The reaction mixture was stirred at 85° C. for three hours under nitrogen. Solvent was removed via rotavap. The residue was purified using C18 column to give desired product 2,2'-((5-amino-6-(2,3-dichlorophenyl)-1,2,4-triazin-3-yl)azonediyl)diethanol (1.18 g, 3.43 mmol, 28.3% yield) as a free base.

Thereafter, 2,2'-((5-amino-6-(2,3-dichlorophenyl)-1,2,4-triazin-3-yl)azonediyl)diethanol (1.18 g, 3.43 mmol) was dissoved in methanol (Volume: 10 ml). To the solution was added HCl (4N in dioxane) (2.57 ml, 10.28 mmol). The mixture was stirred at room temperature for ten minutes. Solvent was removed and the residue was dried under high vacuum to give 2,2'-((5-amino-6-(2,3-dichlorophenyl)-1,2,4-triazin-3-yl)azonediyl)diethanol HCl salt (1.3 g, 3.42 mmol, 100% yield) as a white solid. MS (EI) for $C_{13}H_{15}Cl_2N_5O_2$ (346.3, MH+). 1H NMR (500 MHz, Methanol-d4) δ 7.67 (dd, J=8.1, 1.6 Hz, 1H), 7.44 (t, J=7.8 Hz, 1H), 7.37 (dd, J=7.6, 1.6 Hz, 1H), 3.83 (s, 8H).

Example 154

EX-VIVO POTENCIES OF 6-(2,3-DICHLOROPHENYL)-1,2,4-TRIAZIN-5-AMINE DERIVATIVE COMPOUNDS IN BLOCKING SODIUM CHANNELS

The potencies of the compounds provided herein to block specific Na+ channels was measured using automated patch clamp electrophysiologically of Nav1.7 sodium channels (human SCN9A gene) stably expressed in CHO cells using the IonWorks™ Barracuda system. Currents were measured from the whole cell patch configuration. From a holding potential of −90 mV, membranes were subjected to a 200 ms pre-pulse to −120 mV, then pulsed to 0 mV to measure blockade of the tonic (resting) state. Inactivated state block was elicited by repolarization to −100 mV (20 ms pulse duration), followed by depolarization to 0 mV (20 ms pulse duration). Peak inward Na+ currents were measured in the presence of vehicle or various concentrations of the test compound to determine the percent block of current. Concentration-response relationships were used to calculate $IC_{50}$ values for the illustrative compounds.

TABLE 1

Efficacy in Blockage of Sodium Channels

| Test article: Compound No. | $V_h$ (mV) | $IC_{50}$ (μM) | | |
|---|---|---|---|---|
| | | 0.1 Hz | 3 Hz | 10 Hz |
| 97 | −120 | >100 | >100 | 74.4 |
| 97 | −70 | 39.5 | 21.5 | 16.5 |
| 79 | −120 | | | |
| 79 | −70 | | | |
| 94 | −120 | | | |
| 94 | −70 | | | |
| 95 | −120 | | | |
| 95 | −70 | | | |
| 98 | −120 | | | |
| 98 | −70 | | | |

TABLE 2

Efficacy in Blockage of Sodium Channels

| Test article: Compound No. | Tonic state $IC_{50}$ (μM) | Inactivated state $IC_{50}$ (μM) |
|---|---|---|
| 103 | >200 | 54.86 |
| 103 (repeat test) | >200 | <50 |
| 104 | >200 | <50 |
| 105 | >150 | >150 |
| 105 (repeat test) | >200 | >300 |
| 106 | >200 | 145.82 |
| 106 (repeat test) | >200 | 220.42 |
| 112 | >200 | >300 |
| 112 | >200 | >300 |
| 20 | >200 | >300 |
| 107 | >200 | >300 |
| 108 | >200 | 184.53 |
| 110 | >200 | 206.09 |
| 115 | >200 | >300 |
| 1 | >200 | 60.13 |
| 1 (repeat test) | 197.29 | <50 |
| 79 | >200 | 95.30 |
| 117 | >200 | 84.53 |
| 111 | >200 | <50 |
| 118 | 111.65 | <50 |
| 119 | 92.42 | <50 |
| 92 | >200 | >300 |
| 113 | 92.55 | <50 |
| 120 | 146.94 | <50 |
| 121 | >200 | 271.88 |
| 122 | >150 | >150 |
| 124 | >200 | 71.85 |
| 125 | >200 | 72.60 |
| 123 | >200 | 111.46 |
| 93 | >200 | >300 |
| 96 | >200 | <50 |
| 97 | >200 | <50 |
| 97 (repeat test) | >200 | 90.53 |
| 97 (repeat test) | >200 | 82.21 |
| 87 | >200 | <50 |
| 127 | >200 | >300 |
| 128 | >200 | >300 |
| 126 | >200 | 284.46 |
| 89 | >200 | 66.61 |
| 88 | 113.17 | <50 |
| 129 | >132 | >132 |
| 130 | >200 | 204.14 |
| 131 | >200 | 187.18 |
| 90 | 182.80 | 56.19 |

TABLE 2-continued

Efficacy in Blockage of Sodium Channels

| Test article: Compound No. | Tonic state IC$_{50}$ (μM) | Inactivated state IC$_{50}$ (μM) |
|---|---|---|
| 132 | >200 | >300 |
| 147 | 150.94 | <50 |
| 147 (repeat test) | 178.80 | <50 |
| 148 | 148.75 | <50 |
| 165 | >200 | 291.43 |
| 165 (repeat test) | >200 | 249.35 |
| 133 | >200 | 73.90 |
| 133 (repeat test) | 165.46 | 59.10 |
| 98 | >200 | 57.48 |
| 98 (repeat test) | >200 | <50 |
| 98 (repeat test) | >200 | <50 |
| 134 | >200 | >300 |
| 134 (repeat test) | >200 | 224.53 |
| 135 | >200 | >300 |
| 135 (repeat test) | >200 | >300 |
| 136 | >200 | 86.56 |
| 136 (repeat test) | >200 | 92.65 |
| 137 | >200 | 292.61 |
| 137 (repeat test) | >200 | 243.36 |
| 138 | >200 | >300 |
| 139 | >200 | 103.48 |
| 140 | >200 | >300 |
| 55 | >200 | 62.30 |
| 73 | 179.10 | <50 |
| 131 Product | 133.70 | <50 |
| 141 | >200 | 149.10 |
| 99 | >200 | >300 |
| 71 | >200 | 187.20 |
| 75 | >200 | 256.10 |
| 80 | 70.00 | <50 |
| 83 | 171.20 | <50 |
| 160 | >200 | 291.90 |
| 161 | 146.70 | 51.40 |
| 84 | 192.10 | <50 |
| 162 | >200 | 193.50 |
| 163 | >200 | >300 |
| 159 | >200 | 288.60 |
| 207 | >200 | 106.72 |
| 207 (repeat test) | >200 | 132.74 |
| 169 | >200 | >300 |
| 209 | >200 | <50 |
| 173 | >200 | 214.45 |
| 175 | >200 | >300 |
| 176 | >200 | 266.93 |
| 176 (repeat test) | >200 | 180.95 |
| 177 | >200 | <50 |
| 178 | >200 | >300 |
| 178 (repeat test) | >200 | >300 |
| 153 | >200 | >300 |
| 180 | >200 | 297.57 |
| 182 | >200 | 199.20 |
| 182 (repeat test) | >200 | 127.12 |
| 185 | >200 | 175.58 |
| 186 | >200 | 100.40 |
| 187 | >200 | 160.15 |
| 188 | >200 | <50 |
| 167 | 107.89 | <50 |
| 167 (repeat test) | 91.48 | <50 |
| 167 (repeat test) | 130.15 | <50 |
| 197 | >200 | <50 |
| 190 | >200 | 272.83 |
| 196 | >200 | >300 |
| 191 | >200 | 243.53 |
| 192 | >200 | >300 |
| 193 | 62.55 | <50 |
| 194 | >200 | >300 |
| 199 | >200 | >300 |
| 200 | >200 | 119.80 |
| 201 | >200 | 201.91 |
| 202 | >200 | >300 |
| 203 | 87.92 | <50 |
| 125 | >200 | 72.60 |
| 165 | >200 | 291.43 |
| 165 (repeat test) | >200 | 249.35 |

In one or more embodiments, preferred are compounds that demonstrate an IC$_{50}$ tonic state value as indicated in the table of greater than (>) a value that is 200 μM. In one or more additional embodiments, preferred are compounds that demonstrate an IC$_{50}$ inactivated state value as provided in the table of less than (<) a value that is 50 μM. These compounds include Compound 1, 118, 119, 113, 122, 88, 129, 90, 147, 148, 133, 73, 131, 80, 83, 161, 84, 167, 193, and 203.

Example 155

PHARMACOKINETICS OF DICHLOROPHENYL)-1,2,4-TRIAZIN-5-AMINE DERIVATIVE COMPOUNDS

Fasted, male Sprague Dawley rats were dosed intravenously or orally. Blood samples were collected at predetermined time points and plasma was separated. Test article concentrations were determined in plasma by a LC/MS/MS method. Non compartmental analysis was performed to estimate the area under the plasma concentration vs. time curve (AUC). Clearance parameters (CL), bioavailabilities (F) and half-lives were calculated. The data in qualitative form for CL and dose normalized AUC is provided in the tables below.

TABLE 3

Pharmacokinetics

| Compound No. | CL (mL/min/kg) | Dose normalized AUC(hr*ng/mL) |
|---|---|---|
| 65 | * | ** |
| 97 | * | ** |
| 128 | * | ** |
| 95 | * | ** |
| 75 | * | ** |
| 129 | * | ** |
| 27 | * | ** |
| 127 | * | ** |
| 94 | * | ** |
| 98 | * | ** |
| 96 | * | ** |
| 120 | * | ** |
| 130 | * | ** |
| 45 | | ** |
| 99 | | ** |
| 182 | | ** |
| 90 | | ** |
| 165 | | ** |
| 165 | | ** |
| 55 | | ** |

Of the compounds tested, those compounds demonstrating the most favorable pharmacokinetics, are compounds 65, 97, 128, 95, 75, 129, 27, 127, 94, 98, 96, 120 and 130, indicated by an asterisk (*) in the table above. Each of the foregoing compounds possesses a substituted tertiary amino group attached at the 3-position of the triazine ring, where the tertiary amino group forms part of a ring system. The substituted ring systems include substituted pyrrolidine, substituted piperazine, substituted piperazine forming part of a bicyclic ring system, e.g., tetrahydro-1H-oxazolo[3,4-a]pyrazin-3(5H)-one (compound 128), tetrahydro-1H-oxazolo[3,4-a]pyrazin-3(5H)-one (compound 127), and hexahydropyrazino[2,1-c][1,4]oxazin-4(3H)-one (compound 130), and azetidine. Specifically, compounds demonstrating the most favorable pharmacokinetics include: (2S,4R)-Methyl 1-(5-amino-6-(2,3-dichlorophenyl)-1,2,4-triazin-3- yl)-4-hydroxypyrrolidine-2-carboxylate (Compound 65), (S)-1-(4-(5-amino-6-(2,3-dichlorophenyl)-1,2,4-triazin-3-yl)piperazin-1-yl)-3-methoxypropan-2-ol (Compound 97), (S)-7-(5-amino-6-(2,3-dichlorophenyl)-1,2,4-triazin-3-yl) tetrahydro-1H-oxazolo[3,4-a]pyrazin-3(5H)-one HCl salt (Compound 128), (S)-1-(4-(5-amino-6-(2,3-dichlorophenyl)-1,2,4-triazin-3-yl)-piperazin-1-yl)-3-(2,2,2-trifluoroethoxy)-propan-2-ol.2HCl (Compound 95), (R)-1-((1-(5-Amino-6-(2,3-dichlorophenyl)-1,2,4-triazin-3-yl)azetidin-3-yl)oxy)-3-methoxypropan-2-ol (Compound 75), 3-N-(3-hydroxyazetin-1-yl) lamotrigine (Compound 129), 1-(4-(5-Amino-6-(2,3-dichlorophenyl)-1,2,4-triazin-3-yl)piperazin-1-yl)-3-(trifluoromethoxy)propan-2-ol (Compound 27), (R)-7-(5-amino-6-(2,3-dichlorophenyl)-1,2,4-triazin-3-yl) tetrahydro-1H-oxazolo[3,4-a]pyrazin-3(5H)-one (Compound 127), (R)-1-(4-(5-amino-6-(2,3-dichlorophenyl)-1,2,4-triazin-3-yl)-piperazin-1-yl)-3-(2,2,2-trifluoroethoxy)-propan-2-ol (Compound 94), (S)-1-(4-(5-amino-6-(2,3-dichlorophenyl)-1,2,4-triazin-3-yl)piperazin-1-yl)-3-methoxypropan-2-ol (Compound 98), (R)-1-(4-(5-amino-6-(2,3-dichlorophenyl)-1,2,4-triazin-3-yl)piperazin-1-yl)-3-methoxypropan-2-ol (Compound 96), 3-N-(4-(tetrahydro-2H-pyran-4-yl)piperazin-1-yl) lamotrigine di HCl (Compound 120), and (R)-8-(5-amino-6-(2,3-dichlorophenyl)-1,2,4-triazin-3-yl)hexahydropyrazino[2,1-c][1,4]oxazin-4(3H)-one HCl salt (Compound 130). The foregoing compounds are, in one or more embodiments, preferred.

Of the foregoing compounds, all of them also fell within the group that exhibited the best exposure after oral dosing as indicated in the above table (**). The compounds that exhibited the best exposure after oral dosing were, in addition to the compounds previously identified above, Compounds 65, 97, 128, 95, 75, 129, 27, 127, 94, 98, 96, 120, 130, 45, 99, 182, 90, 165, 55, 119, 118, 201, 202, 89, 73, 200, 79, 47, 126, 92, 49, 57, 188, and 207. These compounds are also, in one or more embodiments, preferred.

Example 156

IN-VIVO EFFICACY STUDIES OF DICHLOROPHENYL)-1,2,4-TRIAZIN-5-AMINE DERIVATIVE COMPOUNDS

TABLE 4

| Compound No. | Model | Dose(s) (mg/kg) | Timepoint(s) tested (h) | ED50 (mg/kg) | MED (mg/kg) |
|---|---|---|---|---|---|
| 1 | AFP | 30, 100, 300, 450 | 0.5 | 589.3 (Ph2) | 450 (Ph2) |
| 167 | AFP | 100 | 0.5 | NA | NA |
| 167 (+ABT) | AFP | 100 | 0.5 | NA | 100 |
| 44 | AFP | 1, 10, 100 | 1 | NA | NA |
| 45 | AFP | 3, 10, 30, 100 | 0.25 | 46.8 (Ph2) | 30 (Ph2) |
|  | RR | 10, 30, 60 | 0.5, 1 | 21.0 (0.5 h) 18.9 (1 h) | 30 |
| 42 | AFP | 30, 100, 300 | 1 | NA | NA |
|  |  | 100 | 0.25 | NA | NA |
|  | SNL: allodynia | 450 | 0.5, 1.5 | NA | NA |
| 95 | AFP | 300 | 0.5 | NA | NA |
|  | AFP | 500 (2 doses @ 250 mg/kg) | 0.5 | NA | 500 (Ph1) |
|  | SNL: allodynia | 30, 100, 300 | 0.5, 1.5 | NA | NA |
| 207 (M3) | AFP | 30, 100, 300, 450 | 0.5 | 476.3 (Ph2) | 300 (Ph2) |

The efficacy of illustrative compounds as provided herein was determined using various animal models as provided in the table above. ED50 and MED (minimum effective dose) values were determined and are reported in Table 4.

Mechanical Allodynia: The efficacy of test compounds in reducing mechanical allodynia was assessed in the chronic constriction injury model in rats. Male SD rats were briefly anesthetized under pentobarbital anesthesia and surgery was performed following the Bennett model of sciatic nerve ligation where the left sciatic nerve was loosely ligated with four chromic gut sutures. 7-14 days post-surgery, rats that are clearly allodynic were randomized to treatment groups (n=10 rats/group). Mechanical allodynia was evaluated using the von Frey up-down method, 30 minutes before and at 1 and 2 hr after a single dose of test compound or of gabapentin. Aminobenzotriazole (100 mg/kg p.o.) was dosed orally 16-24 hours prior to treatment with test compounds.

The efficacy of the compounds when evaluated in additional well-known animal models, AFP, RR, and hyperalgesia, was also explored. Preferred compounds of those evaluated, in terms of their potencies, are compounds 167 (6-(2,3-dichlorophenyl)-N³-(2-(2-(2-(trifluoromethoxy) ethoxy)ethoxy)ethyl)-1,2,4-triazine-3,5-diamine) and 98 ((S)-1-(4-(5-amino-6-(2,3-dichlorophenyl)-1,2,4-triazin-3-yl)piperazin-1-yl)-3-methoxypropan-2-ol).

What is claimed is:
1. A 6-(2,3-dichlorophenyl)-1,2,4-triazine-5 amine compound having a structure of Formula B,

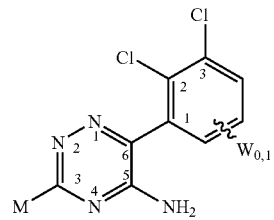

Formula B wherein M is $NR_6R_7$,
wherein $R_6$ and $R_7$ are each independently selected from the group consisting of H, $(CH_2CH_2O)_mR_8$, —$CH_2CH_2$-(3-7 membered heterocycloalkyl), —$C(O)$—$CH_2(CH_2CH_2O)_mR_{10}$, —$CH_2CR_9HCH_2O$ $(CH_2CH_2O)_m(CH_2)_{0,1}R_{10}$, —$CR_{11}R_{12}CH_2OH$, —$CR_{11}R_{12}CH_2O(CH_2CH_2O)_{1-7}R_{10}$, —$CH$—$[CH_2OH]_2$; —$CCH_3(CH_2OH)_2$, —$CCH_3(CH_2OH)$ $CH_2O(CH_2CH_2O)_{1-7}R_{10}$, alkylamino, hydroxyalkylamino, —CH₂CH₂NCH₃C(O)CH₂(OCH₂CH₂)₁₋₇R₁₀,
—CH₂CH₂NCH₃C(O)CH₂OCH₂C(O)NH₂,
—CH₂CH₂NCH₃(CH₂CH₂O)₁₋₇R₁₀, —CR₁₁R₁₂CH(O), —CR₁₁R₁₂(CH₂)₁ or ₂SO₂⁻CH₂CH₂O)₁₋₇R₁₀,
—CCH₃(CH₂OCH₂CH₂OCH₃)₂,
—OCH₂CR₉HCH₂OR₁₀, —CH₂CR₉HCH₂NHC(O)CH₂O(CH₂CH₂O)ₘR₁₀, —CH₂CR₉HCH₂NHC(O)CH₂OCH₂C(O)NH₂, and —(OCH₂CH₂)ₘOR₁₀, with the proviso that R₆ and R₇ are not both H, wherein when R₆ is H and W is 0, R₇ does not equal (CH₂CH₂O)₂₋₁₁CH₃, m is an integer selected from 0-29, R₈ is selected from H, a C₁-C₆ alkyl, fluoro-substituted methyl, —CH₂COOR₁₀, —CH₂COCH₃, —C(O)OCH₃, C₁-C₆ alkyl substituted with one or more of hydroxyl, amino, alkylamino, amido, alkylamide, amidoalkylamine, acylamino, carboxyalkylamino, sulfonamide, alkylsulfone, alkoxyalkyl sulfone, alkyloxyalklsulfoxide, a 3-7 membered heterocycloalkyl, a 5-6 membered heteroaryl, carboxyl, —NHCH₂CH₂OCH₃, —NHCHR₉COOR₁₁; and —CH—[CH₂O—(CH₂CH₂O)₂₋₈CH₃]₂, wherein when R₆ is H and m is 0, R₈ does not equal H;

R₉ is selected from H, lower alkyl, and hydroxyl,

R₁₀ is selected from H, lower alkyl, and fluoro-substituted methyl,

R₁₁ and R₁₂ are each independently selected from H and lower alkyl,

R₁₃ is cyclopropyl or cyclobutyl, and

W is an optional substituent selected from the group consisting of halo, hydroxyl, and (—OCH₂CH₂)ₙOR, where n is an integer selected from 1-7 and R is selected from H, lower alkyl and fluoro-substituted methyl, or a pharmaceutically acceptable salt thereof.

2. The compound of claim 1, wherein the dichlorophenyl ring possesses an additional substituent at any one of positions 4, 5 or 6, where the substituent is selected from halo, hydroxyl, and (—OCH₂CH₂)ₙOR, where n is an integer from 1-7 and R is selected from H, lower alkyl, methyl, and fluoro-substituted methyl.

3. The compound of claim 1, wherein R or R₁₀ is selected from methyl and —CF₃.

4. The compound of claim 1, wherein W is fluoro.

5. The compound of claim 4, wherein W is a fluoro group positioned at the 5-position of the phenyl ring.

6. The compound of claim 1, wherein R₆ is H.

7. The compound of claim 6, wherein R₇ is selected from the group consisting of —(CH₂CH₂O)ₘR₈, —CH₂CH₂-(3-7 membered heterocycloalkyl), —C(O)—CH₂(CH₂CH₂O)ₘR₁₀, —CH₂CR₉HCH₂O(CH₂CH₂O)ₘ(CH₂)₀,₁R₁₀, —CR₁₁R₁₂CH₂OH, —CR₁₁R₁₂CH₂O(CH₂CH₂O)₁₋₇R₁₀, —CH—[CH₂OH]2, —CCH₃(CH₂OH)₂, —CCH₃(CH₂OH)CH₂O(CH₂CH₂O)₁₋₇R₁₀, —CH₂CH₂NCH₃C(O)CH₂(OCH₂CH₂)₁₋₇R₁₀, —CH₂CH₂NCH₃C(O)CH₂OCH₂C(O)NH₂, —CH₂CH₂NCH₃(CH₂CH₂O)₁₋₇R₁₀, —CR₁₁R₁₂CH(O), —CR₁₁R₁₂(CH₂)₁ or ₂SO₂—CH₂CH₂O)₁₋₇R₁₀, —CCH₃(CH₂OCH₂CH₂OCH₃)₂, —OCH₂CR₉HCH₂OR₁₀, —CH₂CR₉HCH₂NHC(O)CH₂O(CH₂CH₂O)ₘR₁₀, —CH₂CR₉HCH₂NHC(O)CH₂OCH₂C(O)NH₂, and —(OCH₂CH₂)ₘOR₁₀.

8. The compound of claim 1, wherein m is selected from 0, 1, 2, 3, 4, 5, 6, and 7.

9. The compound of claim 1, wherein R₆ is H and R₇ is —(CH₂CH₂O)ₘR₈, where m is selected from 1, 2, 3, 4, 5, 6, and 7, and R₈ is selected from H, methyl, isopropyl, fluoro-substituted methyl, carboxyl, and a 3-7 membered heterocycloalkyl.

10. The compound of claim 9, wherein the 3-7 membered ring heterocycloalkyl is selected from tetrazole, oxetane and piperazine.

11. The compound of claim 1, having the following structure

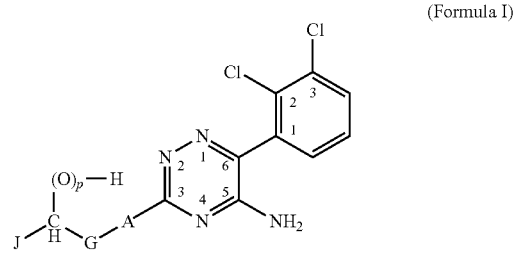

(Formula I)

wherein:

A is

G is selected from the group consisting of ~O~, ~CH₂~,

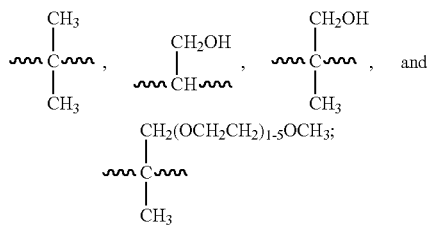

p is 0 or 1 (where a value of 0 indicates the absence of oxygen and a value of 1 indicates its presence); and J is selected from the group consisting of ~CH(OH)CH₂OH, ~CH(OH)CH₂OCH₃, ~OCH₂CH₂OH, ~CH₂OCF₃, ~CH₂OCH₃, ~OCF₃, —OH, ~OCH(CH₂OCH₃)₂, ~OCH(CH₂OH)₂, ~(OCH₂CH₂)₀₋₂₉OR¹, where R¹ is methyl or a fluoro-substituted methyl, ~CH₂OCH₂CH₃, ~CH₂OCH(CH₃)₂,

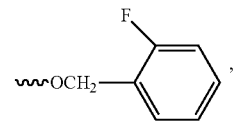

and ~OCH₂C(OH)HCH₂OCH₃, or a pharmaceutically acceptable salt thereof.

12. The compound of claim 11, wherein R¹ is selected from the group consisting of ~CF₃, ~CF₂H, and ~CFH₂.

13. The compound of claim 1, wherein the compound is selected from the group consisting of:

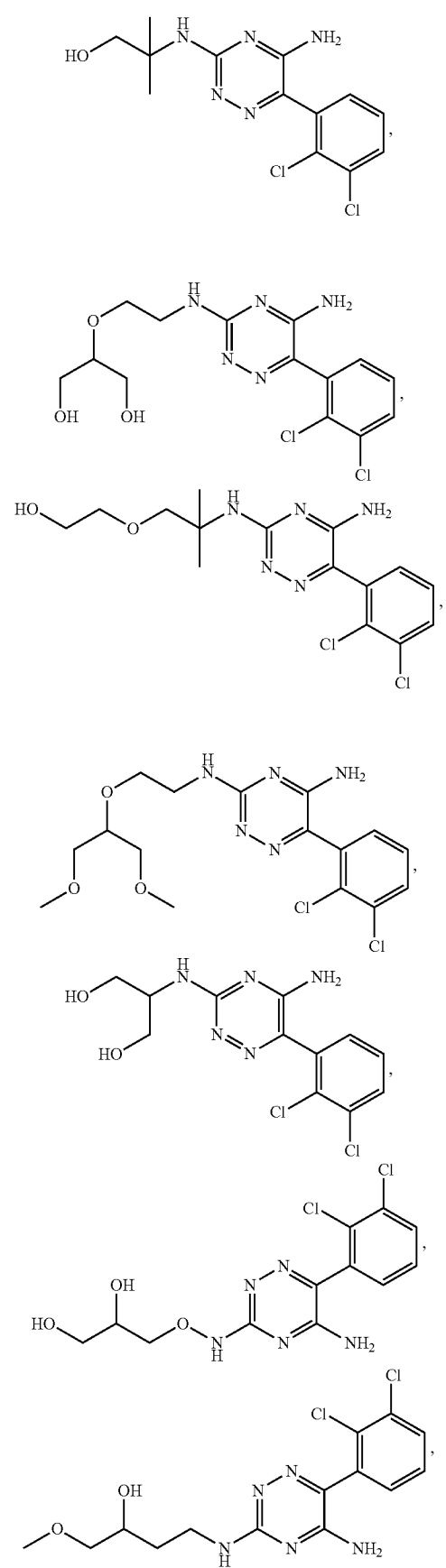
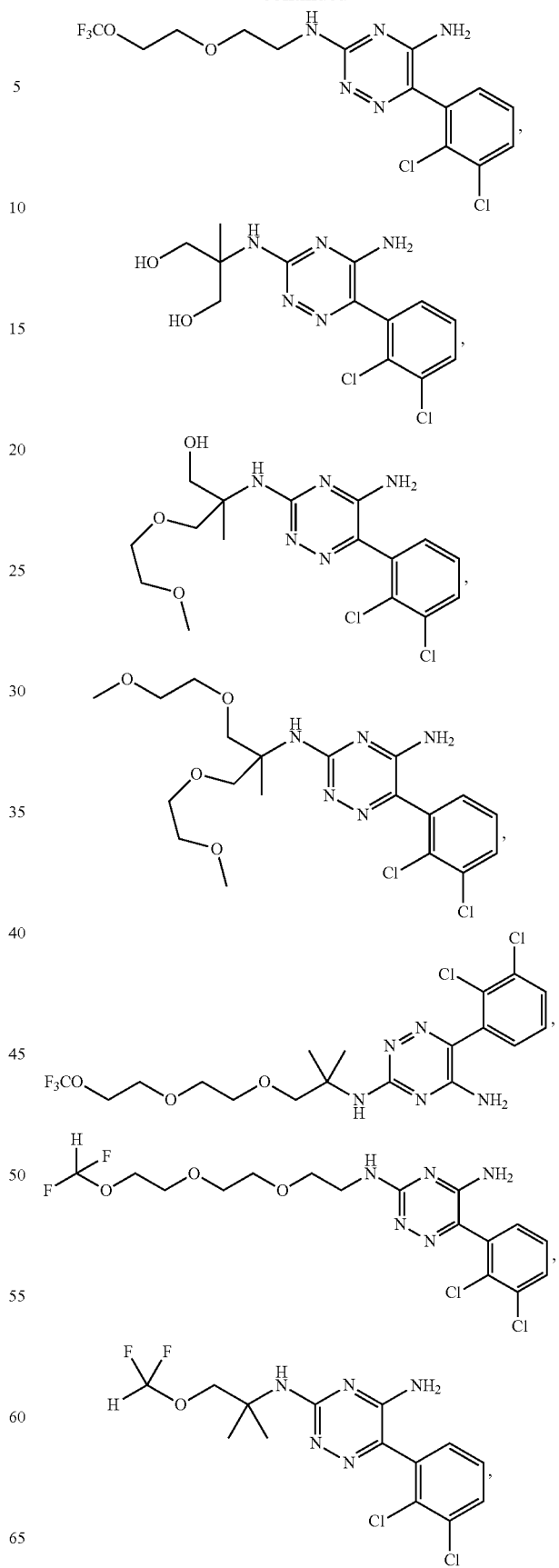

-continued

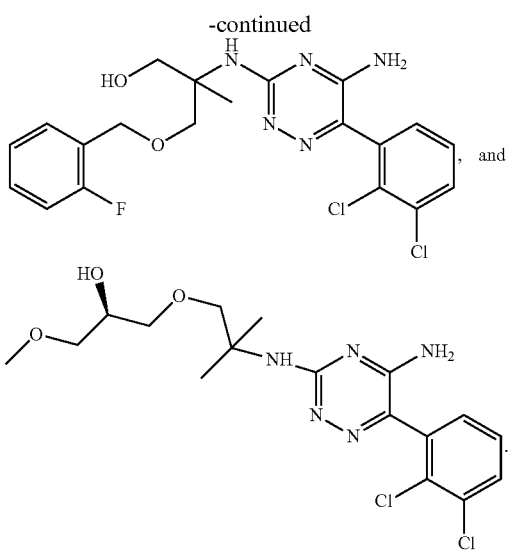
, and

14. The compound of claim 1 having a structure:

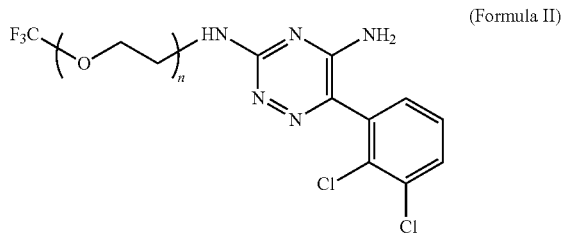
(Formula II)

wherein (n) is an integer of 1 to 30, or pharmaceutically acceptable salts thereof.

15. The compound of claim 1 having a structure selected from the group consisting of:

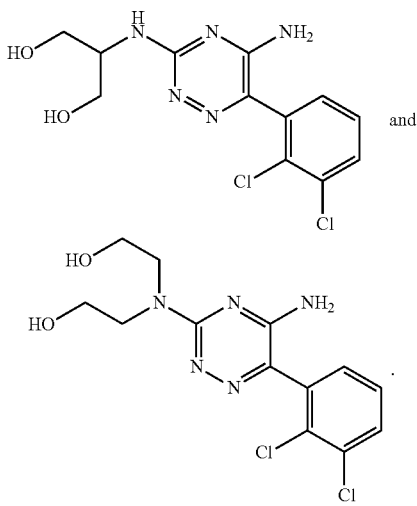

16. A composition comprising the compound of claim 1, and a pharmaceutically acceptable excipient.

17. A method for the treatment of one or more of epilepsy, neuropathic pain, bipolar disorder or a malarial infection comprising:
administering to a therapeutically effective amount of the-composition of claim 16 to a subject in need thereof.

* * * * *